United States Patent
Lewis et al.

(10) Patent No.: US 8,916,569 B2
(45) Date of Patent: Dec. 23, 2014

(54) COMPOUNDS AND METHODS FOR INHIBITING PHOSPHATE TRANSPORT

(71) Applicant: Ardelyx, Inc., Fremont, CA (US)

(72) Inventors: Jason G. Lewis, Castro Valley, CA (US); Jeffrey W. Jacobs, San Mateo, CA (US); Nicholas Reich, Berkeley, CA (US); Michael R. Leadbetter, San Leandro, CA (US); Noah Bell, Berkeley, CA (US); Han-Ting Chang, Livermore, CA (US); Tao Chen, Palo Alto, CA (US); Marc Navre, Belmont, CA (US); Dominique Charmot, Campbell, CA (US); Christopher Carreras, Belmont, CA (US); Eric Labonte, Redwood City, CA (US)

(73) Assignee: Ardelyx, Inc., Fremont, CA (US)

(*) Notice: Subject to any disclaimer, the term of this patent is extended or adjusted under 35 U.S.C. 154(b) by 0 days.

(21) Appl. No.: 13/734,547

(22) Filed: Jan. 4, 2013

(65) Prior Publication Data
US 2013/0336920 A1    Dec. 19, 2013

Related U.S. Application Data

(63) Continuation of application No. PCT/US2011/043267, filed on Jul. 7, 2011.

(60) Provisional application No. 61/362,117, filed on Jul. 7, 2010, provisional application No. 61/443,632, filed on Feb. 16, 2011.

(51) Int. Cl.
| | | |
|---|---|---|
| A61K 31/4418 | (2006.01) | |
| A61K 31/444 | (2006.01) | |
| A61K 31/505 | (2006.01) | |
| A61K 31/506 | (2006.01) | |
| C07D 213/36 | (2006.01) | |
| C07D 239/26 | (2006.01) | |
| C07D 401/10 | (2006.01) | |
| C07D 403/10 | (2006.01) | |
| C07D 401/12 | (2006.01) | |
| A61K 31/44 | (2006.01) | |
| A61K 31/541 | (2006.01) | |
| C07D 405/14 | (2006.01) | |
| A61K 31/4545 | (2006.01) | |
| A61K 31/551 | (2006.01) | |
| C07D 239/34 | (2006.01) | |
| A61K 31/5377 | (2006.01) | |
| C07D 403/12 | (2006.01) | |
| A61K 31/785 | (2006.01) | |
| A61K 45/06 | (2006.01) | |
| C07D 239/42 | (2006.01) | |
| C07D 405/12 | (2006.01) | |
| C07D 417/12 | (2006.01) | |
| C07D 213/81 | (2006.01) | |
| C07D 417/14 | (2006.01) | |
| C07D 401/14 | (2006.01) | |
| C07D 213/82 | (2006.01) | |
| A61K 31/59 | (2006.01) | |

(52) U.S. Cl.
CPC .............. *C07D 213/81* (2013.01); *A61K 31/44* (2013.01); *A61K 31/541* (2013.01); *C07D 405/14* (2013.01); *A61K 31/506* (2013.01); *C07D 401/10* (2013.01); *A61K 31/4545* (2013.01); *A61K 31/551* (2013.01); *C07D 239/34* (2013.01); *C07D 401/12* (2013.01); *A61K 31/5377* (2013.01); *C07D 403/12* (2013.01); *A61K 31/785* (2013.01); *A61K 45/06* (2013.01); *C07D 239/42* (2013.01); *C07D 405/12* (2013.01); *C07D 417/12* (2013.01); *C07D 417/14* (2013.01); *C07D 401/14* (2013.01); *C07D 213/82* (2013.01); *A61K 31/59* (2013.01)
USPC ........... 514/256; 514/357; 514/340; 546/329; 546/264; 546/340; 544/335; 544/333

(58) Field of Classification Search
None
See application file for complete search history.

(56) References Cited

U.S. PATENT DOCUMENTS

| 6,300,363 B1 | 10/2001 | Stevens et al. |
| 6,608,070 B1 | 8/2003 | Nakao et al. |

(Continued)

FOREIGN PATENT DOCUMENTS

| EP | 1273575 A1 | 1/2003 |
| EP | 1614676 A1 | 1/2006 |

(Continued)

OTHER PUBLICATIONS

Stec, et al., Bioorg. & Med. Chem. Lett., 18:5118 (2008).*

(Continued)

*Primary Examiner* — Michael Barker
(74) *Attorney, Agent, or Firm* — Cooley LLP

(57) ABSTRACT

Compounds having activity as phosphate transport inhibitors, more specifically, inhibitors of intestinal apical membrane Na/phosphate co-transport, are disclosed. The compounds have the following structure (I):

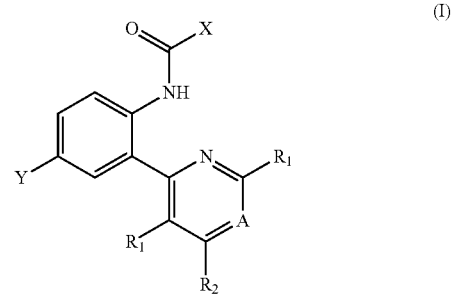

including stereoisomers, pharmaceutically acceptable salts and prodrugs thereof, wherein X, Y, A, $R_1$ and $R_2$ are as defined herein. Methods associated with preparation and use of such compounds, as well as pharmaceutical compositions comprising such compounds, are also disclosed.

44 Claims, No Drawings

(56) References Cited

U.S. PATENT DOCUMENTS

| | | |
|---|---|---|
| 2002/0133036 A1 | 9/2002 | Peerce |
| 2003/0195193 A1 | 10/2003 | Hirayama et al. |
| 2003/0216449 A1 | 11/2003 | Weinstock et al. |
| 2004/0019113 A1 | 1/2004 | Jozefiak et al. |
| 2005/0261346 A1 | 11/2005 | Zhu et al. |
| 2008/0026037 A1 | 1/2008 | Christensen et al. |
| 2009/0227566 A1 | 9/2009 | Argade et al. |
| 2013/0336918 A1 | 12/2013 | Lewis et al. |
| 2013/0336919 A1 | 12/2013 | Lewis et al. |
| 2013/0336921 A1 | 12/2013 | Lewis et al. |
| 2014/0023611 A1 | 1/2014 | Lewis et al. |

FOREIGN PATENT DOCUMENTS

| | | |
|---|---|---|
| WO | WO 01/05398 A1 | 1/2001 |
| WO | WO 01/21160 A2 | 3/2001 |
| WO | WO 01/21160 A3 | 3/2001 |
| WO | WO 03/057225 A2 | 7/2003 |
| WO | WO 2012/006473 A2 | 1/2012 |
| WO | WO 2012/006474 A2 | 1/2012 |
| WO | WO 2012/006475 A1 | 1/2012 |
| WO | WO 2012/006477 A1 | 1/2012 |
| WO | WO 2012/054110 A2 | 4/2012 |

OTHER PUBLICATIONS

Chou, Y-L et al., "Structure-Activity Relationships of Substituted Benzothiophene-anthranilamide Factor Xa Inhibitors", Bioorganic & Medicinal Chemistry Letters, Pergamon. GB, vol. 13, Jan. 1, 2003, pp. 507-511.

Ertl et al., "Fast Calculation of Molecular Polar Surface Area as a Sum of Fragment-Based Contributions and Its Application to the Prediction of Drug Transport Properties", *J. Med. Chem.* (2000) 43:3714-3717.

Eto et al., "Nicotinamide prevents the development of hyperphosphataemia by suppressing intestinal sodium-dependent phosphate transporter in rats with adenine-induced renal failure", *Nephrol Dial Transplant* (2005) 20:1378-1384.

STN/CAPLUS Accession No. 2012:1449104, citing Cooper, M., "An investigation of intramolecular nucleophilic substitution in indole," Dissertation, Department of Chemistry, University of Manchester (1978).

Zakeri-Milani et al., "The relation between molecular properties of drugs and their transport across the intestinal membrane", *DARU* vol. 14, No. 4 2006.

International Report on Patentability for PCT/US2011/043267 mailed Jan. 17, 2013.

International Report on Patentability for PCT/US2011/043261 mailed Jan. 17, 2013.

International Report on Patentability for PCT/US2011/043262 mailed Jul. 4, 2013.

International Report on Patentability for PCT/US2011/043266 mailed Jan. 17, 2013.

International Report on Patentability for PCT/US2011/043263 mailed Jan. 17, 2013.

International Search Report and Written Opinion for PCT/US2011/043267 mailed Apr. 5, 2012.

International Search Report and Written Opinion for PCT/US2011/043261 mailed Nov. 21, 2011.

International Search Report and Written Opinion for PCT/US2011/043262 mailed Nov. 18, 2011.

International Search Report and Written Opinion for PCT/US2011/043266 mailed Nov. 21, 2011.

International Search Report and Written Opinion for PCT/US2011/043263 mailed Nov. 21, 2011.

Supplementary European Search Report in EU Application No. 11834773.1 mailed Nov. 28, 2013.

Supplementary European Search Report in EU Application No. 11804369.4 dated Nov. 8, 2013.

Supplementary European Search Report in EU Application No. 11804373.6 dated Dec. 5, 2013.

Supplementary European Search Report in EU Application No. 11804371.0 dated Apr. 10, 2014.

Communication pursuant to Rules 70(2) and 70a(2) EPC in EU Application No. 11804371.0 dated Apr. 29, 2014.

Office Action in U.S. Appl. No. 13/734,562 issued Oct. 2, 2013.

Notice of Allowance in U.S. Appl. No. 13/734,562, dated Apr. 22, 2014.

Official Communication in U.S. Appl. No. 13/734,562, dated Jun. 10, 2014.

Office Action in U.S. Appl. No. 13/734,551 issued Sep. 30, 2013.

Notice of Allowance in U.S. Appl. No. 13/734,551 dated Apr. 11, 2014.

Office Action in U.S. Appl. No. 13/734,701 issued Oct. 1, 2013.

Notice of Allowance in U.S. Appl. No. 13/734,701, dated Apr. 22, 2014.

\* cited by examiner

COMPOUNDS AND METHODS FOR INHIBITING PHOSPHATE TRANSPORT

CROSS-REFERENCE TO RELATED APPLICATIONS

This application is a continuation of International PCT Patent Application No. PCT/US2011/043267, filed Jul. 7, 2011, now pending, which claims the benefit under 35 U.S.C. §119(e) of U.S. Provisional Patent Application No. 61/362,117 filed Jul. 7, 2010; and U.S. Provisional Patent Application No. 61/443,632 filed Feb. 16, 2011. The foregoing applications are incorporated herein by reference in their entireties.

BACKGROUND

1. Field

The present invention is directed to novel phosphate transport inhibitors, more specifically, inhibitors of intestinal apical membrane Na/phosphate co-transport, and methods for their preparation and use as therapeutic or prophylactic agents.

2. Description of the Related Art

Patients with inadequate renal function, hypoparathyroidism, or certain other medical conditions (such as hereditary hyperphosphatemia, Albright hereditary osteodystrophy, amyloidosis, etc.) often have hyperphosphatemia, or elevated serum phosphate levels (wherein the level, for example, is more than about 6 mg/dL). Hyperphosphatemia, especially if present over extended periods of time, leads to severe abnormalities in calcium and phosphorus metabolism, often manifested by secondary hyperparathyroidism, bone disease and ectopic calcification in the cardiovascular system, joints, lungs, eyes and other soft tissues. Higher serum phosphorus levels are strongly associated with the progression of renal failure, cardiovascular calcification and mortality in end-stage renal disease (ESRD) patients. High-normal serum phosphorus levels have been associated with cardiovascular events and mortality among individuals who have chronic kidney disease (CKD) and among those who have normal kidney function (see, e.g., Joy, M. S., P. C. Karagiannis and F. W. Peyerl, Outcomes of Secondary Hyperparathyroidism in Chronic Kidney Disease and the Direct Costs of Treatment, J. Manag. Care Pharm., 13(5):397-411 (2007)) The progression of kidney disease can be slowed by reducing phosphate retention. Thus, for renal failure patients who are hyperphosphatemic and for chronic kidney disease patients who have serum phosphate levels within the normal range or only slightly elevated, therapy to reduce phosphate retention is beneficial.

For patients who experience hyperphosphatemia, calcium salts have been widely used to bind intestinal phosphate and prevent its absorption. Different types of calcium salts, including calcium carbonate, acetate, citrate, alginate, and ketoacid salts have been utilized for phosphate binding. A problem with all of these therapeutics is the hypercalcemia, which often results from absorption of high amounts of ingested calcium. Hypercalcemia causes serious side effects such as cardiac arrhythmias, renal failure, and skin and vascular calcification. Frequent monitoring of serum calcium levels is required during therapy with calcium-based phosphate binders. Other calcium and aluminum-free phosphate binders, such as sevelamer, a crosslinked polyamine polymer, have drawbacks that include the amount and frequency of dosing required to be therapeutically active. The relatively modest phosphate binding capacity of those drugs in vivo obliges patients to escalate the dose (up to 7 grs per day or more). Such quantities have been shown to produce gastrointestinal discomfort, such as dyspepsia, abdominal pain and, in some extreme cases, bowel perforation.

An alternative approach to the prevention of phosphate absorption from the intestine in patients with elevated phosphate serum levels is through inhibition of the intestinal transport system which mediates phosphate uptake in the intestine. It is understood that phosphate absorption in the upper intestine is mediated at least in part by a carrier-mediated mechanism which couples the absorption of phosphate to that of sodium. Inhibition of intestinal phosphate transport will reduce body phosphorus overload. In patients with advanced kidney disease (e.g. stage 4 and 5), the body phosphorus overload manifests itself by serum phosphate concentration above normal levels, i.e. hyperphosphatemia. Hyperphosphatemia is directly related to mortality and morbidity. Inhibition of intestinal phosphate transport will reduce serum phosphate concentration and therefore improve outcome in those patients. In chronic kidney disease patients stage 2 and 3, the body phosphorus overload does not necessarily lead to hyperphosphatemia, i.e. patients remain normophosphatemic, but there is a need to reduce body phosphorus overload even at those early stages to avoid associated bone and vascular disorders, and ultimately improve mortality rate. Similarly, inhibition of intestinal phosphate transport would be particularly advantageous in patients that have a disease that is treatable by inhibiting the uptake of phosphate from the intestines. Inhibition of phosphate absorption from the glomerular filtrate within the kidneys would also be advantageous for treating chronic renal failure. Furthermore, inhibition of phosphate transport may slow the progression of renal failure and reduce risk of cardiovascular events.

While progress has been made in this field, there remains a need in the art for novel phosphate transport inhibitors. The present invention fulfills this need and provides further related advantages.

BRIEF SUMMARY

In brief, the present invention is directed to compounds having activity as phosphate transport inhibitors, more specifically, inhibitors of intestinal apical membrane Na/phosphate co-transport, including stereoisomers, pharmaceutically acceptable salts and prodrugs thereof, and the use of such compounds to inhibit sodium-mediated phosphate uptake and to thereby treat any of a variety of conditions or diseases in which modulation of sodium-mediated phosphate uptake provides a therapeutic benefit.

In one embodiment, compounds having the following structure (I) are provided:

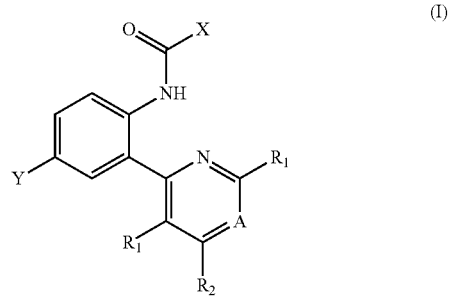

or a stereoisomer, prodrug or pharmaceutically acceptable salt thereof, wherein:

A is —CR$_1$— or —N—;

X is substituted aryl or substituted heteroaryl;

Y is halogen, optionally substituted alkylamino, optionally substituted alkoxy, optionally substituted thioalkyl, optionally substituted cycloalkyl, optionally substituted heterocyclyl, optionally substituted aryl, —O(optionally substituted cycloalkyl), —O(optionally substituted heterocyclyl) or —O(optionally substituted aryl);

each R$_1$ is, independently, hydrogen, halogen, C$_{1-6}$alkyl or C$_{1-6}$haloalkyl;

R$_2$ is —C(=O)NR$_{2a}$R$_{2b}$, —NR$_{2a}$C(=O)R$_{2b}$, —C(=O)R$_{2b}$, —NR$_{2a}$R$_{2b}$, —OR$_{2b}$ or —R$_{2b}$;

R$_{2a}$ is hydrogen or optionally substituted C$_{1-6}$alkyl; and

R$_{2b}$ is optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroarylalkyl.

In another embodiment, a pharmaceutical composition is provided comprising a compound having structure (I), or a stereoisomer, pharmaceutically acceptable salt or prodrug thereof, and a pharmaceutically acceptable carrier, diluent or excipient. In further embodiments, the pharmaceutical composition further comprises one or more additional biologically active agents. In more specific embodiments, the additional biologically active agent is selected from vitamin D$_2$ (ergocalciferol), vitamin D$_3$ (cholecalciferol), active vitamin D (calcitriol) and active vitamin D analogs (e.g. doxercalciferol, paricalcitol). In other more specific embodiments, the additional biologically active agent is a phosphate binder, and the compound does not interfere with the phosphate binder. For example, in certain embodiments, the phosphate binder is selected from the group consisting of Renvela, Renagel, Fosrenol, calcium carbonate, calcium acetate (e.g. Phoslo), MCI-196, Zerenex™, Fermagate, APS1585, SBR-759 and PA-21. In other further embodiments, the compound is substantially active as an inhibitor of Na/phosphate co-transport and the Na/phosphate co-transport is mediated by NaPi2b.

In another embodiment, a method of inhibiting phosphate transport in a mammal is provided, comprising administering to the mammal an effective amount of a compound having structure (I), or a stereoisomer, pharmaceutically acceptable salt or prodrug thereof, or a pharmaceutical composition comprising such compound. In further embodiments, the method inhibits sodium-mediated phosphate uptake. In other further embodiments, the method is selected from the group consisting of: (a) a method for treating hyperphosphatemia; (b) a method for treating a renal disease; (c) a method for delaying time to dialysis; (d) a method for attenuating intima localized vascular calcification; (e) a method for reducing the hyperphosphatemic effect of active vitamin D; (f) a method for reducing FGF23 levels; (g) a method for attenuating hyperparathyroidism; (h) a method for improving endothelial dysfunction induced by postprandial serum phosphate; (i) a method for reducing urinary phosphorous; (j) a method for normalizing serum phosphorus levels; (k) a method for treating proteinura; and (l) a method for reducing serum PTH and phosphate concentrations or levels. In certain embodiments, the renal disease is chronic kidney disease or end stage renal disease. In other certain embodiments, the method for treating a renal disease further comprises administering to the mammal an effective amount of a phosphate binder.

In another embodiment, a method of treating hyperphosphatemia in a mammal in need thereof is provided, comprising administering to the mammal an effective amount of a compound having structure (I), or a stereoisomer, pharmaceutically acceptable salt or prodrug thereof, or a pharmaceutical composition comprising such compound.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms (C$_{1-12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$-R$_c$ where R$_b$ is an alkylene chain as defined above and is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_d$ is an alkylene chain as defined above and R$_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_g R_h$, —$NR_g C(=O)R_h$, —$NR_g C(=O)NR_g R_h$, —$NR_g C(=O)OR_h$, —$NR_g SO_2 R_h$, —$OC(=O)NR_g R_h$, —$OR_g$, —$SR_g$, —$SOR_g$, —$SO_2 R_g$, —$OSO_2 R_g$, —$SO_2 OR_g$, =$NSO_2 R_g$, and —$SO_2 NR_g R_h$. "Substituted" also means any of the above groups in which one or more hydrogen atoms are replaced with —$C(=O)R_g$, —$C(=O)OR_g$, —$C(=O)NR_g R_h$, —$CH_2 SO_2 R_g$, —$CH_2 SO_2 NR_g R_h$, —$(CH_2 CH_2 O)_{1-10} R_g$, —$(CH_2 CH_2 O)_{2-10} R_g$, —$(OCH_2 CH_2)_{1-10} R_g$ and —$(OCH_2 CH_2)_{2-10} R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. The above non-hydrogen groups are generally referred to herein as "substituents" or "non-hydrogen substituents". In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to inhibit phosphate transport, inhibit sodium-mediated phosphate uptake, reduce serum PTH, calcium, calcitriol, and phosphate concentrations or levels, treat renal disease or treat hyperphosphatemia in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

As noted above, in one embodiment of the present invention, compounds having activity as phosphate transport inhibitors, more specifically, inhibitors of intestinal apical membrane Na/phosphate co-transport, are provided, the compounds having the following structure (I):

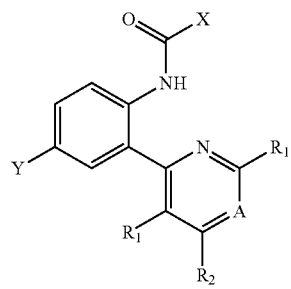

(I)

or a stereoisomer, prodrug or pharmaceutically acceptable salt thereof,
wherein:
A is —$CR_1$— or —N—;
X is substituted aryl or substituted heteroaryl;
Y is halogen, optionally substituted alkylamino, optionally substituted alkoxy, optionally substituted thioalkyl, optionally substituted cycloalkyl, optionally substituted heterocyclyl, optionally substituted aryl, —O(optionally substituted cycloalkyl), —O(optionally substituted heterocyclyl) or —O(optionally substituted aryl);
each $R_1$ is, independently, hydrogen, halogen, $C_{1-6}$alkyl or $C_{1-6}$haloalkyl;
$R_2$ is —C(=O)$NR_{2a}R_{2b}$, —$NR_{2a}$C(=O)$R_{2b}$, —C(=O)$R_{2b}$, —$NR_{2a}R_{2b}$, —$OR_{2b}$ or —$R_{2b}$;
$R_{2a}$ is hydrogen or optionally substituted $C_{1-6}$alkyl; and
$R_{2b}$ is optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroarylalkyl.

In further embodiments, Y is halogen, such as chloro.
In other further embodiments, Y is alkylamino, such as diethylamino.
In other further embodiments, Y is alkoxy.
In other further embodiments, Y is heterocyclyl, such as 1-piperidinyl and the compound has the structure:

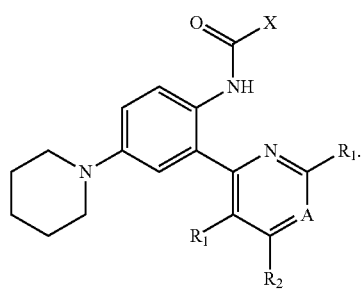

In other further embodiments, Y is —O(cycloalkyl).
In other further embodiments, X is —$ZR_3$, where Z is aryl or heteroaryl and $R_3$ represents a non-hydrogen substituent as defined above, or as more specifically defined below.
In more specific embodiments, Z is aryl, such as phenyl and the compound has the structure:

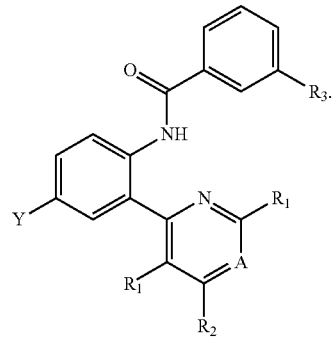

In other more specific embodiments, Z is heteroaryl, such as pyridinyl and the compound has the structure:

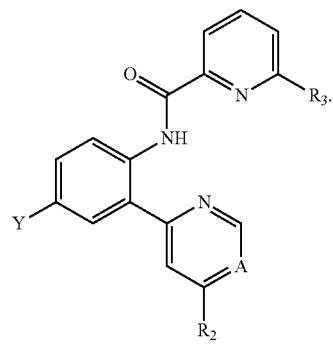

In more specific embodiments of the foregoing, $R_3$ is:
(a) -(optionally substituted $C_{1-6}$alkyl)-S(O)$_{0-2}$(optionally substituted $C_{1-6}$alkyl)C(=O)$NR_7R_4$,
(b) -(optionally substituted $C_{1-6}$alkyl)-S(O)$_{0-2}$(optionally substituted $C_{1-6}$alkyl)$NR_7R_4$,
(c) -(optionally substituted $C_{1-6}$alkyl)-S(O)$_{0-2}$(optionally substituted $C_{1-6}$alkyl)C(=O)$OR_5$,
(d) -(optionally substituted $C_{1-6}$alkyl)-S(O)$_{0-2}$(optionally substituted $C_{1-6}$alkyl)$OR_5$,
(e) -(optionally substituted $C_{1-6}$alkyl)-S(O)$_{0-2}$(optionally substituted $C_{1-6}$alkyl)$R_6$,
(f) -(optionally substituted $C_{1-6}$alkyl)-S(O)$_{0-2}R_6$,
(g) -(optionally substituted $C_{1-6}$alkyl)-S(O)$_{0-2}NR_7R_4$,
(h) -(optionally substituted $C_{1-6}$alkyl)-S(O)$_{0-2}$(CH$_2$CH$_2$O)$_x$ $R_5$, or
(i) -(optionally substituted $C_{1-6}$alkyl)-S(O)$_{0-2}$(CH$_2$CH$_2$O)$_x$ (CH$_2$)$_2$NHSO$_2$(phenyl)$R_5$,
wherein:
$R_4$ is hydrogen, hydroxyl, alkoxy, optionally substituted $C_{1-6}$alkyl, optionally substituted aryl, optionally substituted heterocyclyl or optionally substituted heteroaryl;
$R_5$ is hydrogen, optionally substituted $C_{1-6}$alkyl, optionally substituted aryl, optionally substituted heterocyclyl or optionally substituted heteroaryl;
$R_6$ is optionally substituted aryl, optionally substituted heterocyclyl or optionally substituted heteroaryl;

$R_7$ is hydrogen or optionally substituted $C_{1-6}$alkyl; and
x is an integer from 2 to 10.

For example, in certain embodiments, $R_3$ is:
(a) —$CH_2S(O)_{0-2}$(optionally substituted $C_{1-6}$alkyl)C(=O)$NR_7R_4$,
(b) —$CH_2S(O)_{0-2}$(optionally substituted $C_{1-6}$alkyl)$NR_7R_4$,
(c) —$CH_2S(O)_{0-2}$(optionally substituted $C_{1-6}$alkyl)C(=O)$OR_5$,
(d) —$CH_2S(O)_{0-2}$(optionally substituted $C_{1-6}$alkyl)$OR_5$,
(e) —$CH_2S(O)_{0-2}$(optionally substituted $C_{1-6}$alkyl)$R_6$,
(f) —$CH_2S(O)_{0-2}R_6$,
(g) —$CH_2S(O)_{0-2}NR_7R_4$,
(h) —$CH_2S(O)_{0-2}(CH_2CH_2O)_xR_5$, or
(i) —$CH_2S(O)_{0-2}(CH_2CH_2O)_x(CH_2)_2NHSO_2$(phenyl)$R_5$.

In other more specific embodiments of the foregoing, $R_3$ is:
(a) -(optionally substituted $C_{1-6}$alkyl)-$CH_2NR_7(CH_2CH_2O)_xR_5$, or
(b) -(optionally substituted $C_{1-6}$alkyl)-$CH_2NR_7(CH_2CH_2O)_x(CH_2)_2NHSO_2$(phenyl)$R_5$,
wherein:
$R_5$ is hydrogen, optionally substituted $C_{1-6}$alkyl, optionally substituted aryl, optionally substituted heterocyclyl or optionally substituted heteroaryl;
$R_7$ is hydrogen or optionally substituted $C_{1-6}$alkyl; and
x is an integer from 2 to 10.

For example, in certain embodiments, $R_3$ is:
(a) —$CH_2NR_7(CH_2CH_2O)_xR_5$, or
(b) —$CH_2NR_7(CH_2CH_2O)_x(CH_2)_2NHSO_2$(phenyl)$R_5$.

In other more specific embodiments of the foregoing, $R_3$ is:
(a) —C(=O)$NR_7$(optionally substituted $C_{1-6}$alkyl)C(=O)$NR_7R_4$,
(b) —C(=O)$NR_7$(optionally substituted $C_{1-6}$alkyl)$NR_7R_4$,
(c) —C(=O)$NR_7$(optionally substituted $C_{1-6}$alkyl)C(=O)$OR_5$,
(d) —C(=O)$NR_7$(optionally substituted $C_{1-6}$alkyl)$OR_5$,
(e) —C(=O)$NR_7$(optionally substituted $C_{1-6}$alkyl)$R_6$,
(f) —C(=O)$NR_7(CH_2CH_2O)_xR_5$, or
(g) —C(=O)$NR_7(CH_2CH_2O)_x(CH_2)_2NHSO_2$(phenyl)$R_5$,
wherein:
$R_4$ is hydrogen, hydroxyl, alkoxy, optionally substituted $C_{1-6}$alkyl, optionally substituted aryl, optionally substituted heterocyclyl or optionally substituted heteroaryl;
$R_5$ is hydrogen, optionally substituted $C_{1-6}$alkyl, optionally substituted aryl, optionally substituted heterocyclyl or optionally substituted heteroaryl;
$R_6$ is optionally substituted aryl, optionally substituted heterocyclyl or optionally substituted heteroaryl;
$R_7$ is hydrogen or optionally substituted $C_{1-6}$alkyl; and
x is an integer from 2 to 10.

In other more specific embodiments of the foregoing, $R_3$ is:
(a) —O(optionally substituted $C_{1-6}$alkyl)C(=O)$NR_7R_4$,
(b) —O(optionally substituted $C_{1-6}$alkyl)$NR_7R_4$,
(c) —O(optionally substituted $C_{1-6}$alkyl)C(=O)$OR_5$,
(d) —O(optionally substituted $C_{1-6}$alkyl)$OR_5$,
(e) —O(optionally substituted $C_{1-6}$alkyl)$R_6$,
(f) —O$(CH_2CH_2O)_xR_5$, or
(g) —O$(CH_2CH_2O)_x(CH_2)_2NHSO_2$(phenyl)$R_5$,
wherein:
$R_4$ is hydrogen, hydroxyl, alkoxy, optionally substituted $C_{1-6}$alkyl, optionally substituted aryl, optionally substituted heterocyclyl or optionally substituted heteroaryl;
$R_5$ is hydrogen, optionally substituted $C_{1-6}$alkyl, optionally substituted aryl, optionally substituted heterocyclyl or optionally substituted heteroaryl;
$R_6$ is optionally substituted aryl, optionally substituted heterocyclyl or optionally substituted heteroaryl;
$R_7$ is hydrogen or optionally substituted $C_{1-6}$alkyl; and
x is an integer from 2 to 10.

In other more specific embodiments of the foregoing, $R_3$ is:
(a) —S(optionally substituted $C_{1-6}$alkyl)C(=O)$NR_7R_4$,
(b) —S(optionally substituted $C_{1-6}$alkyl)$NR_7R_4$,
(c) —S(optionally substituted $C_{1-6}$alkyl)C(=O)$OR_5$,
(d) —S(optionally substituted $C_{1-6}$alkyl)$OR_5$,
(e) —S(optionally substituted $C_{1-6}$alkyl)$R_6$,
(f) —S$(CH_2CH_2O)_xR_5$, or
(g) —S$(CH_2CH_2O)_x(CH_2)_2NHSO_2$(phenyl)$R_5$,
wherein:
$R_4$ is hydrogen, hydroxyl, alkoxy, optionally substituted $C_{1-6}$alkyl, optionally substituted aryl, optionally substituted heterocyclyl or optionally substituted heteroaryl;
$R_5$ is hydrogen, optionally substituted $C_{1-6}$alkyl, optionally substituted aryl, optionally substituted heterocyclyl or optionally substituted heteroaryl;
$R_6$ is optionally substituted aryl, optionally substituted heterocyclyl or optionally substituted heteroaryl;
$R_7$ is hydrogen or optionally substituted $C_{1-6}$alkyl; and
x is an integer from 2 to 10.

In other more specific embodiments of the foregoing, $R_3$ is:
(a) —$NR_7$(optionally substituted $C_{1-6}$alkyl)C(=O)$NR_7R_4$,
(b) —$NR_7$(optionally substituted $C_{1-6}$alkyl)$NR_7R_4$,
(c) —$NR_7$(optionally substituted $C_{1-6}$alkyl)C(=O)$OR_5$,
(d) —$NR_7$(optionally substituted $C_{1-6}$alkyl)$OR_5$,
(e) —$NR_7$(optionally substituted $C_{1-6}$alkyl)$R_6$,
(f) —$NR_7(CH_2CH_2O)_xR_5$, or
(g) —$NR_7(CH_2CH_2O)_x(CH_2)_2NHSO_2$(phenyl)$R_5$,
wherein:
$R_4$ is hydrogen, hydroxyl, alkoxy, optionally substituted $C_{1-6}$alkyl, optionally substituted aryl, optionally substituted heterocyclyl or optionally substituted heteroaryl;
$R_5$ is hydrogen, optionally substituted $C_{1-6}$alkyl, optionally substituted aryl, optionally substituted heterocyclyl or optionally substituted heteroaryl;
$R_6$ is optionally substituted aryl, optionally substituted heterocyclyl or optionally substituted heteroaryl;
$R_7$ is hydrogen or optionally substituted $C_{1-6}$alkyl; and
x is an integer from 2 to 10.

In other more specific embodiments of the foregoing, $R_3$ is:
(a) -(optionally substituted $C_{1-6}$alkyl)-$(OCH_2CH_2)_yOR_5$, or
(b) -(optionally substituted $C_{1-6}$alkyl)-$(OCH_2CH_2)_yO(CH_2)_2NHSO_2$(phenyl)$R_5$,
wherein:
$R_5$ is hydrogen, optionally substituted $C_{1-6}$alkyl, optionally substituted aryl, optionally substituted heterocyclyl or optionally substituted heteroaryl; and
y is an integer from 1 to 10.

For example, in certain embodiments, $R_3$ is:
(a) —$(CH_2)_3(OCH_2CH_2)_yOR_5$, or
(b) —$(CH_2)_3(OCH_2CH_2)_yO(CH_2)_2NHSO_2$(phenyl)$R_5$.

In other further embodiments, A is —CH—.

In other further embodiments, A is N.

In other further embodiments, each $R_1$ is hydrogen.

In other further embodiments, $R_2$ is —C(=O)$NR_{2a}R_{2b}$. In more specific embodiments, $R_{2a}$ is hydrogen and $R_{2b}$ is:

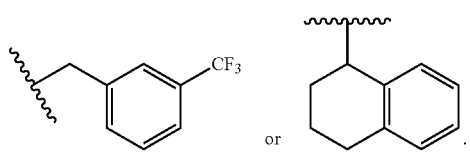 [SMILES: *Cc1cccc(C(F)(F)F)c1 ; *C1CCCc2ccccc21]

It is understood that any embodiment of the compounds of structure (I), as set forth above, and any specific substituent set forth herein for a X, Y, Z, A, $R_1$, $R_2$, $R_{2a}$, $R_{2b}$, $R_3$, $R_4$, $R_5$, $R_6$ or $R_7$ group in the compounds of structure (I), as set forth above, may be independently combined with other embodiments and/or substituents of compounds of structure (I) to form embodiments of the inventions not specifically set forth above. In addition, in the event that a list of substitutents is listed for any particular substituent in a particular embodiment and/or claim, it is understood that each individual substituent may be deleted from the particular embodiment and/or claim and that the remaining list of substituents will be considered to be within the scope of the invention.

In accordance with the present disclosure, it has been discovered that phosphate absorption from the intestine in patients with elevated phosphate serum levels may be limited, and preferably substantially prevented, through inhibition of the intestinal transport system which mediates phosphate uptake in the intestine. This inhibition may be achieved by the administration of certain compounds, and/or pharmaceutical compositions comprising them, which may advantageously be designed such that little, or substantially none, of the compound is absorbed into the blood stream (that is, it is designed to be non-systemic or substantially non-systemic). In this regard, the compounds have features that give rise to little or substantially no systemic availability. In other words, the compounds are not absorbed into the bloodstream at meaningful levels and therefore have no activity there, but instead have their activity localized substantially within the GI tract.

Therefore, in certain illustrative embodiments as further described herein, the compounds of the invention generally require a combination of structural and/or functional features relating or contributing to their activity in the GI tract and/or their substantial non-systemic bioavailability. Such features may include, for example, one or more of (i) specific tPSA and/or MW values (e.g., at least about 190 Å$^2$ and/or at least about 736 Daltons, respectively), (ii) specific levels of fecal recovery of the compound and/or its metabolites after administration (e.g., greater than 50% at 72 hours); (iii) specific numbers of NH and/or OH and/or potentially hydrogen bond donor moieties (e.g., greater than about five); (iv) specific numbers of rotatable bonds (e.g., greater than about five); (iv) specific permeability features (e.g., $P_{app}$ less than about 100× $10^{-6}$ cm/s); and/or any of a number of other features and characteristics as described herein.

The compounds of the present invention offer numerous advantages in the treatment of GI tract and other disorders. For example, the compounds are active on the phosphate transporter apically located in the intestine and essentially do not reach other phosphate transporters expressed in other tissues and organs. For instance the NaPi1 transporter is primarily expressed in the apical membrane of intestinal enterocytes, but is also found in salivary glands, mammary glands, lung, kidney, pancreas, ovary, prostate, testis and liver (Feild et al., 1999, Biochem Biophys Res Commun, v. 258, no. 3, p. 578-582; Bai et al., 2000, Am J Physiol Cell Physiol, v. 279, no. 4, p. C1135-C1143; Virkki et al., 2007, Am J Physiol Renal Physiol, v. 293, no. 3, p. F643-F654). Genome wide single-nucleotide polymorphism analysis in patients with pulmonary alveolar microlithiasis (PAM) has revealed a link between a mutated NaPi2b gene and disorder in which microliths are formed in the lung alveolar space. Homozygous inactivating mutations of pulmonary NaPi2b have also been implicated in the pathophysiology of PAM (Huqun et al., 2007, Am J Respir Crit Care Med, v. 175, no. 3, p. 263-268). Consistent with this human study, calcification nodules were evident in NaPi2b conditional knockout mice but not in wild type animals after NaPi2b deletion. In contrast, analysis of kidney and ileum samples revealed no pathologic abnormalities associated with Npt2b deletion (Sabbagh et al., 2009, J Am Soc. Nephrol., 20: 2348-2358).

The essentially non-systemic NaPi2b inhibitors of the present invention do not interfere with the pulmonary function of NaPi2b and, therefore, potential pulmonary toxicity is minimized. In addition, certain patient populations to whom the compounds of the invention may be administered are expected to have limited kidney clearance rate secondary to a declining kidney function. Thus, systemic compounds with some kidney clearance contribution in their excretion pathway can accumulate in the plasma, potentially leading to undesired side-effects in those patients with chronic kidney disease (Sica, 2008, J Clin Hypertens. (Greenwich.), v. 10, no. 7, p. 541-548). The compounds of the invention do not give rise to these same concerns because of their limited systemic availability.

As further detailed below, phosphate absorption in the upper intestine is mediated, at least in part, by a carrier-mediated mechanism which couples the absorption of phosphate to that of sodium. Accordingly, inhibition of intestinal phosphate transport will reduce body phosphorus overload. In patients with advanced kidney disease (e.g. stage 4 and 5), the body phosphorus overload manifests itself by serum phosphate concentration above normal levels, i.e. hyperphosphatemia. Hyperphosphatemia is directly related to mortality and morbidity. Inhibition of intestinal phosphate transport will reduce serum phosphate concentration and therefore improve outcome in those patients. In stage 2 and 3 chronic kidney disease patients, the body phosphorus overload does not necessarily lead to hyperphosphatemia, i.e. patients remain normophosphatemic, but there is a need to reduce body phosphorus overload even at those early stages to avoid associated bone and vascular disorders, and ultimately improve mortality rate. Similarly, inhibition of intestinal phosphate transport will be particularly advantageous in patients that have a disease that is treatable by inhibiting the uptake of phosphate from the intestines. Inhibition of phosphate absorption from the glomerular filtrate within the kidneys would also be advantageous for treating chronic renal failure. Furthermore, inhibition of phosphate transport may slow the progression of renal failure and reduce risk of cardiovascular events.

Without being held to any particular theory, it is generally believed that, in vertebrates, phosphate (Pi) transporters use the inwardly directed electrochemical gradient of Na+ ions, established by the Na/K ATPase transporter, to drive Pi influx. These transporters fall in three distinct and unrelated Pi transporters proteins named type I, II and III. NaPi type I transporters comprise NaPi-I, mainly expressed in the proximal and distal renal tubules. NaPi type II transporters comprise NaPi2a, NaPi2b, and NaPi2c. NaPi2a is localized in the apical membrane of proximal renal tubule, but is also detected in rat brain, osteoclasts and osteoblast-like cells. NaPi2b is expressed in the apical membrane of enterocytes, but also found in lung, colon, testis and liver (see, e.g., Virkki, L. V., et al., Phosphate Transporters: A Tale of Two Solute Carrier Families, Am. J. Physiol. Renal. Physiol., 293(3): F643-54 (2007)). Type III NaPi transporters comprise PiT-1 and PiT-2, which are now emerging as important players in bone Pi metabolism and vascular calcification.

NaPi2a is believed to play a key role in phosphorus homeostasis by controlling the reabsorption of Pi in the renal proximal tubule. This is exemplified in NaPi2a KO mice, which develop hyperphosphaturia and hypophosphatemia. NaPi2b is believed responsible for transepithelial absorption in the small intestine and is regulated by dietary Pi and vitamin D (Calcitriol (1,25-Dihydroxycholecalciferol)). NaPi2c is expressed in renal tubule and other tissues (see, e.g., Virkki, L. V., et al., Id.).

The basic transport mechanism of NaPi2a and NaPi2b is the same (see, e.g., Murer, H., et al., Proximal Tubular Phosphate Reabsorption: Molecular Mechanisms, Physiol. Rev., 80(4):1373-409 (2000)); both are electrogenic with a stoichiometry of about 3:1 $Na^+:HPO_4^{2-}$, meaning that 3 $Na^+$ are co-transported with one phosphate anion. The additional Na cations translocated are excreted on the basolateral membrane via the K/Na ATPase active transporters to preserve cell polarization. Renal Pi transporter NaPi2a activity is increased in the kidney in response to low dietary Pi (see, e.g., Murer, et al., Id.). This results from an increase in transporter expression on the apical membrane of the kidney tubule. Histochemical analysis suggests a "recruitment" phenomenon. It is to be noted that, in contrast, the type I NaPi transporter does not respond to change in dietary P. The change in NaPi2a expression is paralleled by alteration in parathyroid hormone PTH plasma concentration and vice-versa (e.g., injection of PTH in rats leads within minutes to a reduction in brush border membrane transporter content). Acid-base change can also alter expression of NaPi2a. Chronic metabolic acidosis in rats significantly decreases NaPi2a protein and mRNA content. The same is observed in CKD rats induced by $5/6^{th}$ nephrectomy. The regulation of apical NaPi2a transporters involves complex membrane retrieval and re-insertion mechanisms. Control in transport activity can also be controlled by changes in intra-tubular and intracellular pH, in transmembrane potential difference and posttranslational modification.

Substantially Impermeable or Substantially Systemically Non-Bioavailable Phosphate Transport Inhibitor Compounds A. Physical and Performance Properties In accordance with the present disclosure, the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically non-bioavailable" and/or "substantially impermeable" as used herein (as well as variations thereof) generally refer to situations in which a statistically significant amount, and in some embodiments essentially all of the compound of the present disclosure, remains in the gastrointestinal lumen. For example, in accordance with one or more embodiments of the present disclosure, preferably at least about 70%, about 80%, about 90%, about 95%, about 98%, about 99%, or even about 99.5%, of the compound remains in the gastrointestinal lumen. In such cases, localization to the gastrointestinal lumen refers to reducing net movement across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" refers to embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.); stated another way, "substantially impermeable" or "substantially systemically non-bioavailable" refers to compounds that exhibit some detectable permeability to an epithelial layer of cells in the GI tract of less than about 20% of the administered compound (e.g., less than about 15%, about 10%, or even about 5%, and for example greater than about 0.5%, or 1%), but then are cleared by the liver (i.e., hepatic extraction) and/or the kidney (i.e., renal excretion).

In this regard it is to be further noted, that in certain embodiments, due to the substantial impermeability and/or substantial systemic non-bioavailability of the compounds of the present invention, greater than about 50%, 60%, 70%, 80% or 90% of a compound of the invention is recoverable from the feces over, for example, a 24, 48 or 72 hour period following administration to a patient in need thereof. In this respect, it is understood that a recovered compound can include the sum of the parent compound and its metabolites derived from the parent compound, e.g., by means of hydrolysis, conjugation, reduction, oxidation, N-alkylation, glucuronidation, acetylation, methylation, sulfation, phosphorylation, or any other modification that adds atoms to or removes atoms from the parent compound, wherein the metabolites are generated via the action of any enzyme or exposure to any physiological environment including, pH, temperature, pressure, or interactions with foodstuffs as they exist in the digestive milieu. Measurement of fecal recovery of compound and metabolites can be carried out using standard methodology.

For example, compound can be administered orally at a suitable dose (e.g., 10 mg/kg) and feces are then collected at predetermined times after dosing (e.g., 24 hours, 48 hours, 72 hours). Parent compound and metabolites can be extracted with organic solvent and analyzed quantitatively using mass spectrometry. A mass balance analysis of the parent compound and metabolites (including, parent=M, metabolite 1 [M+16], and metabolite 2 [M+32]) can be used to determine the percent recovery in the feces.

In certain preferred embodiments, the phosphate transport inhibitors of the present invention are not competitive inhibitors with respect to phosphate of Na/phosphate co-transport. In certain other preferred embodiments, the phosphate transport inhibitors of the invention are non-competitive inhibitors. Non-competitive inhibitors maintain their degree of inhibition irrespective of the local phosphate concentration. This feature is an important aspect in providing an efficient blockade of intestinal transport in postprandial state, where the local concentration of dietary phosphate can attain concentration as high as 10 mM. It is believed that competitive inhibitors are too sensitive to local phosphate concentration and unable to block phosphate uptake following a high phosphorus meal. Various methods are available for determining whether a phosphate transport inhibitor is non-competitive or competitive. For example, a phosphate uptake assay can be performed and the $IC_{50}$ values for a compound at different phosphate concentrations can be determined (e.g., "Enzyme kinetics", I. Segel, 1975, John-Wiley & Sons, p. 123). $IC_{50}$ values for non-competitive inhibitors will remain the same or similar with respect to the phosphate concentration, whereas $IC_{50}$ values for competitive inhibitors will increase (i.e lose potency) as phosphate concentration increases.

(i) Permeability

In this regard it is to be noted that, in various embodiments, the ability of the compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacokinetics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews*, 46, 2001 3-26, incorporated herein by reference.) Accordingly, substantially systemically non-bioavailable compounds (e.g., substantially systemically non-bioavailable phosphate transport inhibitor compounds) can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.)

In some embodiments, for example, a substantially impermeable or substantially systemically non-bioavailable phosphate transport inhibitor compound of the present disclosure can be constructed to feature one or more of the following characteristics: (i) a MW greater than about 500 Da, about 1000 Da, about 2500 Da, about 5000 Da, about 10,000 Da or more (in the non-salt form of the compound); (ii) a total number of NH and/or OH and/or other potential hydrogen bond donors greater than about 5, about 10, about 15 or more; (iii) a total number of O atoms and/or N atoms and/or other potential hydrogen bond acceptors greater than about 5, about 10, about 15 or more; (iv) a Moriguchi partition coefficient greater than about $10^5$ (i.e., Log P greater than about 5, about 6, about 7, etc.), or alternatively less than about 10 (i.e., a Log P of less than 1, or even 0); and/or (v) a total number of rotatable bonds greater than about 5, about 10 or about 15, or more.

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. (For Caco2 cell monolayer penetration test details, see for example the description of the Caco2 Model provided in Example 31 of U.S. Pat. No. 6,737,423, the entire contents of which are incorporated herein by reference, and the text of Example 31 in particular, which may be applied for example to the evaluation or testing of the compounds of the present disclosure.) PSA is expressed in $Å^2$ (squared angstroms) and is computed from a three-dimensional molecular representation. A fast calculation method is also available (see, e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see, e.g., Table 1, below):

TABLE 1

| name | % FA[a] | TPSA[b] |
|---|---|---|
| metoprolol | 102 | 50.7 |
| nordiazepam | 99 | 41.5 |
| diazepam | 97 | 32.7 |
| oxprenolol | 97 | 50.7 |
| phenazone | 97 | 26.9 |
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

(from Ertl et al., *J. Med. Chem.*, 2000, 43:3714-3717). Accordingly, in some embodiments, the compounds of the present disclosure may be constructed to exhibit a tPSA value greater than about 100 $Å^2$, about 120 $Å^2$, about 130 $Å^2$, or about 140 $Å^2$, and in some instances about 150 $Å^2$, about 160 $Å^2$, about 170 $Å^2$, about 180 $Å^2$, about 190 $Å^2$, about 200 $Å^2$, about 225 $Å^2$, about 250 $Å^2$, about 270 $Å^2$, about 300 $Å^2$, about 350 $Å^2$, about 400 $Å^2$, about 450 $Å^2$, about 500 $Å^2$, about 750 Å², or even about 1000 Å², such that the compounds are substantially impermeable or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. A synthetic membrane impregnated with, for example, lecithin and/or dodecane to mimic the net permeability characteristics of a gastrointestinal mucosa may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo. (See, for example, Wohnsland et al., *J. Med. Chem.*, 2001, 44:923-930; Schmidt et al., Millipore Corp. Application Note, 2002, no AN1725EN00, and no AN1728EN00, incorporated herein by reference.)

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., *J. Med. Chem.*, 2001, 44. 923-930, the contents of which is incorporated herein by reference).

As previously noted, in accordance with the present disclosure, phosphate transport inhibitors may be modified to hinder their net absorption through a layer of gut epithelial cells, rendering them substantially systemically non-bioavailable. In some particular embodiments, the compounds of the present disclosure comprise a phosphate transport inhibitor linked, coupled or otherwise attached to a non-absorbable moiety, which may be an oligomer moiety, a polymer moiety, a hydrophobic moiety, a hydrophilic moiety, and/or a charged moiety, which renders the overall compound substantially impermeable or substantially systemically non-bioavailable. In some preferred embodiments, the phosphate transport inhibitor is coupled to a multimer or polymer portion or moiety, such that the resulting molecule is substantially impermeable or substantially systemically non-bioavailable. The multimer or polymer portion or moiety may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, preferably in the range of about 5000 to about 200,000 Da, and more preferably may have a molecular weight that is sufficiently high to essentially preclude any net absorption through a layer of gut epithelial cells of the compound. In these or other particular embodiments, the phosphate transport inhibitor is modified to substantially hinder its net absorption through a layer of gut epithelial cells.

(ii) Persistent Inhibitory Effect

In other embodiments, the substantially impermeable or substantially systemically non-bioavailable compounds utilized in the treatment methods of the present disclosure may additionally exhibit a persistent inhibitor effect. This effect manifests itself when the inhibitory action of a compound at a certain concentration in equilibrium with epithelial cells (e.g., at or above its inhibitory concentration, IC) does not revert to baseline (i.e., phosphate transport without inhibitor) after the compound is depleted by simple washing of the luminal content.

This effect can be interpreted as a result of the tight binding of the compounds to the phosphate transport protein at the intestinal apical side of the gut epithelial cell. The binding can be considered as quasi-irreversible to the extent that, after the compound has been contacted with the gut epithelial cell and subsequently washed off said gut epithelial cell, the flux of phosphate transport is still significantly lower than in the control without the compound. This persistent inhibitory effect has the clear advantage of maintaining drug activity within the GI tract even though the residence time of the active in the upper GI tract is short, and when no enterobiliary recycling process is effective to replenish the compound concentration near its site of action.

Such a persistent inhibitory effect has an obvious advantage in terms of patient compliance, but also in limiting drug exposure within the GI tract.

The persistence effect can be determined using in vitro methods; in one instance, cell lines expressing phosphate transporters are split in different vials and treated with a phosphate transport inhibiting compound and phosphate solution to measure the rate of phosphate uptake. The cells in one set of vials are washed for different periods of time to remove the inhibitor, and phosphate uptake measurement is repeated after the washing. Compounds that maintain their inhibitory effect after multiple/lengthy washing steps (compared to the inhibitory effect measured in the vials where washing does not occur) are persistent inhibitors. Persistence effect can also be characterized ex vivo by using the everted sac technique, whereby transport of phosphate is monitored using an excised segment of GI perfused with a solution containing the inhibitor and shortly after flushing the bathing solution with a buffer solution free from inhibitor. A persistence effect can also be characterized in vivo by observing the time needed for phosphate balance to return to normal when the inhibitor treatment is discontinued. The limit of the method resides in the fact that apical cells (and therefore apical phosphate transporters) are sloughed off after a period of 3 to 4 days, the typical turnover time of gut epithelial cells. A persistence effect can be achieved by increasing the residence time of the active compound at the apical surface of the gut epithelial cells; this can be obtained by designing phosphate transport inhibitors with several phosphate transport inhibiting moieties built-in the small molecule or oligomer (wherein "several" as used herein typically means at least about 2, about 4, about 6 or more). Examples of such structures in the context of analogs of the antibiotic vancomycin are given in Griffin, et al., *J. Am. Chem. Soc.*, 2003, 125, 6517-6531. Alternatively the compound comprises groups that contribute to increase the affinity towards the gut epithelial cell so as to increase the time of contact with the gut epithelial cell surface. Such groups are referred to as being "mucoadhesive." More specifically, the Core or L moiety can be substituted by such mucoadhesive groups, such as polyacrylates, partially deacetylated chitosan or polyalkylene glycol. (See also Patil, S. B. et al., *Curr. Drug. Deliv.*, 2008, October 5(4), pp. 312-8.)

(iii) GI Enzyme Resistance

Because the compounds utilized in the treatment methods of the present disclosure are preferably substantially systemically non-bioavailable, and/or preferably exhibit a persistent inhibitory effect, it is also desirable that, during their prolonged residence time in the gut, these compounds resist the hydrolytic conditions prevailing in the upper GI tract. In such embodiments, compounds of the present disclosure are resistant to phase 1 and phase 2 metabolism. For example, administered compounds are preferably resistant to the activity of P450 enzymes, glucurosyl transferases, sulfotransferases, glutathione S-transferases, and the like, in the intestinal mucosa, as well as gastric (e.g., gastric lipase, and pepsine), pancreatic (e.g., trypsin, triglyceride pancreatic lipase, phospholipase A2, endonucleases, nucleotidases, and alpha-amylase), and brush-border enzymes (e.g., alkaline phosphatase, glycosidases, and proteases) generally known in the art.

The compounds that are utilized in methods of the present disclosure are also preferably resistant to metabolism by the bacterial flora of the gut; that is, the compounds are not substrates for enzymes produced by bacterial flora. In addition, the compounds administered in accordance with the methods of the present disclosure may be substantially inactive towards the gastrointestinal flora, and do not disrupt bacterial growth or survival. As a result, in various embodiments herein, the minimal inhibitory concentration (or "MIC") against GI flora is desirably greater than about 15 µg/ml, about 30 µg/ml, about 60 µg/ml, about 120 µg/ml, or even about 240 µg/ml, the MIC in various embodiments being for example between about 16 and about 32 µg/ml, or between about 64 and about 128 µg/ml, or greater than about 256 µg/ml.

To one skilled in the art of medicinal chemistry, metabolic stability can be achieved in a number of ways. Functionality susceptible to P450-mediated oxidation can be protected by, for example, blocking the point of metabolism with a halogen or other functional group. Alternatively, electron withdrawing groups can be added to a conjugated system to generally provide protection to oxidation by reducing the electrophilicity of the compound. Proteolytic stability can be achieved by avoiding secondary amide bonds, or by incorporating changes in stereochemistry or other modifications that prevent the drug from otherwise being recognized as a substrate by the metabolizing enzyme.

(iv) $C_{max}$ and $IC_{50}$

It is also to be noted that, in various embodiments of the present disclosure, one or more of the compounds detailed herein, when administered either alone or in combination with one or more additional pharmaceutically active compounds or agents to a patient in need thereof has a $C_{max}$ that is less than the $IC_{50}$ for NaPi2b, more specifically, less than about 10× (10 times) the $IC_{50}$, and, more specifically still, less than about 100× (100 times) the $IC_{50}$.

Additionally, or alternatively, it is also to be noted that, in various embodiments of the present disclosure, one or more of the compounds detailed herein, when administered either alone or in combination with one or more additional pharmaceutically active compounds or agents to a patient in need thereof, may have a $C_{max}$ of less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

Additionally, or alternatively, it is also to be noted that, in various embodiments of the present disclosure, one or more of the compounds detailed herein, when administered either alone or in combination with one or more additional pharmaceutically active compounds or agents to a patient in need thereof, may have a $IC_{50}$ of less than about 10 µM, about 7.5 µM, about 5 µM, about 2.5 µM, about 1 µM, or about 0.5 µM, the $IC_{50}$ being for example within the range of about 0.5 µM to about 10 µM, or about 0.5 µM to about 7.5 µM, or about 0.5 µM to about 5 µM, or about 0.5 µM to about 2.5 µM.

Additionally, or alternatively, it is also to be noted that, in various embodiments of the present disclosure, one or more of compounds detailed herein, when administered to a patient in need thereof, may have a ratio of $IC_{50}:C_{max}$, wherein $IC_{50}$ and $C_{max}$ are expressed in terms of the same units, of at least about 10, about 50, about 100, about 250, about 500, about 750, or about 1000.

Additionally, or alternatively, it is also to be noted that, in various embodiments of the present disclosure, wherein one or more of the compounds as detailed herein is orally administered to a patent in need thereof, within the therapeutic range or concentration, the maximum compound concentration detected in the serum, defined as $C_{max}$, is lower than the NaPi2b inhibitory concentration $IC_{50}$ of said compound. As previously noted, as used herein, $IC_{50}$ is defined as the quantitative measure indicating the concentration of the compound required to inhibit 50% of the NaPi2b transport activity in a cell based assay.

Pharmaceutical Compositions and Methods of Treatment

For the purposes of administration, the compounds of the present invention may be administered to a patient or subject as a raw chemical or may be formulated as pharmaceutical compositions. Pharmaceutical compositions of the present invention generally comprise a compound of the invention and a pharmaceutically acceptable carrier, diluent or excipient. The compound is present in the composition in an amount which is effective to treat a particular disease or condition of interest, as described herein, and preferably with acceptable toxicity to the patient. The activity of compounds can be determined by one skilled in the art, for example, as described in the Example below. Appropriate concentrations and dosages can be readily determined by one skilled in the art.

A compound or composition of the invention may be used in a method for treating essentially any disease or other condition in a patient which would benefit from phosphate uptake inhibition in the gastrointestinal tract.

For example, by way of explanation, but not limitation, kidney damage reduces the production and activity of renal 1-alpha hydroxylase, leading to lower 1,25-dihydroxy vitamin D. Decreased vitamin D levels limit gastrointestinal calcium absorption, leading to a decline in serum calcium levels. The combination of lower 1,25-dihydroxy vitamin D and lower serum calcium levels synergistically stimulate parathyroid tissue to produce and secrete PTH. A loss of nephrons also impairs Pi excretion, but serum P levels are actively defended by the actions of PTH and FGF-23, and by higher serum P levels, which considerably enhance urinary $PO_4$ excretion. However, tubular actions of PTH and FGF-23 cannot maintain serum P levels in the face of continual nephron loss. Once renal insufficiency progresses to the loss of about 40-50% of renal function, the decrease in the amount of functioning renal tissue does not allow excretion of the full amount of ingested phosphate required to maintain homeostasis. As a result, hyperphosphatemia develops. In addition, a rise in serum P levels impedes renal 1-alpha hydroxylase activity, further suppressing activated vitamin D levels, and further stimulating PTH, leading to secondary hyperparathyroidism (sHPTH).

Phosphorus imbalance, however, does not necessarily equate with hyperphosphatemia. In fact, the vast majority of CKD patients not yet on dialysis are normophosphatemic but their phosphorus balance is positive with the excess phosphorus being disposed in the vasculature in the form of ectopic calcification, e.g. intima localized vascular calcification. Clinically, patients with CKD have elevated levels of FGF-23 that are significantly associated with deteriorating renal function and with decreased calcitriol levels, and it has been hypothesized that the synthesis of FGF-23 is induced by the presence of excess P in the body consecutive to renal failure.

Furthermore, an unrecognized effect on cardiovascular disease is postprandial phosphatemia, i.e. serum P excursion secondary to meal intake. Further still, studies have investigated the acute effect of phosphorus loading on endothelial function in vitro and in vivo. Exposing bovine arotic endothelial cells to a phosphorus load increased production of reactive oxygen species and decreased nitric oxide, a known vasodilator agent. In the acute P loading study in healthy volunteers described above, it was found that the flow mediated dilation correlated inversely with postprandial serum P (Shuto et al., 2009b, J. Am. Soc. Nephrol., v. 20, no. 7, p. 1504-1512).

Accordingly, in certain more specific embodiments, a compounds or composition of the invention can be used in a method selected from the group consisting of: (a) a method for treating hyperphosphatemia; (b) a method for treating a renal disease (e.g., chronic kidney disease or end stage renal disease); (c) a method for delaying time to dialysis; (d) a method for attenuating intima localized vascular calcification; (e) a method for reducing the hyperphosphatemic effect of active vitamin D; (f) a method for reducing FGF23 levels; (g) a method for attenuating hyperparathyroidism; (h) a method for improving endothelial dysfunction induced by postprandial serum phosphate; (i) a method for reducing urinary phosphorous; (j) a method for normalizing serum phosphorus levels; (k) a method for treating proteinura; and (l) a method for reducing serum PTH, calcium, calcitriol and/or phosphate concentrations or levels.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

In certain embodiments, a typical dosage of the substantially impermeable or substantially systemically non-bioavailable, compound may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of the compounds and compositions described herein may vary from once-a-day (QD) to twice-a-day (BID) or thrice-a-day (TID), etc., the precise frequency of administration varying with, for example, the patient's condition, the dosage, etc.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

For example, in certain embodiments, the additional biologically active agent included in a pharmaceutical composition (or method) of the invention is selected, for example, from vitamin $D_2$ (ergocalciferol), vitamin $D_3$ (cholecalciferol), active vitamin D (calcitriol) and active vitamin D analogs (e.g. doxercalciferol, paricalcitol).

In other specific embodiments, the additional biologically active agent included in a pharmaceutical composition (or method) of the invention is a phosphate binder, such as Renvela, Renagel, Fosrenol, calcium carbonate, calcium acetate (e.g. Phoslo), MCI-196, Zerenex™, Fermagate, APS1585, SBR-759, PA-21, and the like.

The compounds of the invention have been found to act synergistically with phosphate binders by providing a higher efficacy than the sum of the efficacy of a NaPi2b inhibitor and that of a phosphate binder administered alone. Without wishing to be bound by theory, it is believed that the synergy results from the distinct mechanisms of action of a phosphate transport inhibitor and a phosphate binder. More specifically, a phosphate transport inhibitor blocks the epithelial inward transport of phosphate ions whereas phosphate binders sequester free phosphate ions in the lumen of the intestine.

The efficacy of a phosphate binder, as measured by its vivo binding capacity (mole of phosphate ions bound per gram of binder) is essentially dictated by: i) the density of binding sites (i.e. amine groups in Renvela/Sevelamer, a polymeric amine material; or multivalent cations such calcium or lanthanum in Phoslo (Calcium acetate) or Fosrenol (lanthanum carbonate)); and ii) the affinity of said binding sites for phosphate ions. Notably only a fraction of the binding sites is available for phosphate binding in vivo as other anions, such as bile acids and fatty acids compete for the binding sites and therefore lowers efficacy. Bound phosphate ions are in equilibrium with free phosphate in the intestinal lumen and are themselves subject to intense pumping from phosphate transport proteins lining up the epithelia. Experiments have shown that the efficacy of phosphate intestinal uptake is remarkably high, exceeding 95% of the phosphate presented to the epithelia. It is believed that the active transport of phosphate contributes to lower the luminal free phosphate concentration and therefore to drive the binding equilibrium of a phosphate binder to lower binding capacity. It is also believed that by reducing the phosphate intestinal transport using a phosphate transport inhibitor, one restores a higher in vivo binding capacity of phosphate sequestering agents. The synergistic effect is thought to be even more pronounced when the contribution of active phosphate transport is increased as a result of, e.g. vitamin D treatment, an agent promoting NaPi2b expression.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples illustrate various methods of making compounds of this invention, i.e., compounds of structure (I), or a stereoisomer, prodrug or pharmaceutically acceptable salt thereof: It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry Reactions, Mechanisms, and Structure, 5th edition (Wiley, December 2000)) or prepared as described in this invention.

The following examples are provided for purposes of illustration, not limitation.

EXAMPLES

Example 1.1

3-(3-((2-(4-((3-(Trifluoromethyl)benzyl)carbamoyl)pyridin-2-yl)-4-(piperidin-1-yl)phenyl)carbamoyl)benzylthio)propanoic acid

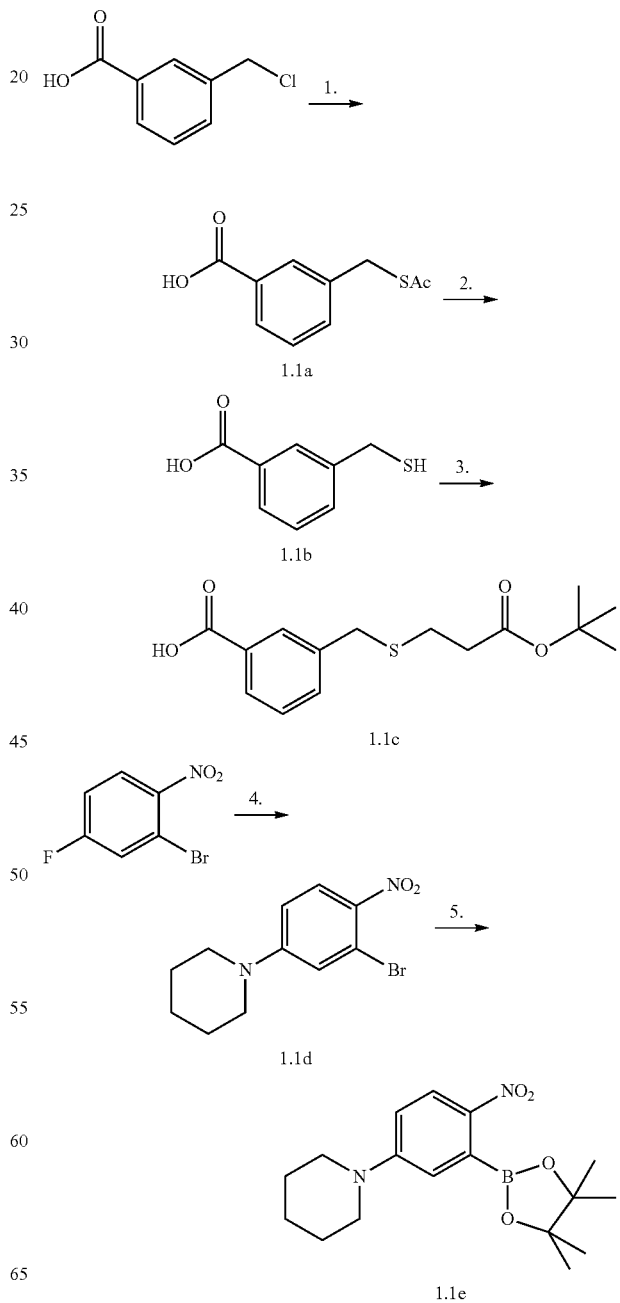

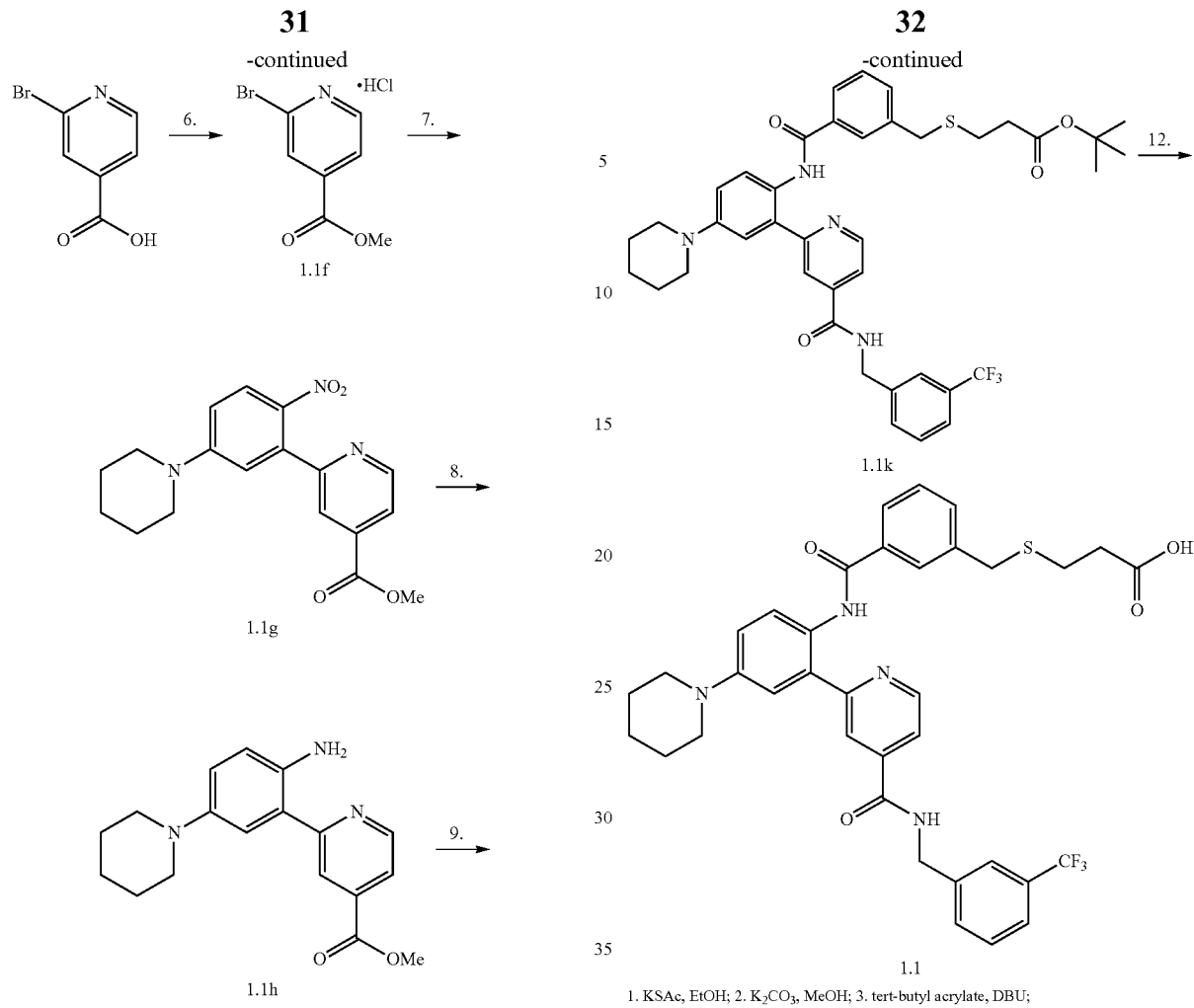
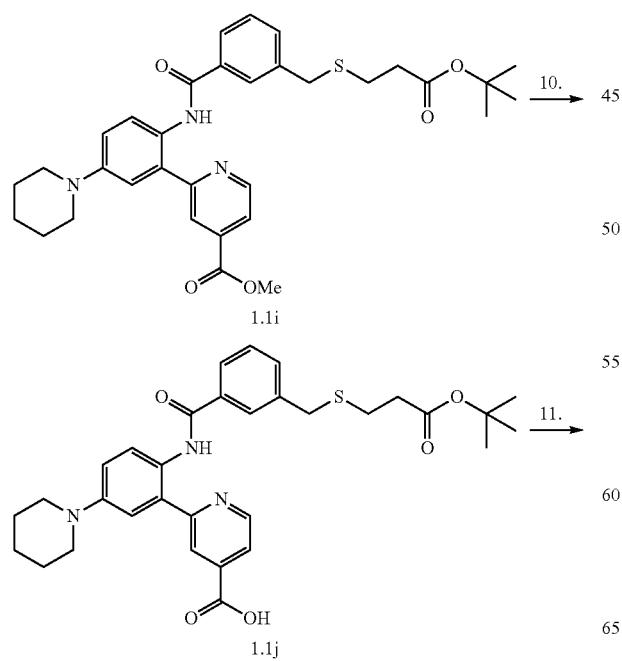

1. KSAc, EtOH; 2. K₂CO₃, MeOH; 3. tert-butyl acrylate, DBU;
4. piperidine, K₂CO₃; 5. 4,4,4′,4′,5,5,5′,5′-octamethyl-2,2′-bi(1,3,2-dioxaborolane), PdCl₂(dppf); 6. MeOH, SOCl₂; 7. Pd(Ph₃P)₄, intermediate 1.1e, DME, Na₂CO₃, water; 8. Fe, NH₄Cl, MeOH; 9. EDC·HCl, DMAP, intermediate 1.1c;
10. LiOH; 11. EDC·HCl, DMAP, 3-(trifluoromethyl)benzylamine; 12. TFA.

Intermediate 1.1a: 3-(acetylthiomethyl)benzoic acid

Into a 250-mL round-bottom flask, was placed a solution of 3-(bromomethyl)benzoic acid (7 g, 32.56 mmol, 1.00 equiv) in ethanol (80 mL), and potassium ethanethioate (9.65 g, 84.65 mmol, 2.60 equiv). The resulting solution was stirred overnight at room temperature. The resulting mixture was concentrated under vacuum. The resulting solution was diluted with 80 mL of water and adjusted to pH 3-4 with 10% hydrochloric acid. The resulting solution was extracted with 3×50 mL of ethyl acetate and the organic layers combined. The resulting mixture was washed with 1×50 mL of brine. The mixture was dried over sodium sulfate and concentrated under vacuum. This resulted in 4.4 g (64%) of 3-(acetylthiomethyl)benzoic acid as a brown solid.

Intermediate 1.1b: 3-(mercaptomethyl)benzoic acid

Into a 500-mL round-bottom flask, was placed a solution of 3-acetylthiomethyl)benzoic acid (16.4 g, 78.10 mmol, 1.00 equiv) in methanol (150 mL), and a solution of potassium carbonate (26.9 g, 194.93 mmol, 2.50 equiv) in water (70 mL). The resulting solution was stirred for 4 h at 60° C. The resulting mixture was concentrated under vacuum. The resulting solution was diluted with 200 mL of water and adjusted to pH 3 with 10% hydrochloric acid. The resulting solution was extracted with 3× (100/20 mL) of ethyl acetate/tetrahydrofuran and the organic layers combined. The resulting mixture was washed with 1×100 mL of brine. The mixture was dried over sodium sulfate and concentrated under vacuum. This resulted in 12 g (91%) of 3-(mercaptomethyl) benzoic acid as a brown solid.

Intermediate 1.1c:
3-((3-tert-butoxy-3-oxopropylthio)methyl)benzoic acid

Into a 500-mL round-bottom flask, was placed a solution of 3-(mercaptomethyl)benzoic acid (12 g, 71.43 mmol, 1.00 equiv) in acetonitrile (200 mL), and tert-butyl acrylate (60 mL), DBU (21.7 g, 142.76 mmol, 2.00 equiv). The resulting solution was stirred overnight at 80° C. in an oil bath. The resulting mixture was concentrated under vacuum. The resulting solution was diluted with 200 mL of water and adjusted to pH 2~3 with 10% hydrochloric acid. The resulting solution was extracted with 3×200 mL of ethyl acetate and the organic layers combined. The mixture was dried over anhydrous sodium sulfate and concentrated under vacuum. The residue was applied onto a silica gel column and eluted with petroleum ether/ethyl acetate (50:1). This resulted in 10.5 g (47%) of 3-((3-tert-butoxy-3-oxopropylthio)methyl)benzoic acid as red oil. $^1$H-NMR (300 MHz, CDCl$_3$, ppm): δ 8.08 (s, 1H), 8.04 (d, J=7.8 Hz, 1H), 7.62 (d, J=7.8 Hz, 1H), 7.46 (t, 1H), 3.81 (s, 2H), 2.68 (t, 2H), 2.50 (t, 2H), 1.48 (s, 9H). MS (ES, m/z): 295 [M−H]—.

Intermediate 1.1d:
1-(3-bromo-4-nitrophenyl)piperidine

Into a 1000-mL round-bottom flask, was placed a solution of 2-bromo-4-fluoro-1-nitrobenzene (30 g, 137.61 mmol, 1.00 equiv) in N,N-dimethylformamide (450 mL), piperidine (13.974 g, 162.68 mmol, 1.20 equiv), and potassium carbonate (56.718 g, 411.00 mmol, 2.99 equiv). The resulting solution was stirred overnight at 75° C. in an oil bath. The solids were filtered out. The resulting mixture was concentrated under vacuum. The resulting solution was diluted with 300 mL of dichloromethane. The resulting mixture was washed with 2×100 mL of water and 2×100 mL of brine. The mixture was dried over anhydrous sodium sulfate and concentrated under vacuum. The residue was applied onto a silica gel column and eluted with ethyl acetate/petroleum ether (1:50). This resulted in 19 g (49%) of 1-(3-bromo-4-nitrophenyl) piperidine as a yellow solid.

Intermediate 1.1e: 1-(4-nitro-3-(4,4,5,5-tetramethyl-1,3,2-dioxaborolan-2-yl)phenyl)-piperidine Into a 50-mL 3-necked round-bottom flask purged and maintained with an inert atmosphere of nitrogen, was placed a solution of 1-(3-bromo-4-nitrophenyl)piperidine (8.00 g, 28.07 mmol, 1.00 equiv) in DMSO (25 mL), PdCl$_2$(dppf) (620 mg, 0.85 mmol, 0.03 equiv), 4,4,5,5-tetramethyl-2-(4,4,5,5-tetramethyl-1,3,2-dioxaborolan-2-yl)-1,3,2-dioxaborolane (10.74 g, 42.45 mmol, 1.50 equiv), and potassium acetate (7.09 g, 72.24 mmol, 2.57 equiv). The resulting solution was stirred overnight at 80° C. in an oil bath. The mixture was concentrated under vacuum. The resulting solution was diluted with 100 mL of water. The resulting solution was extracted with 2×200 mL of ethyl acetate and the organic layers combined. The resulting mixture was washed with 2×100 mL of water and 2×100 mL of brine. The Mixture was dried over anhydrous sodium sulfate and concentrated under vacuum. The residue was applied onto a silica gel column and eluted with ethyl acetate/petroleum ether (1:50~1:10). This resulted in 8.0 g (86%) of 1-(4-nitro-3-(4,4,5,5-tetramethyl-1,3,2-dioxaborolan-2-yl)phenyl)piperidine as a yellow solid. $^1$H-NMR (300 MHz, CDCl$_3$, ppm): δ 8.047-8.077 (d, J=9.0 Hz, 1H), 6.770-6.829 (m, 2H), 3.453 (s, 4H), 1.586-1.702 (m, 6H), 1.499 (s, 12H). MS (ES, m/z): 333.15 [M+H]$^+$.

Intermediate 1.1f: methyl 2-bromoisonicotinate hydrochloride

Into a 500-mL round bottom flask, was placed a solution of 2-bromoisonicotinic acid (10 g, 49.75 mmol, 1.00 equiv) in methanol (200 mL). This was followed by dropwise addition of thionyl chloride (24 g, 203.39 mmol, 4.09 equiv) with stirring at 0° C.-5° C. The resulting solution was stirred for 5 h at 70° C. in an oil bath. The resulting mixture was concentrated under vacuum, to yield 10 g (80%) of methyl 2-bromoisonicotinate hydrochloride as a white solid.

Intermediate 1.1g: methyl 2-(2-nitro-5-(piperidin-1-yl)phenyl)isonicotinate

Into a 250-mL 3-neck round bottom flask purged and maintained with an inert atmosphere of nitrogen, were placed a solution of 1-(4-nitro-3-(4,4,5,5-tetramethyl-1,3,2-dioxaborolan-2-yl)phenyl)piperidine (4 g, 12.05 mmol, 1.00 equiv) in ethylene glycol dimethyl ether (60 mL), methyl 2-bromoisonicotinate hydrochloride (2.6 g, 12.09 mmol, 1.02 equiv), a solution of sodium carbonate (6.4 g, 60.38 mmol, 5.01 equiv) in water (30 mL), and Pd(PPh$_3$)$_4$ (1.4 g, 1.21 mmol, 0.10 equiv). The resulting solution was stirred for 3 h at 95° C. The resulting solution was diluted with 100 mL of water. The resulting solution was extracted with 3×100 mL of ethyl acetate and the organic layers combined. The resulting mixture was washed with 3×100 mL of brine. The mixture was dried over anhydrous sodium sulfate and concentrated under vacuum. The residue was applied onto a silica gel column and eluted with petroleum ether/ethyl acetate (10:1). This resulted in 1.8 g (44%) of methyl 2-(2-nitro-5-(piperidin-1-yl)phenyl)isonicotinate as a red semi-solid.

Intermediate 1.1h: methyl 2-(2-amino-5-(piperidin-1-yl)phenyl)isonicotinate

Into a 100-mL round bottom flask, was placed a solution of methyl 2-(2-nitro-5-(piperidin-1-yl)phenyl)isonicotinate (1.8 g, 5.28 mmol, 1.00 equiv) in methanol (15 mL), and a solution of NH$_4$Cl (850 mg, 15.89 mmol, 3.00 equiv) in water (7.9 mL). This was followed by the addition of iron (2.9 g, 51.79 mmol, 9.99 equiv) in several batches at 70° C. The resulting solution was stirred for 4 h at 70° C. in an oil bath. The solids were filtered out. The resulting mixture was concentrated under vacuum. The resulting solution was diluted with 10 mL of water, extracted with 3×20 mL of ethyl acetate, and the organic layers combined. The resulting mixture was washed with 3×10 mL of brine, dried over anhydrous sodium sulfate, and concentrated under vacuum. This resulted in 1.4 g (85%) of methyl 2-(2-amino-5-(piperidin-1-yl)phenyl) isonicotinate as a black semi-solid.

Intermediate 1.1i: methyl 2-(2-(3-((3-tert-butoxy-3-oxopropylthio)methyl)benzamido)-5-(piperidin-1-yl) phenyl)isonicotinate Into a 50-mL round bottom flask, was placed a solution of methyl 2-(2-amino-5-(piperidin-1-yl)phenyl)isonicotinate (800 mg, 2.57 mmol, 1.00 equiv) in dichloromethane (2 mL), EDC.HCl (608 mg, 3.09 mmol, 1.20 equiv), 4-dimethylaminopyridine (380 mg, 3.11 mmol, 1.20 equiv), and 3-((3-tert-butoxy-3-oxopropylthio)methyl)benzoic acid (837 mg, 2.83 mmol, 1.00 equiv). The resulting solution was stirred for 4 h at room temperature. The mixture was concentrated under vacuum. The residue was applied onto a silica gel column and eluted with petroleum ether/ethyl acetate (10:1-5:1). This resulted in 600 mg (40%) of methyl 2-(2-(3-((3-tert-butoxy-3-oxopropylthio)methyl)benzamido)-5-(piperidin-1-yl)phenyl)isonicotinate as yellow oil.

Intermediate 1.1j: 2-(2-(3-((3-tert-butoxy-3-oxopropylthio)methyl)benzamido)-5-(piperidin-1-yl)phenyl)isonicotinic acid Into a 50-mL round bottom flask, was placed a solution of methyl 2-(2-(3-((3-tert-butoxy-3-oxopropylthio)methyl)benzamido)-5-(piperidin-1-yl)phenyl)isonicotinate (160 mg, 0.27 mmol, 1.00 equiv) in tetrahydrofuran (5 mL), and a solution of lithium hydroxide hydrate (160 mg, 3.81 mmol, 14.02 equiv) in water (5 mL). The resulting solution was stirred overnight at room temperature. The resulting mixture was concentrated under vacuum. The solution was adjusted to pH 3 with hydrochloric acid (2 mol/L). The resulting solution was extracted with 3×10 mL of ethyl acetate and the organic layers combined. The resulting mixture was washed with 3×10 mL of brine. The mixture was dried over anhydrous sodium sulfate and concentrated under vacuum. This resulted in 140 mg (90%) of 2-(2-(3-((3-tert-butoxy-3-oxopropylthio)methyl)benzamido)-5-(piperidin-1-yl)phenyl)isonicotinic acid as a yellow semi-solid.

Intermediate 1.1k: tert-butyl 3-(3-((2-(4-((3-(trifluoromethyl)benzyl)carbamoyl)pyridin-2-yl)-4-(piperidin-1-yl)phenyl)carbamoyl)benzylthio)propanoate Into a 50 mL round bottom flask, was placed 2-(2-(3-((3-tert-butoxy-3-oxopropylthio)methyl)benzamido)-5-(piperidin-1-yl)phenyl)isonicotinic acid (220 mg, 0.38 mmol, 1.00 equiv), 3-(trifluoromethyl)benzylamine (134 mg, 0.77 mmol, 2.00 equiv), EDC.HCl (124 mg, 0.63 mmol, 1.65 equiv), 4-dimethylaminopyridine (76 mg, 0.62 mmol, 1.63 equiv), and dichloromethane (10 mL). The resulting solution was stirred overnight at room temperature. The reaction progress was monitored by LCMS. The resulting mixture was washed with 5×30 mL of aqueous NH$_4$Cl. The mixture was dried over anhydrous sodium sulfate and concentrated under vacuum. This resulted in 360 mg (90%) of tert-butyl 3-(3-((2-(4-((3-(trifluoromethyl)benzyl)carbamoyl)pyridin-2-yl)-4-(piperidin-1-yl)phenyl)carbamoyl)benzylthio)propanoate as yellow oil.

Example 1.1

3-(3-((2-(4-((3-(trifluoromethyl)benzyl)carbamoyl)pyridin-2-yl)-4-(piperidin-1-yl)phenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-(piperidin-1-yl)phenyl)carbamoyl)-benzylthio)propanoate (360 mg, 0.49 mmol, 1.00 equiv) in dichloromethane (2 mL), and 2,2,2-trifluoroacetic acid (2 mL). The resulting solution was stirred for 1 h at room temperature. The reaction progress was monitored by LCMS. The resulting mixture was concentrated under vacuum. The crude product was purified by reverse phase HPLC eluting with a water/CH$_3$CN gradient containing 0.05% TFA. The product was obtained as 217.9 mg (66%) of a white solid. $^1$H-NMR (300 MHz, DMSO-d$_6$+DCl, ppm): δ 9.06~9.04 (d, J=5.7 Hz, 1H), 8.86 (s, 1H), 8.75 (s, 1H), 8.74~8.47 (m, 1H), 8.44~8.10 (m, 2H), 7.88 (s, 2H), 7.88~7.84 (d, J=7.8 Hz, 2H), 7.75~7.48 (m, 4H), 4.60 (s, 2H), 3.86 (s, 2H), 3.78 (s, 4H), 2.63~2.58 (m, 2H), 2.31~1.75 (m, 6H). MS (ES, m/z): 677 [M+H]$^+$.

Example 1.2

3-((3-((4-(Piperidin-1-yl)-2-(4-(((6-(trifluoromethyl)pyridin-3-yl)methyl)carbamoyl)pyridin-2-yl)phenyl)carbamoyl)benzyl)thio)propanoic acid

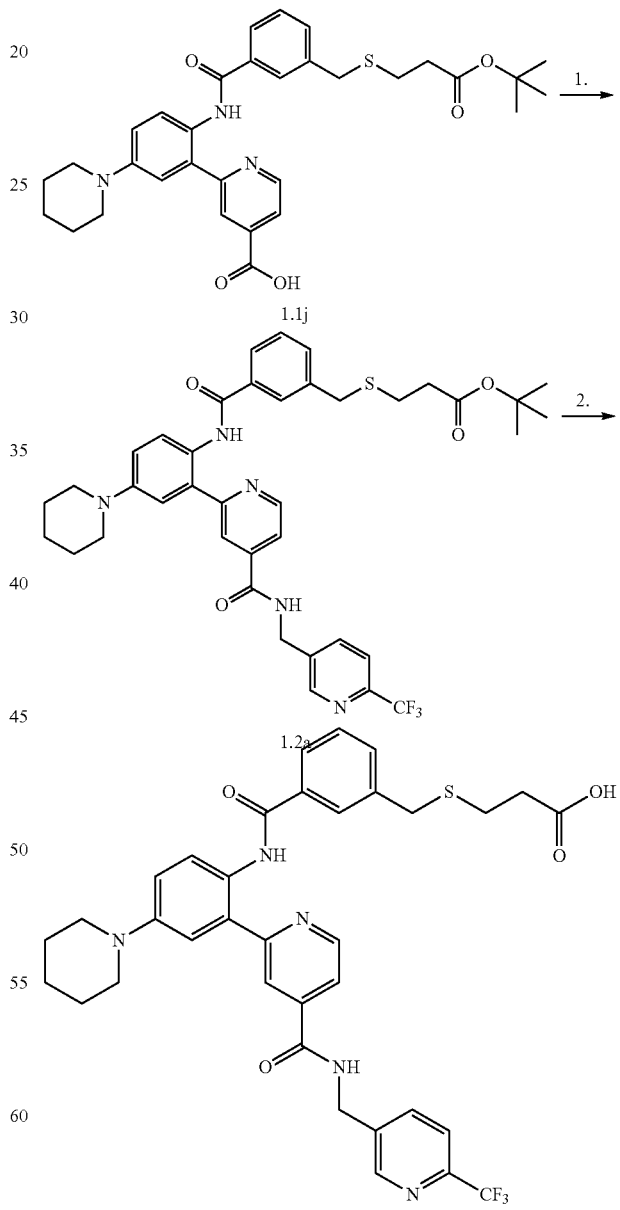

Scheme 2.

1.1j 1.2

1. (6-(trifluoromethyl)pyridin-3-yl)methanamine, HATU, DIEA, DMF;
2. CF$_3$CO$_2$H.

Intermediate 1.2a: tert-butyl 3-((3-((4-(piperidin-1-yl)-2-(4-(((6-(trifluoromethyl)pyridin-3-yl)methyl)carbamoyl)pyridin-2-yl)phenyl)carbamoyl)benzyl)thio)propanoate Into a 8-mL sealed tube, was placed a solution of 2-(2-(3-((3-tert-butoxy-3-oxopropylthio)methyl)benzamido)-5-(piperidin-1-yl)phenyl)isonicotinic acid 1.1j (90 mg, 0.16 mmol, 1.00 equiv) in N,N-dimethylformamide (2 mL), HATU (90 mg, 0.24 mmol, 1.51 equiv), N,N-diisopropylethylamine (30.6 mg, 0.24 mmol, 1.52 equiv), and (6-(trifluoromethyl)pyridin-3-yl)methanamine (54 mg, 0.31 mmol, 1.96 equiv). The resulting solution was stirred overnight at room temperature. The resulting mixture was concentrated under vacuum. The residue was dissolved in ethyl acetate. The resulting mixture was washed with water and brine. The mixture was dried over anhydrous sodium sulfate and concentrated under vacuum to yield 114.7 mg (crude) of tert-butyl 3-(3-((2-(4-(((6-(trifluoromethyl)pyridin-3-yl)methyl)carbamoyl)pyridin-2-yl)-4-(piperidin-1-yl)phenyl)carbamoyl)benzylthio)propanoate as red oil.

Example 1.2

3-(3-((2-(4-(((6-(trifluoromethyl)pyridin-3-yl)methyl)carbamoyl)pyridin-2-yl)-4-(piperidin-1-yl)phenyl)carbamoyl)benzylthio)propanoic acid, trifluoroacetate salt Example 1.2 was prepared from intermediate 1.2a using the procedure used to prepare Example 1.1 from intermediate 1.1k. $^1$H-NMR (300 MHz, CD$_3$OD, ppm): δ 9.064 (d, J=5.1 Hz, 1H), 8.777 (d, J=9.0 Hz, 1H), 8.425 (s, 1H), 8.108-8.163 (m, 2H), 7.997 (s, 1H), 7.896-7.811 (m, 3H), 7.704-7.667 (m, 1H), 7.620-7.595 (m, 1H), 7.547-7.496 (m, 1H), 4.764 (s, 2H), 3.912 (s, 2H), 3.690-3.656 (m, 4H), 2.751-2.690 (m, 2H), 2.614-2.568 (m, 2H), 2.046 (s, 4H), 1.823 (s, 2H). MS (ES, m/z): 678 [M+H]$^+$.

Example 1.3

3-((3-((2-(4-((4-(Tert-butyl)benzyl)carbamoyl)pyridin-2-yl)-4-(piperidin-1-yl)phenyl)carbamoyl)benzyl)thio)propanoic acid Scheme 3.

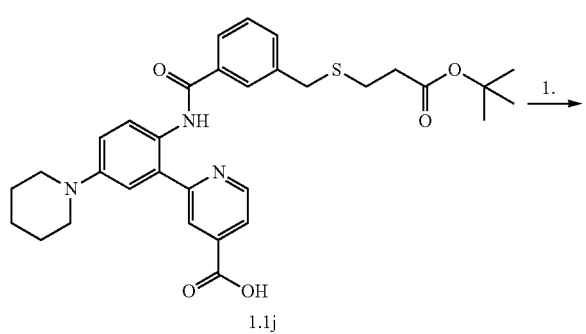

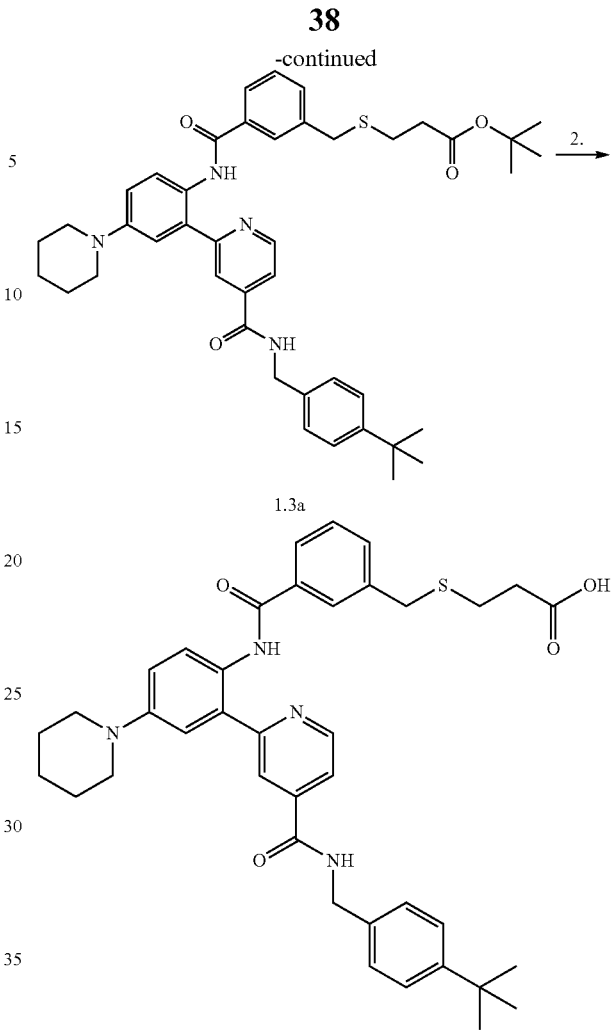

1. 4-tertbutyl-benzylamine, EDC HCl, DMAP; 2. CF$_3$CO$_2$H.

Intermediate 1.3a: methyl tert-butyl 3-(3-((2-(4-((4-tert-butylbenzyl)carbamoyl)pyridin-2-yl)-4-(piperidin-1-yl)phenyl)carbamoyl)benzylthio)propanoate Into a 50-mL round bottom flask, was placed a solution of 2-(2-(3-((3-tert-butoxy-3-oxopropylthio)methyl)benzamido)-5-(piperidin-1-yl)phenyl)isonicotinic acid 1.1j (90.0 mg, 0.16 mmol, 1.00 equiv) in dichloromethane (15 mL), N-(3-dimethylaminopropyl)-N'-ethylcarbodiimide hydrochloride (45.0 mg, 0.23 mmol, 1.50 equiv), N,N-dimethylpyridin-4-amine (28.0 mg, 0.23 mmol, 1.50 equiv), and (4-tert-butylbenzylamine (25.2 mg, 0.15 mmol, 1.00 equiv). The resulting solution was stirred for 8 h at 25° C. in an oil bath. The resulting solution was diluted with 10 mL of water. The resulting solution was extracted with 2×20 mL of ethyl acetate and the organic layers combined. The resulting mixture was washed with brine, dried over sodium sulfate, and concentrated under vacuum. This resulted in 100 mg (89%) of tert-butyl 3-(3-((2-(4-((4-tert-butylbenzyl)carbamoyl)pyridin-2-yl)-4-(piperidin-1-yl)phenyl)carbamoyl)benzylthio)propanoate as a yellow solid.

Example 1.3

3-((3-((2-(4-((4-(tert-butyl)benzyl)carbamoyl)pyridin-2-yl)-4-(piperidin-1-yl)phenyl)carbamoyl)benzyl)thio)propanoic acid Into a 50-mL round bottom flask, was placed a solution of tert-butyl 3-(3-((2-(4-((4-tert-butylbenzyl)carbamoyl)pyridin-2-yl)-4-(piperidin-1-yl)phenyl)carbamoyl)benzylthio)propanoate (100 mg, 0.14 mmol, 1.00 equiv) in dichloromethane (2 mL), and trifluoroacetic acid (160 mg, 1.40 mmol, 10.00 equiv). The resulting solution was stirred overnight at 25° C. in an oil bath. The resulting mixture was concentrated under vacuum. The crude product (95 mg) was purified by reverse phase HPLC eluting with a water/CH₃CN gradient containing 0.05% TFA. The product was obtained as 50 mg (46%) of a white solid. ¹H-NMR (300 MHz, CD₃OD, ppm): δ 9.03-9.05 (d, J=5.4 Hz, 1H), 8.80-8.83 (d, J=9.3 Hz, 1H), 8.42 (s, 1H), 8.16-8.17 (d, J=2.7 Hz, 1H), 8.00 (s, 1H), 7.90-7.90 (d, J=1.5 Hz, 1H), 7.87-7.89 (m, 2H), 7.71-7.75 (dd, J=9.02 Hz, J=2.7 Hz, 1H), 7.60-7.62 (m, 1H), 7.50-7.55 (m, 1H), 7.40-7.42 (m, 2H), 7.31-7.39 (m, 2H), 4.61 (s, 2H), 3.91 (s, 2H), 3.70-3.73 (m, 4H), 2.70 (m, 2H), 2.56-2.51 (m, 2H), 2.06-2.09 (m, 4H), 1.84-1.86 (m, 1H), 1.32-1.33 (m, 9H). MS (ES, m/z): 665 [M+H]⁺.

Examples 1.4 Through 1.49

The compounds listed in Table 1 were prepared from intermediate 1.1j and the requisite amines or amine hydrochloride salts using the methods described for the preparation of Example 1.1 (Method 1) and Example 1.2 (Method 2). Mass spectral data (ES, positive ion mode) is provided for each compound.

TABLE 1

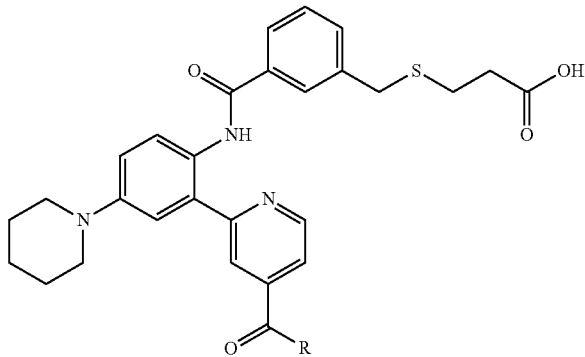

| Example No. | R | Method | MS [M + H] | Salt Form |
|---|---|---|---|---|
| 1.4 | benzylamino | 1 | 609 | Not Applicable (NA)[1] |
| 1.5 | 3-(trifluoromethyl)phenethylamino | 1 | 691 | NA |
| 1.6 | heptylamino | 1 | 617 | Trifluoroacetate |
| 1.7 | cyclohexylmethylamino | 2 | 615 | Trifluoroacetate |
| 1.8 | isobutylamino | 1 | 575 | Trifluoroacetate |

TABLE 1-continued

| Example No. | R | Method | MS [M + H] | Salt Form |
|---|---|---|---|---|
| 1.9 | 2-phenylpyrrolidin-1-yl | 1 | 649 | Trifluoroacetate |
| 1.10 | 4-(dimethylamino)benzylamino | 2 | 652 | Trifluoroacetate |
| 1.11 | 2-aminobenzylamino | 1 | 624 | NA |
| 1.12 | naphthalen-1-ylmethylamino | 1 | 659 | NA |
| 1.13 | 1,2,3,4-tetrahydronaphthalen-1-ylamino | 2 | 649 | NA |
| 1.14 | 4-(piperidin-1-yl)benzylamino | 2 | 692 | Trifluoroacetate |

TABLE 1-continued
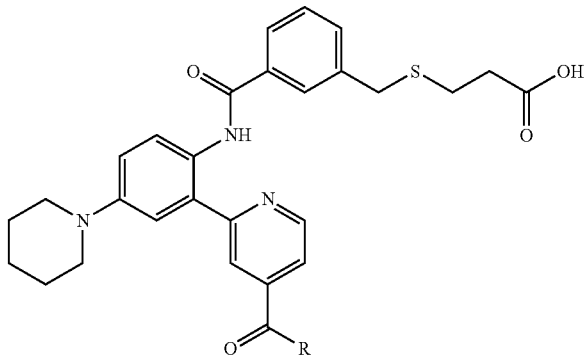
| Example No. | R | Method | MS [M + H] | Salt Form |
|---|---|---|---|---|
| 1.15 | | 1 | 692 | NA |
| 1.16 | | 2 | 708 | Trifluoroacetate |
| 1.17 | | 1 | 657 | Trifluoroacetate |
| 1.18 | | 1 | 613 | Trifluoroacetate |
| 1.19 | | 2 | 635 | Trifluoroacetate |
| 1.20 | | 1 | 652 | Trifluoroacetate |
| 1.21 | | 1 | 675 | Trifluoroacetate |
| 1.22 | | 1 | 681 | Trifluoroacetate |

TABLE 1-continued

| Example No. | R | Method | MS [M + H] | Salt Form |
|---|---|---|---|---|
| 1.23 |  | 1 | 653 | Trifluoroacetate |
| 1.24 |  | 1 | 651 | NA |
| 1.25 | 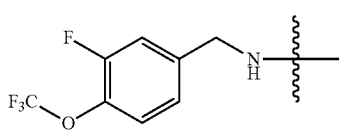 [SMILES: *NCc1ccc(OC(F)(F)F)c(F)c1] | 1 | 711 | Trifluoroacetate |
| 1.26 | 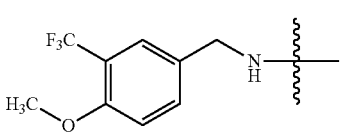 [SMILES: *NCc1ccc(OC)c(C(F)(F)F)c1] | 1 | 711 | NA |
| 1.27 | 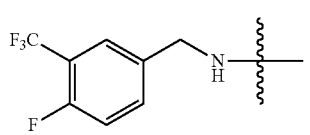 [SMILES: *NCc1ccc(F)c(C(F)(F)F)c1] | 1 | 707 | Trifluoroacetate |
| 1.28 | 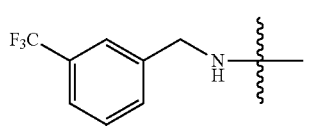 | 1 | 695 | Trifluoroacetate |
| 1.29 | 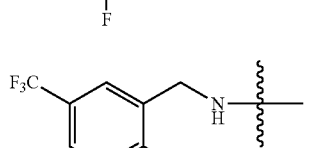 | 1 | 695 | NA |
| 1.30 | | 1 | 695 | NA |

TABLE 1-continued

| Example No. | R | Method | MS [M + H] | Salt Form |
|---|---|---|---|---|
| 1.31 | 2-F, 3-CF₃-benzyl-NH- | 1 | 695 | Trifluoroacetate |
| 1.32 | 3,5-bis(CF₃)-benzyl-NH- | 1 | 745 | NA |
| 1.33 | 3-CF₃, 4-Cl-benzyl-NH- | 1 | 711 | Trifluoroacetate |
| 1.34 | indan-1-yl-NH- | 1 | 635 | Trifluoroacetate |
| 1.35 | indan-2-yl-NH- | 1 | 635 | Trifluoroacetate |
| 1.36 | diphenylmethyl-NH- | 1 | 685 | NA |
| 1.37 | 3-CF₃-benzyl-N(CH₃)- | 1 | 691 | NA |

TABLE 1-continued

| Example No. | R | Method | MS [M + H] | Salt Form |
|---|---|---|---|---|
| 1.38 | 3-methylbenzyl(methyl)amino | 1 | 637 | Trifluoroacetate |
| 1.39 | 4-(benzyloxy)benzylamino | 1 | 715 | NA |
| 1.40 | 4-phenoxybenzylamino | 1 | 701 | NA |
| 1.41 | (biphenyl-4-yl)methylamino | 1 | 685 | Trifluoroacetate |
| 1.42 | (biphenyl-3-yl)methylamino | 1 | 685 | Trifluoroacetate |
| 1.43 | 2-(trifluoromethoxy)benzylamino | 1 | 693 | Trifluoroacetate |
| 1.44 | 4-(trifluoromethoxy)benzylamino | 1 | 693 | Trifluoroacetate |

TABLE 1-continued
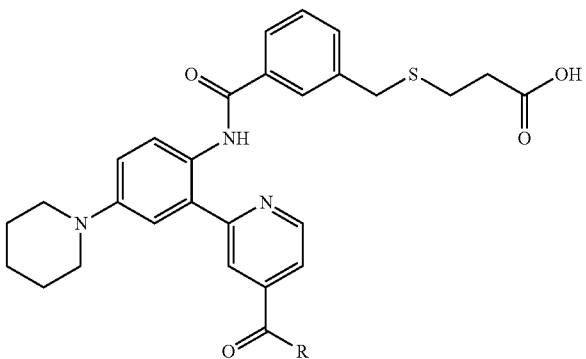
| Example No. | R | Method | MS [M + H] | Salt Form |
|---|---|---|---|---|
| 1.45 | 3-(trifluoromethoxy)benzyl-NH- | 1 | 693 | Trifluoroacetate |
| 1.46 | 3-methylbenzyl-NH- | 1 | 623 | NA |
| 1.47 | 4-(trifluoromethyl)benzyl-NH- | 1 | 677 | Trifluoroacetate |
| 1.48 | 2-(trifluoromethyl)benzyl-NH- | 1 | 677 | NA |
| 1.49 | 3,4-dimethylbenzyl-NH- | 1 | 637 | NA |
[1] Not Applicable (NA): compound isolated as a zwitterion, or free base, or conjugate acid

Example 2

3,3'-(((((((4,4'-((Dodecane-1,12-diylbis(azanediyl))
bis(carbonyl))bis(pyridine-4,2-diyl))bis(4-(piperidin-
1-yl)-2,1-phenylene))bis(azanediyl))bis(carbonyl))
bis(3,1-phenylene))bis(methylene))bis(sulfanediyl))
dipropanoic acid

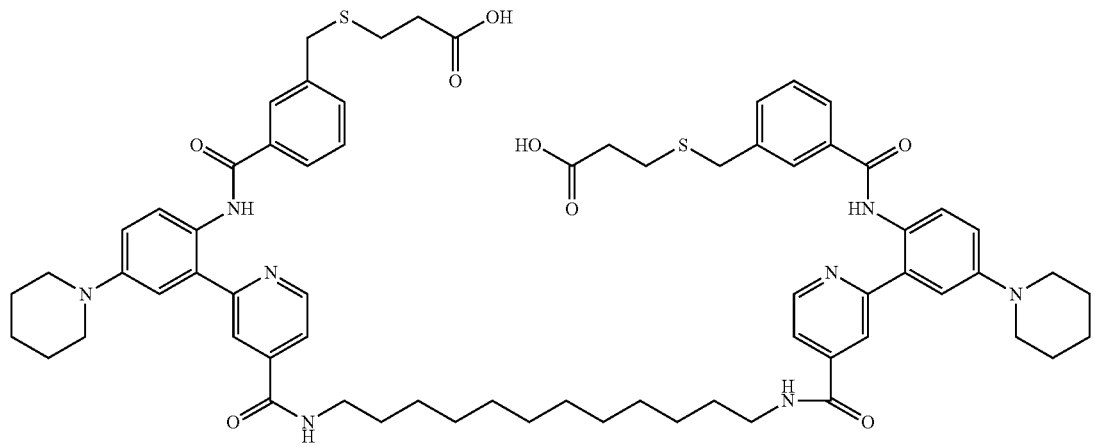

A stirred mixture of 27 mg of intermediate 1.1j, 4.8 mg of 1,12-diaminododecane, and 26 μL of diisopropylamine in 0.5 mL of DMF was treated with 21 mg of HATU. After 20 minutes the solvent was evaporated at reduced pressure and the residue was partitioned between ethyl acetate and aqueous sodium bicarbonate solution. The organic extracts were washed twice with water and once with brine. The solution was dried ($Na_2SO_4$) and the solvent was evaporated. The residue was dissolved in 300 μL of dichloromethane and treated with 300 μL of TFA. The solvent was evaporated and the residue was purified by reverse-phase HPLC to yield 16 mg of 3,3'-(((((((4,4'-((dodecane-1,12-diylbis(azanediyl))bis(carbonyl))bis(pyridine-4,2-diyl))bis(4-(piperidin-1-yl)-2,1-phenylene))bis(azanediyl))bis(carbonyl))bis(3,1-phenylene))bis(methylene))bis-(sulfanediyl))dipropanoic acid. $^1$H-NMR (400 MHz, $CD_3OD$, ppm): δ 8.97 (dd, J=5.2 Hz, J'=0.8 Hz, 2H), 8.79 (d, J=9.0 Hz, 2H), 8.34 (s, 2H), 8.16 (d, J=2.7 Hz, 2H), 7.96 (t, J=1.7 Hz, 2H), 7.84 (dt, J=8.2 Hz, J'=1.3 Hz, 2H), 7.78 (dd, J=5.3 Hz, J'=1.6 Hz, 2H), 7.70 (dd, J=9.2 Hz, J'=2.8 Hz, 2H), 7.56 (dt, J=8.0 Hz, J'=1.2 Hz, 2H), 7.48 (t, J=7.6 Hz, 2H), 3.87 (s, 4H), 3.69 (t, J=5.5 Hz, 8H), 3.39 (t, J=7.2 Hz, 4H), 2.71 (dt, J=7.2 Hz, J'=1.0 Hz, 4H), 2.55 (dt, J=7.1 Hz, J'=1.0 Hz, 4H), 2.05 (m, 8H), 1.81 (m, 4H), 1.62 (m, 4H), 1.40-1.25 (m, 16H). MS (ES, m/z) 1203.6 [M+H]$^+$.

Example 3.1

3-((3-((4-(Piperidin-1-yl)-2-(6-((3-(trifluoromethyl)
benzyl)amino)pyrimidin-4-yl)phenyl)carbamoyl)
benzyl)thio)propanoic acid Scheme 4.

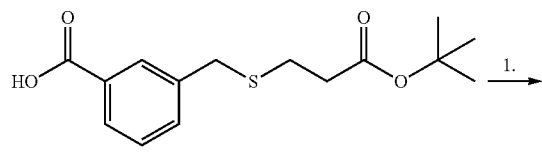
1.1c

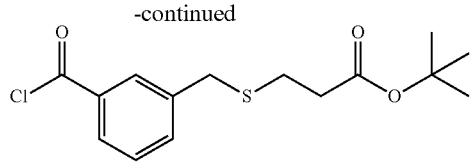
3.1a

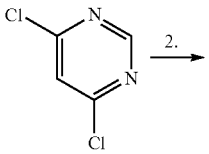

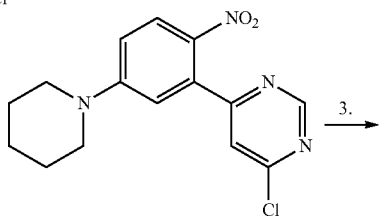
3.1b

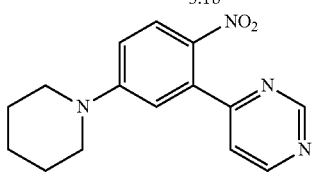
3.1c

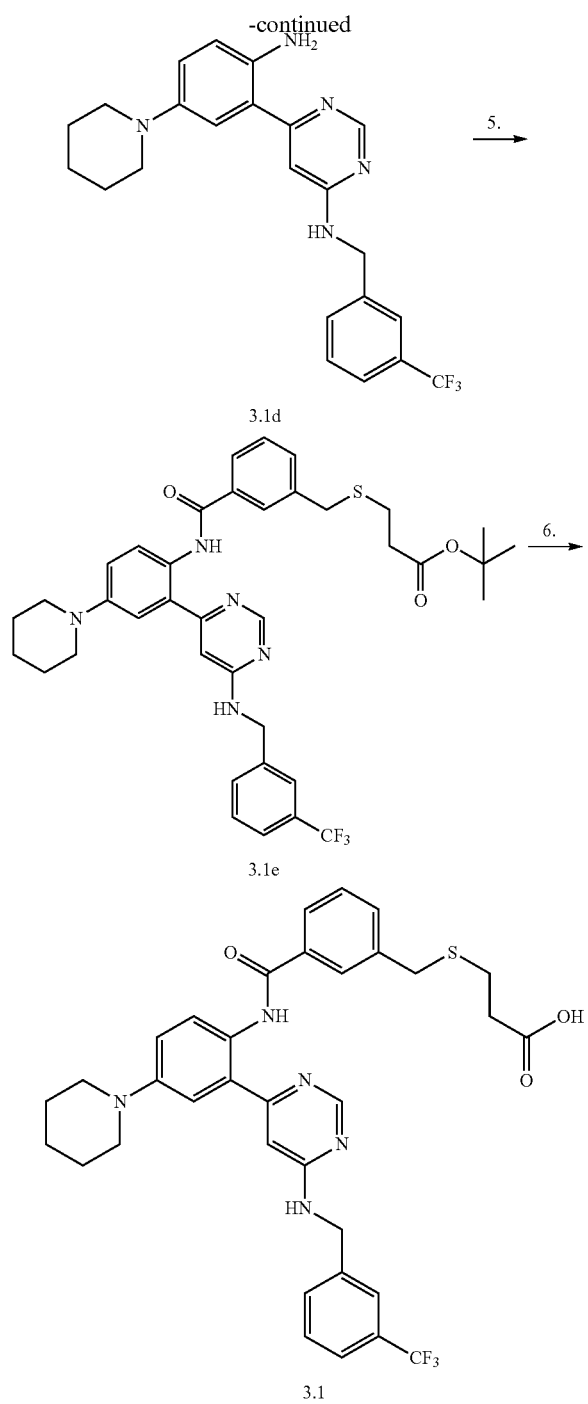

3.1

1. oxalyl chloride, DMF; 2. Intermediate 1.1e, Pd(OAc)₂, PPh₃, Na₂CO₃;
3. 3-(trifluoromethyl)benzylamine, 50° C.; 4. H₂, Pd/C; 5. intermediate 3.1a;
6. TFA.

Intermediate 3.1a: tert-butyl 3-((3-(chlorocarbonyl)benzyl)thio)propanoate

Into a 100-mL round-bottom flask, was placed a solution of 3-((3-tert-butoxy-3-oxopropylthio)methyl)benzoic acid 1.1c (3.00 g, 10.14 mmol, 1.00 equiv) in dichloromethane (50 mL). This was followed by the addition of oxalyl dichloride (4.50 g, 35.43 mmol, 3.00 equiv) dropwise with stirring at 0° C. To this was added N,N-dimethylformamide (one drop). The resulting solution was stirred for 1.5 h at room temperature. The resulting mixture was concentrated under vacuum. This resulted in 3.18 g (99%) of tert-butyl 3-(3-(chlorocarbonyl)benzylthio)propanoate as red oil.

Intermediate 3.1b. 4-chloro-6-(2-nitro-5-(piperidin-1-yl)phenyl)pyrimidine

Into a 250-mL 3-necked round-bottom flask purged and maintained with an inert atmosphere of nitrogen, was placed a solution of 1-(4-nitro-3-(4,4,5,5-tetramethyl-1,3,2-dioxaborolan-2-yl)phenyl)piperidine (5 g, 15.06 mmol, 1.00 equiv) in 1,4-dioxane (150 mL), water (25 mL), 4,6-dichloropyrimidine (5.54 g, 37.69 mmol, 2.50 equiv), Pd(PPh₃)₂Cl₂ (500 mg, 0.75 mmol, 0.05 equiv), triphenylarsine (460 mg, 1.50 mmol, 0.10 equiv), and K₃PO₄ (4.79 g, 22.59 mmol, 1.50 equiv). The resulting solution was stirred overnight at 75° C. The resulting mixture was concentrated under vacuum. The residue was applied onto a silica gel column and eluted with ethyl acetate/petroleum ether (1:10). This resulted in 2.5 g (47%) of 4-chloro-6-(2-nitro-5-(piperidin-1-yl)phenyl)pyrimidine as a yellow solid.

Intermediate 3.1c: 6-(2-nitro-5-(piperidin-1-yl)phenyl)-N-(3-(trifluoromethyl)benzyl)-pyrimidin-4-amine Into a 50-mL round-bottom flask, was placed a solution of 4-chloro-6-(2-nitro-5-(piperidin-1-yl)phenyl)pyrimidine (191 mg) in N,N-dimethylformamide (10 mL), and 3-(trifluoromethyl)benzylamine (210 mg). The resulting solution was stirred overnight at 50° C. The resulting mixture was dissolved in 50 mL of ethyl acetate and washed with 2×50 mL of water. The mixture was dried over anhydrous sodium sulfate and concentrated under vacuum. The residue was purified by silica gel chromatography to give 186 mg of product as yellow oil.

Intermediate 3.1d: 6-(2-amino-5-(piperidin-1-yl)phenyl)-N-(3-(trifluoromethyl)benzyl)-pyrimidin-4-amine A mixture of 6-(2-nitro-5-(piperidin-1-yl)phenyl)-N-(3-(trifluoromethyl)benzyl)pyrimidin-4-amine (184 mg) and 5% Pd/C (35 mg) in ethanol was stirred for 1 h under an atmosphere of hydrogen. The mixture was filtered and the solvent was evaporated.

Intermediate 31e: tert-butyl 3-((3-((4-(piperidin-1-yl)-2-(6-((3-(trifluoromethyl)benzyl)amino)pyrimidin-4-yl)phenyl)carbamoyl)benzyl)thio)propanoate A solution of 6-(2-amino-5-(piperidin-1-yl)phenyl)-N-(3-(trifluoromethyl)benzyl)pyrimidin-4-amine (122 mg) in 1.0 mL of dichloromethane was treated with 54 mg of tert-butyl 3-((3-(chlorocarbonyl)benzyl)thio)propanoate. The mixture was stirred overnight. The solvent was evaporated and the residue was purified by silica gel chromatography to give 120 mg of product as a yellow oil.

Example 3.1

3-((3-((4-(piperidin-1-yl)-2-(6-((3-(trifluoromethyl)benzyl)amino)-pyrimidin-4-yl)phenyl)carbamoyl)benzyl)thio)propanoic acid To a solution of tert-butyl 3-((3-((4-(piperidin-1-yl)-2-(6-((3-(trifluoromethyl)benzyl)amino)pyrimidin-4-yl)phenyl)

carbamoyl)benzyl)thio)propanoate in 1 mL of dichloroethane was added 1 mL of TFA. The mixture was stirred 1 h, and then the solvent was evaporated. The residue was purified by chromatography on silica gel to give 100 mg of a yellow solid. ¹H NMR (400 MHz, DMSO-d₆) δ 8.82 (s, 1H), 7.82 (s, 1H), 7.78-7.60 (m, 4H), 7.59-7.50 (m, 4H), 7.45 (t, J=7.6 Hz, 1H), 7.34-7.15 (m, 2H), 6.97 (s, 1H), 4.76 (s, 2H), 3.84 (s, 2H), 3.26 (s, 4H), 2.64-2.54 (m, 2H), 2.53-2.45 (m, 2H), 1.73-1.62 (m, 4H), 1.62-1.50 (m, 2H). MS (ES, m/z): 650.28 [M+H]⁺.

Example 3.2

3-((3-((4-(Piperidin-1-yl)-2-(6-((3-methylbenzyl)amino)pyrimidin-4-yl)phenyl)carbamoyl)benzyl)thio)propanoic acid

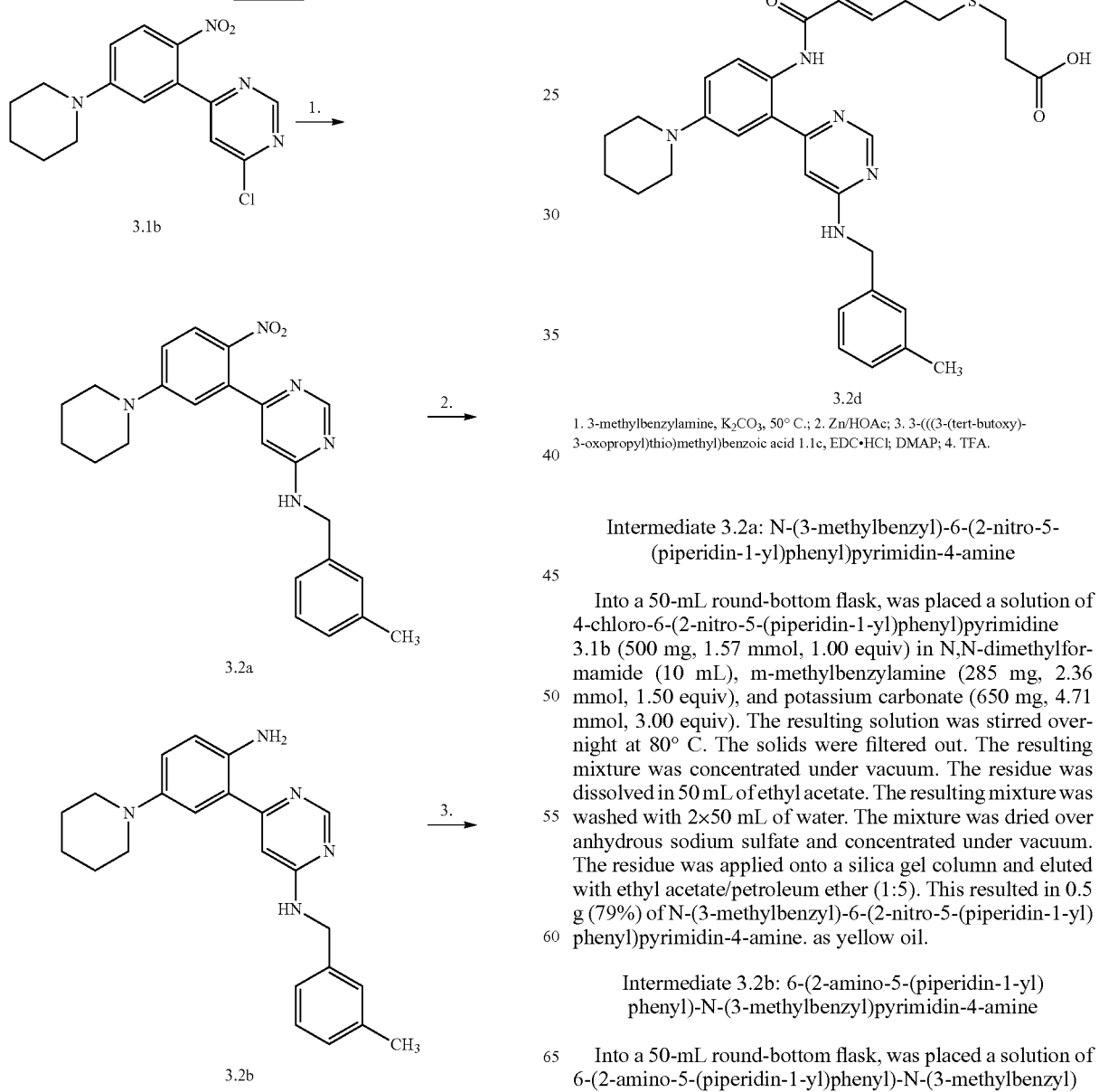

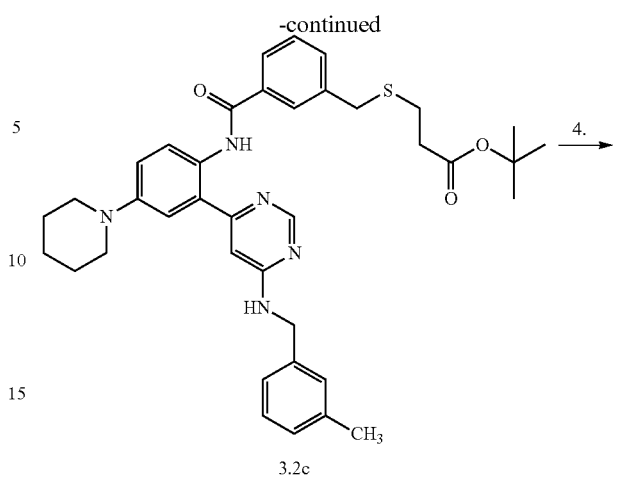

1. 3-methylbenzylamine, K₂CO₃, 50° C.; 2. Zn/HOAc; 3. 3-(((3-(tert-butoxy)-3-oxopropyl)thio)methyl)benzoic acid 1.1c, EDC•HCl; DMAP; 4. TFA.

Intermediate 3.2a: N-(3-methylbenzyl)-6-(2-nitro-5-(piperidin-1-yl)phenyl)pyrimidin-4-amine Into a 50-mL round-bottom flask, was placed a solution of 4-chloro-6-(2-nitro-5-(piperidin-1-yl)phenyl)pyrimidine 3.1b (500 mg, 1.57 mmol, 1.00 equiv) in N,N-dimethylformamide (10 mL), m-methylbenzylamine (285 mg, 2.36 mmol, 1.50 equiv), and potassium carbonate (650 mg, 4.71 mmol, 3.00 equiv). The resulting solution was stirred overnight at 80° C. The solids were filtered out. The resulting mixture was concentrated under vacuum. The residue was dissolved in 50 mL of ethyl acetate. The resulting mixture was washed with 2×50 mL of water. The mixture was dried over anhydrous sodium sulfate and concentrated under vacuum. The residue was applied onto a silica gel column and eluted with ethyl acetate/petroleum ether (1:5). This resulted in 0.5 g (79%) of N-(3-methylbenzyl)-6-(2-nitro-5-(piperidin-1-yl)phenyl)pyrimidin-4-amine. as yellow oil.

Intermediate 3.2b: 6-(2-amino-5-(piperidin-1-yl)phenyl)-N-(3-methylbenzyl)pyrimidin-4-amine Into a 50-mL round-bottom flask, was placed a solution of 6-(2-amino-5-(piperidin-1-yl)phenyl)-N-(3-methylbenzyl)pyrimidin-4-amine (400 mg, 0.99 mmol, 1.00 equiv) in acetic acid (5 mL). This was followed by the addition of zinc (630 mg, 9.84 mmol, 10.00 equiv) in several batches at 70° C. The resulting solution was stirred for 2 h at 60° C. The solids were filtered out. The resulting mixture was concentrated under vacuum. The solution was adjusted to pH 8 with aqueous ammonia (1 mol/L). The resulting solution was extracted with 2×50 mL of ethyl acetate and the organic layers combined, dried over anhydrous sodium sulfate, and concentrated under vacuum. The residue was applied onto a silica gel column and eluted with dichloromethane:methanol (1:50). This resulted in 200 mg (49%) of 6-(2-amino-5-(piperidin-1-yl)phenyl)-N-(3-methylbenzyl)pyrimidin-4-amine as a black solid.

Intermediate 3.2c: tert-butyl 3-((3-((4-(piperidin-1-yl)-2-(6-((3-methyl benzyl)amino)-pyrimidin-4-yl)phenyl)carbamoyl)benzyl)thio)propanoate Into a 50-mL round-bottom flask, was placed a solution of 3-((3-tert-butoxy-3-oxopropylthio)methyl)benzoic acid (143 mg, 0.48 mmol, 1.00 equiv) in dichloromethane (10 mL), EDC.HCl (139 mg, 0.72 mmol, 1.50 equiv), 4-dimethylaminopyridine (89 mg, 0.69 mmol, 1.50 equiv), and 6-(2-amino-5-(piperidin-1-yl)phenyl)-N-(3-methylbenzyl) pyrimidin-4-amine (180 mg, 0.48 mmol, 1.00 equiv). The resulting solution was stirred overnight at room temperature. The resulting mixture was concentrated under vacuum. The residue was applied onto a silica gel column and eluted with petroleum ether/ethyl acetate (5:1). This resulted in 200 mg (57%) of product as yellow oil.

Example 3.2

3-((3-((2-(6-((3-methylbenzyl)amino)pyrimidin-4-yl)-4-(piperidin-1-yl)-phenyl)carbamoyl)benzyl)thio) propanoic acid Into a 100-mL round-bottom flask, was placed a solution of tert-butyl 3-(3-(2-(6-(3-methylbenzylamino)pyrimidin-4-yl)-4-(piperidin-1-yl)phenylcarbamoyl)benzylthio)propanoate (180 mg, 0.28 mmol, 1.00 equiv) in dichloromethane (5 mL), and 2,2,2-trifluoroacetic acid (2 mL). The resulting solution was stirred for 3 h at room temperature. The resulting mixture was concentrated under vacuum. The crude product was purified by reverse phase HPLC eluting with a water/CH$_3$CN gradient containing 0.05% TFA. The product was obtained as 84 mg (51%) of a yellow solid. $^1$H-NMR (300 MHz, DMSO-d$_6$, ppm): δ 9.42 (s, 1H), 8.84 (s, 1H), 7.80 (s, 1H), 7.71 (m, 2H), 7.52 (m, 1H), 7.45 (m, 1H), 7.24 (m, 6H), 6.90 (s, 1H), 5.42 (s, 2H), 4.64 (m, 1H), 3.82 (s, 2H), 3.26 (m, 4H), 2.59 (m, 2H), 1.67 (m, 6H). MS (ES, m/z): 596 [M+H]$^+$.

Example 3.3

3-((3-((4-(Piperidin-1-yl)-2-(6-((3-(trifluoromethyl) phenethyl)amino)pyrimidin-4-yl)phenyl)carbamoyl) benzyl)thio)propanoic acid

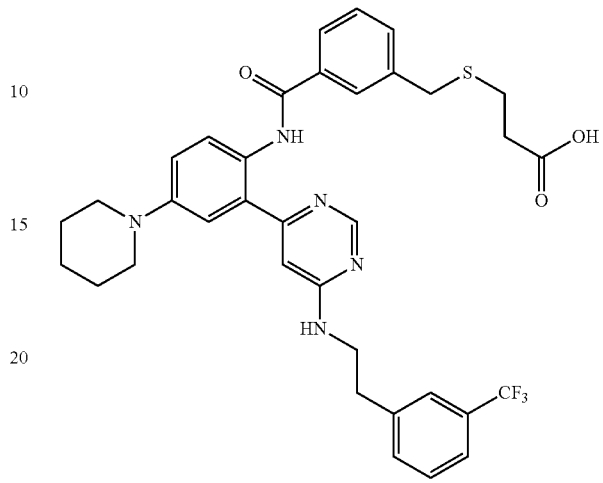

This compound was prepared using the procedure described for the preparation of Example 3.2, except that 3-(trifluoromethyl)phenethylamine was used in place of 3-methylbenzylamine. $^1$H-NMR (300 MHz, CD$_3$OD, ppm): δ 8.67 (s, 1H), 7.86 (s, 1H), 7.76 (m, 2H), 7.47 (m, 9H), 6.82 (s, 1H), 3.85 (s, 4H), 3.38 (m, 4H), 3.01 (m, 2H), 2.66 (m, 2H), 2.56 (m, 2H), 1.83 (m, 4H), 1.72 (m, 2H). MS (ES, m/z): 664 [M+H]$^+$.

Example 3.4

3-((3-((2-(6-((3,4-Dimethylbenzyl)amino)pyrimidin-4-yl)-4-(piperidin-1-yl)phenyl)carbamoyl)benzyl) thio)propanoic acid

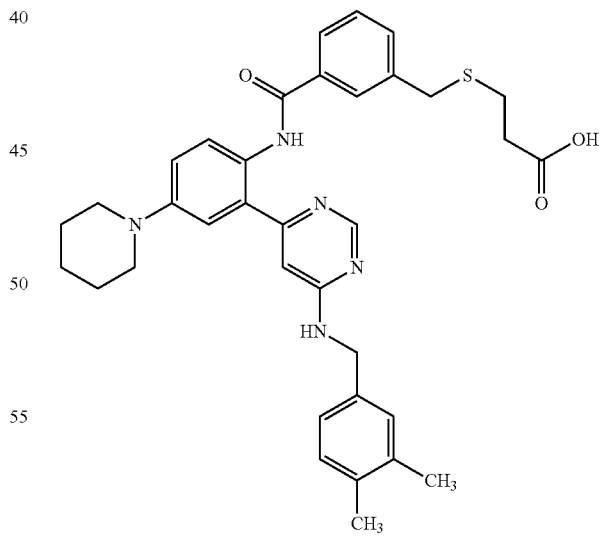

This compound was prepared using the procedure described for the preparation of Example 3.2, except that 3,4-dimethylbenzylamine was used in place of 3-methylbenzylamine. $^1$H-NMR (300 MHz, DMSO-d$_6$, ppm): δ 8.83 (s, 1H), 7.79 (s, 1H), 7.71 (m, 2H), 7.53 (m, 1H), 7.47 (m, 1H), 7.26 (m, 2H), 7.06 (m, 2H), 6.96 (m, 1H), 6.88 (s, 1H), 4.58 (s, 2H), 3.82 (s, 2H), 3.26 (m, 4H), 2.57 (m, 2H), 2.18 (m, 6H), 1.66 (m, 6H). MS (ES, m/z): 610 [M+H]$^+$.

Example 3.5

3-((3-((2-(6-((4-Chloro-3-(trifluoromethyl)benzyl)amino)pyrimidin-4-yl)-4-(piperidin-1-yl)phenyl)carbamoyl)benzyl)thio)propanoic acid

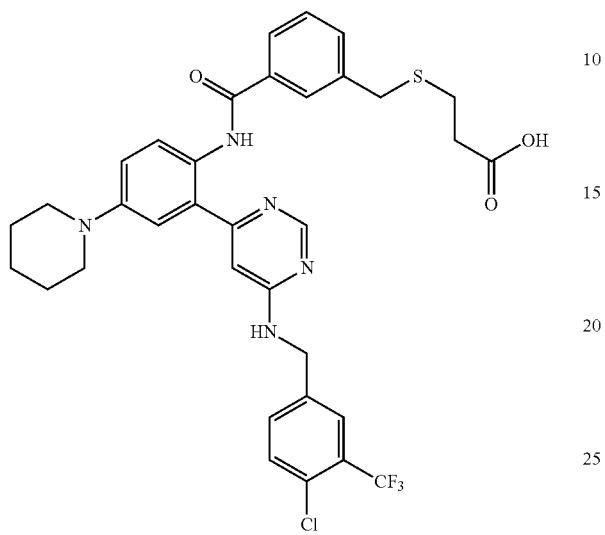

This compound was prepared using the procedure described for the preparation of Example 3.2, except that 4-chloro-3-(trifluoromethyl)benzylamine was used in place of 3-methylbenzylamine $^1$H-NMR (300 MHz, CD$_3$OD, ppm): δ 8.75 (s, 1H), 7.86 (s, 1H), 7.77 (m, 3H), 7.48 (m, 8H), 6.91 (s, 1H), 4.79 (s, 2H), 3.84 (s, 2H), 3.42 (m, 4H), 2.70 (m, 2H), 2.56 (m, 2H), 1.85 (m, 4H), 1.73 (m, 2H). MS (ES, m/z): 684 [M+H]$^+$.

Example 3.6

3-((3-((2-(6-((3,4-Dimethoxybenzyl)amino)pyrimidin-4-yl)-4-(piperidin-1-yl)phenyl)carbamoyl)benzyl)thio)propanoic acid

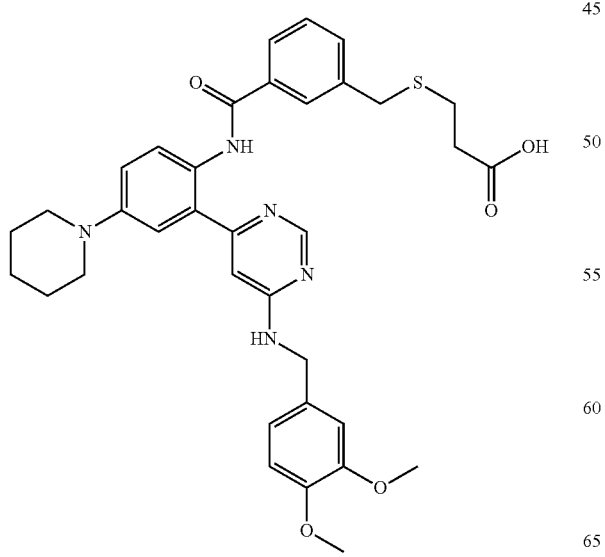

This compound was prepared using the procedure described for the preparation of Example 3.2, except that 3,4-dimethoxybenzylamine was used in place of 3-methylbenzylamine. $^1$H-NMR (400 MHz, DMSO-d$_6$, ppm): δ 8.85 (s, 1H), 7.79 (s, 1H), 7.73 (m, 2H), 7.54 (m, 1H), 7.44 (m, 1H), 7.25 (m, 1H), 7.23 (m, 1H), 6.88 (m, 2H), 6.83 (m, 1H), 6.76 (m, 1H), 4.58 (s, 2H), 4.39 (s, 1H), 3.82 (s, 2H), 3.72 (m, 3H), 3.68 (s, 3H), 3.25 (m, 4H), 2.58 (m, 2H), 1.66 (m, 4H), 1.58 (m, 2H). MS (ES, m/z): 642 [M+H]$^+$.

Example 3.7

3-((3-((2-(6-(Benzylamino)pyrimidin-4-yl)-4-(piperidin-1-yl)phenyl)carbamoyl)benzyl)thio)propanoic acid

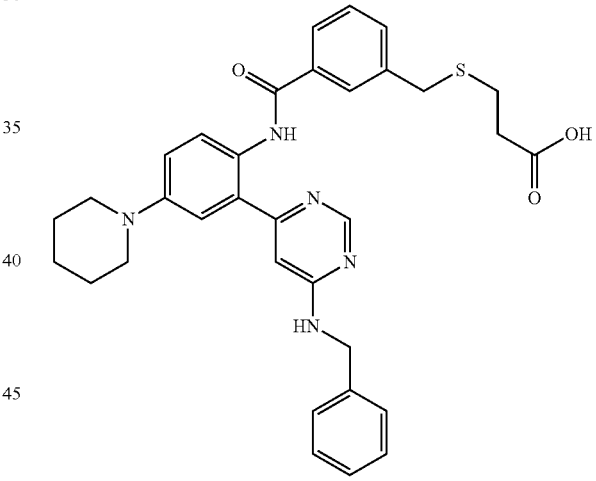

This compound was prepared using the procedure described for the preparation of Example 3.2, except that benzylamine was used in place of 3-methylbenzylamine. $^1$H-NMR (400 MHz, DMSO d$_6$, ppm): δ 9.55 (s, 1H), 8.85 (s, 1H), 7.80 (s, 1H), 7.74 (m, 1H), 7.72 (m, 1H), 7.55 (m, 1H), 7.45 (m, 1H), 7.28 (m, 7H), 6.91 (s, 1H), 4.68 (m, 2H), 4.52 (s, 1H), 3.82 (s, 2H), 3.27 (s, 4H), 2.57 (m, 2H), 1.67 (m, 4H), 1.58 (m, 2H). MS (ES, M/Z): 582 [M+H]$^+$.

Example 3.8

3-((3-((4-(Piperidin-1-yl)-2-(6-((3-(trifluoromethyl)benzyl)oxy)pyrimidin-4-yl)phenyl)carbamoyl)benzyl)thio)propanoic acid

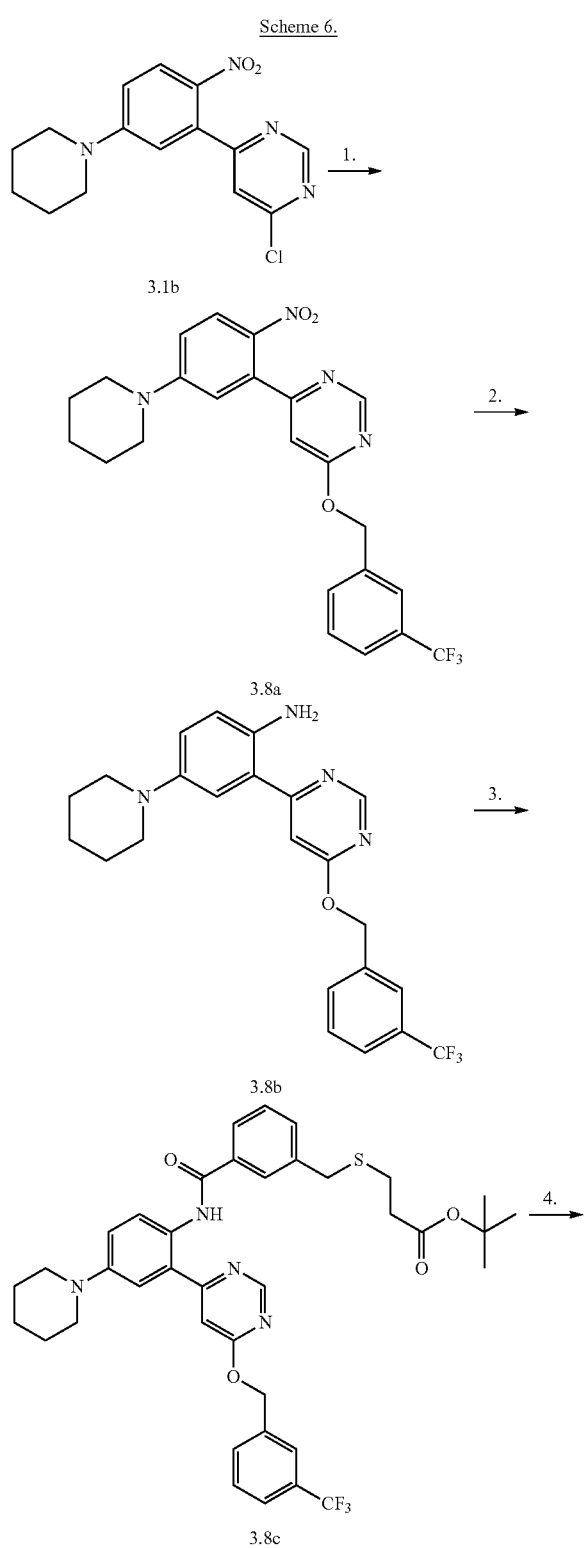

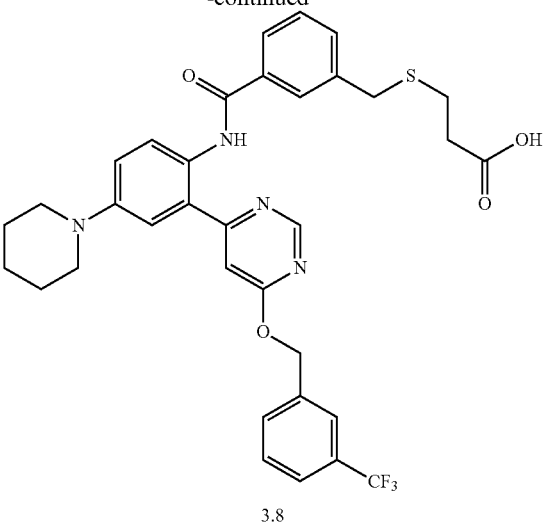

1. 3-(trifluoromethyl)benzyl alcohol, NaH; 2. sodium dithionite; 3. Intermediate 3.1a; 4. TFA.

Intermediate 3.8a: 4-(2-nitro-5-(piperidin-1-yl)phenyl)-6-((3-(trifluoromethyl)benzyl)-oxy)pyrimidine To a solution of 99 mg of 3-(trifluoromethyl)benzyl alcohol in 2 mL of DMF was added 27 mg of a 50% dispersion of sodium hydride in oil. After 15 min the solution was treated with 150 mg of intermediate 3.1b. After an additional 2 h the reaction mixture was partitioned between water and ethyl acetate. The organic extracts were washed with brine and dried ($Na_2SO_4$). The solvent was evaporated to give a yellow syrup that was used directly in the next step.

Intermediate 3.8b: 4-(piperidin-1-yl)-2-(6-((3-(trifluoromethyl)benzyl)oxy)pyrimidin-4-yl)aniline All of the product from the preceding step was dissolved in 4 mL of dioxane and a solution of 410 mg of sodium dithionite and 158 mg of sodium bicarbonate in 4 mL of water was added dropwise. After 3 h a fresh solution of 410 mg of sodium dithionite and 158 mg of sodium bicarbonate in 4 mL of water was added dropwise, and the mixture was stirred an additional 4 h. It was partitioned between ethyl acetate and water, and the aqueous phase was extracted with ethyl acetate. The combined organic extracts were washed with brine and dried ($Na_2SO_4$). The solvent was evaporated and the residue was chromatographed on silica gel to give 75 mg of a yellow syrup.

Intermediate 3.8c: tert-butyl 3-((3-((4-(piperidin-1-yl)-2-(6-((3-(trifluoromethyl)benzyl)oxy)pyrimidin-4-yl)phenyl)carbamoyl)benzyl)thio)propanoate To a 5° C. solution of 75 mg of 4-(piperidin-1-yl)-2-(6-((3-(trifluoromethyl)benzyl)oxy)pyrimidin-4-yl)aniline in dichloromethane was added 65 mg of intermediate 3.1a. The mixture was stirred overnight and then the solvent was evaporated. The residue was purified by chromatography on silica gel to give 75 mg of a yellow syrup.

Example 3.8

3-((3-((4-(piperidin-1-yl)-2-(6-((3-(trifluoromethyl) benzyl)oxy)pyrimidin-4-yl)phenyl)carbamoyl)benzyl)thio)propanoic acid This compound was prepared from intermediate 3.8c using the same procedure used to prepare Example 1.1 from intermediate 1.1k. MS (ES, m/z): 651.1 [M+H]$^+$ Example 3.9

3-((3-((4-(Piperidin-1-yl)-2-(6-(3-(trifluoromethyl) phenoxy)pyrimidin-4-yl)phenyl)carbamoyl)benzyl) thio)propanoic acid Scheme 7.

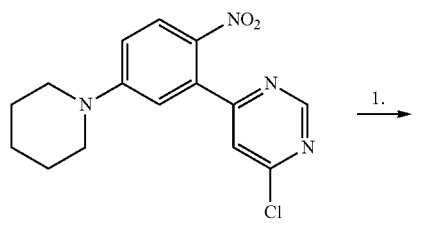

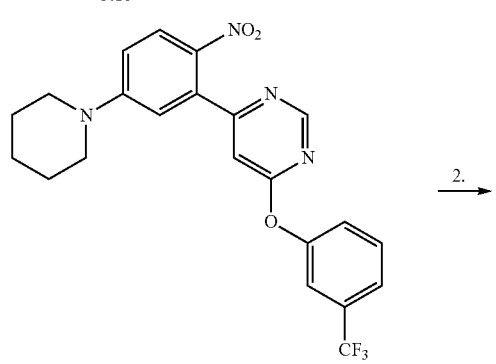

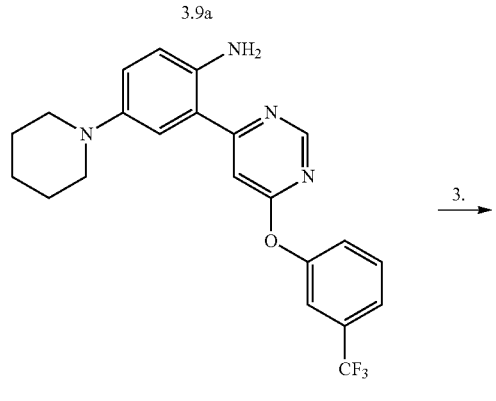

1. 3-(trifluoromethyl)phenol, K$_2$CO$_3$;
2. H$_2$, Pd/C;
3. Intermediate 3.1a, then TFA.

Intermediate 3.9a: 4-(2-nitro-5-(piperidin-1-yl)phenyl)-6-(3-(trifluoromethyl)phenoxy)-pyrimidine To a solution of 160 mg of 3-(trifluoromethyl)phenol in 2 mL of DMF was added 104 mg of potassium carbonate and 160 mg of intermediate 3.1b. After stirring overnight at 50° C. the reaction mixture was partitioned between water and ethyl acetate. The organic extracts were washed with brine and dried (Na$_2$SO$_4$). The solvent was evaporated to give a yellow syrup that was used directly in the next step.

Intermediate 3.9b: 4-(piperidin-1-yl)-2-(6-(3-(trifluoromethyl)phenoxy)pyrimidin-4-yl)-aniline A solution of 4-(2-nitro-5-(piperidin-1-yl)phenyl)-6-(3-(trifluoromethyl)phenoxy)pyrimidine in a mixture of methanol and ethyl acetate was treated with 35 mg of 5% Pd/C and stirred for 2 h under a hydrogen atmosphere. The mixture was filtered and the solvent was evaporated. The residue was purified by chromatography to give the product as 170 mg of a yellow syrup.

Example 3.9

3-((3-((4-(piperidin-1-yl)-2-(6-(3-(trifluoromethyl) phenoxy)pyrimidin-4-yl)-phenyl)carbamoyl)benzyl) thio)propanoic acid This compound was prepared from intermediate 3.9 using the procedure described for the conversion of intermediate 1.1k to Example 1.1.

Example 3.10

3-((3-((4-(Piperidin-1-yl)-2-(6-((3-(trifluoromethyl)
phenyl)amino)pyrimidin-4-yl)phenyl)carbamoyl)
benzyl)thio)propanoic acid Scheme 8.

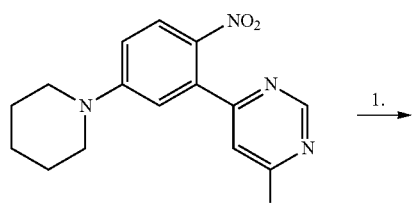

3.1b

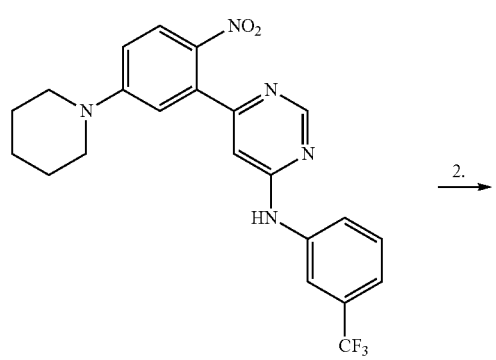

3.10a

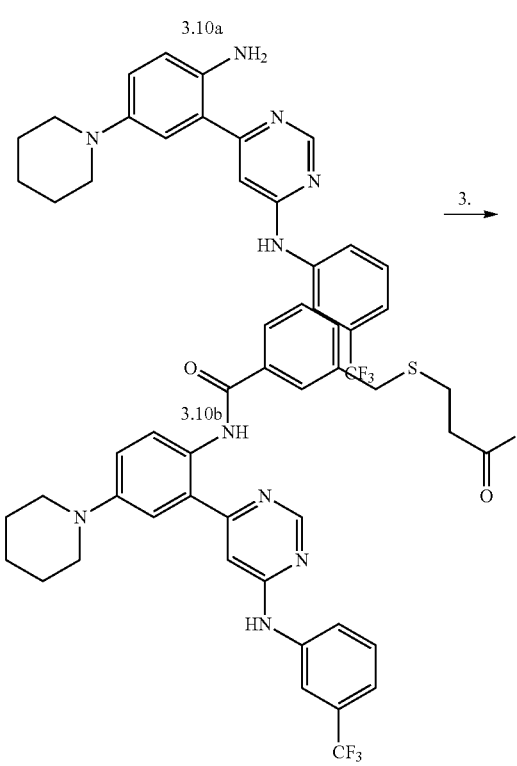

3.10

1. 3-(trifluoromethyl)aniline, hydrochloric acid;
2. H₂, Pd/C;
3. Intermediate 3.1a, then TFA Intermediate 3.10a: 6-(2-nitro-5-(piperidin-1-yl)phenyl)-N-(3-(trifluoromethyl)phenyl)-pyrimidin-4-amine A solution of 15 mg of 3-(trifluoromethyl)aniline and 27 mg intermediate 3.1b in 1 mL of DMF was treated with 1 drop of concentrated hydrochloric acid and heated to 90° C. for 1 h. The solution was cooled and partitioned between ethyl acetate and water. The organic extracts were washed with brine and dried over $Na_2SO_4$. The solvent was evaporated at reduced pressure to give 28 mg of product.

Intermediate 3.10b: 6-(2-amino-5-(piperidin-1-yl)phenyl)-N-(3-(trifluoromethyl)phenyl)-pyrimidin-4-amine This compound was prepared from intermediate 3.10a using the procedure used for the preparation of intermediate 3.9b from intermediate 3.9a.

Example 3.10

3-((3-((4-(piperidin-1-yl)-2-(6-((3-(trifluoromethyl)
phenyl)amino)-pyrimidin-4-yl)phenyl)carbamoyl)
benzyl)thio)propanoic acid This compound was prepared from intermediate 3.10b using the procedure described for the preparation of Example 3.8 from intermediate 3.8b. MS (ES, m/z): 636.3 [M+H]⁺

Example 4.1

N1-(2-(Diethylamino)ethyl)-N1-methyl-N3-(4-(piperidin-1-yl)-2-(4-((3-(trifluoromethyl)benzyl)carbamoyl)pyridin-2-yl)phenyl)isophthalamide Scheme 9.

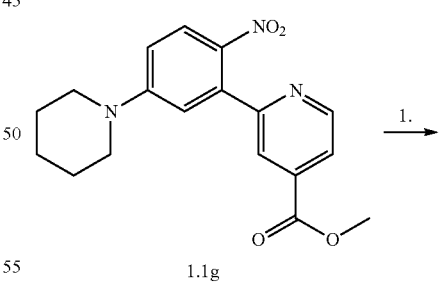

1.1g

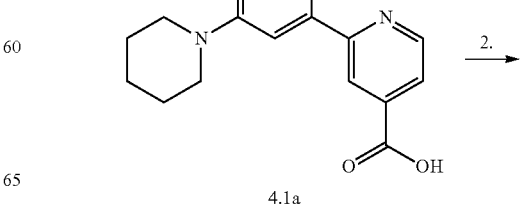

4.1a

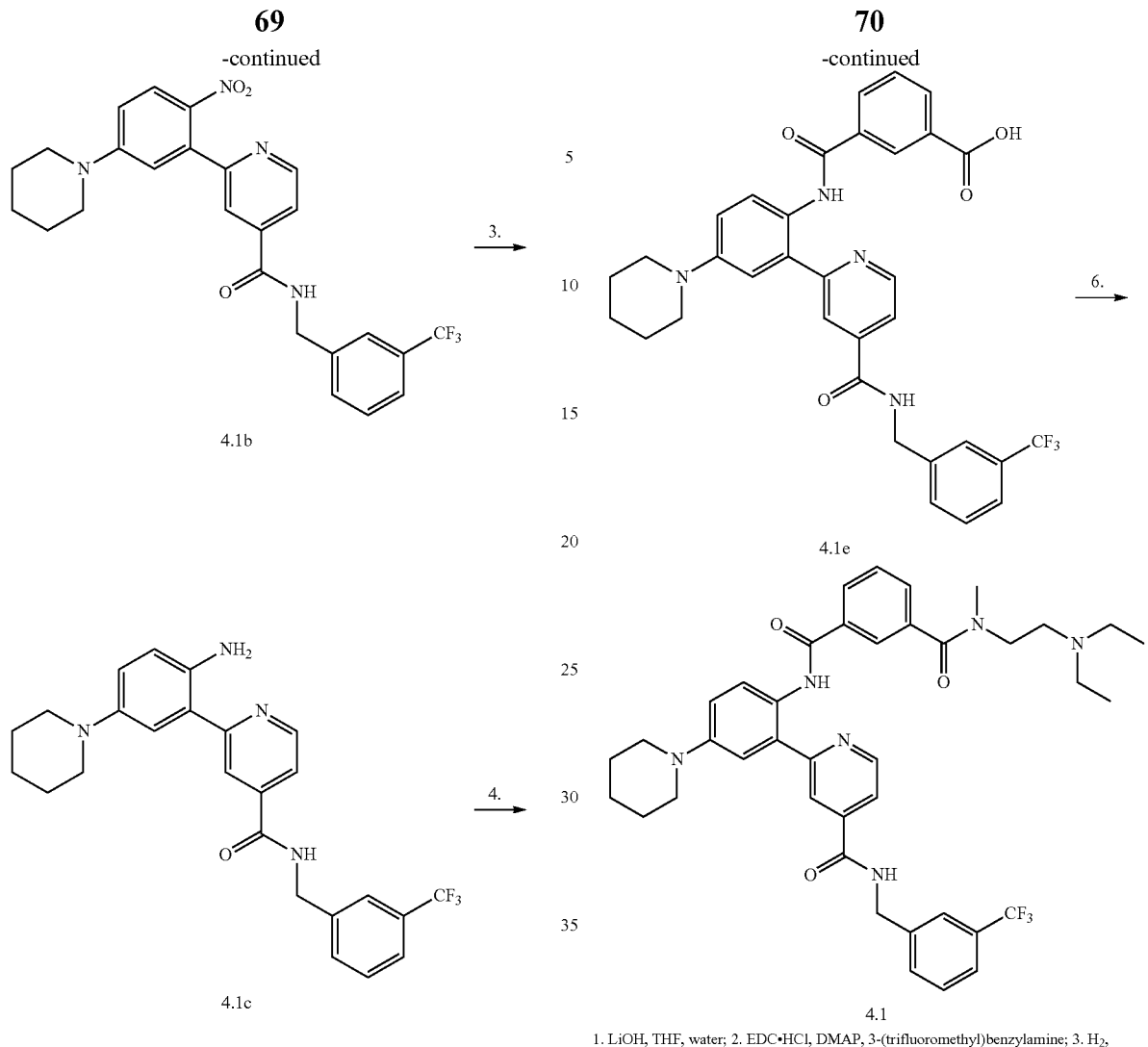
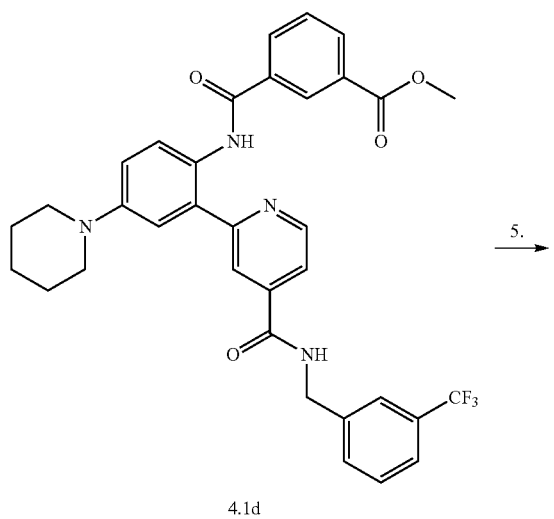

1. LiOH, THF, water; 2. EDC•HCl, DMAP, 3-(trifluoromethyl)benzylamine; 3. H₂, Pd/C; 4. isophthalic acid monomethyl ester, EDC•HCl, DMAP; 5. LiOH; 6. EDC•HCl, DMAP, Et₂NCH₂CH₂NHMe.

Intermediate 4.1a:
2-(2-nitro-5-(piperidin-1-yl)phenyl)isonicotinic acid

Into a 50-mL round-bottom flask, was placed a solution of methyl 2-(2-nitro-5-(piperidin-1-yl)phenyl)isonicotinate 1.1g (1 g, 2.93 mmol, 1.00 equiv) in tetrahydrofuran/water (1:1) (20 mL), lithium hydroxide hydrate (1.26 g, 30.00 mmol, 10.23 equiv). The resulting solution was stirred overnight at 25° C. in an oil bath. The resulting mixture was concentrated under vacuum. The resulting solution was diluted with 10 mL of water. The resulting solution was extracted with 2×20 mL of ethyl acetate and the aqueous layers combined. The solution was adjusted to pH 5 with hydrochloric acid. The resulting solution was extracted with 2×50 mL of ethyl acetate and the organic layers combined, dried over anhydrous sodium sulfate, and concentrated under vacuum. This resulted in 0.8 g (83%) of 2-(2-nitro-5-(piperidin-1-yl)phenyl)isonicotinic acid as a yellow solid.

Intermediate 4.1b: N-(3-(trifluoromethyl)benzyl)-2-(2-nitro-5-(piperidin-1-yl)phenyl)-isonicotinamide Into a 50-mL round bottom flask, was placed a solution of 2-(2-nitro-5-(piperidin-1-yl)phenyl)isonicotinic acid (1 g, 3.06 mmol, 1.00 equiv) in dichloromethane (20 mL), EDC.HCl (970 mg, 5.05 mmol, 1.65 equiv), 4-dimethylaminopyridine (620 mg, 5.08 mmol, 1.66 equiv), and (3-(trifluoromethyl)phenyl)methanamine (590 mg, 3.37 mmol, 1.10 equiv). The resulting solution was stirred overnight at 25° C. in an oil bath. The reaction progress was monitored by LCMS. The mixture was concentrated under vacuum. The residue was applied onto a silica gel column and eluted with petroleum ether/ethyl acetate (10:1~3:1). This resulted in 800 mg (51%) of N-(3-(trifluoromethyl)benzyl)-2-(2-nitro-5-(piperidin-1-yl)phenyl)isonicotinamide as a yellow solid.

Intermediate 4.1c: N-(3-(trifluoromethyl)benzyl)-2-(2-amino-5-(piperidin-1-yl)phenyl)-isonicotinamide Into a 250 mL round bottom flask, was placed a solution of 1-(2-(2-nitro-5-(piperidin-1-yl)phenyl)pyridin-4-yl)ethanone (1 g, 2.07 mmol, 1.00 equiv) in methanol/ethyl acetate (3:2) (35 mL). The mixture was treated with Pd/C (10%) (1 g) and stirred under a hydrogen atmosphere for 1.5 h at room temperature. The solids were filtered out. The resulting mixture was concentrated under vacuum. This resulted in 0.9 g (96%) of N-(3-(trifluoromethyl)benzyl)-2-(2-amino-5-(piperidin-1-yl)phenyl)isonicotinamide as a yellow solid.

Intermediate 4.1d: 3-((2-(4-((3-(trifluoromethyl) benzyl)carbamoyl)pyridin-2-yl)-4-(piperidin-1-yl) phenyl)carbamoyl)benzoate Into a 50-mL round bottom flask, was placed a solution of N-(3-(trifluoromethyl)benzyl)-2-(2-amino-5-(piperidin-1-yl)phenyl)-isonicotinamide (300 mg, 0.66 mmol, 1.00 equiv) in dichloromethane (15 mL), EDC.HCl (153 mg, 0.80 mmol, 1.21 equiv), 4-dimethylaminopyridine (96.75 mg, 0.79 mmol, 1.20 equiv), and 3-(methoxycarbonyl)benzoic acid (130.8 mg, 0.73 mmol, 1.10 equiv). The resulting solution was stirred overnight at 25° C. in an oil bath. The reaction progress was monitored by LCMS. The resulting solution was diluted with 50 mL of dichloromethane. The resulting mixture was washed with 2×50 mL of NH$_4$Cl aq. and 1×50 mL of brine. The resulting mixture was concentrated under vacuum. The residue was applied onto a silica gel column and eluted with petroleum ether/ethyl acetate (3:1~2:1). This resulted in 360 mg (88%) of methyl 3-((2-(4-((3-(trifluoromethyl)benzyl)carbamoyl)pyridin-2-yl)-4-(piperidin-1-yl) phenyl)carbamoyl)benzoate as a yellow solid.

Intermediate 4.1e: 3-((2-(4-((3-(trifluoromethyl)benzyl)carbamoyl)pyridin-2-yl)-4-(piperidin-1-yl)phenyl)carbamoyl)benzoic acid Into a 50-mL round-bottom flask, was placed a solution of methyl 3-((2-(4-((3-(trifluoromethyl)benzyl)carbamoyl)pyridin-2-yl)-4-(piperidin-1-yl)phenyl)carbamoyl)benzoate (360 mg, 0.58 mmol, 1.00 equiv) in tetrahydrofuran/water (2:3) (35 mL), and lithium hydroxide hydrate (251.2 mg, 5.98 mmol, 10.25 equiv). The resulting solution was stirred overnight at 25° C. in an oil bath. The reaction progress was monitored by LCMS. The resulting mixture was concentrated under vacuum. The resulting solution was diluted with 50 mL of water adjusted to pH 2-3 with hydrogen chloride (2 mol/L). The resulting solution was extracted with 3×50 mL of ethyl acetate and the organic layers combined. The mixture was dried over anhydrous sodium sulfate and concentrated under vacuum. This resulted in 325 mg (92%) of 3-((2-(4-((3-(trifluoromethyl)benzyl)carbamoyl)pyridin-2-yl)-4-(piperidin-1-yl)phenyl)carbamoyl)-benzoic acid as a yellow oil.

Example 4.1

N1-(2-(diethylamino)ethyl)-N1-methyl-N3-(4-(piperidin-1-yl)-2-(4-((3-(trifluoromethyl)benzyl)carbamoyl)pyridin-2-yl)phenyl)isophthalamide Into a 10-mL round bottom flask, was placed a solution of 3-((2-(4-((3-(trifluoromethyl)benzyl)carbamoyl)pyridin-2-yl)-4-(piperidin-1-yl)phenyl)carbamoyl)-benzoic acid (100 mg, 0.17 mmol, 1.00 equiv) in dichloromethane (5 mL), EDC.HCl (63.75 mg, 0.33 mmol, 2.00 equiv), 4-dimethylaminopyridine (40.5 mg, 0.33 mmol, 2.00 equiv), N1,N1-diethyl-N2-methylethane-1,2-diamine (64.8 mg, 0.56 mmol, 3.00 equiv). The resulting solution was stirred overnight at 25° C. in an oil bath. The reaction progress was monitored by LCMS. The resulting solution was diluted with 50 mL of dichloromethane. The resulting mixture was washed with 3×70 mL of NH$_4$Cl (aq). The mixture was dried over anhydrous sodium sulfate and concentrated under vacuum. The crude product (150 mg) was purified by reverse phase HPLC eluting with a water/CH$_3$CN gradient containing 0.05% TFA. The product was obtained as 47.8 mg (34%) of a yellow solid. $^1$H-NMR (300 MHz, DMSO-d$_6$, ppm): δ 12.36 (s, 1H), 9.57 (t, 1H), 9.28 (s, 1H), 8.90 (d, J=5.1 Hz, 1H), 8.30 (m, 2H), 7.98 (d, J=7.2 Hz, 2H), 7.84 (d, J=4.8 Hz, 1H), 7.65 (m, 7H), 7.28 (d, J=8.4 Hz, 1H), 4.66 (d, J=6.0 Hz, 2H), 3.82 (m, 2H), 3.31 (m, 9H), 2.97 (s, 4H), 1.71 (m, 6H), 1.24 (m, 6H). MS (ES, m/z): 715 [M+H]$^+$.

Example 4.2

N1-(2-(4-((3-(Trifluoromethyl)benzyl)carbamoyl) pyridin-2-yl)-4-(piperidin-1-yl)phenyl)-N3-(3-(2-methoxyethylamino)-3-oxopropyl)-N3-methylisophthalamide

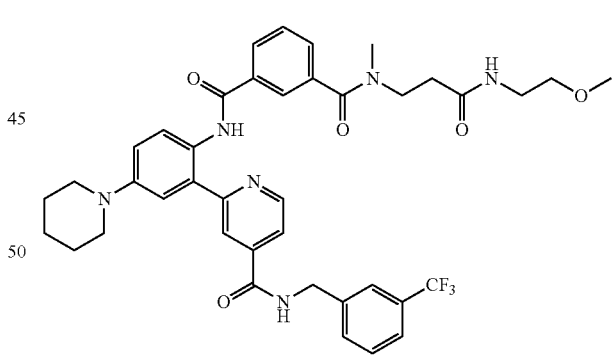

Into a 10-mL vial, was placed a solution of 3-((2-(4-((3-(trifluoromethyl)benzyl)carbamoyl)pyridin-2-yl)-4-(piperidin-1-yl)phenyl)carbamoyl)-benzoic acid 4.1e (80 mg, 0.13 mmol, 1.00 equiv) in dichloromethane (5 mL), EDC.HCl (51.1 mg, 0.27 mmol), 4-dimethylaminopyridine (32.4 mg, 0.27 mmol, 2.00 equiv), and N-(2-methoxyethyl)-3-(methylamino)propanamide (31.2 mg, 0.20 mmol, 1.47 equiv). The resulting solution was stirred for 6 h at 25° C. in an oil bath. The reaction progress was monitored by LCMS. The resulting solution was diluted with 50 mL of dichloromethane. The resulting mixture was washed with 3×70 mL of NH$_4$Cl. The mixture was dried over sodium sulfate and concentrated under vacuum. The crude product (100 mg) was purified by reverse phase HPLC eluting with a water/CH$_3$CN gradient containing 0.05% TFA. This yielded 50.4 mg (44%) of N1-(2-(4-((3-(trifluoromethyl)benzyl)carbamoyl)pyridin-2-yl)-4-(piperidin-1-yl)phenyl)-N3-(3-(2-methoxyethylamino)-3-oxopropyl)-N3-methylisophthalamide as a yellow solid. $^1$H-NMR (300 MHz, DMSO-d$_6$+D$_2$O, ppm) δ 8.89 (d, J=5.1 Hz, 1H), 8.43 (t, 1H), 8.31 (s, 1H), 7.94 (t, J=9.3 Hz, 4H), 7.83 (m, 7H), 4.58 (s, 2H), 3.32-3.65 (m, 7H), 3.07-3.17 (m, 6H), 2.85-2.95 (m, 3H), 2.31 (s, 2H), 1.63-1.85 (m, 6H). MS (ES, m/z): 745 [M+H]$^+$.

Example 4.3

N1-(2-(2-Hydroxyethoxy)ethyl)-N1-methyl-N3-(4-(piperidin-1-yl)-2-(4-((3-(trifluoromethyl)benzyl)carbamoyl)pyridin-2-yl)phenyl)isophthalamide

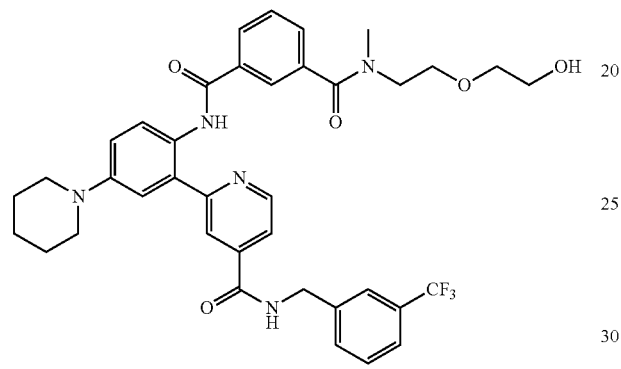

This compound was prepared from 3-((2-(4-((3-(trifluoromethyl)benzyl)carbamoyl)pyridin-2-yl)-4-(piperidin-1-yl)phenyl)carbamoyl)-benzoic acid 4.1e using the procedure described for the preparation of N1-(2-(4-((3-(trifluoromethyl)benzyl)carbamoyl)pyridin-2-yl)-4-(piperidin-1-yl)phenyl)-N3-(3-(2-methoxyethylamino)-3-oxopropyl)-N3-methylisophthalamide 4.2. 2-(2-(Methylamino)-ethoxy)ethanol was used as the amine component in this coupling. $^1$H-NMR: (300 MHz, DMSO-d$_6$+D$_2$O, ppm): δ 9.58 (s, 1H), 8.91 (d, J=5.1 Hz, 1H), 8.46 (d, J=9 Hz, 1H), 8.36 (s, 1H), 7.87-7.96 (m, 4H), 7.545-7.689 (m, 7H), 4.61 (s, 2H), 3.29-3.49 (m, 12H), 2.97 (d, J=21.9 Hz, 3H), 1.84 (s, 4H), 1.68 (s, 2H). MS (ES, m/z): 704 [M+H]$^+$.

Example 4.4

N1-(2-Morpholinoethyl)-N3-(4-(piperidin-1-yl)-2-(4-((3-(trifluoromethyl)benzyl)carbamoyl)pyridin-2-yl)phenyl)isophthalamide

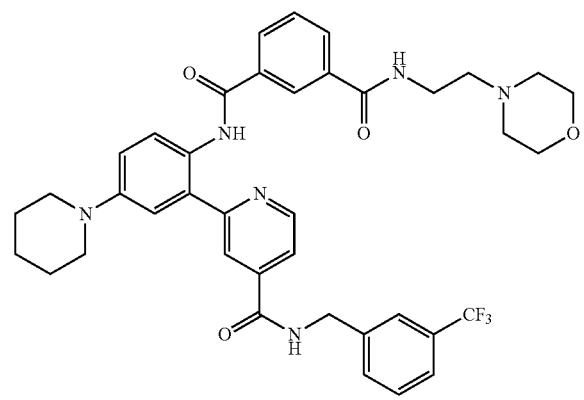 [SMILES: O=C(NCCN1CCOCC1)c1cccc(C(=O)Nc2ccc(N3CCCCC3)cc2-c2cc(C(=O)NCc3cccc(C(F)(F)F)c3)ccn2)c1]

This compound was prepared from 3-((2-(4-((3-(trifluoromethyl)benzyl)carbamoyl)pyridin-2-yl)-4-(piperidin-1-yl)phenyl)carbamoyl)-benzoic acid 4.1e using the procedure described for the preparation of N1-(2-(4-((3-(trifluoromethyl)benzyl)carbamoyl)pyridin-2-yl)-4-(piperidin-1-yl)phenyl)-N3-(3-(2-methoxyethylamino)-3-oxopropyl)-N3-methylisophthalamide 4.2. 2-Morpholinoethanamine was used as the amine component in this coupling. $^1$H-NMR (300 MHz, DMSO-d$_6$, ppm) δ 12.60 (s, 1H), 9.68 (s, 1H), 9.57 (t, 1H), 9.00 (d, J=5.1 Hz, 1H), 8.95 (t, 1H), 8.50 (s, 1H), 8.36 (s, 2H), 8.09 (t, 2H), 7.85 (d, J=5.1 Hz, 1H), 7.64 (m, 6H), 7.28 (s, 1H), 4.63 (d, J=6.0 Hz, 2H), 4.02 (m, 4H), 3.69 (m, 6H), 3.43 (m, 8H), 1.65 (m, 6H). MS (ES, m/z): 715 [M+H]$^+$.

Example 4.5

Tert-butyl 4-(2-(N-methyl-3-((4-(piperidin-1-yl)-2-(4-((3-(trifluoromethyl)benzyl)carbamoyl)pyridin-2-yl)phenyl)carbamoyl)benzamido)ethyl)piperazine-1-carboxylate

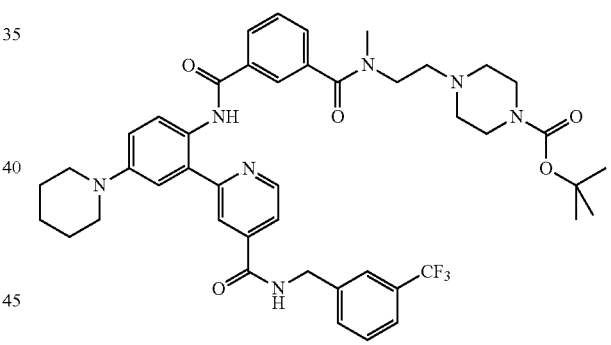

This compound was prepared from 3-((2-(4-((3-(trifluoromethyl)benzyl)carbamoyl)pyridin-2-yl)-4-(piperidin-1-yl)phenyl)carbamoyl)-benzoic acid 4.1e using the procedure described for the preparation of N1-(2-(4-((3-(trifluoromethyl)benzyl)carbamoyl)pyridin-2-yl)-4-(piperidin-1-yl)phenyl)-N3-(3-(2-methoxyethylamino)-3-oxopropyl)-N3-methylisophthalamide 4.2. Tert-Butyl 4-(2-(methylamino)ethyl)piperazine-1-carboxylate was used as the amine component in this coupling. $^1$H-NMR (300 MHz, CD$_3$OD, ppm): δ 8.98 (d, J=5.1 Hz, 1H), 8.75 (d, J=9.0 Hz, 1H), 8.46 (s, 1H), 8.18~8.11 (m, 3H), 7.89~7.53 (m, 8H), 4.72 (s, 2H), 4.00~3.11 (m, 16H), 3.08 (s, 3H), 2.04 (d, J=4.8 Hz, 4H), 1.83 (d, J=5.7 Hz, 2H), 1.49 (s, 9H). MS (ES, m/z): 828 [M+H]$^+$.

Example 4.6

2-(2-(3-(4-Acetylpiperazine-1-carbonyl)benzamido)-5-(piperidin-1-yl)phenyl)-N-(3-(trifluoromethyl)benzyl)isonicotinamide

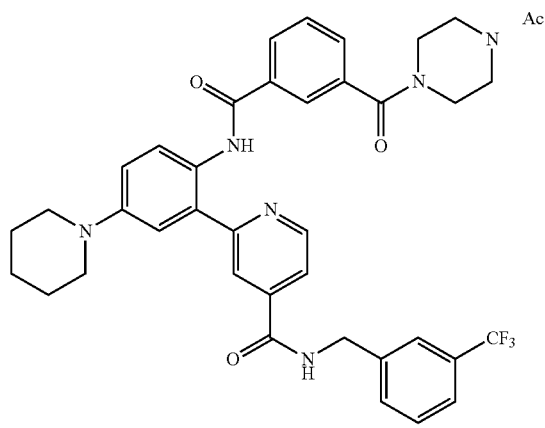 [SMILES: O=C(NCc1cccc(C(F)(F)F)c1)c1ccnc(-c2cc(N3CCCCC3)ccc2NC(=O)c2cccc(C(=O)N3CCNCC3)c2)c1 ; "Ac"]

This compound was prepared from 3-((2-(4-((3-(trifluoromethyl)benzyl)carbamoyl)pyridin-2-yl)-4-(piperidin-1-yl)phenyl)carbamoyl)-benzoic acid 4.1e using the procedure described for the preparation of N1-(2-(4-((3-(trifluoromethyl)benzyl)carbamoyl)pyridin-2-yl)-4-(piperidin-1-yl)phenyl)-N3-(3-(2-methoxyethylamino)-3-oxopropyl)-N3-methylisophthalamide 4.2. N-Acetylpiperazine was used as the amine component in this coupling. $^1$H-NMR (400 MHz, DMSO-d$_6$, ppm): δ 12.48 (s, 1H), 9.57 (m, 1H), 8.93 (d, J=5.2 Hz, 1H), 8.39 (d, J=11.2 Hz, 2H), 7.99~7.46 (m, 11H), 4.63 (d, J=6.0 Hz, 2H), 3.55~3.42 (m, 12H), 2.21 (s, 3H), 1.79 (s, 4H), 1.62 (s, 2H). MS (ES, m/z): 713 [M+H]$^+$.

Example 4.7

2-(2-(3-(4-Acetamidopiperidine-1-carbonyl)benzamido)-5-(piperidin-1-yl)phenyl)-N-(3-(trifluoromethyl)benzyl)isonicotinamide

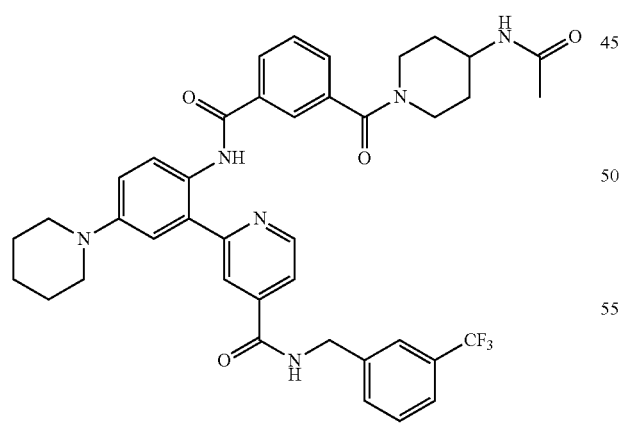

This compound was prepared from 3-((2-(4-((3-(trifluoromethyl)benzyl)carbamoyl)pyridin-2-yl)-4-(piperidin-1-yl)phenyl)carbamoyl)benzoic acid 4.1e using the procedure described for the preparation of N1-(2-(4-((3-(trifluoromethyl)benzyl)carbamoyl)pyridin-2-yl)-4-(piperidin-1-yl)phenyl)-N3-(3-(2-methoxyethylamino)-3-oxopropyl)-N3-methylisophthalamide 4.2. N-(piperidin-4-yl)acetamide was used as the amine component in this coupling. $^1$H-NMR (300 MHz, CD$_3$OD, ppm): δ 8.98 (d, J=3.5 Hz, 1H), 8.85 (d, J=9.0 Hz, 1H), 8.47 (s, 1H), 8.24 (d, J=2.4 Hz, 1H), 8.12~8.09 (m, 2H), 7.90~7.88 (m, 1H), 7.77~7.68 (m, 5H), 6.62~7.55 (m, 2H), 4.72 (s, 2H), 4.58 (s, 1H), 3.99~3.93 (m, 1H), 3.73~3.70 (m, 5H), 3.27~3.12 (m, 2H), 2.09~2.02 (m, 5H), 1.94 (s, 3H), 1.85 (d, J=4.8 Hz, 1H), 1.60~1.35 (m, 2H). MS (ES, m/z): 727 [M+H]$^+$.

Example 4.8

N1-Ethyl-N1-(2-morpholinoethyl)-N3-(4-(piperidin-1-yl)-2-(4-((3-(trifluoromethyl)benzyl)carbamoyl)pyridin-2-yl)phenyl)isophthalamide

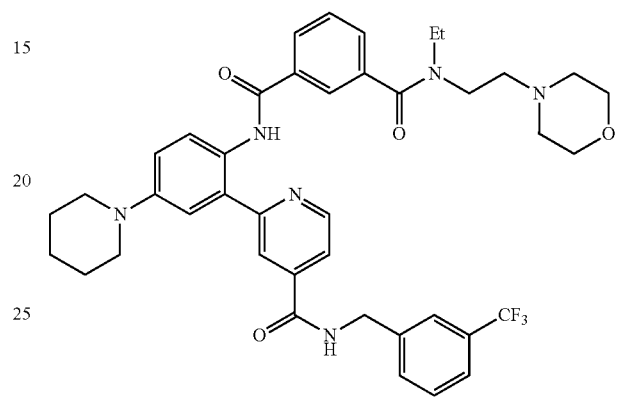

To a mixture of 25 mg of 3-((4-(piperidin-1-yl)-2-(4-((3-(trifluoromethyl)benzyl)carbamoyl)pyridin-2-yl)phenyl)carbamoyl)benzoic acid 4.1e, 17 mg of diisopropylethylamine and 9 mg of N-ethyl-2-morpholinoethanamine in 1 mL of DMF was added 17 mg of HATU. The mixture was stirred at 25° C. for 1 h. The solution was injected onto a preparative reverse phase HPLC and the product was eluted with 0.5% TFA in a gradient of water and acetonitrile. The yield was 11.2 mg of product. $^1$H-NMR (400 MHz, DMSO-d$_6$, ppm) δ 12.46 (s, 1H), 9.90 (s, 1H), 9.57 (t, J=6.1 Hz, 1H), 8.90 (d, J=5.1 Hz, 1H), 8.36, (s, 2H), 8.03-7.92 (m, 2H), 7.87 (dd, J=5.1, 1.3 Hz, 1H), 7.75-7.53 (m, 26H), 7.39 (s, 1H), 4.63 (d, J=5.8 Hz, 2H), 4.03 (s, 2H), 3.82 (s, 2H), 3.60 (s, 4H), 3.40 (d, J=23.1 Hz, 6H), 3.24 (s, 4H), 1.77 (s, 4H), 1.61 (s, 2H), 1.08 (t, J=6.5 Hz, 10H). MS (ES, m/z): 743 [M+H]$^+$.

Example 4.9

(S)-2-(2-(3-(3-Acetamidopyrrolidine-1-carbonyl)benzamido)-5-(piperidin-1-yl)phenyl)-N-(3-(trifluoromethyl)benzyl)isonicotinamide

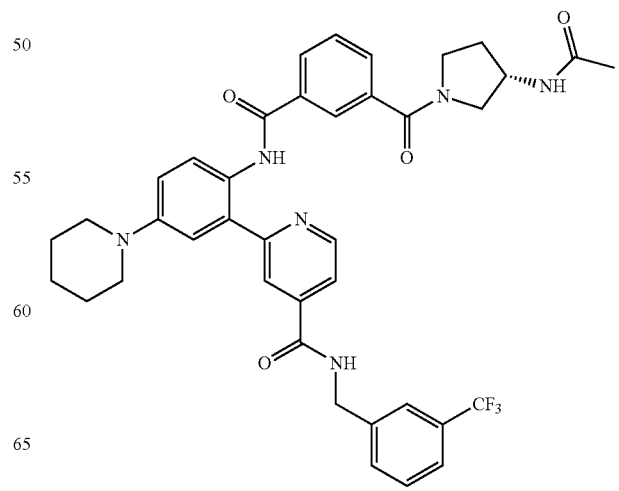

This compound was prepared from 3-((2-(4-((3-(trifluoromethyl)benzyl)carbamoyl)pyridin-2-yl)-4-(piperidin-1-yl)phenyl)carbamoyl)benzoic acid 4.1e using the procedure described for the preparation of N1-methyl-N1-(2-morpholinoethyl)-N3-(4-(piperidin-1-yl)-2-(4-((3-(trifluoromethyl)benzyl)carbamoyl)pyridin-2-yl)phenyl)isophthalamide 4.8, except that CH₃CN was substituted for DMF as the reaction solvent and (S)—N-(pyrrolidin-3-yl)acetamide was used as the amine component. ¹H-NMR (300 MHz, CD₃OD, ppm): δ 8.88 (d, J=3.5 Hz, 1H), 8.69~8.663 (m, 1H), 8.33 (s, 1H), 8.10~8.05 (m, 2H), 8.00~7.97 (m, 1H), 7.76 (d, J=5.2 Hz, 1H), 7.71~7.66 (m, 1H), 7.60~7.43 (m, 6H), 4.60 (s, 2H), 4.40~4.16 (m, 1H), 3.71~3.21 (m, 8H), 2.22~1.71 (m, 11H). MS (ES, m/z): 713 [M+H]⁺.

Example 4.10

(S)-2-(2-(3-(3-Acetamidopyrrolidine-1-carbonyl)benzamido)-5-(piperidin-1-yl)phenyl)-N-(3-(trifluoromethyl)benzyl)isonicotinamide

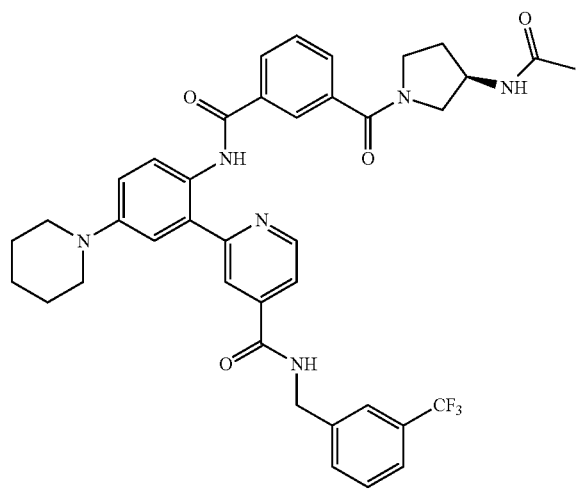 [SMILES: CC(=O)N[C@@H]1CCN(C(=O)c2cccc(C(=O)Nc3ccc(N4CCCCC4)cc3-c3cc(C(=O)NCc4cccc(C(F)(F)F)c4)ccn3)c2)C1]

This compound was prepared from 3-((2-(4-((3-(trifluoromethyl)benzyl)carbamoyl)pyridin-2-yl)-4-(piperidin-1-yl)phenyl)carbamoyl)-benzoic acid 4.1e using the procedure described for the preparation of N1-methyl-N1-(2-morpholinoethyl)-N3-(4-(piperidin-1-yl)-2-(4-((3-(trifluoromethyl)benzyl)carbamoyl)-pyridin-2-yl)phenyl)isophthalamide 4.8, except that CH₃CN was substituted for DMF as the reaction solvent and (R)—N-(pyrrolidin-3-yl)acetamide was used as the amine component. ¹H-NMR (300 MHz, CD₃OD, ppm): δ 8.99 (d, J=6.0 Hz, 1H), 8.70 (d, J=9.6 Hz, 1H), 8.41 (s, 1H), 8.21 (d, J=6.0 Hz, 1H), 8.12 (d, J=7.8 Hz, 1H), 8.01 (s, 1H), 7.88~7.78 (m, 2H), 7.72~7.54 (m, 6H), 4.72 (s, 1H), 4.51~4.28 (m, 1H), 3.91~3.52 (m, 8H), 2.30~4.79 (m, 11H). MS (ES, m/z): 713 [M+H]⁺.

Example 4.11

N1-Cyclopropyl-N1-(2-morpholinoethyl)-N3-(4-(piperidin-1-yl)-2-(4-((3-(trifluoromethyl)benzyl)carbamoyl)pyridin-2-yl)phenyl)isophthalamide

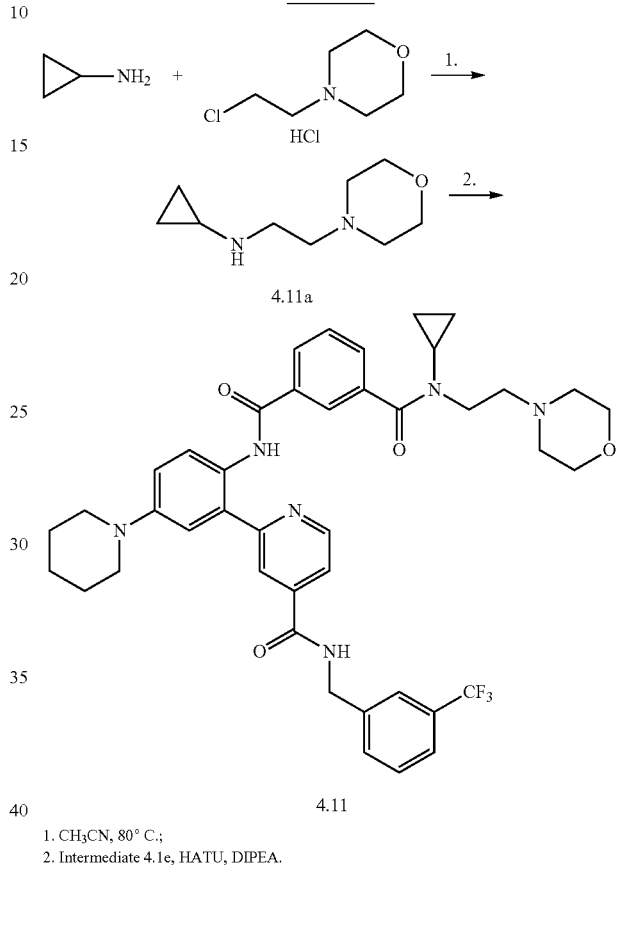

1. CH₃CN, 80° C.;
2. Intermediate 4.1e, HATU, DIPEA.

Intermediate 4.11a:
N-(2-morpholinoethyl)cyclopropanamine, hydrochloride salt A solution of 100 mg of N-(2-chloroethyl)morpholine and 307 mg of cyclopropylamine in 5 mL of CH₃CN was refluxed for 2 h. The mixture was cooled to 25° C. and treated with excess K₂CO₃. After stirring for 1 h the suspension was filtered and the solvent was evaporated. The residual solvent was removed at high vacuum and the residue was dissolved in a large excess of methanolic HCl. The solvent was evaporated to give 102 mg of the product.

Example 4.11

N1-cyclopropyl-N1-(2-morpholinoethyl)-N3-(4-(piperidin-1-yl)-2-(4-((3-(trifluoromethyl)benzyl)carbamoyl)pyridin-2-yl)phenyl)isophthalamide This compound was prepared from 3-((2-(4-((3-(trifluoromethyl)benzyl)carbamoyl)pyridin-2-yl)-4-(piperidin-1- yl)phenyl)carbamoyl)benzoic acid 4.1e using the procedure described for the preparation of N1-methyl-N1-(2-morpholinoethyl)-N3-(4-(piperidin-1-yl)-2-(4-((3-(trifluoromethyl)benzyl)carbamoyl)pyridin-2-yl)phenyl)isophthalamide 4.8. N-(2-morpholinoethyl)cyclopropanamine hydrochloride was used as the amine component in this coupling. MS (ES, m/z): 755 [M+H]$^+$

Example 4.12

N1-Benzyl-N1-(2-morpholinoethyl)-N3-(4-(piperidin-1-yl)-2-(4-((3-(trifluoromethyl)benzyl)carbamoyl)pyridin-2-yl)phenyl)isophthalamide

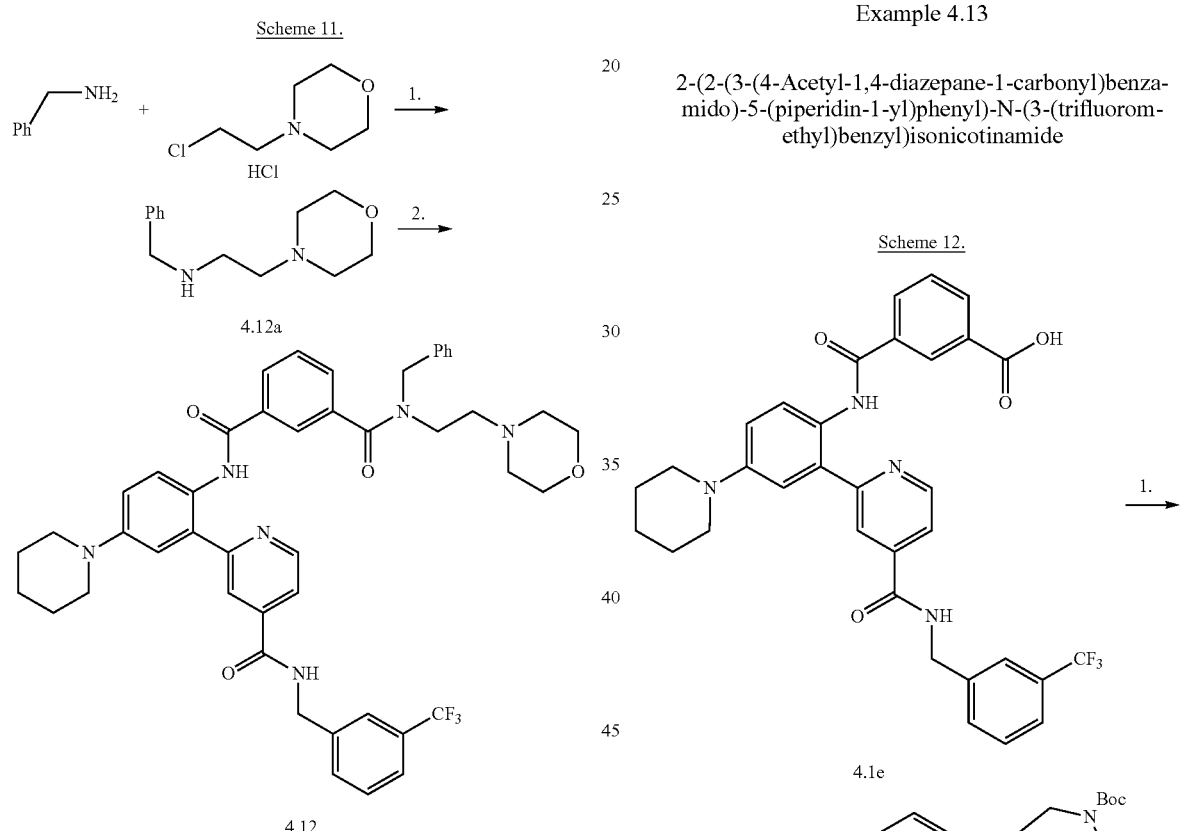

1. CH$_3$CN, 80° C.;
2. Intermediate 4.1e, HATU, DIPEA.

Intermediate 4.12a:
N-benzyl-2-morpholinoethanamine, hydrochloride salt

A solution of 100 mg of N-(2-chloroethyl)morpholine and 575 mg of benzylamine in 5 mL of CH$_3$CN was refluxed for 2 h. The mixture was cooled to 25° C. and partitioned between dichloromethane and an aqueous sodium bicarbonate solution. The organic extracts were dried and the solvent was evaporated. The residual solvent was removed at high vacuum and the residue was dissolved in a large excess of methanolic HCl. The solvent was evaporated to give 60 mg of the product.

Example 4.12

N1-benzyl-N1-(2-morpholinoethyl)-N3-(4-(piperidin-1-yl)-2-(4-((3-(trifluoromethyl)benzyl)carbamoyl)pyridin-2-yl)phenyl)isophthalamide This compound was prepared from 3-((2-(4-((3-(trifluoromethyl)benzyl)carbamoyl)pyridin-2-yl)-4-(piperidin-1-yl)phenyl)carbamoyl)benzoic acid 4.1e using the procedure described for the preparation of N1-methyl-N1-(2-morpholinoethyl)-N3-(4-(piperidin-1-yl)-2-(4-((3-(trifluoromethyl)benzyl)carbamoyl)pyridin-2-yl)phenyl)isophthalamide 4.8. N-benzyl-2-morpholinoethanamine was used as the amine component in this coupling. MS (ES, m/z): 805 [M+H]$^+$

Example 4.13

2-(2-(3-(4-Acetyl-1,4-diazepane-1-carbonyl)benzamido)-5-(piperidin-1-yl)phenyl)-N-(3-(trifluoromethyl)benzyl)isonicotinamide

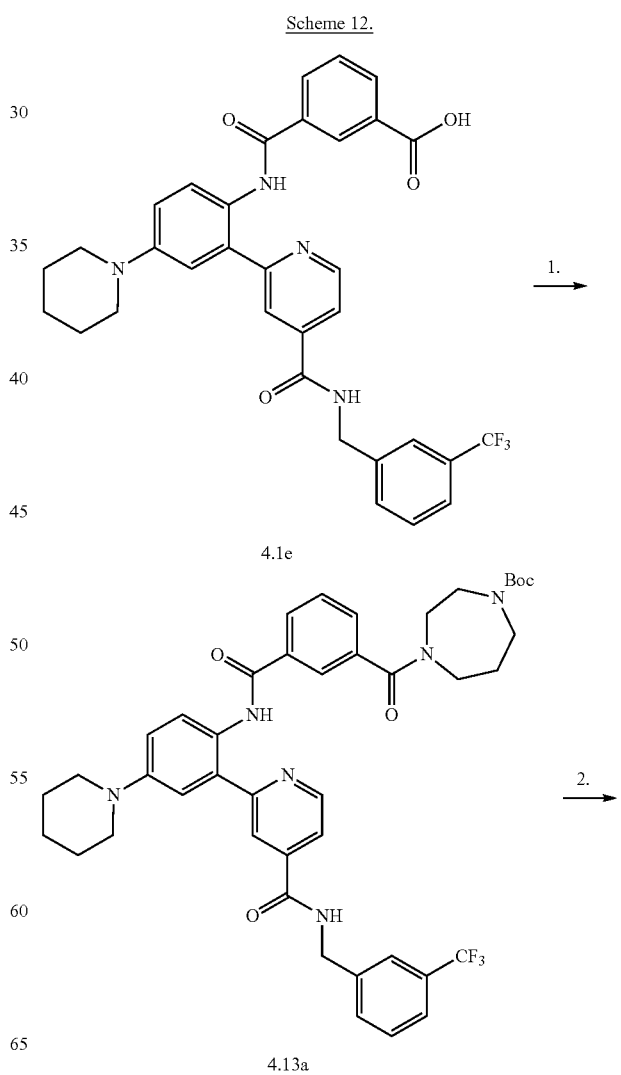

81

-continued

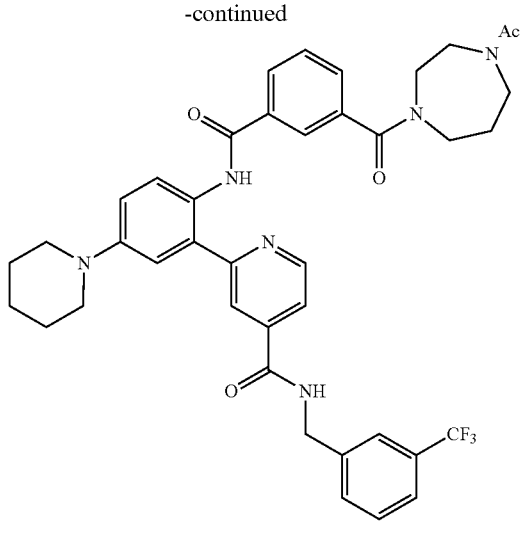

4.13

1. tert-butyl 1,4-diazepane-1-carboxylate, EDC•HCl, DMAP; 2. TFA, then AcCl.

Intermediate 4.13a: tert-butyl 4-(3-((4-(piperidin-1-yl)-2-(4-((3-(trifluoromethyl)benzyl)-carbamoyl)pyridin-2-yl)phenyl)carbamoyl)benzoyl)-1,4-diazepane-1-carboxylate This compound was prepared from 3-((2-(4-((3-(trifluoromethyl)benzyl)carbamoyl)pyridin-2-yl)-4-(piperidin-1-yl)phenyl)carbamoyl)benzoic acid 4.1e and tert-butyl 1,4-diazepane-1-carboxylate using the procedure used to prepare N1-(2-(diethylamino)ethyl)-N1-methyl-N3-(4-(piperidin-1-yl)-2-(4-((3-(trifluoromethyl)benzyl)carbamoyl)pyridin-2-yl)phenyl)-isophthalamide 4.1.

Example 4.13

2-(2-(3-(4-acetyl-1,4-diazepane-1-carbonyl)benzamido)-5-(piperidin-1-yl)phenyl-N-(3-(trifluoromethyl)benzyl)isonicotinamide The Boc protecting group was removed from 2-(2-(3-(4-acetyl-1,4-diazepane-1-carbonyl)benzamido)-5-(piperidin-1-yl)phenyl)-N-(3-(trifluoromethyl)benzyl)isonicotinamide by treatment with a 1:1 solution of dichloromethane and TFA. The product was acylated using acetyl chloride and pyridine in dichloromethane as solvent under standard conditions. $^1$H-NMR (300 MHz, CDCl$_3$, ppm): δ 14.26 (s, 1H), 9.55 (s, 1H), 9.31 (s, 1H), 9.15 (d, J=8.4 Hz, 1H), 8.94 (s, 1H), 8.87 (d, J=4.8 Hz, 1H), 8.14~8.06 (m, 3H), 7.73 (s, 1H), 7.68~7.60 (m, 3H), 7.52~7.41 (m, 3H), 4.76 (d, J=5.7 Hz, 2H), 3.93~3.47 (m, 10H), 2.19~2.13 (m, 10H), 1.73 (s, 3H). MS (ES, m/z): 727 [M+H]$^+$.

82

Example 4.14

(S)-2-(2-(3-(3-((2-Methoxyethyl)carbamoyl)piperidine-1-carbonyl)benzamido)-5-(piperidin-1-yl)phenyl)-N-(3-(trifluoromethyl)benzyl)isonicotinamide Scheme 13.

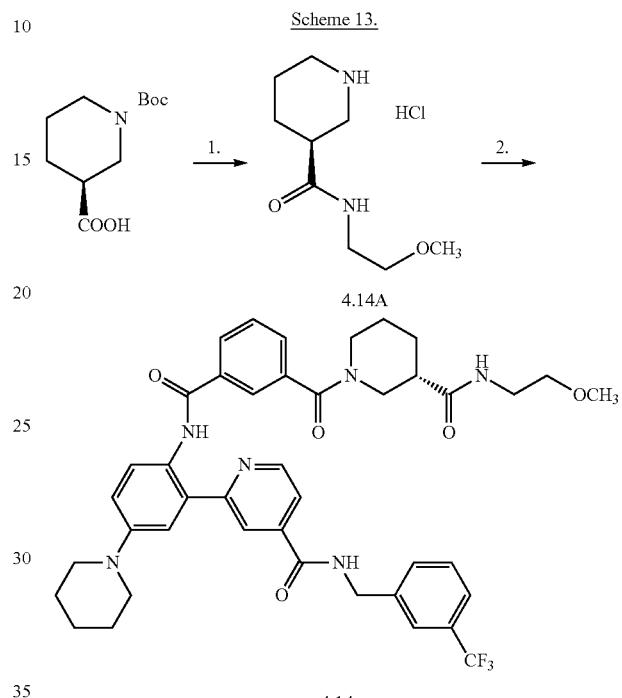

4.14

1. EDC•HCl, triethylamine, HOBt, then HCl;
2. HATU, diisopropylethylamine, intermediate 4.1e.

Intermediate 4.14a: (S)—N-(2-methoxyethyl)piperidine-3-carboxamide

A 0° C. solution of 500 mg of (S)-1-(tert-butoxycarbonyl)piperidine-3-carboxylic acid, 328 mg of 2-methoxyethylamine, 736 mg of HOBt, and 1.82 mL of triethylamine in 9 mL of dichloromethane was treated with 836 mg of EDC.HCl. The mixture was stirred at 25° C. overnight and the solvent was evaporated at reduced pressure. The residue was dissolved in ethyl acetate, and the solution was sequentially washed with water, an aqueous solution of citric acid, an aqueous sodium bicarbonate solution, and brine. The solution was dried (Na$_2$SO$_4$) and the solvent was evaporated. The residue was dissolved in a 4 M solution of HCl in dioxane. After 1 h the mixture was evaporated to give 406 mg of the product.

Example 4.14

(S)-2-(2-(3-(3-((2-methoxyethyl)carbamoyl)piperidine-1-carbonyl)-benzamido)-5-(piperidin-1-yl)phenyl)-N-(3-(trifluoromethyl)benzyl)isonicotinamide A solution of 31.4 mg of 3-((2-(4-((3-(trifluoromethyl)benzyl)carbamoyl)pyridin-2-yl)-4-(piperidin-1-yl)phenyl)

carbamoyl)benzoic acid 4.1e, 31.1 mg of intermediate 4.14a, 68 μL, of diisopropylethylamine, and 22.4 mg of HATU in 150 μL of DMF was stirred for 2 h. The product was isolated by reverse phase chromatography. MS (ES, m/z): 771.8 [M+H]+

Example 4.15

(R)-2-(2-(3-(3-((2-Methoxyethyl)carbamoyl)piperidine-1-carbonyl)benzamido)-5-(piperidin-1-yl)phenyl)-N-(3-(trifluoromethyl)benzyl)isonicotinamide

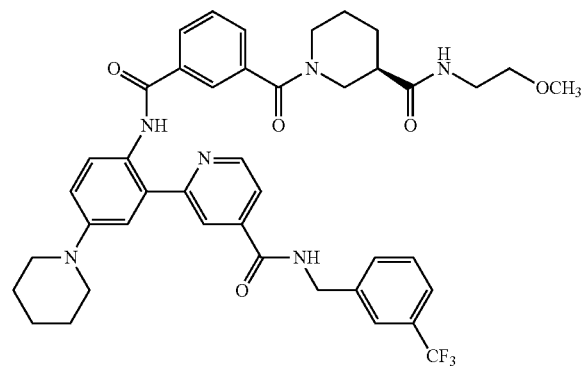 [SMILES: COCCNC(=O)[C@@H]1CCCN(C(=O)c2cccc(C(=O)Nc3ccc(N4CCCCC4)cc3-c3cc(C(=O)NCc4cccc(C(F)(F)F)c4)ccn3)c2)C1]

This compound was prepared using the methods described in Example 4.14. MS (ES, m/z): 771.8 [M+H]+

Example 4.16

2-(2-(3-(((3-((2-Morpholinoethyl)amino)-3-oxopropyl)thio)methyl)benzamido)-5-(piperidin-1-yl)phenyl)-N-(3-(trifluoromethyl)benzyl)isonicotinamide

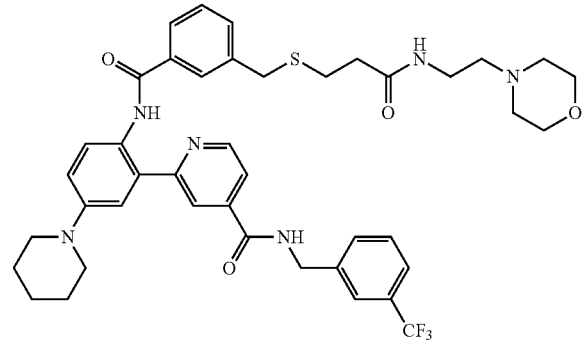 [SMILES: O=C(CCSCc1cccc(C(=O)Nc2ccc(N3CCCCC3)cc2-c2cc(C(=O)NCc3cccc(C(F)(F)F)c3)ccn2)c1)NCCN1CCOCC1]

A solution of 25 mg of 3-(3-((2-(4-((3-(trifluoromethyl)benzyl)carbamoyl)pyridin-2-yl)-4-(piperidin-1-yl)phenyl)carbamoyl)benzylthio)propanoic acid 1.1, 19 mg of diisopropylethylamine, and 6 mg of 2-morpholinoethylamine in 1 mL of DMF was treated with 15 mg of HATU and stirred for 24 h. The product was isolated by reverse phase HPLC eluting with 0.05% TFA in a water/acetonitrile gradient to give 11.3 mg of product. MS (ES, m/z): 789 [M+H]+

Example 4.17

2-(2-(3-(((3-((2-Methoxyethyl)amino)-3-oxopropyl)thio)methyl)benzamido)-5-(piperidin-1-yl)phenyl)-N-(3-(trifluoromethyl)benzyl)isonicotinamide

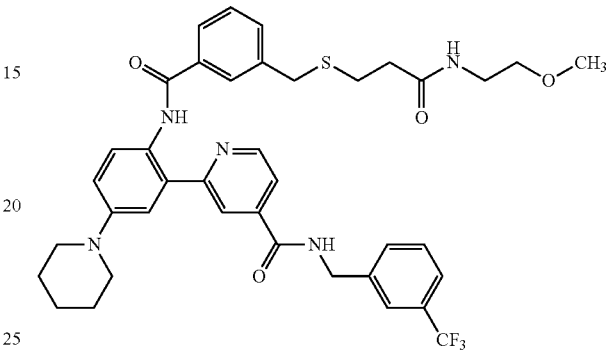

This compound was prepared using the procedure described for the preparation of 2-(2-(3-(((3-((2-morpholinoethyl)amino)-3-oxopropyl)thio)methyl)benzamido)-5-(piperidin-1-yl)-phenyl)-N-(3-(trifluoromethyl)benzyl)isonicotinamide 4.16, using 2-methoxyethylamine in place of 2-morpholinoethylamine. MS (ES, m/z): 734 [M+H]+

Example 4.18

2-(3-((3-((4-(Piperidin-1-yl)-2-(4-((3-(trifluoromethyl)benzyl)carbamoyl)pyridin-2-yl)phenyl)carbamoyl)benzyl)thio)propanamido)acetic acid

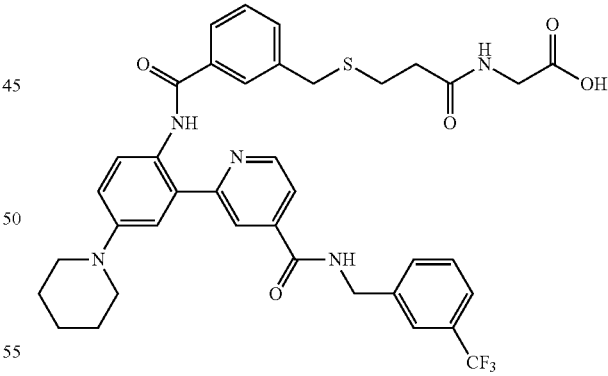

Tert-butyl glycinate was coupled to 3-(3-((2-(4-((3-(trifluoromethyl)benzyl)carbamoyl)pyridin-2-yl)-4-(piperidin-1-yl)phenyl)carbamoyl)-benzylthio)propanoic acid 1.1 using the procedure described for the synthesis of 2-(2-(3-(((3-((2-morpholinoethyl)amino)-3-oxopropyl)thio)methyl)benzamido)-5-(piperidin-1-yl)-phenyl)-N-(3-(trifluoromethyl)benzyl)isonicotinamide 4.16. This material was dissolved in 2 mL of 1:1 dichloromethane/TFA and stirred for 1 h. The solvent was evaporated to give 4.6 mg of product. MS (ES, m/z): 734 [M+H]+

Example 4.19

2-(2-(3-(29-Hydroxy-5-oxo-9,12,15,18,21,24,27-heptaoxa-2-thia-6-azanonacosyl)benzamido)-5-(piperidin-1-yl)phenyl)-N-(3-(trifluoromethyl)benzyl)isonicotinamide

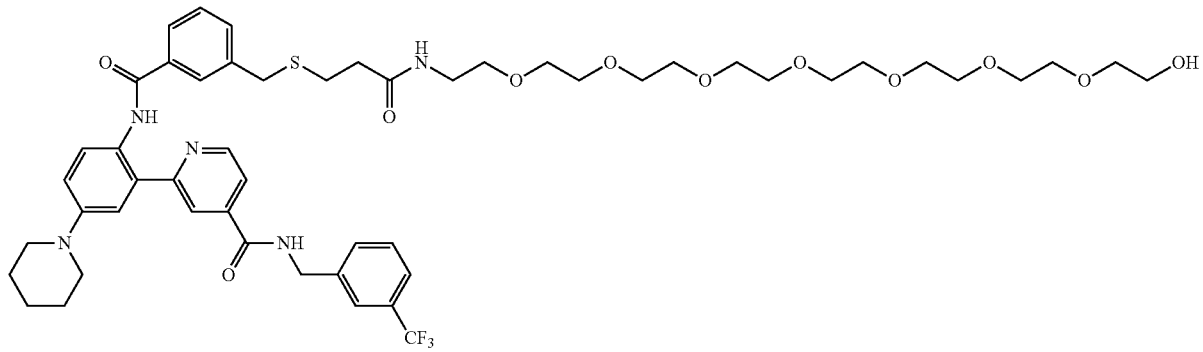 [SMILES: O=C(CCSCc1cccc(C(=O)Nc2ccc(N3CCCCC3)cc2-c2cc(C(=O)NCc3cccc(C(F)(F)F)c3)ccn2)c1)NCCOCCOCCOCCOCCOCCOCCOCCO]

A solution of 50 mg of 3-(3-((2-(4-((3-(trifluoromethyl)benzyl)carbamoyl)pyridin-2-yl)-4-(piperidin-1-yl)phenyl)carbamoyl)benzylthio)propanoic acid 1.1, 57 mg of diisopropylethylamine, 27 mg of 23-amino-3,6,9,12,15,18,21-heptaoxatricosan-1-ol, 18 mg of EDCI, and 19 mg of HOBt in 2 mL of DMF was stirred for 24 h. The product was isolated by reverse phase HPLC eluting with 0.05% TFA in a water/acetonitrile gradient to give 5.1 mg of product. MS (ES, m/z): 1028 [M+H]$^+$

Example 4.20.1

N1-Methyl-N1-(2-morpholinoethyl)-N3-(4-(piperidin-1-yl)-2-(4-((3-(trifluoromethyl)benzyl)carbamoyl)pyridin-2-yl)phenyl)isophthalamide

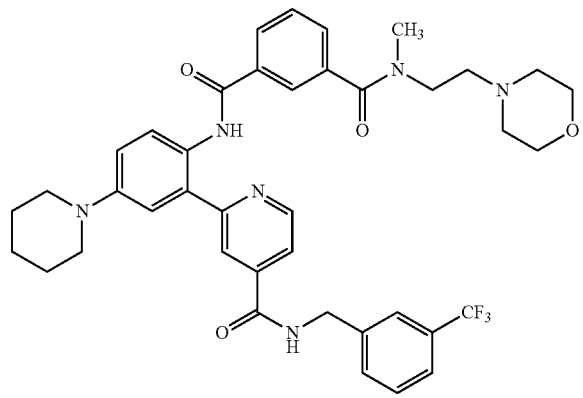

This compound was prepared by coupling N-methyl-2-morpholinoethylamine to 3-((4-(piperidin-1-yl)-2-(4-((3-(trifluoromethyl)benzyl)carbamoyl)pyridin-2-yl)phenyl)carbamoyl)benzoic acid 4.1e, using the procedure described for the preparation of N1-ethyl-N1-(2-morpholinoethyl)-N3-(4-(piperidin-1-yl)-2-(4-((3-(trifluoromethyl)benzyl)carbamoyl)pyridin-2-yl)phenyl)isophthalamide 4.8. MS (ES, m/z): 743 [M+H]$^+$

Example 4.20.2

N1-(2-((2-Methoxyethyl)(methyl)amino)ethyl)-N1-methyl-N3-(4-(piperidin-1-yl)-2-(4-((3-(trifluoromethyl)benzyl)carbamoyl)pyridin-2-yl)phenyl)isophthalamide Scheme 14.

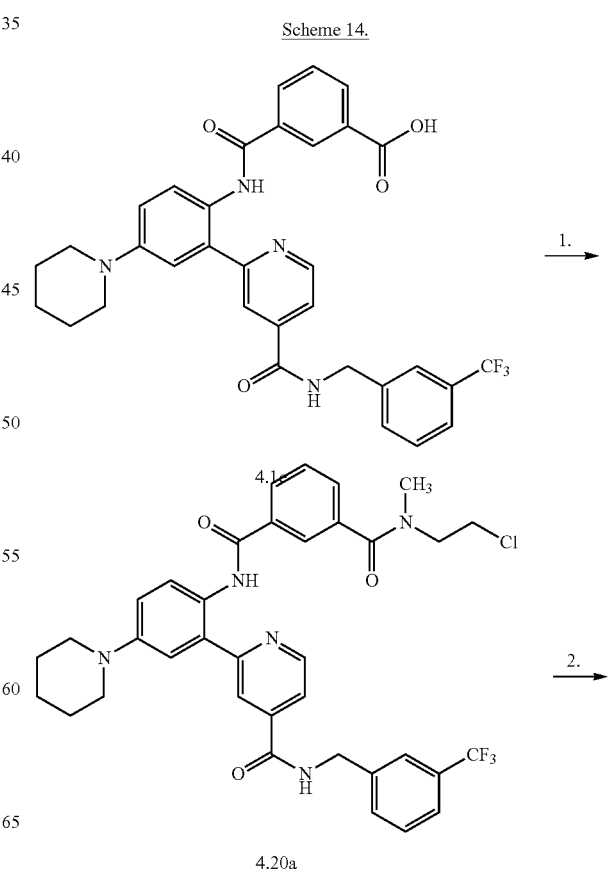

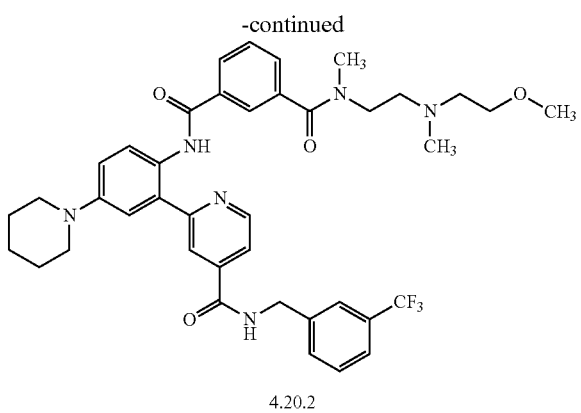

4.20.2

1. N-methyl-N-(2-chloroethyl)amine hydrochloride, diisopropylamine, HATU;
2. N-methyl-2-(methoxyethyl)amine.

Intermediate 4.20a

N1-(2-chloroethyl)-N1-methyl-N3-(4-(piperidin-1-yl)-2-(4-((3-(trifluoromethyl)benzyl)carbamoyl)pyridin-2-yl)phenyl)isophthalamide A solution of 50 mg of 3-((2-(4-((3-(trifluoromethyl)benzyl)carbamoyl)pyridin-2-yl)-4-(piperidin-1-yl)phenyl)carbamoyl)benzoic acid 4.1e, 9.3 mg of N-methyl-N-(2-chloroethyl)amine hydrochloride, 43 µL of diisopropylethylamine, and 35 mg of HATU in 1000 µL of DMF was stirred for 1 h. The mixture was diluted with 20 mL of water, and the resulting precipitate was collected by filtration. It was dissolved in dichloromethane and the solution was washed with water and dried ($Na_2SO_4$). The solvent was evaporated to give 42 mg of product.

Example 4.20.2

N1-(2-((2-methoxyethyl)(methyl)amino)ethyl)-N1-methyl-N3-(4-(piperidin-1-yl)-2-(4-((3-(trifluoromethyl)benzyl)carbamoyl)pyridin-2-yl)phenyl)-isophthalamide A mixture of 21 mg of N1-(2-chloroethyl)-N1-methyl-N3-(4-(piperidin-1-yl)-2-(4-((3-(trifluoromethyl)benzyl)carbamoyl)pyridin-2-yl)phenyl)isophthalamide 4.20a and 4.1 mg of N-methyl-2-(methoxyethyl)amine in 1 mL of acetonitrile was refluxed for 2 h. The product was isolated by reverse phase HPLC, eluting with 0.05% TFA in a water/acetonitrile gradient to give 18.8 mg. $^1$H NMR (400 MHz, DMSO-$d_6$) δ 12.34 (s, 1H), 9.55 (t, J=6.0 Hz, 1H), 9.40 (s, 1H), 8.90 (d, J=5.0 Hz, 1H), 8.33 (s, 1H), 8.28 (d, J=7.3 Hz, 1H), 8.05-7.93 (m, 2H), 7.84 (d, J=5.1 Hz, 1H), 7.75-7.54 (m, 6H), 7.25 (s, 1H), 4.63 (d, J=5.9 Hz, 2H), 3.88-3.81 (m, 2H), 3.75-3.66 (m, 2H), 3.64-3.55 (m, 2H), 3.56-3.42 (m, 2H), 3.42-3.22 (m, 7H), 3.01-2.88 (m, 6H), 1.80-1.66 (m, 4H), 1.58 (s, 2H). MS (ES, m/z): 727 [M+H]$^+$.

Example 4.21

N1-(2-((2-Hydroxyethyl)(methyl)amino)ethyl)-N1-methyl-N3-(4-(piperidin-1-yl)-2-(4-((3-(trifluoromethyl)benzyl)carbamoyl)pyridin-2-yl)phenyl)isophthalamide

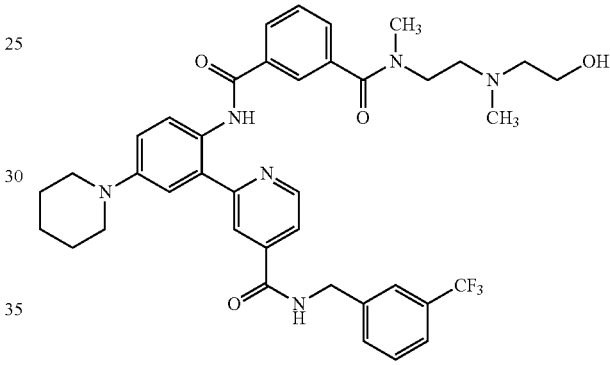

This compound was prepared by the procedure described for the preparation of N1-(2-((2-methoxyethyl)(methyl)amino)ethyl)-N1-methyl-N3-(4-(piperidin-1-yl)-2-(4-((3-(trifluoromethyl)benzyl)carbamoyl)pyridin-2-yl)phenyl)isophthalamide 4.20.2, using 2-(methylamino) ethanol in place of N-methyl-2-(methoxyethyl)amine. MS (ES, m/z): 717 [M+H]$^+$.

Examples 4.22 Through 4.30

The compounds in the Table 2 were prepared by the following procedure: A 60° C. solution of 20 mg of 3-((2-(4-((3-(trifluoromethyl)benzyl)carbamoyl)pyridin-2-yl)-4-(piperidin-1-yl)phenyl)carbamoyl)benzoic acid 4.1e, 1.2 equivalents of the requisite amine, 14.4 mg of HATU, and 28.3 mg of diisopropylethylamine in 150 µL of DMF was stirred for 1 h. The product was isolated by reverse phase HPLC, eluting with 0.05% TFA in a gradient of water/acetonitrile.

Scheme 14-1.

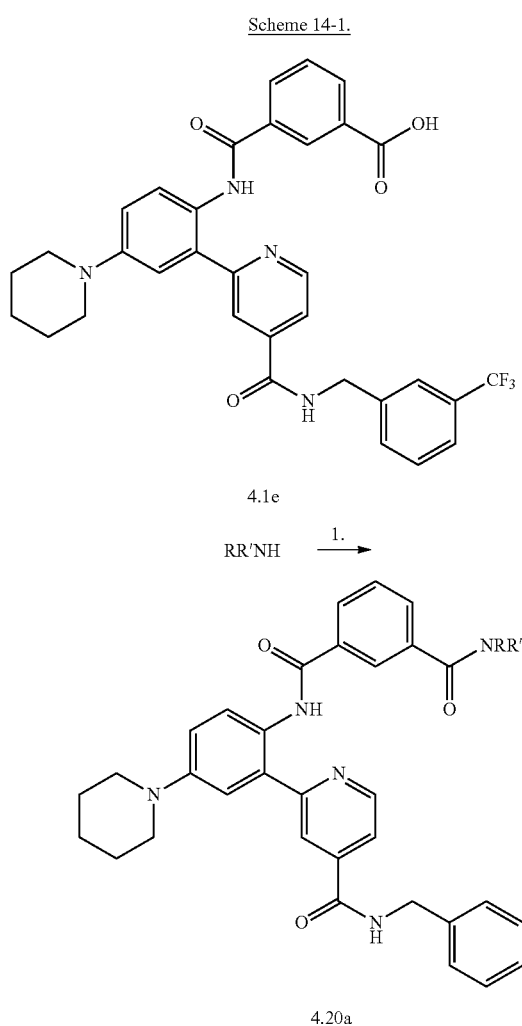

1. diisopropylethylamine, HATU, DMF.

TABLE 2

| Example No. | RR'NH | Mass Spectrum |
|---|---|---|
| 4.22 | H₃C-NH-CH₂CH₂-NH-Boc | 759.45 [M + H] |
| 4.23 | morpholine-piperidine | 755.29 [M + H] |
| 4.24 | H₃C-NH-CH₂-(2-imidazolyl) | 696.13 [M + H] |
| 4.25 | H₃C-NH-CH₂-(1-methyl-2-imidazolyl) | 710.22 [M + H] |

TABLE 2-continued

| Example No. | RR'NH | Mass Spectrum |
|---|---|---|
| 4.26 | H₃C-NH-CH₂-(1-methyl-5-imidazolyl) | 710.19 [M + H] |
| 4.27 | H₃C-NH-CH₂-(3-pyridyl) | 707.26 [M + H] |
| 4.28 | H₃C-NH-CH₂CH₂-(1-imidazolyl) | 710.16 [M + H] |
| 4.29 | HO-CH₂CH₂-(4-piperidinyl) | 714.56 [M + H] |
| 4.30 | HO-CH₂-(4-piperidinyl) | 700.53 [M + H] |

Example 4.31

2-(1-(3-(4-(Piperidin-1-yl)-2-(4-(3-(trifluoromethyl)benzylcarbamoyl)pyridin-2-yl)phenylcarbamoyl)benzoyl)piperidin-4-yl)acetic acid

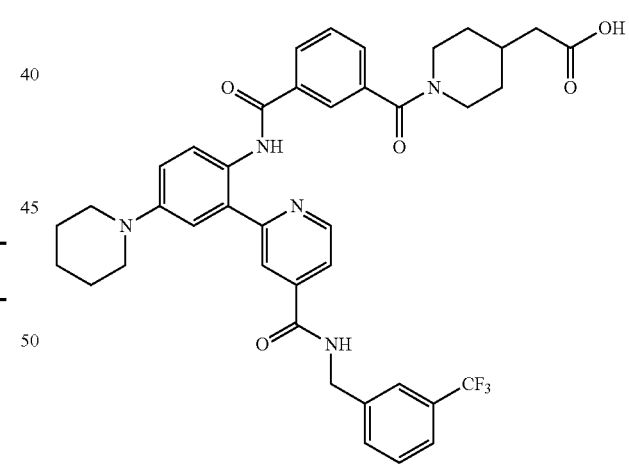

To a mixture of 20 mg of 3-((4-(piperidin-1-yl)-2-(4-((3-(trifluoromethyl)-benzyl)carbamoyl)pyridin-2-yl)phenyl)carbamoyl)benzoic acid 4.1e, 28 mg of diisopropylethylamine, and 6.5 mg of ethyl 2-(piperidin-4-yl)acetate in 1 mL of DMF was added 17 mg of HATU. The mixture was stirred at 60° C. for 1 h. The solution was diluted with water and extracted with ethyl acetate. The organic phase was washed with water, then brine. It was dried and the solvent was evaporated at reduced pressure. It was dissolved in 4:1 methanol/water and treated with 19.4 mg of LiOH.H₂O. After stirring for 20 h the product was isolated by reverse phase HPLC, eluting with 0.5% TFA in a gradient of water and acetonitrile to give 10.9 mg of product. MS (ES, m/z): 728.7 [M+H]+.

Example 4.32

3-((N-Methyl-3-(4-(piperidin-1-yl)-2-(4-(3-(trifluoromethyl)benzylcarbamoyl)pyridin-2-yl)phenylcarbamoyl)benzamido)methyl)benzoic acid

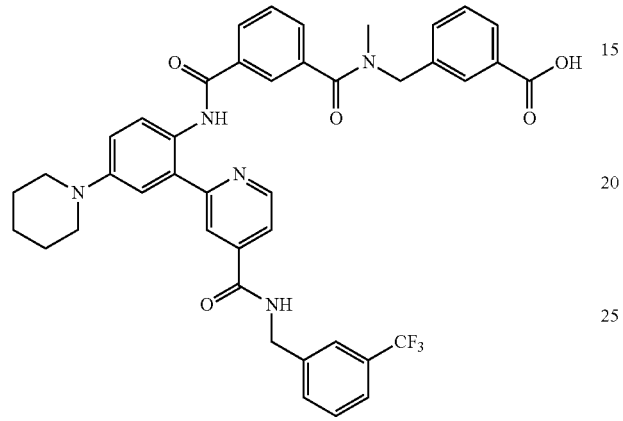

This compound was prepared using the procedure described for the preparation of Example 4.31, using 3-((methylamino)methyl)benzoic acid methyl ester as the amine component. MS (ES, m/z): 750.5 [M+H]+.

Examples 5.1 and 6.1

3-((3-((2-(4-(3-Phenylpropanoyl)pyridin-2-yl)-4-(piperidin-1-yl)phenyl)carbamoyl)benzyl)thio)propanoic acid and 3-((3-((2-(4-(1-hydroxy-3-phenylpropyl)pyridin-2-yl)-4-(piperidin-1-yl)phenyl)carbamoyl)benzyl)thio)propanoic acid Scheme 15.

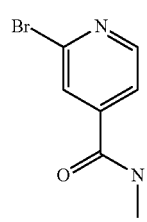

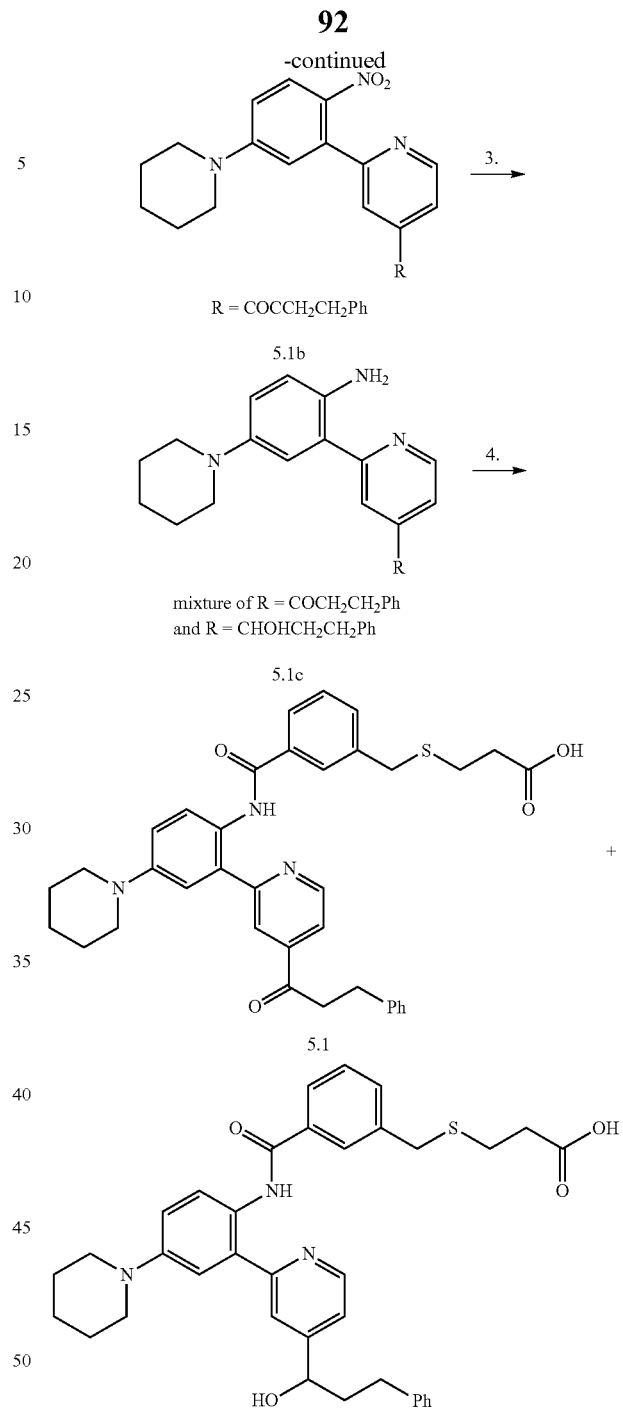

1. PhCH2CH2MgCl;
2. Intermediate 1.1e, Pd(OAc)2, Ph3P, Na2CO3;
3. H2, Pd/C;
4. Intermediate 1.1c, HATU, then TFA.

Intermediate 5.1a:
1-(2-bromopyridin-4-yl)-3-phenylpropan-1-one 1.0 mL of 1.0 N phenylethylmagnesium chloride in THF was added dropwise to a −78° C. solution of 200 mg of 2-bromo-N-methoxy-N-methylisonicotinamide in 6 mL of THF. The solution was allowed to warm to 25° C. After 10 minutes the solution was cooled back to −78° C. and an additional 1.0 mL of 1.0 N phenylmagnesium chloride in THF was added. The mixture was warmed to 25° C. and after 10 minutes 10 mL of 1.0 N hydrochloric acid was added. The solution was then made basic with excess aqueous sodium hydroxide solution and the mixture was partitioned between ethyl acetate and water. The aqueous phase was washed with ethyl acetate and the combined organic extracts were dried over sodium sulfate. The solvent was evaporated and the residue was chromatographed on silica gel to give 168 mg of product.

Intermediate 5.1b: 1-(2-(2-nitro-5-(piperidin-1-yl) phenyl)pyridin-4-yl)-3-phenylpropan-1-one A solution of 200 mg of 1-(4-nitro-3-(4,4,5,5-tetramethyl-1,3,2-dioxaborolan-2-yl)phenyl)piperidine 1.1e, 168 mg of 1-(2-bromopyridin-4-yl)-3-phenylpropan-1-one 5.1a, 12 mg of Pd(OAc)$_2$, 58 mg of PPh$_3$ in 1.25 mL of 2 N aqueous Na$_2$CO$_3$ solution and 3 mL of dimethoxyethane was refluxed for 4 h. The mixture was diluted with ethyl acetate and washed with water twice. The combined organic layer was dried over Na$_2$SO$_4$ and the solvent was evaporated. The residue was chromatographed on silica gel eluting with a gradient of 0% to 7% ethyl acetate in dichloromethane to give 196 mg of product.

Intermediates 5.1c: 1-(2-(2-amino-5-(piperidin-1-yl) phenyl)pyridin-4-yl)-3-phenylpropan-1-one and 1-(2-(2-amino-5-(piperidin-1-yl)phenyl)pyridin-4-yl)-3-phenylpropan-1-ol This mixture was prepared using the procedure described for the conversion of 6-(2-nitro-5-(piperidin-1-yl)phenyl)-N-(3-(trifluoromethyl)benzyl)pyrimidin-4-amine 3.1c to 6-(2-amino-5-(piperidin-1-yl)phenyl)-N-(3-(trifluoromethyl) benzyl)pyrimidin-4-amine 3.1d. After chromatography on silica gel, mg of a mixture of starting material, 1-(2-(2-amino-5-(piperidin-1-yl)phenyl)pyridin-4-yl)-3-phenylpropan-1-one and 1-(2-(2-amino-5-(piperidin-1-yl)phenyl)pyridin-4-yl)-3-phenylpropan-1-ol was obtained.

Examples 5.1 and 6.1

3-((3-((2-(4-(3-phenylpropanoyl)pyridin-2-yl)-4-(piperidin-1-yl)phenyl)carbamoyl)benzyl)thio)propanoic acid and 3-((3-((2-(4-(1-hydroxy-3-phenylpropyl)pyridin-2-yl)-4-(piperidin-1-yl)phenyl) carbamoyl)benzyl)thio)propanoic acid The mixture of products from the previous synthetic step was converted to a mixture containing 3-((3-((2-(4-(3-phenylpropanoyl)pyridin-2-yl)-4-(piperidin-1-yl)phenyl)-carbamoyl)benzyl)thio)propanoic acid 5 and 3-((3-((2-(4-(1-hydroxy-3-phenylpropyl)pyridin-2-yl)-4-(piperidin-1-yl) phenyl)carbamoyl)benzyl)thio)propanoic acid 6 using intermediate 3.1a and following procedures described in the preparation of Example 3.1. These two examples were isolated from the mixture by chromatography on silica gel, eluting with a gradient of 0% to 20% ethyl acetate in dichloromethane. Each product was then further purified by reverse phase HPLC. The mass spectrum (ES) of 3-((3-((2-(4-(3-phenylpropanoyl)pyridin-2-yl)-4-(piperidin-1-yl)phenyl) carbamoyl)benzyl)-thio)propanoic acid 5 exhibited m/z=608.3 [M+H]$^+$. The mass spectrum (ES) of 3-((3-((2-(4-(1-hydroxy-3-phenylpropyl)pyridin-2-yl)-4-(piperidin-1-yl) phenyl)carbamoyl)-benzyl)thio)propanoic acid 6 exhibited m/z=610.3 [M+H]$^+$.

Example 5.2

N1-Benzyl-N1-(2-morpholinoethyl)-N3-(4-(piperidin-1-yl)-2-(4-((3-(trifluoromethyl)benzyl)carbamoyl)pyridin-2-yl)phenyl)isophthalamide

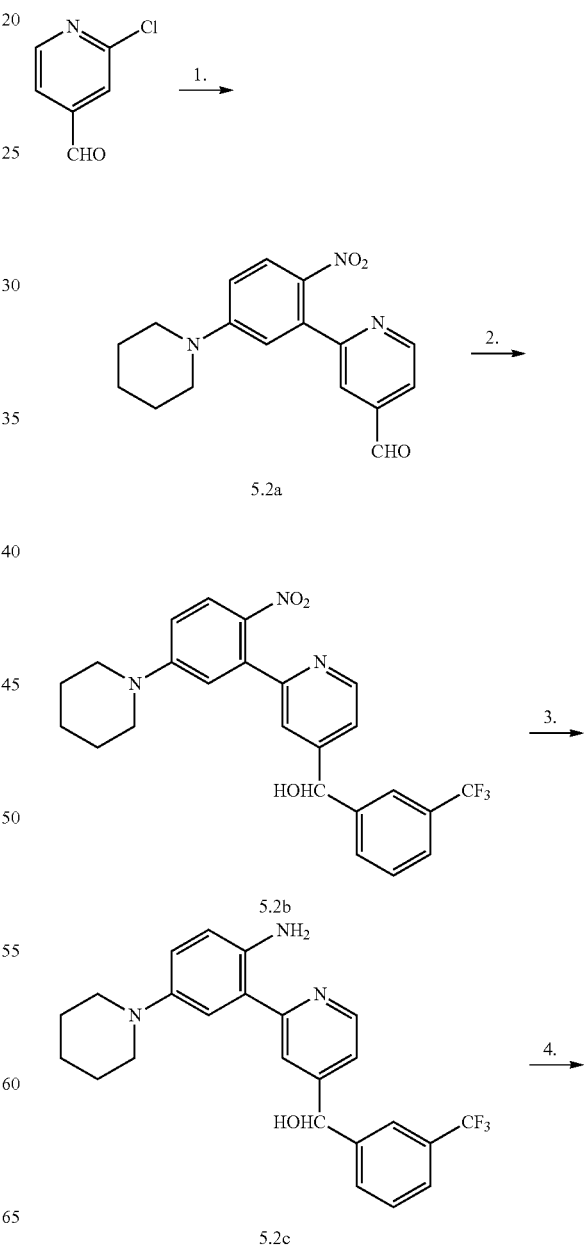

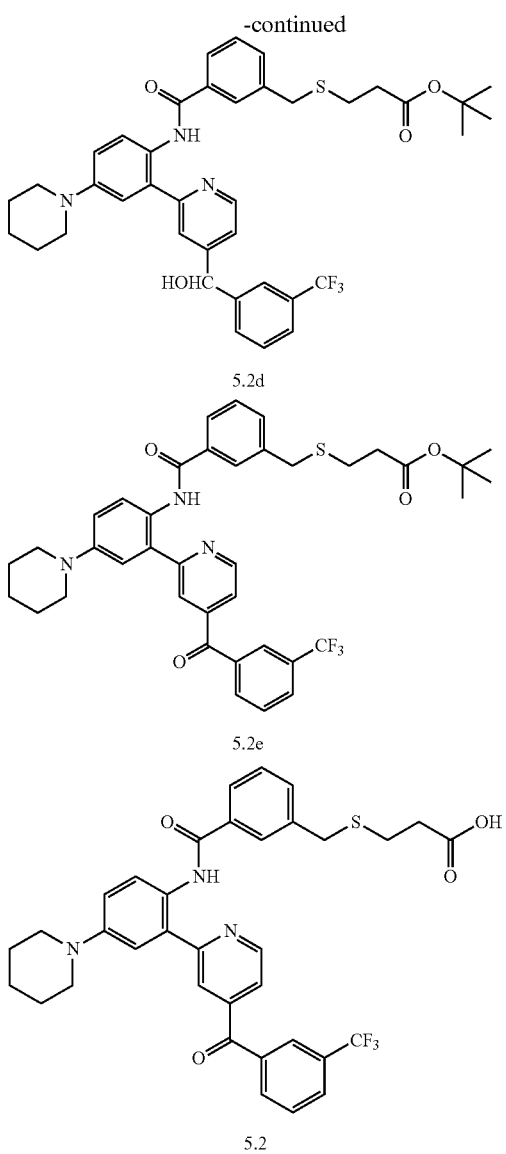

5.2d 5.2e 5.2

1. Intermediate 1.1e, 1-(4-nitro-3-(4,4,5,5-tetramethyl-1,3,2-dioxaborolan-2-yl) phenyl)piperidine, Pd(OAc)₂, PPh₃, DME, Na₂CO₃;
2. 3-(trifluoromethyl)phenylmagnesium chloride;
3. H₂, Pd/C;
4. Intermediate 1.1c: 3-((3-tert-butoxy-3-oxopropylthio)methyl)benzoic acid, HATU, DMF;
5. Py•SO₃;
6. TFA.

Intermediate 5.2a: 2-(2-nitro-5-(piperidin-1-yl)phenyl)isonicotinaldehyde

A mixture of 200 mg of 1-(4-nitro-3-(4,4,5,5-tetramethyl-1,3,2-dioxaborolan-2-yl)phenyl)piperidine 1e, 85 mg of 2-chloroisonicotinaldehyde, 6.7 mg of Pd(OAc)₂, 31 mg of PPh₃, 1.25 mL of 2 N aqueous Na₂CO₃ solution, and 3 mL of DME were refluxed 2 h. The mixture was diluted with ethyl acetate and washed 3× with water. The organic extracts were washed with brine and dried (Na₂SO₄). The solvent was evaporated and the residue was chromatographed on silica gel eluting with 10% ethyl acetate in dichloromethane. This gave 114 mg of product. MS (ES, m/z): 312.0 [M+H]⁺.

Intermediate 5.2b: (2-(2-nitro-5-(piperidin-1-yl)phenyl)pyridin-4-yl)(3-(trifluoromethyl)-phenyl)methanol To a −78° solution of 110 mg of 2-(2-nitro-5-(piperidin-1-yl)phenyl)isonicotinaldehyde in 4 mL of THF was added 0.82 mL of a 1.0 M solution of 3-(trifluoromethyl)phenylmagnesium chloride in THF. After 5 min the solution was warmed to 0° C. and treated with 10 mL of a saturated aqueous solution of NaHCO₃. The mixture was extracted with ethyl acetate and the organic extracts were washed with water and then with brine. The solution was dried (Na₂SO₄) and the solvent was evaporated. The residue was purified by silica gel chromatography eluting with 1:1 ethyl acetate/hexanes to give 123 mg of product. MS (ES, m/z) 458.2 [M+H]⁺.

Intermediate 5.2c: (2-(2-amino-5-(piperidin-1-yl)phenyl)pyridin-4-yl)(3-(trifluoromethyl)-phenyl)methanol A mixture of 123 mg of (2-(2-nitro-5-(piperidin-1-yl)phenyl)pyridin-4-yl)(3-(trifluoromethyl)phenyl)methanol 5.2b, 30 mg of moist 10% Pd/C, and 3 mL of methanol was stirred under a hydrogen atmosphere for 5 h. The mixture was filtered and the solvent was evaporated to provide 1.05 mg of product. MS (ES, m/z) 428.2 [M+H]⁺.

Intermediate 5.2d: tert-butyl 3-((3-((2-(4-(hydroxy(3-(trifluoromethyl)phenyl)methyl)-pyridin-2-yl)-4-(piperidin-1-yl)phenyl)carbamoyl)benzyl)thio)propanoate A solution of mg of (2-(2-amino-5-(piperidin-1-yl)phenyl)pyridin-4-yl)(3-(trifluoromethyl)phenyl)-methanol 5.2c, and 41 mg of 3-((3-tert-butoxy-3-oxopropylthio)methyl)benzoic acid 1.1c, 67 mg of diisopropylethylamine in 1.5 mL of DMF was treated with 57 mg of HATU. After stirring at 60° C. for 2 h the mixture was diluted with ethyl acetate and washed once with a saturated aqueous solution of sodium bicarbonate, three times with water, and once with brine. After drying (Na₂SO₄) the solvent was evaporated to give 107 mg of product. MS (ES, m/z) 706.2 [M+H]⁺.

Intermediate 5.2e: tert-butyl 3-((3-((4-(piperidin-1-yl)-2-(4-(3-(trifluoromethyl)benzoyl)-pyridin-2-yl)phenyl)carbamoyl)benzyl)thio)propanoate A −10° C. solution of 23 mg of tert-butyl 3-((3-((2-(4-(hydroxy(3-(trifluoromethyl)phenyl)methyl)pyridin-2-yl)-4-(piperidin-1-yl)phenyl)carbamoyl)benzyl)thio)propanoate 5.2d, 17 mg of diisopropylethylamine, and 10 mg of DMSO in 0.4 mL of dichloromethane was treated with 10 mg of pyridine sulfur trioxide complex. After stirring for 1 h the reaction mixture was applied directly to a silica gel column and eluted with a gradient of 0% to 10% ethyl acetate in dichloromethane. Evaporation of the solvent yielded 9.5 mg of product. MS (ES, m/z) 704.2 [M+H]⁺.

Example 5.2

3-((3-((4-(piperidin-1-yl)-2-(4-(3-(trifluoromethyl)benzoyl)pyridin-2-yl)phenyl)carbamoyl)benzyl)thio)propanoic acid A solution of 9.5 mg of 3-((3-((4-(piperidin-1-yl)-2-(4-(3-(trifluoromethyl)benzoyl)pyridin-2-yl)phenyl)carbamoyl)benzyl)-thio)propanoate. 5.2e in 600 μL of 1:1 dichloromethane/TFA was stirred 45 minutes and then the solvent was evaporated. The residue was purified by reverse phase chromatography eluting with a water/acetonitrile gradient containing 0.05% TFA to afford 5 mg of product. $^1$H-NMR (400 MHz, CD$_3$OD, ppm) δ 9.10 (d, J=5 Hz, 1H), 8.75 (d, J=9 Hz, 1H), 8.28 (s, 1H), 8.18 (s, 1H), 8.10-8.05 (m, 2H), 7.99-8.02 (m, 3H), 7.87 (d, J=8 Hz, 1H), 7.76-7.71 (m, 3H), 7.58 (d, J=8 Hz, 1H), 7.49 (d, J=8 Hz, 1H), 3.89 (s, 2H), 3.70-3.60 (m, 4H), 2.70 (t, J=7 Hz, 2H), 2.55 (t, J=7 Hz, 2H), 2.10-2.00 (m, 4H), 1.85-1.75 (m, 2H). $^{19}$F-NMR analysis revealed the presence of two peaks at δ-64 and δ-77 in a 1:2 ratio, suggesting that the compound was isolated as a salt containing two equivalents of TFA. MS (ES, m/z) 648.3 [M+H]$^+$.

Example 6.2

3-((3-((2-(4-(Hydroxy(3-(trifluoromethyl)phenyl)methyl)pyridin-2-yl)-4-(piperidin-1-yl)phenyl)carbamoyl)benzyl)thio)propanoic acid

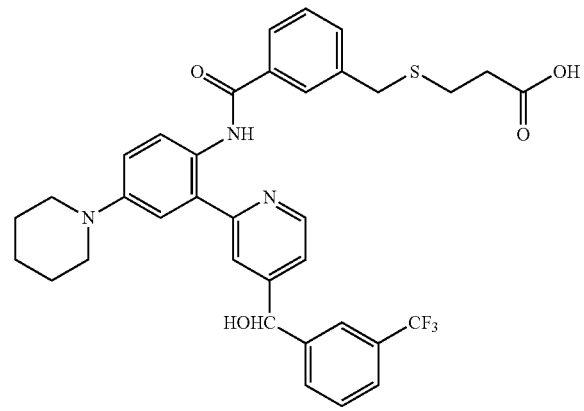

This compound was prepared from (2-(2-amino-5-(piperidin-1-yl)phenyl)pyridin-4-yl)(3-(trifluoromethyl)phenyl)methanol 5.2c using the procedures described in Example 5.2, but omitting the oxidation step (Step 5.2e). MS (ESI, m/z) 650.3 [M+H]$^+$.

Example 7

3-((3-((4-(Piperidin-1-yl)-2-(4-(((3-(trifluoromethyl)benzyl)amino)methyl)pyridin-2-yl)phenyl)carbamoyl)benzyl)thio)propanoic acid Scheme 17:

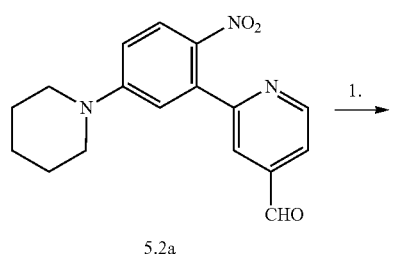

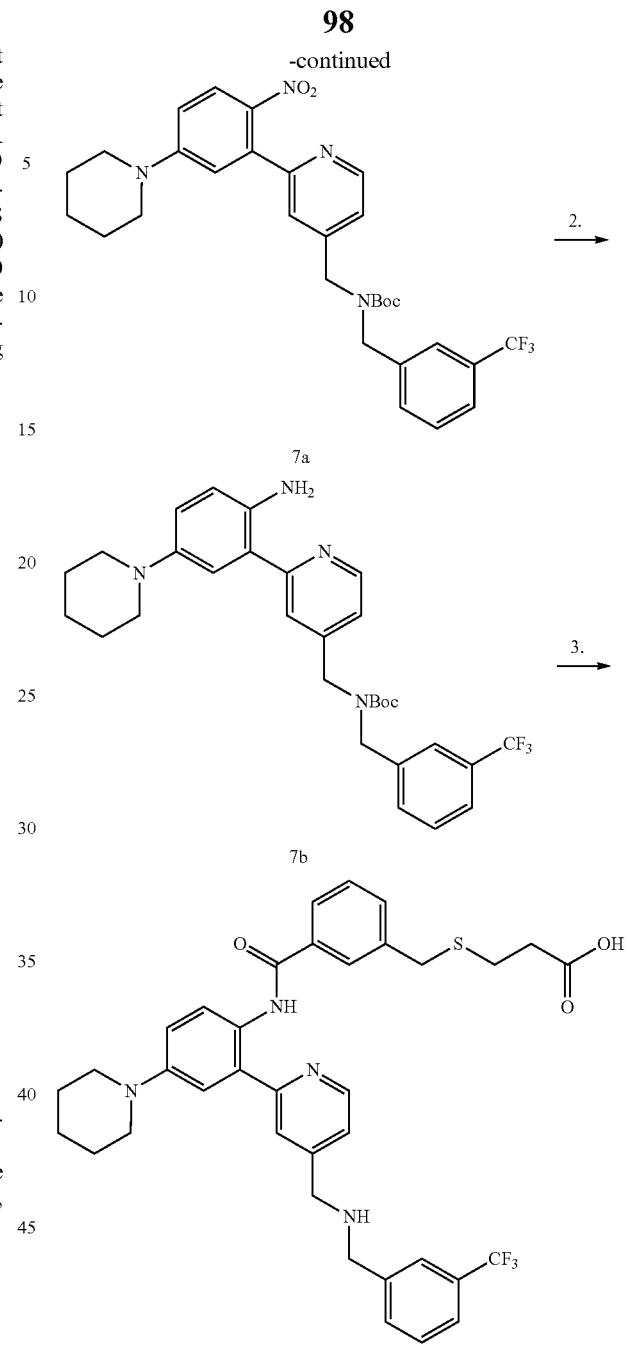

1. 3-(trifluoromethyl)benzylamine, NaBH(OAc)$_3$, then Boc$_2$O: 2. H$_2$, Pd/C; 3. 3-((3-tert-butoxy-3-oxopropylthio)methyl)benzoic acid 1.1c, HATU, diisopropylamine, then TFA.

Intermediate 7a: tert-butyl ((2-(2-nitro-5-(piperidin-1-yl)phenyl)pyridin-4-yl)methyl)(3-(trifluoromethyl)benzyl)carbamate A solution of 120 mg of 2-(2-nitro-5-(piperidin-1-yl)phenyl)isonicotinaldehyde 5.2a and 70 mg of 3-(trifluoromethyl)benzylamine in 4 mL of dichloromethane was treated with 207 mg of NaBH(OAc)$_3$. After 17 h the mixture was diluted with 10 mL of a saturated aqueous solution of sodium bicarbonate. The phases were separated and the aqueous phase was washed 3 times with dichloromethane. The combined organic extracts were dried (Na$_2$SO$_4$), and the solvent was evaporated to give 220 mg of a product giving MS (ES, m/z) 471.2 [M+H]$^+$. The product was dissolved in 3 mL of dichloromethane and treated with 109 mg of Boc$_2$O and stirred for 17 h. The solvent was evaporated and the product was purified by silica gel chromatography to give 93 mg of tert-butyl ((2-(2-nitro-5-(piperidin-1-yl)phenyl)pyridin-4-yl)methyl)(3-(trifluoromethyl)-benzyl)carbamate 7a.

Intermediate 7b: tert-butyl ((2-(2-amino-5-(piperidin-1-yl)phenyl)pyridin-4-yl)methyl)(3-(trifluoromethyl)benzyl)carbamate This compound was prepared using the procedure described for the conversion of (2-(2-nitro-5-(piperidin-1-yl)phenyl)pyridin-4-yl)(3-(trifluoromethyl)phenyl)methanol 5.2b to 2-(2-amino-5-(piperidin-1-yl)phenyl)pyridin-4-yl)(3-(trifluoromethyl)phenyl)methanol 5.2c. MS (ES, m/z) 541.2 [M+H]$^+$.

Example 7

3-((3-((4-(piperidin-1-yl)-2-(4-(((3-(trifluoromethyl)benzyl)amino)methyl)-pyridin-2-yl)phenyl)carbamoyl)benzyl)thio)propanoic acid This compound was prepared using the procedure described for the preparation of 3-((3-((4-(piperidin-1-yl)-2-(6-(3-(trifluoromethyl)phenoxy)pyrimidin-4-yl)phenyl)carbamoyl)benzyl)thio)propanoic acid 3.9 from 4-(piperidin-1-yl)-2-(6-(3-(trifluoromethyl)phenoxy)pyrimidin-4-yl)aniline 3.9b. MS (ES, m/z) 662.2 [M+H]$^+$.

Example 8.1

3-((3-((4-(Piperidin-1-yl)-2-(4-((3-(trifluoromethyl)benzyl)carbamoyl)pyridin-2-yl)phenyl)carbamoyl)benzyl)thio)benzoic acid Scheme 18:

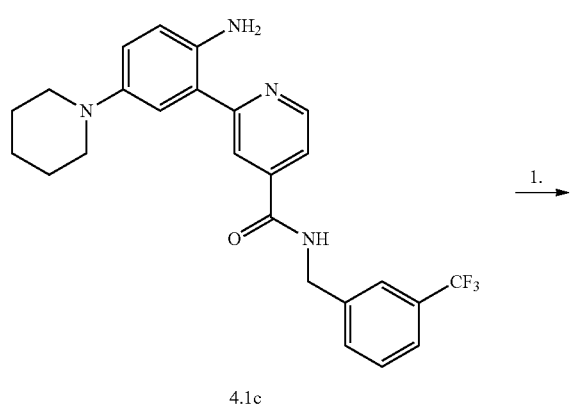

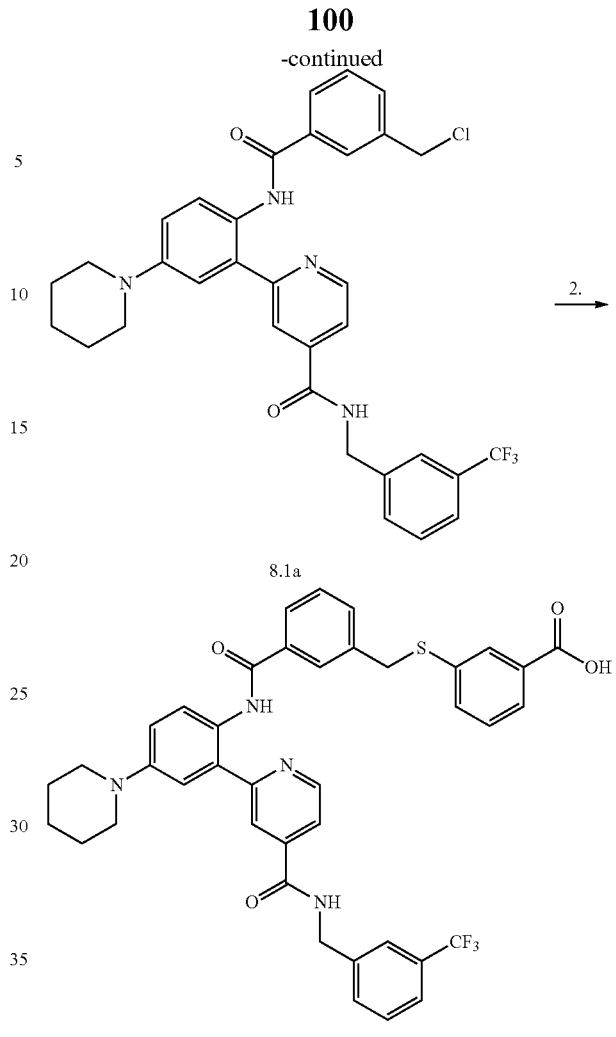

1. 3-(chloromethyl)benzoyl chloride, diisopropylethylamine;
2. 3-mercaptobenzoic acid, K$_2$CO$_3$.

Intermediate 8.1a. 2-(2-(3-(chloromethyl)benzamido)-5-(piperidin-1-yl)phenyl)-N-(3-(trifluoromethyl)benzyl)isonicotinamide 3-(Chloromethyl)benzoyl chloride was added dropwise to a 0° C. solution of 900 mg of N-(3-(trifluoromethyl)benzyl)-2-(2-amino-5-(piperidin-1-yl)phenyl)isonicotinamide 4.1c 1.02 g of diisopropylethylamine in 10 mL of a 1:1 mixture of dichloromethane and THF. The mixture was warmed to 25° C. and stirred for 1 h, after which it was washed five times with aqueous hydrochloric acid, once with a saturated aqueous solution of sodium bicarbonate, and once with water. The solution was dried and the solvent was evaporated to give 1.24 g of product as a yellow solid.

Example 8.1

3-((3-((4-(piperidin-1-yl)-2-(4-((3-(trifluoromethyl)benzyl)carbamoyl)-pyridin-2-yl)phenyl)carbamoyl)benzyl)thio)benzoic acid A mixture of 250 mg of 2-(2-(3-(chloromethyl)benzamido)-5-(piperidin-1-yl)phenyl)-N-(3-(trifluoromethyl)benzyl)-isonicotinamide 8.1a, 70 mg of 3-mercaptobenzoic acid, 10 mL of acetone, and 171 mg of $K_2CO_3$ was stirred for 16 h and then filtered. The solvent was removed by evaporation. The residue was dissolved in dichloromethane and the resulting solution was washed with aqueous hydrochloric acid. The solution was dried, and the solvent was evaporated. The residue was purified by silica gel chromatography to give 113 mg of product. MS (ES, m/z) 725 $[M+H]^+$.

Examples 8.2 Through 8.24

The compounds presented in Table 3 were prepared as follows: A mixture of 2-(2-(3-(chloromethyl)benzamido)-5-(piperidin-1-yl)phenyl)-N-(3-(trifluoromethyl)benzyl)-isonicotinamide 8.1a (0.05 mmol), the requisite thiol (0.055 mmol), and $K_2CO_3$ in 500 μL of DMF were stirred for 18 h under nitrogen. The mixture was filtered, and the filtrate was purified by reverse-phase HPLC eluting with a water/acetonitrile gradient containing 0.1% TFA. The purity and identity of the products was confirmed by LCMS (Table 3) and $^1H$ NMR (data not shown).

TABLE 3

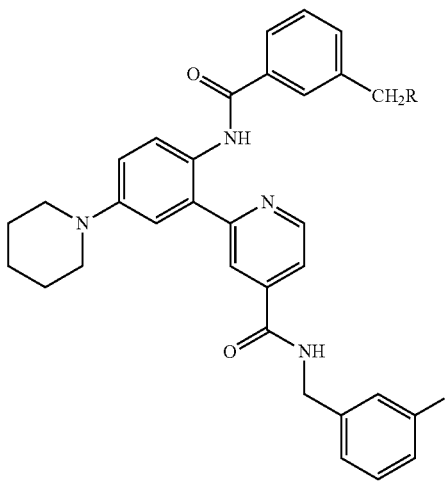

| Example No. | R | Mass Spectrum |
|---|---|---|
| 8.2 | —SCH₂CH₂OH | 649.30 [M + H] |
| 8.3 | —SCH₂CH₂CH₂OH | 663.31 [M + H] |
| 8.4 | —SCH₂CH₂CH₂CH₂OH | 677.32 [M + H] |
| 8.5 | —SCH₂CH₂CH₂COOH | 691.33 [M + H] |
| 8.6 | —SC(CH₃)₂COOH | 691.32 [M + H] |
| 8.7 | —S(CH₂CH₂O)₄CH₂CH₂COOH | 853.55 [M + H] |
| 8.8 | —S—C₆H₄—CH₂CH₂COOH | 753.33 [M + H] |
| 8.9 | —S—C₆H₄—CH₂CH₂CH₂COOH | 767.35 [M + H] |
| 8.10 | —S—CH₂—CH(NHBoc)—COOH | 792.14 [M + H] |
| 8.11 | (N-acetyl-penicillamine thiolate) | 762.32 [M + H] |
| 8.12 | (N-isobutyryl-cysteine thiolate) | 762.33 [M + H] |
| 8.13 | —SCH₂CH₂SO₃Na | 713.29 [M + H] |
| 8.14 | 2-thio-4-hydroxy-pyrimidine-5-COOH | 743.25 [M + H] |
| 8.15 | 2-thio-pyridine-5-COOH | 726.27 [M+ H] |
| 8.16 | (4-methyl-thiazol-2-yl)thio-CH₂COOH | 760.18 [M + H] |
| 8.17 | —S—C₆H₄—CH₂COOH (para) | 739.32 [M+ H] |
| 8.18 | —S—C₆H₄—CH₂COOH (meta) | 739.32 [M+ H] |

TABLE 3-continued

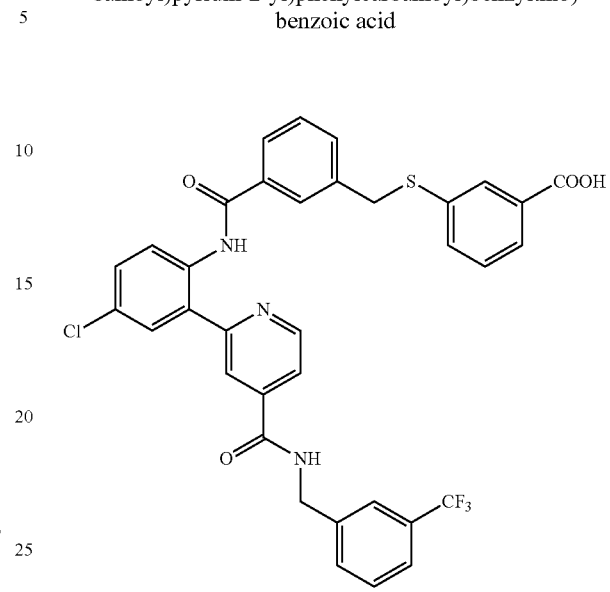

| Example No. | R | Mass Spectrum |
|---|---|---|
| 8.19 | —S—(3-CH$_2$CH$_2$CH$_2$COOH-phenyl) | 767.33 [M + H] |
| 8.20 | —S—(3-CH$_2$C(CH$_3$)$_2$COOH-phenyl) | 781.40 [M + H] |
| 8.21 | —S—(4-COOH, 3-Br-phenyl) | 803.44 [M + H] |
| 8.22 | —SCH$_2$CH$_2$(OCH$_2$CH$_2$)$_8$COOH | 1029 [M + H] |
| 8.23 | —S—(4-COOH-phenyl) | 725 [M + H] |
| 8.24 | —S—(2-COOH-phenyl) | 725 [M + H] |

Example 8.25

3-(3-(4-Chloro-2-(4-(3-(trifluoromethyl)benzylcarbamoyl)pyridin-2-yl)phenylcarbamoyl)benzylthio)benzoic acid

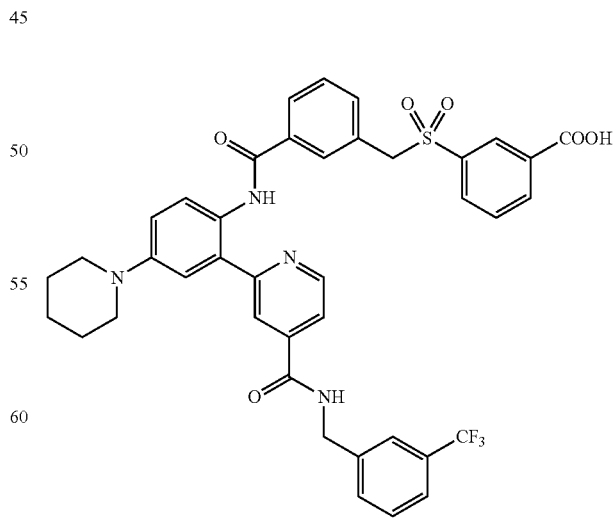

A mixture of 173 mg of 2-(5-chloro-2-(3-(chloromethyl)benzamido)phenyl)-N-(3-(trifluoromethyl)benzyl)isonicotinamide, which was made from intermediate 21b in a similar manner as the synthesis of 8.1a, 52 mg of 3-mercaptobenzoic acid, and 128 mg of K$_2$CO$_3$ in 2 mL of DMF was stirred for 2 h and then poured into 20 mL of water. The solution was acidified with hydrochloric acid. A precipitate formed and was collected by filtration and dried. The resulting solid was dissolved in acetone and filtered. Evaporation of the solvent gave 92 mg of product. MS (ES, m/z) 676 [M+H]$^+$.

Example 8.26

3-((3-((4-(Piperidin-1-yl)-2-(4-((3-(trifluoromethyl)benzyl)carbamoyl)pyridin-2-yl)phenyl)carbamoyl)benzyl)sulfonyl)benzoic acid A solution of 25 mg of 3-((3-((4-(piperidin-1-yl)-2-(4-((3-(trifluoromethyl)benzyl)carbamoyl)pyridin-2-yl)phenyl)

carbamoyl)benzyl)thio)benzoic acid 8.25 in 2 mL of a 2:1:1 mixture of THF, methanol, and water was treated with 110 mg of Oxone®. The mixture was stirred for 2 h and then it was diluted with ethyl acetate. The organic phase was washed with water, which caused a precipitate to form. The precipitate was redissolved by adding methanol. The organic phase was separated and filtered. Evaporation of the solvent gave a white solid. This solid was dissolved in methanol and treated with 5 mg of 5% Pd/C. The mixture was stirred under a hydrogen atmosphere for 15 minutes, and then it was filtered. The solvent was evaporated and the residue was purified by reverse phase HPLC, eluting with 0.05% TFA in a water/acetonitrile gradient. The process yielded 8.6 mg of product. MS (ES, m/z) 757 [M+H]$^+$.

Example 8.27

3-((3-((4-(Piperidin-1-yl)-2-(4-((3-(trifluoromethyl)benzyl)carbamoyl)pyridin-2-yl)phenyl)carbamoyl)benzyl)thio)benzoic acid

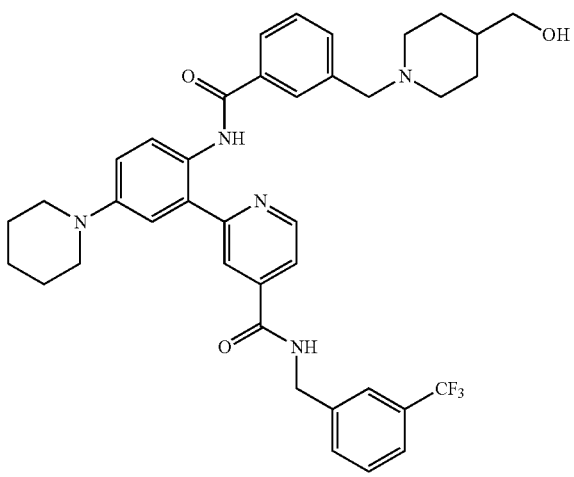 [SMILES: O=C(NCc1cccc(C(F)(F)F)c1)c1ccnc(-c2cc(N3CCCCC3)ccc2NC(=O)c2cccc(CN3CCC(CO)CC3)c2)c1]

A mixture of 20 mg of 2-(2-(3-(chloromethyl)benzamido)-5-(piperidin-1-yl)phenyl)-N-(3-(trifluoromethyl)benzyl)isonicotinamide 8.1a, 4.6 mg of 4-(hydroxymethyl)piperidine, and 9.1 mg of K$_2$CO$_3$ in 2 mL of DMF was stirred for 12 h. The product (12 mg) was isolated by reverse phase chromatography eluting with 0.05% TFA in a water/acetonitrile gradient. MS (ES, m/z) 686.3 [M+H]$^+$.

Example 8.28

2-(2-(3-((4-(2-Hydroxyethyl)piperidin-1-yl)methyl)benzamido)-5-(piperidin-1-yl)phenyl)-N-(3-(trifluoromethyl)benzyl)isonicotinamide

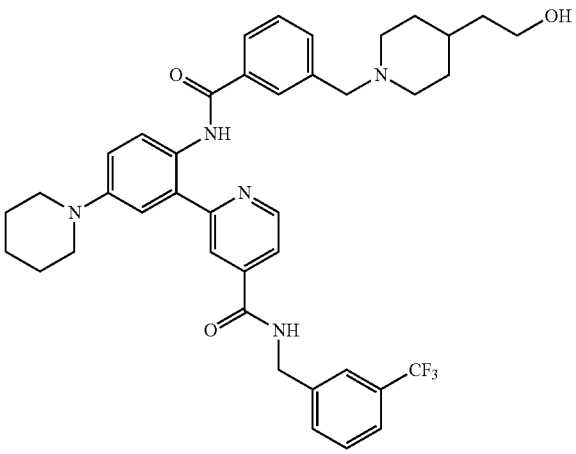 [SMILES: O=C(NCc1cccc(C(F)(F)F)c1)c1ccnc(-c2cc(N3CCCCC3)ccc2NC(=O)c2cccc(CN3CCC(CCO)CC3)c2)c1]

A mixture of 20 mg of 2-(2-(3-(chloromethyl)benzamido)-5-(piperidin-1-yl)phenyl)-N-(3-(trifluoromethyl)benzyl)isonicotinamide 8.1a, 5.2 mg of 2-(piperidin-4-yl)ethanol, and 9.1 mg of K$_2$CO$_3$ in 2 mL of DMF was stirred for 12 h. The product was isolated by reverse phase chromatography eluting with 0.05% TFA in a water/acetonitrile gradient. MS (ES, m/z) 700.27 [M+H]$^+$.

Example 9.1

1-(3-((4-(Piperidin-1-yl)-2-(4-((3-(trifluoromethyl)benzyl)carbamoyl)pyridin-2-yl)phenyl)carbamoyl)benzyl)-1H-indole-4-carboxylic acid

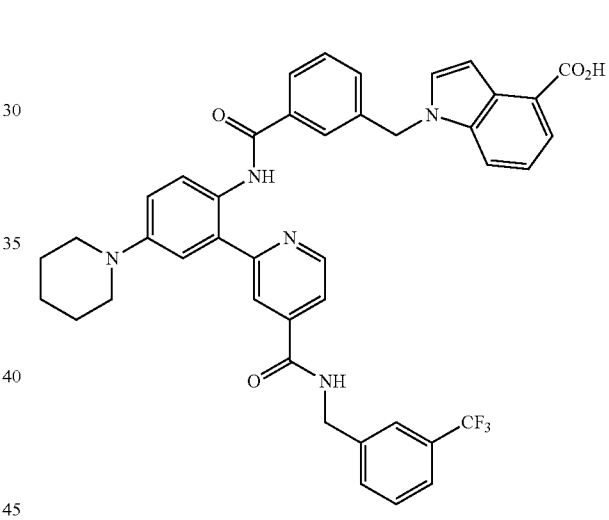

A mixture of 10.5 mg of methyl 1H-indole-4-carboxylate, 18.2 mg of 2-(2-(3-(chloromethyl)benzamido)-5-(piperidin-1-yl)phenyl)-N-(3-(trifluoromethyl)benzyl)-isonicotinamide 8.1a, and excess potassium carbonate in 300 µL of DMF was stirred for 24 h. The solvent was evaporated and the residue was purified by silica gel chromatography. The product was dissolved in 1 mL of 4:1 THF/water and treated with 10 mg of LiOH.H$_2$O. After stirring 4 days at 70° C. the reaction mixture was acidified with 3.0 N hydrochloric acid and then extracted with ethyl acetate. The aqueous phase was washed with ethyl acetate, and the combined organic extracts washed with brine and dried (NaSO$_4$). The residue was purified by reverse phase HPLC eluting with 0.1% TFA in a water/acetonitrile gradient to give 10.6 mg of product. MS (ES, m/z) 732.4 [M+H]$^+$.

Example 9.2

1-Oxo-1-(1-(3-((4-(piperidin-1-yl)-2-(4-((3-(trifluoromethyl)benzyl)carbamoyl)pyridin-2-yl)-phenyl)carbamoyl)benzyl)-1H-indol-4-yl)-5,8,11-trioxa-2-azatetradecan-14-oic acid

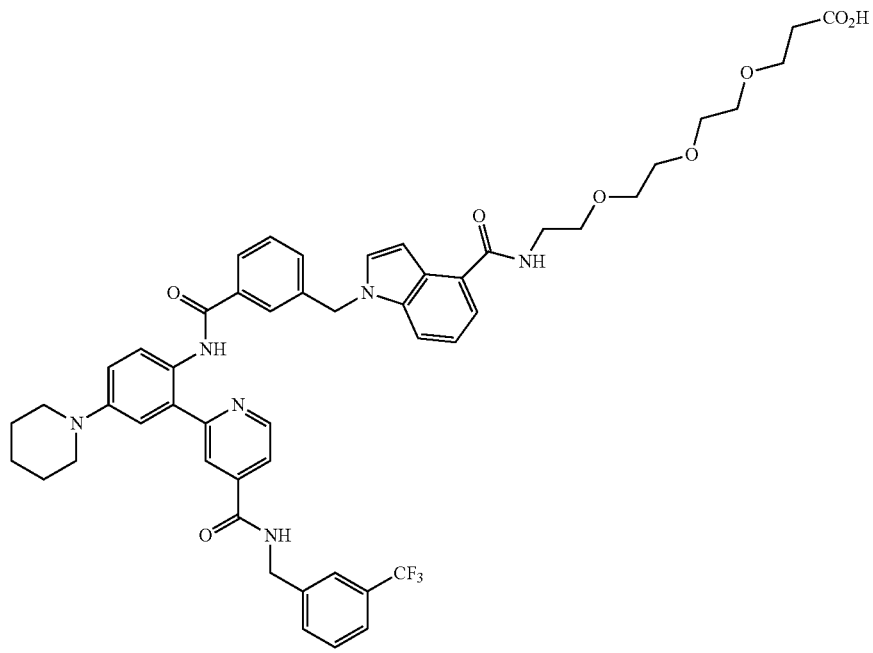 [SMILES: O=C(O)CCOCCOCCOCCNC(=O)c1cccc2c1ccn2Cc1cccc(C(=O)Nc2ccc(N3CCCCC3)cc2-c2cc(C(=O)NCc3cccc(C(F)(F)F)c3)ccn2)c1]

A mixture of 3 mg of 1-(3-((4-(piperidin-1-yl)-2-(4-((3-(trifluoromethyl)-benzyl)carbamoyl)pyridin-2-yl)phenyl)carbamoyl)benzyl)-1H-indole-4-carboxylic acid 9.1, 1.7 mg of 3-(2-(2-(2-aminoethoxy)ethoxy)ethoxy)propanoic acid, and 2.5 mg of HATU in 300 µL of DMF was treated with 1.5 µL of diisopropylethylamine. After 2 h the solvent was evaporated and the residue was partitioned between ethyl acetate and water. The aqueous phase was washed with ethyl acetate, and the combined organic extracts were washed with brine and dried ($Na_2SO_4$). The solvent was evaporated and a fraction of the product was dissolved in 1:1 dichloromethane/TFA. After stirring for 1 h the solvent was evaporated and the residue was purified by reverse phase HPLC eluting with 0.05% TFA in a water/acetonitrile gradient to yield 1.4 mg of the title compound. $^1$H NMR (400 MHz, DMSO-$d_6$) δ 12.62 (s, 1H), 9.57 (t, J=5.7 Hz, 1H), 8.98 (d, J=5.1 Hz, 1H), 8.51 (d, J=8.7 Hz, 1H), 8.40 (s, 1H), 7.93 (s, 1H), 7.89 (d, J=5.1 Hz, 1H), 7.78 (d, J=7.4 Hz, 1H), 7.72 (s, 1H), 7.65 (m, 2H), 7.60-7.52 (m, 3H), 7.48 (t, J=7.7 Hz, 1H), 7.24-7.14 (m, 3H), 7.03-6.94 (m, 1H), 4.64 (d, J=5.8 Hz, 2H), 4.36 (s, 2H), 3.47 (s, 4H), 2.15 (t, J=7.3 Hz, 2H), 1.83 (br, 4H), 1.81-1.67 (m, 2H), 1.64 (br, 2H). MS (ES, m/z) 935.32 [M+H]$^+$

Example 9.3

3-(((3-((4-(Piperidin-1-yl)-2-(4-((3-(trifluoromethyl)benzyl)carbamoyl)pyridin-2-yl)phenyl)carbamoyl)benzyl)thio)meth)benzoic acid Scheme 19:

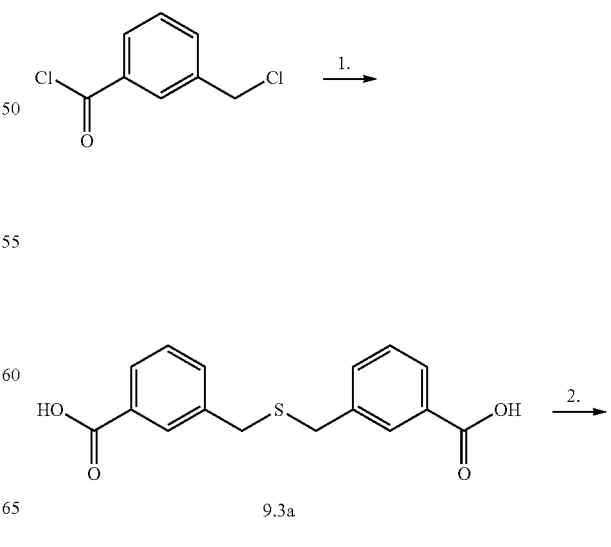

9.3a

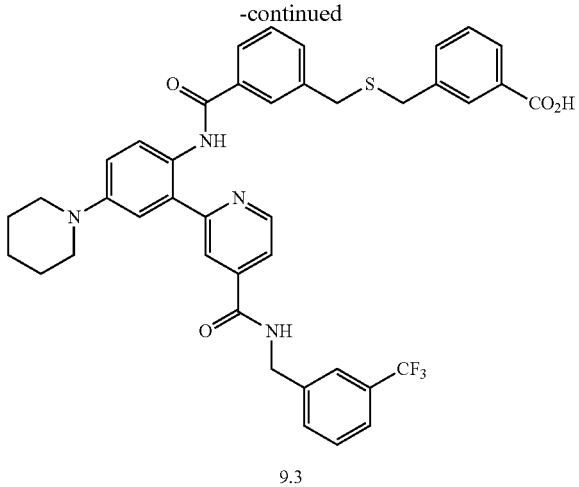

1. Na₂S;
2. HATU, diisopropylethylamine.

Intermediate 9.3a:
3,3'-(thiobis(methylene))dibenzoic acid

A mixture of 284 μL of 3-(chloromethyl)benzoyl chloride, 78 mg of Na₂S, 36 μl of water, and 276 mg K₂CO₃ in DMF was stirred 18 h at RT The mixture was filtered and the solvent was evaporated at reduced pressure. The residue was triturated with dichloromethane to give 100 mg of product.

Example 9.3

3-(((3-((4-(piperidin-1-yl)-2-(4-((3-(trifluoromethyl) benzyl)carbamoyl)-pyridin-2-yl)phenyl)carbamoyl) benzyl)thio)methyl)benzoic acid A solution of 15 mg of thiobis(methylene))dibenzoic acid 9.3a, 7.5 mg of N-(3-(trifluoromethyl)benzyl)-2-(2-amino-5-(piperidin-1-yl)phenyl)isonicotinamide. 4.1c, and 17 mg of HATU in DMF was treated with 26 μL of diisopropylethylamine. After 18 h the product was isolated by reverse phase HPLC, eluting with 0.05% TFA in a water/acetonitrile gradient. The procedure gave 7.5 mg of product. MS (ES, m/z) 739.3 [M+H]⁺.

Example 10.1

1-Oxo-1-(3-(((3-((4-(piperidin-1-yl)-2-(4-((3-(trifluoromethyl)benzyl)carbamoyl)pyridin-2-yl)phenyl) carbamoyl)benzyl)thio)methyl)phenyl)-5,8,11-trioxa-2-azatetradecan-14-oic acid Scheme 20.

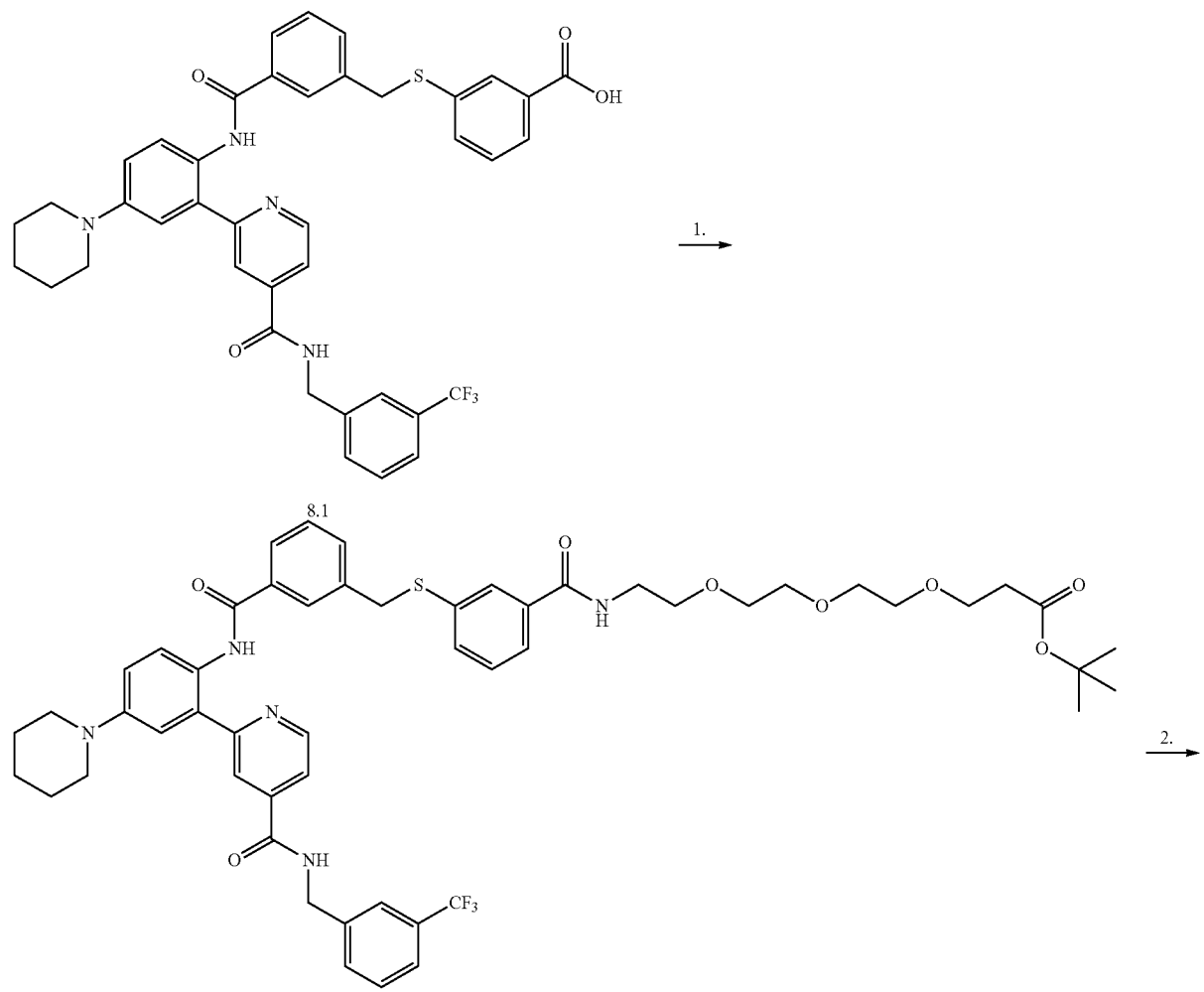

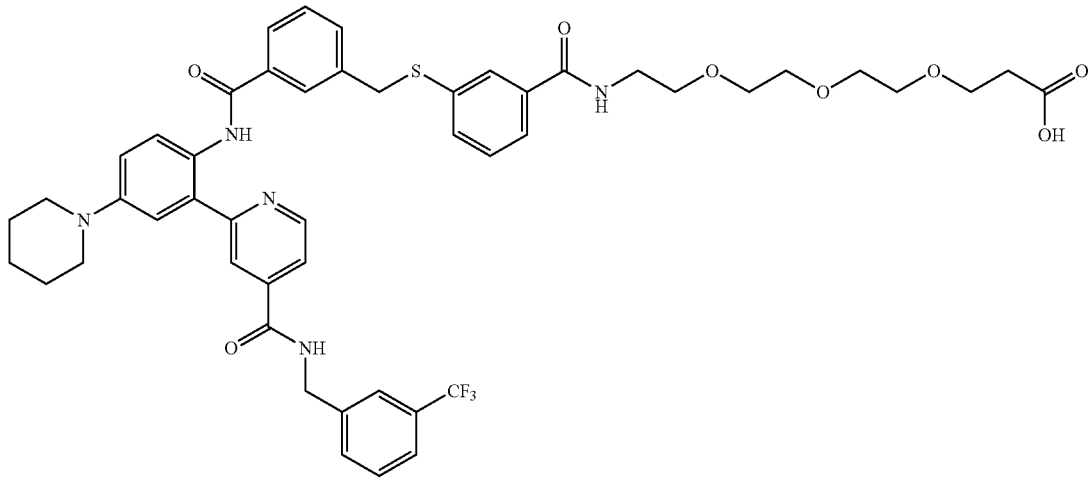

10.1

1. H₂NCH₂CH₂(OCH₂CH₂)₃CO₂(t-Bu), diisopropylethylamine, HATU;
2. TFA.

Intermediate 10.1b: tert-butyl 1-oxo-1-(3-(3-(4-(piperidin-1-yl)-2-(4-(3-(trifluoromethyl)-benzylcarbamoyl)pyridin-2-yl)phenylcarbamoyl)benzylthio)phenyl)-5,8,11-trioxa-2-azatetradecan-14-oate A solution of 25 mg of 3-(3-(4-(piperidin-1-yl)-2-(4-(3-(trifluoromethyl)-benzylcarbamoyl)pyridin-2-yl)phenylcarbamoyl)benzylthio)benzoic acid 8.1, 12 mg of tert-butyl 3-(2-(2-(2-aminoethoxy)ethoxy)ethoxy)propanoate, and 17.8 mg of diisopropylethylamine in 1 mL of DMF was treated with 15 mg of HATU. The mixture was stirred for 1 h and then the product was isolated by reverse phase HPLC eluting with 0.05% TFA in a water/acetonitrile gradient.

Example 10.1

1-oxo-1-(3-(3-(4-(piperidin-1-yl)-2-(4-(3-(trifluoromethyl)benzyl-carbamoyl)pyridin-2-yl)phenylcarbamoyl)benzylthio)phenyl)-5,8,11-trioxa-2-azatetradecan-14-oic acid tert-Butyl 1-oxo-1-(3-(((3-((4-(piperidin-1-yl)-2-(4-((3-(trifluoromethyl)benzyl)-carbamoyl)pyridin-2-yl)phenyl) carbamoyl)benzyl)thio)methyl)-phenyl)-5,8,11-trioxa-2-azatetradecan-14-oate 10.1b from the previous step was dissolved in 1 mL of 1:1 dichloromethane/TFA. After 45 minutes the solvent was evaporated in a stream of nitrogen and the residue was dissolved in 1:1 acetonitrile/water. Lyophilization gave 18 mg of product. $^1$H NMR (400 MHz, CD₃OD) δ 8.94 (d, J=5.2 Hz, 1H), 8.81 (d, J=9.2 Hz, 1H), 8.43 (s, 1H), 8.15 (s, 1H), 7.96 (s, 1H), 7.88-7.83 (m, 2H), 7.82 (t, J=1.8 Hz, 1H), 7.73-7.70 (m, 2H), 7.67 (d, J=7.4 Hz, 1H), 7.64-7.60 (m, 1H), 7.60-7.54 (m, 3H), 7.52-7.44 (m, 2H), 7.34 (t, J=7.8 Hz, 1H), 4.72 (d, J=4.2 Hz, 2H), 4.34 (s, 2H), 3.72-3.68 (m, 4H), 3.65 (t, J=6.3 Hz, 2H), 3.61-3.55 (m, 8H), 3.54-3.48 (m, 4H), 2.47 (t, J=6.3 Hz, 2H), 2.10-2.02 (m, 4H), 1.82 (s, 2H). MS (ES, m/z) 928 [M+H]⁺

Examples 10.2 Through 10.8

The compounds presented in Table 4 were prepared using the procedure described for the preparation of intermediate 10.1a TABLE 4
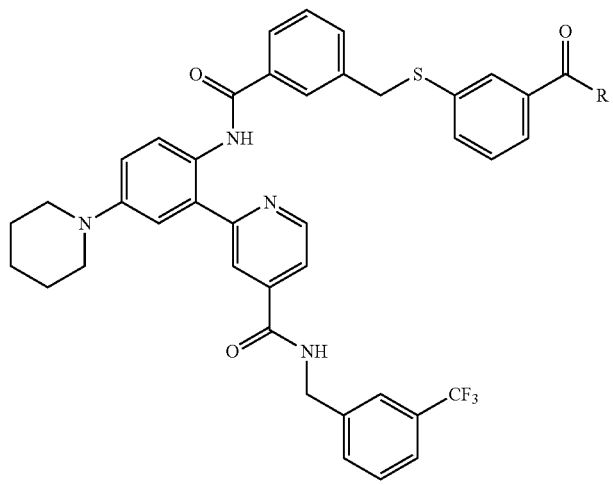
| Example No. | R | Mass Spectrum |
|---|---|---|
| 10.2 | —N(CH₃)-(1-methylpiperidin-4-yl) | 835 [M + H] |
| 10.3 | 4-methylpiperazin-1-yl | 807 [M + H] |
| 10.4 | —NH-(1-methylpiperidin-4-yl) | 821 [M + H] |
| 10.5 | —NH-CH₂CH₂-OCH₃ | 782 [M + H] |
| 10.6 | —NH-CH₂CH₂-morpholin-4-yl | 837 [M + H] |
| 10.7 | —N(CH₃)-CH₂CH₂-morpholin-4-yl | 851 [M + H] |
| 10.8 | —N(CH₃)-CH₂CH₂-N(CH₂CH₃)₂ | 837 [M + H] |

Examples 10.9 Through 10.12

The compounds presented in Table 5 were prepared using the method described for the synthesis of 1-oxo-1-(3-(((3-((4-(piperidin-1-yl)-2-(4-((3-(trifluoromethyl)benzyl)-carbamoyl)pyridin-2-yl)phenyl)carbamoyl)benzyl)thio)methyl)phenyl)-5,8,11-trioxa-2-azatetradecan-14-oic acid 10.1 from 3-(((3-((4-(piperidin-1-yl)-2-(4-((3-(trifluoromethylbenzyl)carbamoyl)pyridin-2-yl)phenyl)carbamoyl)benzyl)thio)methyl)-benzoic acid 9.3. The products were assayed by NMR and LCMS to confirm identity and purity.

TABLE 5

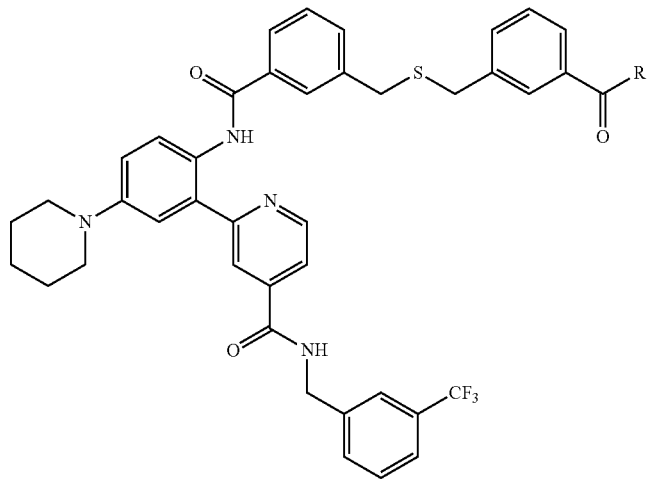

| Example No. | R | Mass Spectrum |
| --- | --- | --- |
| 10.9 | —NHCH₂COOH | 782 [M + H] |
| 10.10 | 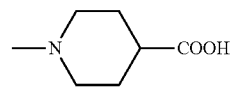 | 836 [M + H] |
| 10.11 | —NH(CH₂)₃COOH | 810 [M + H] |
| 10.12 | —NH(CH₂)₂COOH | 796 [M + H] |

Example 11.1

N2-Methyl-N2-(2-morpholinoethyl)-N6-(4-(piperidin-1-yl)-2-(4-((3-(trifluoromethyl)benzyl)carbamoyl)pyridin-2-yl)phenyl)pyridine-2,6-dicarboxamide

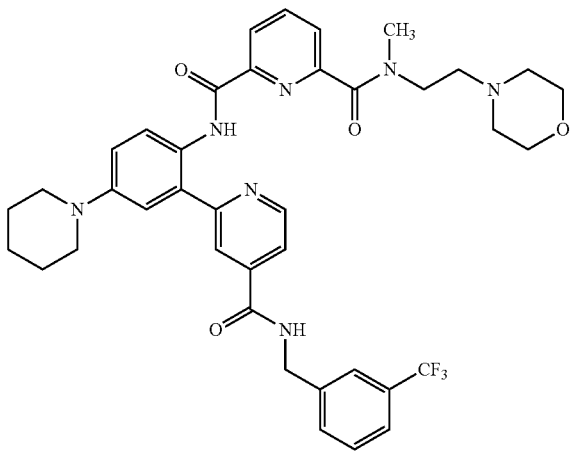 [SMILES: CN(CCN1CCOCC1)C(=O)c1cccc(C(=O)Nc2ccc(N3CCCCC3)cc2-c2cc(C(=O)NCc3cccc(C(F)(F)F)c3)ccn2)n1]

A solution of 25 mg of N-(3-(trifluoromethyl)benzyl)-2-(2-amino-5-(piperidin-1-yl)phenyl)isonicotinamide 4.1c, 28 mg of pyridine-2,6-dicarboxylic acid, and 4.3 mg of diisopropylethylamine in 1 mL of DMF was treated with 21 mg of HATU. After 2 h the mixture was separated by reverse phase HPLC, eluting with 0.05% TFA in a water/acetonitrile gradient. The isolated monoamide adduct of pyridine-2,6-dicarboxylic acid and 4.1c was dissolved in 2 mL of DMF and treated with 10 mg of N-methyl-2-morpholinoethanamine, 28 mg of diisopropylethylamine, and 23 mg of HATU. After 2 h the product was isolated by reverse phase HPLC. MS (ES, m/z) 730 [M+H]$^+$

Example 11.2

N1,5-Dimethyl-N1-(2-morpholinoethyl)-N3-(4-(piperidin-1-yl)-2-(4-((3-(trifluoromethyl)benzyl)carbamoyl)pyridin-2-yl)phenyl)isophthalamide

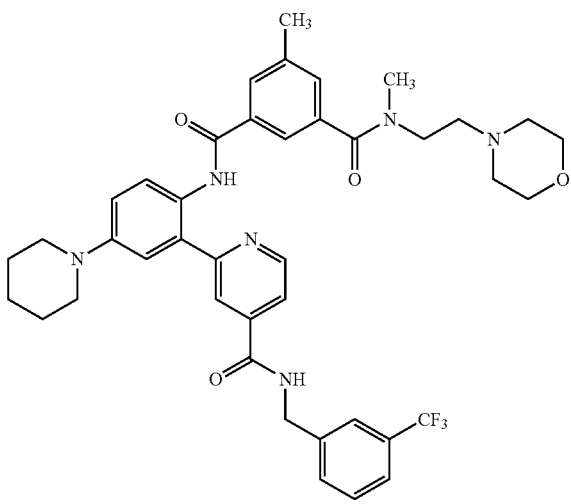 [SMILES: Cc1cc(C(=O)Nc2ccc(N3CCCCC3)cc2-c2cc(C(=O)NCc3cccc(C(F)(F)F)c3)ccn2)cc(C(=O)N(C)CCN2CCOCC2)c1]

This compound was prepared using the method described for the preparation of Example 11.2, using 5-methyl-isophthalic acid in place of pyridine-2,6-dicarboxylic acid. MS (ES, m/z) 743 [M+H]$^+$

Example 11.3

2-Methoxy-N1-methyl-N1-(2-morpholinoethyl)-N3-(4-(piperidin-1-yl)-2-(4-((3-(trifluoromethyl)benzyl)carbamoyl)pyridin-2-yl)phenyl)isophthalamide

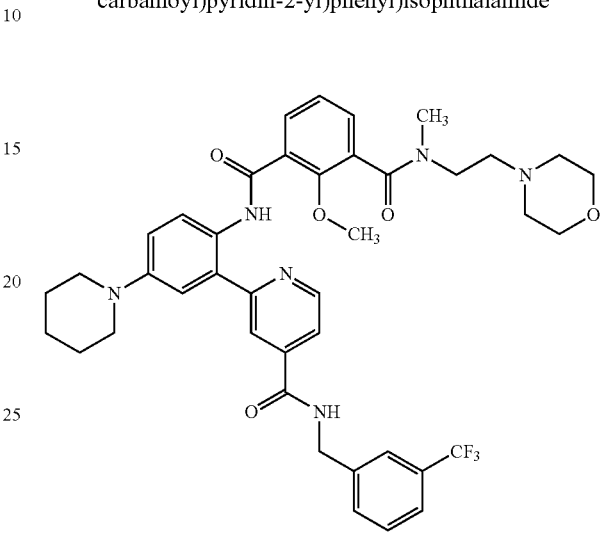

This compound was prepared using the method described for the preparation of Example 11.2, using 2-methoxy-isophthalic acid in place of pyridine-2,6-dicarboxylic acid. MS (ES, m/z) 759 [M+H]$^+$

Example 11.4

5-Methoxy-N1-methyl-N1-(2-morpholinoethyl)-N3-(4-(piperidin-1-yl)-2-(4-((3-(trifluoromethyl)benzyl)carbamoyl)pyridin-2-yl)phenyl)isophthalamide

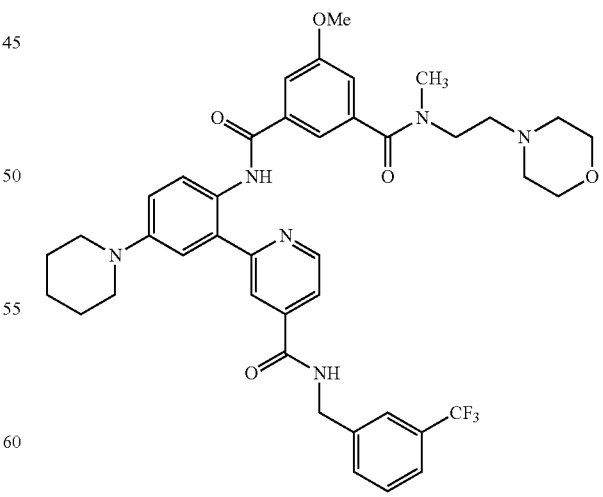

This compound was prepared using the method described for the preparation of Example 11.2, using 5-methoxy-isophthalic acid in place of pyridine-2,6-dicarboxylic acid. MS (ES, m/z) 759 [M+H]$^+$

Example 12.1

(S)-2-(2-(3-((3-((2-Methoxyethyl)carbamoyl)piperidin-1-yl)methyl)benzamido)-5-(piperidin-1-yl)phenyl)-N-(3-(trifluoromethyl)benzyl)isonicotinamide

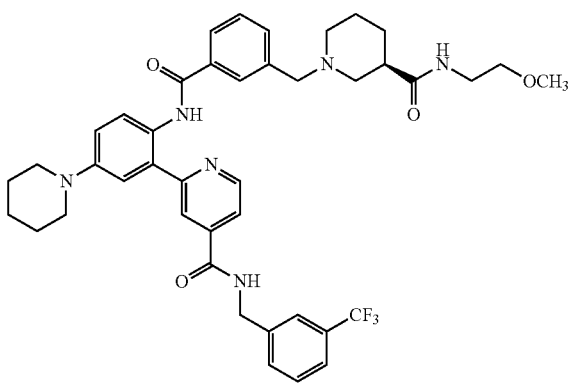 [SMILES: COCCNC(=O)[C@@H]1CCCN(Cc2cccc(C(=O)Nc3ccc(N4CCCCC4)cc3-c3cc(C(=O)NCc4cccc(C(F)(F)F)c4)ccn3)c2)C1]

A mixture of 20 mg of 2-(2-(3-(chloromethyl)benzamido)-5-(piperidin-1-yl)phenyl)-N-(3-(trifluoromethyl)benzyl)isonicotinamide 8.1a, 8.8 mg of (S)—N-(2-methoxyethyl)piperidine-3-carboxamide and 13.7 mg of $K_2CO_3$ in 0.33 mL of DMF was stirred for 2 h. The product was isolate by preparative reverse phase HPLC eluting with 0.05% TFA in a water/acetonitrile gradient to give 23 mg of product. MS (ES, m/z) 757.3 $[M+H]^+$

Example 12.2

(R)-2-(2-(3-((3-((2-Methoxyethyl)carbamoyl)piperidin-1-yl)methyl)benzamido)-5-(piperidin-1-yl)phenyl)-N-(3-(trifluoromethyl)benzyl)isonicotinamide

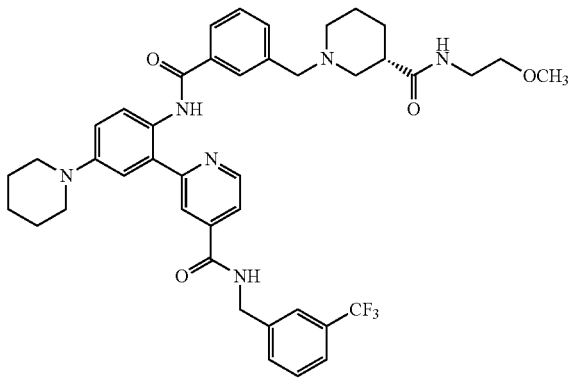 [SMILES: COCCNC(=O)[C@H]1CCCN(Cc2cccc(C(=O)Nc3ccc(N4CCCCC4)cc3-c3cc(C(=O)NCc4cccc(C(F)(F)F)c4)ccn3)c2)C1]

This compound was prepared by the procedure described for the preparation of its enantiomer. MS (ES, m/z) 757.3 $[M+H]^+$

Example 14

3-((3-((4-Morpholino-2-(4-((3-(trifluoromethyl)benzyl)carbamoyl)pyridin-2-yl)phenyl)carbamoyl)benzyl)thio)propanoic acid Scheme 20.

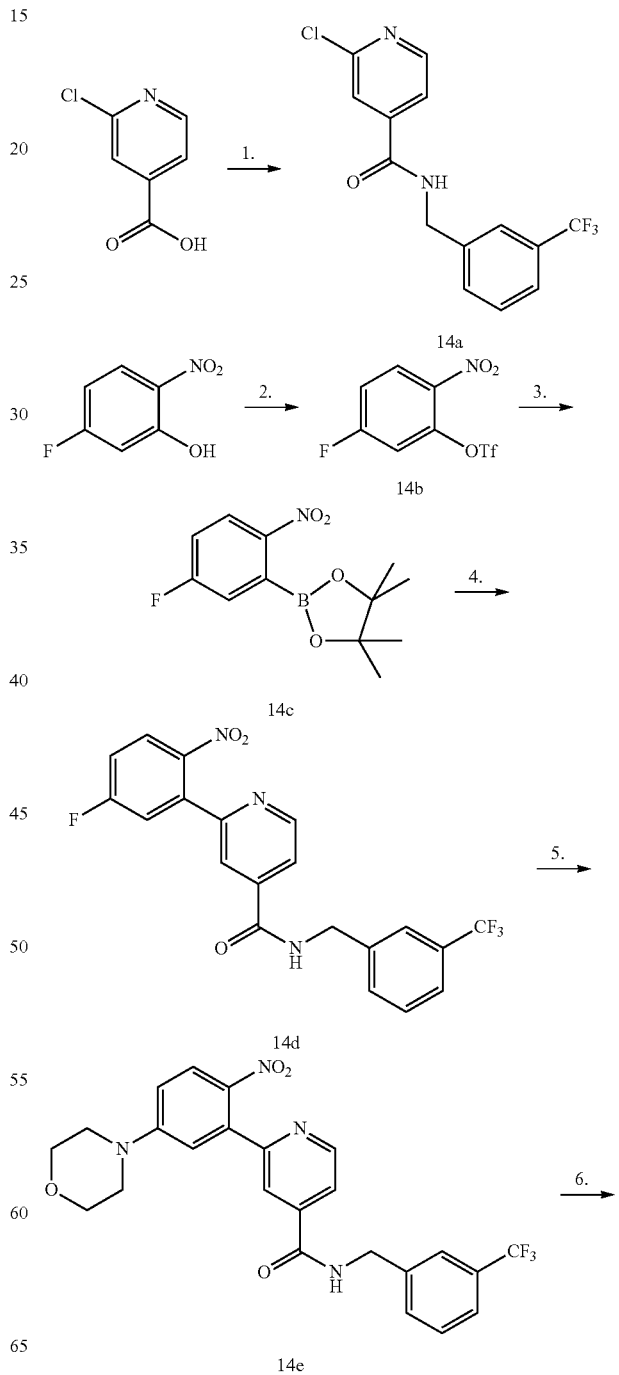

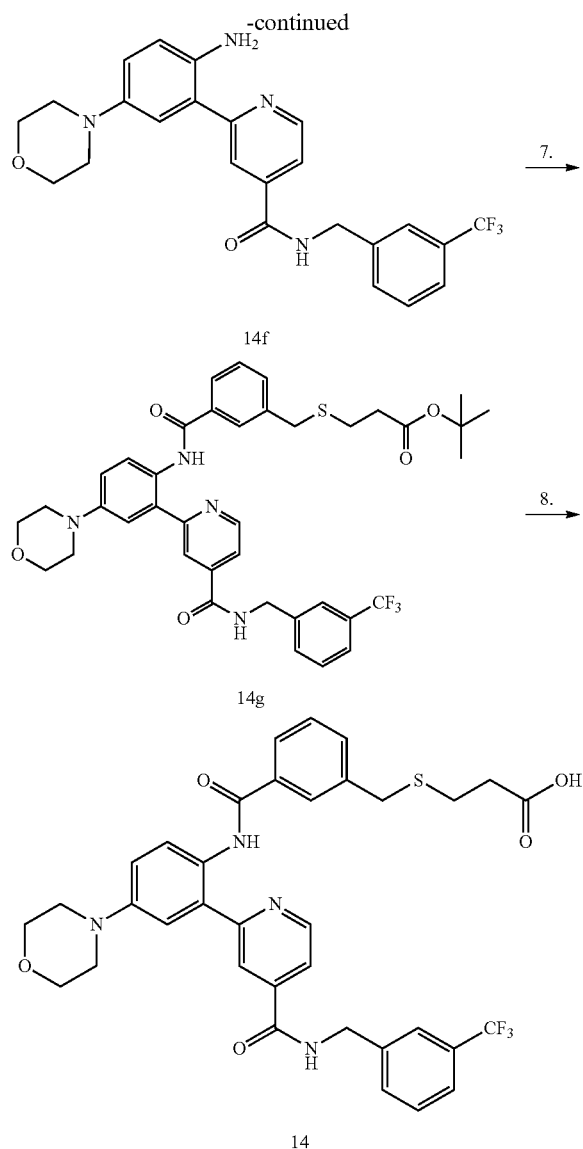

1. 3-Trifluoromethyl benzylamine, EDC•HCl, DMAP;
2. Tf₂O, pyridine;
3. Pd(dppf)Cl₂/KOAc, 1,4-dioxane, 4,4,4',4',5,5,5',5'-octamethyl-2,2'-bi(1,3,2-dioxaborolane);
4. Pd(dppf)Cl₂, X-PHOS, K₃PO₄, DME/H₂O, intermediate 14a;
5. K₂CO₃, DMF, morpholine;
6. Pd/C, H₂, MeOH;
7. EDC•HCl, DMAP, DMF, 3-((3-tert-butoxy-3-oxopyropylthio)methyl)benzoic acid 1.1c;
8. CF₃COOH, DCM.

Intermediate 14a: N-(3-(trifluoromethyl)benzyl)-2-chloroisonicotinamide

Into a 500-mL round bottom flask, was placed a solution of 2-chloroisonicotinic acid (18 g, 113.92 mmol, 2.00 equiv) in dichloromethane (200 mL), 3-(trifluoromethyl)benzylamine (10 g, 57.14 mmol, 1.00 equiv), EDC.HCl (22 g, 115.18 mmol, 2.00 equiv), and 4-dimethylaminopyridine (14 g, 114.75 mmol, 2.00 equiv). The resulting solution was stirred for 3 h at 25° C. The resulting solution was diluted with 500 mL of dichloromethane. The resulting mixture was washed with 2×50 mL of aqueous NH₄Cl, 1×50 mL of 10% sodium bicarbonate, and 1×50 mL of brine. The mixture was dried over anhydrous sodium sulfate and concentrated under vacuum. The residue was applied onto a silica gel column and eluted with petroleum ether/ethyl acetate (5:1). The product was obtained as 11.8 g (63%) of a white solid.

Intermediate 14b: 5-fluoro-2-nitrophenyl trifluoromethanesulfonate

Into a 250-mL round bottom flask, was placed a solution of 5-fluoro-2-nitrophenol (5 g, 31.85 mmol, 1.00 equiv) in pyridine (25 mL). This was followed by the addition of trifluoromethanesulfonic anhydride (9.6 g, 34.04 mmol, 1.07 equiv) dropwise with stirring at 0° C. The resulting solution was stirred for 1 h at 0° C., overnight at room temperature. The resulting solution was diluted with 100 mL of water. The resulting solution was extracted with 3×100 mL of dichloromethane and the organic layers combined. The resulting mixture was washed with 3×100 mL of water. The mixture was dried over anhydrous sodium sulfate and concentrated under vacuum. The product was obtained as 5 g (54%) of a yellow oil.

Intermediate 14c: 2-(5-fluoro-2-nitrophenyl)-4,4,5,5-tetramethyl-1,3,2-dioxaborolane Into a 250-mL round bottom flask purged and maintained with an inert atmosphere of nitrogen, was placed a solution of 5-fluoro-2-nitrophenyl trifluoromethanesulfonate (18 g, 62.28 mmol, 1.00 equiv) in 1,4-dioxane (150 mL), 4,4,4',4',5,5,5',5'-octamethyl-2,2'-bi(1,3,2-dioxaborolane) (24 g, 94.49 mmol, 1.50 equiv), Pd(dppf)Cl₂ (1.5 mg, 0.03 equiv), and potassium acetate (12.6 g, 128.44 mmol, 2.00 equiv). The resulting solution was stirred overnight at 80° C. The mixture was concentrated under vacuum. The residue was applied onto a silica gel column and eluted with petroleum ether/ethyl acetate (1:5~ethyl acetate). The product was obtained as 10 g (60%) of a yellow solid.

Intermediate 14d

N-(3-(trifluoromethyl)benzyl)-2-(5-fluoro-2-nitrophenyl)-isonicotinamide

Into a 500-mL round bottom flask purged and maintained with an inert atmosphere of nitrogen, was placed a solution of 2-(5-fluoro-2-nitrophenyl)-4,4,5,5-tetramethyl-1,3,2-dioxaborolane (11.8 g, 44.19 mmol, 3.00 equiv) in 330 mL of 10:1 DME/H₂O, N-(3-(trifluoromethyl)benzyl)-2-chloroisonicotinamide (5 g, 15.92 mmol, 1.00 equiv), Pd(PPh₃)₂Cl₂ (2.54 g, 3.62 mmol, 0.20 equiv), X-PHOS (2.5 g, 6.36 mmol, 0.20 equiv), and K₃PO₄ (20 g, 59.17 mmol, 4.00 equiv). The resulting solution was stirred overnight at 80° C. The resulting mixture was concentrated under vacuum. The residue was applied onto a silica gel column and eluted with ethyl acetate/petroleum ether (1:5~1). The product was obtained as 2 g (27%) of a brown oil.

Intermediate 14e: N-(3-(trifluoromethyl)benzyl)-2-(5-morpholino-2-nitrophenyl)-isonicotinamide Into a 50-mL round bottom flask, was placed a solution of N-(3-(trifluoromethyl)benzyl)-2-(5-fluoro-2-nitrophenyl)

isonicotinamide 14d (200 mg, 0.48 mmol, 1.00 equiv) in N,N-dimethylformamide (2 mL), morpholine (80 mg, 0.90 mmol, 1.70 equiv), and potassium carbonate (0.2 g, 3.00 equiv). The resulting solution was stirred overnight at 80° C. The solids were filtered out. The resulting mixture was concentrated under vacuum to yield 0.1 g of crude product as a yellow oil.

Intermediate 14f: N-(3-(trifluoromethyl)benzyl)-2-(2-amino-5-morpholinophenyl)-isonicotinamide Into a 50-mL round bottom flask, was placed a solution of N-(3-(trifluoromethyl)benzyl)-2-(5-morpholino-2-nitrophenyl)isonicotinamide (100 mg, 0.21 mmol, 1.00 equiv) in methanol (5 mL). The solution was treated with Pd/C (100 mg), and stirred under an atmosphere of hydrogen overnight at room temperature. The solids were filtered out. The resulting mixture was concentrated under vacuum to yield 50 mg (53%) of product as a yellow oil.

Intermediate 14g: tert-butyl 3-(3-((2-(4-((3-(trifluoromethyl)benzyl)carbamoyl)pyridin-2-yl)-4-morpholinophenyl)carbamoyl)benzylthio)propanoate Into a 50-mL round bottom flask, was placed a solution of N-(3-(trifluoromethyl)benzyl)-2-(2-amino-5-morpholinophenyl)isonicotinamide (200 mg, 0.44 mmol, 1.00 equiv) in N,N-dimethylformamide (5 mL), 3-((3-tert-butoxy-3-oxopropylthio)methyl)benzoic acid 1.1c (200 mg, 0.68 mmol, 1.50 equiv), EDC.HCl (160 mg, 0.84 mmol, 2.00 equiv), and 4-dimethylaminopyridine (60 mg, 0.49 mmol, 1.00 equiv). The resulting solution was stirred for 2 h at room temperature. After a conventional aqueous/organic workup, the resulting mixture was concentrated under vacuum to yield 100 mg of crude product as a yellow oil.

Example 14

3-(3-((2-(4-((3-(trifluoromethyl)benzyl)carbamoyl)pyridin-2-yl)-4-morpholinophenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-morpholinophenyl)carbamoyl)benzylthio)propanoate (100 mg, 0.14 mmol, 1.00 equiv) in dichloromethane (5 mL), and trifluoroacetic acid (0.1 mL). The resulting solution was stirred overnight at room temperature. The reaction progress was monitored by LCMS. The resulting mixture was concentrated under vacuum. The crude product (100 mg) was purified by reverse phase HPLC eluting with a water/CH$_3$CN gradient containing 0.05% TFA. The product was obtained as 14 mg (15%) of a yellow solid. $^1$H-NMR (300 MHz, CDCl$_3$, ppm): δ 13.55 (s, 1H), 9.09 (s, 1H), 8.96-8.78 (m, 2H), 8.72 (s, 1H), 8.65 (s, 1H), 8.25-8.09 (m, 3H), 8.05-7.90 (m, 8H), 4.73 (d, J=5.4 Hz, 2H), 4.13 (s, 4H), 3.82 (s, 2H), 3.47 (s, 4H), 2.75-2.57 (m, 4H). MS (ES, m/z): 679 [M+H]$^+$.

Example 15

3-((3-((4-Isopropoxy-2-(4-((3-(trifluoromethyl)benzyl)carbamoyl)pyridin-2-yl)phenyl)carbamoyl)benzyl)thio)propanoic acid

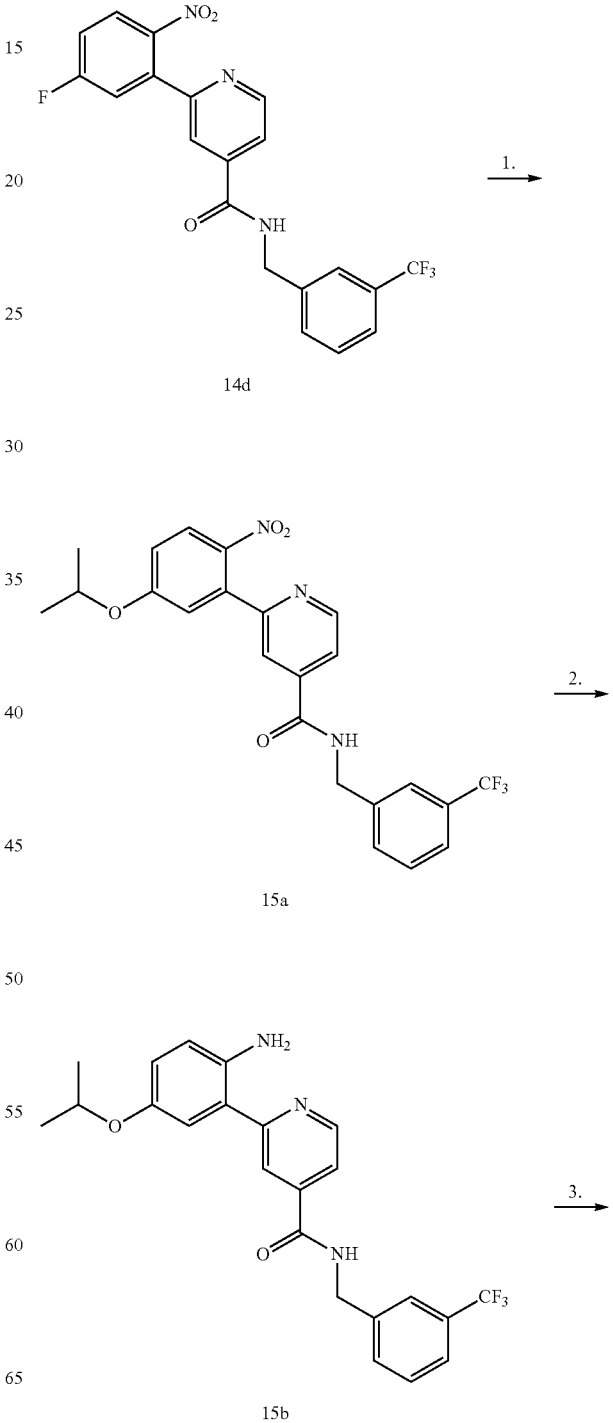

Scheme 21.

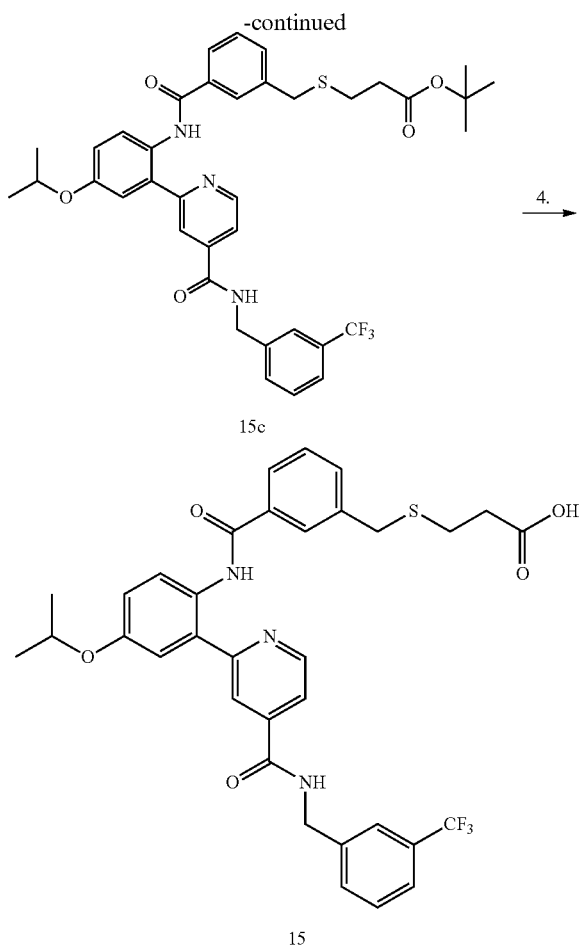

1. isopropanol, NaH, DMF;
2. Pd/C H₂, MeOH, DCM;
3. EDC·HCl,DMAP/DCM, 3-((3-tert-butoxy-3-oxopropylthio)methyl)benzoic acid 1.1c;
4. TFA, DCM.

Intermediate 15a: N-(3-(trifluoromethyl)benzyl)-2-(5-isopropoxy-2-nitrophenyl)-isonicotinamide Into a 50-mL round bottom flask, was placed a solution of propan-2-ol (2 mL) in N,N-dimethylformamide (5 mL), sodium hydride (72 mg, 3.00 mmol, 5.00 equiv), and N-(3-(trifluoromethyl)benzyl)-2-(5-fluoro-2-nitrophenyl)isonicotinamide 14d (250 mg, 0.58 mmol, 1.00 equiv, 98%). The resulting solution was stirred for 3 h at 60° C. in an oil bath. The resulting solution was diluted with 200 mL of ethyl acetate and washed with 3×30 mL of brine. The mixture was dried over anhydrous sodium sulfate and concentrated under vacuum to yield 280 mg (99%) of product as a brown oil.

Intermediate 15b: N-(3-(trifluoromethyl)benzyl)-2-(2-amino-5-isopropoxyphenyl)-isonicotinamide Into a 100-mL round bottom flask, was placed a solution of N-(3-(trifluoromethyl)benzyl)-2-(5-isopropoxy-2-nitrophenyl)isonicotinamide (270 mg, 0.53 mmol, 1.00 equiv, 90%) in dichloromethane/methanol (3/6 mL). The solution was treated with Pd/C (270 mg), and stirred under an atmosphere of hydrogen for 2 h at room temperature. The solids were filtered out. The filtrate was concentrated under vacuum to yield 230 mg (91%) of product as a brown oil.

Intermediate 15c: tert-butyl 3-(3-((2-(4-((3-(trifluoromethyl)benzyl)carbamoyl)pyridin-2-yl)-4-isopropoxyphenyl)carbamoyl)benzylthio)propanoate Into a 50-mL round bottom flask, was placed a solution of N-(3-(trifluoromethyl)benzyl)-2-(2-amino-5-isopropoxyphenyl)isonicotinamide (230 mg, 0.48 mmol, 1.00 equiv, 90%) in dichloromethane (8 mL), 3-((3-tert-butoxy-3-oxopropylthio)methyl)benzoic acid 1.1c (317 mg, 0.86 mmol, 2.00 equiv, 80%), EDC.HCl (206 mg, 1.07 mmol, 2.00 equiv), and 4-dimethylaminopyridine (131 mg, 1.07 mmol, 2.00 equiv). The resulting solution was stirred for 2 h at 25° C. The resulting solution was diluted with 100 mL of ethyl acetate and washed with 1×20 mL of aqueous NH₄Cl, 1×20 mL of 10% sodium bicarbonate, and 1×20 mL of brine. The mixture was dried over sodium sulfate and concentrated under vacuum. The residue was applied onto a silica gel column and eluted with ethyl acetate/petroleum ether (1:2). The product was obtained as 240 mg (60%) of a brown oil.

Example 15

3-(3-((2-(4-((3-(trifluoromethyl)benzyl)carbamoyl)pyridin-2-yl)-4-isopropoxyphenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-isopropoxyphenyl)carbamoyl)-benzylthio)propanoate (230 mg, 0.28 mmol, 1.00 equiv, 85%) in dichloromethane (5 mL), and trifluoroacetic acid (1 mL). The resulting solution was stirred for 2 h at room temperature. The resulting mixture was concentrated under vacuum. The crude product (180 mg) was purified by reverse phase HPLC eluting with a water/CH₃CN gradient containing 0.05% TFA. The product was obtained as 139.8 mg (76%) of a white solid.
$^1$H-NMR (400 MHz, DMSO-d₆, ppm): δ 12.52 (s, 1H), 12.23 (s, 1H), 9.57 (t, J=8 Hz, 1H), 8.96 (d, J=4 Hz, 1H), 8.41-8.36 (m, 2H), 7.88-7.84 (m, 2H), 7.79-7.63 (m, 2H), 7.60-7.52 (m, 2H), 7.50-7.48 (m, 4H), 7.16-7.13 (d, J=12 Hz, 1H), 4.76-4.70 (m, 1H), 4.62 (d, J=6 Hz, 2H), 3.88 (s, 2H), 2.63-2.53 (m, 4H), 1.30 (s, 6H). MS (ES, m/z): 652 [M+H]⁺.

Example 16

3-((3-((4-((tetrahydro-2H-pyran-4-yl)oxy)-2-(4-((3-(trifluoromethyl)benzyl)-carbamoyl)pyridin-2-yl)phenyl)carbamoyl)benzyl)thio)propanoic acid Scheme 22.

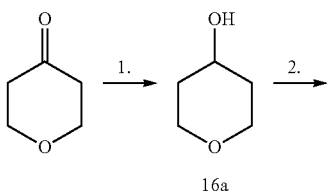

16a

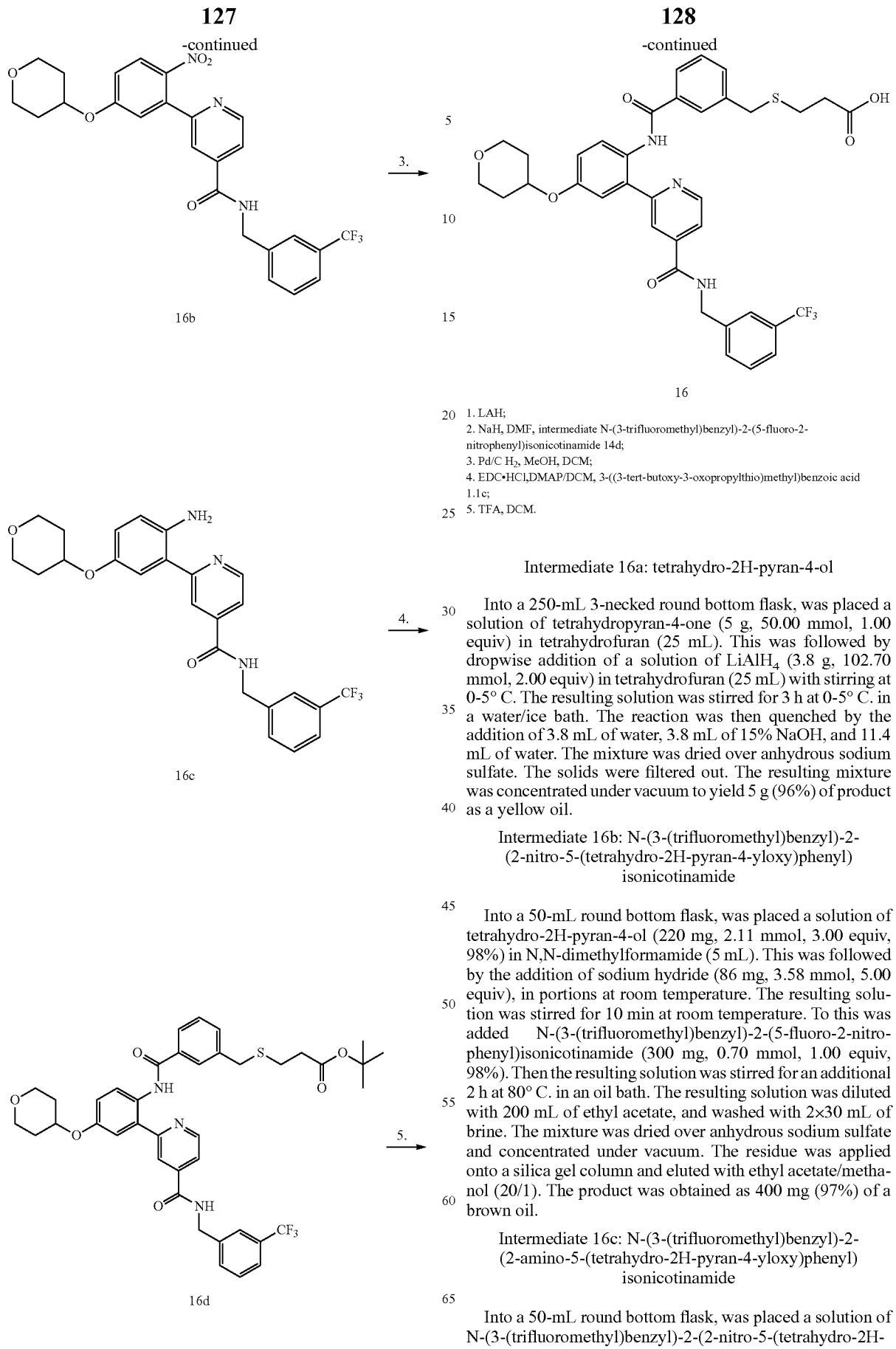

1. LAH;
2. NaH, DMF, intermediate N-(3-trifluoromethyl)benzyl)-2-(5-fluoro-2-nitrophenyl)isonicotinamide 14d;
3. Pd/C H₂, MeOH, DCM;
4. EDC•HCl,DMAP/DCM, 3-((3-tert-butoxy-3-oxopropylthio)methyl)benzoic acid 1.1c;
5. TFA, DCM.

Intermediate 16a: tetrahydro-2H-pyran-4-ol

Into a 250-mL 3-necked round bottom flask, was placed a solution of tetrahydropyran-4-one (5 g, 50.00 mmol, 1.00 equiv) in tetrahydrofuran (25 mL). This was followed by dropwise addition of a solution of LiAlH₄ (3.8 g, 102.70 mmol, 2.00 equiv) in tetrahydrofuran (25 mL) with stirring at 0-5° C. The resulting solution was stirred for 3 h at 0-5° C. in a water/ice bath. The reaction was then quenched by the addition of 3.8 mL of water, 3.8 mL of 15% NaOH, and 11.4 mL of water. The mixture was dried over anhydrous sodium sulfate. The solids were filtered out. The resulting mixture was concentrated under vacuum to yield 5 g (96%) of product as a yellow oil.

Intermediate 16b: N-(3-(trifluoromethyl)benzyl)-2-(2-nitro-5-(tetrahydro-2H-pyran-4-yloxy)phenyl)isonicotinamide Into a 50-mL round bottom flask, was placed a solution of tetrahydro-2H-pyran-4-ol (220 mg, 2.11 mmol, 3.00 equiv, 98%) in N,N-dimethylformamide (5 mL). This was followed by the addition of sodium hydride (86 mg, 3.58 mmol, 5.00 equiv), in portions at room temperature. The resulting solution was stirred for 10 min at room temperature. To this was added N-(3-(trifluoromethyl)benzyl)-2-(5-fluoro-2-nitrophenyl)isonicotinamide (300 mg, 0.70 mmol, 1.00 equiv, 98%). Then the resulting solution was stirred for an additional 2 h at 80° C. in an oil bath. The resulting solution was diluted with 200 mL of ethyl acetate, and washed with 2×30 mL of brine. The mixture was dried over anhydrous sodium sulfate and concentrated under vacuum. The residue was applied onto a silica gel column and eluted with ethyl acetate/methanol (20/1). The product was obtained as 400 mg (97%) of a brown oil.

Intermediate 16c: N-(3-(trifluoromethyl)benzyl)-2-(2-amino-5-(tetrahydro-2H-pyran-4-yloxy)phenyl)isonicotinamide Into a 50-mL round bottom flask, was placed a solution of N-(3-(trifluoromethyl)benzyl)-2-(2-nitro-5-(tetrahydro-2H- pyran-4-yloxy)phenyl)isonicotinamide (400 mg, 0.76 mmol, 1.00 equiv, 95%) in methanol/dichloromethane (10/5 mL). The solution was treated with Pd/C (400 mg), and stirred under an atmosphere of hydrogen for 2 h at room temperature. The solids were filtered out. The resulting mixture was concentrated under vacuum to yield 270 mg (68%) of product as a brown oil.

Intermediate 16d: tert-butyl 3-(3-((2-(4-((3-(trifluoromethyl)benzyl)carbamoyl)pyridin-2-yl)-4-(tetrahydro-2H-pyran-4-yloxy)phenyl)carbamoyl)benzylthio)propanoate Into a 50-mL round bottom flask, was placed a solution of N-(3-(trifluoromethyl)benzyl)-2-(2-amino-5-(tetrahydro-2H-pyran-4-yloxy)phenyl)isonicotinamide (270 mg, 0.52 mmol, 1.00 equiv, 90%) in dichloromethane (10 mL), 3-((3-tert-butoxy-3-oxopropylthio)methyl)benzoic acid (339 mg, 0.92 mmol, 2.00 equiv, 80%), EDC.HCl (220 mg, 1.15 mmol, 2.00 equiv), and 4-dimethylaminopyridine (140 mg, 1.15 mmol, 2.00 equiv). The resulting solution was stirred for 3 h at 25° C. The resulting solution was diluted with 150 mL of dichloromethane and was washed with 1×20 mL of aqueous NH₄Cl, 1×20 mL of 10% sodium bicarbonate, and 1×20 mL of brine. The mixture was dried over sodium sulfate and concentrated under vacuum. The residue was applied onto a silica gel column and eluted with ethyl acetate/petroleum ether (1:1)~dichloromethane:methanol (20:1). The product was obtained as 190 mg (42%) of a brown oil.

Example 16

3-(3-((2-(4-((3-(trifluoromethyl)benzyl)carbamoyl)pyridin-2-yl)-4-(tetrahydro-2H-pyran-4-yloxy)phenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-(tetrahydro-2H-pyran-4-yloxy)phenyl)carbamoyl)benzylthio)propanoate (190 mg, 0.20 mmol, 1.00 equiv, 80%) in dichloromethane (5 mL), and trifluoroacetic acid (1 mL). The resulting solution was stirred for 3 h at room temperature. The resulting mixture was concentrated under vacuum. The crude product (100 mg) was purified by reverse phase HPLC eluting with a water/CH₃CN gradient containing 0.05% TFA. The product was obtained as 82.4 mg (57%) of as a yellow solid. ¹H-NMR (300 MHz, CD₃OD, ppm): δ 8.94 (d, J=3 Hz, 1H), 8.30 (s, 1H), 8.22 (d, J=9 Hz, 1H), 7.89-7.85 (m, 2H), 7.77 (d, J=9 Hz, 1H), 7.70 (s, 1H), 7.66-7.52 (m, 4H), 7.48-7.43 (m, 2H), 7.19-7.15 (q, J=9 Hz, 1H), 4.69 (s, 3H), 4.01-3.95 (m, 2H), 3.86 (s, 2H), 3.66-3.58 (m, 2H), 2.73-2.68 (m, 2H), 2.59-2.54 (m, 2H), 2.06 (m, 2H), 1.80-1.76 (m, 2H). MS (ES, m/z): 694 [M+H]⁺.

Example 17

3-(3-((2-(4-((3-(trifluoromethyl)benzyl)carbamoyl)pyridin-2-yl)-4-(bis(2-methoxyethyl)amino)phenyl)carbamoyl)benzylthio)propanoic acid Scheme 23.

-continued

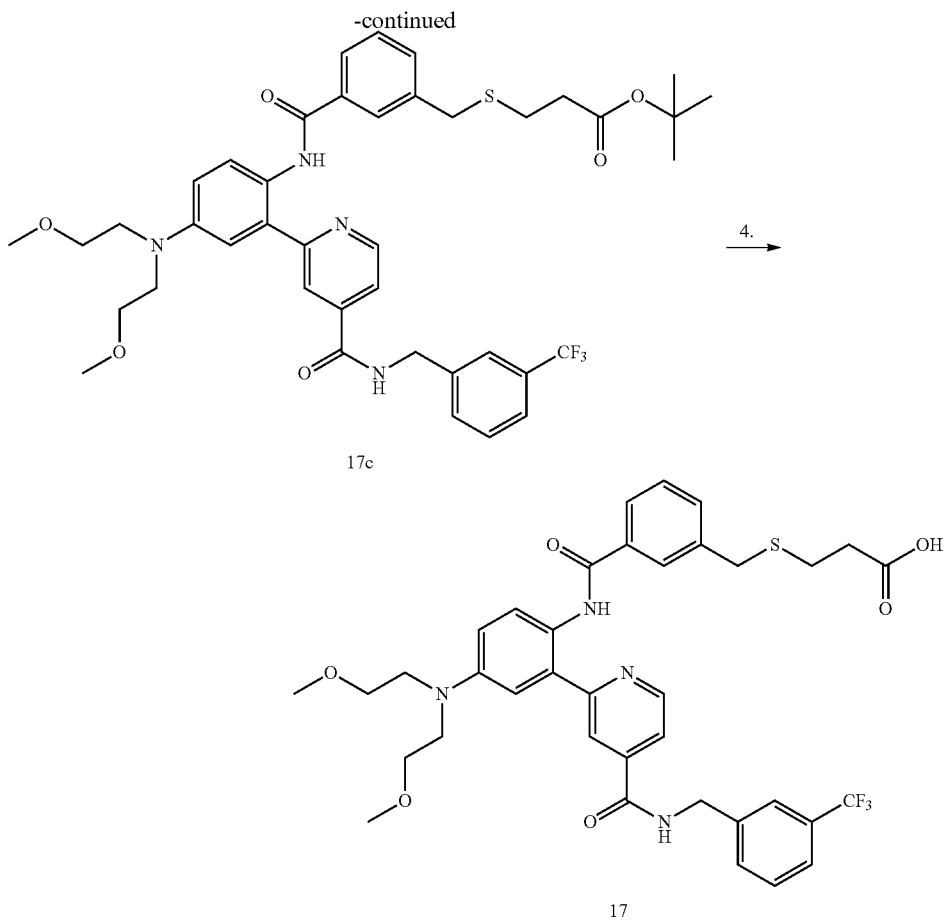

17c

17

1. Diisopropyethylamine, bis(2-methoxyethyl)amine, DMF; 2. Pd/C H₂, MeOH, DCM; 3. EDC·HCl, DMAP, DCM, 3-((3-tert-butoxy-3-oxopropylthio)methyl)benzoic acid 1.1c; 4. TFA, DCM.

Intermediate 17a: N-(3-(trifluoromethyl)benzyl)-2-(5-(bis(2-methoxyethyl)amino)-2-nitrophenyl)isonicotinamide Into a 10-mL vial, was placed a solution of bis(2-methoxyethyl)amine (285.6 mg, 2.15 mmol, 3.00 equiv) in N,N-dimethylformamide (3 mL), and N,N-diisopropylethylamine (277 mg, 2.14 mmol, 2.99 equiv). This was followed by the addition of a solution of N-(3-(trifluoromethyl)benzyl)-2-(5-fluoro-2-nitrophenyl)isonicotinamide (300 mg, 0.72 mmol, 1.00 equiv) in N,N-dimethylformamide (2 mL). The resulting solution was stirred for 48 h at 80° C. in an oil bath. The reaction progress was monitored by LCMS. The resulting solution was diluted with 50 mL of water. The resulting solution was extracted with 3×50 mL of ethyl acetate and the organic layers combined. The resulting mixture was washed with 2×70 mL of brine. The mixture was dried over anhydrous sodium sulfate and concentrated under vacuum. The residue was applied onto a silica gel column and eluted with ethyl acetate/petroleum ether (1:5~1). The product was obtained as 270 mg (71%) of a yellow to green oil.

Intermediate 17b: N-(3-(trifluoromethyl)benzyl)-2-(2-amino-5-(bis(2-methoxyethyl)-amino)phenyl)isonicotinamide Into a 50-mL round bottom flask, was placed a solution of N-(3-(trifluoromethyl)benzyl)-2-(5-(bis(2-methoxyethyl) amino)-2-nitrophenyl)-isonicotinamide (270 mg, 0.51 mmol, 1.00 equiv) in methanol (10 mL). The solution was treated with Pd/C (300 mg), and stirred under an atmosphere of hydrogen for 2 h at room temperature in a water bath. The solids were filtered out. The resulting mixture was concentrated under vacuum to yield 180 mg (71%) of product as a yellow to green oil.

Intermediate 17c: tert-butyl 3-(3-((2-(4-((3-(trifluoromethyl)benzyl)carbamoyl)pyridin-2-yl)-4-(bis(2-methoxyethyl)amino)phenyl)carbamoyl)benzylthio)propanoate Into a 10-mL vial, was placed a solution of 3-((3-tert-butoxy-3-oxopropylthio)methyl)benzoic acid (188.64 mg, 0.64 mmol, 2.00 equiv) in dichloromethane (5 mL), EDC.HCl (120.8 mg, 0.63 mmol, 1.98 equiv), 4-dimethylaminopyridine (77.6 mg, 0.64 mmol, 2.00 equiv), and N-(3-(trifluoromethyl)benzyl)-2-(2-amino-5-(bis(2-methoxyethyl)amino)phenyl)-isonicotinamide (160 mg, 0.32 mmol, 1.00 equiv). The resulting solution was stirred for 2 h at 25° C. in an oil bath. The reaction progress was monitored by LCMS. The resulting solution was diluted with 50 mL of dichloromethane, and washed with 3×50 mL of aqueous NH₄Cl. The mixture was dried over anhydrous sodium sulfate and concentrated under vacuum. The residue was applied onto a silica gel column and eluted with ethyl acetate/petroleum ether (1:5~1). The product was obtained as 160 mg (64%) of a yellow solid.

Example 17

3-(3-((2-(4-((3-(trifluoromethyl)benzyl)carbamoyl)pyridin-2-yl)-4-(bis(2-methoxyethyl)amino)phenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-(bis(2-methoxyethyl)amino)phenyl)-carbamoyl)benzylthio)propanoate (160 mg, 0.21 mmol, 1.00 equiv) in dichloromethane (8 mL), and trifluoroacetic acid (2 mL). The resulting solution was stirred for 4 h at 25° C. in an oil bath. The reaction progress was monitored by LCMS. The resulting mixture was concentrated under vacuum. The crude product (125 mg) was purified by reverse phase HPLC eluting with a water/CH₃CN gradient containing 0.05% TFA. The product was obtained as 81.1 mg (41%) of as a yellow solid.
¹H-NMR (300 MHz, DMSO, ppm): δ 11.86 (s, 1H), 9.49 (t, J=5.7 Hz, 1H), 8.94 (d, J=5.1 Hz, 1H), 8.25 (s, 1H), 8.12 (d, J=6.5 Hz, 1H), 7.82 (s, 2H), 7.71 (m, 2H), 7.62 (m, 5H), 7.15 (d, J=2.4 Hz, 1H), 6.90 (m, 1H), 4.61 (d, J=6.0 Hz, 2H), 3.87 (s, 2H), 3.56 (m, 8H), 3.27 (s, 6H), 2.63 (m, 2H), 2.51 (m, 2H). MS (ES, m/z): 725 [M+H]⁺.

Example 18

3-((3-((4-Fluoro-2-(4-((3-(trifluoromethyl)benzyl)carbamoyl)pyridin-2-yl)phenyl)carbamoyl)benzyl)thio)propanoic acid Scheme 24.

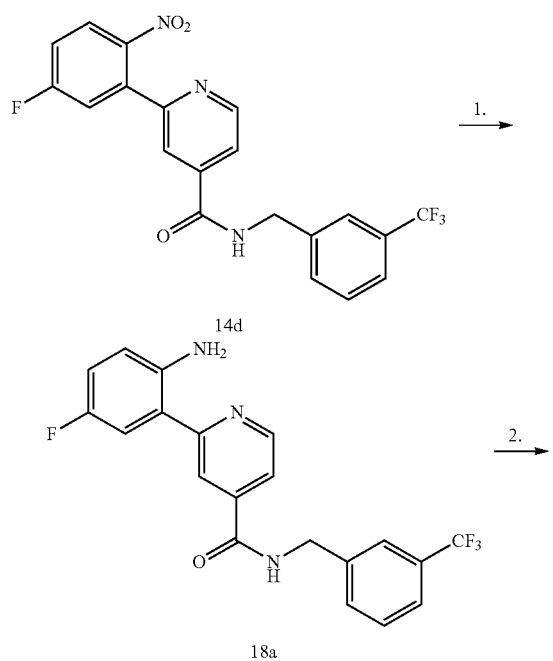

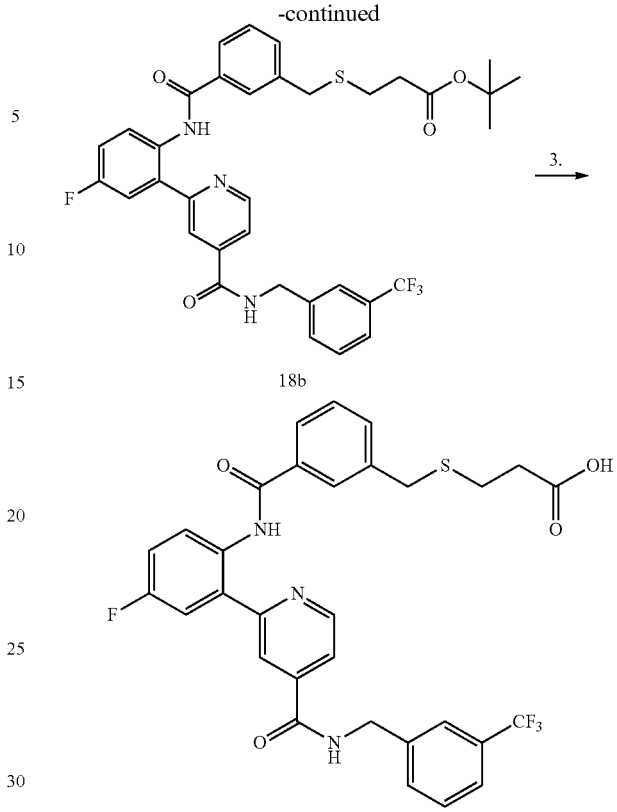

1. Pd/C H₂, MeOH; 2. EDC•HCl, DMAP, DMF, 3-((3-tert-butoxy-3-oxopropylthio)methyl)benzoic acid 1.1c; 3. CF₃COOH, DCM.

Intermediate 18a: N-(3-(trifluoromethyl)benzyl)-2-(2-amino-5-fluorophenyl)-isonicotinamide Into a 50-mL round bottom flask, was placed a solution of N-(3-(trifluoromethyl)benzyl)-2-(5-fluoro-2-nitrophenyl)isonicotinamide 14d (200 mg, 0.48 mmol, 1.00 equiv) in methanol (5 mL). The solution was treated with Pd/C (0.2 g), and stirred under an atmosphere of hydrogen for 2 h at room temperature. The reaction progress was monitored by LCMS. The solids were filtered out. The resulting mixture was concentrated under vacuum to yield 200 mg of crude product as a yellow oil.

Intermediate 18b: tert-butyl 3-(3-((2-(4-((3-(trifluoromethyl)benzyl)carbamoyl)pyridin-2-yl)-4-fluorophenyl)carbamoyl)benzylthio)propanoate Into a 50-mL round bottom flask, was placed a solution of N-(3-(trifluoromethyl)benzyl)-2-(2-amino-5-fluoro-phenyl)isonicotinamide (200 mg, 0.51 mmol, 1.00 equiv) in N,N-dimethylformamide (2 mL), 3-((3-tert-butoxy-3-oxopropylthio)methyl)benzoic acid (200 mg, 0.68 mmol, 1.50 equiv), EDC.HCl (0.18 g, 0.94 mmol, 2.00 equiv), and 4-dimethylaminopyridine (58 mg, 0.48 mmol, 1.00 equiv). The resulting solution was stirred for 2 h at room temperature. The reaction progress was monitored by LCMS. The resulting mixture was concentrated under vacuum. The residue was applied onto a silica gel column and eluted with ethyl acetate/petroleum ether (1:5~ethyl acetate). The product was obtained as 100 mg (29%) of a yellow solid.

Example 18

3-(3-((2-(4-((3-(trifluoromethyl)benzyl)carbamoyl)pyridin-2-yl)-4-fluoro-phenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-fluorophenyl)carbamoyl)benzylthio)propanoate (100 mg, 0.15 mmol, 1.00 equiv) in dichloromethane (5 mL), and trifluoroacetic acid (1 mL). The resulting solution was stirred overnight at room temperature. The resulting mixture was concentrated under vacuum. The crude product (100 mg) was purified by reverse phase HPLC eluting with a water/CH$_3$CN gradient containing 0.05% TFA. The product was obtained as 22.7 mg (25%) of a yellow solid. $^1$H-NMR (300 MHz, DMSO, ppm): δ 12.78 (s, 1H), 9.55-9.54 (m, 1H), 9.00-8.99 (m, 1H), 8.58-8.53 (m, 1H), 8.43 (s, 1H), 7.94-7.39 (m, 11H), 4.65-4.63 (t, J=3 Hz, 2H), 3.89 (s, 2H), 2.63-2.59 (m, 2H). MS (ES, m/z): 612 [M+H]$^+$.

Example 19

3-((3-((4-(Dipropylamino)-2-(4-((3-(trifluoromethyl)benzyl)carbamoyl)pyridin-2-yl)phenyl)carbamoyl)benzyl)thio)propanoic acid Scheme 25:

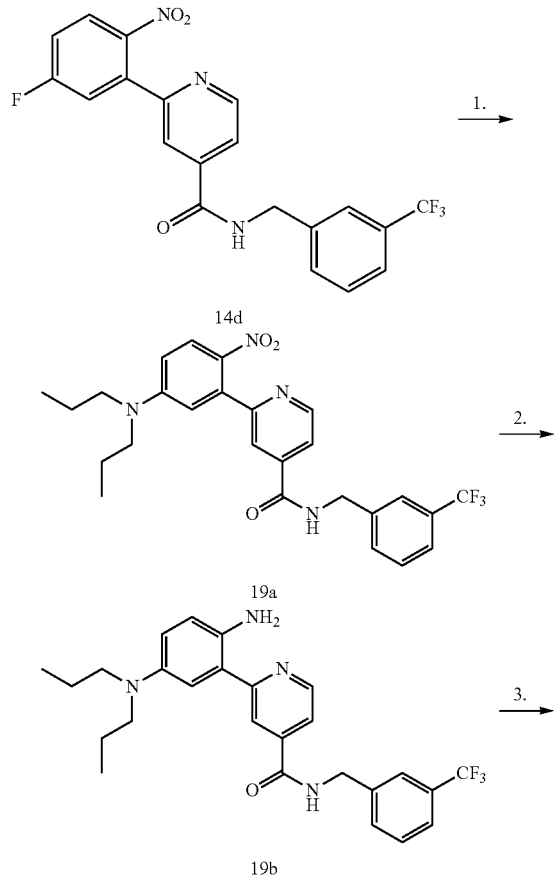

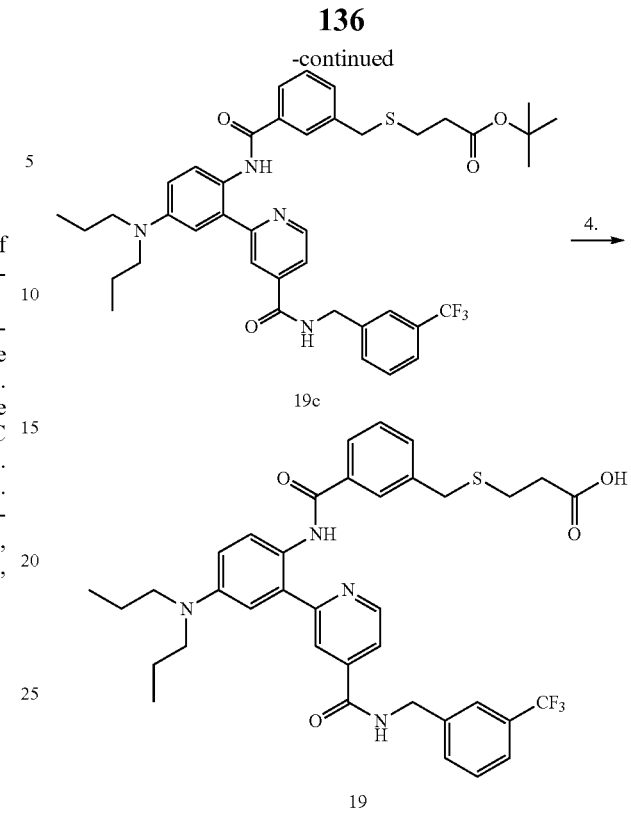

1. dipropylamine, 2. Pd/C H$_2$, MeOH; 3. EDC·HCl, DMAP, DMF, 3-((3-tert-butoxy-3-oxopropylthio)methyl)benzoic acid 1.1c; 4. CF$_3$COOH, DCM.

Intermediate 19a: N-(3-(trifluoromethyl)benzyl)-2-(5-(dipropylamino)-2-nitrophenyl)-isonicotinamide Into a 10-mL vial, was placed a solution of dipropylamine (216.9 mg, 2.15 mmol, 3.00 equiv) in N,N-dimethylformamide (3 mL), N,N-diisopropylethylamine (277 mg, 2.15 mmol, 3.00 equiv), and a solution of N-(3-(trifluoromethyl)benzyl)-2-(5-fluoro-2-nitrophenyl)isonicotinamide 14d (300 mg, 0.72 mmol, 1.00 equiv) in N,N-dimethylformamide (2 mL). The resulting solution was stirred for 8 h at 90° C. to 100° C. in an oil bath. The resulting solution was diluted with 50 mL of water. The resulting solution was extracted with 3×50 mL of ethyl acetate and the organic layers combined. The resulting mixture was washed with 2×70 mL of brine, dried over sodium sulfate, and concentrated under vacuum. The crude product was obtained as 400 mg of a yellow to green oil.

Intermediate 19b: N-(3-(trifluoromethyl)benzyl)-2-(2-amino-5-(dipropylamino)phenyl)-isonicotinamide Into a 50-mL round bottom flask, was placed a solution of N-(3-(trifluoromethyl)benzyl)-2-(5-(dipropylamino)-2-nitrophenyl)isonicotinamide (400 mg, 0.80 mmol, ~1.00 equiv) in methanol (20 mL). The solution was treated with Pd/C (400 mg, 10%), and stirred under an atmosphere of hydrogen for 4 h at room temperature. The solids were filtered out. The resulting mixture was concentrated under vacuum. The product was obtained as 300 mg (80%) of a yellow to green oil.

Intermediate 19c: tert-butyl 3-(3-((2-(4-((3-(trifluoromethyl)benzyl)carbamoyl)pyridin-2-yl)-4-(dipropylamino)phenyl)carbamoyl)benzylthio)propanoate Into a 10-mL vial, was placed a solution of 3-((3-tert-butoxy-3-oxopropylthio)methyl)benzoic acid (355.2 mg, 1.20 mmol, 2.00 equiv) in dichloromethane (5 mL), EDC.HCl (228 mg, 1.19 mmol, 2.00 equiv), 4-dimethylaminopyridine (146.4 mg, 2.00 mmol), and N-(3-(trifluoromethyl)benzyl)-2-(2-amino-5-(dipropylamino)phenyl)isonicotinamide (300 mg, 0.64 mmol, 1.00 equiv). The resulting solution was stirred for 2 h at 25° C. in an oil bath. The resulting solution was diluted with 50 mL of dichloromethane and washed with 3×50 mL of aqueous NH$_4$Cl. The mixture was dried over anhydrous sodium sulfate and concentrated under vacuum. The residue was applied onto a silica gel column and eluted with ethyl acetate/petroleum ether (1:5-1:3). The product was obtained as 320 mg (67%) of a yellow to green oil.

Example 19

3-((3-((4-(dipropylamino)-2-(4-((3-(trifluoromethyl)benzyl)carbamoyl)-pyridin-2-yl)phenyl)carbamoyl)benzyl)thio)propanoic acid Into a 50-mL round bottom flask, was placed a solution of tert-butyl 3-(3-((2-(4-((3-(trifluoromethyl)-benzyl)carbamoyl)pyridin-2-yl)-4-(dipropylamino)phenyl)carbamoyl)benzylthio)-propanoate (320 mg, 0.43 mmol, 1.00 equiv) in dichloromethane (10 mL), and trifluoroacetic acid (1 mL). The resulting solution was stirred overnight at 25° C. in an oil bath. The reaction progress was monitored by LCMS. The resulting mixture was concentrated under vacuum. The crude product (200 mg) was purified by reverse phase HPLC eluting with a water/CH$_3$CN gradient containing 0.05% TFA. The product was obtained as 108 mg (30%) of a yellow solid. $^1$H-NMR (300 MHz, DMSO, ppm): δ 9.52 (t, J=6 Hz, 1H), 8.96 (d, J=5.1 Hz, 1H), 8.27 (s, 2H), 7.85 (s, 2H), 7.74 (m, 2H), 7.53 (m, 5H), 7.02 (s, 2H), 4.61 (d, J=5.7 Hz, 2H), 3.87 (s, 2H), 3.39 (s, 4H), 2.61 (m, 2H), 2.50 (m, 2H), 1.53 (t, J=9.3 Hz, 4H), 0.89 (t, J=7.2 Hz, 6H). MS (ES, m/z): 693 [M+H]$^+$.

Example 20

3-((3-((4-(Pyrrolidin-1-yl)-2-(4-((3-(trifluoromethyl)benzyl)carbamoyl)pyridin-2-yl)phenyl)carbamoyl)benzyl)thio)propanoic acid Scheme 26:

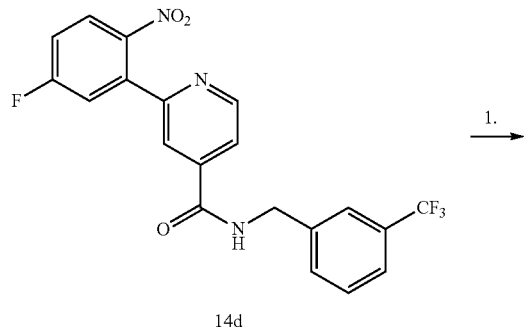

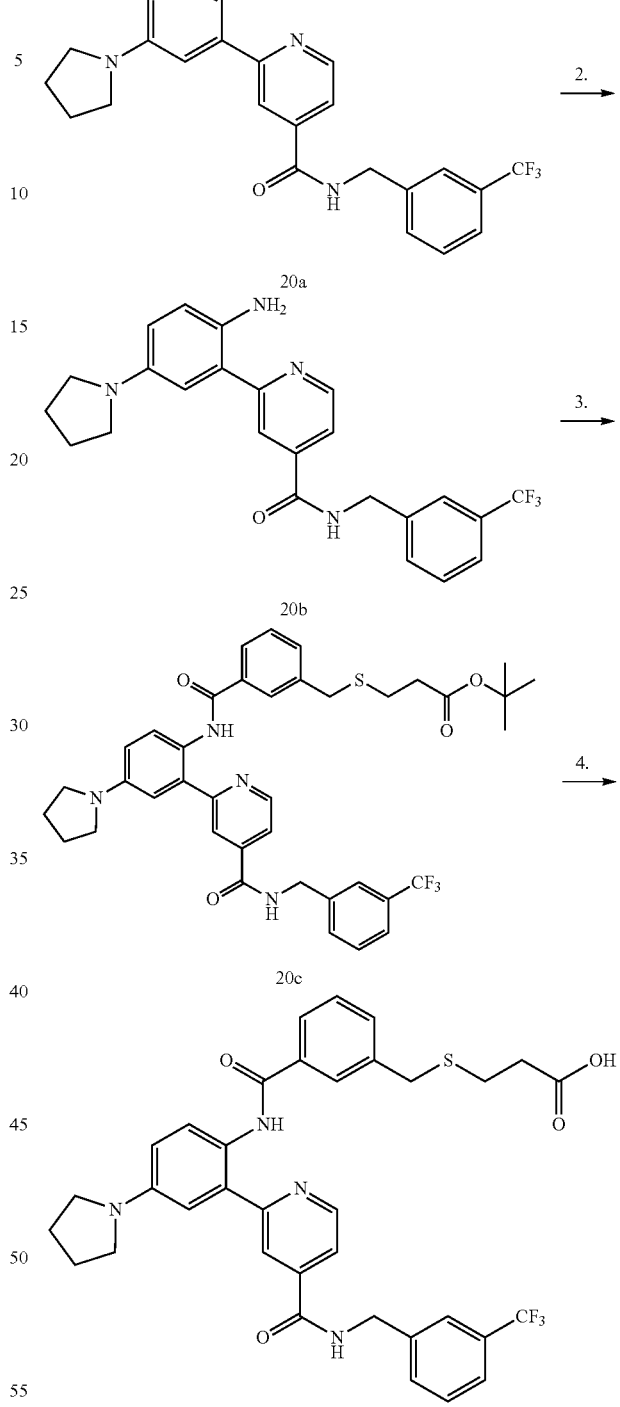

1. pyrrolidine, 2. Pd/C H$_2$, MeOH; 3. EDC•HCl, DMAP, DMF, 3-((3-tert-butoxy-3-oxopropylthio)methyl)benzoic acid 1.1c; 4. CF$_3$COOH, DCM.

Intermediate 20a: N-(3-(trifluoromethyl)benzyl)-2-(2-nitro-5-(pyrrolidin-1-yl)phenyl)-isonicotinamide Into a 10-mL vial, was placed a solution of pyrrolidine (152.5 mg, 2.15 mmol, 3.00 equiv) in N,N-dimethylformamide (5 mL), potassium carbonate (296.2 mg, 2.15 mmol, 3.00 equiv), and N-(3-(trifluoromethyl)benzyl)-2-(5-fluoro-2-nitrophenyl)isonicotinamide 14d (300 mg, 0.72 mmol, 1.00 equiv). The resulting solution was stirred for 4 h at 90° C. in an oil bath. The resulting solution was diluted with 50 mL of water. The resulting solution was extracted with 3×50 mL of ethyl acetate and the organic layers combined. The mixture was dried over anhydrous sodium sulfate and concentrated under vacuum to yield 400 mg of crude product as a yellow to green oil.

Intermediate 20b: N-(3-(trifluoromethyl)benzyl)-2-(2-amino-5-(pyrrolidin-1-yl)phenyl)-isonicotinamide Into a 50-mL round bottom flask, was placed a solution of N-(3-(trifluoromethyl)benzyl)-2-(2-nitro-5-(pyrrolidin-1-yl)phenyl)isonicotinamide (400 mg, 0.85 mmol, 1.00 equiv) in methanol (20 mL). The solution was treated with Pd/C (400 mg) and stirred under an atmosphere of hydrogen for 3.5 h at room temperature. The solids were filtered out. The resulting mixture was concentrated under vacuum. The product was obtained as 300 mg (80%) of a yellow to green solid.

Intermediate 20c: tert-butyl 3-(3-((2-(4-((3-(trifluoromethyl)benzyl)carbamoyl)pyridin-2-yl)-4-(pyrrolidin-1-yl)phenyl)carbamoyl)benzylthio)propanoate Into a 10-mL vial, was placed a solution of 3-((3-tert-butoxy-3-oxopropylthio)methyl)benzoic acid (402.6 mg, 1.36 mmol, 2.00 equiv) in dichloromethane (5 mL), EDC.HCl (258.5 mg, 1.35 mmol, 2.00 equiv), 4-dimethylaminopyridine (165.9 mg, 1.36 mmol, 2.00 equiv), and N-(3-(trifluoromethyl)benzyl)-2-(2-amino-5-(pyrrolidin-1-yl)phenyl)isonicotinamide (300 mg, 0.68 mmol, 1.00 equiv). The resulting solution was stirred for 5 h at 25° C. in an oil bath. The resulting solution was diluted with 50 mL of dichloromethane and washed with 2×70 mL of aqueous NH₄Cl. The mixture was dried over anhydrous sodium sulfate and concentrated under vacuum. The residue was applied onto a silica gel column and eluted with ethyl acetate/petroleum ether (1:10-1:3). The crude product was obtained as 600 mg of a yellow solid.

Example 20

3-((3-((4-(pyrrolidin-1-yl)-2-(4-((3-(trifluoromethyl)benzyl)carbamoyl)-pyridin-2-yl)phenyl)carbamoyl)benzyl)thio)propanoic acid Into a 50-mL round bottom flask, was placed a solution of tert-butyl 3-(3-((2-(4-((3-(trifluoromethyl)benzyl)carbamoyl)pyridin-2-yl)-4-(pyrrolidin-1-yl)phenyl)carbamoyl)-benzylthio)propanoate (600 mg, 0.84 mmol, 1.00 equiv) in dichloromethane (20 mL), and trifluoroacetic acid (2 mL). The resulting solution was stirred for 2.5 h at 25° C. in an oil bath. The reaction progress was monitored by LCMS. The resulting mixture was concentrated under vacuum. The crude product (120 mg) was purified by reverse phase HPLC eluting with a water/CH₃CN gradient containing 0.05% TFA. The product was obtained as 96.2 mg (15%) of a yellow solid.

¹H-NMR (300 MHz, DMSO, ppm): δ 11.92 (s, 1H), 9.51 (t, J=11.7 Hz, 1H), 8.95 (d, J=5.4 Hz, 1H), 8.28 (s, 1H), 8.15 (d, J=8.7 Hz, 1H), 7.82 (d, J=5.4 Hz, 2H), 7.73 (t, J=12.3 Hz, 2H), 7.55 (m, 5H), 6.96 (d, J=2.4 Hz, 1H), 6.76 (m, 1H), 4.62 (d, J=5.7 Hz, 2H), 3.87 (s, 2H), 3.33 (s, 4H), 2.62 (m, 2H), 2.50 (m, 2H), 1.99 (s, 4H). MS (ES, m/z): 663 [M+H]⁺.

Example 21

3-((3-((4-Chloro-2-(4-((3-(trifluoromethyl)benzyl)carbamoyl)pyridin-2-yl)phenyl)carbamoyl)benzyl)thio)propanoic acid Scheme 27:

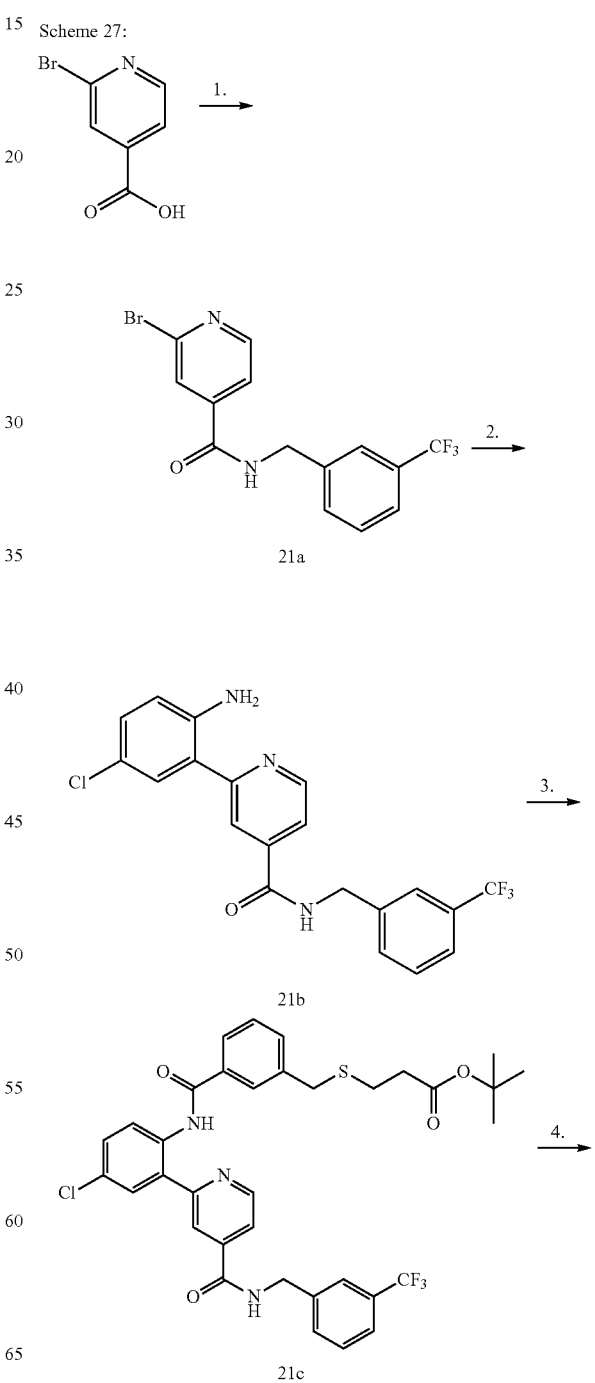

-continued

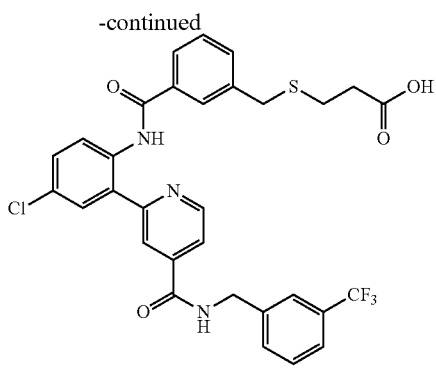

21

1. 3-(trifluormethyl)benzylamine, EDC•HCl, DMAP; 2. 4-chloro-2-(4,4,5,5-tetramethyl-1,3,2-dioxaborolan-2-yl)aniline, (Ph₃P)₄Pd, Na₂CO₃, DME; 3. 3-((3-tert-butoxy-3-oxopropylthio)methyl)benzoic acid 1.1c, EDC•HCl, DMAP; 4. TFA.

Intermediate 21a: N-(3-(trifluoromethyl)benzyl)-2-bromoisonicotinamide

Into a 250-mL round bottom flask, was placed a solution of 2-bromoisonicotinic acid (1.4 g, 6.93 mmol, 1.20 equiv) in dichloromethane (50 mL), EDC.HCl (1.64 g, 8.56 mmol, 1.50 equiv), 4-dimethylaminopyridine (1.04 g, 8.51 mmol, 1.50 equiv), and 3-(trifluoromethyl)benzylamine (1.0 g, 5.71 mmol, 1.00 equiv). The resulting solution was stirred overnight at 25° C. in an oil bath. The resulting solution was diluted with 100 mL of dichloromethane. The resulting mixture was washed with 2×50 mL of sat. NH₄Cl, 2×50 mL of sat. Na₂CO₃, and 2×50 mL of brine. The mixture was dried over anhydrous sodium sulfate and concentrated under vacuum. The residue was applied onto a silica gel column and eluted with ethyl acetate/petroleum ether (1:10-1:5). The product was obtained as 1.2 g (59%) of a white solid.

Intermediate 21b: N-(3-(trifluoromethyl)benzyl)-2-(2-amino-5-chlorophenyl)-isonicotinamide Into a 50-mL round bottom flask purged and maintained with an inert atmosphere of nitrogen, was placed a solution of 4-chloro-2-(4,4,5,5-tetramethyl-1,3-dioxolan-2-yl)benzenamine (300 mg, 1.17 mmol, 1.00 equiv) in ethylene glycol dimethyl ether (15 mL), N-(3-(trifluoromethyl)benzyl)-2-bromoisonicotinamide (432 mg, 1.20 mmol, 1.00 equiv), a solution of sodium carbonate (636 mg, 6.00 mmol, 5.00 equiv) in water (3.0 mL), and Pd(PPh₃)₄ (138 mg, 0.12 mmol, 0.10 equiv). The resulting solution was stirred for 2 h at 85° C. in an oil bath. The resulting mixture was concentrated under vacuum. The resulting solution was diluted with 10 mL of water. The resulting solution was extracted with 3×10 mL of ethyl acetate and the organic layers combined, and washed with brine. The mixture was dried over sodium sulfate and concentrated under vacuum. The residue was applied onto a silica gel column and eluted with petroleum ether/ethyl acetate (10:1-5:1). The product was obtained as 260 mg (55%) of a yellow solid.

Intermediate 21c: tert-butyl 3-(3-((2-(4-((3-(trifluoromethyl)benzyl)carbamoyl)pyridin-2-yl)-4-chlorophenyl)carbamoyl)benzylthio)propanoate Into a 100-mL round bottom flask, was placed a solution of 3-((3-tert-butoxy-3-oxopropylthio)methyl)benzoic acid (210 mg, 0.71 mmol, 1.20 equiv) in dichloromethane (35 mL), EDC.HCl (170.6 mg, 0.89 mmol, 1.50 equiv), 4-dimethylaminopyridine (108.8 mg, 0.89 mmol, 1.50 equiv), and N-(3-(trifluoromethyl)benzyl)-2-(2-amino-5-chlorophenyl)isonicotinamide (240 mg, 0.59 mmol, 1.00 equiv). The resulting solution was stirred for 6 h at 25° C. in an oil bath. The resulting solution was diluted with 100 mL of dichloromethane and washed with 2×50 mL of aqueous NH₄Cl and brine. The mixture was dried over anhydrous sodium sulfate and concentrated under vacuum to yield 350 mg (86%) of product as a yellow solid.

Example 21

3-(3-((2-(4-((3-(trifluoromethyl)benzyl)carbamoyl)pyridin-2-yl)-4-chlorophenyl)carbamoyl)benzylthio)propanoic acid Into a 50-mL round bottom flask, was placed a solution of tert-butyl 3-(3-((2-(4-((3-(trifluoromethyl)benzyl)carbamoyl)pyridin-2-yl)-4-chlorophenyl)carbamoyl)benzylthio)propanoate (350 mg, 0.51 mmol, 1.00 equiv) in dichloromethane (5.0 mL), and trifluoroacetic acid (581.4 mg, 5.10 mmol, 10.00 equiv). The resulting solution was stirred overnight at 15° C. The resulting mixture was concentrated under vacuum. The crude product (340 mg) was purified by reverse phase HPLC eluting with a water/CH₃CN gradient containing 0.05% TFA. The product was obtained 250 mg (78%) of a white solid. ¹H-NMR (300 MHz, DMSO-d₆, ppm): δ 12.988 (s, 1H), 12.228 (s, 1H), 9.595-9.560 (m, 1H), 9.020-9.003 (d, J=5.1 Hz, 1H), 8.631-8.601 (d, J=9.0 Hz, 1H), 8.448 (s, 1H), 8.118-8.126 (d, J=2.4 Hz, 1H), 7.917-7.899 (d, J=5.4 Hz, 2H), 7.837-7.812 (d, J=7.5 Hz, 1H), 7.727-7.510 (m, 6H), 4.662-4.643 (d, J=5.7 Hz, 2H), 3.904 (s, 2H), 2.637-2.594 (m, 2H), 2.538 (m, 2H). MS (ES, m/z): 628 [M+H]⁺

Example 22

3-((3-((2-(4-((3-(Trifluoromethyl)benzyl)carbamoyl)pyridin-2-yl)phenyl)carbamoyl)benzyl)thio)propanoic acid Scheme 28:

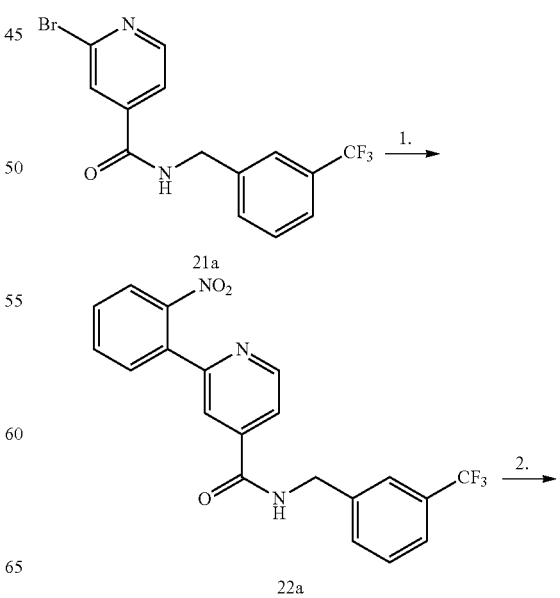

-continued

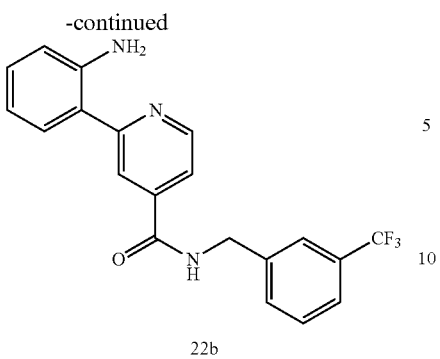

22b

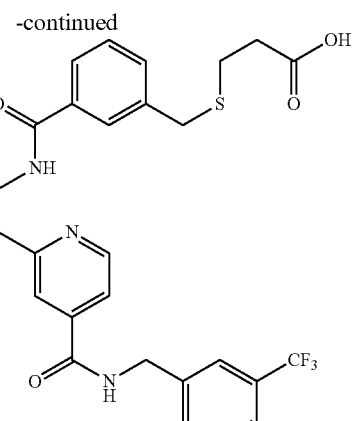

22

1. 2-nitrophenylboronic acid, (Ph₃)₄Pd, DME, Na₂CO₃; 2. Fe, CH₃COOH;
3. methyl acrylate, DBU, acetonitrile; 4. oxaloyl chloride, DCM; 5. methyl 3-((3-(chlorocarbonyl)benzyl)thio)propanoate, pyridine; 6. LiOH.

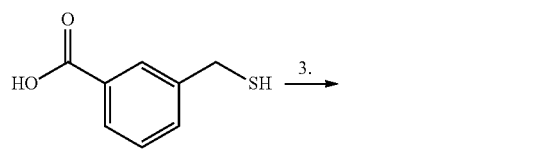

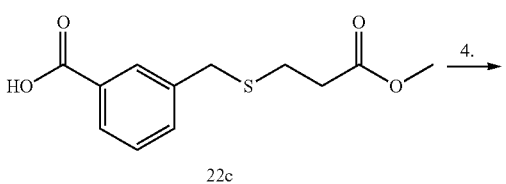

22c

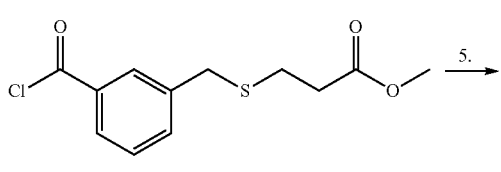

22d

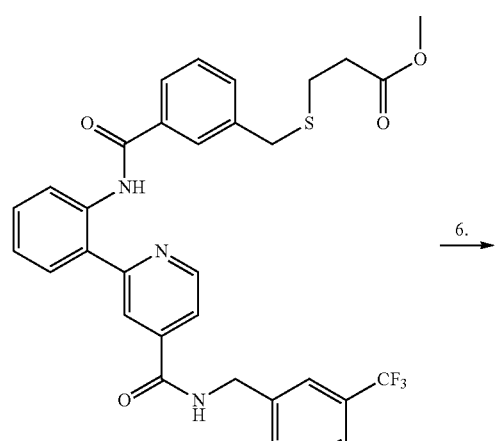

22e

Intermediate 22a: N-(3-(trifluoromethyl)benzyl)-2-(2-nitrophenyl) isonicotinamide Into a 250-mL 3-necked round bottom flask purged and maintained with an inert atmosphere of nitrogen, was placed a solution of 2-nitrophenylboronic acid (500 mg, 2.99 mmol, 1.00 equiv) in ethylene glycol dimethyl ether (30 mL), N-(3-(trifluoromethyl)benzyl)-2-bromoisonicotinamide 21a (1.08 g, 3.01 mmol, 1.00 equiv), Pd(PPh₃)₄ (334.7 mg, 0.30 mmol, 0.10 equiv), and a solution of sodium carbonate (1.6 g, 15.09 mmol, 5.00 equiv) in water (4 mL). The resulting solution was stirred for 1.5 h at 80° C. The reaction progress was monitored by TLC (ethyl acetate/petroleum ether=1:1). The resulting solution was diluted with 50 mL of water. The resulting solution was extracted with 2×100 mL of ethyl acetate and the organic layers combined and dried over magnesium sulfate. The solids were filtered out. The resulting mixture was concentrated under vacuum. The residue was applied onto a silica gel column and eluted with petroleum ether/EtOAc (20:1-5:1). The product was obtained as 1.0 g (83%) of a light yellow solid.

Intermediate 22b: N-(3-(trifluoromethyl)benzyl)-2-(2-aminophenyl)isonicotinamide Into a 100-mL round bottom flask, was placed a solution of N-(3-(trifluoromethyl)benzyl)-2-(2-nitrophenyl)isonicotinamide (350 mg, 0.87 mmol, 1.00 equiv) in ethanol/H₂O (1/1) (30 mL), iron (489 mg, 8.73 mmol, 10.00 equiv), and acetic acid (0.1 mL). The resulting solution was heated to reflux for 0.5 h. The solids were filtered out. The resulting solution was extracted with of ethyl acetate and the organic layers combined and dried over magnesium sulfate. The solids were filtered out. The resulting mixture was concentrated under vacuum. The product was obtained as 260 mg (80%) of a yellow solid.

Intermediate 22c: 3-((3-methoxy-3-oxopropylthio)methyl)benzoic acid

To a solution of 3-(mercaptomethyl)benzoic acid (500 mg, 2.97 mmol, 1.00 equiv) in acetonitrile (10.0 mL) was added methyl acrylate (10.0 mL) and 1,8-Diazabicyclo[5.4.0]undec-7-ene (1.0 g, 6.57 mmol, 2.00 equiv) and the resulting solution was heated to reflux overnight. The reaction was concentrated under vacuum and the residue was applied onto a silica gel column with ethyl acetate/petroleum ether (0~1:6) to afford 220 mg (28%) of 3-((3-methoxy-3-oxopropylthio) methyl)benzoic acid as light-red oil.

Intermediate 22d: methyl
3-(3-(chlorocarbonyl)benzylthio)propanoate

To a solution of 3-((3-methoxy-3-oxopropylthio)methyl) benzoic acid (61.6 mg, 0.24 mmol, 1.00 equiv) in dichloromethane (5 mL) was added dropwise oxalyl dichloride (121.76 mg, 0.96 mmol, 4.00 equiv) followed by a few drops of N,N-dimethylformamide. The resulting solution was heated to reflux for 30 min, then concentrated under vacuum to afford 60 mg (crude) of methyl 3-(3-(chlorocarbonyl)benzylthio)propanoate as a yellow oil.

Intermediate 22e: methyl 3-(3-((2-(4-((3-(trifluoromethyl)benzyl)carbamoyl)pyridin-2-yl)phenyl)carbamoyl)benzylthio)propanoate Into a 100-mL round bottom flask, was placed a solution of N-(3-(trifluoromethyl)benzyl)-2-(2-aminophenyl)isonicotinamide (240 mg, 0.65 mmol, 1.00 equiv) in tetrahydrofuran (5 mL), and pyridine (77 mg, 0.97 mmol, 1.50 equiv). This was followed by dropwise addition of a solution of methyl 3-(3-(chlorocarbonyl)benzylthio)propanoate (194 mg, 0.71 mmol, 1.10 equiv) in tetrahydrofuran (5 mL) with stirring. The resulting solution was stirred for 2 h at room temperature. The reaction was then quenched with 30 mL of water. The resulting solution was extracted with 3×10 mL of ethyl acetate and the organic layers combined and dried over magnesium sulfate. The resulting mixture was concentrated under vacuum to yield 250 mg (64%) of product as a light yellow solid.

Example 22

3-(3-((2-(4-((3-(trifluoromethyl)benzyl)carbamoyl) pyridin-2-yl)phenyl)-carbamoyl)benzylthio)propanoic acid Into a 100-mL 3-necked round bottom flask, was placed a solution of methyl 3-(3-((2-(4-((3-(trifluoromethyl)benzyl) carbamoyl)pyridin-2-yl)phenyl)carbamoyl)benzylthio)propanoate (250 mg, 0.41 mmol, 1.00 equiv) in tetrahydrofuran (8 mL), and a solution of LiOH (98 mg, 4.08 mmol, 10.00 equiv) in water (2 mL). The resulting solution was stirred for 2 h at room temperature. The reaction progress was monitored by LCMS. The reaction was then quenched with 50 mL of water. The solution was adjusted to pH 3 with hydrochloric acid. The resulting solution was extracted with of ethyl acetate and the organic layers combined and dried over anhydrous sodium sulfate. The solids were filtered out. The resulting mixture was concentrated under vacuum. The crude product (120 mg) was purified by reverse phase HPLC eluting with a water/CH$_3$CN gradient containing 0.05% TFA. The product was obtained 50 mg (20%) of a white solid. $^1$H-NMR (400 MHz, DMSO-d$_6$, ppm): δ 13.02 (s, 1H), 9.60-9.56 (t, 1H), 9.01-8.99 (d, 1H), 8.60-8.57 (d, 1H), 8.42 (s, 1H), 8.05-8.03 (d, 1H), 7.93-7.82 (m, 3H), 7.72-7.51 (m, 7H), 7.35-7.30 (t, 1H), 4.65-4.63 (d, 2H), 3.91 (s, 2H), 2.64-2.59 (m, 3H). MS (ES, m/z): 594 [M+H]$^+$.

Example 24

N1-(2-(4-(1-Benzyl-1H-1,2,3-triazol-4-yl)pyridin-2-yl)-4-(piperidin-1-yl)phenyl)-N3-methyl-N3-(2-morpholinoethyl)isophthalamide

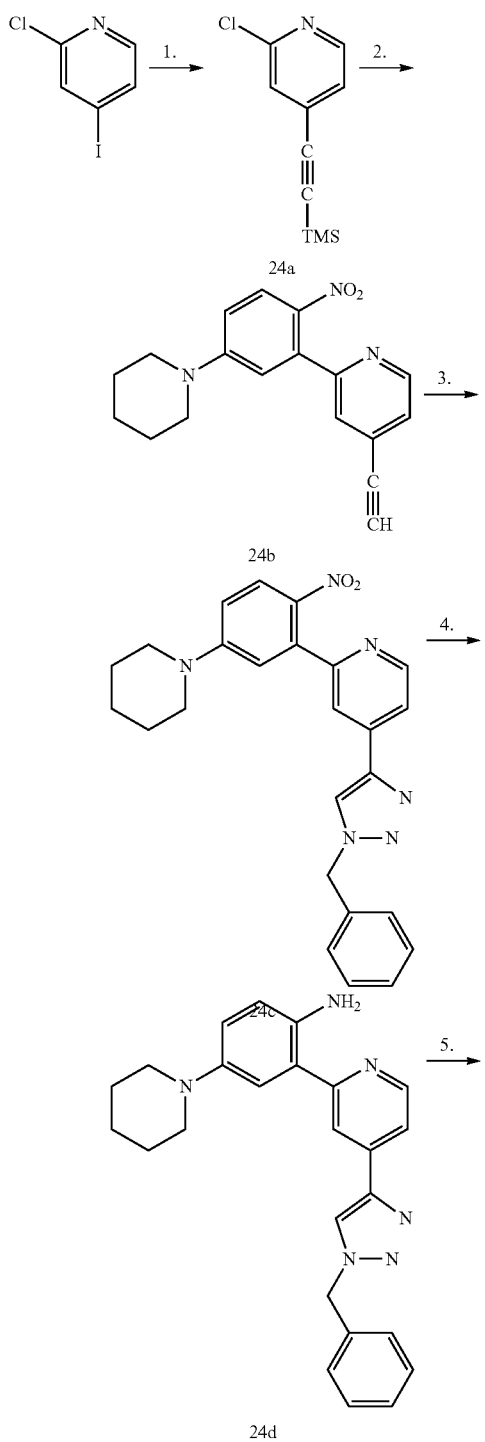

-continued

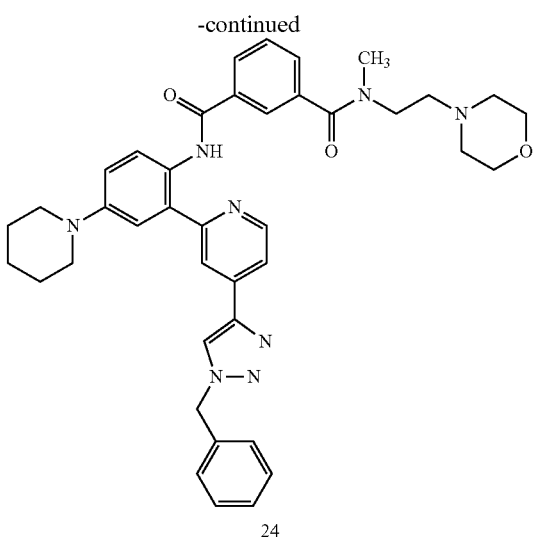

24

1. TMSC≡CH, CuI, (Ph₃P)₂PdCl₂, triethylamine; 2. boronic ester 1.1e, Pd(OAc)₂, XPHOS, Na₂CO₃; 3. benzyl azide, CuSO₄; 4. H₂, Pd/C; 5. 3-(methyl(2-morpholinoethyl)carbamoyl)benzoic acid, EDC·HCl, DMAP.

Intermediate 24a: 2-chloro-4-((trimethylsilyl)ethynyl)pyridine

A solution 0.835 mL of triethylamine in 10 mL of THF was degassed and treated with 16 mg of Ph₃P, 70 mg of (Ph₃P)₂PdCl₂, and 479 mg of 2-chloro-4-iodopyridine. The solution was stirred 1 h then treated with 236 mg of TMSC≡CH and 11.4 mg of CuI. After stirring overnight the solvent was evaporated and the residue was dissolved in dichloromethane. The solution was washed with water and then with brine. The solution was dried (Na₂SO₄) and then the solvent was evaporated at reduced pressure. The residue was chromatographed on silica gel eluting with a gradient of 0% to 20% ethyl acetate in hexanes to give 516 mg of product. MS (ESI, m/z) 210.1 [M+H]⁺.

Intermediate 24b: 4-ethynyl-2-(2-nitro-5-(piperidin-1-yl)phenyl)pyridine

A degassed mixture of 2-chloro-4-((trimethylsilyl)ethynyl)pyridine 24a, boronic ester 1.1e, 4.9 mL of 2 M aqueous Na₂CO₃, and 12 mL of DME was treated with 45 mg of XPHOS and 11 mg of Pd(OAc)₂. The mixture was stirred at 75° C. for 1.5 h. The solvent was evaporated at reduced pressure and the residue was dissolved in 100 mL of dichloromethane. The solution was washed with water and dried over Na₂SO₄. The solvent was evaporated and the residue was purified by silica gel chromatography eluting with a 0-20% gradient of EtOAc in CH₂Cl₂ to give 275 mg of product. MS (ESI, m/z) 308.1 [M+H]⁺.

Intermediate 24c: 4-(1-benzyl-1H-1,2,3-triazol-4-yl)-2-(2-nitro-5-(piperidin-1-yl)phenyl)-pyridine A solution of 50 mg of 4-ethynyl-2-(2-nitro-5-(piperidin-1-yl)phenyl)pyridine, 20 μL of benzyl azide, 16.3 μL of 1 M aqueous sodium ascorbate solution, 5.4 μL of 0.3 M CuSO₄ solution, 326 μL of tert-butanol, and 326 μL of water was stirred for 2 days and then the solvent was evaporated at reduced pressure. The residue was dissolved in dichloromethane. The solution was washed with water and dried.

The solvent was evaporated at reduced pressure and the residue was chromatographed on silica gel eluting with a 0% to 4% gradient of methanol in dichloromethane. The process yielded 22 mg of product.

Intermediate 24d: 2-(4-(1-benzyl-1H-1,2,3-triazol-4-yl)pyridin-2-yl)-4-(piperidin-1-yl)-aniline A solution of 22 mg of 4-(1-benzyl-1H-1,2,3-triazol-4-yl)-2-(2-nitro-5-(piperidin-1-yl)phenyl)pyridine 24c in 1 mL of methanol was treated with 10 mg of Pd/C and stirred under a hydrogen atmosphere for 1 h. The mixture was filtered through celite and the solvent was evaporated to give 22 mg of product.

Example 24

N1-(2-(4-(1-benzyl-1H-1,2,3-triazol-4-yl)pyridin-2-yl)-4-(piperidin-1-yl)-phenyl)-N3-methyl-N3-(2-morpholinoethyl)isophthalamide A solution of 22 mg of 2-(4-(1-benzyl-1H-1,2,3-triazol-4-yl)pyridin-2-yl)-4-(piperidin-1-yl)aniline 24d, 15.2 mg of 3-(methyl(2-morpholinoethyl)carbamoyl)benzoic acid, 22.6 mg of HATU, and 27.9 mg of diisopropylethylamine in 0.3 mL of DMF was stirred for 1 h. The solution was filtered and the product was isolated from the filtrate by reverse phase chromatography eluting with 0.05% TFA in a water/acetonitrile gradient. This procedure gave 13.4 mg of product. ¹H NMR (400 MHz, DMSO-d₆, ppm): δ 8.97 (s, 1H), 8.78 (d, J=5.0 Hz, 1H), 8.35 (s, 1H), 8.32-8.26 (m, 1H), 8.03-7.94 (m, 2H), 7.91 (d, J=5.2 Hz, 1H), 7.70-7.50 (m, 3H), 7.35 (mj, 4H), 7.28-7.19 (m, 1H), 5.69 (s, 2H), 4.09-3.90 (m, 3H), 3.85-3.76 (m, 2H), 3.71-3.53 (m, 4H), 2.91 (s, 3H), 1.69 (s, 4H), 1.55 (s, 2H). MS (ESI, m/z) 685.3 [M+H]⁺.

Example 25

N1-(4-(Diethylamino)-2-(4-((3-(trifluoromethyl)benzyl)carbamoyl)pyridin-2-yl)phenyl)-N3-methyl-N3-(2-morpholinoethyl)isophthalamide Scheme 30:

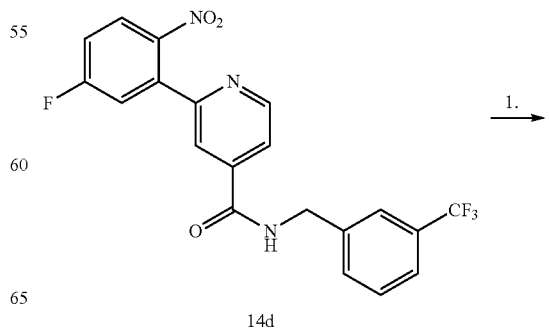

14d

149

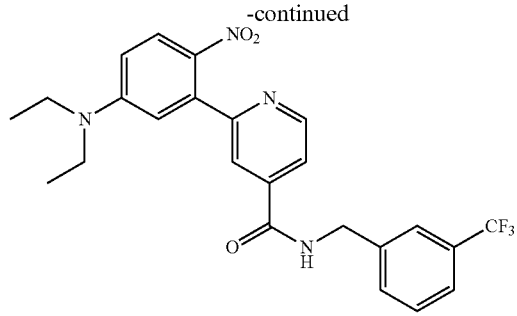

25a

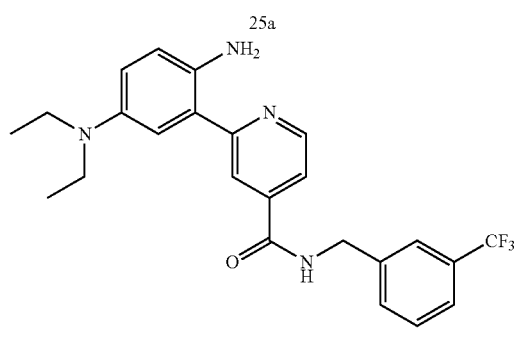

25b

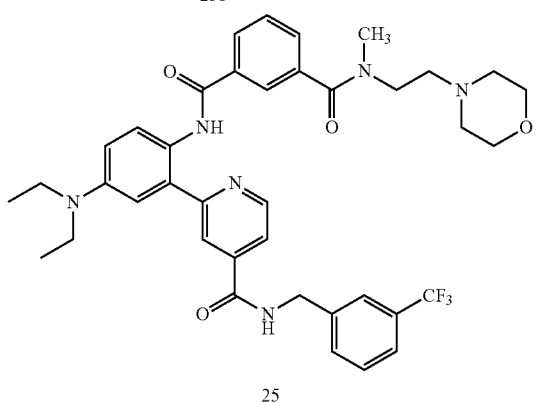

25

1. diethylamine, 2. Pd/C H₂, MeOH; 3. HATU, DIEA, DMF,
3-(methyl(2-morpholineoethyl)carbamoyl)benzoic acid.

Intermediate 25a: N-(3-(trifluoromethyl)benzyl)-2-(5-(diethylamino)-2-nitrophenyl)-isonicotinamide A 25° C. mixture of 500 mg of 2-(5-fluoro-2-nitrophenyl)-N-(3-(trifluoromethyl)benzyl)isonicotinamide 14d, 131 mg of diethylamine, and 329 mg of K₂CO₃ in 4 mL of DMF was stirred for 16 h and then stirred for an additional 24 h at 60° C. The mixture was diluted with ethyl acetate, and the resulting solution was washed with water, and then with brine. The solution was dried (Na₂SO₄) and the solvent was removed at reduced pressure. The residue was purified by chromatography on silica gel to give 500 mg of a yellow solid.

Intermediate 25b: N-(3-(trifluoromethyl)benzyl)-2-(2-amino-5-(diethylamino)phenyl)-isonicotinamide A mixture of 500 mg of N-(3-(trifluoromethyl)benzyl)-2-(5-(diethylamino)-2-nitrophenyl)isonicotinamide, 120 mg of 10% Pd/C, and 30 mL of methanol was stirred for 2 h under a hydrogen atmosphere. The mixture was filtered and concentrated to give 0.42 g of product.

150

Example 25

N1-(4-(diethylamino)-2-(4-((3-(trifluoromethyl)benzyl)carbamoyl)pyridin-2-yl)phenyl)-N3-methyl-N3-(2-morpholinoethyl)isophthalamide A mixture of 80 mg of N-(3-(trifluoromethyl)benzyl)-2-(2-amino-5-(diethylamino)phenyl)isonicotinamide, 64 mg of 3-(methyl(2-morpholinoethyl)carbamoyl)benzoic acid, 83 mg of HATU, and 190 μL of diisopropylethylamine in 0.5 mL of DMF was stirred at 60° C. for 2 h. The product was isolated by reverse phase chromatography eluting with 0.05% TFA in a water/acetonitrile gradient. This procedure gave 17.6 mg of product. ¹H NMR (400 MHz, CD₃OD, ppm): δ 9.54 (t, J=5.9 Hz, 1H), 8.98 (dd, J=5.2, 0.6 Hz, 1H), 8.88 (d, J=9.0 Hz, 1H), 8.49 (s, 1H), 8.26 (d, J=2.6 Hz, 1H), 8.20 (s, 1H), 8.16-8.10 (m, 1H), 7.90 (dd, J=5.2, 1.5 Hz, 1H), 7.80 (d, J=7.8 Hz, 1H), 7.75-7.63 (m, 4H), 7.63-7.50 (m, 2H), 4.74-4.67 (m, 2H), 4.21-4.03 (m, 2H), 3.99 (t, J=5.7 Hz, 2H), 3.90-3.69 (m, 4H), 3.76 (q, J=7.2 Hz, 4H), 3.54 (t, J=5.9 Hz, 2H), 3.34-3.18 (m, 2H), 3.10 (s, 3H), 1.22 (t, J=7.2 Hz, 6H). MS (ESI, m/z) 717.24 [M+H]⁺.

Example 26

N1-(4-Cyclobutoxy-2-(4-((3-(trifluoromethyl)benzyl)carbamoyl)pyridin-2-yl)phenyl)-N3-methyl-N3-(2-morpholinoethyl)isophthalamide Scheme 31:

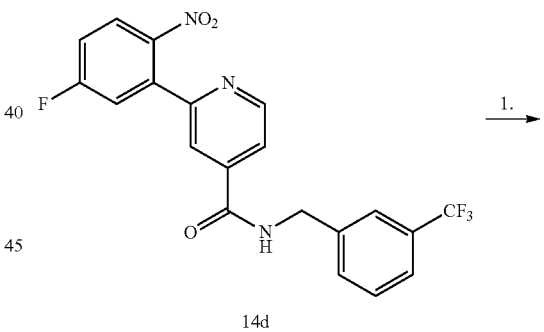

14d

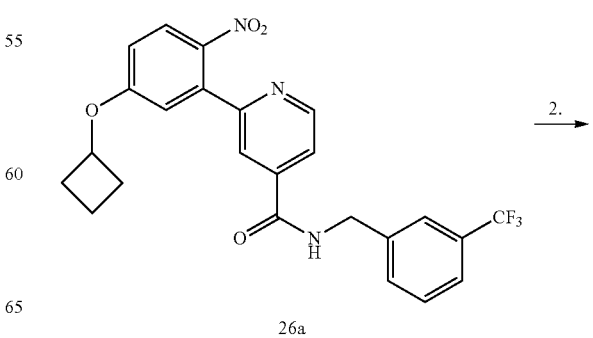

26a

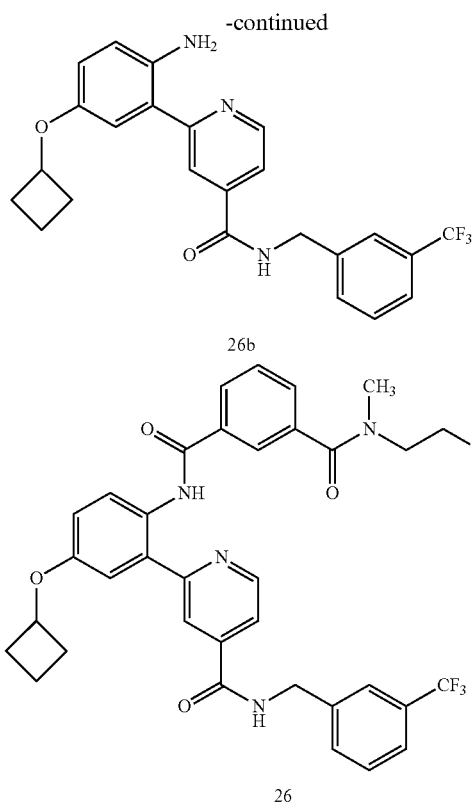

1. cyclobutanol, NaH, 2. Pd/C H₂, MeOH; 3. HATU, DIEA, DMF, 3-(methyl(2-morpholineoethyl)carbamoyl)benzoic acid;

Intermediate 26a: 2-(5-cyclobutoxy-2-nitrophenyl)-N-(3-(trifluoromethyl)benzyl)-isonicotinamide A 25° C. solution of 26 mg of cyclobutanol in 0.5 mL of DMF was treated with 10 mg of 60% NaH in oil. After stirring for 15 minutes, 75 mg of 2-(5-fluoro-2-nitrophenyl)-N-(3-(trifluoromethyl)benzyl)isonicotinamide 14d was added. The mixture was stirred overnight and then it was quenched with water. It was diluted with ethyl acetate, and the resulting solution was washed with water, then with brine. The solution was dried (Na₂SO₄) and the solvent was removed at reduced pressure. The residue was purified by chromatography on silica gel to give 62 mg of a syrup.

Intermediate 26b: 2-(2-amino-5-cyclobutoxyphenyl)-N-(3-(trifluoromethyl)benzyl)-isonicotinamide A mixture of 62 mg of 2-(5-cyclobutoxy-2-nitrophenyl)-N-(3-(trifluoromethyl)benzyl)isonicotinamide, 10 mg of 10% Pd/C, and 4 mL of methanol was stirred for 2 h under a hydrogen atmosphere. The mixture was filtered and concentrated to give 46 mg of product.

Example 26

N1-(4-cyclobutoxy-2-(4-((3-(trifluoromethyl)benzyl)carbamoyl)pyridin-2-yl)phenyl)-N3-methyl-N3-(2-morpholinoethyl)isophthalamide A mixture of 26 mg of 2-(2-amino-5-cyclobutoxyphenyl)-N-(3-(trifluoromethyl)benzyl)isonicotinamide, 21 mg of 3-(methyl(2-morpholinoethyl)carbamoyl)benzoic acid, 27 mg of HATU, and 63 μL of DIEA in 0.2 mL of DMF was stirred at 60° C. for 2 h. The product was isolated by reverse phase chromatography eluting with 0.05% TFA in a water/acetonitrile gradient. This procedure gave 24 mg of a yellow solid. ¹H NMR (400 MHz, CD₃OD, ppm): δ 9.46 (t, J=5.8 Hz, 1H), 8.85 (d, J=5.3 Hz, 1H), 8.26 (s, 1H), 8.15 (d, J=9.0 Hz, 1H), 8.05 (s, 1H), 8.01 (d, J=7.8 Hz, 1H), 7.85-7.80 (m, 1H), 7.80-7.47 (m, 6H), 7.31 (d, J=2.7 Hz, 1H), 7.00 (dd, J=8.9, 2.6 Hz, 1H), 4.83-4.71 (m, 1H), 4.67 (s, 2H), 4.09 (s, 2H), 3.96 (m, 2H), 3.77 (m, 4H), 3.52 (t, J=4.9 Hz, 2H), 3.24 (s, 2H), 3.07 (s, 3H), 2.59-2.39 (m, 2H), 2.25-2.04 (m, 2H), 1.93-1.60 (m, 2H). MS (ESI, m/z) 716.26 [M+H]⁺.

Example 27

3-((3-((4-Thiomorpholino-2-(4-((3-(trifluoromethyl)benzyl)carbamoyl)pyridin-2-yl)phenyl)carbamoyl)benzyl)thio)propanoic acid

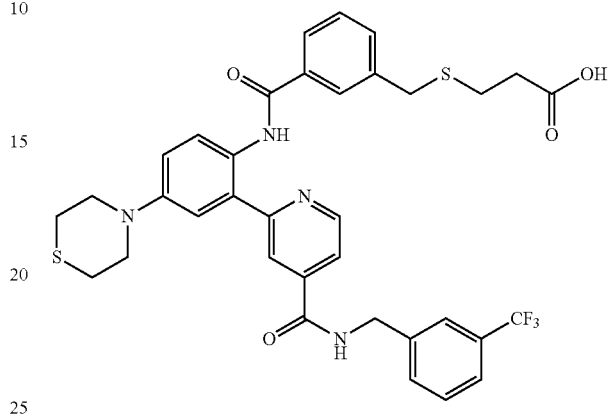

This compound was prepared according to the procedure described for the synthesis of 3-((3-((4-morpholino-2-(4-((3-(trifluoromethyl)benzyl)carbamoyl)pyridin-2-yl)phenyl)carbamoyl)benzyl)thio)propanoic acid 14, using thiomorpholine in place of morpholine. ¹H-NMR (300 MHz, DMSO-d₆, ppm): δ 12.22 (s, 1H), 9.54 (t, 1H), 8.32 (d, J=3 Hz, 1H), 8.27 (m, 2H), 7.85 (m, 2H), 7.75 (m, 2H), 7.50 (m, 6H), 7.15 (m, 1H), 4.62 (d, J=6 Hz, 2H), 3.87 (s, 2H), 3.58 (m, 4H), 2.74 (m, 4H), 2.62 (m, 2H), 2.50 (m, 1H). MS (ES, m/z): 695 [M+H]⁺.

Example 28

3-((3-((4-(Hexahydrocyclopenta[c]pyrrol-2(1H)-yl)-2-(4-((3-(trifluoromethyl)-benzyl)carbamoyl)pyridin-2-yl)phenyl)carbamoyl)benzyl)thio)propanoic acid

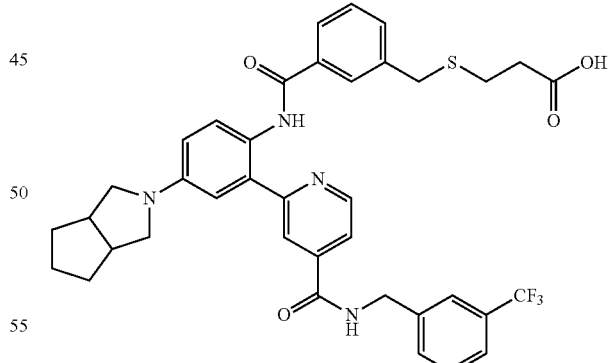

This compound was prepared according to the procedure described for the synthesis of 3-((3-((4-morpholino-2-(4-((3-(trifluoromethyl)benzyl)carbamoyl)pyridin-2-yl)phenyl)-carbamoyl)benzyl)thio)propanoic acid 14, using octahydrocyclopenta[c]pyrrole in place of morpholine. ¹H-NMR (300 MHz, DMSO-d₆+D₂O, ppm): δ 9.54 (s, 1H), 8.92 (d, J=3 Hz, 1H), 8.25 (s, 1H), 8.11 (d, J=9 Hz, 1H), 7.73 (m, 2H), 7.58 (m, 2H), 7.49 (m, 2H), 7.45 (m, 2H), 7.02 (s, 1H), 6.80 (d, J=9 Hz, 1H), 4.60 (s, 2H), 3.84 (s, 2H), 3.05 (d, J=6 Hz, 2H), 2.77 (m, 2H), 2.56 (m, 3H), 1.80 (m, 2H), 1.52 (m, 3H). MS (ES, m/z): 703 [M+H]⁺.

Example 29

3-((3-((4-Ethoxy-2-(4-((3-(trifluoromethyl)benzyl)carbamoyl)pyridin-2-yl)phenyl)carbamoyl)benzyl)thio)propanoic acid

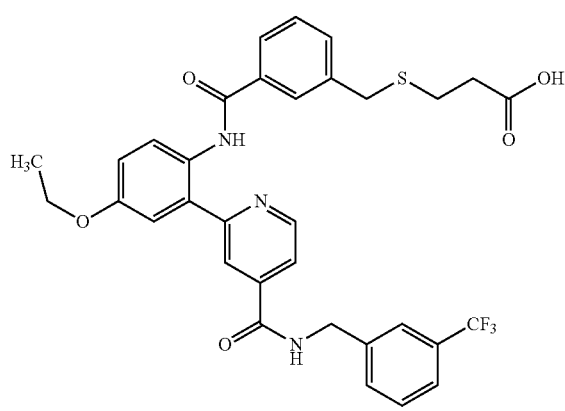 [SMILES: CCOc1ccc(NC(=O)c2cccc(CSCCC(=O)O)c2)c(-c2cc(C(=O)NCc3cccc(C(F)(F)F)c3)ccn2)c1]

This compound was prepared according to the procedure described for the synthesis of 3-((3-((4-morpholino-2-(4-((3-(trifluoromethyl)benzyl)carbamoyl)pyridin-2-yl)phenyl)carbamoyl)benzyl)thio)propanoic acid 14, using ethanol in place of morpholine. $^1$H-NMR (300 MHz, DMSO, ppm): δ 12.49 (s, 1H), 9.57 (m, 1H), 8.98-8.96 (m, 1H), 8.41-8.38 (m, 2H), 7.88-7.54 (m, 10H), 7.16-7.10 (m, 2H), 4.63 (m, 2H), 4.14-4.12 (m, 2H), 3.88 (s, 2H), 2.60-2.58 (m, 2H), 1.37-1.35 (t, J=3 Hz, 3H). MS (ES, m/z): 638 [M+H]$^+$.

Example 30

3-((3-((4-Methoxy-2-(4-((3-(trifluoromethyl)benzyl)carbamoyl)pyridin-2-yl)phenyl)carbamoyl)benzyl)thio)propanoic acid

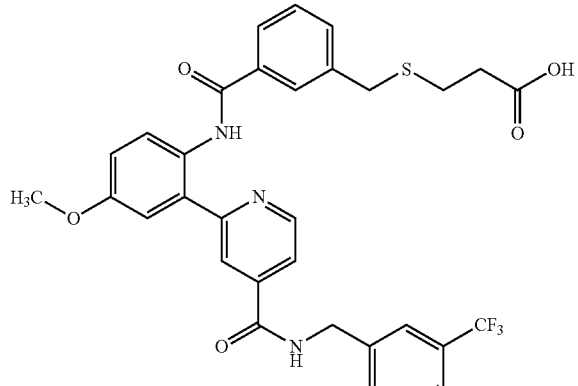

This compound was prepared according to the procedure described for the synthesis of 3-((3-((4-morpholino-2-(4-((3-(trifluoromethyl)benzyl)carbamoyl)pyridin-2-yl)phenyl)carbamoyl)benzyl)thio)propanoic acid 14, using methanol in place of morpholine. $^1$H-NMR (300 MHz, DMSO-d$_6$, ppm): δ 12.40 (s, 1H), 9.55 (m, 1H), 8.98-8.96 (m, 1H), 8.39-8.36 (m, 2H), 7.87-7.47 (m, 10H), 7.16-7.14 (m, 1H), 4.62-4.61 (m, 2H), 1H), 3.88 (s, 2H), 3.86 (s, 3H), 2.62-2.58 (m, 2H). MS (ES, m/z): 624 [M+H]$^+$.

Example 31

3-((3-((4-(4-Methoxypiperidin-1-yl)-2-(4-((3-(trifluoromethyl)benzyl)carbamoyl)-pyridin-2-yl)phenyl)carbamoyl)benzyl)thio)propanoic acid

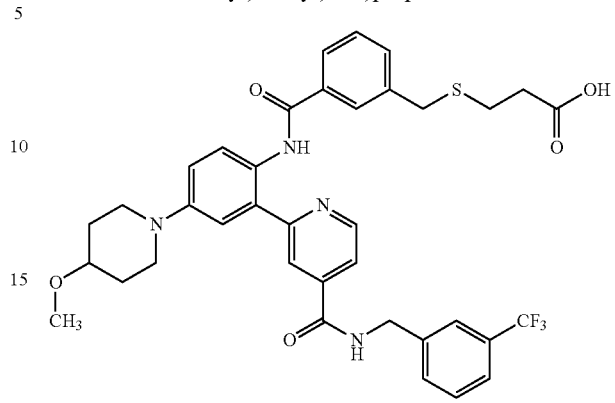

This compound was prepared according to the procedure described for the synthesis of 3-((3-((4-morpholino-2-(4-((3-(trifluoromethyl)benzyl)carbamoyl)pyridin-2-yl)phenyl)-carbamoyl)benzyl)thio)propanoic acid 14, using 4-methoxypiperidine in place of morpholine and using triethylamine in place of potassium carbonate in the nucleophilic aromatic substitution step. $^1$H-NMR (300 MHz, CD$_3$OD, ppm) δ 8.98 (d, J=4.1 Hz, 1H), 8.47 (d, J=9 Hz, 1H) 8.33 (s, 1H), 7.94 (s, 1H), 7.84 (m, 2H), 7.72-7.46 (m, 7H), 7.38 (d, J=7.5 Hz, 1H), 4.71 (s, 3H), 3.89 (s, 2H), 3.72 (m, 2H), 3.55 (m, 1H), 3.33 (s, 3H), 3.26 (m, 2H), 2.74 (t, 2H), 2.56 (t, 2H), 2.20 (m, 2H), 1.88 (m, 2H). MS (ES, m/z): 707 [M+H]$^+$.

Example 32

3-((3-((4-(2,2,2-Trifluoroethoxy)-2-(4-((3-(trifluoromethyl)benzyl)carbamoyl)pyridin-2-yl)phenyl)carbamoyl)benzyl)thio)propanoic acid Scheme 32:

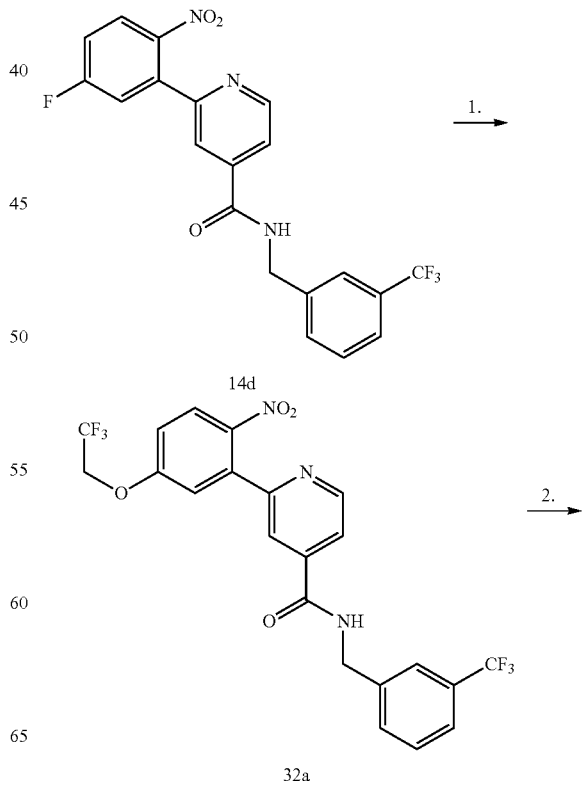

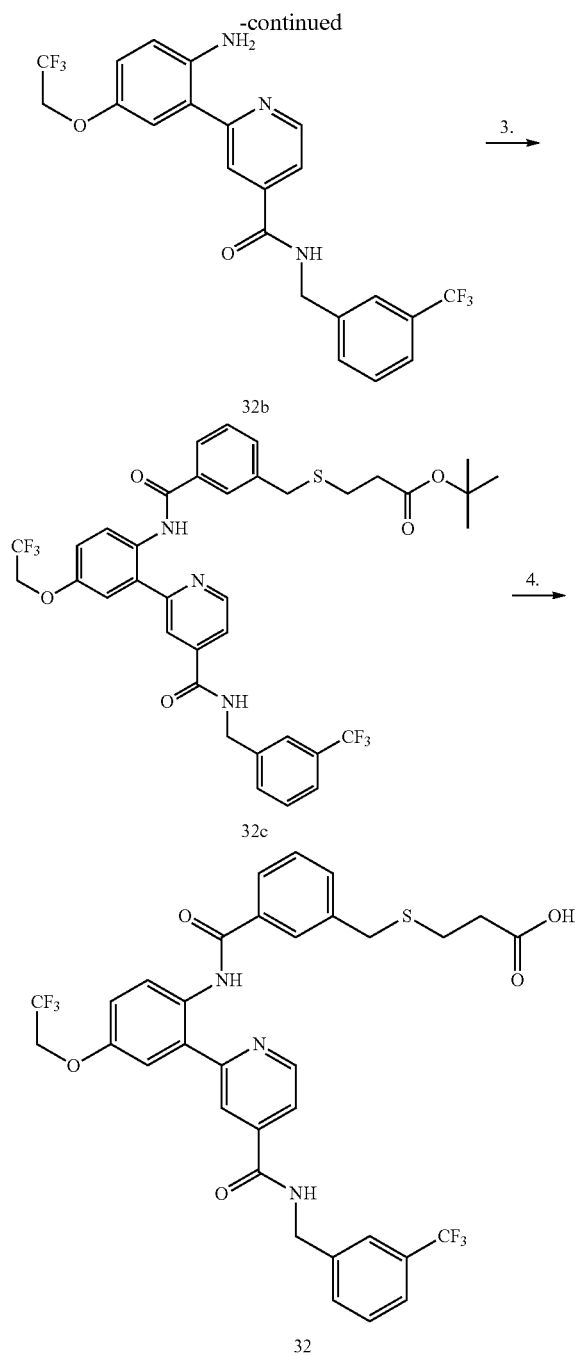

1. 2,2,2-trifluoroethanol, NaH, THF; 2. H₂, Pd/C; 3. 3-((3-tert-butoxy-3-oxopropylthio)methyl)benzoic acid, 1.1c, EDC, DMAP; 4. TFA Intermediate 32a: N-(3-(trifluoromethyl)benzyl)-2-(2-nitro-5-(2,2,2-trifluoroethoxy)-phenyl)isonicotinamide Into a 50-mL round-bottom flask, was placed a solution of 2,2,2-trifluoroethanol (150 mg, 1.50 mmol, 2.00 equiv) in tetrahydrofuran (10 mL). This was followed by the addition of sodium hydride (180 mg, 7.50 mmol, 10.00 equiv), in portions at 0° C. The resulting solution was stirred for 20 min at 0° C. in an ice/salt bath. To this was added N-(3-(trifluoromethyl)benzyl)-2-(5-fluoro-2-nitrophenyl)isonicotinamide 14d (300 mg, 0.72 mmol, 1.00 equiv). The resulting solution was stirred overnight at room temperature. The resulting solution was diluted with 20 mL of water. The resulting solution was extracted with 3×20 mL of dichloromethane and the organic layers combined and dried over sodium sulfate and concentrated under vacuum. This resulted in 200 mg (crude) of N-(3-(trifluoromethyl)benzyl)-2-(2-nitro-5-(2,2,2-trifluoroethoxy)phenyl)isonicotinamide as a yellow solid.

Intermediate 32b: N-(3-(trifluoromethyl)benzyl)-2-(2-amino-5-(2,2,2-trifluoroethoxy)-phenyl)isonicotinamide Into a 50-mL round-bottom flask, was placed a solution of N-(3-(trifluoromethyl)benzyl)-2-(2-nitro-5-(2,2,2-trifluoroethoxy)phenyl)isonicotinamide (200 mg, 0.40 mmol, 1.00 equiv) in methanol (5 mL). The solution was treated with Pd/C (0.2 g), and stirred under an atmosphere of hydrogen for 2 h at room temperature. The solids were filtered out. The resulting mixture was concentrated under vacuum. This resulted in 200 mg (crude) of N-(3-(trifluoromethyl)benzyl)-2-(2-amino-5-(2,2,2-trifluoroethoxy)phenyl)isonicotinamide as a yellow solid.

Intermediate 32c: tert-butyl 3-(3-((2-(4-((3-(trifluoromethyl)benzyl)carbamoyl)pyridin-2-yl)-4-(2,2,2-trifluoroethoxy)phenyl)carbamoyl)benzylthio)propanoate Into a 50-mL round-bottom flask, was placed a solution of N-(3-(trifluoromethyl)benzyl)-2-(2-amino-5-(2,2,2-trifluoroethoxy)phenyl)isonicotinamide (200 mg, 0.43 mmol, 1.00 equiv) in N,N-dimethylformamide (3 mL), 3-(3-tert-butoxy-3-oxopropylthio)methyl)benzoic acid (200 mg, 0.74 mmol, 1.50 equiv), EDC.HCl (190 mg, 0.99 mmol, 2.00 equiv), and 4-dimethylaminopyridine (60 mg, 0.49 mmol, 1.00 equiv). The resulting solution was stirred for 2 h at room temperature. This resulted in 300 mg (crude) of tert-butyl 3-(3-((2-(4-((3-(trifluoromethyl)benzyl)carbamoyl)pyridin-2-yl)-4-(2,2,2-trifluoroethoxy)phenyl)-carbamoyl)benzylthio)propanoate as a yellow solid.

Example 32

3-(3-((2-(4-((3-(trifluoromethyl)benzyl)carbamoyl)pyridin-2-yl)-4-(2,2,2-trifluoroethoxy)phenyl)carbamoyl)benzylthio)propanoic acid Into a 50-mL round-bottom flask, was placed a solution of tert-butyl 3-(3-((2-(4-((3-(trifluoromethyl)benzyl)carbamoyl)pyridin-2-yl)-4-(2,2,2-trifluoro ethoxy)phenyl)-carbamoyl)benzylthio)propanoate (200 mg, 0.27 mmol, 1.00 equiv) in dichloromethane (5 mL), and trifluoroacetic acid (2 mL). The resulting solution was stirred overnight at room temperature. The reaction progress was monitored by LCMS. The resulting mixture was concentrated under vacuum. The crude product (200 mg) was purified by reverse phase HPLC eluting with a water/CH₃CN gradient containing 0.05% TFA. The product was obtained as 68 mg (37%) of a light yellow solid. ¹H-NMR (300 MHz, DMSO-d₆, ppm): δ 12.61 (s, 1H), 9.57-9.54 (m, 1H), 8.99-8.98 (m, 1H), 8.49-8.41 (m, 2H), 7.89-7.79 (m, 10H), 7.30-7.26 (m, 1H), 4.92-4.84 (dd, J=18 Hz, 9

Hz, 2H), 4.65-4.63 (d, J=5.4 Hz, 2H), 3.89 (s, 2H), 2.63-2.59 (m, 4H). MS (ES, m/z): 692 [M+H]⁺.

Example 33

3-((3-((4-Methoxy-2-(4-((3-(trifluoromethyl)benzyl)carbamoyl)pyridin-2-yl)phenyl)carbamoyl)benzyl)thio)propanoic acid

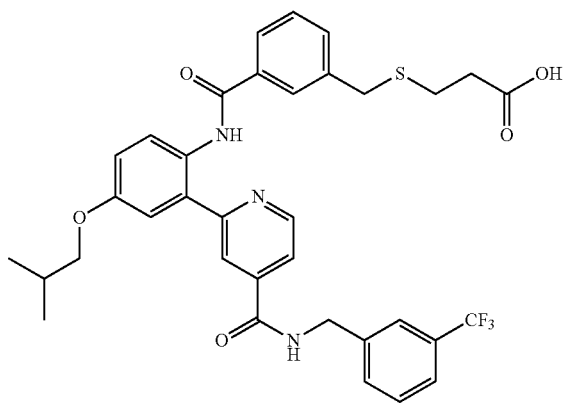 [SMILES: CC(C)COc1ccc(NC(=O)c2cccc(CSCCC(=O)O)c2)c(-c2cc(C(=O)NCc3cccc(C(F)(F)F)c3)ccn2)c1]

This compound was prepared according to the procedure described for the synthesis of 3-(3-((2-(4-((3-(trifluoromethyl)benzyl)carbamoyl)pyridin-2-yl)-4-(2,2,2-trifluoroethoxy)-phenyl)carbamoyl)benzylthio)propanoic acid 32, using isobutanol in place of trifluoroethanol. ¹H-NMR (300 MHz, DMSO-d₆, ppm): δ 12.44 (s, 1H), 9.56 (m, 1H), 8.97 (m, 1H), 8.36 (m, 2H), 7.87-7.52 (m, 10H), 7.16 (m, 1H), 4.63 (d, 2H), 3.87 (m, 4H), 2.59 (m, 2H), 2.06 (m, 2H), 1.03 (m, 6H). MS (ES, m/z): 666 [M+H]⁺.

Example 34

3-((3-((4-(2-Methoxyethoxy)-2-(4-((3-(trifluoromethyl)benzyl)carbamoyl)pyridin-2-yl)phenyl)carbamoyl)benzyl)thio)propanoic acid

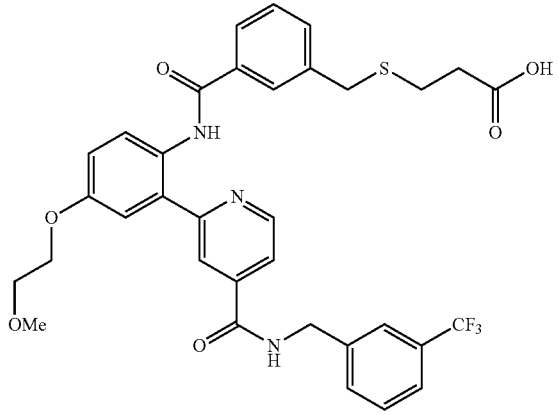 [SMILES: COCCOc1ccc(NC(=O)c2cccc(CSCCC(=O)O)c2)c(-c2cc(C(=O)NCc3cccc(C(F)(F)F)c3)ccn2)c1]

This compound was prepared according to the procedure described for the synthesis of 3-(3-((2-(4-((3-(trifluoromethyl)benzyl)carbamoyl)pyridin-2-yl)-4-(2,2,2-trifluoroethoxy)phenyl)carbamoyl)benzylthio)propanoic acid 32 using 2-methoxyethanol in place of trifluoroethanol. ¹H-NMR (400 MHz, DMSO-d₆, ppm): δ 12.55 (s, 1H), 9.60-9.58 (m, 1H), 8.99-8.97 (m, 1H), 8.43-8.39 (m, 2H), 7.89-7.49 (m, 11H), 7.18-7.15 (m, 1H), 4.64-4.63 (m, 2H), 4.22-4.20 (t, J=6 Hz, J=3 Hz, 2H), 3.89 (s, 2H), 3.71-3.69 (t, J=6 Hz, J=3 Hz, 2H), 3.33 (s, 3H), 2.63-2.59 (m, 2H). MS (ES, m/z): 668 [M+H]⁺.

Example 35

3-((3-((4-(Ethylthio)-2-(4-((3-(trifluoromethyl)benzyl)carbamoyl)pyridin-2-yl)phenyl)carbamoyl)benzyl)thio)propanoic acid Scheme 33:

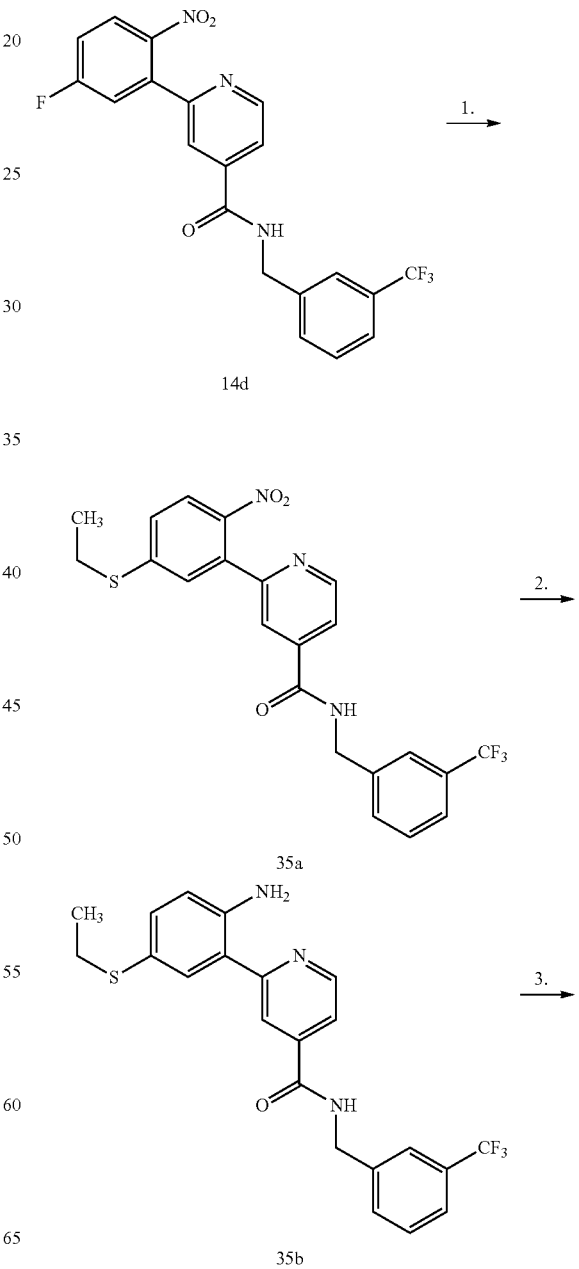

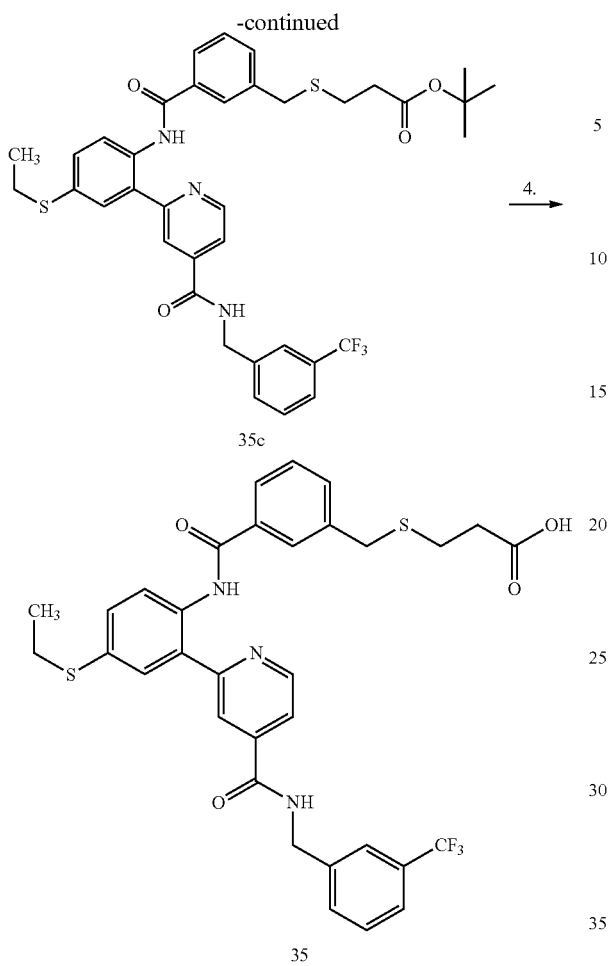

1. EtSNa, DMSO; 2. Pd/C H₂, MeOH, DCM; 3. EDC•HCl, DMAP/DCM, 3-(((3-(tert-butoxy)-3-oxopropyl)thio)methyl)benzoic acid 1.1c; 4. TFA, DCM.

Intermediate 35a: N-(3-(trifluoromethyl)benzyl)-2-(5-(ethylthio)-2-nitrophenyl)-isonicotinamide Into a 50-mL round-bottom flask, was placed a solution of N-(3-(trifluoromethyl)benzyl)-2-(5-fluoro-2-nitrophenyl)isonicotinamide 14d (300 mg, 0.72 mmol, 1.00 equiv) in DMSO (5 mL), and sodium ethanethiolate (100 mg, 1.19 mmol, 1.70 equiv). The resulting solution was stirred for overnight at 90° C. in an oil bath. The mixture was concentrated under vacuum. The residue was diluted with 20 mL of water. The resulting solution was extracted with 3×20 mL of dichloromethane and the organic layers combined. The mixture was dried over anhydrous sodium sulfate and concentrated under vacuum. This resulted in 300 mg (crude) of N-(3-(trifluoromethyl)benzyl)-2-(5-(ethylthio)-2-nitrophenyl)isonicotinamide as a yellow solid.

Intermediate 35b: N-(3-(trifluoromethyl)benzyl)-2-(2-amino-5-(ethylthio)phenyl)-isonicotinamide Into a 50-mL round-bottom flask, was placed a solution of N-(3-(trifluoromethyl)benzyl)-2-(5-(ethylthio)-2-nitrophenyl)isonicotinamide (300 mg, 0.65 mmol, 1.00 equiv) in methanol (5 mL). The solution was treated with Pd/C (300 mg), and stirred under an atmosphere of hydrogen for 2 h at room temperature. The solids were filtered out. The resulting mixture was concentrated under vacuum. This resulted in 200 mg (71%) of N-(3-(trifluoromethyl)benzyl)-2-(2-amino-5-(ethylthio)phenyl)isonicotinamide as a yellow solid.

Intermediate 35c: tert-butyl 3-(3-((2-(4-((3-(trifluoromethyl)benzyl)carbamoyl)pyridin-2-yl)-4-(ethylthio)phenyl)carbamoyl)benzylthio)propanoate Into a 50-mL round-bottom flask, was placed a solution of N-(3-(trifluoromethyl)benzyl)-2-(2-amino-5-(ethylthio)phenyl)isonicotinamide (200 mg, 0.46 mmol, 1.00 equiv) in N,N-dimethylformamide (5 mL), 3-((3-tert-butoxy-3-oxopropylthio)methyl)benzoic acid (200 mg, 0.68 mmol, 1.50 equiv), EDC.HCl (190 mg, 0.99 mmol, 2.00 equiv), and 4-dimethylaminopyridine (60 mg, 0.49 mmol, 1.00 equiv). The resulting solution was stirred for 2 h at room temperature. The resulting mixture was concentrated under vacuum. This resulted in 300 mg (crude) of tert-butyl 3-(3-((2-(4-((3-(trifluoromethyl)benzyl)carbamoyl)pyridin-2-yl)-4-(ethylthio)phenyl)carbamoyl)-benzylthio)propanoate as a yellow solid.

Example 35

3-(3-(4-(ethylthio)-2-(4-(3-(trifluoromethyl)benzylcarbamoyl)pyridin-2-yl)phenylcarbamoyl)benzylthio)propanoic acid Into a 50-mL round-bottom flask, was placed a solution of tert-butyl 3-(3-(4-(ethylthio)-2-(4-(3-(trifluoromethyl)benzylcarbamoyl)pyridin-2-yl)phenylcarbamoyl)benzylthio) propanoate (200 mg, 0.28 mmol, 1.00 equiv) in dichloromethane (5 mL), and trifluoroacetic acid (2 mL). The resulting solution was stirred overnight at room temperature. The reaction progress was monitored by LCMS. The resulting mixture was concentrated under vacuum. The crude product (0.2 g) was purified by reverse phase HPLC eluting with a water/CH₃CN gradient containing 0.05% TFA. The product was obtained 40.4 mg (21%) of a light yellow solid. ¹H-NMR (400 MHz, DMSO-d₆, ppm): δ 12.85 (s, 1H), 12.28 (s, 1H), 9.60-9.57 (m, 1H), 9.01-8.99 (m, 1H), 8.55-8.53 (m, 1H), 8.39 (s, 1H), 7.96-7.51 (m, 11H), 4.65-4.64 (d, J=5.2 Hz, 2H), 3.90 (s, 2H), 3.08-3.03 (m, 2H), 2.63-2.59 (t, J=5.1 Hz, 2H), 1.28-1.24 (t, J=5.7 Hz, 3H). MS (ES, m/z): 654 [M+H]⁺.

Example 36

3-((3-((4-Phenoxy-2-(4-((3-(trifluoromethyl)benzyl)carbamoyl)pyridin-2-yl)phenyl)carbamoyl)benzyl)thio)propanoic acid

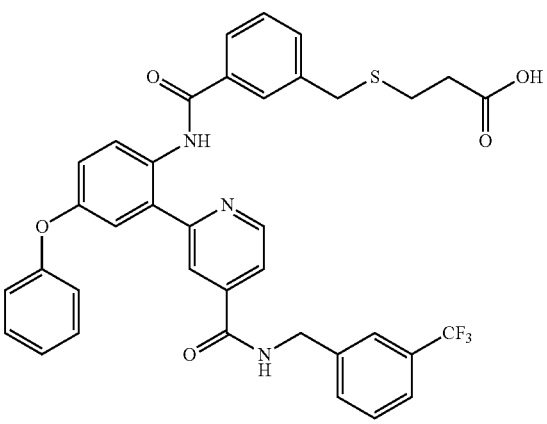 [SMILES: O=C(O)CCSCc1cccc(C(=O)Nc2ccc(Oc3ccccc3)cc2-c2cc(C(=O)NCc3cccc(C(F)(F)F)c3)ccn2)c1]

This compound was prepared according to the procedure described for the synthesis of 3-(3-((2-(4-((3-(trifluoromethyl)benzyl)carbamoyl)pyridin-2-yl)-4-(2,2,2-trifluoroethoxy)phenyl)carbamoyl)benzylthio)propanoic acid 32 using phenol in place of trifluoroethanol. $^1$H-NMR-(300 MHz, CD$_3$OD, ppm): δ 8.97 (m, 1H), 8.47-8.50 (d, 1H), 8.24 (s, 1H), 7.96 (s, 1H), 7.81-7.86 (m, 2H), 7.36-7.69 (m, 6H), 7.36-7.40 (m, 2H), 7.05-7.15 (m, 4H), 4.66 (s, 2H), 3.89 (s, 2H), 2.70-2.74 (m, 2H), 2.56-2.61 (m, 2H). MS (ES, m/z): 686 [M+H]$^+$.

Example 37

(S)—N1-Methyl-N1-(2-morpholinoethyl)-N3-(4-(piperidin-1-yl)-2-(4-((1,2,3,4-tetrahydronaphthalen-1-yl)carbamoyl)pyridin-2-yl)phenyl)isophthalamide Scheme 34.

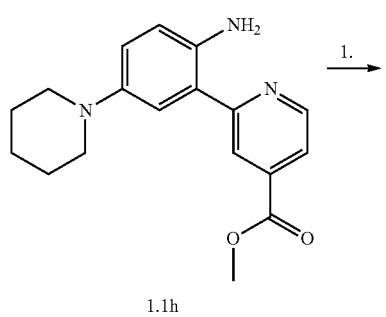

1.1h

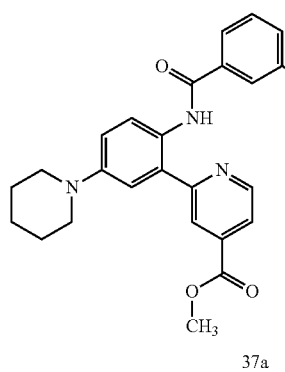

37a

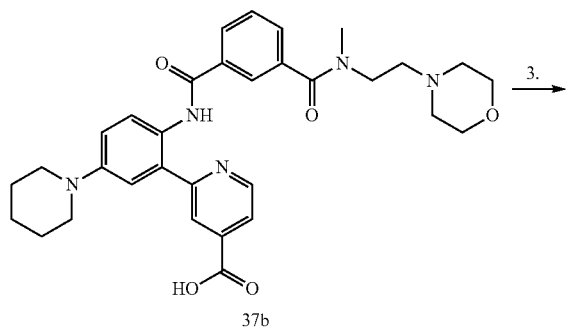

37b

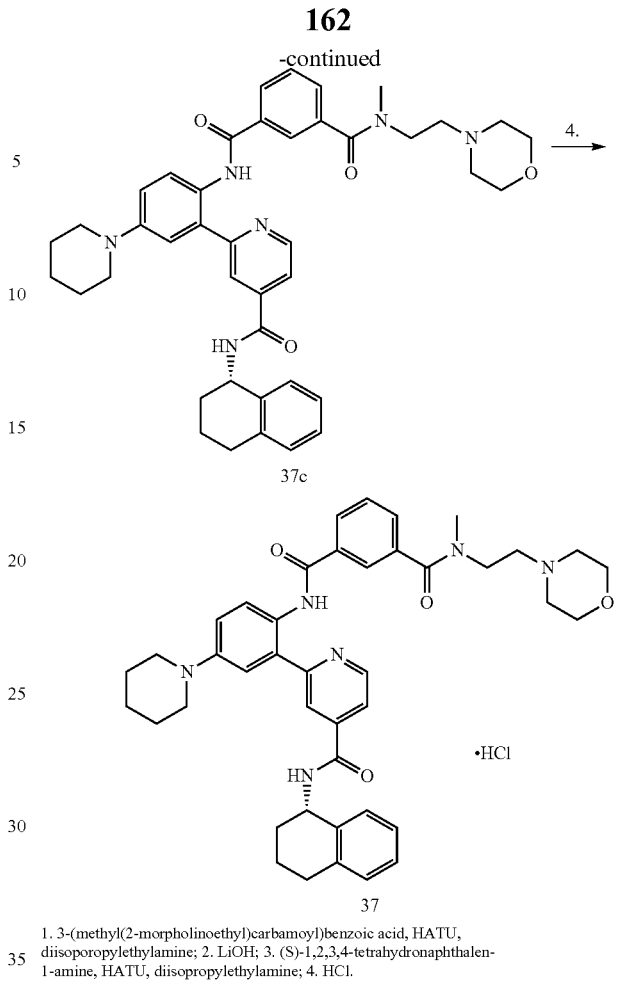

1. 3-(methyl(2-morpholinoethyl)carbamoyl)benzoic acid, HATU, diisoporopylethylamine; 2. LiOH; 3. (S)-1,2,3,4-tetrahydronaphthalen-1-amine, HATU, diisopropylethylamine; 4. HCl.

Intermediate 37a: methyl 2-(2-(3-(methyl(2-morpholinoethyl)carbamoyl)benzamido)-5-(piperidin-1-yl)phenyl)isonicotinate A solution of 150 mg of methyl 2-(2-amino-5-(piperidin-1-yl)phenyl)isonicotinate 1.1h, 169 mg of 3-(methyl(2-morpholinoethyl)carbamoyl)benzoic acid, and 249 mg of diisopropylethylamine in 3 mL of DMF was treated with 202 mg of HATU. The mixture was stirred for 2 h and then it was diluted with 20 mL of water. The resulting precipitate was collected by filtration and dissolved in dichloromethane. The solution was washed with water and then dried over Na$_2$SO$_4$. The solvent was evaporated to give the product as 231 mg of an orange oil.

Intermediate 37b: 2-(2-(3-(methyl(2-morpholinoethyl)carbamoyl)benzamido)-5-(piperidin-1-yl)phenyl)isonicotinic acid A solution of 231 mg of methyl 2-(2-(3-(methyl(2-morpholinoethyl)carbamoyl)benzamido)-5-(piperidin-1-yl)phenyl)isonicotinate in 9 mL of 2:1 dioxane/water was treated with 33 mg of lithium hydroxide hydrate. After stirring for 1 h the solvent was evaporated and the residue was partitioned between dichloromethane and 3 N hydrochloric acid. The aqueous phase was evaporated to give the product as 280 mg of a yellow solid.

Example 37c (S)—N1-methyl-N1-(2-morpholinoethyl)-N3-(4-(piperidin-1-yl)-2-(4-((1,2,3,4-tetrahydronaphthalen-1-yl)carbamoyl)pyridin-2-yl)phenyl)isophthalamide A solution of 550 mg of 2-(2-(3-(methyl(2-morpholinoethyl)carbamoyl)benzamido)-5-(piperidin-1-yl)phenyl)isonicotinic acid, 142 mg of (S)-1,2,3,4-tetrahydronaphthalen-1-amine, and 497 mg of diisopropylethylamine in 6 mL of DMF was treated with 366 mg of HATU. After stirring for 2 h the product was isolated by reverse phase HPLC, eluting with 0.05% TFA in a water/acetonitrile gradient. The procedure gave 220 mg of product.

Example 37

S)—N1-methyl-N1-(2-morpholinoethyl)-N3-(4-(piperidin-1-yl)-2-(4-(1,2,3,4-tetrahydronaphthalen-1-ylcarbamoyl)pyridin-2-yl)phenyl)isophthalamide trihydrochloride Into a 100-mL round-bottom flask, was placed a solution of (S)—N1-methyl-N1-(2-morpholinoethyl)-N3-(4-(piperidin-1-yl)-2-(4-(1,2,3,4-tetrahydronaphthalen-1-yl-carbamoyl)pyridin-2-yl)phenyl)isophthalamide (1.02 g, 1.46 mmol, 1.00 equiv) in methanol (30 mL). Hydrogen chloride gas was bubbled through the reaction mixture for 15 minutes. The resulting solution was stirred for 2 min at 5° C. in a water/ice bath. The resulting mixture was concentrated under vacuum. The resulting mixture was washed with 2×20 mL of diethyl ether. This resulted in 1.12 g (93%) of (S)—N1-methyl-N1-(2-morpholinoethyl)-N3-(4-(piperidin-1-yl)-2-(4-(1,2,3,4-tetrahydronaphthalen-1-yl-carbamoyl)pyridin-2-yl)phenyl)isophthalamide trihydrochloride as a yellow solid. $^{1}$H-NMR (300 MHz, CD$_{3}$OD, ppm): δ 9.00 (d, J=5.4 Hz, 1H), 8.60~8.58 (m, 2H), 8.51 (s, 1H), 8.34 (s, 1H), 8.20~7.91 (m, 3H), 7.84 (d, J=7.2 Hz, 1H), 7.72~7.67 (m, 1H), 7.25~7.16 (m, 4H), 5.39~5.37 (m, 1H), 4.14~3.88 (m, 6H), 3.84~3.76 (m, 6H), 3.56~3.55 (m, 2H), 3.28~3.24 (m, 2H), 3.12 (s, 3H), 2.91~2.83 (m, 2H), 2.14~1.86 (m, 10H). MS (ES, m/z): 701 [M+H]$^{+}$.

Example 38

Tert-butyl 4-(2-(methyl(3-((4-(piperidin-1-yl)-2-(4-((3-(trifluoromethyl)benzyl)-carbamoyl)pyridin-2-yl)phenyl)carbamoyl)benzyl)amino)ethyl)piperazine-1-carboxylate Scheme 35.

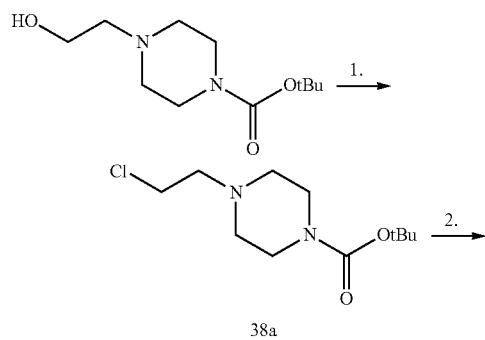

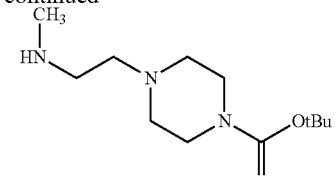

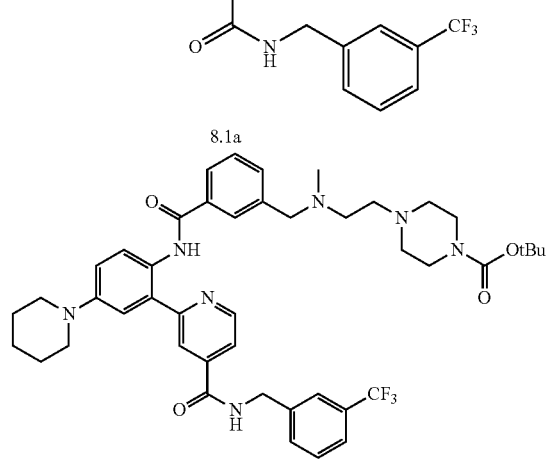

1. SOCl$_2$; 2. methylaminie; 3. K$_2$CO$_3$, KI, DMF, acetone, intermediate 38b.

Intermediate 38a: tert-butyl 4-(2-chloroethyl)piperazine-1-carboxylate

Into a 50-mL round-bottom flask, was placed a solution of tert-butyl 4-(2-hydroxyethyl)piperazine-1-carboxylate (2.31 g, 10.03 mmol, 1.00 equiv) in dichloromethane (20 mL) and a solution of thionyl chloride (1.5 mL, 2.00 equiv) in dichloromethane (3 mL) was added dropwise at 0° C. The resulting solution was stirred overnight at 25° C. The resulting mixture was concentrated under vacuum. The resulting solution was diluted with 10 mL of water. The resulting solution was extracted with 2×25 mL of ethyl acetate and the organic layers combined. The resulting mixture was washed with 2×15 mL of sodium bicarbonate aq. and 2×10 mL of brine. The mixture was dried over anhydrous sodium sulfate and concentrated under vacuum. The residue was applied onto a silica gel column and eluted with ethyl acetate/petroleum ether (1:5). This resulted in 1.16 g (46%) of tert-butyl 4-(2-chloroethyl)piperazine-1-carboxylate as a off-white solid.

Intermediate 38b: tert-butyl 4-(2-(methylamino)ethyl)piperazine-1-carboxylate Into a 50-mL sealed tube, was placed tert-butyl 4-(2-chloroethyl)piperazine-1-carboxylate (300 mg, 1.21 mmol, 1.00 equiv), methylamine (in ethanol) (10 mL), and NaI (100 mg).

The resulting solution was stirred for 12 h at 70° C. in an oil bath. The resulting mixture was concentrated under vacuum. The resulting solution was diluted with 3 mL of water and adjusted to pH 7-8 with sodium bicarbonate (5%). The resulting solution was extracted with 2×5 mL of dichloromethane and the organic layers combined. The resulting mixture was washed with 1×3 mL of water and 1×3 mL of brine. The resulting mixture was concentrated under vacuum. This resulted in 180 mg (crude) of tert-butyl 4-(2-(methylamino) ethyl)piperazine-1-carboxylate as brown oil.

Example 38 tert-butyl 4-(2-(methyl(3-((4-(piperidin-1-yl)-2-(4-((3-(trifluoromethyl)benzyl)carbamoyl)pyridin-2-yl) phenyl)carbamoyl)benzyl)amino)ethyl)-piperazine-1-carboxylate Into a 50-mL round-bottom flask, was placed a solution of N-(3-(trifluoromethyl)benzyl)-2-(2-(3-(chloromethyl)benzamido)-5-(piperidin-1-yl)phenyl)-isonicotinamide (100 mg, 0.17 mmol, 1.00 equiv) in N,N-dimethylformamide (2.5 mL), acetone (2.5 mL), tert-butyl 4-(2-(methylamino)ethyl) piperazine-1-carboxylate (48 mg, 0.20 mmol, 1.20 equiv), potassium carbonate (68 mg, 0.49 mmol, 3.00 equiv), and potassium iodide (6 mg, 0.04 mmol, 0.20 equiv). The resulting solution was stirred for 2.5 h at 70° C. in an oil bath. The resulting mixture was concentrated under vacuum. The crude product (100 mg) was purified by reverse phase HPLC eluting with a water/CH$_3$CN gradient containing 0.05% TFA. The product was obtained as 75.5 mg (49%) of a yellow solid. $^1$H-NMR (300 MHz, DMSO-d$_6$, ppm): δ 12.28 (s, 1H), 9.58-9.54 (m, 1H), 8.94-8.92 (d, J=5.1 Hz, 1H), 8.33-8.27 (m, 2H), 8.04 (s, 1H), 7.96-7.93 (d, J=7.8 Hz, 1H), 7.85-7.84 (d, J=4.2 Hz, 1H), 7.71-7.55 (m, 7H), 7.31-7.28 (d, J=8.1 Hz, 1H), 4.64-4.62 (d, J=5.7 Hz, 2H), 4.29 (s, 2H), 3.44-3.31 (m, 8H), 3.20 (s, 2H), 3.06 (s, 2H), 3.27-3.26 (m, 6H), 1.73 (s, 4H), 1.60 (s, 2H), 1.39 (s, 9H). MS (ES, m/z): 814 [M+H]$^+$.

Example 39

2-(2-(3-((Methyl(2-(4-methylpiperazin-1-yl)ethyl) amino)methyl)benzamido)-5-(piperidin-1-yl)phenyl)-N-(3-(trifluoromethyl)benzyl)isonicotinamide

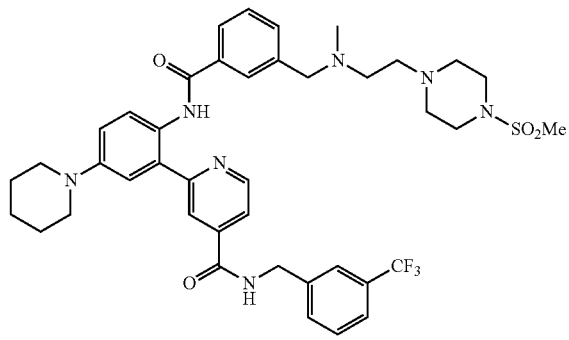 [SMILES: CN(CCN1CCN(S(C)(=O)=O)CC1)Cc1cccc(C(=O)Nc2ccc(N3CCCCC3)cc2-c2cc(C(=O)NCc3cccc(C(F)(F)F)c3)ccn2)c1]

Into a 25-mL round-bottom flask, was placed 160 mg of tert-butyl 4-(2-(methyl(3-((4-(piperidin-1-yl)-2-(4-((3-(trifluoromethyl)benzyl)carbamoyl)pyridin-2-yl)phenyl)-carbamoyl)benzyl)amino)ethyl)piperazine-1-carboxylate Example 38 and 10 mL of 1:1 dichloromethane/TFA. After stirring for 2 hours, the solvent was evaporated. The residue was partitioned between ethyl acetate and aqueous sodium bicarbonate solution. The organic phase was dried and the solvent was evaporated. The residue was treated with triethylamine (78 mg, 0.77 mmol, 6.00 equiv), and dichloromethane (2 mL). This was followed by dropwise addition of a solution of methanesulfonyl chloride (21.9 mg, 0.19 mmol, 1.50 equiv) in dichloromethane (1 mL) with stirring at 0° C. The resulting solution was stirred for 4 h at 25° C. The resulting mixture was concentrated under vacuum. The crude product (200 mg) was purified by reverse phase HPLC eluting with a water/CH$_3$CN gradient containing 0.05% TFA. The product was obtained as 45 mg (28%) of a yellow solid. $^1$H-NMR (300 MHz, DMSO-d$_6$, ppm): δ 12.31 (s, 1H), 9.55-9.59 (t, J=6.6 Hz, 1H), 8.93-8.94 (d, J=3 Hz, 1H), 8.35 (s, 1H), 8.27-8.30 (d, J=9 Hz, 1H), 8.09 (s, 1H), 7.96-7.98 (d, J=6 Hz, 1H), 7.85-7.86 (d, J=3 Hz, 1H), 7.56-7.76 (m, 7H), 7.31-7.34 (d, J=9 Hz, 1H), 4.62-4.64 (d, J=6 Hz, 2H), 4.39 (s, 2H), 3.34 (s, 4H), 3.22-3.24 (d, J=6 Hz, 6H), 2.90 (s, 5H), 2.74 (s, 3H), 2.69 (s, 4H), 1.75 (s, 4H), 1.60-1.61 (d, J=3 Hz, 2H). MS (ES, m/z): 792 [M+H]$^+$.

Example 40

2-(2-(3-((Methyl(2-(4-methylpiperazin-1-yl)ethyl) amino)methyl)benzamido)-5-(piperidin-1-yl)phenyl)-N-(3-(trifluoromethyl)benzyl)isonicotinamide

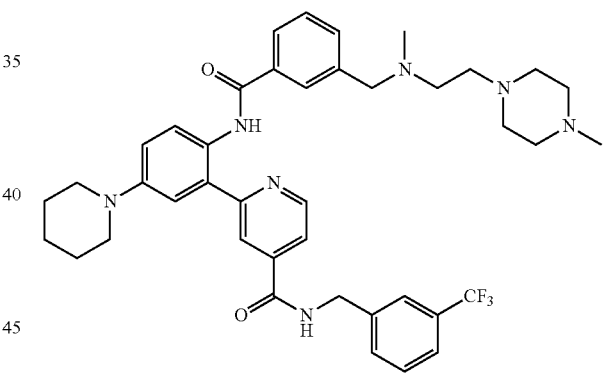

Into a 25-mL round-bottom flask, was placed 190 mg of tert-butyl 4-(2-(methyl(3-((4-(piperidin-1-yl)-2-(4-((3-(trifluoromethyl)benzyl)carbamoyl)pyridin-2-yl)phenyl)-carbamoyl)benzyl)amino)ethyl)piperazine-1-carboxylate and 10 mL of 1:1 dichloromethane/TFA. After stirring for 2 hours, the solvent was evaporated. The residue was dissolved in 10 mL of aqueous sodium bicarbonate solution. The mixture was stirred for 20 minutes at room temperature. The resulting solution was extracted with 3×10 mL of ethyl acetate and the organic layers combined. The mixture was dried over anhydrous sodium sulfate and concentrated under vacuum. This resulted in 150 mg of N-(3-(trifluoromethyl)benzyl)-2-(2-(3-((methyl(2-(piperazin-1-yl)ethyl)amino)methyl)-benzamido)-5-(piperidin-1-yl)phenyl)isonicotinamide. Into a 50-mL round-bottom flask, was placed a solution of N-(3-(trifluoromethyl)benzyl)-2-(2-(3-((methyl(2-(piperazin-1-yl)ethyl)amino)methyl)benzamido)-5-(piperidin-1-yl)-phenyl)isonicotinamide (150 mg, 0.21 mmol, 1.00 equiv) in formaldehyde solution (5 mL), sodium cyanoborohydride (16 mg, 0.25 mmol, 1.20 equiv), and acetic acid (cat.). The resulting solution was stirred for 2 h at room temperature. The resulting solution was diluted with 2 mL of water. The resulting solution was extracted with 2×5 mL of ethyl acetate and the organic layers combined and dried over sodium sulfate and concentrated under vacuum. The crude product (150 mg) was purified by reverse phase HPLC eluting with a water/CH₃CN gradient containing 0.05% TFA. The product was obtained as 21.3 mg (8%) of a yellow solid. ¹H-NMR (300 MHz, DMSO-d₆, ppm): δ 12.18 (s, 1H), 9.57 (s, 1H), 9.56-9.54 (d, J=6.0 Hz, 1H), 8.93-8.91 (d, J=5.1 Hz, 1H), 8.32 (s, 1H), 8.23-8.20 (d, J=9.0 Hz, 1H), 8.08 (s, 1H), 7.98-7.96 (d, J=7.8 Hz, 1H), 7.84-7.82 (m, 6H), 7.50 (s, 1H), 7.22 (s, 1H), 4.81-4.80 (m, 1H), 4.68-4.60 (m, 3H), 4.44 (s, 3H), 3.41-3.38 (d, J=10.5 Hz, 2H), 3.28-3.20 (m, 6H), 2.98-2.94 (d, J=12 Hz, 4H), 2.78-2.73 (m, 7H), 2.51-2.49 (m, 2H), 1.76 (s, 4H), 1.59-1.57 (d, J=4.5 Hz, 2H). MS (ES, m/z): 728 [M+H]⁺.

Example 41

2-(2-(3-(((2-(4-Acetylpiperazin-1-yl)ethyl)(methyl)amino)methyl)benzamido)-5-(piperidin-1-yl)phenyl)-N-benzylisonicotinamide The free base of N-benzyl-2-(2-(3-((methyl(2-(piperazin-1-yl)ethyl)amino)methyl)benzamido)-5-(piperidin-1-yl)phenyl)isonicotinamide was prepared as described in the preparation of 2-(2-(3-((methyl(2-(4-methylpiperazin-1-yl)ethyl)amino)methyl)benzamido)-5-(piperidin-1-yl)phenyl)-N-(3-(trifluoromethyl)-benzyl)isonicotinamide 40. Into a 50-mL round-bottom flask, was placed a solution of this free base (150 mg, 0.21 mmol, 1.00 equiv) in tetrahydrofuran (5 mL), acetyl acetate (26 mg, 0.25 mmol, 1.20 equiv), and pyridine (33 mg, 0.42 mmol, 2.00 equiv). The resulting solution was stirred for 2 h at room temperature. The resulting mixture was concentrated under vacuum. The crude product (200 mg) was purified by reverse phase HPLC eluting with a water/CH₃CN gradient containing 0.05% TFA. The product was obtained as 44 mg (17%) of a yellow solid. ¹H-NMR (300 MHz, DMSO-d₆, ppm): δ 12.25 (s, 1H), 9.56-9.52 (m, 1H), 8.93-8.91 (d, J=5.1 Hz, 1H), 8.33-8.26 (m, 2H), 8.04 (s, 1H), 7.96-7.93 (d, J=7.8 Hz, 1H), 7.85-7.83 (d, J=6.3 Hz, 1H), 7.70-7.55 (m, 6H), 7.29-7.26 (d, J=8.7 Hz, 1H), 4.64-4.62 (d, J=5.7 Hz, 2H), 4.29 (s, 2H), 3.54 (s, 4H), 3.30-3.21 (m, 6H), 3.03 (s, 2H), 2.80-2.73 (m, 3H), 2.66 (s, 3H), 1.99 (s, 3H), 1.73 (s, 4H), 1.60-1.59 (d, J=4.8 Hz, 1H). MS (ES, m/z): 756 [M+H]⁺.

Example 42

2-(2-(3-((N-Methyl-2-morpholinoacetamido)methyl)benzamido)-5-(piperidin-1-yl)phenyl)-N-(3-(trifluoromethyl)benzyl)isonicotinamide

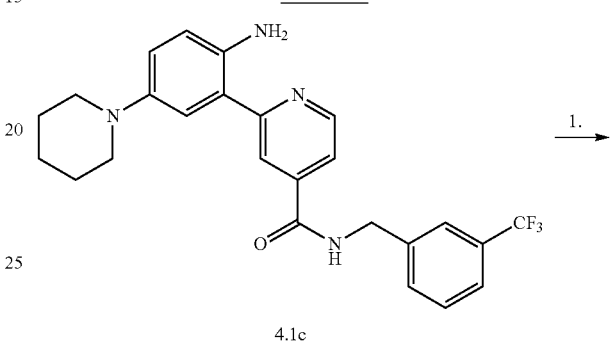

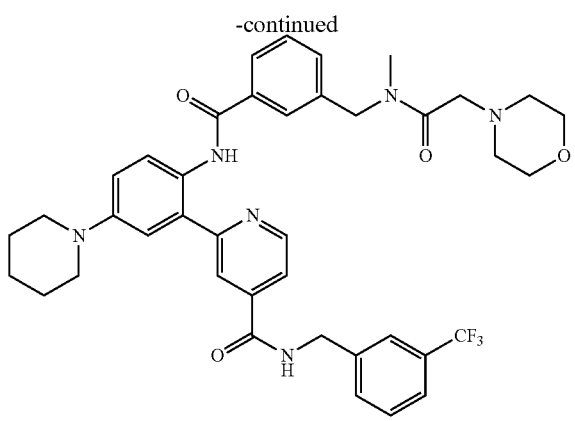

42

1. 3-(bromomethyl)benzoyl chloride, pyridine; 2. MeNH₂; 3. EDC•HCl, DMAP, DCM, morpholinoacetic acid.

Intermediate 42a: 2-(2-(3-(bromomethyl)benzamido)-5-(piperidin-1-yl)phenyl)-N-(3-(trifluoromethyl)benzyl)isonicotinamide This compound was prepared from 3-(bromomethyl)benzoyl chloride and Intermediate 4.1c using the procedure described for the synthesis of 2-(2-(3-(chloromethyl)benzamido)-5-(piperidin-1-yl)phenyl)-N-(3-(trifluoromethyl)benzyl)isonicotinamide 8.1a.

Intermediate 42b: N-(3-(trifluoromethyl)benzyl)-2-(2-(3-((methylamino)methyl)-benzamido)-5-(piperidin-1-yl)phenyl)isonicotinamide Into a 100-mL round-bottom flask, was placed a solution of methylamine in methanol (126 mg, 1.22 mmol, 4.00 equiv, 30%), potassium carbonate (124 mg, 0.90 mmol, 3.00 equiv), potassium iodide (10 mg, 0.06 mmol, 0.20 equiv), and a solution of N-(3-(trifluoromethyl)benzyl)-2-(2-(3-(bromomethyl)benzamido)-5-(piperidin-1-yl)phenyl)isonicotinamide (200 mg, 0.31 mmol, 1.00 equiv) in N,N-dimethylformamide (15 mL). The resulting solution was stirred for 3 h at 70° C. in an oil bath. The resulting solution was diluted with 250 mL of water. The resulting solution was extracted with 4×20 mL of ethyl acetate and the organic layers combined. The resulting mixture was washed with 2×50 mL of brine, dried over sodium sulfate, and concentrated under vacuum. This resulted in 200 mg (crude) of N-(3-(trifluoromethyl)benzyl)-2-(2-(3-((methylamino)methyl)benzamido)-5-(piperidin-1-yl)phenyl)isonicotinamide as a yellow solid.

Example 42

2-(2-(3-((N-methyl-2-morpholinoacetamido)methyl)benzamido)-5-(piperidin-1-yl)phenyl)-N-(3-(trifluoromethyl)benzyl)isonicotinamide Into a 50-mL round-bottom flask, was placed a solution of 2-morpholinoacetic acid (25.0 mg, 0.17 mmol, 1.00 equiv) in dichloromethane (10 mL), EDC.HCl (50.0 mg, 0.26 mmol, 1.50 equiv), 4-dimethylaminopyridine (32.0 mg, 0.26 mmol, 1.50 equiv), and N-(3-(trifluoromethyl)benzyl)-2-(2-(3-((methylamino)methyl)benzamido)-5-(piperidin-1-yl)phenyl)isonicotinamide (1000 mg, 1.66 mmol, 1.00 equiv). The resulting solution was stirred for 6 h at 25° C. in an oil bath. The resulting solution was diluted with 50 mL of dichloromethane. The resulting mixture was washed with 2×30 mL of aqueous NH₄Cl. The resulting mixture was washed with brine. The mixture was dried over sodium sulfate and concentrated under vacuum. The crude product (120 mg) was purified by reverse phase HPLC eluting with a water/CH₃CN gradient containing 0.05% TFA. The product was obtained as 47.4 mg (26%) of a pale-yellow solid. $^1$H-NMR (300 MHz, CD₃OD, ppm): δ 8.90-8.98 (m, 1H), 8.57-8.64 (m, 1H), 8.40 (s, 1H), 7.84-8.00 (m, 4H), 7.54-7.72 (m, 7H), 4.72-4.76 (m, 4H), 4.36-4.38 (m, 2H), 3.96 (m, 4H), 3.58-3.61 (m, 4H), 3.01 (s, 3H), 1.99-2.00 (m, 4H), 1.75 (m, 2H). MS (ES, m/z) 729 [M+H]⁺.

Example 43

2-Methyl-1-(3-((4-(piperidin-1-yl)-2-(4-((3-(trifluoromethyl)benzyl)carbamoyl)pyridin-2-yl)phenyl)carbamoyl)phenyl)-5,8,11-trioxa-2-azatetradecan-14-oic acid Scheme 37.

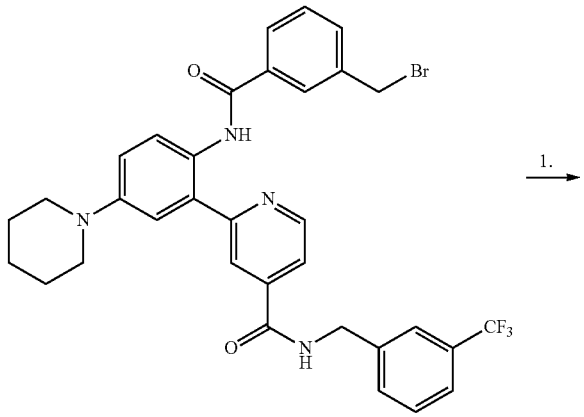

42a

-continued

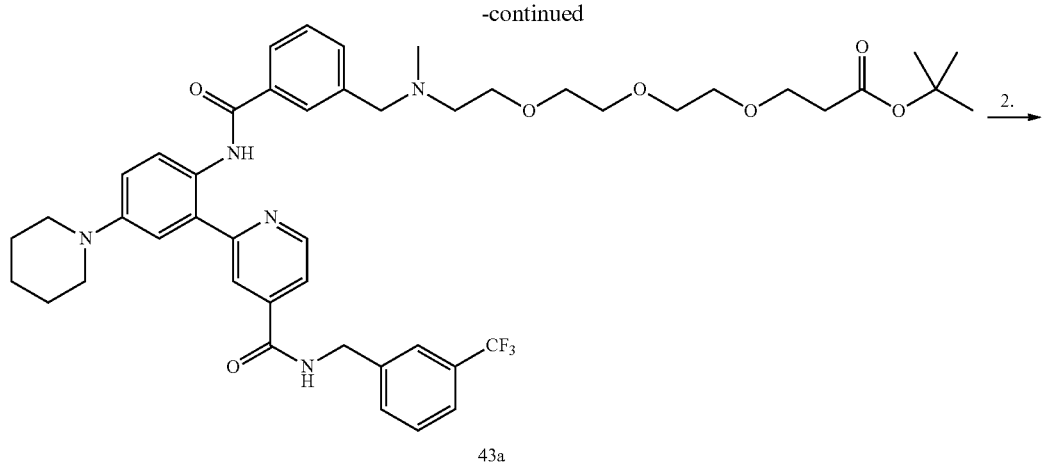

1. tert-butyl 5,8,11-trioxa-2-azatetradecan-14-oate, $K_2CO_3$, KI, DMF; 2. $CF_3COOH$, DCM.

Intermediate 43a: tert-butyl 3-(2-(2-(2-((3-((2-(4-((3-(trifluoromethyl)benzyl)carbamoyl)-pyridin-2-yl)-4-(piperidin-1-yl)phenyl)carbamoyl)-benzyl)(methyl)amino)ethoxy)ethoxy)-ethoxy)propanoate Into a 8-mL round-bottom flask, was placed a solution of tert-butyl 3-(2-(2-(2-(methylamino)ethoxy)ethoxy)ethoxy) propanoate (89.3 mg, 0.31 mmol, 1.00 equiv) in N,N-dimethylformamide (6 mL), potassium carbonate (84.7 mg, 0.61 mmol, 1.99 equiv), potassium iodide (10.2 mg, 0.06 mmol, 0.20 equiv), and N-(3-(trifluoromethyl)benzyl)-2-(2-(3-(bromomethyl)benzamido)-5-(piperidin-1-yl)phenyl)isonicotinamide (200 mg, 0.31 mmol, 1.00 equiv). The resulting solution was stirred overnight at 70° C. The solids were filtered out. The resulting mixture was concentrated under vacuum. The residue was dissolved in 20 mL of dichloromethane. The resulting mixture was washed with 2×20 mL of water. The resulting mixture was washed with 1×20 mL of brine, dried over sodium sulfate, and concentrated under vacuum. This resulted in 264 mg (crude) of product as yellow oil.

Example 43
2-methyl-1-(3-((4-(piperidin-1-yl)-2-(4-((3-(trifluoromethyl)benzyl)-carbamoyl)pyridin-2-yl)phenyl)carbamoyl)phenyl)-5,8,11-trioxa-2-azatetradecan-14-oic acid Into a 50-mL round-bottom flask, was placed a solution of tert-butyl 3-(2-(2-(2-((3-((2-(4-((3-(trifluoromethyl)benzyl)carbamoyl)pyridin-2-yl)-4-(piperidin-1-yl)phenyl)-carbamoyl)benzyl)(methyl)amino)ethoxy)ethoxy)ethoxy)propanoate (264 mg, 0.31 mmol, 1.00 equiv) in dichloromethane (2 mL), and trifluoroacetic acid (1 mL). The resulting solution was stirred for 2 h at room temperature. The resulting mixture was concentrated under vacuum. The crude product (200 mg) was purified by reverse phase HPLC eluting with a water/$CH_3CN$ gradient containing 0.05% TFA. The product was obtained as 46 mg (13%) of as a yellow solid. $^1$H-NMR (300 MHz, $CD_3OD$, ppm): δ 8.941-8.924 (d, J=5.1 Hz, 1H), 8.665-8.635 (d, J=9.0 Hz, 1H), 8.436 (s, 1H), 8.159-8.081 (m, 3H), 7.888-7.863 (m, 1H), 7.792-7.563 (m, 7H), 4.720 (s, 2H), 4.533 (s, 2H), 3.895-3.862 (m, 6H), 3.685-3.560 (m, 14H), 3.410 (s, 2H), 2.910 (s, 3H), 2.509-2.468 (m, 2H), 2.020-2.004 (s, 4H), 1.816-1.799 (s, 2H). MS (ES, m/z): 806 [M+H]$^+$.

Example 44
tert-Butyl 4-(3-((4-(piperidin-1-yl)-2-(4-((3-(trifluoromethyl)benzyl)carbamoyl)pyridin-2-yl)phenyl)carbamoyl)benzyl)-1,4-diazepane-1-carboxylate

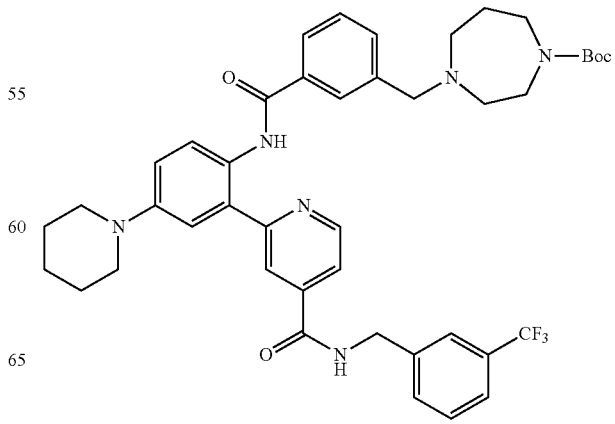

Example 44 tert-butyl 4-(3-((2-(4-(((3-(trifluoromethyl)benzyl) carbamoyl)pyridin-2-yl)-4-(piperidin-1-yl)phenyl) carbamoyl)benzyl)-1,4-diazepane-1-carboxylate Into a 100-mL round-bottom flask, was placed a solution of N-(3-(trifluoromethyl)benzyl)-2-(2-(3-(bromomethyl)benzamido)-5-(piperidin-1-yl)phenyl)isonicotinamide (400 mg, 0.61 mmol, 1.00 equiv) in N,N-dimethylformamide (20 mL), potassium carbonate (248 mg, 1.79 mmol, 2.92 equiv), potassium iodide (20 mg, 0.12 mmol, 0.20 equiv), and tert-butyl 1,4-diazepane-1-carboxylate (240 mg, 1.20 mmol, 1.95 equiv). The resulting solution was stirred for 3 h at 70° C. in an oil bath. The resulting solution was diluted with 300 mL of water. The resulting solution was extracted with 4×200 mL of ethyl acetate and the organic layers combined. The resulting mixture was washed with 2×200 mL of brine. The mixture was dried over sodium sulfate and concentrated under vacuum. The residue was applied onto a silica gel column with dichloromethane:methanol (20:1~10:1). The product was obtained as 400 mg (85%) of a yellow solid. $^1$H-NMR (300 MHz, CD$_3$OD, ppm): δ 8.875-8.887 (d, J=3.6 Hz, 1H), 8.287-8.298 (d, J=3.3 Hz, 1H), 8.253 (s, 1H), 7.936 (s, 1H), 7.772-7.936 (m, 2H), 7.433-7.711 (m, 7H), 7.106-7.146 (dd, J=2.7 Hz, J'=9.0 Hz, 1H), 4.689 (s, 2H), 3.740 (s, 2H), 3.482 (m, 4H), 3.197-3.232 (m, 4H), 2.656-2.693 (m, 4H), 1.720-1.847 (m, 6H), 1.614-1.649 (m, 2H), 1.420-1.459 (m, 9H). MS (ES, m/z): 771 [M+H]$^+$; 793 [M+Na]$^+$.

Example 45

2-(2-(3-((4-Methyl-1,4-diazepan-1-yl)methyl)benzamido)-5-(piperidin-1-yl)phenyl)-N-(3-(trifluoromethyl)benzyl)isonicotinamide

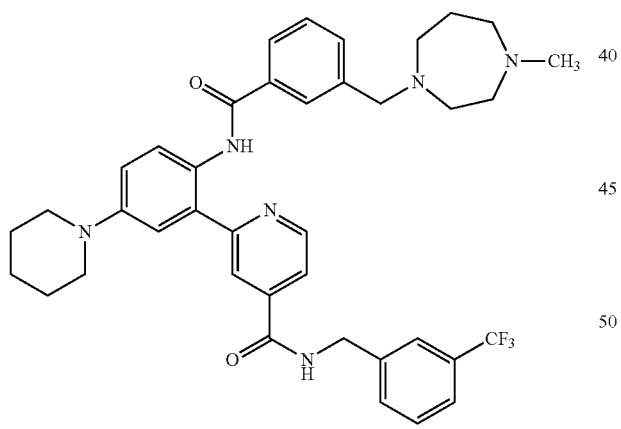

Into a 50-mL round-bottom flask, was placed a solution of N-(3-(trifluoromethyl)benzyl)-2-(2-(3-(bromomethyl)benzamido)-5-(piperidin-1-yl)phenyl)isonicotinamide (100 mg, 0.15 mmol, 1.00 equiv) in N,N-dimethylformamide (2 mL), 1-methyl-1,4-diazepane (65.4 mg, 0.57 mmol, 3.74 equiv), KI (12.7 mg, 0.08 mmol, 0.50 equiv), and potassium carbonate (42.4 mg, 0.31 mmol, 2.00 equiv). The resulting solution was stirred for 3 h at 70° C. in an oil bath. The reaction progress was monitored by LCMS. The resulting solution was diluted with 20 mL of water. The resulting solution was extracted with 3×20 mL of ethyl acetate and the organic layers combined. The resulting mixture was washed with 3×20 mL of brine, dried over anhydrous sodium sulfate, and concentrated under vacuum. The crude product was purified by reverse phase HPLC eluting with a water/CH$_3$CN gradient containing 0.05% TFA. The product was obtained as 40 mg (23%) of a yellow solid. $^1$H-NMR (400 MHz, CD$_3$OD, ppm): δ 8.95-8.93 (d, J=4.2 Hz, 1H), 8.75-8.73 (d, J=6.6 Hz, 1H), 8.46 (s, 1H), 8.18-8.17 (d, J=4.2 Hz, 1H), 8.09 (s, 1H), 8.02-8.00 (d, J=8 Hz, 1H), 7.90-7.88 (m, 1H), 7.75-7.55 (m, 1H), 4.72 (s, 2H), 4.19 (s, 2H), 3.70-3.67 (t, J=5.6 Hz, 4H), 3.55-3.49 (m, 4H), 3.18-3.16 (t, J=5.6 Hz, 2H), 2.95 (s, 3H), 2.22-2.18 (m, 2H), 2.07-2.05 (t, J=5.2 Hz, 4H), 1.84-1.83 (d, J=5.2 Hz, 1H). MS (ES, m/z): 685 [M+H]$^+$.

Example 46

2-(2-(3-((4-Acetamidopiperidin-1-yl)methyl)benzamido)-5-(piperidin-1-yl)phenyl)-N-(3-(trifluoromethyl)benzyl)isonicotinamide

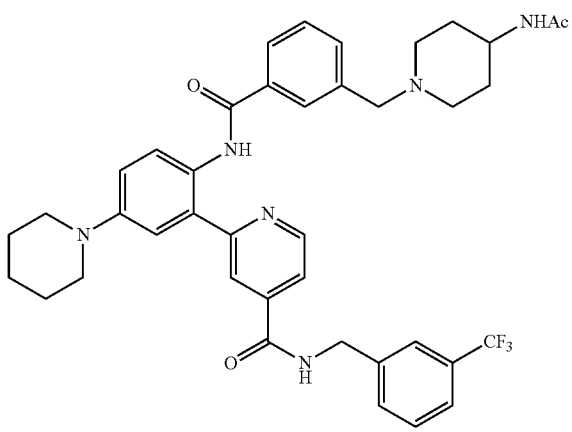 [SMILES: CC(=O)NC1CCN(Cc2cccc(C(=O)Nc3ccc(N4CCCCC4)cc3-c3cc(C(=O)NCc4cccc(C(F)(F)F)c4)ccn3)c2)CC1]

Into a 50-mL round-bottom flask, was placed a solution of N-(3-(trifluoromethyl)benzyl)-2-(2-(3-(bromomethyl)benzamido)-5-(piperidin-1-yl)phenyl)isonicotinamide (100 mg, 0.15 mmol, 1.00 equiv) in N,N-dimethylformamide (2 mL), N-(piperidin-4-yl)acetamide (52.5 mg, 0.37 mmol, 2.41 equiv), potassium iodide (12.7 mg, 0.08 mmol, 0.50 equiv), and potassium carbonate (42.4 mg, 0.31 mmol, 2.00 equiv). The resulting solution was stirred for 3 h at 70° C. in an oil bath. The reaction progress was monitored by LCMS. The resulting solution was diluted with 20 mL of water. The resulting solution was extracted with 3×20 mL of ethyl acetate and the organic layers combined. The resulting mixture was washed with 3×20 mL of brine. The mixture was dried over anhydrous sodium sulfate and concentrated under vacuum. The crude product was purified by reverse phase HPLC eluting with a water/CH$_3$CN gradient containing 0.05% TFA. The product was obtained as 80.4 mg (50%) of a yellow solid. $^1$H-NMR (400 MHz, CD$_3$OD, ppm): δ 8.93-8.92 (d, J=5.2 Hz, 1H), 8.67-8.65 (d, J=8.8 Hz, 1H), 8.44 (s, 1H), 8.13-8.09 (m, 3H), 7.88-7.87 (m, 1H), 7.78-7.67 (m, 5H), 7.62-7.54 (m, 1H), 4.72 (s, 2H), 4.44 (s, 2H), 3.91 (s, 1H), 3.66-3.63 (t, J=5.2 Hz, 4H), 3.57-3.54 (m, 2H), 3.20-3.14 (m, 2H), 2.17-2.13 (m, 2H), 2.05-2.00 (m, 4H), 1.93 (s, 3H), 1.82-1.70 (m, 4H). MS (ES, m/z): 713 [M+H]+.

Example 47

(S)-2-(2-(3-((3-Acetamidopyrrolidin-1-yl)methyl)benzamido)-5-(piperidin-1-yl)phenyl)-N-(3-(trifluoromethyl)benzyl)isonicotinamide

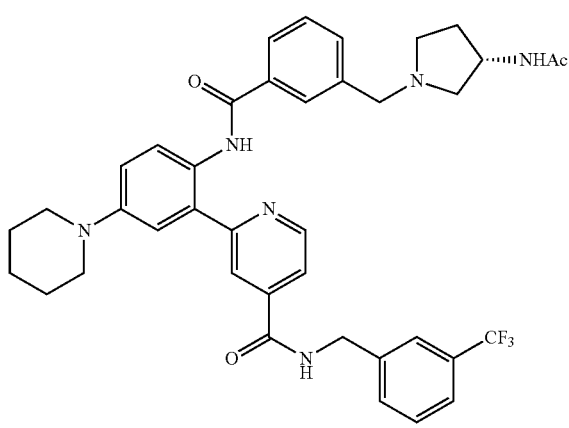 [SMILES: CC(=O)N[C@H]1CCN(Cc2cccc(C(=O)Nc3ccc(N4CCCCC4)cc3-c3cc(C(=O)NCc4cccc(C(F)(F)F)c4)ccn3)c2)C1]

Into a 50-mL round-bottom flask, was placed a solution of N-(3-(trifluoromethyl)benzyl)-2-(2-(3-(bromomethyl)benzamido)-5-(piperidin-1-yl)phenyl)isonicotinamide (100 mg, 0.15 mmol, 1.00 equiv) in N,N-dimethylformamide (10 mL), potassium carbonate (62 mg, 0.45 mmol, 2.92 equiv), potassium iodide (5 mg, 0.03 mmol, 0.20 equiv), and (S)—N-(pyrrolidin-3-yl)acetamide (38.5 mg, 0.30 mmol, 1.96 equiv). The resulting solution was stirred for 3 h at 70° C. in an oil bath. The resulting solution was diluted with 150 mL of water. The resulting solution was extracted with 4×100 mL of ethyl acetate and the organic layers combined. The resulting mixture was washed with 2×200 mL of brine. The mixture was dried over sodium sulfate and concentrated under vacuum. The crude product (100 mg) was purified by reverse phase HPLC eluting with a water/CH3CN gradient containing 0.05% TFA. The product was obtained as 38.7 mg (24%) of a light yellow solid. $^1$H-NMR (300 MHz, CD$_3$OD, ppm): δ 8.921-8.938 (d, J=5.1 Hz, 1H), 8.623-8.653 (d, J=9.0 Hz, 1H), 8.429 (s, 1H), 8.070-8.138 (m, 3H), 7.859-7.881 (m, 1H), 7.536-7.799 (m, 7H), 4.719 (s, 2H), 4.526-4.593 (m, 2H), 4.377-7.420 (m, 1H), 3.612-3.648 (t, J=5.4 Hz, 4H), 2.500 (m, 1H), 2.007-2.022 (m, 5H), 1.946 (s, 3H), 1.803-1.818 (m, 2H). MS (ES, m/z): 699 [M+H]+.

Example 48

(S)-2-(2-(3-((3-Acetamidopyrrolidin-1-yl)methyl)benzamido)-5-(piperidin-1-yl)phenyl)-N-(3-(trifluoromethyl)benzyl)isonicotinamide

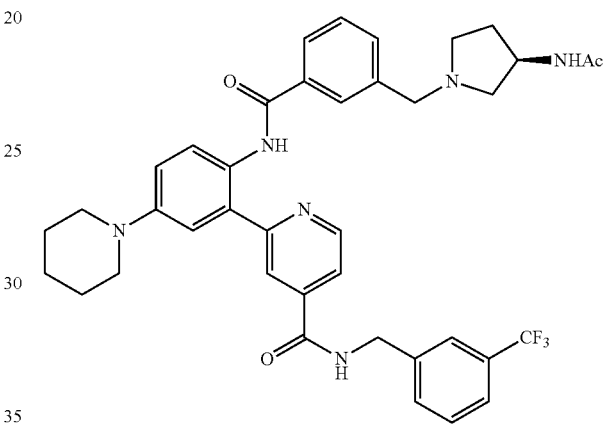

Into a 50-mL round-bottom flask, was placed a solution of N-(3-(trifluoromethyl)benzyl)-2-(2-(3-(bromomethyl)benzamido)-5-(piperidin-1-yl)phenyl)isonicotinamide (100 mg, 0.15 mmol, 1.00 equiv) in N,N-dimethylformamide (10 mL), potassium carbonate (62 mg, 0.45 mmol, 2.92 equiv), potassium iodide (5 mg, 0.03 mmol, 0.20 equiv), and (R)—N-(pyrrolidin-3-yl)acetamide (38.5 mg, 0.30 mmol, 1.96 equiv). The resulting solution was stirred for 3 h at 70° C. in an oil bath. The resulting solution was diluted with 150 mL of water. The resulting solution was extracted with 4×100 mL of ethyl acetate and the organic layers combined. The resulting mixture was washed with 2×200 mL of brine. The mixture was dried over sodium sulfate and concentrated under vacuum. The crude product (100 mg) was purified by reverse phase HPLC eluting with a water/CH3CN gradient containing 0.05% TFA. The product was obtained as 48 mg (30%) of a light yellow solid. $^1$H-NMR (300 MHz, CD$_3$OD, ppm): δ 8.925-8.942 (d, J=5.1 Hz, 1H), 8.642-8.672 (d, J=9.0 Hz, 1H), 8.435 (s, 1H), 8.075-8.141 (m, 3H), 7.863-7.880 (m, 1H), 7.537-7.801 (m, 7H), 4.720 (s, 2H), 4.524-4.594 (m, 2H), 4.374-4.418 (m, 1H), 3.628-3.663 (m, 4H), 2.501 (m, 1H), 2.016-2.031 (m, 5H), 1.947 (m, 3H), 1.810-1.826 (m, 2H). MS (ES, m/z): 699 [M+H]⁺.

Example 49

2-(2-(3-((4-Acetyl-1,4-diazepan-1-yl)methyl)benzamido)-5-(piperidin-1-yl)phenyl)-N-(3-(trifluoromethyl)benzyl)isonicotinamide

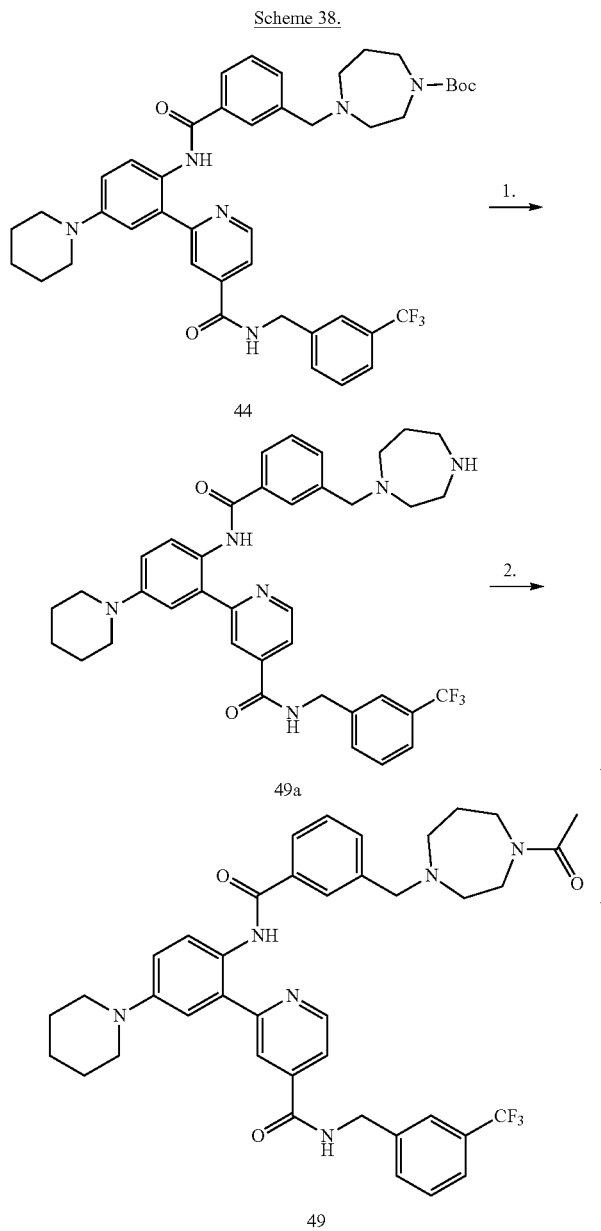

Scheme 38.

44

49a

49

1. CF₃COOH, DCM; 2. (CH₃CO)₂O, Py, THF.

Intermediate 49: 2-(2-(3-((1,4-diazepan-1-yl)methyl)benzamido)-5-(piperidin-1-yl)-phenyl)-N-(3-(trifluoromethyl)benzyl)isonicotinamide Into a 50-mL round-bottom flask, was placed a solution of tert-butyl 4-(3-((2-(4-((3-(trifluoromethyl)benzyl)carbamoyl)pyridin-2-yl)-4-(piperidin-1-yl)phenyl)carbamoyl)benzyl)-1,4-diazepane-1-carboxylate (100 mg, 0.13 mmol, 1.00 equiv) in dichloromethane (15 mL), and trifluoroacetic acid (147.9 mg, 1.30 mmol, 10.00 equiv). The resulting solution was stirred for 3 h at 15° C. The resulting mixture was concentrated under vacuum to yield 130 mg of crude product as a red solid.

Example 49

2-(2-(3-((4-acetyl-1,4-diazepan-1-yl)methyl)benzamido)-5-(piperidin-1-yl)-phenyl)-N-(3-(trifluoromethyl)benzyl)isonicotinamide Into a 50-mL round-bottom flask, was placed a solution of PH-RDX-002-1161-1 (149 mg, 0.19 mmol, 1.00 equiv) in tetrahydrofuran (15 mL), pyridine (31 mg, 0.39 mmol, 2.00 equiv), and acetyl acetate (33 mg, 0.23 mmol, 1.20 equiv). The resulting solution was stirred for 3 h at room temperature. The resulting mixture was concentrated under vacuum. The resulting solution was diluted with 20 mL of water. The resulting solution was extracted with 2×20 mL of ethyl acetate and the organic layers combined. The resulting mixture was washed with brine. The mixture was dried over sodium sulfate and concentrated under vacuum. The crude product (160 mg) was purified by reverse phase HPLC eluting with a water/CH₃CN gradient containing 0.05% TFA. The product was obtained as 92.2 mg (46%) of a pale-yellow solid. ¹H-NMR (300 MHz, CD₃OD, ppm): δ 8.907-8.924 (d, J=5.1 Hz, 1H), 8.562-8.592 (d, J=9.0 Hz, 1H), 8.402 (s, 1H), 8.082-8.146 (m, 2H), 7.986-7.994 (d, J=2.4 Hz, 1H), 7.854-7.877 (m, 1H), 7.662-7.791 (m, 4H), 7.536-7.601 (m, 3H), 4.717 (s, 2H), 4.508-4.519 (d, J=3.3 Hz, 2H), 3.656-3.698 (t, J=6.3 Hz, 2H), 3.569-3.604 (t, J=5.3 Hz, 4H), 3.466-3.480 (m, 2H), 2.249-2.265 (m, 2H), 2.152 (s, 3H), 1.993 (m, 4H), 1.784-1.802 (m, 2H). MS (ES, m/z): 713 [M+H]⁺; 357 [(M+2H)/2]⁺.

Example 50

2-(2-(3-((4-Acetylpiperazin-1-yl)methyl)benzamido)-5-(piperidin-1-yl)phenyl)-N-(3-(trifluoromethyl)benzyl)isonicotinamide

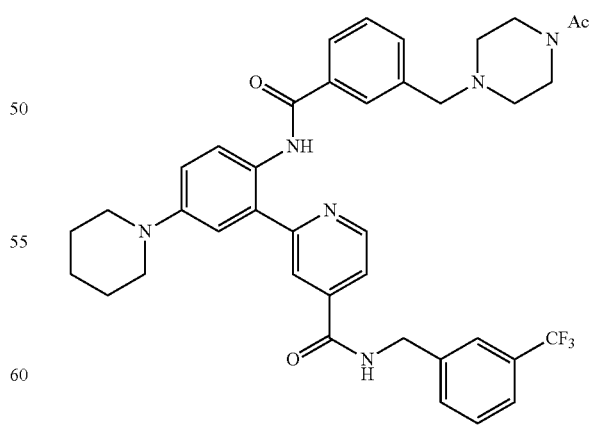

Into a 50-mL round-bottom flask, was placed a solution of N-(3-(trifluoromethyl)benzyl)-2-(2-(3-(bromomethyl)benzamido)-5-(piperidin-1-yl)phenyl)isonicotinamide (100 mg, 0.15 mmol, 1.00 equiv) in N,N-dimethylformamide (2 mL), 1-(piperazin-1-yl)ethanone (59 mg, 0.46 mmol, 3.00 equiv), potassium iodide (12.7 mg, 0.08 mmol, 0.50 equiv), and potassium carbonate (42.4 mg, 0.31 mmol, 2.00 equiv). The resulting solution was stirred for 3 h at 70° C. in an oil bath. The reaction progress was monitored by LCMS. The resulting solution was diluted with 20 mL of water. The resulting solution was extracted with 3×20 mL of ethyl acetate and the organic layers combined. The resulting mixture was washed with 3×20 mL of brine, dried over anhydrous sodium sulfate, and concentrated under vacuum. The crude product was purified by reverse phase HPLC eluting with a water/CH$_3$CN gradient containing 0.05% TFA. The product was obtained as 54.8 mg (34%) of a yellow solid. $^1$H-NMR (400 MHz, CD$_3$OD, ppm): 8.94-8.92 (d, J=4.2 Hz, 1H), 8.66-8.64 (d, J=6.6 Hz, 1H), 8.43 (s, 1H), 8.14-8.09 (m, 3H), 7.88-7.87 (m, 1H), 7.79-7.54 (m, 7H), 4.72 (s, 2H), 4.47 (s, 2H), 3.82 (s, 3H), 3.65-3.62 (t, J=4.2 Hz, 1H), 3.33-3.29 (m, 5H), 2.15 (s, 3H), 2.04-2.01 (t, J=5.2 Hz, 4H), 1.82-1.81 (d, J=5.2 Hz, 1H). MS (ES, m/z): 699 [M+H]$^+$.

Example 51

2-(2-(3-(((3-((2-Methoxyethyl)amino)-3-oxopropyl)(methyl)amino)methyl)benzamido)-5-(piperidin-1-yl)phenyl)-N-(3-(trifluoromethyl)benzyl)isonicotinamide Scheme 39.

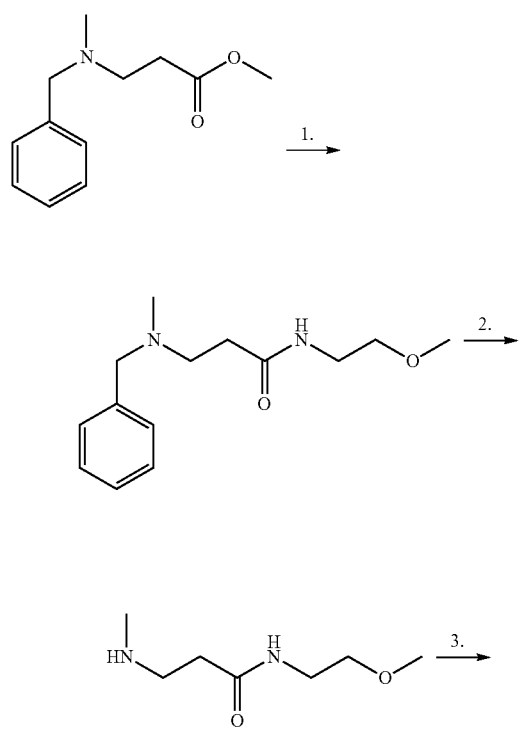

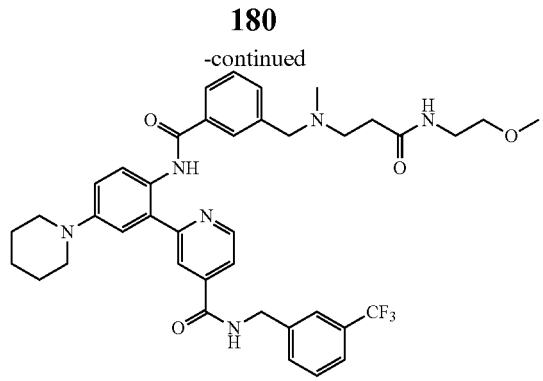

1. 2-methoxyethanamine; 2. Pd/C, MeOH; 3.Intermediate 42a, K$_2$CO$_3$, KI

3-(benzyl(methyl)amino)-N-(2-methoxyethyl)propanamide

To methyl 3-(benzyl(methyl)amino)propanoate (1.5 g, 7.24 mmol, 1.00 equiv) was added 2-methoxyethanamine (11 g, 146.45 mmol, 20.00 equiv) and the mixture was stirred for 2 days at 100° C. in sealed tube. The resulting mixture was concentrated under vacuum and purified via silica gel chromatography (dichloromethane/methanol 30:1) to afford 1.1 g (61%) of the product as a yellow oil.

N-(2-methoxyethyl)-3-(methylamino)propanamide

To a solution of 3-(benzyl(methyl)amino)-N-(2-methoxyethyl)propanamide (1.1 g, 4.39 mmol, 1.00 equiv) in methanol (50 mL) was added 5% palladium-on-carbon (50 mg) and the suspension stirred under a hydrogen atmosphere for 2 h. The solids were filtered out and the mixture was concentrated under vacuum to afford 200 mg (28%) of the product as a white solid.

Example 51
2-(2-(3-(((3-((2-methoxyethyl)amino)-3-oxopropyl)(methyl)amino)-methyl)benzamido)-5-(piperidin-1-yl)phenyl)-N-(3-(trifluoromethyl)benzyl)-isonicotinamide Into a 8-mL round-bottom flask, was placed a solution of N-(3-(trifluoromethyl)benzyl)-2-(2-(3-(bromomethyl)benzamido)-5-(piperidin-1-yl)phenyl)-isonicotinamide 42a (250 mg, 0.31 mmol, 1.00 equiv, 80%) in N,N-dimethylformamide (6 mL), N-(2-methoxyethyl)-3-(methylamino)propanamide (185 mg, 1.04 mmol, 3.00 equiv, 90%), potassium carbonate (106 mg, 0.77 mmol, 2.00 equiv), and potassium iodide (32 mg, 0.19 mmol, 0.50 equiv). The resulting solution was stirred for 5 h at 60° C. The resulting solution was diluted with 100 mL of ethyl acetate. The resulting mixture was washed with 1×20 mL of 10% sodium bicarbonate. The resulting mixture was washed with 1×20 mL of brine, dried over sodium sulfate, and concentrated under vacuum. The crude product was purified by Flash-Prep-HPLC with water:methanol (0.05% TFA) (10:90). The product was obtained as 63.7 mg (23%) of a yellow solid. $^1$H-NMR (300 MHz, CD$_3$OD, ppm): δ 8.87 (d, J=6 Hz, 1H), 8.29 (m, 2H), 8.06 (m, 2H), 7.70 (m, 8H), 7.31 (d, J=9 Hz, 1H), 4.70 (s, 2H), 4.50 (m, 2H), 3.43

(m, 2H), 3.39 (m, 6H), 2.89 (s, 3H), 2.76 (m, 2H), 1.86 (m, 4H), 1.73 (m, 2H). MS (ES, m/z): 731 [M+H]+.

Example 52 tert-Butyl 4-(2-(methyl((6-((4-(piperidin-1-yl)-2-(4-((3-(trifluoromethyl)benzyl)carbamoyl)pyridin-2-yl)phenyl)carbamoyl)pyridin-2-yl)methyl)amino)ethyl)piperazine-1-carboxylate Scheme 40.

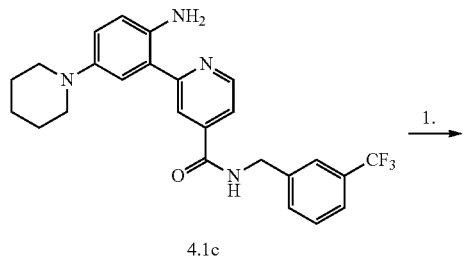

4.1c

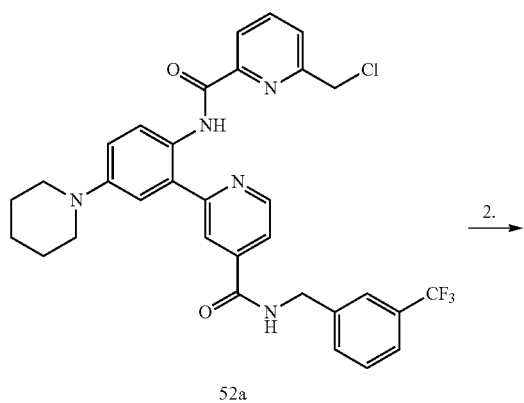

52a

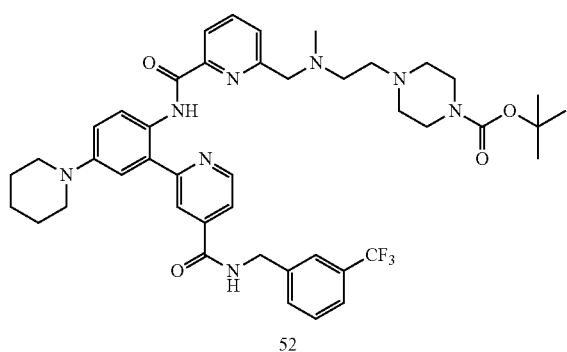

52

1. 6-(chloromethyl)picolinic acid EDC·HCl, DMAP, DCM, 25° C;
2. K₂CO₃, KI, DMF, tert-butyl 4-(2-(methylamino)ethyl)piperazine-1-carboxylate, 65° C.

Intermediate 52a: N-(3-(trifluoromethyl)benzyl)-2-(2-(2-(chloromethyl)picolinamido)-5-(piperidin-1-yl)phenyl)isonicotinamide Into a 50-mL 1-neck bottle, was placed a solution of N-(3-(trifluoromethyl)benzyl)-2-(2-amino-5-(piperidin-1-yl)phenyl)isonicotinamide (1.83 g, 4.03 mmol, 1.00 equiv) in dichloromethane (30 mL), 6-(chloromethyl)picolinic acid (1.04 g, 6.05 mmol, 1.50 equiv), EDC.HCl (1.54 g, 8.06 mmol, 2.00 equiv), and 4-dimethylaminopyridine (490 mg, 4.02 mmol, 1.00 equiv). The resulting solution was stirred for 4 h at 25° C. The resulting mixture was concentrated under vacuum. The residue was applied onto a silica gel column and eluted with dichloromethane:methanol (100:1). The product was obtained as 2 g (82%) of a yellow solid. ¹H-NMR (300 MHz, DMSO-d₆, ppm): δ 13.01 (s, 1H), 9.54 (t, J=8.7 Hz, 1H), 9.09 (d, J=5.1 Hz, 1H), 8.51 (d, J=9.0 Hz, 1H), 8.25 (s, 1H), 8.12-8.04 (m, 2H), 7.87-7.37 (m, 6H), 7.36 (s, 1H), 7.14 (dd, J=9.0 Hz, 1H), 4.95 (s, 2H), 4.65 (t, J=4.8 Hz, 2H), 3.34-3.20 (m, 4H), 1.67-1.55 (m, 6H). MS (ES, m/z): 608 [M+H]+.

Example 52

N-(3-(trifluoromethyl)benzyl)-2-(2-(2-(chloromethyl)picolinamido)-5-(piperidin-1-yl)phenyl)isonicotinamide Into a 8-mL sealed tube, was placed a solution of 6-(chloromethyl)-N-(4-(piperidin-1-yl)-2-(4-(3-(trifluoromethyl)benzylcarbamoyl)pyridin-2-yl)phenyl)picolinamide (166 mg, 0.27 mmol, 1.00 equiv) in N,N-dimethylformamide (5 mL), tert-butyl 4-(2-(methylamino)ethyl)piperazine-1-carboxylate (100 mg, 0.41 mmol, 1.50 equiv), potassium carbonate (114 mg, 0.82 mmol, 3.00 equiv), and potassium iodide (9 mg, 0.05 mmol, 0.20 equiv). The resulting solution was stirred for 3 h at 65° C. The resulting solution was diluted with 10 mL of water. The resulting solution was extracted with 3×30 mL of ethyl acetate and the organic layers combined. The resulting mixture was washed with 3×30 mL of brine. The mixture was dried over sodium sulfate and concentrated under vacuum. The residue was applied onto a silica gel column with dichloromethane:methanol (100:1-40:1). This resulted in 180 mg (81%) of tert-butyl 4-(2-(methyl((6-(4-(piperidin-1-yl)-2-(4-(3-(trifluoromethyl)benzylcarbamoyl)pyridin-2-yl)-phenylcarbamoyl)pyridin-2-yl)methyl)amino)ethyl)piperazine-1-carboxylate as a yellow solid. ¹H-NMR (400 MHz, DMSO-d₆, ppm): δ 12.88 (s, 1H), 9.54 (t, J=6.0 Hz, 1H), 9.04 (d, J=4.8 Hz, 1H), 8.51 (d, J=9.2 Hz, 1H), 8.24 (s, 1H), 8.01 (d, J=4.0 Hz, 2H), 7.88 (dd, J=4.8 Hz, 1H), 7.56-7.72 (m, 5H), 7.34 (d, J=3.6 Hz, 1H), 7.14 (dd, J=9.2 Hz, 1H), 4.64 (d, J=5.6 Hz, 2H), 3.78 (s, 2H), 3.20-3.78 (m, 8H), 1.67-2.56 (m, 11H), 1.57-1.66 (m, 6H), 1.35 (s, 9H). MS (ES, m/z): 815 [M+H].

Example 53

6-((N-Methyl-2-morpholinoacetamido)methyl)-N-(4-(piperidin-1-yl)-2-(4-((3-(trifluoromethyl)benzyl)carbamoyl)pyridin-2-yl)phenyl)picolinamide Scheme 41.

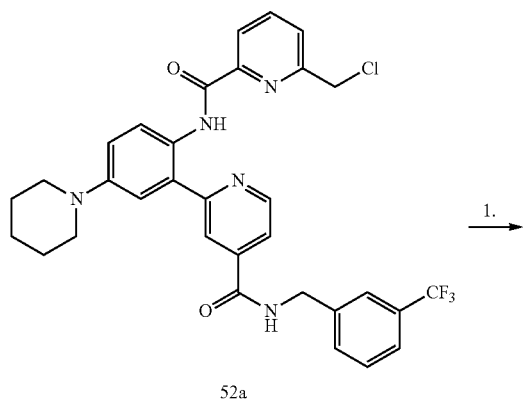

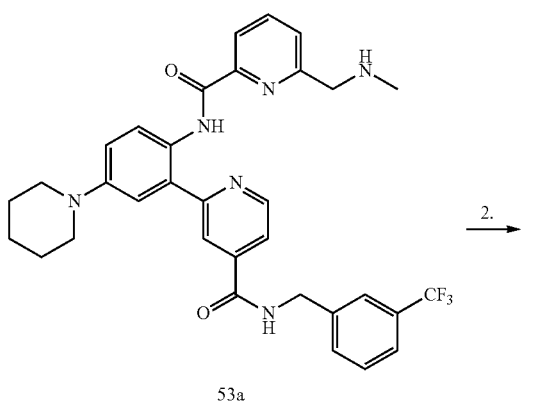

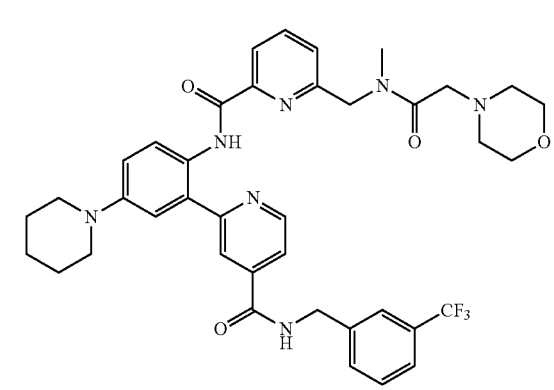

1. CH₃NH₂, DCM; 2. EDC·HCl, DMAP, DCM, morpholinoacetic acid.

Intermediate 53a: N-(3-(trifluoromethyl)benzyl)-2-(2-(2-((methylamino)methyl)-picolinamido)-5-(piperidin-1-yl)phenyl)isonicotinamide Into a 10-mL vial, was placed a solution of N-(3-(trifluoromethyl)benzyl)-2-(2-(2-(chloromethyl)picolinamido)-5-(piperidin-1-yl)phenyl)isonicotinamide (150 mg, 0.25 mmol, 1.00 equiv) in dichloromethane (5 mL), methylamine (2 mL). The resulting solution was stirred for 48 h at 25° C. in an oil bath. The reaction progress was monitored by LCMS. The resulting mixture was concentrated under vacuum. The residue was applied onto a silica gel column and eluted with ethyl acetate/petroleum ether (1:10-1:5). The product was obtained as 110 mg (74%) of a yellow solid.

Example 53

N-(3-(trifluoromethyl)benzyl)-2-(2-(2-((N-methyl-2-morpholinoacetamido)-methyl)picolinamido)-5-(piperidin-1-yl)phenyl)isonicotinamide Into a 50-mL vial, was placed N-(3-(trifluoromethyl)benzyl)-2-(2-(2-((methylamino)methyl)picolinamido)-5-(piperidin-1-yl)phenyl)isonicotinamide (100 mg, 0.17 mmol, 1.00 equiv) in dichloromethane (10 mL), 2-morpholinoacetic acid (28.9 mg, 0.20 mmol, 1.20 equiv), EDC.HCl (47.4 mg, 0.25 mmol, 1.50 equiv), and 4-dimethylaminopyridine (30.4 mg, 0.25 mmol, 1.50 equiv). The resulting solution was stirred for 4 h at 25° C. in an oil bath. The reaction progress was monitored by LCMS. The resulting solution was diluted with 50 mL of dichloromethane. The resulting mixture was washed with 3×50 mL of aqueous NH₄Cl, dried over anhydrous sodium sulfate, and concentrated under vacuum. The crude product (200 mg) was purified by reverse phase HPLC eluting with a water/CH₃CN gradient containing 0.05% TFA. The product was obtained as 116 mg (59%) of a yellow solid. ¹H-NMR (400 MHz, CD₃OD, ppm): δ 9.12 (m, 1H), 8.86 (d, J=9.2 Hz, 1H), 8.34 (d, J=2.0 Hz, 1H), 8.17 (m, 1H), 8.12 (m, 1H), 8.01 (m, 1H), 7.95 (m, 1H), 7.80 (m, 3H), 7.60 (m, 3H), 4.96 (m, 2H), 4.72 (s, 2H), 4.50 (m, 2H), 3.98 (m, 4H), 3.70 (m, 4H), 3.1 (s, 3H), 2.10 (m, 4H), 1.98 (s, 2H). MS (ES, m/z): 730 [M+H]⁺.

Example 54
2-Methyl-1-(6-((4-(piperidin-1-yl)-2-(4-((3-(trifluoromethyl)benzyl)carbamoyl)pyridin-2-yl)phenyl)carbamoyl)pyridin-2-yl)-5,8,11-trioxa-2-azatetradecan-14-oic acid
Scheme 42.
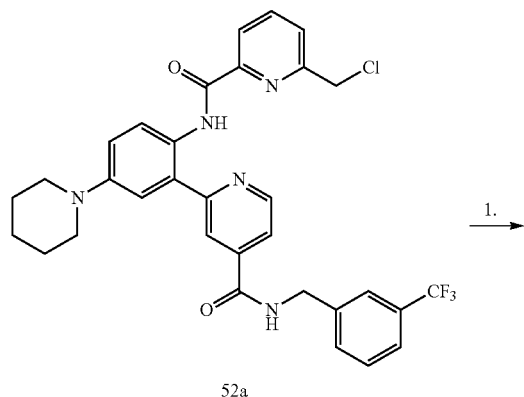
52a
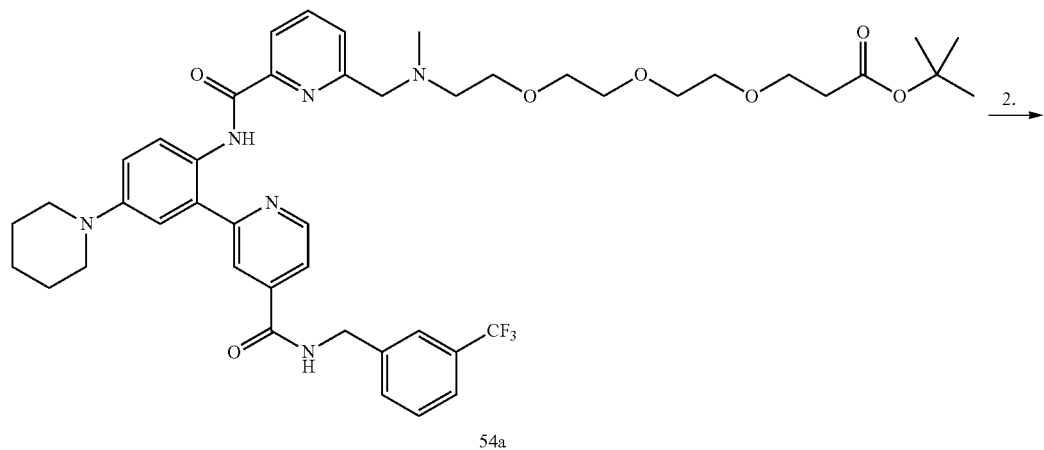
54a
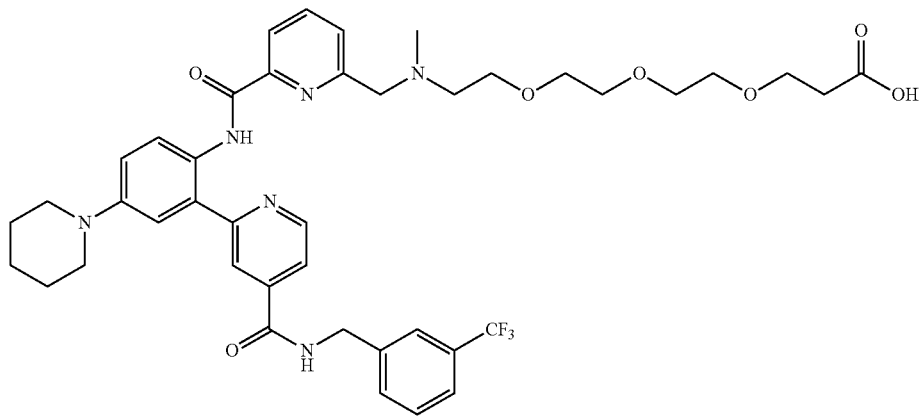
54
1. K₂CO₃, KI, DMF, tert-butyl 5,8,11-trioxa-2-azatetradecan-14-oate; 2. CF₃COOH, DCM.

Intermediate 54a: tert-butyl 3-(2-(2-(2-(((6-((2-(4-((3-(trifluoromethyl)benzyl)carbamoyl)-pyridin-2-yl)-4-(piperidin-1-yl)phenyl)carbamoyl)pyridin-2-yl)methyl)(methyl)amino)-ethoxy)ethoxy)ethoxy)propanoate Into a 10-mL round-bottom flask, was placed a solution of N-(3-(trifluoromethyl)benzyl)-2-(2-(2-(chloromethyl)picolinamido)-5-(piperidin-1-yl)phenyl)isonicotinamide (200 mg, 0.33 mmol, 1.00 equiv) in N,N-dimethylformamide (10 mL), tert-butyl 3-(2-(2-(2-(methylamino)ethoxy)ethoxy)ethoxy)propanoate (191.7 mg, 0.66 mmol, 2.00 equiv), potassium carbonate (90.9 mg, 0.66 mmol, 2.00 equiv), and potassium iodide (109.4 mg, 0.66 mmol, 2.00 equiv). The resulting solution was stirred overnight at 60° C. in an oil bath. The resulting solution was diluted with 50 mL of water. The resulting solution was extracted with 2×50 mL of dichloromethane and the organic layers combined. The mixture was dried over anhydrous sodium sulfate and concentrated under vacuum. The crude product was obtained as 300 mg of a yellow oil.

Example 54

3-(2-(2-(2-(((6-((2-(4-((3-(trifluoromethyl)benzyl)carbamoyl)pyridin-2-yl)-4-(piperidin-1-yl)phenyl)carbamoyl)pyridin-2-yl)methyl)(methyl)amino)ethoxy)ethoxy)-ethoxy)propanoic acid Into a 50-mL vial, was placed a solution of tert-butyl 3-(2-(2-(2-(((6-((2-(4-((3-(trifluoromethyl)benzyl)carbamoyl)pyridin-2-yl)-4-(piperidin-1-yl)phenyl)carbamoyl)pyridin-2-yl)methyl)(methyl)amino)ethoxy)ethoxy)-propanoate (200 mg, 0.23 mmol, 1.00 equiv) in dichloromethane (10 mL), and 2,2,2-trifluoroacetic acid (2 mL). The resulting solution was stirred for 3 h at 25° C. in an oil bath. The reaction progress was monitored by LCMS. The resulting mixture was concentrated under vacuum. The residue was dissolved in 50 mL of ethyl acetate. The resulting mixture was washed with 4×30 mL of brine, dried over sodium sulfate, and concentrated under vacuum. The crude product (200 mg) was purified by reverse phase HPLC eluting with a water/CH$_3$CN gradient containing 0.05% TFA. The product was obtained as 84.9 mg (31%) of a yellow solid. $^1$H-NMR (300 MHz, DMSO-d$_6$, ppm): δ 12.34 (s, 1H), 9.89 (s, 1H), 9.54 (m, 1H), 9.02 (m, 1H), 8.19 (m, 4H), 7.84 (m, 2H), 7.57 (m, 5H), 7.29 (s, 1H), 4.60 (t, J=5.7 Hz, 6H), 3.77 (t, J=4.8 Hz, 2H), 3.48 (m, 16H), 2.84 (s, 3H), 2.51 (m, 2H), 1.9 (s, 4H), 1.7 (s, 2H). MS (ES, m/z): 807 [M+H]$^+$.

Example 55

(R)-6-((3-Acetamidopyrrolidin-1-yl)methyl)-N-(4-(piperidin-1-yl)-2-(4-((3-(trifluoromethyl)benzyl)carbamoyl)pyridin-2-yl)phenyl)picolinamide 2,2,2-trifluoroacetate

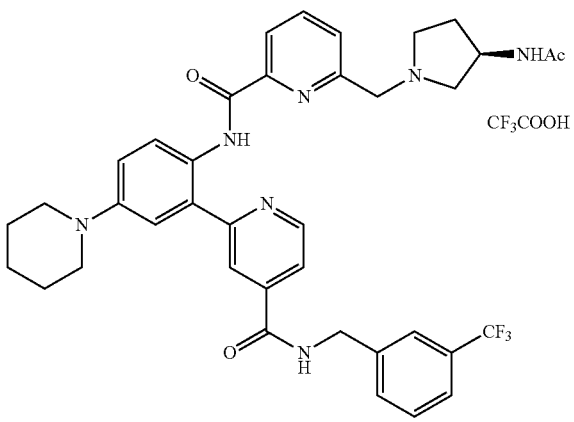

Into a 50-mL round-bottom flask, was placed a solution of N-(3-(trifluoromethyl)benzyl)-2-(2-(2-(chloromethyl)picolinamido)-5-(piperidin-1-yl)phenyl)isonicotinamide (100 mg, 0.15 mmol, 1.00 equiv, 90%) in N,N-dimethylformamide (3 mL), (R)—N-(pyrrolidin-3-yl)acetamide (42 mg, 0.33 mmol, 2.00 equiv), potassium carbonate (45 mg, 0.33 mmol, 2.00 equiv), and potassium iodide (14 mg, 0.08 mmol, 0.50 equiv). The resulting solution was stirred for 3 h at 60° C. in an oil bath. The resulting solution was diluted with 100 mL of ethyl acetate. The resulting mixture was washed with 3×20 mL of brine, dried over anhydrous sodium sulfate, and concentrated under vacuum. The crude product (100 mg) was purified by reverse phase HPLC eluting with a water/CH$_3$CN gradient containing 0.05% TFA. The product was obtained as 33.4 mg (27%) of a yellow solid. $^1$H-NMR (300 MHz, CD$_3$OD, ppm): δ 8.90 (d, J=6 Hz, 1H), 8.40 (s, 1H), 8.26 (m, 1H), 8.21-8.09 (m, 2H), 7.98 (d, J=3 Hz, 1H), 7.82 (d, J=6 Hz, 1H), 7.71-7.50 (m, 6H), 4.65 (m, 4H), 4.20 (m, 1H), 3.85 (m, 1H), 3.66-3.63 (m, 4H), 2.50 (m, 1H), 2.00 (m, 4H), 1.80 (m, 3H), 1.68 (m, 3H). MS (ES, m/z): 700 [M+H]$^+$.

Example 56

(S)-6-((3-Acetamidopyrrolidin-1-yl)methyl)-N-(4-(piperidin-1-yl)-2-(4-((3-(trifluoromethyl)benzyl)carbamoyl)pyridin-2-yl)phenyl)picolinamide

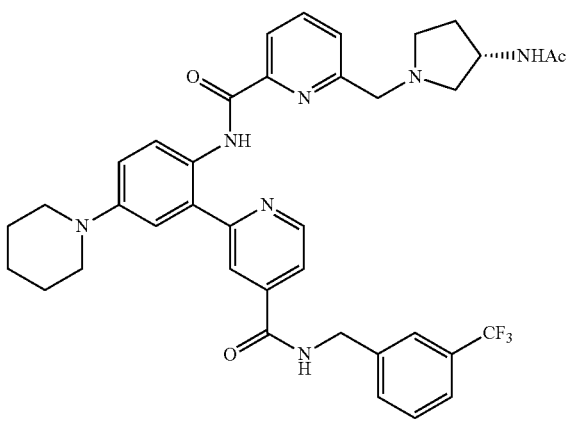 [SMILES: CC(=O)N[C@H]1CCN(Cc2cccc(C(=O)Nc3ccc(N4CCCCC4)cc3-c3cc(C(=O)NCc4cccc(C(F)(F)F)c4)ccn3)n2)C1]

Into a 50-mL round-bottom flask, was placed a solution of N-(3-(trifluoromethyl)benzyl)-2-(2-(2-(chloromethyl)picolinamido)-5-(piperidin-1-yl)phenyl)isonicotinamide (100 mg, 0.15 mmol, 1.00 equiv, 90%) in N,N-dimethylformamide (3 mL), (S)—N-(pyrrolidin-3-yl)acetamide (42 mg, 0.33 mmol, 2.00 equiv), potassium carbonate (45 mg, 0.33 mmol, 2.00 equiv), and potassium iodide (14 mg, 0.08 mmol, 0.50 equiv). The resulting solution was stirred for 3 h at 60° C. in an oil bath. The resulting solution was diluted with 100 mL of ethyl acetate. The resulting mixture was washed with 2×20 mL of brine, dried over anhydrous sodium sulfate, and concentrated under vacuum. The crude product (100 mg) was purified by reverse phase HPLC eluting with a water/CH$_3$CN gradient containing 0.05% TFA. The product was obtained as 47.8 mg (39%) of a yellow solid. $^1$H-NMR (300 MHz, CD$_3$OD, ppm): δ 8.92 (d, J=6 Hz, 1H), 8.42 (s, 1H), 8.19 (m, 1H), 8.15 (m, 1H), 8.10 (m, 1H), 8.04 (m, 1H), 7.83 (d, J=6 Hz, 1H), 7.74 (m, 3H), 7.61 (m, 2H), 7.52 (m, 1H), 4.65 (m, 4H), 4.22 (m, 1H), 3.80 (m, 1H), 3.69-3.54 (m, 5H), 3.44 (m, 1H), 2.49 (m, 1H), 2.05-2.00 (m, 5H), 1.83-1.66 (m, 5H). MS (ES, m/z): 700 [M+H]$^+$.

Example 57

6-((4-Acetamidopiperidin-1-yl)methyl)-N-(4-(piperidin-1-yl)-2-(4-((3-(trifluoromethyl)benzyl)carbamoyl)pyridin-2-yl)phenyl)picolinamide

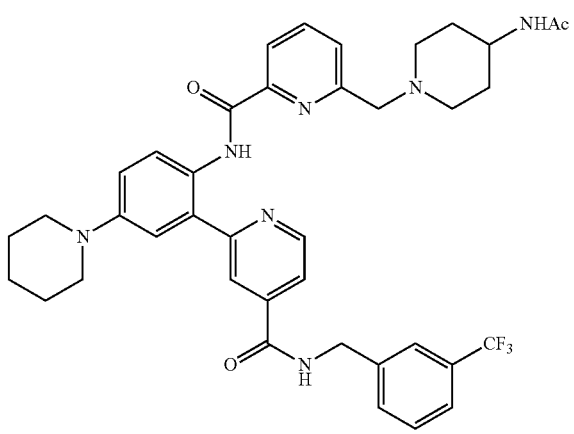 [SMILES: CC(=O)NC1CCN(Cc2cccc(C(=O)Nc3ccc(N4CCCCC4)cc3-c3cc(C(=O)NCc4cccc(C(F)(F)F)c4)ccn3)n2)CC1]

Into a 50-mL round-bottom flask, was placed a solution of 6-(chloromethyl)-N-(4-(piperidin-1-yl)-2-(4-(3-(trifluoromethyl)benzylcarbamoyl)pyridin-2-yl)phenyl)picolinamide (100 mg, 0.16 mmol, 1.00 equiv) in N,N-dimethylformamide (2 mL), N-(piperidin-4-yl)acetamide (35 mg, 0.25 mmol, 1.50 equiv), potassium carbonate (70 mg, 0.51 mmol, 3.00 equiv), and potassium iodide (6 mg, 0.04 mmol, 0.20 equiv). The resulting solution was stirred overnight at 60° C. The reaction progress was monitored by LCMS. The solids were filtered out. The mixture was concentrated under vacuum. The crude product (200 mg) was purified by reverse phase HPLC eluting with a water/CH$_3$CN gradient containing 0.05% TFA. The product was obtained as 70.8 mg (51%) of a yellow solid. $^1$H-NMR (300 MHz, DMSO-d$_6$, ppm): δ 12.49 (s, 1H), 9.86 (m, 1H), 9.54 (m, 1H), 9.06 (m, 1H), 8.37-8.19 (d, J=9 Hz, 1H), 8.24-8.19 (m, 3H), 7.97-7.95 (d, J=6 Hz, 1H), 7.86-7.83 (m, 2H), 7.70-7.49 (m, 5H), 7.26 (m, 1H), 4.64-4.51 (m, 4H), 3.82 (m, 1H), 3.54-3.24 (m, 8H), 1.95-1.58 (m, 13H). MS (ES, m/z): 714 [M+H]$^+$.

Example 58

6-((4-Acetylpiperazin-1-yl)methyl)-N-(4-(piperidin-1-yl)-2-(4-((3-(trifluoromethyl)benzyl)carbamoyl)pyridin-2-yl)phenyl)picolinamide

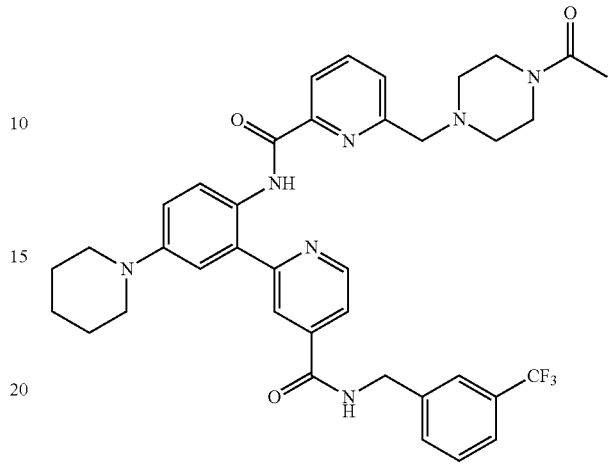

Into a 8-mL sealed tube, was placed a solution of 6-(chloromethyl)-N-(4-(piperidin-1-yl)-2-(4-(3-(trifluoromethyl)benzylcarbamoyl)pyridin-2-yl)phenyl)picolinamide (120 mg, 0.20 mmol, 1.00 equiv) in N,N-dimethylformamide (5 mL), 1-(piperazin-1-yl)ethanone (37.9 mg, 0.30 mmol, 1.50 equiv), potassium carbonate (82 mg, 0.59 mmol, 3.00 equiv), and potassium iodide (7 mg, 0.04 mmol, 0.20 equiv). The resulting solution was stirred for 3 h at 65° C. The reaction was then quenched with 10 mL of water. The resulting solution was extracted with 3×30 mL of ethyl acetate and the organic layers combined. The resulting mixture was washed with 3×30 mL of brine, dried over sodium sulfate, and concentrated under vacuum. The crude product (100 mg) was purified by reverse phase HPLC eluting with a water/CH$_3$CN gradient containing 0.05% TFA. The product was obtained as 89.2 mg (56%) of a yellow solid. $^1$H-NMR (300 MHz, DMSO-d$_6$, ppm): δ 12.56 (s, 1H), 9.54 (t, J=6.0 Hz, 1H), 9.08 (d, J=5.1 Hz, 1H), 8.38 (d, J=8.7 Hz, 1H), 8.25-8.17 (m, 3H), 7.84 (d, J=3.9 Hz, 2H), 7.71-7.58 (m, 5H), 7.51 (s, 1H), 4.63 (d, J=5.7 Hz, 2H), 4.49 (s, 2H), 3.31-3.21 (m, 10H), 2.01 (s, 3H), 1.72-1.59 (m, 6H). MS (ES, m/z): 700 [M+H]$^+$.

Example 59

6-((4-Acetyl-1,4-diazepan-1-yl)methyl)-N-(4-(piperidin-1-yl)-2-(4-((3-(trifluoromethyl)benzyl)carbamoyl)pyridin-2-yl)phenyl)picolinamide Scheme 43.

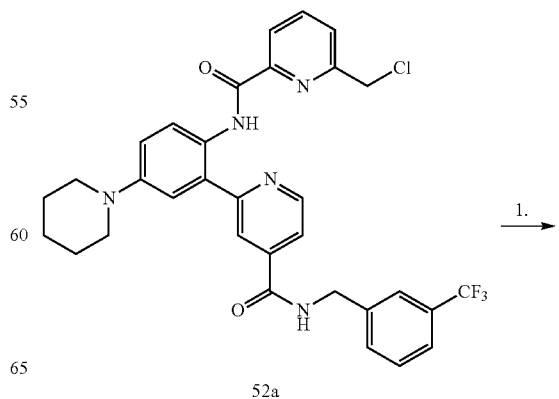

52a

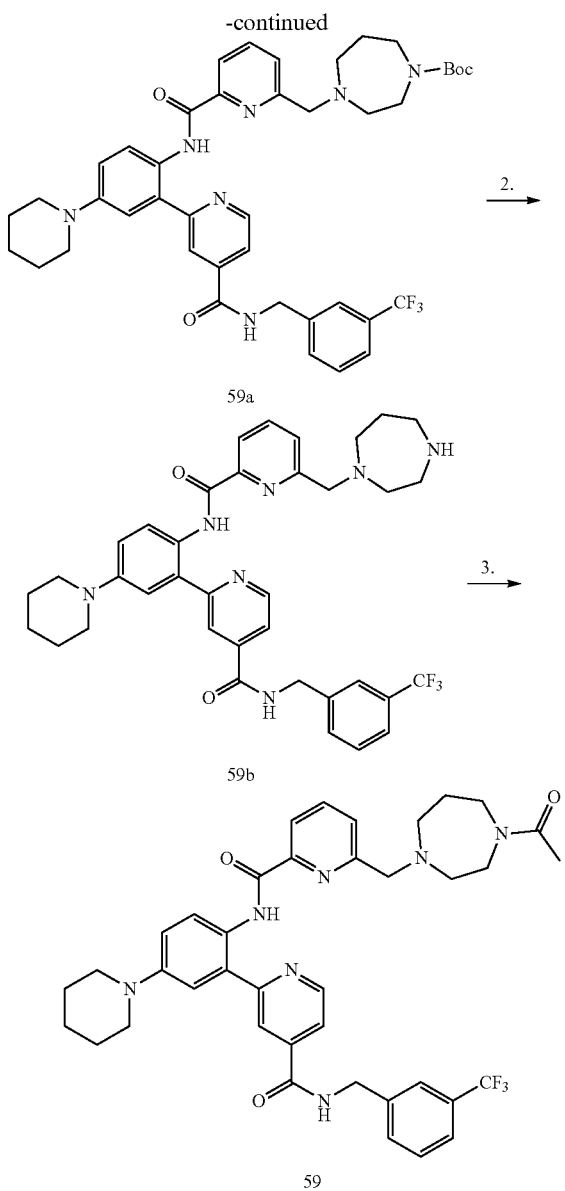

59
1. tert-butyl 1,4-diazepane-1-carboxylate, KI, K₂CO₃; 2 TFA, DMF; 3 TEA, AcCl, Intermediate 59a: tert-butyl 4-((6-((4-(piperidin-1-yl)-2-(4-((3-(trifluoromethyl)benzyl)-carbamoyl)pyridin-2-yl)phenyl)carbamoyl)pyridin-2-yl)methyl)-1,4-diazepane-1-carboxylate This compound was prepared using the procedure described for the preparation of 6-((4-acetylpiperazin-1-yl)methyl)-N-(4-(piperidin-1-yl)-2-(4-((3-(trifluoromethyl)benzyl)carbamoyl)pyridin-2-yl)phenyl)picolinamide 58, substituting tert-butyl 1,4-diazepane-1-carboxylate for -(piperazin-1-yl)ethanone.

Intermediate 59b: 6-((1,4-diazepan-1-yl)methyl)-N-(4-(piperidin-1-yl)-2-(4-(3-(trifluoromethyl)benzylcarbamoyl)pyridin-2-yl)phenyl)picolinamide Into a 50-mL round-bottom flask, was placed a solution of tert-butyl 4-((6-((4-(piperidin-1-yl)-2-(4-(3-(trifluoromethyl) benzylcarbamoyl)pyridin-2-yl)phenylcarbamoyl)pyridin-2-yl)methyl)-1,4-diazepane-1-carboxylate (150 mg, 0.18 mmol, 1.00 equiv, 95%) in dichloromethane (5 mL), and trifluoroacetic acid (1 mL). The resulting solution was stirred overnight at room temperature. The resulting solution was diluted with 50 mL of dichloromethane. The solution was adjusted to pH 9 with aqueous sodium bicarbonate. The resulting solution was extracted with 3×50 mL of dichloromethane and the organic layers combined, dried over anhydrous sodium sulfate, and concentrated under vacuum. The product was obtained as 120 mg (97%) of a yellow solid.

Example 59

6-((4-acetyl-1,4-diazepan-1-yl)methyl)-N-(4-(piperidin-1-yl)-2-(4-(3-(trifluoromethyl)benzylcarbamoyl)pyridin-2-yl)phenyl)picolinamide Into a 50-mL round-bottom flask, was placed a solution of 6-((1,4-diazepan-1-yl)methyl)-N-(4-(piperidin-1-yl)-2-(4-(3-(trifluoromethyl)benzylcarbamoyl)pyridin-2-yl)phenyl)picolinamide (135 mg, 0.19 mmol, 1.00 equiv, 95%) in dichloromethane (5 mL), triethylamine (40 mg, 0.39 mmol, 2.00 equiv, 99%), and acetyl chloride (18 mg, 0.23 mmol, 1.20 equiv, 99%). The resulting solution was stirred for 3 h at room temperature. The resulting solution was diluted with 50 mL of dichloromethane. The resulting mixture was washed with 1×50 mL of brine. The mixture was dried over anhydrous sodium sulfate and concentrated under vacuum. The resulting mixture was washed with 2×10 mL of hexane. The product was obtained as 120 mg (87%) of a yellow solid. $^1$H-NMR (400 MHz, DMSO-$d_6$, ppm): δ 12.86 (s, 1H), 9.54-9.51 (t, 1H), 9.00 (s, 1H), 8.51-8.49 (d, J=6 Hz, 1H), 8.23 (s, 1H), 8.00 (s, 2H), 7.88-7.86 (d, 1H), 7.72-7.55 (m 5H), 7.33 (s, 1H), 7.14-7.11 (d, J=9 Hz, 1H), 4.63 (s, 2H), 3.91-3.88 (s, J=9 Hz, 2H), 3.52-3.50 (m, 4H), 3.21-3.19 (m, 4H), 2.78-2.63 (m, 4H), 2.01-1.98 (d, J=9 Hz, 3H), 1.79-1.55 (m, 8H). MS (ES, m/z): 714 [M+H]⁺.

Example 60

6-(((2-(4-Acetylpiperazin-1-yl)ethyl)(methyl)amino)methyl)-N-(4-(piperidin-1-yl)-2-(4-((3-(trifluoromethyl)benzyl)carbamoyl)pyridin-2-yl)phenyl)picolinamide

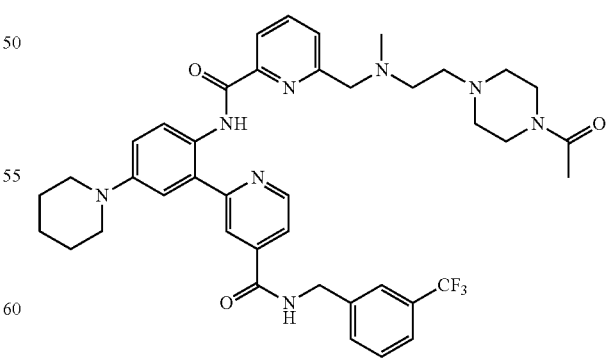

The tert-butoxycarbonyl group of tert-butyl 4-(2-(methyl ((6-((4-(piperidin-1-yl)-2-(4-((3-(trifluoromethyl)benzyl) carbamoyl)pyridin-2-yl)phenyl)carbamoyl)pyridin-2-yl)-methyl)amino)ethyl)piperazine-1-carboxylate 52 was cleaved by stirring for 1 hour in 1:1 dichloromethane/TFA and the resultant amine converted to the free base by partitioning between ethyl acetate and aqueous sodium bicarbonate solution. Into a 50-mL round-bottom flask, was placed a solution of this amine (110 mg, 0.15 mmol, 1.00 equiv) in dichloromethane (5 mL), and N,N-diisopropylethylamine (30 mg, 0.23 mmol, 1.50 equiv). This was followed by dropwise addition of a solution of acetyl chloride (14.4 mg, 0.18 mmol, 1.20 equiv) in dichloromethane (1 mL) with stirring at 0° C. The resulting solution was stirred for 3 h at room temperature. The resulting mixture was concentrated under vacuum. The crude product (200 mg) was purified by reverse phase HPLC eluting with a water/CH$_3$CN gradient containing 0.05% TFA. The product was obtained as 90.3 mg (44%) of as a yellow solid. $^1$H-NMR (300 MHz, DMSO-d$_6$, ppm): δ 12.77 (s, 1H), 9.56 (t, J=5.7 Hz, 1H), 9.06 (d, J=5.1 Hz, 1H), 8.49 (d, J=8.7 Hz, 1H), 8.28 (s, 1H), 8.15-8.09 (m, 2H), 7.90-7.79 (m, 2H), 7.72-7.56 (m, 5H), 7.34 (s, 1H), 4.64 (d, J=5.7 Hz, 2H), 4.20 (s, 2H), 3.56 (s, 4H), 3.34 (s, 4H), 3.18-2.95 (m, 7H), 2.56-2.49 (m, 4H), 1.96 (s, 3H), 1.74 (s, 4H), 1.60 (d, J=4.2 Hz, 2H). MS (ES, m/z): 757 [M+H]$^+$.

Example 61

6-((Methyl(2-(4-methylpiperazin-1-yl)ethyl)amino)methyl)-N-(4-(piperidin-1-yl)-2-(4-((3-(trifluoromethyl)benzyl)carbamoyl)pyridin-2-yl)phenyl)picolinamide

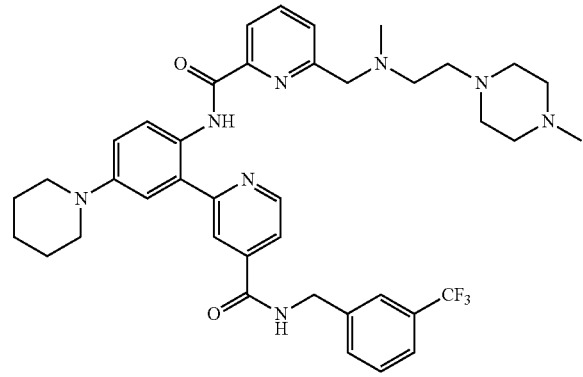 [SMILES: CN1CCN(CCN(C)Cc2cccc(C(=O)Nc3ccc(N4CCCCC4)cc3-c3cc(C(=O)NCc4cccc(C(F)(F)F)c4)ccn3)n2)CC1]

The tert-butoxycarbonyl group of tert-butyl 4-(2-(methyl((6-((4-(piperidin-1-yl)-2-(4-((3-(trifluoromethyl)benzyl)carbamoyl)pyridin-2-yl)phenyl)carbamoyl)pyridin-2-yl)methyl)amino)ethyl)piperazine-1-carboxylate 52 was cleaved by stirring for 1 hour in 1:1 dichloromethane/TFA and the resultant amine converted to the free base by partitioning between ethyl acetate and aqueous sodium bicarbonate solution. Into a 8-mL sealed tube, was placed a solution of 6-((methyl(2-(piperazin-1-yl)ethyl)amino)methyl)-N-(4-(piperidin-1-yl)-2-(4-(3-(trifluoromethyl)benzylcarbamoyl)pyridin-2-yl)phenyl)picolinamide (100 mg, 0.14 mmol, 1.00 equiv) in tetrahydrofuran (3 mL), NaBH(OAc)$_3$ (90 mg, 0.42 mmol, 3.00 equiv), and formaldehyde (2 mL). The resulting solution was stirred for overnight at 40° C. The resulting mixture was concentrated under vacuum. The crude product (100 mg) was purified by reverse phase HPLC eluting with a water/CH$_3$CN gradient containing 0.05% TFA. The product was obtained as 53.7 mg (27%) of as a yellow solid. $^1$H-NMR (300 MHz, DMSO-d$_6$, ppm): δ 12.44 (s, 1H), 9.82 (s, 1H), 9.58 (t, J=5.4 Hz, 1H), 9.06 (d, J=5.1 Hz, 1H), 8.33 (d, J=9.0 Hz, 1H), 8.26 (s, 1H), 8.21-8.15 (m, 2H), 7.90-7.84 (m, 2H), 7.71-7.55 (m, 4H), 7.47 (s, 1H), 7.25 (d, J=8.1 Hz, 1H), 4.64-4.58 (m, 4H), 3.36-3.29 (m, 8H), 2.97 (s, 4H), 2.86 (s, 3H), 2.76 (s, 5H), 2.33-2.27 (m, 2H), 1.71-1.58 (m, 6H). MS (ES, m/z): 729 [M+H]$^+$.

Example 62

6-((Methyl(2-(4-(methylsulfonyl)piperazin-1-yl)ethyl)amino)methyl)-N-(4-(piperidin-1-yl)-2-(4-((3-(trifluoromethyl)benzyl)carbamoyl)pyridin-2-yl)phenyl)picolinamide

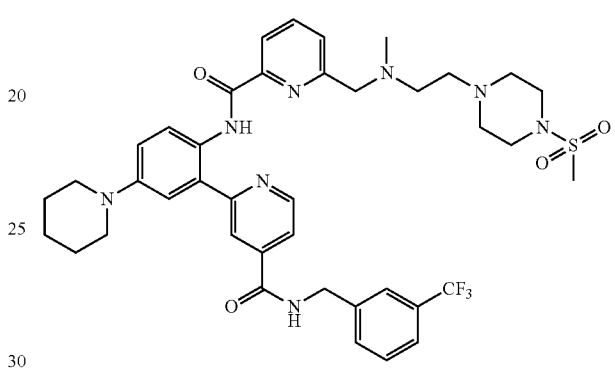

The tert-butoxycarbonyl group of tert-butyl 4-(2-(methyl((6-((4-(piperidin-1-yl)-2-(4-((3-(trifluoromethyl)benzyl)carbamoyl)pyridin-2-yl)phenyl)carbamoyl)pyridin-2-yl)methyl)amino)ethyl)piperazine-1-carboxylate 52 was cleaved by stirring for 1 hour in 1:1 dichloromethane/TFA and the resultant amine converted to the free base by partitioning between ethyl acetate and aqueous sodium bicarbonate solution. Into a 50-mL round-bottom flask, was placed a solution of 6-((methyl(2-(piperazin-1-yl)ethyl)amino)methyl)-N-(4-(piperidin-1-yl)-2-(4-(3-(trifluoromethyl)benzylcarbamoyl)pyridin-2-yl)phenyl)-picolinamide (110 mg, 0.15 mmol, 1.00 equiv) in dichloromethane (5 mL). To this was added triethylamine (23.3 mg, 0.23 mmol, 1.50 equiv). This was followed by dropwise addition of a solution of methanesulfonyl chloride (21.2 mg, 0.18 mmol, 1.20 equiv) in dichloromethane (2 mL) with stirring at 0° C. The resulting solution was stirred for 3 h at room temperature. The resulting mixture was concentrated under vacuum. The crude product (100 mg) was purified by reverse phase HPLC eluting with a water/CH$_3$CN gradient containing 0.05% TFA. The product was obtained as 58.1 mg (28%) of a yellow solid. $^1$H-NMR (300 MHz, DMSO-d$_6$, ppm): δ 12.62 (s, 1H), 9.56 (t, J=6.0 Hz, 1H), 9.05 (d, J=5.4 Hz, 1H), 8.42 (d, J=9.0 Hz, 1H), 8.27 (s, 1H), 8.16 (dd, J=4.8 Hz, 2H), 7.88-7.81 (m, 2H), 7.71 (s, 1H), 7.67-7.54 (m, 4H), 7.30 (d, J=7.8 Hz, 1H), 4.63 (d, J=5.7 Hz, 2H), 4.35 (s, 2H), 3.32 (s, 4H), 3.18 (s, 6H), 2.99 (s, 2H), 2.88-2.84 (m, 7H), 2.68 (s, 3H), 1.73-1.59 (m, 6H). MS (ES, m/z): 793 [M+H]$^+$.

Example 63
N-(2-Methoxyethyl)-4-(2-(methyl((6-((4-(piperidin-1-yl)-2-(4-((3-(trifluoromethyl)benzyl)carbamoyl)pyridin-2-yl)phenyl)carbamoyl)pyridin-2-yl)methyl)amino)ethyl)piperazine-1-carboxamide
Scheme 44.
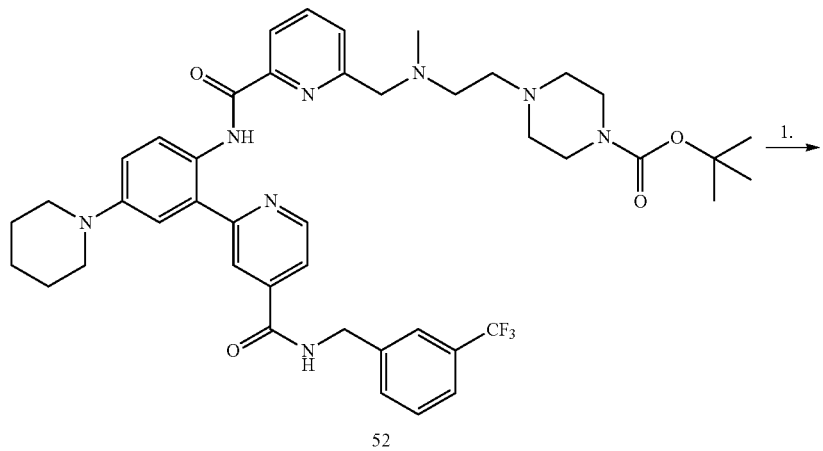
52
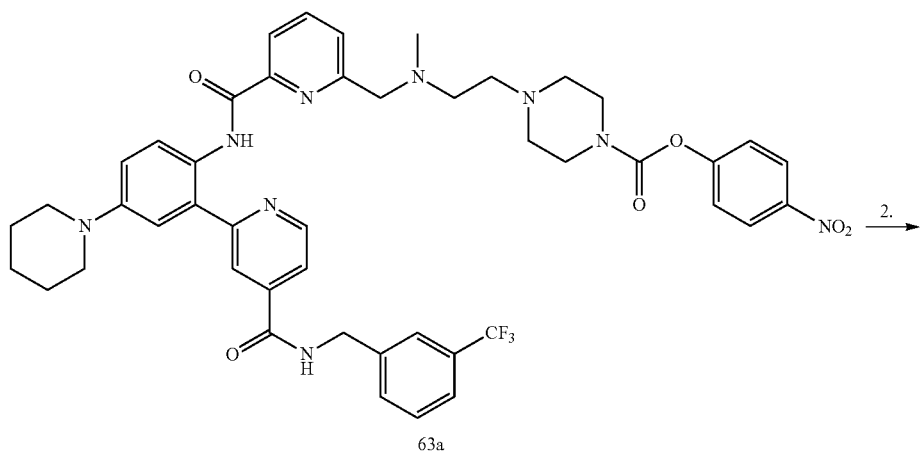
63a
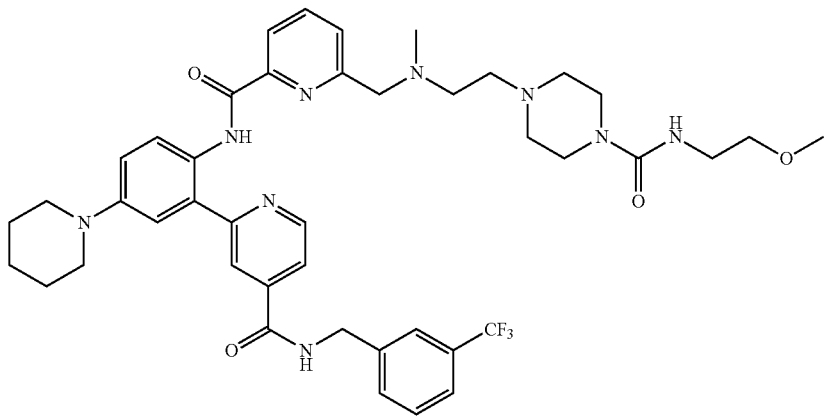
63
1. TFA, then 4-nitrophenyl chloroformate; 2. DIEA, DMF, methoxyethylamine.

Intermediate 63a: 4-nitrophenyl 4-(2-(methyl((6-(4-(piperidin-1-yl)-2-(4-(3-(trifluoromethyl)benzylcarbamoyl)pyridin-2-yl)phenylcarbamoyl)pyridin-2-yl)methyl)-amino)ethyl)piperazine-1-carboxylate The tert-butoxycarbonyl group of tert-butyl 4-(2-(methyl ((6-((4-(piperidin-1-yl)-2-(4-((3-(trifluoromethyl)benzyl) carbamoyl)pyridin-2-yl)-phenyl)carbamoyl)pyridin-2-yl) methyl)amino)ethyl)piperazine-1-carboxylate 52 was cleaved by stirring for 1 hour in 1:1 dichloromethane/TFA and the resultant amine converted to the free base by partitioning between ethyl acetate and aqueous sodium bicarbonate solution. Into a 50-mL round-bottom flask, was placed a solution of 6-((methyl(2-(piperazin-1-yl)ethyl)amino)methyl)-N-(4-(piperidin-1-yl)-2-(4-(3-(trifluoromethyl)benzylcarbamoyl)pyridin-2-yl)phenyl)picolinamide (100 mg, 0.14 mmol, 1.00 equiv) in dichloromethane (2 mL), and 4-nitrophenyl chloroformate (28 mg, 0.14 mmol, 1.00 equiv). The resulting solution was stirred for 2 h at room temperature. The mixture was concentrated under vacuum. The crude product was obtained as 0.1 g of a yellow solid.

Example 63

N-(2-methoxyethyl)-4-(2-(methyl((6-(4-(piperidin-1-yl)-2-(4-(3-(trifluoromethyl)benzylcarbamoyl)pyridin-2-yl)phenylcarbamoyl)pyridin-2-yl)methyl)amino)ethyl)piperazine-1-carboxamide Into a 50-mL round-bottom flask, was placed a solution of 4-nitrophenyl 4-(2-(methyl((6-(4-(piperidin-1-yl)-2-(4-(3-(trifluoromethyl)benzylcarbamoyl)pyridin-2-yl)phenylcarbamoyl)pyridin-2-yl)methyl)-amino)ethyl)piperazine-1-carboxylate (100 mg, 0.11 mmol, 1.00 equiv) in N,N-dimethylformamide (5 mL), 2-methoxyethanamine (10 mg, 0.13 mmol, 1.00 equiv), and N,N-diisopropylethylamine (45 mg, 0.35 mmol, 3.00 equiv). The resulting solution was stirred overnight at room temperature. The mixture was concentrated under vacuum. The crude product (0.1 g) was purified by reverse phase HPLC eluting with a water/CH$_3$CN gradient containing 0.05% TFA. The product was obtained as 23.2 mg (18%) of a yellow solid. $^1$H-NMR (300 MHz, DMSO-d$_6$, ppm): δ 12.76 (s, 1H), 9.54-9.52 (m, 1H), 9.05-9.03 (m, 1H), 8.48-8.45 (m, 1H), 8.26 (m, 1H), 8.14-8.12 (m, 2H), 7.88-7.86 (m, 1H), 7.79-7.24 (m, 7H), 6.71 (m, 1H), 4.65-4.63 (d, J=5.7 Hz, 2H), 4.09 (m, 3H), 3.69-3.01 (m, 23H), 1.71-1.59 (m, 6H). MS (ES, m/z): 816 [M+H]$^+$.

Example 64

N1-(2-(2-Hydroxyethoxy)ethyl)-N3-(4-(piperidin-1-yl)-2-(6-((3-(trifluoromethyl)benzyl)amino)pyrimidin-4-yl)phenyl)isophthalamide Scheme 45.

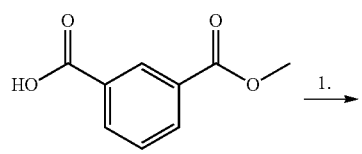

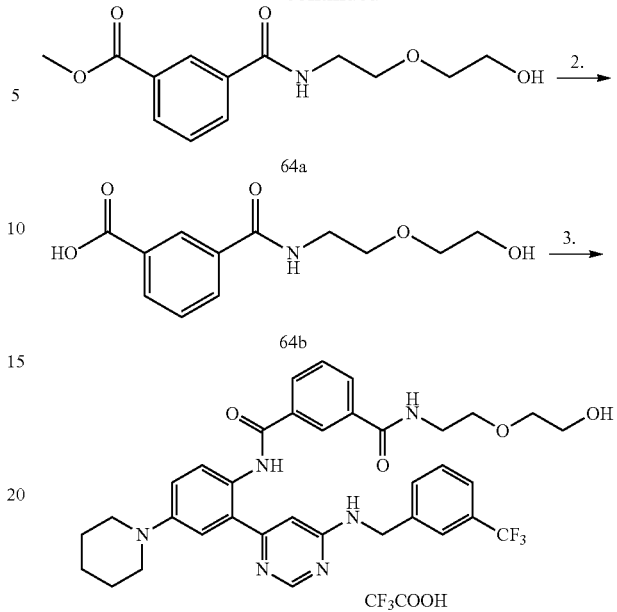

1. HATU, diisopropylethylamine; 2. LiOH; 3. EDC•HCl/HOBT/TEA, DMF, imtermediate 3.1d Intermediate 64a: methyl 3-((2-(2-hydroxyethoxy)ethyl)carbamoyl)benzoate Into a 1000-mL round bottom flask, was placed a solution of 3-(methoxycarbonyl)benzoic acid (20 g, 111.11 mmol, 1.00 equiv) in N,N-dimethylformamide (500 mL), HATU (63.2 g, 166.32 mmol, 1.50 equiv), N,N-diisopropylethylamine (21.5 g, 166.67 mmol, 1.50 equiv), 2-(2-aminoethoxy)ethanol (23.3 g, 221.90 mmol, 2.00 equiv). The resulting solution was stirred for overnight at 25° C. The resulting mixture was concentrated under vacuum. The resulting solution was dissolved in 200 mL of ethyl acetate. The resulting mixture was washed with 10×200 mL of brine. The mixture was dried over anhydrous sodium sulfate and concentrated under vacuum. The residue was applied onto a silica gel column with dichloromethane:methanol (100:1). This resulted in 15 g (51%) of methyl 3-((2-(2-hydroxyethoxy) ethyl)carbamoyl)benzoate as red oil.

Intermediate 64b: 3-((2-(2-hydroxyethoxy)ethyl)carbamoyl)benzoic acid

Into a 500-mL round bottom flask, was placed a solution of methyl 3-((2-(2-hydroxyethoxy)ethyl)carbamoyl)benzoate (10 g, 37.45 mmol, 1.00 equiv) in tetrahydrofuran (40 mL), and a solution of lithium hydroxide hydrate (23.4 g, 558.33 mmol, 15.00 equiv) in water (30 mL). The resulting solution was stirred for overnight at room temperature. The resulting mixture was concentrated under vacuum. The solution was adjusted to pH 3-4 with hydrochloric acid (2 mol/L). The resulting solution was extracted with 3×10 mL of ethyl acetate and the organic layers combined. The resulting mixture was washed with 2×10 mL of brine, dried over anhydrous sodium sulfate, and concentrated under vacuum. The residue was applied onto a silica gel column and eluted with dichloromethane:methanol (50:1). This resulted in 5 g (53%) of 3-((2-(2-hydroxyethoxy)ethyl)carbamoyl)benzoic acid as a yellowish solid. $^1$H-NMR (300 MHz DMSO-d$_6$, ppm): δ 13.25 (s, 1H), 8.71 (m, 1H), 8.48 (d, J=8.5 Hz 1H), 8.06 (m, 2H), 7.62 (m, 1H), 4.59 (s, 1H), 3.41~3.60 (m, 8H). MS (ES, m/z): 254 [M+H]$^+$.

Example 64

N1-(2-(2-hydroxyethoxy)ethyl)-N3-(4-(piperidin-1-yl)-2-(6-((3-(trifluoromethyl)benzyl)amino)pyrimidin-4-yl)phenyl)isophthalamide Into a 100-mL round bottom flask, was placed a solution of 6-(2-amino-5-(piperidin-1-yl)phenyl)-N-(3-(trifluoromethyl)benzyl)pyrimidin-4-amine (300 mg, 0.70 mmol, 1.00 equiv) in N,N-dimethylformamide (6 mL). This was followed by the addition of 3-(2-(2-hydroxyethoxy)ethylcarbamoyl) benzoic acid (302.2 mg, 1.19 mmol, 1.70 equiv) at room temperature. To this was added triethylamine (156 mg, 1.54 mmol, 2.20 equiv). To the mixture was added EDC.HCl (148.2 mg, 0.78 mmol, 1.10 equiv) at room temperature, followed by HOBT (104.4 mg, 0.77 mmol, 1.10 equiv) at room temperature. The resulting solution was stirred overnight at room temperature. The resulting mixture was concentrated under vacuum. The crude product was purified by reverse phase HPLC eluting with a water/CH$_3$CN gradient containing 0.05% TFA. The product was obtained as 83.6 mg (15%) of a yellow solid. $^1$H-NMR (300 MHz, CD$_3$OD, ppm): δ 8.76 (s, 1H), 8.40 (s, 1H), 8.039 (t, J=8.1 Hz, 2H), 7.74 (s, 1H), 7.63~7.57 (m, 3H), 7.53~7.50 (m, 2H), 7.47~7.40 (m, 2H), 6.93 (s, 1H), 4.81 (s, 2H), 3.71~3.58 (m, 8H), 3.43~3.39 (m, 4H), 1.84~1.81 (m, 6H). MS (ES, m/z): 663 [M+H]$^+$.

Example 65

N1-(4-Chloro-2-(6-((3-(trifluoromethyl)benzyl) amino)pyrimidin-4-yl)phenyl)-N3-(2-(2-hydroxyethoxy)ethyl)isophthalamide Scheme 46.

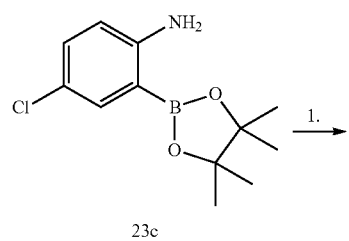

23c

1.

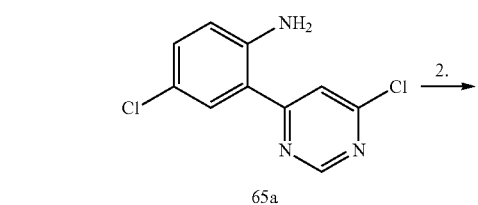

65a

2.

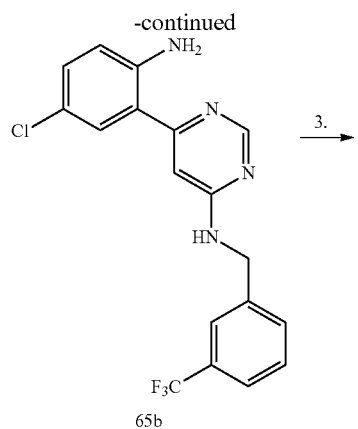

65b

3.

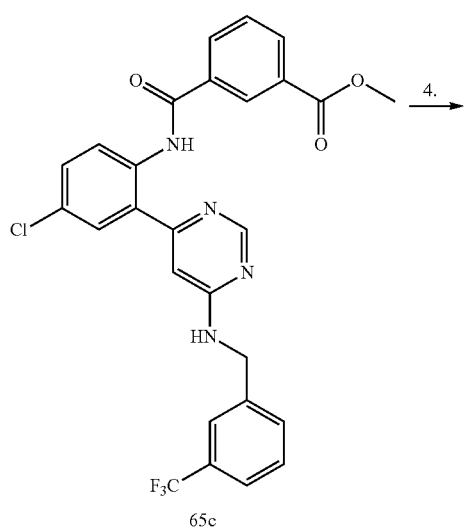

65c

4.

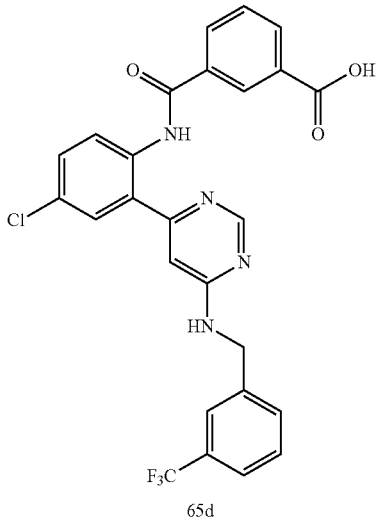

65d

5.

-continued

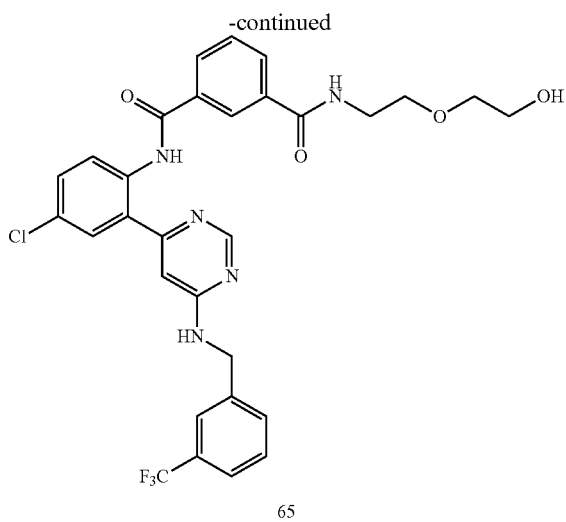

65

1. Pd(PhP₃)₂Cl₂, AsPh₃, K₃PO₄, dioxane/HCl; 2. 3-(trifluromethyl)-benzenamine; 3. monomethyl isophthalate, EDC, DMAP/DCM; 4. LiOH, THF, H₂O; 5. HATU/DIPEA, DMF, 2-(2-aminoethoxy)ethanol.

Intermediate 65a: 4-chloro-2-(6-chloropyrimidin-4-yl)aniline

Into a 250-mL round bottom flask, was placed a solution of 4-chloro-2-(4,4,5,5-tetramethyl-1,3,2-dioxaborolan-2-yl)benzenamine (3 g, 11.83 mmol, 1.00 equiv) in dioxane (120 mL), water (20 mL), 4,6-dichloropyrimidine (4.4 g, 29.53 mmol, 2.50 equiv), triphenylarsine (360 mg, 1.18 mmol, 0.10 equiv), K₃PO₄ (3.8 g, 17.90 mmol, 1.50 equiv), Pd(PPh₃)₂Cl₂ (390 mg, 0.56 mmol, 0.05 equiv). The resulting solution was stirred for 3 h at 75° C. in an oil bath. The resulting mixture was concentrated under vacuum. The residue was applied onto a silica gel column with ethyl acetate/petroleum ether (1:50~1:10). This resulted in 1.5 g (53%) of 4-chloro-2-(6-chloropyrimidin-4-yl)benzenamine as a yellow solid.

Intermediate 65b: 6-(2-amino-5-chlorophenyl)-N-(3-(trifluoromethyl)benzyl)pyrimidin-4-amine Into a 50-mL round bottom flask, was placed a solution of 4-chloro-2-(6-chloropyrimidin-4-yl)benzenamine (1.5 g, 6.25 mmol, 1.00 equiv) in N,N-dimethylformamide (30 mL), potassium carbonate (2.7 g, 19.54 mmol, 3.00 equiv), 3-(trifluoromethyl)benzylamine (1.7 g, 9.70 mmol, 1.50 equiv). The resulting solution was stirred overnight at 80° C. in an oil bath. The resulting mixture was concentrated under vacuum. The resulting solution was diluted with 20 mL of ethyl acetate. The resulting mixture was washed with 2×20 mL of water. The mixture was dried over anhydrous sodium sulfate and concentrated under vacuum. The residue was applied onto a silica gel column with ethyl acetate/petroleum ether (1:2). This resulted in 1 g (42%) of N-(3-(trifluoromethyl)benzyl)-6-(2-amino-5-chlorophenyl)pyrimidin-4-amine as yellow oil Intermediate 65c: methyl 3-((2-(6-(3-(trifluoromethyl)benzylamino)pyrimidin-4-yl)-4-chlorophenyl)carbamoyl)benzoate Into a 100-mL round bottom flask, was placed a solution of N-(3-(trifluoromethyl)benzyl)-6-(2-amino-5-chlorophenyl)pyrimidin-4-amine (500 mg, 1.32 mmol, 1.00 equiv) in dichloromethane (30 mL), EDC.HCl (380 mg, 1.98 mmol, 1.50 equiv), N,N-dimethylpyridin-4-amine (242 mg, 1.98 mmol, 1.50 equiv), and 3-(methoxycarbonyl)benzoic acid (357 mg, 1.98 mmol, 1.50 equiv). The resulting solution was stirred for 2 h at 30° C. in an oil bath. The resulting mixture was concentrated under vacuum. The residue was applied onto a silica gel column and eluted with petroleum ether/ethyl acetate (2:1). The product was obtained as 400 mg (56%) of a yellow solid.

Intermediate 65d: 3-((2-(6-(3-(trifluoromethyl)benzylamino)pyrimidin-4-yl)-4-chlorophenyl)carbamoyl)benzoic acid Into a 100-mL round bottom flask, was placed a solution of methyl 3-((2-(6-(3-(trifluoromethyl)benzylamino)pyrimidin-4-yl)-4-chlorophenyl)carbamoyl)benzoate (400 mg, 0.74 mmol, 1.00 equiv) in tetrahydrofuran (30 mL), water (30 mL), and lithium hydroxide hydrate (317 mg, 7.55 mmol, 10.00 equiv). The resulting solution was stirred for 4 h at 30° C. in an oil bath. The solution was adjusted to pH 1 with hydrochloric acid (1 mol/L). The resulting solution was extracted with 20 mL of ethyl acetate and the organic layers combined, dried over anhydrous sodium sulfate, and concentrated under vacuum. The product was obtained as 350 mg (90%) of a white solid.

Example 65

N1-(2-(6-(3-(trifluoromethyl)benzylamino)pyrimidin-4-yl)-4-chlorophenyl)-N3-(2-(2-hydroxyethoxy)ethyl)isophthalamide Into a 50-mL round bottom flask, was placed a solution of N-(3-(trifluoromethyl)benzyl)-6-(2-amino-5-chlorophenyl)pyrimidin-4-amine (200 mg, 0.53 mmol, 1.00 equiv) in N,N-dimethylformamide (20 mL), HATU (290 mg, 0.76 mmol, 2.00 equiv), N,N-diisopropylethylamine (200 mg, 1.55 mmol, 4.00 equiv), and N1-(2-(6-(3-(trifluoromethyl)benzylamino)pyrimidin-4-yl)-4-chlorophenyl)-N3-(2-(2-hydroxyethoxy)ethyl)isophthalamide (60 mg, 0.10 mmol, 1.50 equiv). The resulting solution was stirred overnight at 30° C. in an oil bath. The reaction progress was monitored by LCMS. The resulting mixture was concentrated under vacuum. The crude product was purified by reverse phase HPLC eluting with a water/CH₃CN gradient containing 0.05% TFA. The product was obtained as 105.9 mg (33%) of a yellow solid. ¹H-NMR (300 MHz, DMSO-d₆, ppm): δ 8.87 (s, 1H), 8.71 (t, J=4.8 Hz, 9.9 Hz, 1H), 8.49 (s, 1H), 8.07 (t, J=7.5 Hz, 15.3 Hz, 2H), 7.83 (s, 1H), 7.58 (m, 6H), 7.07 (s, 1H), 4.75 (s, 2H), 3.57 (m, 2H), 3.49 (m, 6H). MS (ES, m/z): 614 [M+H]⁺.

Example 66

3-((3-((4-Chloro-2-(6-((3-(trifluoromethyl)benzyl)amino)pyrimidin-4-yl)phenyl)carbamoyl)benzyl)thio)propanoic acid

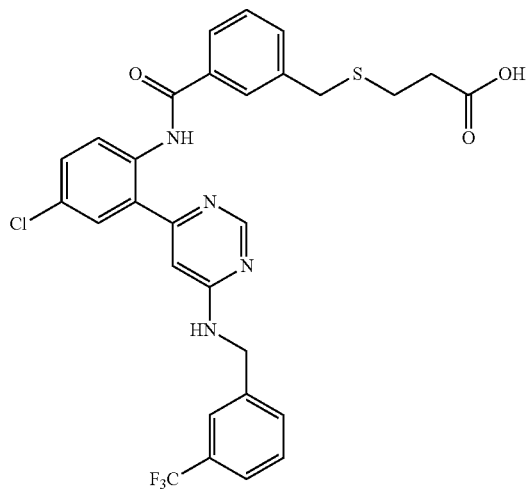 [SMILES: O=C(O)CCSCc1cccc(C(=O)Nc2ccc(Cl)cc2-c2cc(NCc3cccc(C(F)(F)F)c3)ncn2)c1]

203

This compound was prepared from 6-(2-amino-5-chlorophenyl)-N-(3-(trifluoromethyl)benzyl)pyrimidin-4-amine 65b using the procedure described for the preparation of 3-((3-((4-(piperidin-1-yl)-2-(6-((3-methylbenzyl)amino)pyrimidin-4-yl)phenyl)carbamoyl)benzyl)thio)propanoic acid 3.2 from 6-(2-amino-5-(piperidin-1-yl)phenyl)-N-(3-methylbenzyl) pyrimidin-4-amine 3.2b. $^1$H-NMR (400 MHz, DMSO-$d_6$, ppm): δ 8.79 (s, 1H), 8.48 (s, 1H), 7.91 (s, 1H), 7.81 (d, J=5.7 Hz, 2H), 7.63 (s, 1H), 7.56 (m, 6H), 7.09 (s, 1H), 4.74 (s, 2H), 3.88 (s, 2H), 2.57 (d, J=4.8 Hz, 2H). MS (ES, m/z): 601 [M+H]$^+$.

Example 67

N-(4-Chloro-2-(6-(3-(trifluoromethyl)benzylamino)pyrimidin-4-yl)phenyl)-3-(4-(dimethylamino)but-1-ynyl)benzamide 2,2,2-trifluoroacetate Scheme 47.

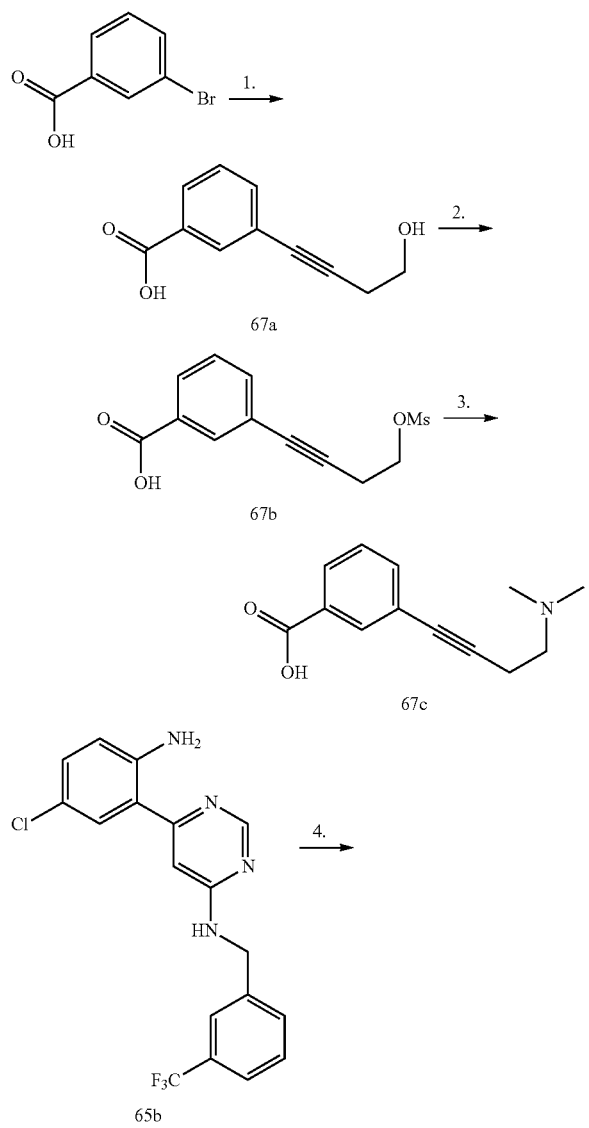

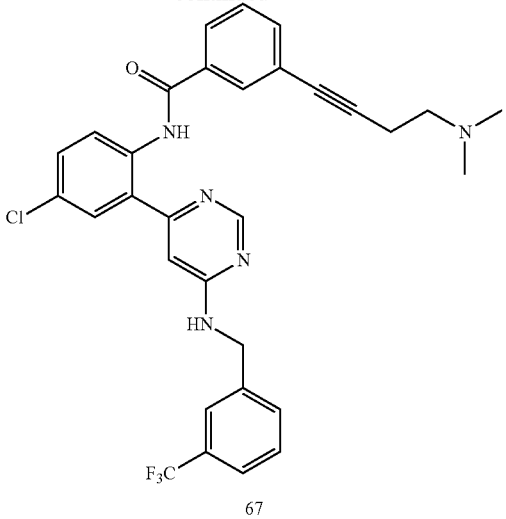

1. homopropargyl alcohol, Pd(Ph$_3$P)$_2$Cl$_2$, CuI, Et$_3$N; 2. methansulfonic anhydride, Et$_3$N; 3. dimethylamine; 4. intermediate 67c, EDC·HCl, DMAP, DCM.

Intermediate 67a: 3-(4-hydroxybut-1-yn-1-yl)benzoic acid

Into a 500-mL round bottom flask purged and maintained with an inert atmosphere of nitrogen, was placed a solution of 3-bromobenzoic acid (10 g, 49.75 mmol, 1.00 equiv) in triethylamine/N,N-dimethylformamide (100/20 mL), but-3-yn-1-ol (6.98 g, 99.57 mmol, 2.00 equiv), copper(I) iodide (1.90 g, 9.97 mmol, 0.20 equiv), Pd(PPh$_3$)$_2$Cl$_2$ (6.98 g, 9.94 mmol, 0.20 equiv). The resulting solution was stirred overnight at 80° C. The resulting mixture was concentrated under vacuum. The resulting solution was diluted with 100 mL of water. The pH value of the solution was adjusted to 11-12 with sodium hydroxide (1 mol/L). The resulting solution was extracted with 3×300 mL of dichloromethane and the aqueous layers combined. The solution was adjusted to pH 1-2 with hydrochloric acid (1 mol/L). The resulting solution was extracted with 5×300 mL of dichloromethane and the organic layers combined, dried over sodium sulfate, and concentrated under vacuum. This resulted in 10 g crude product as brown oil.

Intermediate 67b: 3-(4-((methylsulfonyl)oxy)but-1-yn-1-yl)benzoic acid

Into a 250-mL round bottom flask, was placed a solution of 3-(4-hydroxybut-1-ynyl)benzoic acid (2 g, 10.52 mmol, 1.00 equiv) in dichloromethane (100 mL), triethylamine (3200 mg, 31.68 mmol, 3.00 equiv), and methanesulfonic anhydride (3700 mg, 21.24 mmol, 2.00 equiv). The resulting solution was stirred for 5 h at room temperature. The resulting mixture was concentrated under vacuum. The residue was applied onto a silica gel column and eluted with dichloromethane/methanol (100:1). This resulted in 3 g crude product as a brown oil.

Example 67c 3-(4-(dimethylamino)but-1-yn-1-yl)benzoic acid trifluoroacetic acid salt Into a 250-mL round bottom flask, was placed a solution of 3-(4-(methylsulfonyloxy)but-1-ynyl)benzoic acid (8.23 g, 30.67 mmol, 1.00 equiv) in ethanol (50 mL), dimethylamine 33% water solution (50 mL). The resulting solution was stirred overnight at 30° C. in an oil bath. The resulting mixture was concentrated under vacuum. The crude product (10 g) was purified by reverse phase HPLC eluting with a water/CH₃CN gradient containing 0.05% TFA. 3-(4-(dimethylamino)but-1-ynyl)benzoic acid trifluoroacetic acid salt was obtained as 2.68 g (40%) of as yellow oil Example 67

N-(4-chloro-2-(6-(3-(trifluoromethyl)benzylamino)pyrimidin-4-yl)phenyl)-3-(4-(dimethylamino)but-1-ynyl)benzamide 2,2,2-trifluoroacetate Into a 50-mL round bottom flask, was placed a solution of 6-(2-amino-5-chlorophenyl)-N-(3-(trifluoromethyl)benzyl)pyrimidin-4-amine 57b (100 mg, 0.26 mmol, 1.00 equiv) in dichloromethane (2 mL), 3-(4-(dimethylamino)but-1-ynyl)benzoic acid (57 mg, 0.26 mmol, 1.00 equiv), EDC.HCl (76 mg, 0.40 mmol, 1.50 equiv), and 4-dimethylaminopyridine (48 mg, 0.39 mmol, 1.50 equiv). The resulting solution was stirred overnight at 25° C. The crude product (100 mg) was purified by reverse phase HPLC eluting with a water/CH₃CN gradient containing 0.05% TFA. The product was obtained as 7.4 mg (4%) of a light yellow solid. ¹H-NMR (300 MHz, DMSO-d₆, ppm): δ 8.666 (s, 1H), 8.5385 (d, J=2.9 Hz, 1H), 8.430 (s, 1H), 8.1125 (d, J=6.9 Hz, 1H), 8.008 (s, 1H), 7.866 (s, 1H), 7.819 (m, 2H), 7.769 (m, 1H), 7.623 (m, 4H), 7.120 (s, 1H), 6.491 (s, 1H), 4.7285 (d, J=5.7 Hz, 2H), 4.090 (t, J=6.9 Hz, 2H), 3.169 (m, 6H), 2.930 (m, 2H). MS (ES, m/z): 578 [M+H]⁺.

Example 68

N-(4-Chloro-2-(6-((3-(trifluoromethyl)benzyl)amino)pyrimidin-4-yl)phenyl)-3-(((2-(diethylamino)ethyl)(methyl)amino)methyl)benzamide Scheme 48.

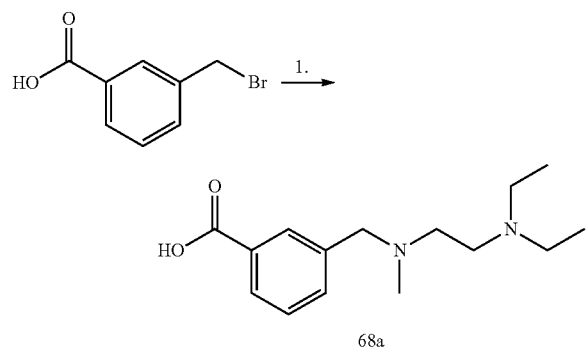

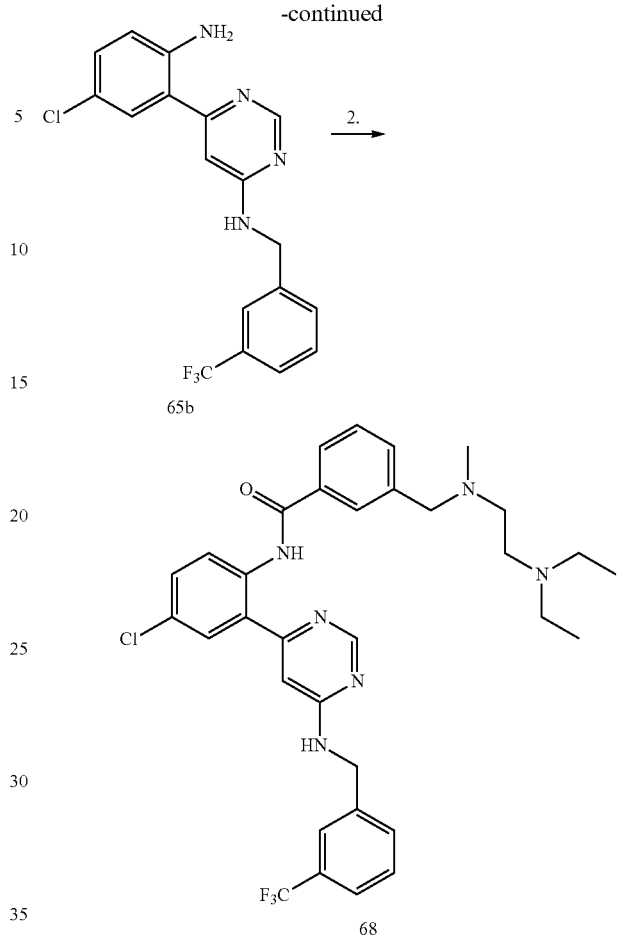

1. N,N-diethyl-N'-methylethylenediamine; 2. HATU, DIPEA, DMF, intermediate 68a.

Intermediate 68a: 3-(((2-(diethylamino)ethyl)(methyl)amino)methyl)benzoic acid

Into a 1000-mL round bottom flask, was placed a solution of N1,N1-diethyl-N2-methylethane-1,2-diamine (9.1 g, 63.00 mmol, 1.50 equiv, 90%) in N,N-dimethylformamide (500 mL), 3-(bromomethyl)benzoic acid (10 g, 46.51 mmol, 1.00 equiv), potassium carbonate (7.8 g, 56.12 mmol, 1.20 equiv), and potassium iodide (1.55 g, 9.34 mmol, 0.20 equiv). The resulting solution was stirred for 2 h at 90° C. in an oil bath. The solids were filtered out. The resulting mixture was concentrated under vacuum. The crude product (10 g) was purified by reverse phase HPLC eluting with 0.05% TFA in a water/CH₃CN gradient. The product was obtained as 6 g (46%) of a white solid. ¹H-NMR (300 MHz, CDCl₃, ppm): δ 8.01 (m, 1H), 7.89-7.87 (m, 1H), 7.28-7.22 (m, 2H), 3.99 (s, 2H), 2.97-2.72 (m, 8H), 2.28 (s, 3H), 1.13-1.01 (m, 6H). MS (ES, m/z): 265 [M+H]⁺.

Example 68

N-(4-chloro-2-(6-((3-(trifluoromethyl)benzyl)amino)pyrimidin-4-yl)phenyl)-3-(((2-(diethylamino)ethyl)(methyl)amino)methyl)benzamide Into a 50-mL round bottom flask, was placed a solution of 6-(2-amino-5-chlorophenyl)-N-(3-(trifluoromethyl)benzyl)

pyrimidin-4-amine 65b (200 mg, 0.53 mmol, 1.00 equiv) in N,N-dimethylformamide (5 mL), 3-(((2-(diethylamino)ethyl)(methyl)amino)methyl)benzoic acid (130 mg, 0.49 mmol, 1.00 equiv), HATU (300 mg, 0.79 mmol, 1.50 equiv), and N,N-diisopropylethylamine (270 mg, 2.09 mmol, 5.00 equiv). The resulting solution was stirred for 2 days at 25° C. in an oil bath. The reaction was then quenched with 50 mL of water. The resulting solution was extracted with 2×100 mL of ethyl acetate and the organic layers combined. The resulting mixture was washed with 2×50 mL of saturated NH$_4$Cl, dried over anhydrous sodium sulfate, and concentrated under vacuum. The crude product (200 mg) was purified by reverse phase HPLC eluting with a water/CH$_3$CN gradient containing 0.05% TFA. The product was obtained as 36.1 mg (9%) of a yellow solid. $^1$H-NMR (300 MHz, DMSO-d$_6$, ppm): δ 8.73 (s, 1H), 8.60 (d, J=9.3 Hz, 1H), 8.41 (s, 1H), 8.19 (m, 1H), 7.92 (m, 3H), 7.64 (m, 7H), 7.14 (s, 1H), 4.73 (d, J=5.7 Hz, 2H), 3.35 (s, 2H), 3.14 (d, J=6.9 Hz, 4H), 1.18 (t, J=7.2 Hz, 6H). MS (ES, m/z): 625 [M+H]$^+$.

Example 69

3-((3-((4-(Piperidin-1-yl)-2-(4-((3-(trifluoromethyl)benzyl)amino)pyridin-2-yl)phenyl)carbamoyl)benzyl)thio)propanoic acid

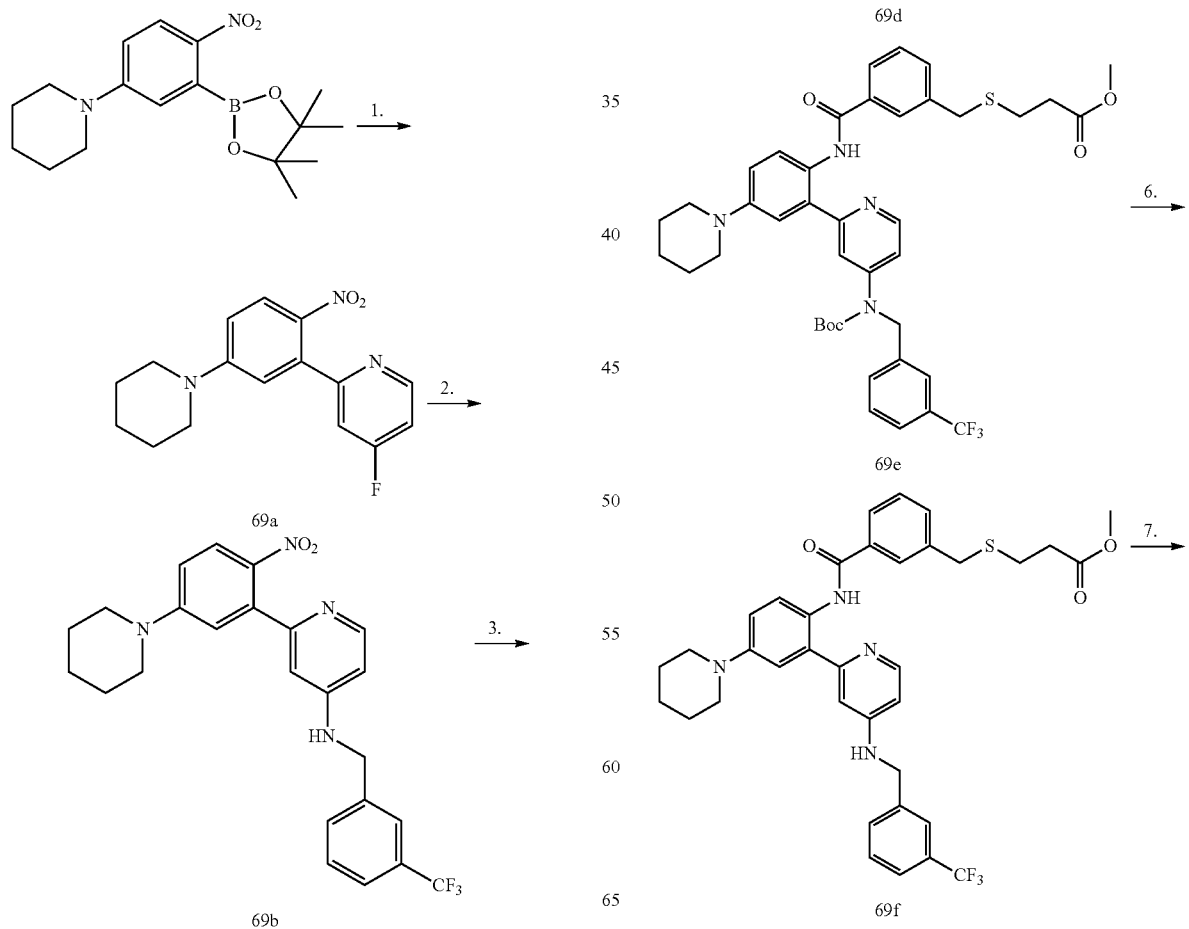

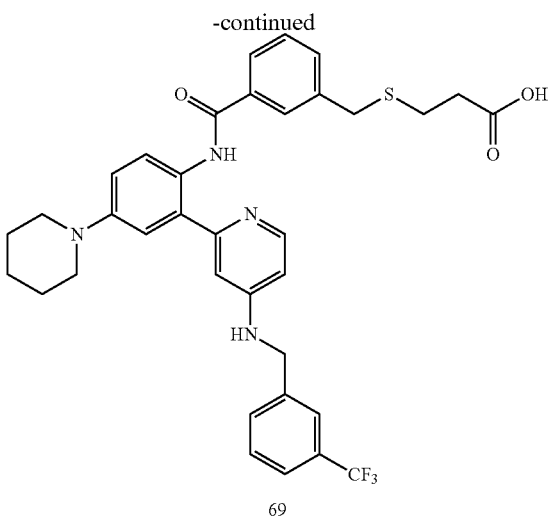

69

1. 2-chloro-4-fluoropyridine, K₃PO₄, SPhos, Pd(PPh₃)₄, DME/H₂O;
2. 3-(trifluoromethyl)benzylamine, K₂CO₃, DMF; 3. (Boc)₂O, DCM; 4. DCM, Zn, AcOH; 5. DCM/THF, pyridine, methyl 3-(3-(chlorocarbonyl)benzylthio)propanoate 22d; 6. TFA, DCM; 7. THF/H₂O, LiOH.

Intermediate 69a: 4-fluoro-2-(2-nitro-5-(piperidin-1-yl)phenyl)pyridine

Into a 500-mL 3-necked round bottom flask purged and maintained with an inert atmosphere of nitrogen, was placed a solution of 1-(4-nitro-3-(4,4,5,5-tetramethyl-1,3,2-dioxaborolan-2-yl)phenyl) piperidine (15 g, 45.18 mmol, 1.00 equiv) in DME/H₂O (100/5 mL), 2-chloro-4-fluoropyridine (7.80 g, 60.00 mmol, 1.20 equiv), K₃PO₄ (31 g, 146.23 mmol, 3.00 equiv), 2-dicyclohexylphosphino-2',6'-dimethoxybiphenyl (SPhos) (2.00 g, 4.88 mmol, 0.10 equiv), and Pd(PPh₃)₄ (2800 mg, 2.42 mmol, 0.05 equiv). The resulting solution was stirred for 1 overnight at 80° C. in an oil bath. The reaction progress was monitored by LCMS. The resulting mixture was concentrated under vacuum. The resulting solution was diluted with 200 mL of H₂O, extracted with 3×300 mL of dichloromethane, and the organic layers combined. The resulting mixture was washed with 1×20 mL of brine, dried over anhydrous sodium sulfate, and concentrated under vacuum. The residue was applied onto a silica gel column and eluted with ethyl acetate/petroleum ether (10:1). The product was obtained as 8 g of a yellow solid.

Intermediate 69b: 2-(2-nitro-5-(piperidin-1-yl)phenyl)-N-(3-(trifluoromethyl)benzyl)-pyridin-4-amine Into a 30-mL round bottom flask, was placed a solution of 4-fluoro-2-(2-nitro-5-(piperidin-1-yl)phenyl)pyridine (500 mg, 1.66 mmol, 1.00 equiv) in N,N-dimethylformamide (10 mL), (3-(trifluoromethyl)benzylamine (581 mg, 3.32 mmol, 2.00 equiv), and potassium carbonate (985 mg, 7.14 mmol, 4.00 equiv). The resulting solution was stirred overnight at 100° C. in an oil bath. The resulting solution was diluted with 30 mL of water. The resulting solution was extracted with 3×30 mL of ethyl acetate and the organic layers combined. The resulting mixture was washed with 2×20 mL of brine and concentrated under vacuum. The residue was applied onto a silica gel column and eluted with ethyl acetate/hexane (1:1). The product was obtained as 500 mg (66%) of a yellow oil.

Intermediate 69c: tert-butyl 2-(2-nitro-5-(piperidin-1-yl)phenyl)pyridin-4-yl(3-(trifluoro-methyl)benzyl)carbamate Into a 100-mL round bottom flask, was placed a solution of 2-(2-nitro-5-(piperidin-1-yl)phenyl)-N-(3-(trifluoromethyl)benzyl)pyridin-4-amine (670 mg, 1.47 mmol, 1.00 equiv) in dichloromethane (40 mL), (Boc)₂O (960 mg, 4.40 mmol, 3.00 equiv), and 4-dimethylaminopyridine (268 mg, 2.20 mmol, 1.50 equiv). The resulting solution was stirred overnight at 35° C. in an oil bath. The resulting mixture was concentrated under vacuum. The resulting solution was diluted with 30/30 mL of H₂O/DCM, and adjusted to pH 7 with sulfuric acid (1 N). The resulting solution was extracted with 3×50 mL of dichloromethane and the organic layers combined, dried over sodium sulfate, and concentrated under vacuum. The product was obtained as 760 mg (93%) of a yellow solid.

Intermediate 69d: tert-butyl 2-(2-amino-5-(piperidin-1-yl)phenyl)pyridin-4-yl(3-(trifluoro-methyl)benzyl)carbamate Into a 100-mL 3-necked round bottom flask purged and maintained with an inert atmosphere of nitrogen, was placed a solution of tert-butyl 2-(2-nitro-5-(piperidin-1-yl)phenyl)pyridin-4-yl(3-(trifluoromethyl)benzyl)carbamate (760 mg, 1.37 mmol, 1.00 equiv) in dichloromethane (10 mL), and Zn (500 mg). This was followed by dropwise addition of acetic acid (0.7 mL) with stirring. The resulting solution was stirred for 3 h at room temperature. The reaction progress was monitored by LCMS. The solids were removed by filtration. The solution was adjusted to pH 8-9 with NaHCO₃ (aq). The resulting solution was extracted with 3×50 mL of dichloromethane and the organic layers combined. The resulting mixture was washed with 1×50 mL of brine, dried over sodium sulfate, and concentrated under vacuum. The product was obtained as 600 mg (83%) of a black solid.

Intermediate 69e: methyl 3-(3-(2-(4-(tert-butoxycarbonyl(3-(trifluoromethyl)benzyl)-amino)pyridin-2-yl)-4-(piperidin-1-yl)phenylcarbamoyl)benzylthio)propanoate Into a 50-mL round bottom flask purged and maintained with an inert atmosphere of nitrogen, was placed a solution of tert-butyl 2-(2-amino-5-(piperidin-1-yl)phenyl)pyridin-4-yl (3-(trifluoromethyl)benzyl)carbamate (600 mg, 1.14 mmol, 1.00 equiv) in DCM/THF (5/20 mL), methyl 3-(3-(chlorocarbonyl)benzylthio)propanoate (580 mg, 2.13 mmol, 1.40 equiv), and pyridine (750 mg, 9.49 mmol, 3.00 equiv). The resulting solution was stirred for 3 h at room temperature. The reaction progress was monitored by LCMS. The resulting solution was diluted with 30 mL of H₂O and adjusted to pH 6-7 with H₂SO₄ (1 N). The resulting solution was extracted with 3×40 mL of dichloromethane and the organic layers combined. The resulting mixture was washed with 1×30 mL of brine. The mixture was dried over anhydrous sodium sulfate and concentrated under vacuum to yield 800 mg (92%) of product as a yellow oil.

Intermediate 69f: methyl 3-(3-(4-(piperidin-1-yl)-2-(4-(3-(trifluoromethyl)benzylamino)-pyridin-2-yl)phenylcarbamoyl)benzylthio)propanoate Into a 50-mL round bottom flask, was placed a solution of methyl 3-(3-(2-(4-(tert-butoxycarbonyl(3-(trifluoromethyl)benzyl)amino)pyridin-2-yl)-4-(piperidin-1-yl)phenylcarbamoyl)-benzylthio)propanoate (800 mg, 1.05 mmol, 1.00 equiv) in dichloromethane (2 mL), and 2,2,2-trifluoroacetic acid (5 mL). The resulting solution was stirred for 3 h at room temperature. The reaction progress was monitored by LCMS. The resulting solution was diluted with 20 mL of NaHCO₃ (aq), extracted with 3×50 mL of dichloromethane, and the organic layers combined. The resulting mixture was washed with 1×50 mL of brine. The resulting mixture was concentrated under vacuum. The residue was applied onto a silica gel column and eluted with petroleum ether:ethyl acetate (5:1). The product was obtained as 200 mg (29%) of a yellow solid.

Example 69

3-(3-(4-(piperidin-1-yl)-2-(4-((3-(trifluoromethyl)benzylamino)pyridin-2-yl)phenylcarbamoyl)benzylthio)propanoic acid Into a 50-mL round bottom flask, was placed a solution of methyl 3-(3-(4-(piperidin-1-yl)-2-(4-(3-(trifluoromethyl)benzylamino)pyridin-2-yl)phenylcarbamoyl)benzylthio)propano ate (300 mg, 0.35 mmol, 1.00 equiv, 78%) in tetrahydrofuran/H₂O (20/5 mL), and LiOH (150 mg, 10.00 equiv, 40%). The resulting solution was stirred for 2 h at room temperature. The reaction progress was monitored by LCMS. The solution was adjusted to pH 6-7 with hydrochloric acid (1 N). The resulting solution was extracted with 3×50 mL of ethyl acetate and the organic layers combined. The resulting mixture was washed with 1×20 mL of ethoxyethane. The resulting mixture was concentrated under vacuum. The crude product (250 mg) was purified by reverse phase HPLC eluting with a water/CH₃CN gradient containing 0.05% TFA to afford the product (27 mg, 10%) as a yellow oil. ¹H-NMR (300 MHz, DMSO-d₆, ppm) δ 13.49 (s, 1H), 10.05 (m, 1H), 8.89 (m, 1H), 8.02 (m, 1H), 7.68 (m, 4H), 7.37 (m, 5H), 7.08 (m, 1H), 6.91 (m, 2H), 6.28 (m, 1H), 3.80 (s, 2H), 3.23 (s, 4H), 2.27 (m, 2H), 1.63 (s, 6H). MS (ES, m/z): 649 [M+H]⁺.

Example 70

3-((3-((4-(Piperidin-1-yl)-2-(4-((3-(trifluoromethyl)phenethyl)amino)pyridin-2-yl)phenyl)carbamoyl)benzyl)thio)propanoic acid

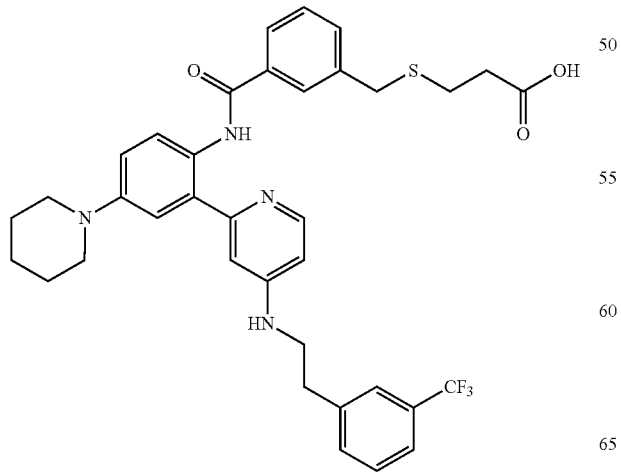

This compound was prepared by the route used to prepare 3-(3-(4-(piperidin-1-yl)-2-(4-(3-(trifluoromethyl)benzylamino)pyridin-2-yl)phenylcarbamoyl)benzylthio)propanoic acid 69, substituting 3-(trifluoromethyl)phenethylamine for 3-(trifluoromethyl)benzylamine. ¹H-NMR (300 MHz, DMSO-d₆, ppm): δ 13.37 (s, 1H), 12.23 (s, 1H), 8.22 (s, 1H), 7.82-7.74 (m, 2H), 7.64-7.50 (m, 6H), 7.12 (m, 3H), 6.99 (s, 1H), 6.70 (s, 1H), 3.82 (s, 2H), 3.47 (s, 2H), 3.21 (t, 4H), 2.92 (t, 2H), 2.58-2.50 (m, 4H), 1.66 (m, 4H), 1.58 (m, 2H). MS (ES, m/z): 663 [M+H]⁺.

Example 71

3-((3-((2-(4-((3,4-Dimethylphenyl)amino)pyridin-2-yl)-4-(piperidin-1-yl)phenyl)carbamoyl)benzyl)thio)propanoic acid Scheme 50.

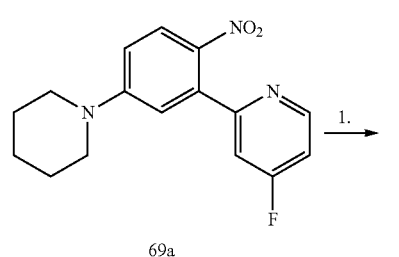

69a

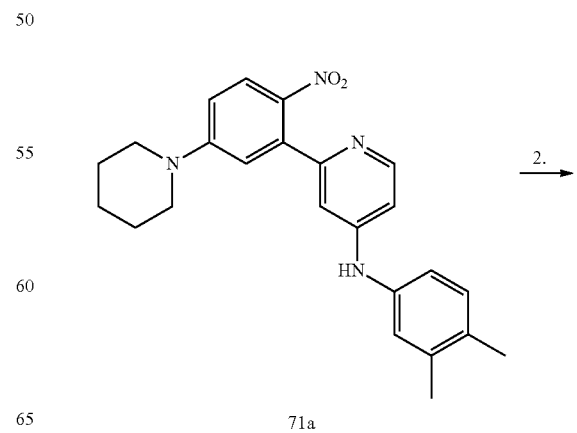

71a

-continued

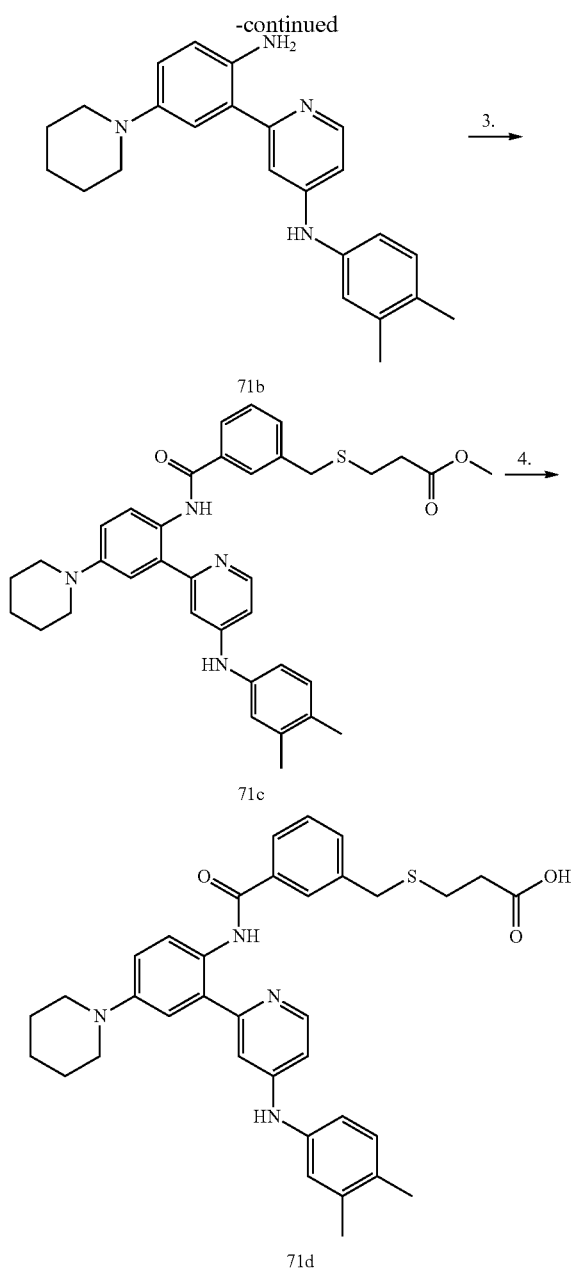

1. 3,4-dimethylaninline, NaH, DMF; 2. Zn/HOAc, EtOH/THF; 3. methyl 3-(3-(chlorocarbonyl)benzylthio)propanoate 22d; 4. LiOH, H₂O/THF.

Intermediate 71a: N-(3,4-dimethylphenyl)-2-(2-nitro-5-(piperidin-1-yl)phenyl)pyridin-4-amine Into a 100-mL 3-necked round bottom flask purged and maintained with an inert atmosphere of nitrogen, was placed a solution of 3,4-dimethylbenzenamine (2 g, 16.53 mmol, 4.98 equiv) in N,N-dimethylformamide (50 mL), and sodium hydride (660 mg, 16.50 mmol, 4.97 equiv, 60%). The resulting solution was stirred for 1 h at room temperature. To this was added 4-fluoro-2-(2-nitro-5-(piperidin-1-yl)phenyl)pyridine (1 g, 3.32 mmol, 1.00 equiv). The resulting solution stirred for an additional 1 h at 50-80° C. in an oil bath. The reaction mixture was cooled. The reaction was then quenched with 150 mL of H₂O. The resulting solution was extracted with 3×60 mL of ethyl acetate and the organic layers combined. The resulting mixture was washed with 1×60 mL of brine, dried over sodium sulfate, and concentrated under vacuum. The residue was applied onto a silica gel column and eluted with ethyl acetate:petroleum ether (1:1). The product was obtained as 500 mg (37%) of a yellow solid.

Intermediate 71b: 2-(2-amino-5-(piperidin-1-yl)phenyl)-N-(3,4-dimethylphenyl)pyridin-4-amine Into a 50-mL 3-necked round bottom flask, was placed a solution of N-(3,4-dimethylphenyl)-2-(2-nitro-5-(piperidin-1-yl)phenyl)pyridin-4-amine (300 mg, 0.75 mmol, 1.00 equiv) in tetrahydrofuran/EtOH (10/1 mL), Zn (485 mg, 7.46 mmol, 10.00 equiv), and acetic acid (1 mL). The resulting solution was stirred for 30 min at room temperature. The solids were filtered out. The solution was adjusted to pH 7-8 with sodium bicarbonate (aq). The resulting solution was extracted with 3×25 mL of dichloromethane and the organic layers combined. The resulting mixture was washed with 1×25 mL of brine, dried over sodium sulfate, and concentrated under vacuum. The product was obtained as 270 mg (97%) of a yellow solid.

Intermediate 71c: methyl 3-(3-((2-(4-(3,4-dimethylphenylamino)pyridin-2-yl)-4-(piperidin-1-yl)phenyl)carbamoyl)benzylthio)propanoate Into a 50-mL 3-necked round bottom flask, was placed a solution of 2-(2-amino-5-(piperidin-1-yl)phenyl)-N-(3,4-dimethylphenyl)pyridin-4-amine (270 mg, 0.72 mmol, 1.00 equiv) in tetrahydrofuran (10 mL), pyridine (170 mg, 2.15 mmol, 2.97 equiv), and methyl 3-(3-(chlorocarbonyl)benzylthio)propanoate (197.6 mg, 0.72 mmol, 1.00 equiv). The resulting solution was stirred for 1.5 h at room temperature. This reaction was used directly in next step without workup.

Example 71

3-(3-((2-(4-(3,4-dimethylphenylamino)pyridin-2-yl)-4-(piperidin-1-yl)-phenyl)carbamoyl)benzylthio)propanoic acid Into a 50-mL 3-necked round bottom flask, was placed a solution of methyl 3-(3-((2-(4-(3,4-dimethylphenylamino)pyridin-2-yl)-4-(piperidin-1-yl)phenyl)carbamoyl)benzylthio)propanoate (440 mg, 0.72 mmol, 1.00 equiv) in tetrahydrofuran (10 mL), and a solution of LiOH H₂O (300 mg, 7.14 mmol, 9.89 equiv) in water (2 mL). The resulting solution was stirred for 18 h at room temperature. The reaction was then quenched with 30 mL of water. The solution was adjusted to pH 6-7 with hydrochloric acid (1 N). The resulting solution was extracted with 3×30 mL of ethyl acetate and the organic layers combined. The resulting mixture was washed with 1×30 mL of brine. The mixture was dried over anhydrous sodium sulfate and concentrated under vacuum. The crude product (250 mg) was purified by reverse phase HPLC eluting with a water/CH₃CN gradient containing 0.05% TFA. The product was obtained as 237.2 mg (55%) of as a yellow solid. ¹H-NMR (300 MHz, DMSO-d₆, ppm): δ 13.76 (s, 1H), 10.22 (s, 1H), 10.11 (s, 1H), 8.21 (d, J=6 Hz, 1H), 7.71 (s, 1H), 7.61 (d, J=6.6 Hz, 1H), 7.51 (d, J=7.5 Hz, 1H), 7.42 (m, 1H), 7.32 (d, J=8.1 Hz, 1H), 7.16 (d, J=9 Hz, 1H), 7.08 (s, 2H), 6.94 (m, 3H), 6.81 (s, 1H), 3.80 (s, 2H), 3.24 (s, 4H), 2.55 (m, 3H), 2.17 (d, 6H), 1.63 (s, 6H). MS (ES, m/z): 595 [M+H]⁺.

Example 72

3-((3-((4-(Piperidin-1-yl)-2-(4-((3-(trifluoromethyl) phenyl)amino)pyridin-2-yl)phenyl)carbamoyl)benzyl)thio)propanoic acid This compound was prepared by the route used to prepare 3-((3-((2-(4-((3,4-dimethylphenyl)amino)pyridin-2-yl)-4-(piperidin-1-yl)phenyl)carbamoyl)benzyl)thio)-propanoic acid 71, substituting 3-(trifluoromethyl)aniline for 3,4-dimethylaniline. ¹H-NMR (300 MHz, DMSO-d₆, ppm) δ 13.08 (s, 1H), 9.36 (s, 1H), 8.54-8.52 (d, 1H), 8.43-8.40 (d, 1H), 7.89 (s, 1H), 7.81-7.78 (d, 1H), 7.56-7.39 (m, 7H), 7.24-7.23 (d, 1H), 7.10-7.04 (m, 2H), 3.89 (s, 2H), 3.17-3.15 (d, 4H), 2.62-2.58 (m, 2H), 1.66-1.56 (d, 6H). MS (ES, m/z): 635 [M+H]⁺.

Example 73

3-((3-((4-(Piperidin-1-yl)-2-(4-(3-(trifluoromethyl) benzamido)pyridin-2-yl)phenyl)carbamoyl)benzyl) thio)propanoic acid Scheme 51.

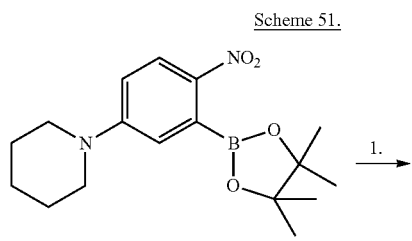

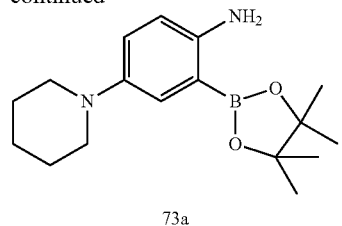

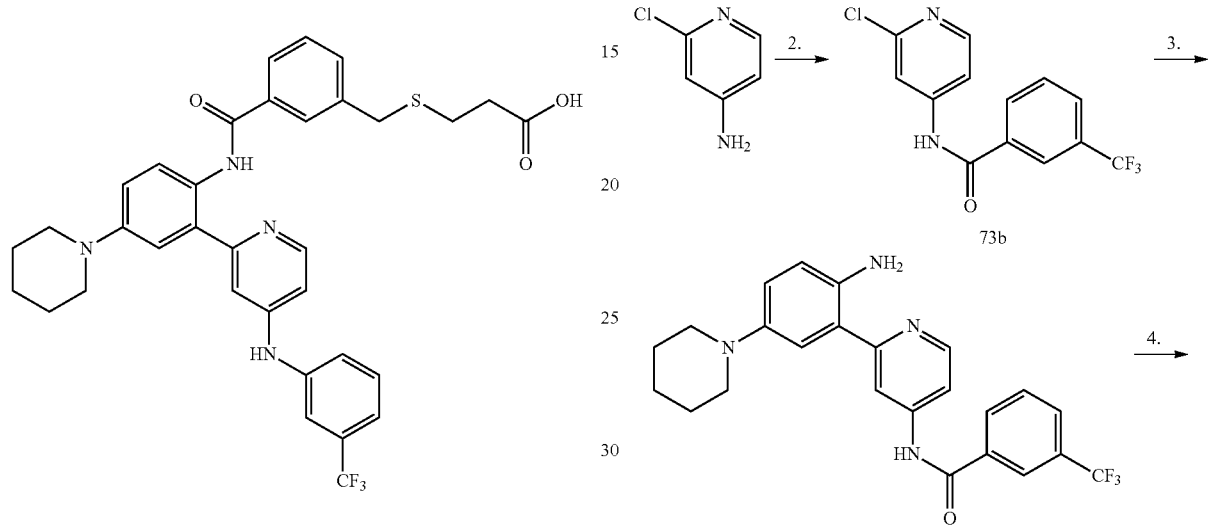

1. H2, Pd/C; 2. 3-(trifluoromethyl)benzoyl chloride; 3. Intermediate 73a, (Ph₃P)₂PdCl₂, X—PHOS, K₃PO₄;
4 DCM, DIEA, methyl 3-((3-(chlorocarbonyl)benzyl)thio)propanoate 22d;
5 LiOH•H₂O, THF/H₂O.

Intermediate 73a: 4-(piperidin-1-yl)-2-(4,4,5,5-tetramethyl-1,3,2-dioxaborolan-2-yl)-aniline Into a 50-mL round-bottom flask, was placed a solution of 1-(4-nitro-3-(4,4,5,5-tetramethyl-1,3,2-dioxaborolan-2-yl) phenyl)piperidine (600.0 mg, 1.81 mmol, 1.00 equiv) in ethyl acetate (30.0 mL), then Palladium carbon (10%) (150 mg) was added next. The gas of $H_2$ was introduced in. The resulting solution was stirred for 1 h at 0~5° C. The Pd/C was filtered out and the filtrate was collected and concentrated under vacuum. This resulted in 545.8 mg (99%) of 4-(piperidin-1-yl)-2-(4,4,5,5-tetramethyl-1,3,2-dioxaborolan-2-yl) benzenamine as a green to yellow solid. The target product was unstable, it was used to the next reaction step rapidly

Intermediate 73b: N-(2-chloropyridin-4-yl)-3-(trifluoromethyl)benzamide

Into a 100-mL round-bottom flask purged and maintained with an inert atmosphere of nitrogen, was placed a solution of 2-chloropyridin-4-amine (1.0 g, 7.78 mmol, 1.00 equiv) and N,N-Diisopropylethylamine (1.0 mL) in dichloromethane (30.0 mL). This was followed by the addition of a solution of 3-(trifluoromethyl)benzoyl chloride (2.6 g, crude) in dichloromethane (5.0 mL) dropwise with stirring at 0° C. The resulting solution was stirred for 2 h at room temperature. The resulting mixture was concentrated under vacuum. The residue was applied onto a silica gel column with ethyl acetate/petroleum ether (0~1:2). This resulted in 2.2 g (92%) of N-(2-chloropyridin-4-yl)-3-(trifluoromethyl)benzamide as a light-yellow syrup

Intermediate 73c: N-(2-(2-amino-5-(piperidin-1-yl) phenyl)pyridin-4-yl)-3-(trifluoromethyl)benzamide Into a 50-mL round-bottom flask purged and maintained with an inert atmosphere of nitrogen, was placed a solution of N-(2-chloropyridin-4-yl)-3-(trifluoromethyl)benzamide (350 mg, 1.16 mmol, 1.00 equiv), 4-(piperidin-1-yl)-2-(4,4, 5,5-tetramethyl-1,3,2-dioxaborolan-2-yl)benzenamine (430 mg, 1.42 mmol, 1.20 equiv), Pd(PPh$_3$)$_2$Cl$_2$ (81.7 mg, 0.12 mmol, 0.10 equiv), K$_3$PO$_4$.7H$_2$O (790 mg, 2.33 mmol, 2.00 equiv), X—PHOS (91.6 mg, 0.23 mmol, 0.20 equiv) in DME/H$_2$O (10:1) (30/3 mL). The resulting solution was stirred for 2 h at 80° C. The reaction progress was monitored by LCMS. The resulting mixture was concentrated under vacuum. The residual solution was diluted with 50 mL of water. The resulting solution was extracted with 2×50 mL of dichloromethane and the organic layers combined and dried over anhydrous sodium sulfate and concentrated under vacuum. The residue was applied onto a silica gel column with dichloromethane/methanol (100~100:1~40:1). This resulted in 350 mg (67%) of N-(2-(2-amino-5-(piperidin-1-yl)phenyl)pyridin-4-yl)-3-(trifluoromethyl)benzamide as a yellow solid

Intermediate 73d: methyl 3-(3-((4-(piperidin-1-yl)-2-(4-(3-(trifluoromethyl)benzamido)-pyridin-2-yl)phenyl)carbamoyl)benzylthio)propanoate Into a 50-mL round bottom flask purged and maintained with an inert atmosphere of nitrogen, was placed a solution of N-(2-(2-amino-5-(piperidin-1-yl)phenyl)pyridin-4-yl)-3-(trifluoromethyl)benzamide (100.0 mg, 0.23 mmol, 1.00 equiv) and N,N-diisopropylethylamine (0.2 mL) in dichloromethane (20 mL). This was followed by dropwise addition of a solution of methyl 3-(3-(chlorocarbonyl)benzylthio)propanoate 22d (74.0 mg, 0.27 mmol, 1.20 equiv) in dichloromethane (2.0 mL) with stirring at 0° C. The resulting solution was stirred for 2 h at room temperature. The resulting mixture was combined with the solution of the previous batch and then concentrated under vacuum. The residue was applied onto a silica gel column and eluted with dichloromethane:methanol (100~100:1~50:1). The product was obtained as 170 mg (70%) of a yellow solid.

Example 73

3-((3-((4-(piperidin-1-yl)-2-(4-(3-(trifluoromethyl) benzamido)pyridin-2-yl)-phenyl)carbamoyl)benzyl) thio)propanoic acid Into a 50-mL round bottom flask, was placed a solution of methyl 3-(3-((4-(piperidin-1-yl)-2-(4-(3-(trifluoromethyl) benzamido)pyridin-2-yl)phenyl)carbamoyl)benzylthio)propanoate (100 mg, 0.15 mmol, 1.00 equiv) and lithium hydroxide hydrate (62.0 mg, 1.48 mmol, 10.00 equiv) in tetrahydrofuran/water (1:1) (10/10 mL). The resulting solution was stirred for 2 h at room temperature. The resulting mixture was combined with the solution of the previous batch and then concentrated under vacuum. The residual solution was adjusted to pH 5~6 with 1 N acetic acid. The resulting solution was extracted with 2×30 mL of dichloromethane and the organic layers combined and dried over anhydrous sodium sulfate. The solvent was removed under vacuum. The crude product (140 mg) was purified by reverse phase HPLC eluting with a water/CH$_3$CN gradient containing 0.05% TFA. The fractions were collected and lyophilized to yield 100 mg (58%) of product as an off-white solid. $^1$H-NMR (300 MHz, DMSO-d$_6$, ppm): δ 11.29 (br, 1H), 8.79 (d, J=6.0 Hz, 1H), 8.42 (s, 1H), 8.31-8.27 (m, 2H), 8.07-7.97 (m, 2H), 7.87-7.74 (m, 3H), 7.53-7.44 (m, 3H), 7.38-7.37 (m, 1H), 3.83 (s, 2H), 3.35 (s, 4H), 2.56 (t, J=6.3 Hz, 2H), 1.74-1.61 (m, 6H). MS (ES, m/z): 663 [M+H]$^+$.

Example 74

3-((3-((2-(4-(3,4-Dimethylbenzamido)pyridin-2-yl)-4-(piperidin-1-yl)phenyl)carbamoyl)benzyl)thio) propanoic acid

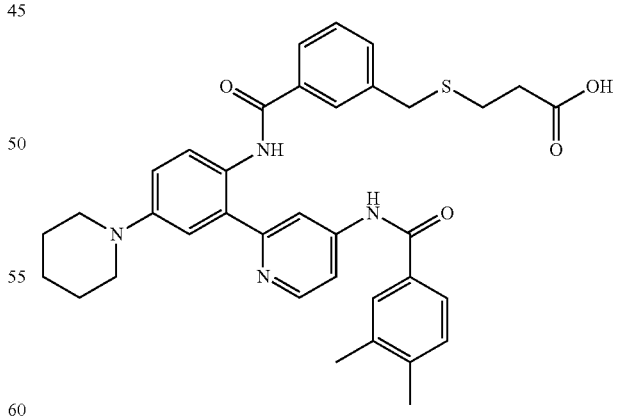

This compound was prepared by the route used to prepare 3-((3-((4-(piperidin-1-yl)-2-(4-(3-(trifluoromethyl)benzamido)pyridin-2-yl)phenyl)carbamoyl)benzyl)thio)propanoic acid 73, substituting 3,4-dimethylbenzoyl chloride for 3-(trifluoromethyl)benzoyl chloride. $^1$H-NMR (300 MHz, CD$_3$OD, ppm): δ 8.71-8.65 (m, 2H), 7.96-7.84 (m, 3H), 7.77-

7.70 (m, 3H), 7.55-7.41 (m, 4H), 7.33 (d, J=8.1 Hz, 1H), 2.63 (s, 2H), 2.60 (d, J=6.9 Hz, 4H), 2.63-2.58 (m, 2H), 2.52-2.46 (m, 2H), 2.38 (s, 6H), 1.90-1.74 (m, 6H). MS (ES, m/z): 623 [M+H]$^+$.

Example 75

2-(2-(3-((4-(2-Hydroxyethyl)-1H-1,2,3-triazol-1-yl)methyl)benzamido)-5-(piperidin-1-yl)phenyl)-N-(3-(trifluoromethyl)benzyl)isonicotinamide

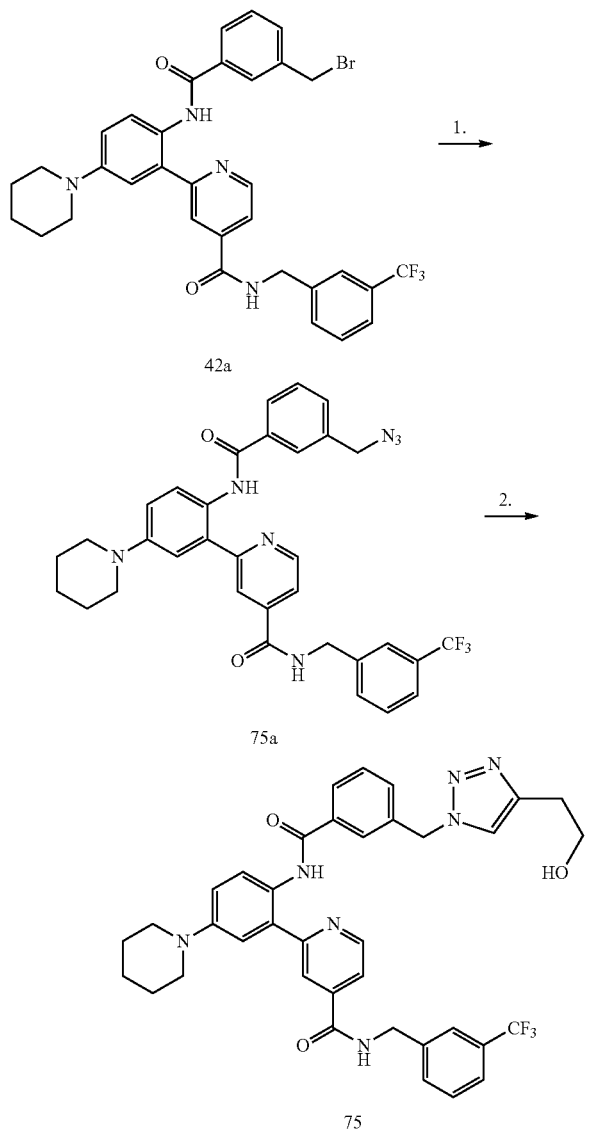

Scheme 52.

75

1. NaN$_3$, DMF; 2. CuI, DMSO, homopropargyl alcohol.

Intermediate 75a: N-(3-(trifluoromethyl)benzyl)-2-(2-(3-(azidomethyl)benzamido)-5-(piperidin-1-yl)phenyl)isonicotinamide Into a 50-mL round-bottom flask, was placed a solution of N-(3-(trifluoromethyl)benzyl)-2-(2-(3-(bromomethyl)benzamido)-5-(piperidin-1-yl)phenyl)isonicotinamide (200 mg, 0.18 mmol, 1.00 equiv, 60%) in N,N-dimethylformamide (5 mL), and NaN$_3$ (70 mg, 1.08 mmol, 5.00 equiv). The resulting solution was stirred for 2 h at 80° C. in an oil bath. The resulting solution was diluted with 25 mL of water. The resulting solution was extracted with 3×50 mL of ethyl acetate and the organic layers combined. The resulting mixture was washed with 1×50 mL of brine, dried over anhydrous sodium sulfate, and concentrated under vacuum. The residue was applied onto a silica gel column and eluted with ethyl acetate/petroleum ether (1:2). The product was obtained as 55 mg (49%) a yellow solid.

Example 75

2-(2-(3-((4-(2-hydroxyethyl)-1H-1,2,3-triazol-1-yl)methyl)benzamido)-5-(piperidin-1-yl)phenyl)-N-(3-(trifluoromethyl)benzyl)isonicotinamide Into a 50-mL round-bottom flask, was placed a solution of N-(3-(trifluoromethyl)benzyl)-2-(2-(3-(azidomethyl)benzamido)-5-(piperidin-1-yl)phenyl)isonicotinamide (55 mg, 0.09 mmol, 1.00 equiv, 95%) in DMSO (3 mL), but-3-yn-1-ol (19 mg, 0.27 mmol, 3.00 equiv), and copper(I) iodide (0.84 mg, 0.05 equiv). The resulting solution was stirred overnight at room temperature. The resulting solution was diluted with 10 mL of 10% NH$_3$.H$_2$O. The resulting solution was extracted with 5×30 mL of ethyl acetate and the organic layers combined, dried over anhydrous sodium sulfate, and concentrated under vacuum. The crude product (60 mg) was purified by reverse phase HPLC eluting with a water/CH$_3$CN gradient containing 0.05% TFA. The product was obtained as 10 mg (14%) of a yellow to green solid. $^1$H-NMR (300 MHz, DMSO-d$_6$, ppm): δ 12.48 (s, 1H), 9.55-9.58 (t, J=6 Hz, 1H), 8.93 (s, 1H), 8.36 (s, 2H), 7.96 (s, 1H), 7.85-7.96 (s, 1H), 7.71-7.77 (m, 3H) 7.64 (s, 1H), 7.55-7.60 (m, 5H), 7.44 (s, 1H), 5.67 (s, 2H), 4.63 (t, 2H), 3.58-3.61 (t, 2H), 3.40 (s, 4H), 2.75-2.77 (t, J=9 Hz, 2H), 1.61-1.78 (d, 6H). MS (ES, m/z): 684 [M+H]$^+$.

Example 76

3-((3-((4-(Piperidin-1-yl)-2-(6-((1-(3-(trifluoromethyl)phenyl)ethyl)amino)pyrimidin-4-yl)phenyl)carbamoyl)benzyl)thio)propanoic acid Scheme 53.

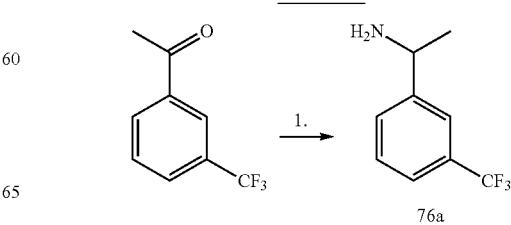

76a

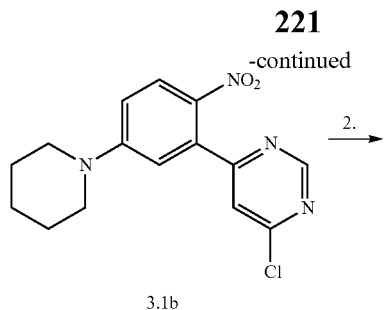

3.1b

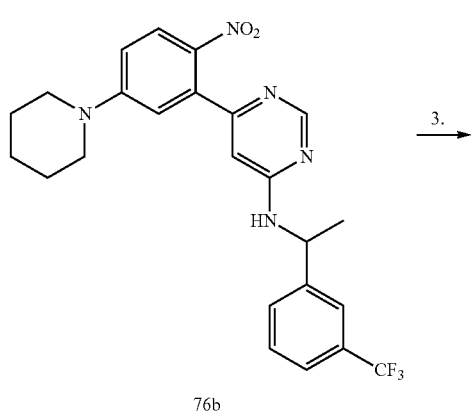

76b

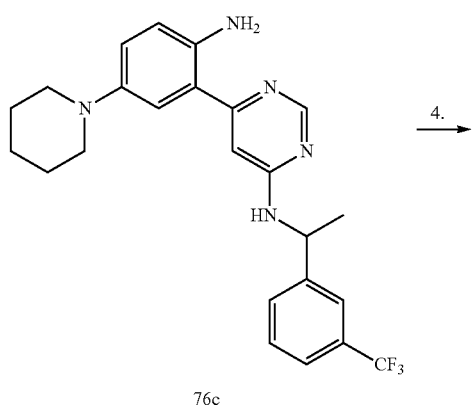

76c

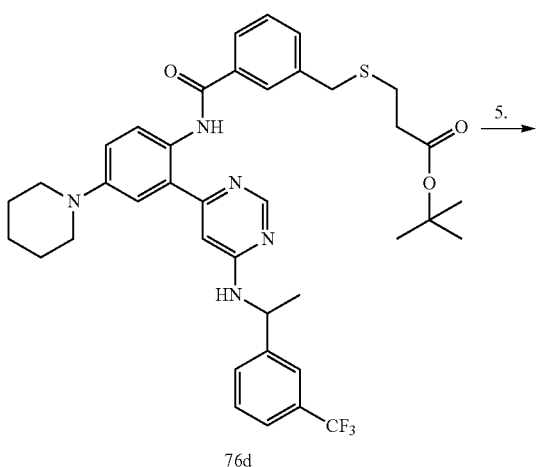

76d

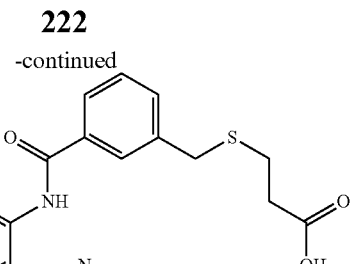

76

1. Ti[OCH(CH₃)₂]₄, NH₃, EtOH, NaBH₄; 2. Intermediate 76a, toluene, BINAP, Cs₂CO₃, Pd(dba)₃CHCl₃; 3. CH₃COOH, Zn; 4. 3-((3-tert-butoxy-3-oxopropylthio)methyl)benzoic acid 1.1c, DCM, DMAP, EDC·HCl; 5. TFA, DCM.

Intermediate 76a: 1-(3-(trifluoromethyl)phenyl)ethanamine

Into a 150 mL 3-necked round bottom flask, was placed ethanol (25 mL) NH₃ gas was added at 0° C. The mixture was stirred for 1 h at 0° C. Into a 150-mL sealed tube, was placed a solution of 1-(3-(trifluoromethyl)phenyl)ethanone (2 g, 10.64 mmol, 1.00 equiv) in ethanol (5 mL), and Ti[OCH(CH₃)₂]₄ (6.04 g, 21.13 mmol, 2.00 equiv). This was followed by the addition of the above solution of NH₃ (gas) in ethanol (25 mL). The mixture was stirred overnight at 48° C. To this was added NaBH₄ (600 mg, 15.79 mmol, 1.48 equiv). The resulting solution was stirred for 3 h at room temperature. The resulting solution was diluted with 10 mL of ammonia and the solids were filtered out. The resulting mixture was concentrated under vacuum. The residue was applied onto a silica gel column and eluted with dichloromethane/methanol (50:1). The product was obtained as 1 g (50%) of a yellow oil.

Intermediate 76b: 6-(2-nitro-5-(piperidin-1-yl)phenyl)-N-(1-(3-(trifluoromethyl)phenyl)-ethyl)pyrimidin-4-amine Into a 100 mL round bottom flask, was placed a solution of 4-chloro-6-(2-nitro-5-(piperidin-1-yl)phenyl)pyrimidine (100 mg, 0.31 mmol, 1.00 equiv) in toluene (10 mL), 1-(3-(trifluoromethyl)phenyl)ethanamine (71 mg, 0.38 mmol, 1.20 equiv), BINAP (9 mg, 0.01 mmol, 0.05 equiv), Cs₂CO₃ (144 mg, 0.44 mmol, 1.40 equiv), and Pd(dba)₃ CHCl₃ (6.5 mg, 0.01 mmol, 0.02 equiv). The resulting solution was stirred for 3 h at 120° C. The resulting mixture was concentrated under vacuum. The residue was applied onto a silica gel column and eluted with ethyl acetate/petroleum ether (1:5). The product was obtained as 80 mg (54%) of a yellow oil.

Intermediate 76c: 6-(2-amino-5-(piperidin-1-yl)phenyl)-N-(1-(3-(trifluoromethyl)phenyl)-ethyl)pyrimidin-4-amine Into a 100-mL round-bottom flask, was placed a solution of 6-(2-nitro-5-(piperidin-1-yl)phenyl)-N-(1-(3-(trifluoromethyl)phenyl)ethyl)pyrimidin-4-amine (400 mg, 0.85 mmol, 1.00 equiv) in acetic acid (5 mL). To this was added zinc (552 mg, 8.62 mmol, 10.00 equiv) in several batches at 70° C. The resulting solution was stirred for 1 h at 70° C. The solids were filtered out. The resulting mixture was concentrated under vacuum. The solution was adjusted to pH 8 with ammonia (1 mol/L). The resulting solution was extracted with 4×50 ml of ethyl acetate and the organic layers combined, dried over sodium sulfate, and concentrated under vacuum. The residue was applied onto a silica gel column and eluted with methanol:dichloromethane (1:50). The product was obtained as 200 mg (53%) of a black solid.

Intermediate 76d: tert-butyl 3-(3-(4-(piperidin-1-yl)-2-(6-(1-(3-(trifluoromethyl)phenyl)-ethylamino)pyrimidin-4-yl)phenylcarbamoyl)benzylthio)propanoate Into a 100-mL round-bottom flask, was placed a solution of 3-((3-tert-butoxy-3-oxopropylthio)methyl)benzoic acid (147 mg, 0.50 mmol, 1.10 equiv) in dichloromethane (5 mL), EDC.HCl (143 mg, 0.74 mmol, 1.50 equiv), 4-dimethylaminopyridine (92 mg, 0.71 mmol, 1.50 equiv), and 6-(2-amino-5-(piperidin-1-yl)phenyl)-N-(1-(3-(trifluoromethyl)phenyl)ethyl)pyrimidin-4-amine (200 mg, 0.45 mmol, 1.00 equiv). The resulting solution was stirred for 3 h at 30° C. The resulting mixture was concentrated under vacuum. The residue was applied onto a silica gel column and eluted with petroleum ether/ethyl acetate (5:1). The product was obtained as 100 mg (31%) of a yellow oil.

Example 76

3-(3-(4-(piperidin-1-yl)-2-(6-(1-(3-(trifluoromethyl)phenyl)ethylamino)-pyrimidin-4-yl)phenylcarbamoyl)benzylthio)propanoic acid Into a 100-mL round-bottom flask, was placed a solution of tert-butyl 3-(3-(4-(piperidin-1-yl)-2-(6-(1-(3-(trifluoromethyl)phenyl)ethylamino)pyrimidin-4-yl)phenylcarbamoyl) benzylthio)-propanoate (90 mg, 0.13 mmol, 1.00 equiv) in dichloromethane (4 mL), and 2,2,2-trifluoroacetic acid (2 mL). The resulting solution was stirred for 2 h at 30° C. The resulting mixture was concentrated under vacuum. The crude product (80 mg) was purified by reverse phase HPLC eluting with a water/CH$_3$CN gradient containing 0.05% TFA. The product was obtained as 46.1 mg (55%) of as a yellow solid. $^1$H-NMR (300 MHz, DMSO-d$_6$, ppm): δ 8.78 (s, 1H), 7.71 (m, 4H), 7.53 (m, 6H), 7.27 (m, 2H), 6.93 (s, 1H), 5.40 (s, 1H), 3.92 (s, 2H), 3.48 (m, 4H), 2.61 (m, 4H), 1.59 (m, 10H). MS (ES, m/z): 663 [M+H]$^+$.

Example 77

3-(3-(4-(piperidin-1-yl)-2-(4-(1-(3-(tri fluoromethyl)phenyl)ethylcarbamoyl)pyridin-2-yl)phenylcarbamoyl)benzylthio)propanoic acid This compound was prepared using the procedure used to prepare 3-(3-((2-(4-(((3-(trifluoromethyl)benzyl)carbamoyl)pyridin-2-yl)-4-(piperidin-1-yl)phenyl)carbamoyl)-benzylthio)propanoic acid 1.1, using 1-(3-(trifluoromethyl)phenyl)ethanamine in place of 3-(trifluoromethyl)benzylamine. $^1$H-NMR (300 MHz, CD$_3$OD, ppm): δ 9.044-9.062 (d, J=5.4 Hz, 1H), 8.786-8.816 (d, J=9.0 Hz, 1H), 8.378 (s, 1H), 8.125-8.133 (d, J=2.4 Hz, 1H), 8.003 (s, 1H), 7.875-7.905 (m, 2H), 7.707-7.754 (m, 3H), 7.499-7.623 (m, 4H), 5.324-5.393 (m, 1H), 3.913 (s, 2H), 3.678-3.714 (m, 4H), 2.709-2.754 (m, 2H), 2.574-2.618 (m, 2H), 2.043-2.060 (m, 4H), 1.831-1.846 (m, 2H), 1.641-1.664 (d, j=6.9 Hz, 3H). MS (ES, m/z): 692 [M+H]$^+$.

Example 78

3-(3-(2-(4-(4-Morpholinobenzylcarbamoyl)pyridin-2-yl)-4-(piperidin-1-yl)-phenylcarbamoyl)benzylthio)propanoic acid

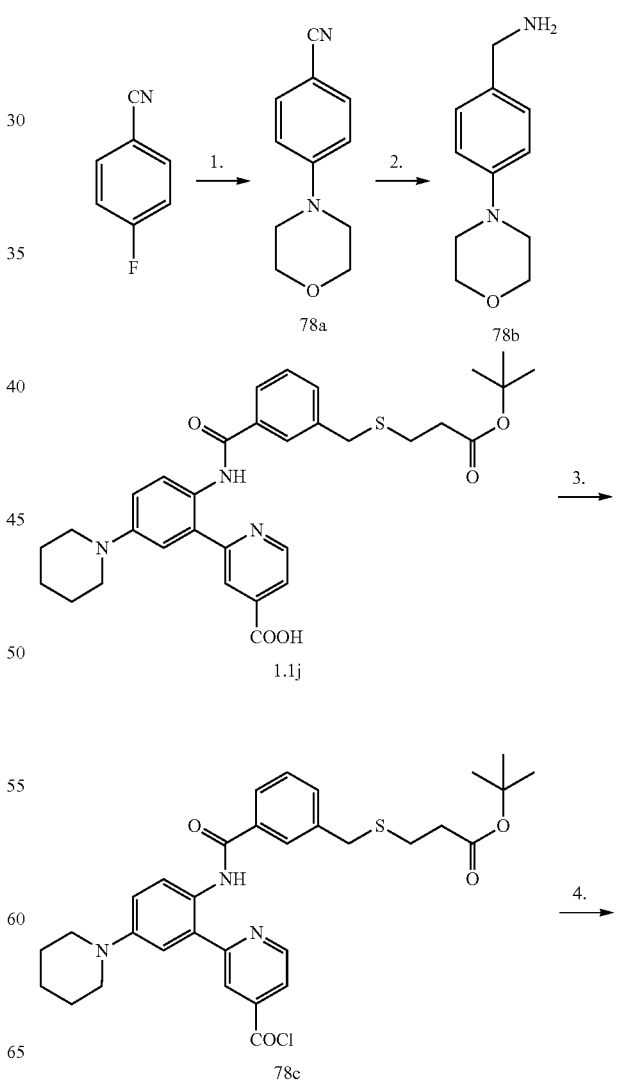

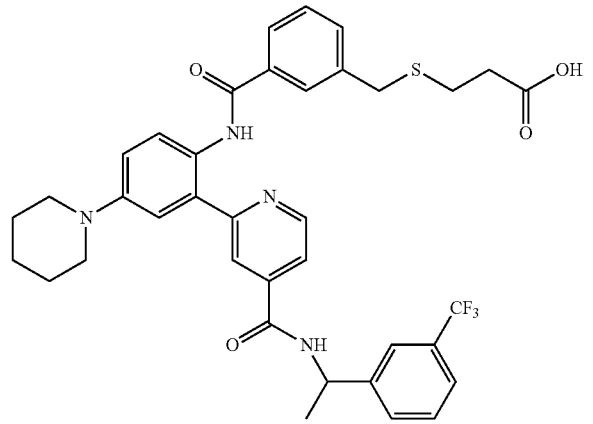 [SMILES: CC(NC(=O)c1ccnc(-c2cc(N3CCCCC3)ccc2NC(=O)c2cccc(CSCCC(=O)O)c2)c1)c1cccc(C(F)(F)F)c1]

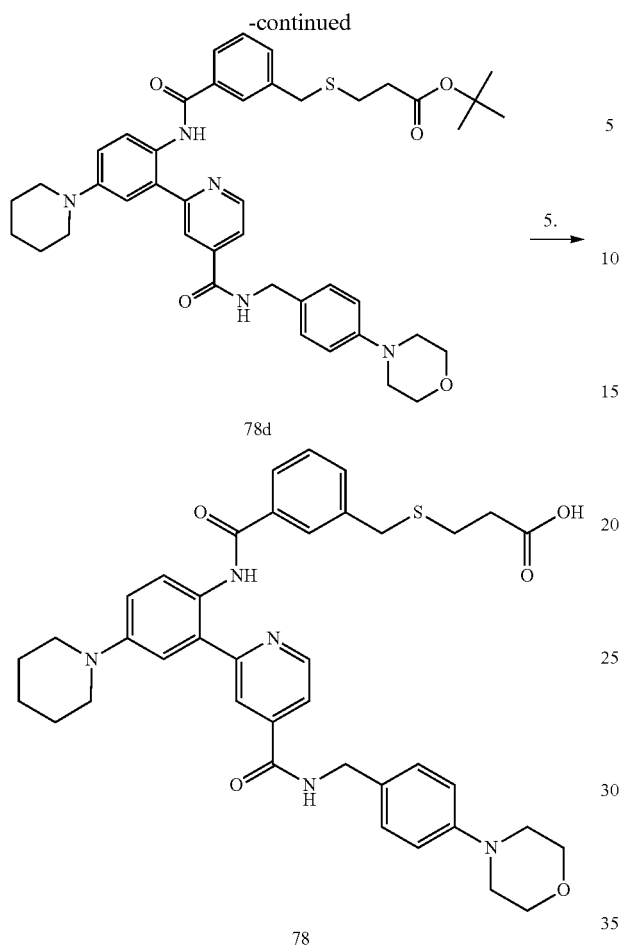

78

1. DMSO, morpholine 2. LiAlH₄, THF; 3. DCM, oxalyl chloride; 4. THF, Intermediate 78b; 5. TFA, DCM.

Intermediate 78a: 4-morpholinobenzonitrile

Into a 50-mL 3-necked round-bottom flask, was placed a solution of 4-fluorobenzonitrile (500 mg, 4.13 mmol, 1.00 equiv) in DMSO (5 mL), and morpholine (1070 mg, 12.30 mmol, 3.00 equiv). The resulting solution was stirred for 4 h at 120° C. in an oil bath. The resulting solution was diluted with 100 mL of H₂O. The solids were collected by filtration. The product was obtained as 617 mg (79%) of a yellow solid.

Intermediate 78b: (4-morpholinophenyl)methanamine

Into a 50-mL round-bottom flask purged and maintained with an inert atmosphere of nitrogen, was placed a solution of 4-morpholinobenzonitrile (200 mg, 1.06 mmol, 1.00 equiv) in tetrahydrofuran (10 mL), and LiAlH₄ (400 mg, 10.53 mmol, 10.00 equiv). The resulting solution was stirred for 3 h at 60° C. The reaction was then quenched with 1 N NaOH. The solids were removed by filtration. The resulting solution was extracted with 3×20 mL of dichloromethane and the organic layers combined, dried over NaSO₄, and concentrated under vacuum. The product was obtained as 120 mg (58%) of a yellow solid. ¹H-NMR (300 MHz, CDCl₃, ppm): δ 7.26 (m, 2H). 6.91 (m, 2H), 3.87 (m, 6H), 3.16 (m, 4H).

Intermediate 78c: tert-butyl 3-(3-(2-(4-(chloro carbonyl)pyridin-2-yl)-4-(piperidin-1-yl)phenylcarbamoyl)benzylthio)propanoate Into a 50-mL round-bottom flask purged and maintained with an inert atmosphere of nitrogen, was placed a solution of 2-(2-(3-((3-tert-butoxy-3-oxopropylthio)methyl)benzamido)-5-(piperidin-1-yl)phenyl)isonicotinic acid (170 mg, 0.30 mmol, 1.00 equiv) in dichloromethane (10 mL), and oxalyl dichloride (112 mg, 0.88 mmol, 3.00 equiv). The resulting solution was stirred for 4 h at room temperature. The resulting mixture was concentrated under vacuum to yield 200 mg of crude product a yellow solid.

Intermediate 78d: tert-butyl 3-(3-(2-(4-(4-morpholinobenzylcarbamoyl)pyridin-2-yl)-4-(piperidin-1-yl) phenylcarbamoyl)benzylthio)propanoate Into a 50-mL round-bottom flask purged and maintained with an inert atmosphere of nitrogen, was placed a solution of tert-butyl 3-(3-(2-(4-(chloro carbonyl)pyridin-2-yl)-4-(piperidin-1-yl)phenylcarbamoyl)-benzylthio)-propanoate (120 mg, 0.20 mmol, 1.00 equiv) in tetrahydrofuran (10 mL), (4-morpholinophenyl)methanamine (68 mg, 0.35 mmol, 1.50 equiv), and DIPEA (32 mg, 0.25 mmol, 3.00 equiv). The resulting solution was stirred for 4 h at room temperature. An additional 68 mg of 4-morpholinophenyl)methanamine was added. The resulting solution was stirred for an additional 2 h at room temperature. The resulting solution was diluted with 10 mL of H₂O. The resulting solution was extracted with 3×50 mL of dichloromethane and the organic layers combined. The resulting mixture was washed with 1×50 mL of brine, dried over anhydrous sodium sulfate, and concentrated under vacuum. This resulted in 200 mg of crude product as a yellow oil.

Example 78

3-(3-(2-(4-(4-morpholinobenzylcarbamoyl)pyridin-2-yl)-4-(piperidin-1-yl)-phenylcarbamoyl)benzylthio) propanoic acid Into a 50-mL round-bottom flask purged and maintained with an inert atmosphere of nitrogen, was placed a solution of tert-butyl 3-(3-(2-(4-(4-morpholinobenzylcarbamoyl)pyridin-2-yl)-4-(piperidin-1-yl)phenylcarbamoyl)-benzylthio) propanoate (170 mg, 0.20 mmol, 1.00 equiv, 86%) in dichloromethane (20 mL), and trifluoroacetic acid (2 mL). The resulting solution was stirred overnight at room temperature. The reaction progress was monitored by LCMS. The solution was adjusted to pH 7-8 with NaHCO₃ (aq). The resulting solution was extracted with 3×30 mL of dichloromethane and the organic layers combined. The resulting mixture was washed with 1×30 mL of brine, dried over NaSO₄ and concentrated under vacuum. The crude product (120 mg) was purified by reverse phase HPLC eluting with a water/CH₃CN gradient containing 0.05% TFA. The product was obtained as 17 mg (13%) of a yellow solid. ¹H-NMR (300 MHz, DMSO-d₆, ppm): δ 8.96 (s, 1H), 8.49 (m, 1H), 8.34 (s, 1H), 7.79 (m, 4H), 7.54 (m, 3H), 7.16 (m, 2H), 6.89 (m, 2H), 4.42 (s, 2H), 3.86 (s, 2H), 3.70 (m, 5H), 3.49 (s, 4H), 3.04 (m, 4H), 2.60 (m, 2H), 1.78 (m, 6H). MS (ES, m/z): 694 [M+H]$^+$.

Example 79

3-(3-((2-(4-((4-(1H-Pyrazol-1-yl)benzyl)carbamoyl)pyridin-2-yl)-4-(piperidin-1-yl)phenyl)carbamoyl)benzylthio)propanoic acid

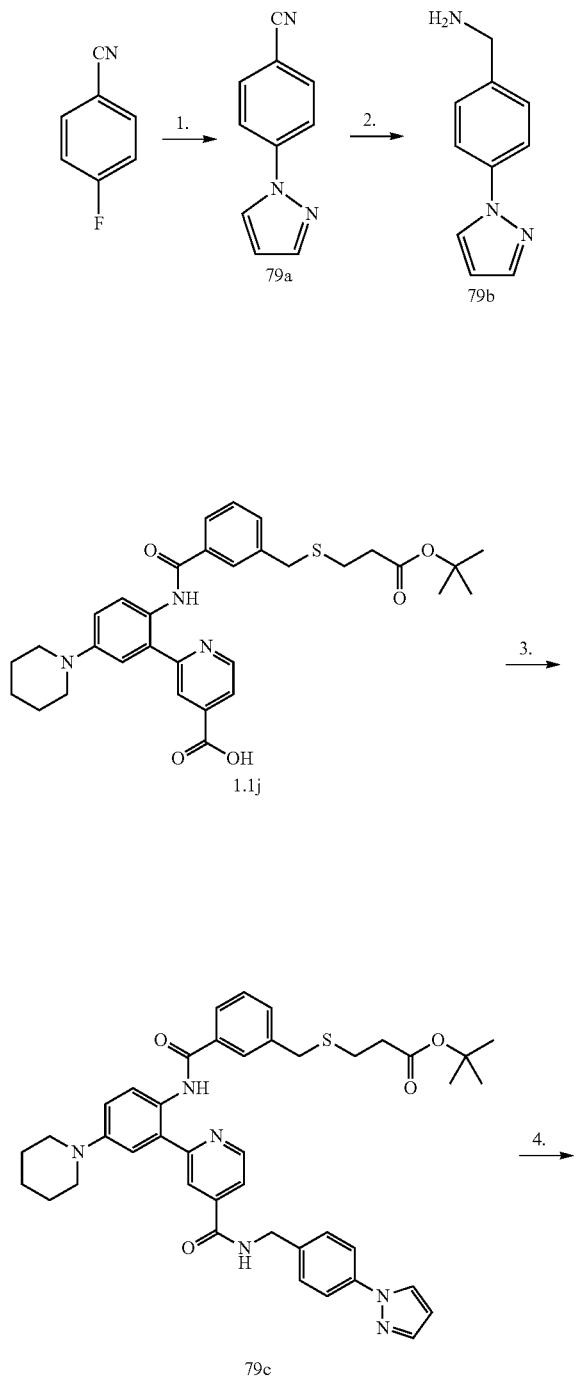

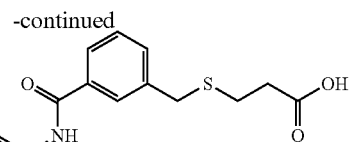

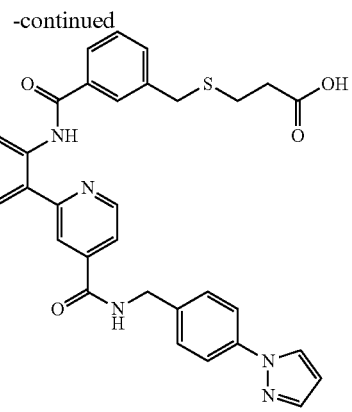

1. DMF, NaOH, 1H-pyrazole; 2. LiAlH$_4$, THF; 3. EDC•HCL, DMAP, DCM, intermediate 79b; 4. TFA, DCM.

Intermediate 79a: 4-(1H-pyrazol-1-yl)benzonitrile

Into a 50-mL 3-necked round-bottom flask purged and maintained with an inert atmosphere of nitrogen, was placed 1H-pyrazole (422 mg, 6.21 mmol, 1.50 equiv), sodium hydroxide (248 mg, 6.20 mmol, 1.50 equiv), and N,N-dimethylformamide (20 mL). The mixture was stirred and heated to 80° C. for 30 min, then to this was added 4-fluorobenzonitrile (500 mg, 4.13 mmol, 1.00 equiv). The resulting solution was stirred for 3 h at 110° C. in an oil bath. The resulting solution was diluted with 50 mL of H$_2$O. The solids were collected by filtration and dried in an oven. The product was obtained as 0.43 g (62%) of a white solid.

Intermediate 79b: (4-(1H-pyrazol-1-yl)phenyl)methanamine

Into a 50-mL 3-necked round-bottom flask purged and maintained with an inert atmosphere of nitrogen, was placed tetrahydrofuran (15 mL). This was followed by dropwise addition of a 4-(1H-pyrazol-1-yl)benzonitrile (250 mg, 1.48 mmol, 1.00 equiv) in tetrahydrofuran (5 mL) with stirring at 0° C. To this was added LiAlH$_4$ (337 mg, 8.87 mmol, 6.00 equiv). The resulting solution was stirred for 3 h at room temperature. The reaction was then quenched by the addition of NaOH (15%, aq). The resulting solution was extracted with 3×50 mL of dichloromethane and the organic layers were combined, dried over anhydrous sodium sulfate, and concentrated under vacuum. The product was obtained as 0.251 mg of a white crude solid.

Intermediate 79c: tert-butyl 3-(3-((2-(4-((4-(1H-pyrazol-1-yl)benzyl)carbamoyl)pyridin-2-yl)-4-(piperidin-1-yl)phenyl)carbamoyl)benzylthio)propanoate Into a 50-mL 3-necked round-bottom flask, was placed 2-(2-(3-((3-tert-butoxy-3-oxopropylthio) methyl)benzamido)-5-(piperidin-1-yl)phenyl)isonicotinic acid (125 mg, 0.22 mmol, 1.00 equiv), (4-(1H-pyrazol-1-yl)phenyl)methanamine (41 mg, 0.24 mmol, 1.10 equiv), EDC.HCl (62 mg, 0.32 mmol, 1.50 equiv), 4-dimethylaminopyridine (40 mg, 0.33 mmol, 1.51 equiv), and dichloromethane (15 mL). The resulting solution was stirred overnight at room temperature. The resulting solution was extracted with 40 mL of dichloromethane and the organic layers combined. The resulting mixture was washed with 2×15 mL of H$_2$O. The mixture was

Example 79

3-(3-((2-(4-((4-(1H-pyrazol-1-yl)benzyl)carbamoyl)pyridin-2-yl)-4-(piperidin-1-yl)phenyl)carbamoyl)benzylthio)propanoic acid Into a 50-mL 3-necked round bottom flask, was placed tert-butyl 3-(3-((2-(4-((4-(1H-pyrazol-1-yl)benzyl)carbamoyl)pyridin-2-yl)-4-(piperidin-1-yl)phenyl)carbamoyl)benzylthio)-propanoate (130 mg, 0.18 mmol, 1.00 equiv), and dichloromethane (2 mL). This was followed by dropwise addition of trifluoroacetic acid (3 mL) with stirring. The resulting solution was stirred for 60 min at room temperature. The solution was adjusted to pH 7 with sodium bicarbonate (aq). The resulting solution was diluted with 30 mL of dichloromethane and washed with 2×10 mL of $H_2O$. The mixture was dried over anhydrous sodium sulfate and concentrated under vacuum. The crude product (300 mg) was purified by reverse phase HPLC eluting with a water/$CH_3CN$ gradient containing 0.05% TFA. The product was obtained as 86.9 mg (72%) of a yellow solid. $^1$H-NMR: (300 MHz, DMSO-$d_6$+$D_2O$, ppm): δ 1.63 (m, 2H), 1.82 (m, 4H), 2.58-2.62 (m, 4H), 3.47 (t, 4H), 3.87 (s, 2H), 4.56 (d, 2H), 6.53 (s, 1H), 7.44-7.54 (m, 4H), 7.72-7.79 (m, 3H), 7.87-7.89 (m, 2H), 8.36 (s, 1H), 8.42 (s, 1H), 8.99 (d, 1H), 9.53 (s, 1H), 11.97 (s, 1H). MS (ES, m/z): 675 [M+H]$^+$.

Example 80

N1-Methyl-N1-(2-morpholinoethyl)-N3-(4-(piperidin-1-yl)-2-(4-((3-(trifluoromethyl)benzyl)carbamoyl)pyridin-2-yl)phenyl)isophthalamide

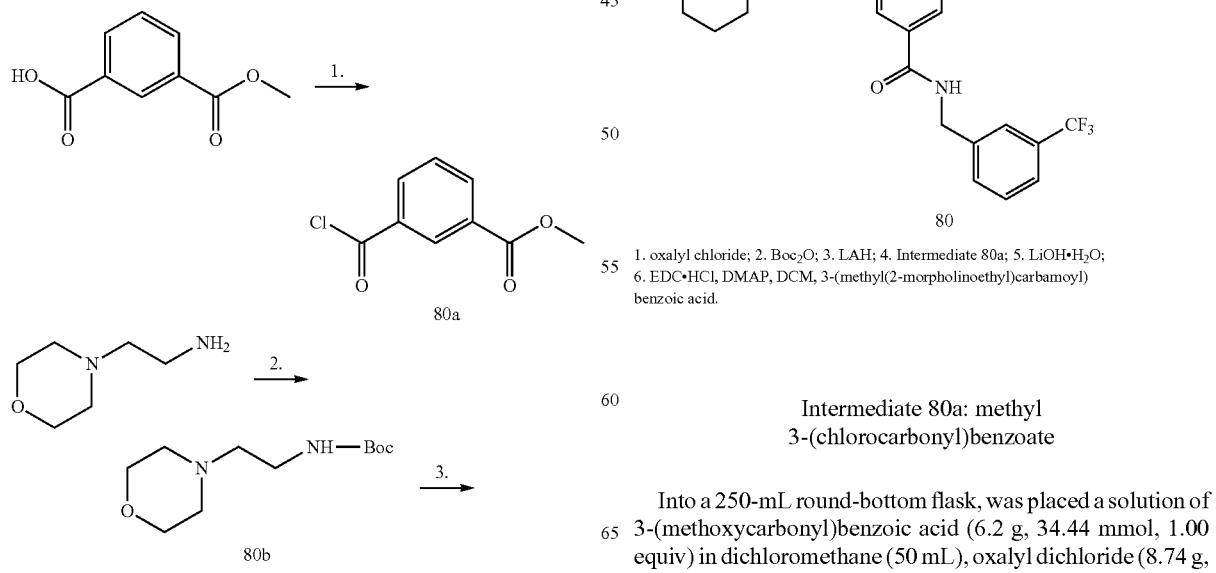

1. oxalyl chloride; 2. Boc$_2$O; 3. LAH; 4. Intermediate 80a; 5. LiOH•H$_2$O; 6. EDC•HCl, DMAP, DCM, 3-(methyl(2-morpholinoethyl)carbamoyl)benzoic acid.

Intermediate 80a: methyl 3-(chlorocarbonyl)benzoate

Into a 250-mL round-bottom flask, was placed a solution of 3-(methoxycarbonyl)benzoic acid (6.2 g, 34.44 mmol, 1.00 equiv) in dichloromethane (50 mL), oxalyl dichloride (8.74 g, 69.37 mmol, 2.00 equiv), and N,N-dimethylformamide (cat.).

The resulting solution was stirred for 1 h at 40° C. in an oil bath. The resulting mixture was concentrated under vacuum. This resulted in 6.6 g (87%) of methyl 3-(chlorocarbonyl) benzoate as brown oil Intermediate 80b: tert-butyl (2-morpholinoethyl)carbamate Into a 250-mL round-bottom flask, was placed a solution of 2-morpholinoethanamine (10 g, 76.92 mmol, 1.00 equiv) in dichloromethane (50 mL). To this was added triethylamine (5.83 g, 57.72 mmol, 0.50 equiv). This was followed by the addition of di-tert-butyl dicarbonate (18.44 g, 84.59 mmol, 1.10 equiv) at 0-5° C. The resulting solution was stirred overnight at 25° C. The resulting solution was diluted with 200 mL of dichloromethane. The resulting mixture was washed with 1×30 mL of 10% sodium bicarbonate and 1×30 mL of brine. The mixture was dried over sodium sulfate and concentrated under vacuum. This resulted in 16 g (81%) of tert-butyl 2-morpholinoethylcarbamate as an off-white solid.

Intermediate 80c: N-methyl-2-morpholinoethanamine

Into a 250-mL 3-necked round-bottom flask, was placed a solution of LiAlH$_4$ (7.72 g, 208.65 mmol, 3.00 equiv) in tetrahydrofuran (60 mL). This was followed by the addition of a solution of tert-butyl 2-morpholinoethylcarbamate (16 g, 62.61 mmol, 1.00 equiv, 90%) in tetrahydrofuran (40 mL) dropwise with stirring at 0-5° C. The resulting solution was stirred for 2 h at 70° C. in a oil bath. The reaction was then quenched by the addition of 7.7 mL of water, 7.7 mL of 15% sodium hydroxide, and 23.1 mL of water. The solids were filtered out. The mixture was dried over sodium sulfate and concentrated under vacuum. The residue was applied onto a silica gel column and eluted with dichloromethane:methanol (0.5% triethylamine) (20:1). This resulted in 4.2 g (42%) of N-methyl-2-morpholinoethanamine as brown oil.

Intermediate 80d: methyl 3-(methyl(2-morpholinoethyl)carbamoyl)benzoate

Into a 100-mL round-bottom flask, was placed a solution of N-methyl-2-morpholinoethanamine (2.1 g, 13.12 mmol, 1.00 equiv, 90%) in dichloromethane (20 mL), and triethylamine (1.47 g, 14.55 mmol, 1.00 equiv). This was followed by the addition of a solution of methyl 3-(chlorocarbonyl)benzoate (3.3 g, 15.00 mmol, 1.20 equiv, 90%) in dichloromethane (10 mL) dropwise with stirring at 0-5° C. The resulting solution was stirred for 3 h at room temperature. The resulting solution was diluted with 100 mL of dichloromethane. The resulting mixture was washed with 1×30 mL of 10% sodium bicarbonate. The resulting mixture was washed with 1×30 mL of brine. The mixture was dried over sodium sulfate and concentrated under vacuum. The residue was applied onto a silica gel column with dichloromethane:methanol (20:1). This resulted in 4.4 g (99%) of methyl 3-(methyl(2-morpholinoethyl)carbamoyl)benzoate as a brown solid.

Intermediate 80e: 3-(methyl(2-morpholinoethyl)carbamoyl)benzoic acid

Into a 100-mL round-bottom flask, was placed a solution of methyl 3-(methyl(2-morpholinoethyl)carbamoyl)benzoate (4.4 g, 13.66 mmol, 1.00 equiv, 95%) in tetrahydrofuran/water (15/10 mL), and lithium hydroxide hydrate (1.77 g, 43.17 mmol, 3.00 equiv). The resulting solution was stirred for 1 h at 25° C. The resulting mixture was concentrated under vacuum. The resulting solution was diluted with 10 mL of water and adjusted to pH 2-3 with hydrochloric acid. The resulting mixture was washed with 2×30 mL of ethyl acetate. The aqueous layers were concentrated under vacuum. The residue was applied onto a silica gel column and eluted with ethyl acetate:methanol (4:1). This resulted in 2.7 g (65%) of 3-(methyl(2-morpholinoethyl)carbamoyl)benzoic acid as a white solid. $^1$H-NMR (300 MHz, CD$_3$OD, ppm): δ 8.17 (m, 2H), 7.78 (m, 1H), 7.61 (m, 1H), 3.98 (m, 6H), 3.56 (m, 5H), 3.47 (m, 1H), 3.10 (s, 3H). MS (ES, m/z): 293 [M+H]$^+$.

Example 80

N1-(2-(4-((3-(trifluoromethyl)benzyl)carbamoyl) pyridin-2-yl)-4-(piperidin-1-yl)phenyl)-N3-methyl-N3-(2-morpholinoethyl)isophthalamide hydrochloride Into a 250-mL round bottom flask, was placed a solution of N-(3-(trifluoromethyl)benzyl)-2-(2-amino-5-(piperidin-1-yl)phenyl)isonicotinamide (1 g, 2.09 mmol, 1.00 equiv, 95%) in dichloromethane (30 mL), 3-(methyl(2-morpholinoethyl) carbamoyl)benzoic acid (960 mg, 3.12 mmol, 1.50 equiv, 95%), EDC.HCl (840 mg, 4.38 mmol, 2.00 equiv), and 4-dimethylaminopyridine (540 mg, 4.43 mmol, 2.00 equiv). The resulting solution was stirred for 3 h at 25° C. The resulting solution was diluted with 200 mL of ethyl acetate. The resulting mixture was washed with 2×30 mL of NH$_4$Cl (aq), 1×30 mL of 10% sodium bicarbonate, and 1×30 mL of brine. The mixture was dried over sodium sulfate and concentrated under vacuum. The residue was applied onto a silica gel column and eluted with ethyl acetate:methanol (20:1). This resulted in 1.30 g of N1-(2-(4-((3-(trifluoromethyl)benzyl)carbamoyl)pyridin-2-yl)-4-(piperidin-1-yl)phenyl)-N3-methyl-N3-(2-morpholinoethyl)isophthalamide as a brown oil. The brown oil was dissolved in 40 mL of methanol. HCl gas was added at 0° C. The mixture was stirred for 20 min at 0° C. The mixture was concentrated under vacuum. The product was obtained as 1.40 g (86%) of a yellow solid. $^1$H-NMR (300 MHz, DMSO-d$_6$+D$_2$O, ppm): δ 9.96 (m, 1H), 8.94 (d, J=6 Hz, 1H), 8.59 (m, 2H), 8.49 (s, 1H), 7.93-8.07 (m, 2H), 7.87-8.03 (m, 2H), 7.54-7.80 (m, 7H), 4.59 (s, 2H), 4.12 (m, 1H), 3.99-4.03 (m, 2H), 3.88 (m, 2H), 3.76-3.79 (m, 2H), 3.58 (m, 2H), 3.43 (m, 2H), 3.15-3.17 (m, 3H), 2.96 (s, 3H), 1.97 (m, 4H), 1.71 (m, 2H). MS (ES, m/z): 729 [M+H]$^+$.

Example 81

N1-(2-(4-Acetylpiperazin-1-yl)ethyl)-N1-methyl-N3-(4-(piperidin-1-yl)-2-(4-(3-(trifluoromethyl)benzylcarbamoyl)pyridin-2-yl)phenyl)isophthalamide

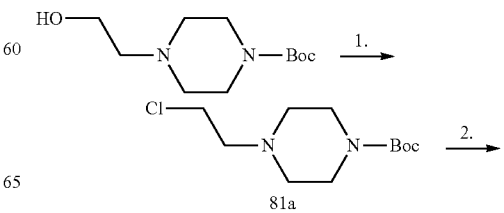

Scheme 57.

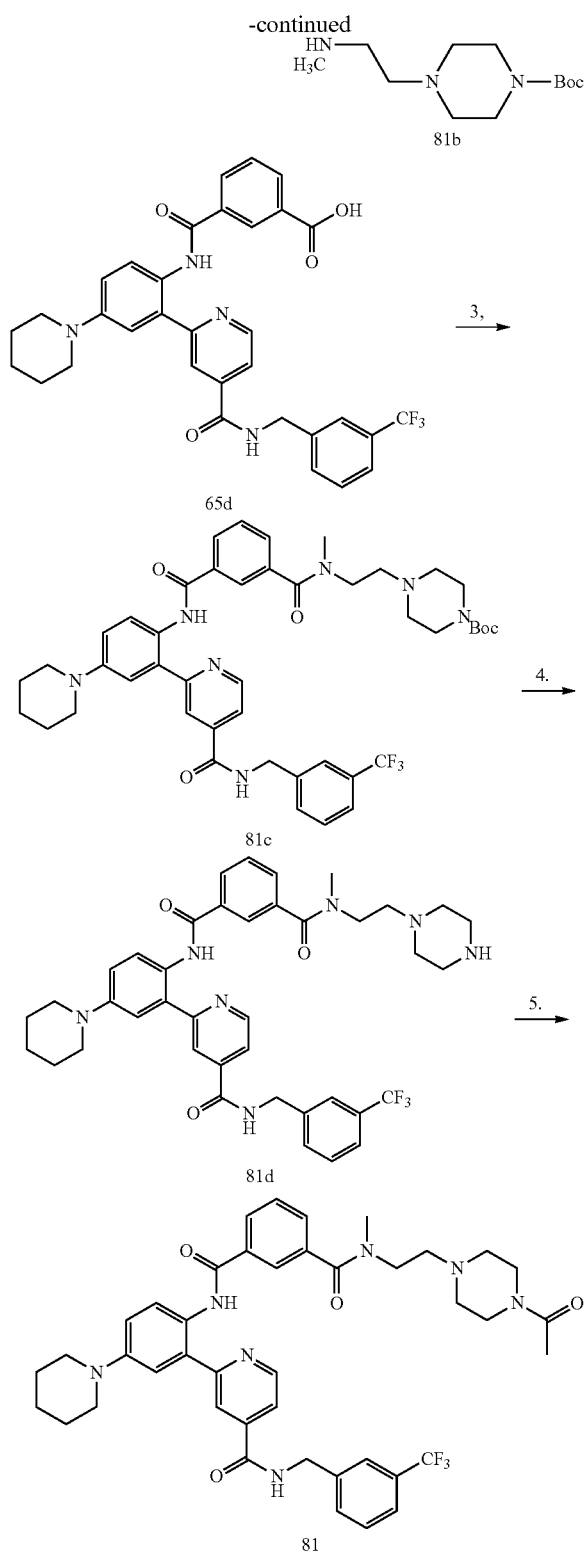

1. SOCl₂; 2. MeNH₂; 3. NaHCO₃, then Et₃N, DCM; 4. TFA; 5. AcCl

Intermediate 81a: tert-butyl
4-(2-chloroethyl)piperazine-1-carboxylate

Into a 50-mL round-bottom flask, was placed a solution of tert-butyl 4-(2-hydroxyethyl)piperazine-1-carboxylate (2.31 g, 10.03 mmol, 1.00 equiv) in dichloromethane (20 mL) and a solution of thionyl chloride (1.5 mL, 2.00 equiv) in dichloromethane (3 mL) was added dropwise under ice-bath. The resulting solution was stirred overnight at 25° C. The resulting mixture was concentrated under vacuum. The resulting solution was diluted with 10 mL of water. The resulting solution was extracted with 2×25 mL of ethyl acetate and the organic layers combined. The resulting mixture was washed with 2×15 mL of sodium bicarbonate aq. and 2×10 mL of brine. The mixture was dried over anhydrous sodium sulfate and concentrated under vacuum. The residue was applied onto a silica gel column with ethyl acetate/petroleum ether (1:5). This resulted in 1.16 g (46%) of tert-butyl 4-(2-chloroethyl)piperazine-1-carboxylate as a off-white solid Intermediate 81b: tert-butyl
4-(2-(methylamino)ethyl)piperazine-1-carboxylate Into a 50-mL sealed tube, was placed tert-butyl 4-(2-chloroethyl)piperazine-1-carboxylate (300 mg, 1.21 mmol, 1.00 equiv), methanamine (in ethanol) (10 mL), NaI (100 mg). The resulting solution was stirred for 12 h at 70° C. in an oil bath. The resulting mixture was concentrated under vacuum. The resulting solution was diluted with 3 mL of water. The pH value of the solution was adjusted to 7-8 with sodium bicarbonate (5%). The resulting solution was extracted with 2×5 mL of dichloromethane and the organic layers combined. The resulting mixture was washed with 1×3 mL of water and 1×3 mL of brine. The resulting mixture was concentrated under vacuum. This resulted in 180 mg (crude) of tert-butyl 4-(2-(methylamino)ethyl)piperazine-1-carboxylate as brown oil Intermediate 81c: tert-butyl 4-(2-(N-methyl-3-((4-(piperidin-1-yl)-2-(4-((3-(trifluoromethyl)benzyl)carbamoyl)pyridin-2-yl)phenyl)carbamoyl)benzamido)ethyl)-piperazine-1-carboxylate Into a 50-mL round-bottom flask, was placed a solution of 3-(4-(piperidin-1-yl)-2-(4-(3-(trifluoromethyl)benzylcarbamoyl)pyridin-2-yl)phenylcarbamoyl)-benzoic acid (100 mg, 0.17 mmol, 1.00 equiv) in dichloromethane (5 mL), EDC.HCl (48 mg, 0.25 mmol, 1.50 equiv), 4-dimethylaminopyridine (31 mg, 0.25 mmol, 1.50 equiv). The mixture was stirred for 5 min at room temperature. To the above was added tert-butyl 4-(2-(methylamino)ethyl)piperazine-1-carboxylate (53 mg, 0.22 mmol, 1.30 equiv). The resulting solution was stirred for 2 h at 25° C. The resulting solution was diluted with 5 mL of water. The resulting solution was extracted with 2×5 mL of dichloromethane and the organic layers combined. The resulting mixture was washed with 1×5 mL of water and 2×5 mL of brine. The mixture was dried over anhydrous sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, WATER WITH 0.05% TFA and CH₃CN (25% CH₃CN up to 45% in 6 min); Detector, Waters2545 UvDector 254&220 nm. 33.6 mg product was obtained. This resulted in 33.6 mg (21%) of PH-RDX-002-1129-0 as a light yellow solid. MS (ES, m/z): 828 [M−+H]⁺. H-NMR (300 MHz, CD₃OD, ppm) 8.98 (d, J=5.1 Hz, 1H), 8.75 (d, J=9.0 Hz, 1H), 8.46 (s, 1H), 8.18~8.11 (m, 3H), 7.89~7.53 (m, 8H), 4.72 (s, 2H), 4.00~3.11 (m, 16H), 3.08 (s, 3H), 2.04 (d, J=4.8 Hz, 4H), 1.83 (d, J=5.7 Hz, 2H), 1.49 (s, 9H)

Intermediate 81d: N1-(2-(4-((3-(trifluoromethyl)benzyl)carbamoyl)pyridin-2-yl)-4-(piperidin-1-yl)phenyl)-N3-methyl-N3-(2-(piperazin-1-yl)ethyl)isophthalamide Compound 81c was dissolved in 1:1 dichloromethane/TFA and stirred for 1 hour. The solvent was evaporated and 250 mg of the residue was placed into a 50-mL round bottom flask with a saturated aqueous solution of sodium bicarbonate aq. (10 mL). The mixture was stirred for 20 minutes at room temperature. The resulting solution was extracted with 3×10 mL of ethyl acetate and the organic layers combined. The mixture was dried over anhydrous sodium sulfate and concentrated under vacuum to yield 150 mg of product.

Example 81

N1-(2-(4-acetylpiperazin-1-yl)ethyl)-N1-methyl-N3-(4-(piperidin-1-yl)-2-(4-(3-(trifluoromethyl)benzyl-carbamoyl)pyridin-2-yl)phenyl)isophthalamide Into a 50-mL round-bottom flask, was placed a solution of N1-methyl-N1-(2-(piperazin-1-yl)ethyl)-N3-(4-(piperidin-1-yl)-2-(4-(3-(trifluoromethyl)benzylcarbamoyl)pyridin-2-yl)phenyl)-isophthalamide (150 mg, 0.21 mmol, 1.00 equiv) in dichloromethane (3 mL), and triethylamine (63 mg, 0.62 mmol, 3.00 equiv). This was followed by dropwise addition of acetyl chloride (25 mg, 0.32 mmol, 1.50 equiv) with stirring at 0° C. The resulting solution was stirred for 2 h at 25° C. The reaction was then quenched with 3 mL of water. The resulting solution was extracted with 2×5 mL of dichloromethane and the organic layers combined. The resulting mixture was washed with 1×5 mL of sodium bicarbonate and 2×5 mL of brine. The mixture was dried over anhydrous sodium sulfate and concentrated under vacuum. The crude product (130 mg) was purified by reverse phase HPLC eluting with a water/CH$_3$CN gradient containing 0.05% TFA. The product was obtained as 56.5 mg (38%) of a light yellow solid. $^1$H-NMR (300 MHz, CD$_3$OD, ppm): δ 8.96 (d, J=5.1 Hz, 1H), 8.70 (d, J=9.0 Hz, 1H), 8.43 (s, 1H), 8.16~8.08 (m, 3H), 7.87~7.86 (m, 1H), 7.79~7.56 (m, 7H), 4.71 (s, 2H), 4.00~3.89 (m, 5H), 3.63~3.52 (m, 1H), 3.23 (s, 3H), 2.17 (s, 3H), 2.01 (s, 1H), 1.81 (d, J=4.8 Hz, 1H). MS (ES, m/z): 770 [M+H]$^+$.

Example 82

N1-Methyl-N1-(2-(4-methylpiperazin-1-yl)ethyl)-N3-(4-(piperidin-1-yl)-2-(4-((3-(trifluoromethyl)benzyl)carbamoyl)pyridin-2-yl)phenyl)isophthalamide

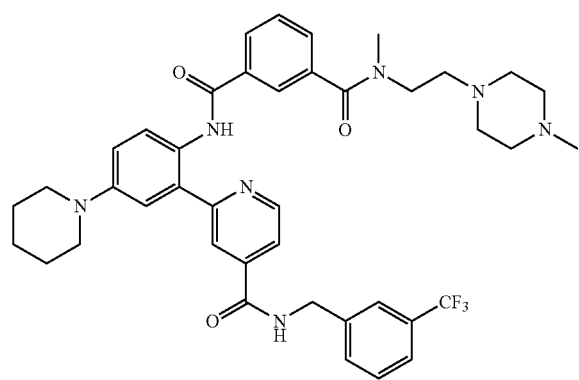 [SMILES: CN1CCN(CCN(C)C(=O)c2cccc(C(=O)Nc3ccc(N4CCCCC4)cc3-c3cc(C(=O)NCc4cccc(C(F)(F)F)c4)ccn3)c2)CC1]

Into a 50-mL round bottom flask, was placed a solution of N1-methyl-N1-(2-(piperazin-1-yl)ethyl)-N3-(4-(piperidin-1-yl)-2-(4-(3-(trifluoromethyl)benzylcarbamoyl)pyridin-2-yl)phenyl)isophthalamide (150 mg, 0.21 mmol, 1.00 equiv) in HCHO (in water) (6 mL), NaBH$_3$CN (15 mg, 1.10 equiv), and acetic acid (5 drops). The resulting solution was stirred for 2 h at 25° C. The resulting solution was diluted with 5 mL of sodium bicarbonate, extracted with 2×5 mL of dichloromethane, and the organic layers combined. The resulting mixture was washed with 1×5 mL of water and 1×5 mL of brine. The mixture was dried over anhydrous sodium sulfate and concentrated under vacuum. The crude product (80 mg) was purified by reverse phase HPLC eluting with a water/CH$_3$CN gradient containing 0.05% TFA. The product was obtained as 13.3 mg (9%) of a light yellow solid. $^1$H-NMR (300 MHz, CD$_3$OD, ppm): δ 8.96 (d, J=5.1 Hz, 1H), 8.76 (d, J=9.3 Hz, 1H), 8.45 (s, 1H), 8.15 (s, 1H), 8.05 (s, 2H), 7.89~7.87 (m, 1H), 7.71~7.62 (m, 5H), 7.59~7.56 (m, 2H), 4.72 (s, 2H), 3.79 (s, 2H), 3.66 (d, J=5.1 Hz, 4H), 3.50~3.34 (m, 2H), 3.15~3.04 (m, 6H), 2.89~2.85 (m, 6H), 2.80~2.60 (m, 2H), 2.04 (d, J=4.5 Hz, 4H), 1.83 (d, J=5.4 Hz, 2H). MS (ES, m/z): 742 [M+H]$^+$.

Example 83

N1-methyl-N1-(2-(4-(methylsulfonyl)piperazin-1-yl)ethyl)-N3-(4-(piperidin-1-yl)-2-(4-(3-(trifluoromethyl)benzylcarbamoyl)pyridin-2-yl)phenyl)isophthalamide

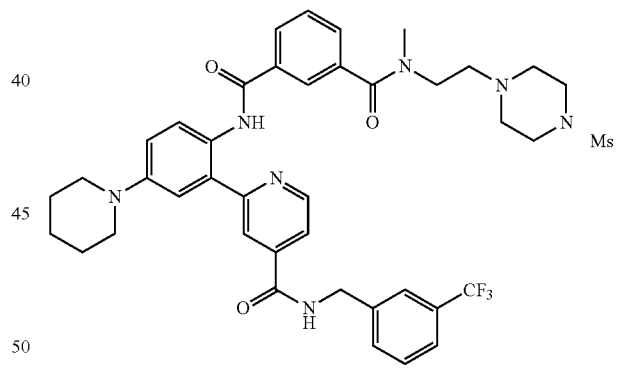

Into a 50-mL round-bottom flask, was placed a solution of N1-methyl-N1-(2-(piperazin-1-yl)ethyl)-N3-(4-(piperidin-1-yl)-2-(4-(3-(trifluoromethyl)benzylcarbamoyl)pyridin-2-yl)phenyl)isophthalamide (100 mg, 0.14 mmol, 1.00 equiv) in dichloromethane (3 mL), triethylamine (42 mg, 0.42 mmol, 3.00 equiv), and methanesulfonyl chloride (17 mg, 0.15 mmol, 1.05 equiv). The resulting solution was stirred for 40 min at 25° C. The reaction was then quenched by the addition of 3 mL of water. The resulting solution was extracted with 2×5 mL of dichloromethane and the organic layers combined. The resulting mixture was washed with 1×5 mL of water and 1×5 mL of brine. The mixture was dried over anhydrous sodium sulfate and concentrated under vacuum.

The crude product (90 mg) was purified by reverse phase HPLC eluting with a water/CH$_3$CN gradient containing 0.05% TFA. The product was obtained as 55.8 mg (50%) of a light yellow solid. $^1$H-NMR (300 MHz, CD$_3$OD, ppm): δ8.97 (d, J=5.1 Hz, 1H), 8.764 (d, J=9.0 Hz, 1H), 8.45 (s, 1H), 8.16~8.10 (m, 3H), 7.89~7.87 (m, 1H), 7.80 (d, J=7.5 Hz, 1H), 7.72~7.67 (m, 4H), 7.62~7.53 (m, 2H), 4.72 (s, 2H), 4.00 (s, 2H), 3.68~3.55 (m, 14H), 3.11 (s, 3H), 2.96 (s, 3H), 2.04 (d, J=4.8 Hz, 1H), 1.83 (d, J=5.1 Hz, 1H). MS (ES, m/z): 806 [M+H]$^+$.

Examples 84 Through 119

The compounds listed in Table 6 were prepared by the procedures disclosed above as typified in Example 1.1 (Method 1), Example 8.1 (Method 2), Example 5.1 (Method 3), Example 71 (Method 4), Example 25 (Method 5), Example 37 (Method 6), Example 26 (Method 7), Example 4.22 (Method 8) or Example 8.25 (Method 9). Mass spectral data (ES, positive ion mode) is provided for each compound.

TABLE 6

| Method | Example No. | Structure | Mass Spectrum |
|---|---|---|---|
| 1 | 84 | 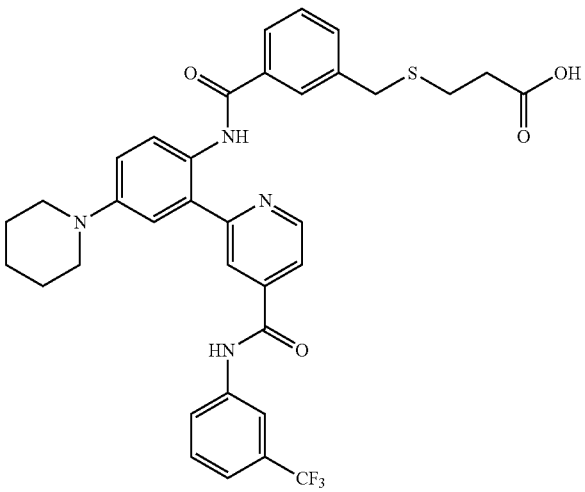 [SMILES: O=C(O)CCSCc1cccc(C(=O)Nc2ccc(N3CCCCC3)cc2-c2cc(C(=O)Nc3cccc(C(F)(F)F)c3)ccn2)c1] | 663.3 [M + H] |
| 1 | 85 | 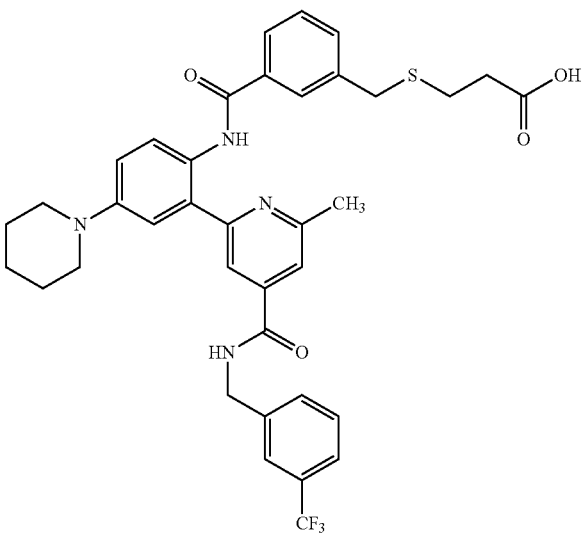 [SMILES: Cc1cc(C(=O)NCc2cccc(C(F)(F)F)c2)cc(-c2cc(N3CCCCC3)ccc2NC(=O)c2cccc(CSCCC(=O)O)c2)n1] | 691.32 [M + H] |

TABLE 6-continued

| Method | Example No. | Structure | Mass Spectrum |
|---|---|---|---|
| 1 | 86 | | 711.28 [M + H] |
| 1 | 87 | | 678.26 [M + H] |
| 1 | 88 | | 695.29 [M + H] |

TABLE 6-continued
| Method | Example No. | Structure | Mass Spectrum |
|---|---|---|---|
| 1 | 89 | 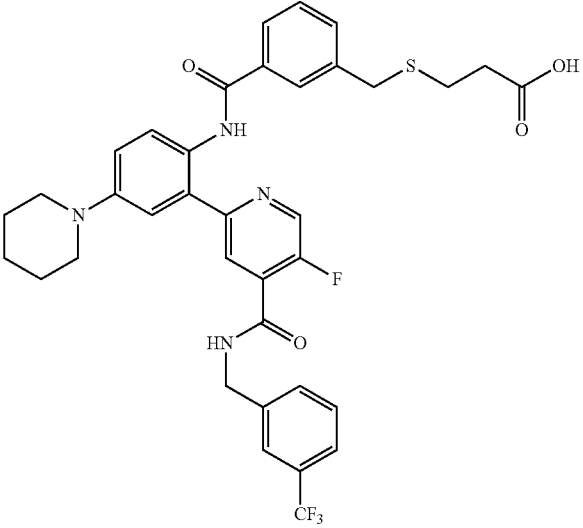 [SMILES: O=C(O)CCSCc1cccc(C(=O)Nc2ccc(N3CCCCC3)cc2-c2cc(C(=O)NCc3cccc(C(F)(F)F)c3)c(F)cn2)c1] | 659.28 [M + H] |
| 1 | 90 | 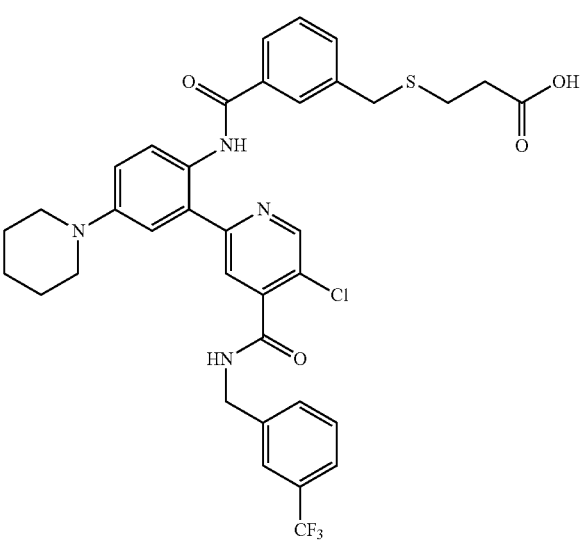 | 711.35 [M + H] |

TABLE 6-continued

| Method | Example No. | Structure | Mass Spectrum |
|---|---|---|---|
| 2 | 91 | | 727.30 [M + H] |
| 2 | 92 | | 691.32 [M + H] |
| 3 (treating the ketone product with deoxo-fluor (Bis-(2-methoxyethyl) aminosulfur-trifluoride) to install the fluorines) | 93 | 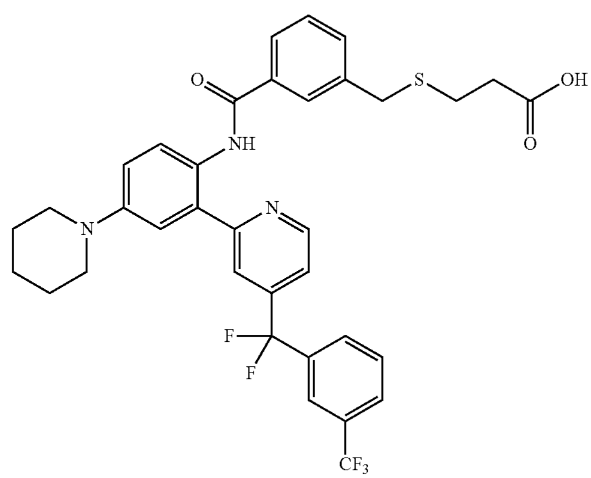 [SMILES: O=C(O)CCSCc1cccc(C(=O)Nc2ccc(N3CCCCC3)cc2-c2cc(C(F)(F)c3cccc(C(F)(F)F)c3)ccn2)c1] | 670.23 [M + H] |

TABLE 6-continued
| Method | Example No. | Structure | Mass Spectrum |
|---|---|---|---|
| 4 | 94 | 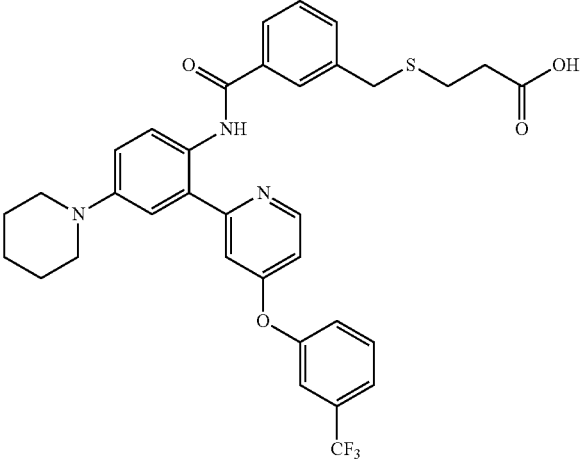 [SMILES: O=C(O)CCSCc1cccc(C(=O)Nc2ccc(N3CCCCC3)cc2-c2cc(Oc3cccc(C(F)(F)F)c3)ccn2)c1] | 636.28 [M + H] |
| 5 | 95 | 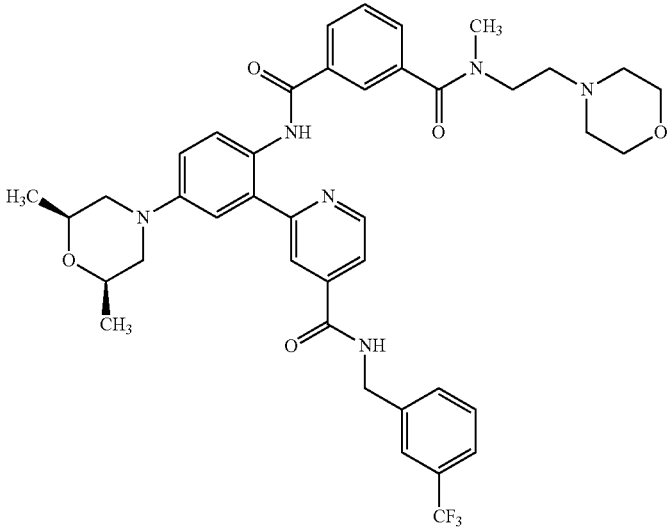 [SMILES: C[C@@H]1CN(c2ccc(NC(=O)c3cccc(C(=O)N(C)CCN4CCOCC4)c3)c(-c3cc(C(=O)NCc4cccc(C(F)(F)F)c4)ccn3)c2)C[C@H](C)O1] | 759.24 [M + H] |
| 5 | 96 | 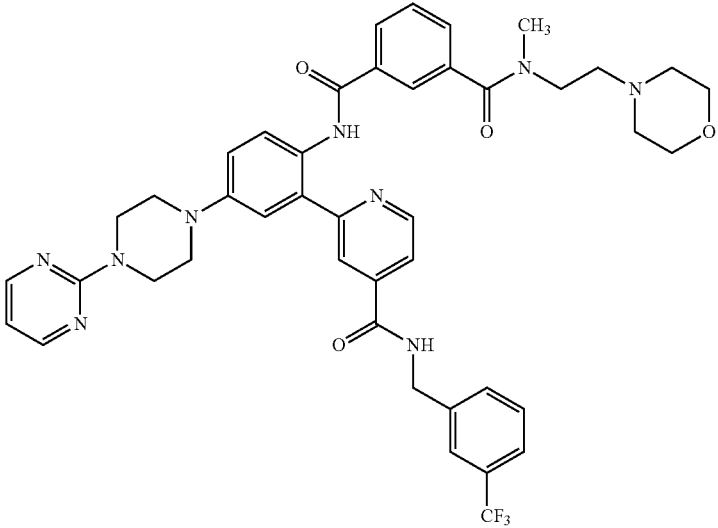 [SMILES: CN(CCN1CCOCC1)C(=O)c1cccc(C(=O)Nc2ccc(N3CCN(c4ncccn4)CC3)cc2-c2cc(C(=O)NCc3cccc(C(F)(F)F)c3)ccn2)c1] | 808.21 [M + H] |

TABLE 6-continued
| Method | Example No. | Structure | Mass Spectrum |
|---|---|---|---|
| 6 | 97 | 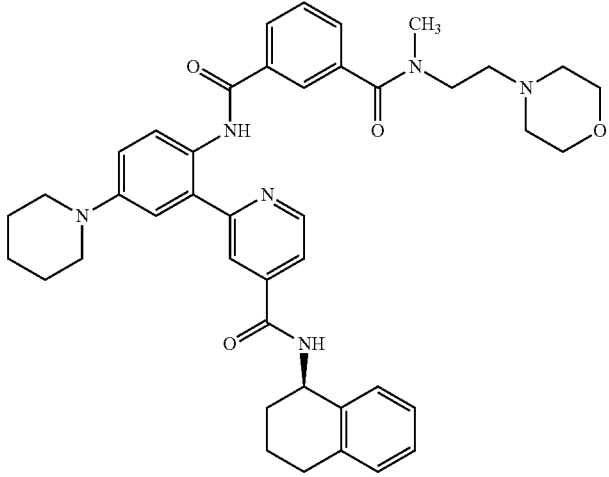 [SMILES: CN(CCN1CCOCC1)C(=O)c1cccc(C(=O)Nc2ccc(N3CCCCC3)cc2-c2cc(C(=O)N[C@@H]3CCCc4ccccc43)ccn2)c1] | 701 [M + H] |
| 4 | 98 | 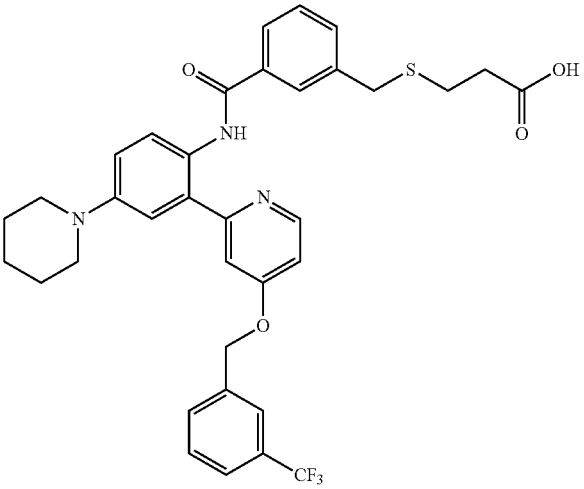 [SMILES: O=C(O)CCSCc1cccc(C(=O)Nc2ccc(N3CCCCC3)cc2-c2cc(OCc3cccc(C(F)(F)F)c3)ccn2)c1] | 650.29 [M + H] |
| 4 | 99 | 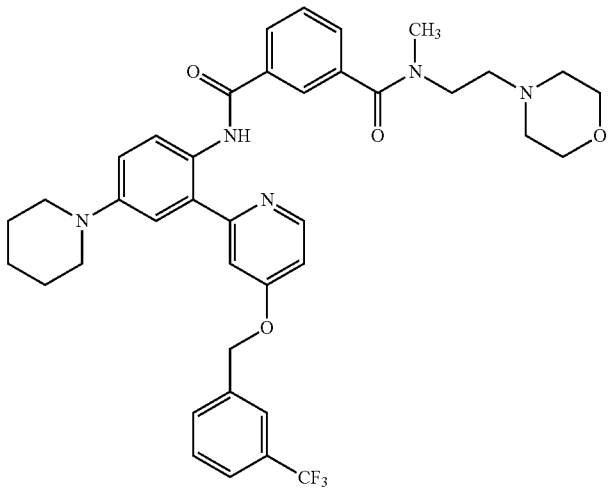 [SMILES: CN(CCN1CCOCC1)C(=O)c1cccc(C(=O)Nc2ccc(N3CCCCC3)cc2-c2cc(OCc3cccc(C(F)(F)F)c3)ccn2)c1] | 702.26 [M + H] |

TABLE 6-continued
| Method | Example No. | Structure | Mass Spectrum |
|---|---|---|---|
| 7 | 101 | 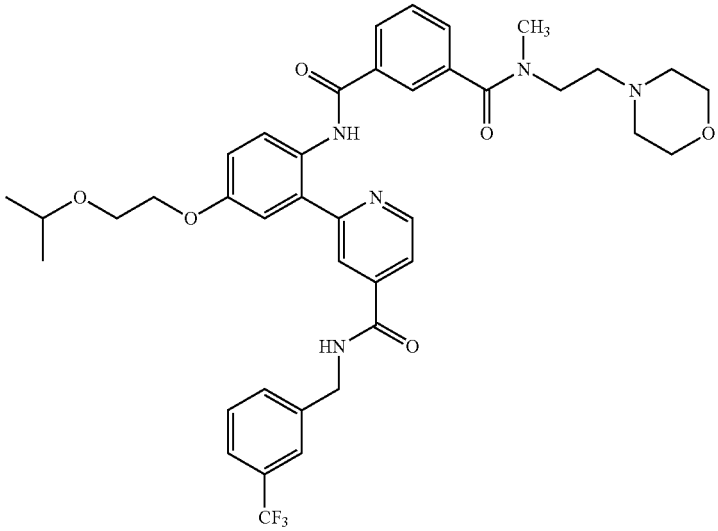 [SMILES: CC(C)OCCOc1ccc(NC(=O)c2cccc(C(=O)N(C)CCN3CCOCC3)c2)c(-c2cc(C(=O)NCc3cccc(C(F)(F)F)c3)ccn2)c1] | 748.29 [M + H] |
| 5 | 102 | 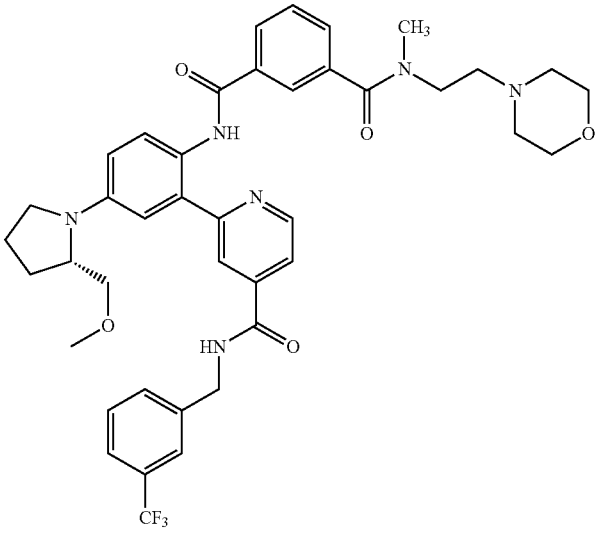 [SMILES: COC[C@@H]1CCCN1c1ccc(NC(=O)c2cccc(C(=O)N(C)CCN3CCOCC3)c2)c(-c2cc(C(=O)NCc3cccc(C(F)(F)F)c3)ccn2)c1] | 759.21 [M + H] |
| 5 | 103 | 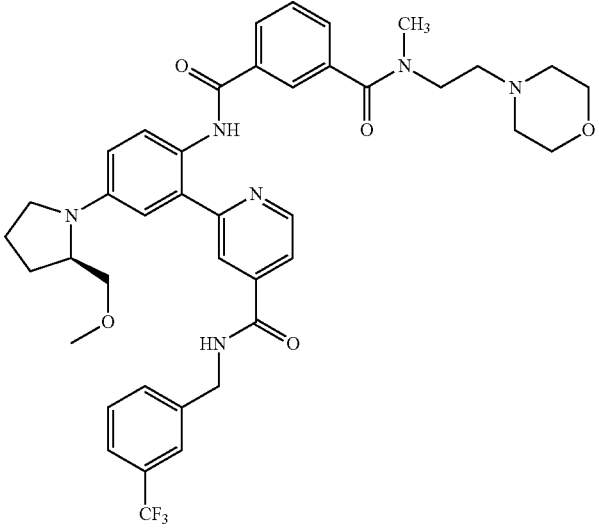 [SMILES: COC[C@H]1CCCN1c1ccc(NC(=O)c2cccc(C(=O)N(C)CCN3CCOCC3)c2)c(-c2cc(C(=O)NCc3cccc(C(F)(F)F)c3)ccn2)c1] | 759.21 [M + H] |

TABLE 6-continued
| Method | Example No. | Structure | Mass Spectrum |
|---|---|---|---|
| 4 | 104 | 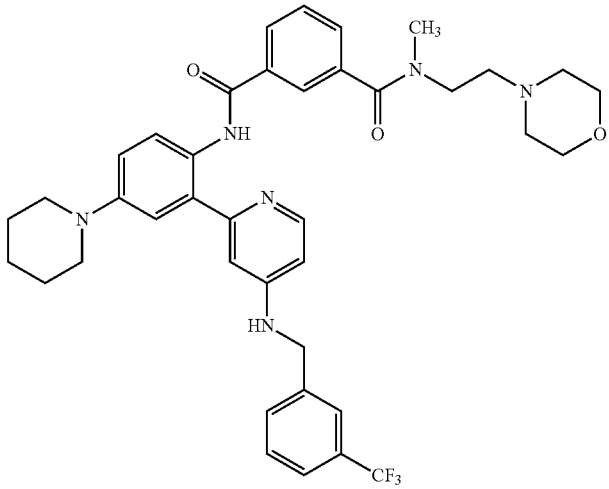 [SMILES: CN(CCN1CCOCC1)C(=O)c1cccc(C(=O)Nc2ccc(N3CCCCC3)cc2-c2cc(NCc3cccc(C(F)(F)F)c3)ccn2)c1] | 701.27 [M + H] |
| 5 | 105 | 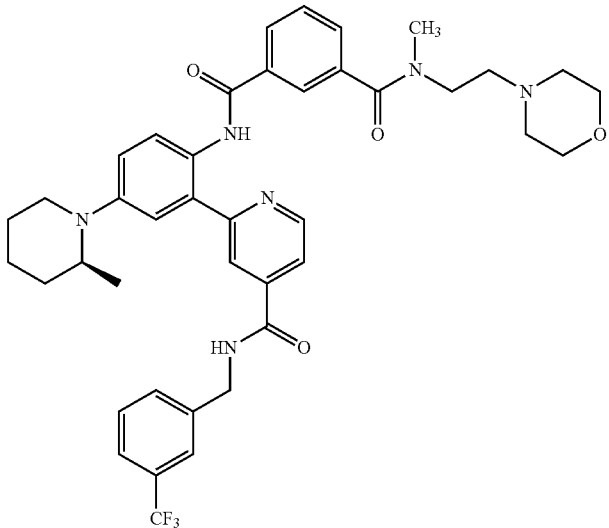 [SMILES: C[C@H]1CCCCN1c1ccc(NC(=O)c2cccc(C(=O)N(C)CCN3CCOCC3)c2)c(-c2cc(C(=O)NCc3cccc(C(F)(F)F)c3)ccn2)c1] | 743.21 [M + H] |
| 3 (treating the ketone product with deoxofluor (Bis-(2-methoxyethyl) aminosulfurtrifluoride) to install the fluorines) | 106 | 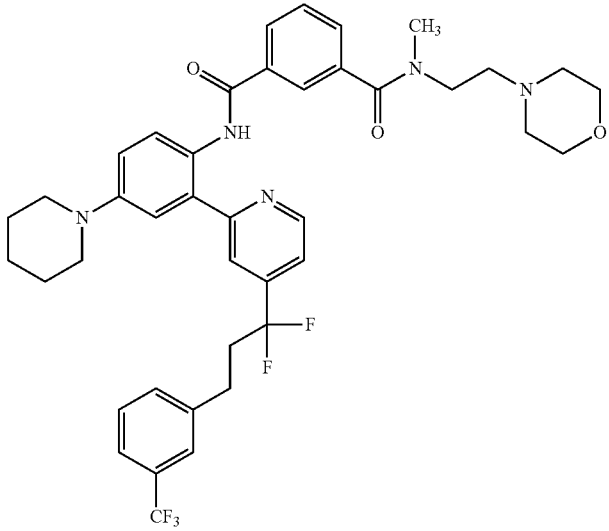 | 682.2 [M + H] |

TABLE 6-continued
| Method | Example No. | Structure | Mass Spectrum |
|---|---|---|---|
| 5 | 108 | 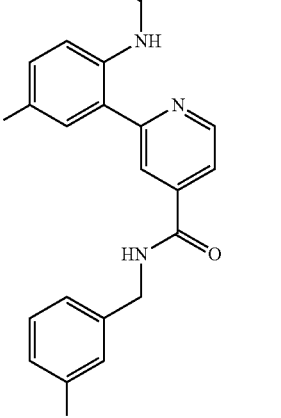 | 757.26 [M + H] |
| 4 | 109 | 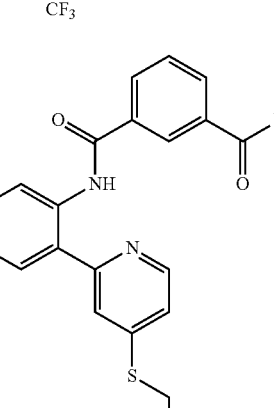 | 650.28 [M + H] |
| 8 | 110 | 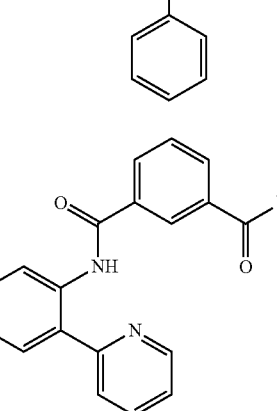 | 721.23 [M + H] |

TABLE 6-continued
| Method | Example No. | Structure | Mass Spectrum |
|---|---|---|---|
| 5 | 111 | 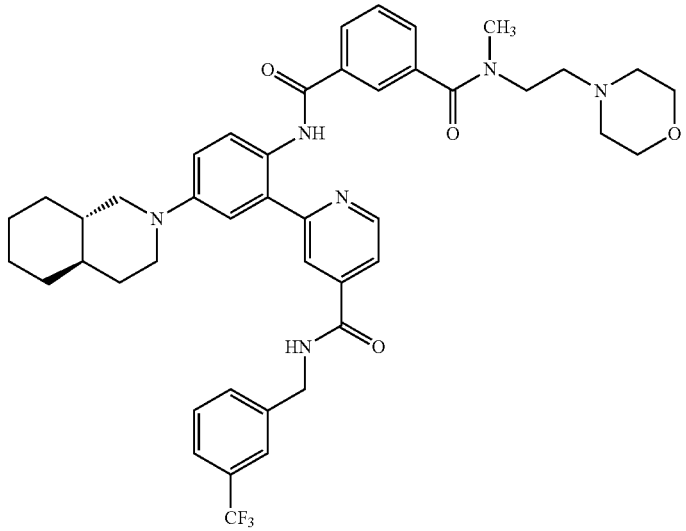 [SMILES: CN(CCN1CCOCC1)C(=O)c1cccc(C(=O)Nc2ccc(N3CC[C@H]4CCCC[C@@H]4C3)cc2-c2cc(C(=O)NCc3cccc(C(F)(F)F)c3)ccn2)c1] | 783.23 [M + H] |
| 8 | 112 | 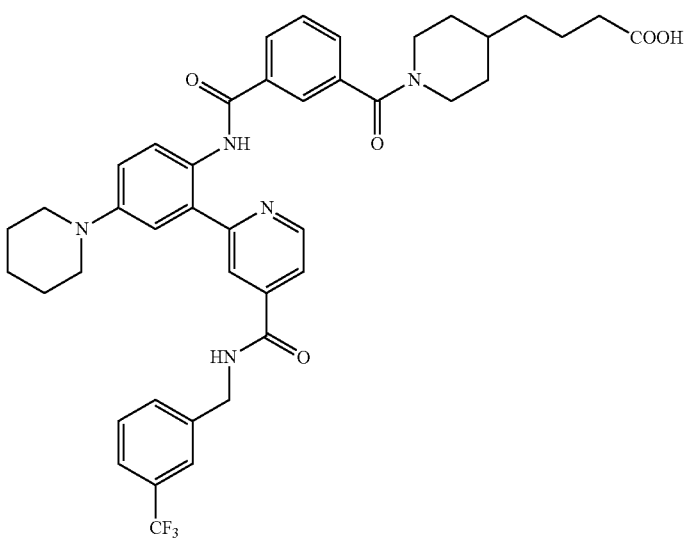 [SMILES: O=C(O)CCCC1CCN(C(=O)c2cccc(C(=O)Nc3ccc(N4CCCCC4)cc3-c3cc(C(=O)NCc4cccc(C(F)(F)F)c4)ccn3)c2)CC1] | 756.64 [M + H] |
| 8 | 113 | 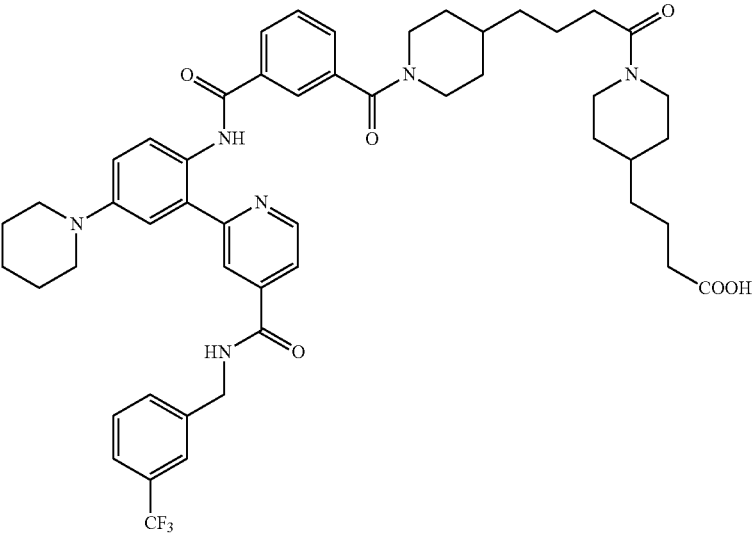 [SMILES: O=C(O)CCCC1CCN(C(=O)CCCC2CCN(C(=O)c3cccc(C(=O)Nc4ccc(N5CCCCC5)cc4-c4cc(C(=O)NCc5cccc(C(F)(F)F)c5)ccn4)c3)CC2)CC1] | 909.91 [M + H] |

TABLE 6-continued

| Method | Example No. | Structure | Mass Spectrum |
|---|---|---|---|
| 5 | 114 | | 783.23 [M + H] |
| 8 | 115 | 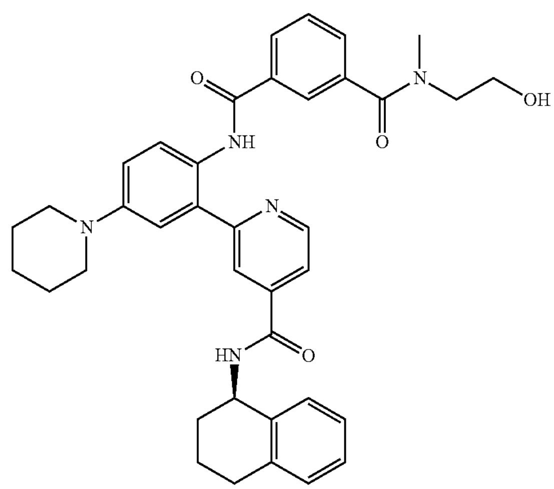 [SMILES: CN(CCO)C(=O)c1cccc(C(=O)Nc2ccc(N3CCCCC3)cc2-c2cc(C(=O)N[C@@H]3CCCc4ccccc43)ccn2)c1] | 632.42 [M + H] |
| 5 | 116 | | 745.26 [M + H] |

TABLE 6-continued

| Method | Example No. | Structure | Mass Spectrum |
|---|---|---|---|
| 5 | 117 | | 836.35 [M + H] |
| 5 | 118 | | 747.19 [M + H] |
| 9 | 119 | 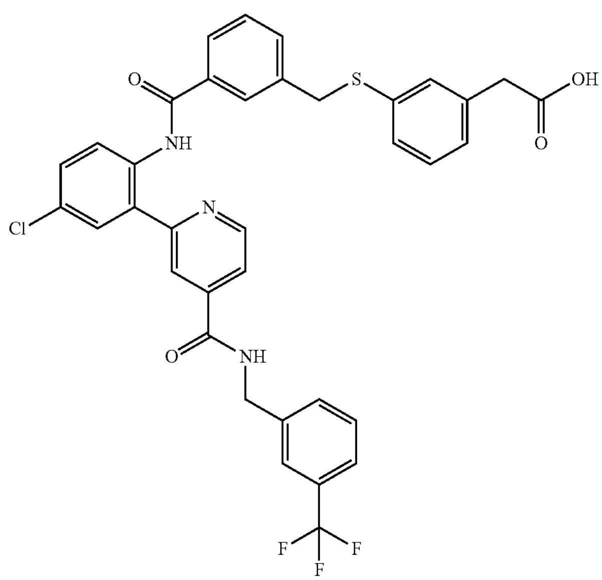 [SMILES: O=C(O)Cc1cccc(SCc2cccc(C(=O)Nc3ccc(Cl)cc3-c3cc(C(=O)NCc4cccc(C(F)(F)F)c4)ccn3)c2)c1] | 690 [M + H] |

Example 120

3-(3-(4-(dimethylamino)-2-(4-(3-(trifluoromethyl)benzylcarbamoyl)pyridin-2-yl)phenylcarbamoyl)benzylthio)propanoic acid

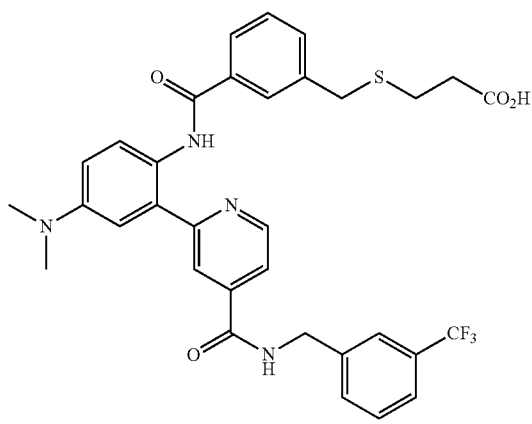 [SMILES: CN(C)c1ccc(NC(=O)c2cccc(CSCCC(=O)O)c2)c(-c2cc(C(=O)NCc3cccc(C(F)(F)F)c3)ccn2)c1]

This compound was prepared according to the procedure described for the synthesis of 3-((3-((4-(Dipropylamino)-2-(4-((3-(trifluoromethyl)benzyl)carbamoyl)pyridin-2-yl)phenyl)carbamoyl)benzyl)thio)propanoic acid Example 19, using dimethylamine in place of dipropylamine. (ES, m/z): 637 [M+H]$^+$(300 MHz, DMSO, ppm): 12.10 (s, 1H), 9.53 (t, J=6.0 Hz, 1H), 8.97 (d, J=5.1 Hz, 1H), 8.33 (s, 1H), 8.26 (d, J=8.7 Hz, 1H), 7.85-7.87 (m, 2H), 7.72-7.77 (m, 2H), 7.45-7.69 (m, 5H), 7.35 (s, 1H), 7.09 (d, J=7.8 Hz, 1H), 4.63 (d, J=5.7 Hz, 2H), 3.87 (s, 2H), 3.04 (s, 6H), 2.53-2.64 (m, 4H).

Example 121

N1-(2-(4-((2-methoxy-4-(trifluoromethyl)benzyl)carbamoyl)pyridin-2-yl)-4-(piperidin-1-yl)phenyl)-N3-methyl-N3-(2-morpholinoethyl)isophthalamide

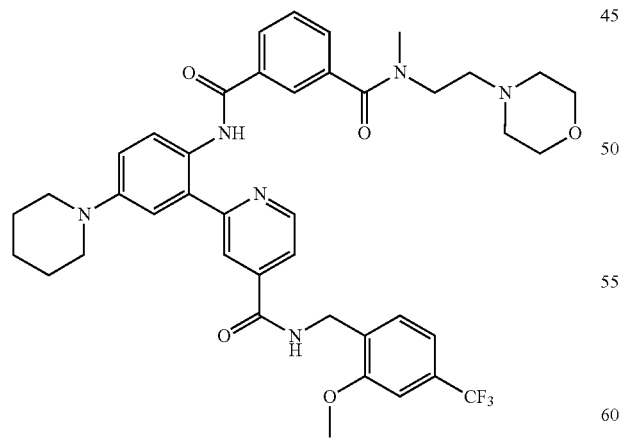

Into a 50-mL round-bottom flask, was placed a solution of 2-(2-(3-(carbamoyl)benzamido)-5-(piperidin-1-yl)phenyl)isonicotinic acid (100 mg, 0.15 mmol, 1.00 equiv, 85%) in dichloromethane (6 mL), (2-methoxy-4-(trifluoromethyl)phenyl)methanamine (36 mg, 0.17 mmol, 1.00 equiv), EDC.HCl (67 mg, 0.35 mmol, 2.00 equiv), 4-dimethylaminopyridine (43 mg, 0.35 mmol, 2.00 equiv). The resulting solution was stirred for 2 h at 25° C. The resulting solution was diluted with 100 mL of ethyl acetate. The resulting mixture was washed with 2×20 mL of NH$_4$Cl aq. and 1×20 mL of 10% sodium bicarbonate. The resulting mixture was washed with 1×20 mL of Brine. The mixture was dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and CH$_3$CN (28% CH$_3$CN up to 39% in 5.5 min); Detector, Waters2545 UvDector 254&270 nm. 79.9 mg product was obtained. This resulted in 79.9 mg (48%) of N1-(2-(4-((2-methoxy-4-(trifluoromethyl)benzyl)carbamoyl)pyridin-2-yl)-4-(piperidin-1-yl)phenyl)-N3-methyl-N3-(2-morpholinoethyl)isophthalamide as a yellow solid. (ES, m/z): 759 [M+H]$^+$ H$^1$-NMR (300 MHz, DMSO d$_6$, ppm): 12.41 (s, 1H), 9.74 (s, 1H), 9.39-9.43 (t, J=12 Hz, 1H), 8.91 (d, J=6 Hz, 1H), 8.30-8.35 (m, 2H), 7.48-8.03 (m, 2H), 7.85 (d, J=6 Hz, 1H), 7.57-7.71 (m, 3H), 7.24-7.42 (m, 3H), 4.53 (s, 2H), 4.17-4.21 (m, 3H), 3.85-3.93 (m, 6H), 3.67 (m, 4H), 3.46 (m, 2H), 3.32 (m, 4H), 3.19 (m, 2H), 2.96 (s, 3H), 1.73 (m, 4H), 1.59 (m, 2H).

Example 122

N1-(2-(4-((4-tert-butylbenzyl)carbamoyl)pyridin-2-yl)-4-(piperidin-1-yl)phenyl)-N3-methyl-N3-(2-morpholinoethyl)isophthalamide

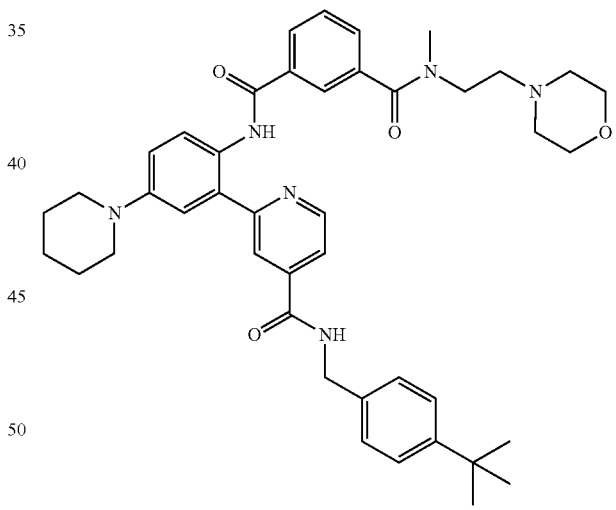

Into a 8-mL round-bottom flask, was placed a solution of 2-(2-(3-(carbamoyl)benzamido)-5-(piperidin-1-yl)phenyl)isonicotinic acid (125 mg, 0.19 mmol, 1.00 equiv, 85%) in dichloromethane (2 mL), (4-tert-butylphenyl)methanamine (36 mg, 0.22 mmol, 1.00 equiv), EDC.HCl (84 mg, 0.44 mmol, 2.00 equiv), 4-dimethylaminopyridine (54 mg, 0.44 mmol, 2.00 equiv). The resulting solution was stirred for 2 h at 25° C. The resulting solution was diluted with 100 mL of ethyl acetate. The resulting mixture was washed with 2×20 mL of NH$_4$Cl aq. and 1×20 mL of 10% sodium bicarbonate. The resulting mixture was washed with 1×20 mL of Brine. The mixture was dried over anhydrous sodium sulfate and concentrated under vacuum. The crude product (130 mg) was purified by Prep-HPLC with the following conditions (1#-Waters 2767-3): Column, SunFire Prep C18, 19*150 mm 5 um; mobile phase, water with 0.05% TFA and CH$_3$CN (28% CH$_3$CN up to 39% in 6 min); Detector, Waters2545 UvDector 254&270 nm. 85.8 mg product was obtained. This resulted in 85.8 mg (44%) of N1-(2-(4-((4-tert-butylbenzyl)carbamoyl)pyridin-2-yl)-4-(piperidin-1-yl)phenyl)-N3-methyl-N3-(2-morpholinoethyl)isophthalamide as a yellow solid. (ES, m/z): 717 [M+H]$^+$; H-NMR (300 MHz, DMSO, ppm): 12.39 (s, 1H), 9.71 (s, 1H), 9.41 (t, J=12 Hz, 1H), 8.89 (d, J=3 Hz, 1H), 8.28 (m, 2H), 7.98-8.02 (m, 2H), 7.83 (d, J=6 Hz, 1H), 7.62-7.69 (m, 3H), 7.24-7.36 (m, 5H), 4.48 (s, 2H), 3.46 (m, 3H), 3.31 (m, 4H), 3.20 (m, 3H), 2.96 (s, 3H), 1.73 (m, 4H), 1.58 (m, 2H), 1.26 (s, 9H).

Example 123

N1-(2-(4-((2-(trifluoromethoxy)benzyl)carbamoyl)pyridin-2-yl)-4-(piperidin-1-yl)phenyl)-N3-methyl-N3-(2-morpholinoethyl)isophthalamide

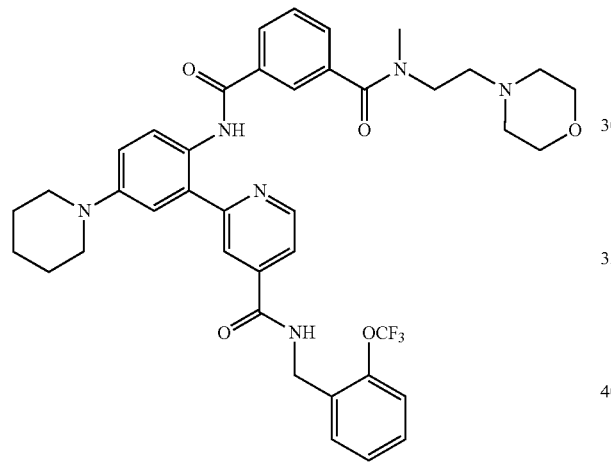

Into a 8-mL round-bottom flask, was placed a solution of 2-(2-(3-(carbamoyl)benzamido)-5-(piperidin-1-yl)phenyl)isonicotinic acid (100 mg, 0.15 mmol, 1.00 equiv, 85%) in dichloromethane (2 mL), (2-(trifluoromethoxy)phenyl)methanamine (33.45 mg, 0.17 mmol, 1.00 equiv), EDC.HCl (67.25 mg, 0.35 mmol, 2.00 equiv), 4-dimethylaminopyridine (42.73 mg, 0.35 mmol, 2.00 equiv). The resulting solution was stirred for 2 h at 25° C. The resulting solution was diluted with 100 mL of ethyl acetate. The resulting mixture was washed with 2×20 mL of NH$_4$Cl aq. and 1×20 mL of 10% sodium bicarbonate. The resulting mixture was washed with 1×20 mL of Brine. The mixture was dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and CH$_3$CN (22% CH$_3$CN up to 40% in 6 min); Detector, Waters2545 UvDector 254&270 nm. 62.2 mg product was obtained. This resulted in 62.2 mg (38%) of N1-(2-(4-((2-(trifluoromethoxy)benzyl)carbamoyl)pyridin-2-yl)-4-(piperidin-1-yl)phenyl)-N3-methyl-N3-(2-morpholinoethyl)isophthalamide as a yellow solid. (ES, m/z): 745 [M+H]$^+$; H-NMR (300 MHz, DMSO, ppm): 12.37 (s, 1H), 9.65 (s, 1H), 9.47 (t, J=12 Hz, 1H), 8.90 (d, J=6 Hz, 1H), 8.28-8.30 (m, 2H), 7.83-8.00 (m, 2H), 7.96 (d, J=6 Hz, 1H), 7.57-7.71 (m, 3H), 7.34-7.48 (m, 4H), 7.27 (m, 1H), 4.59 (s, 2H), 3.66 (m, 3H), 3.46 (m, 4H), 3.30 (m, 2H), 2.96 (s, 3H), 1.72 (m, 4H), 1.58-1.60 (m, 2H).

Example 124

N1-(2-(4-((2-methoxybenzyl)carbamoyl)pyridin-2-yl)-4-(piperidin-1-yl)phenyl)-N3-methyl-N3-(2-morpholinoethyl)isophthalamide

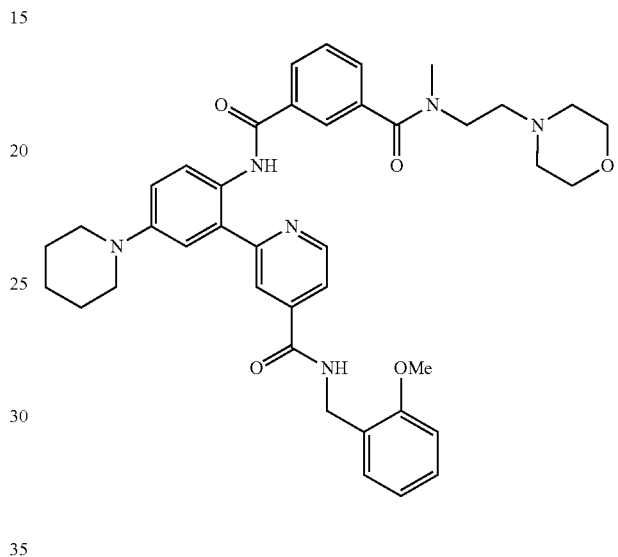

Into a 8-mL round-bottom flask, was placed a solution of 2-(2-(3-(carbamoyl)benzamido)-5-(piperidin-1-yl)phenyl)isonicotinic acid (100 mg, 0.15 mmol, 1.00 equiv, 85%) in dichloromethane (2 mL), (2-methoxyphenyl)methanamine (30 mg, 0.22 mmol, 1.00 equiv), EDC.HCl (67.25 mg, 0.35 mmol, 2.00 equiv), 4-dimethylaminopyridine (42.73 mg, 0.35 mmol, 2.00 equiv). The resulting solution was stirred for 2 h at 25° C. The resulting solution was diluted with 100 mL of ethyl acetate. The resulting mixture was washed with 2×20 mL of NH$_4$Cl aq. and 1×20 mL of 10% sodium bicarbonate. The resulting mixture was washed with 1×20 mL of Brine. The mixture was dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and CH$_3$CN (20% CH$_3$CN up to 33% in 6 min); Detector, Waters2545 UvDector 254&270 nm. 85.8 mg product was obtained. This resulted in 85.8 mg (55%) of N1-(2-(4-((2-methoxybenzyl)carbamoyl)pyridin-2-yl)-4-(piperidin-1-yl)phenyl)-N3-methyl-N3-(2-morpholinoethyl)isophthalamide as a yellow solid. LC-MS (ES, m/z): 691 [M+H]$^+$; H-NMR (300 MHz, CD$_3$OD, ppm): 12.48 (s, 1H), 9.81 (s, 1H), 9.29 (t, J=12 Hz, 1H), 8.90 (d, J=6 Hz, 1H), 8.35 (m, 2H), 8.03-7.99 (m, 2H), 7.86 (d, J=3 Hz, 1H), 7.72-7.63 (m, 2H), 7.34-7.19 (m, 3H), 7.00 (m, 1H), 6.92-6.87 (t, J=15 Hz, 1H), 4.49 (m, 4H), 4.36 (m, 5H), 4.24

(m, 3H), 4.03 (m, 5H), 3.66 (m, 4H), 3.34 (m, 6H), 3.20 (m, 2H), 2.96 (s, 3H), 1.74 (m, 6H).

Example 125

N1-(2-(4-((2-methoxy-5-(trifluoromethyl)benzyl) carbamoyl)pyridin-2-yl)-4-(piperidin-1-yl)phenyl)-N3-methyl-N3-(2-morpholinoethyl)isophthalamide

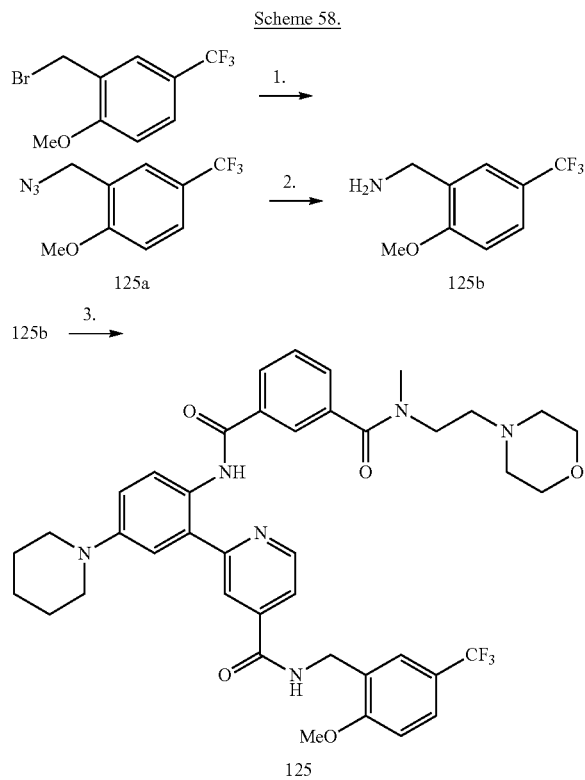

1. NaN$_3$, DMF 2. PPh$_3$, THF, H$_2$O 3. 37b EDC·HCl, DMAP, DCM.

Intermediate 125a

Into a 50-mL round-bottom flask, was placed a solution of 2-(bromomethyl)-1-methoxy-4-(trifluoromethyl)benzene (230 mg, 0.86 mmol, 1.00 equiv) in N,N-dimethylformamide (5 mL), sodiumazide (167 mg, 2.57 mmol, 3.00 equiv). The resulting solution was stirred for 3 h at 75° C. in an oil bath. The resulting solution was diluted with 100 mL of ethyl acetate. The resulting mixture was washed with 4×20 mL of brine. The mixture was dried over anhydrous sodium sulfate and concentrated under vacuum. This resulted in 160 mg (73%) of 2-(azidomethyl)-1-methoxy-4-(trifluoromethyl) benzene as brown oil.

Intermediate 125b

Into a 50-mL round-bottom flask, was placed a solution of 2-(azidomethyl)-1-methoxy-4-(trifluoromethyl)benzene (160 mg, 0.62 mmol, 1.00 equiv, 90%) in tetrahydrofuran/water (4/0.5 mL), triphenylphosphine (399 mg, 1.52 mmol, 2.20 equiv). The resulting solution was stirred for 3 h at 40° C. in an oil bath. The resulting mixture was concentrated under vacuum. The residue was applied onto a silica gel column with ethylacetate:methanol (10:1). This resulted in 180 mg (70%) of (2-methoxy-5-(trifluoromethyl)phenyl)methanamine as a off-white solid.

Example 125

N1-(2-(4-((2-methoxy-5-(trifluoromethyl)benzyl) carbamoyl)pyridin-2-yl)-4-(piperidin-1-yl)phenyl)-N3-methyl-N3-(2-morpholinoethyl)isophthalamide A solution of 2-(2-(3-(carbamoyl)benzamido)-5-(piperidin-1-yl)phenyl)isonicotinic acid (100 mg, 0.15 mmol, 1.00 equiv, 85%) in dichloromethane (6 mL), (2-methoxy-5-(trifluoromethyl)phenyl)methanamine (120 mg, 0.29 mmol, 1.00 equiv, 50%), EDC.HCl (67 mg, 0.35 mmol, 2.00 equiv), 4-dimethylaminopyridine (43 mg, 0.35 mmol, 2.00 equiv). The resulting solution was stirred for 2 h at 25° C. The resulting solution was diluted with 100 mL of ethyl acetate. The resulting mixture was washed with 2×20 mL of NH$_4$Cl and 1×20 mL of 10% sodium bicarbonate. The resulting mixture was washed with 1×20 mL of Brine. The mixture was dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and CH$_3$CN (26% CH$_3$CN up to 36% in 6 min); Detector, Waters2545 UvDector 254&270 nm. 80.6 mg product was obtained. This resulted in 80.6 mg (48%) of N1-(2-(4-((2-methoxy-5-(trifluoromethyl)benzyl) carbamoyl)pyridin-2-yl)-4-(piperidin-1-yl)phenyl)-N3-methyl-N3-(2-morpholinoethyl)isophthalamide Example 125 as a yellow solid. LC-MS (ES, m/z): 759 [M+H]$^+$; H-NMR (300 MHz, DMSO, ppm): 12.48 (s, 1H), 9.70 (s, 1H), 9.38 (t, J=12 Hz, 1H), 8.90 (d, J=6 Hz, 1H), 8.32 (m, 2H), 7.98-8.03 (m, 2H), 7.84 (d, J=6 Hz, 1H), 7.59-7.71 (m, 4H), 7.27 (m, 1H), 4.54 (s, 2H), 3.31-3.86 (m, 10H), 3.19 (m, 2H), 3.97 (s, 3H), 1.59-1.72 (m, 6H).

Example 126

(S)—N1-methyl-N1-(3-morpholinopropyl)-N3-(4-(piperidin-1-yl)-2-(4-(1,2,3,4-tetrahydronaphthalen-1-ylcarbamoyl)pyridin-2-yl)phenyl)isophthalamide

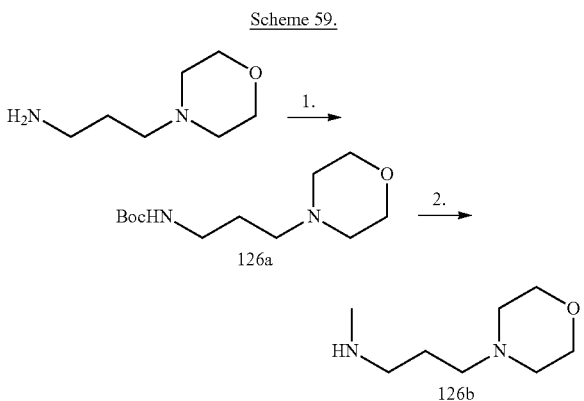

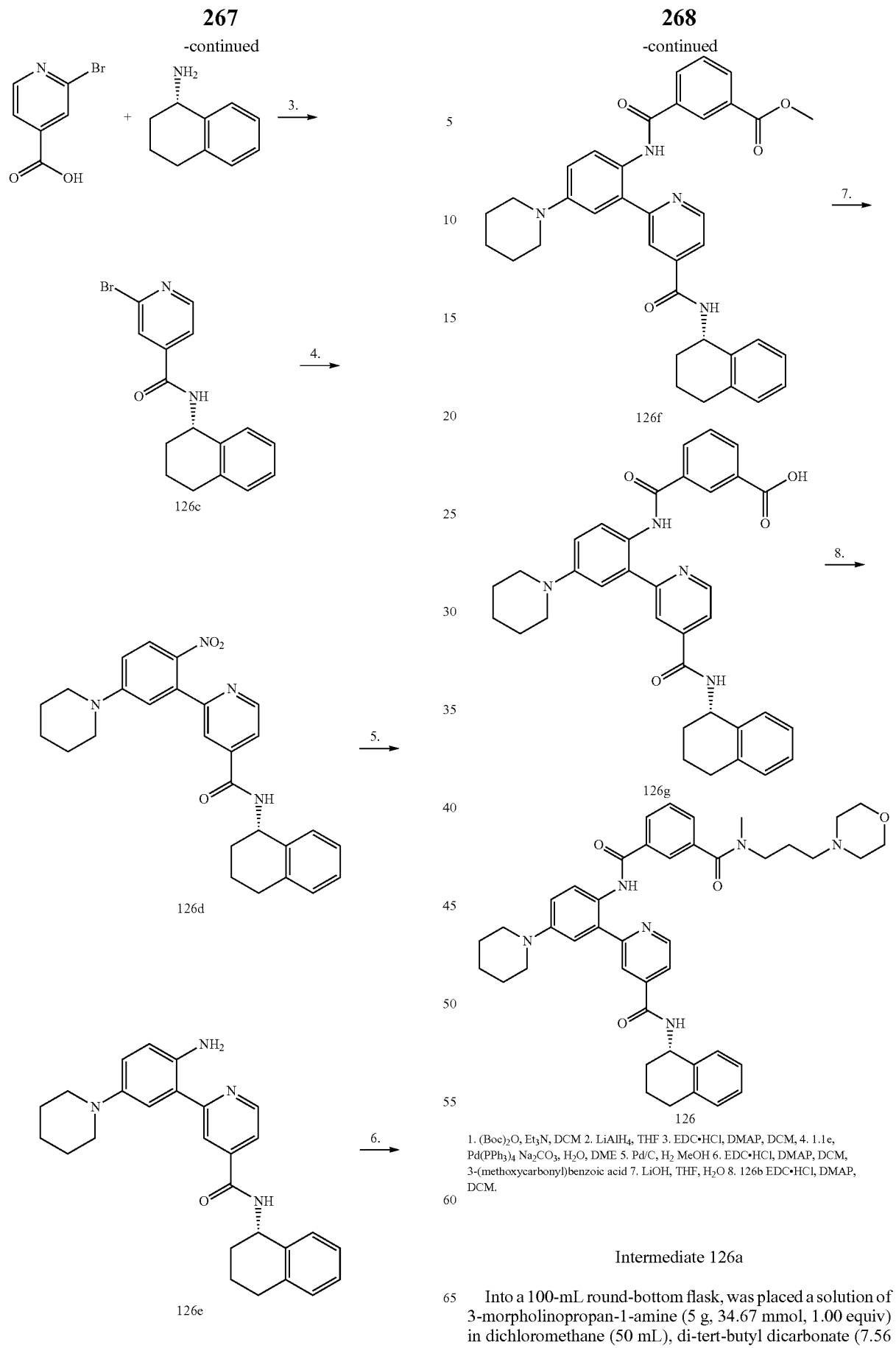
1. (Boc)₂O, Et₃N, DCM 2. LiAlH₄, THF 3. EDC·HCl, DMAP, DCM, 4. 1.1e, Pd(PPh₃)₄ Na₂CO₃, H₂O, DME 5. Pd/C, H₂ MeOH 6. EDC·HCl, DMAP, DCM, 3-(methoxycarbonyl)benzoic acid 7. LiOH, THF, H₂O 8. 126b EDC·HCl, DMAP, DCM.
Intermediate 126a
Into a 100-mL round-bottom flask, was placed a solution of 3-morpholinopropan-1-amine (5 g, 34.67 mmol, 1.00 equiv) in dichloromethane (50 mL), di-tert-butyl dicarbonate (7.56 g, 34.67 mmol, 1.00 equiv.), triethylamine (7 g, 70.00 mmol, 2.00 equiv). The resulting solution was stirred overnight at 25° C. The resulting mixture was concentrated under vacuum. This resulted in 6.8 g (80%) of tert-butyl 3-morpholinopropylcarbamate as light yellow oil.

Intermediate 126b

Into a 100-mL round-bottom flask, was placed a solution of tert-butyl 3-morpholinopropylcarbamate (3 g, 12.28 mmol, 1.00 equiv) in tetrahydrofuran (50 mL). This was followed by the addition of LiAlH$_4$ (0.93 g, 24.60 mmol, 2.00 equiv) in several batches. The resulting solution was stirred for 1 h at 75° C. in an oil bath. The reaction was then quenched by the addition of 8 mL of water. The solids were filtered out. The resulting mixture was concentrated under vacuum. This resulted in 1.3 g (67%) of N-methyl-3-morpholinopropan-1-amine as light yellow oil.

Intermediate 126c

Into a 250-mL round-bottom flask, was placed a solution of 2-bromoisonicotinic acid (10 g, 49.50 mmol, 1.10 equiv) in dichloromethane (60 mL), (S)-1,2,3,4-tetrahydronaphthalen-1-amine (6.6 g, 44.90 mmol, 1.00 equiv), EDC.HCl (12.9 g, 67.29 mmol, 1.50 equiv), 4-dimethylaminopyridine (8.3 g, 68.03 mmol, 1.50 equiv). The resulting solution was stirred for 3 h at room temperature. The resulting solution was diluted with 20 mL of water. The resulting solution was extracted with 2×20 ml of dichloromethane and the organic layers combined. The resulting mixture was washed with 1×10 mL of hydrogen chloride (10%) and 1×20 ml of water. The resulting mixture was washed with 1×20 mL of brine. The mixture was dried over anhydrous sodium sulfate and concentrated under vacuum. This resulted in 13.2 g (89%) of (S)-2-bromo-N-(1,2,3,4-tetrahydronaphthalen-1-yl)isonicotinamide as a off-white solid.

Intermediate 126d

Into a 250-mL round-bottom flask purged and maintained with an inert atmosphere of nitrogen, was placed a solution of 1-(4-nitro-3-(4,4,5,5-tetramethyl-1,3,2-dioxaborolan-2-yl)phenyl)piperidine (6.5 g, 19.58 mmol, 1.00 equiv) in ethylene glycol dimethyl ether (100 mL), (S)-2-bromo-N-(1,2,3,4-tetrahydronaphthalen-1-yl)isonicotinamide (6.5 g, 19.64 mmol, 1.00 equiv), Pd(PPh$_3$)$_4$ (1.13 g, 0.98 mmol, 0.05 equiv), a solution of sodium carbonate (6.2 g, 58.49 mmol, 3.00 equiv) in water (20 mL). The resulting solution was stirred for 3 h at 80° C. in an oil bath. The resulting solution was extracted with 2×30 mL of ethyl acetate and the organic layers combined. The resulting mixture was washed with 1×20 mL of water and 1×20 ml of Brine. The mixture was dried over anhydrous sodium sulfate and concentrated under vacuum. The residue was applied onto a silica gel column with ethyl acetate/petroleum ether (2:52:1). This resulted in 7.6 g (85%) of 2-(2-nitro-5-(piperidin-1-yl)phenyl)-N—((S)-1,2,3,4-tetrahydronaphthalen-1-yl)isonicotinamide as a yellow solid.

Intermediate 126e

Into a 250-mL round-bottom flask, was placed a solution of 2-(2-nitro-5-(piperidin-1-yl)phenyl)-N—((S)-1,2,3,4-tetrahydronaphthalen-1-yl)isonicotinamide (7.6 g, 16.67 mmol, 1.00 equiv) in methanol (120 mL), Palladium carbon (0.76 g). Hydrogen gas was introduced into the reaction vessel. The resulting solution was stirred overnight at room temperature. The solids were filtered out. The resulting mixture was concentrated under vacuum. This resulted in 5.3 g (75%) of 2-(2-amino-5-(piperidin-1-yl)phenyl)-N—((S)-1,2,3,4-tetrahydronaphthalen-1-yl)isonicotinamide as a brown solid. (ES, m/z): 427 [M+H]$^+$ (300 MHz, CD$_3$OD, ppm): 8.726~8.745 (m, 1H), 8.072 (s, 1H), 7.630~7.682 (m, 2H), 7.266~7.306 (m, 2H), 7.145~7.198 (m, 3H), 6.984~7.022 (m, 1H), 6.831~6.86 (d, J=8.7 Hz, 1H), 5.378 (m, 1H), 3.014~3.049 (m, 4H), 2.837~2.885 (m, 2H), 1.915~2.033 (m, 4H), 1.721~1.796 (m, 4H).

Intermediate 126f

Into a 250-mL round-bottom flask, was placed a solution of 2-(2-amino-5-(piperidin-1-yl)phenyl)-N—((S)-1,2,3,4-tetrahydronaphthalen-1-yl)isonicotinamide (4.3 g, 10.09 mmol, 1.00 equiv) in dichloromethane (100 mL), 3-(methoxycarbonyl)benzoic acid (2.08 g, 11.56 mmol, 1.10 equiv), EDCI (2.87 g, 14.97 mmol, 1.50 equiv), 4-dimethylaminopyridine (1.83 g, 14.98 mmol, 1.50 equiv). The resulting solution was stirred for 2 h at room temperature. The resulting solution was diluted with 10 mL of water. The resulting solution was extracted with 2×20 ml of dichloromethane and the organic layers combined. The resulting mixture was washed with 1×20 mL of water and 1×20 ml of Brine. The mixture was dried over anhydrous sodium sulfate and concentrated under vacuum. This resulted in 5.8 g (98%) of methyl 3-((2-(4-(((S)-1,2,3,4-tetrahydronaphthalen-1-yl)carbamoyl)pyridin-2-yl)-4-(piperidin-1-yl)phenyl)carbamoyl)benzoate as a brown solid.

Intermediate 126g

Into a 250-mL round-bottom flask, was placed a solution of methyl 3-((2-(4-(((S)-1,2,3,4-tetrahydronaphthalen-1-yl)carbamoyl)pyridin-2-yl)-4-(piperidin-1-yl)phenyl)carbamoyl)benzoate (5.8 g, 9.86 mmol, 1.00 equiv) in tetrahydrofuran (50 mL), a solution of lithium hydroxide hydrate (1.2 g, 28.57 mmol, 5.00 equiv) in water (20 mL). The resulting solution was stirred for 16 h at 70° C. in an oil bath. The resulting mixture was concentrated under vacuum. The pH value of the solution was adjusted to 3~4 with hydrogen chloride (10%). The solids were collected by filtration. The solid was dried in an oven under reduced pressure. This resulted in 5 g (88%) of 3-((2-(4-(((S)-1,2,3,4-tetrahydronaphthalen-1-yl)carbamoyl)pyridin-2-yl)-4-(piperidin-1-yl)phenyl)carbamoyl)benzoic acid as a brown solid. LC-MS (ES, m/z): 575 [M+H]$^+$; H-NMR (300 MHz, CDCl$_3$, ppm): 13.36 (s, 1H), 8.85 (s, 1H), 8.59 (s, 2H), 8.31 (s, 1H), 8.11 (s, 2H), 7.81~7.46 (m, 4H), 7.08 (d, J=−13.5 Hz, 4H), 5.38 (s, 1H), 3.23 (s, 4H), 2.74 (s, 2H), 2.10~1.60 (m, 10H).

Example 126

(S)—N1-methyl-N1-(3-morpholinopropyl)-N3-(4-(piperidin-1-yl)-2-(4-(1,2,3,4-tetrahydronaphthalen-1-ylcarbamoyl)pyridin-2-yl)phenyl)isophthalamide A solution of 3-((2-(4-(((S)-1,2,3,4-tetrahydronaphthalen-1-yl)carbamoyl)pyridin-2-yl)-4-(piperidin-1-yl)phenyl)carbamoyl)benzoic acid (150 mg, 0.26 mmol, 1.00 equiv) in dichloromethane (3 mL), N-methyl-3-morpholinopropan-1-amine (42 mg, 0.27 mmol, 1.00 equiv), EDC.HCl (75 mg, 0.39 mmol, 1.50 equiv), 4-dimethylaminopyridine (48 mg, 0.39 mmol, 1.50 equiv). The resulting solution was stirred for 2 h at 25° C. The resulting solution was diluted with 3 mL of water. The resulting solution was extracted with 2×5 mL of dichloromethane and the organic layers combined. The resulting mixture was washed with 1×5 mL of water and 2×5 mL of Brine. The mixture was dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and CH$_3$CN (24% CH$_3$CN up to 34% in 6 min); Detector, Waters2545 UvDector 254&220 nm. 97 mg product was obtained. This resulted in 97 mg (35%) of (S)—N1-methyl-N1-(3-morpholinopropyl)-N3-(4-(piperidin-1-yl)-2-(4-(1,2,3,4-tetrahydronaphthalen-1-ylcarbamoyl)pyridin-2-yl)phenyl)isophthalamide. Example 126 as a yellow solid. (ES, m/z): 715 [M+H]$^+$ (400 MHz, CD$_3$OD, ppm): 8.91 (s, 1H), 8.73 (d, J=8.8 Hz, 1H), 8.41 (s, 1H), 8.14~8.09 (m, 3H), 7.873~7.857 (m, 1H), 7.753~7.69 (m, 3H), 7.27 (d, J=7.2 Hz, 1H), 7.19~7.13 (m, 3H), 5.40 (d, J=6.4 Hz, 1H), 4.18 (s, 2H), 3.90~3.50 (m, 9H), 3.46~3.17 (m, 5H), 3.07 (s, 3H), 2.89~2.78 (s, 2H), 2.26~2.03 (m, 8H), 1.98~1.81 (m, 4H).

Example 127

N1-(4-(butyl(methyl)amino)-2-(4-(3-(trifluoromethyl)benzylcarbamoyl)pyridin-2-yl)phenyl)-N3-methyl-N3-(2-morpholinoethyl)isophthalamide

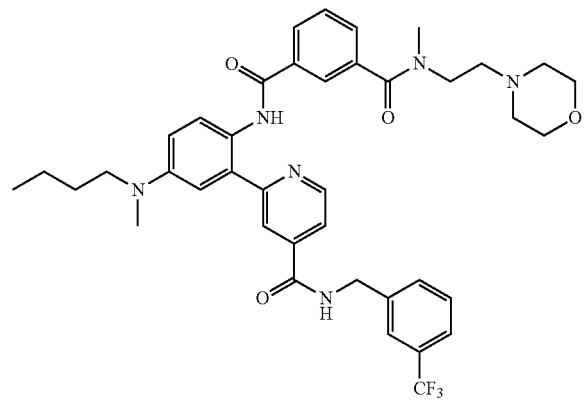 [SMILES: CCCCN(C)c1ccc(NC(=O)c2cccc(C(=O)N(C)CCN3CCOCC3)c2)c(-c2cc(C(=O)NCc3cccc(C(F)(F)F)c3)ccn2)c1]

Into a 50-mL round-bottom flask, was placed a solution of N-(3-(trifluoromethyl)benzyl)-2-(2-amino-5-(butyl(methyl)amino)phenyl)isonicotinamide (250 mg, 0.55 mmol, 1.00 equiv) in dichloromethane (10 mL), 3-(methyl(2-morpholinoethyl)carbamoyl)benzoic acid (190 mg, 0.65 mmol, 1.19 equiv), 4-dimethylaminopyridine (133 mg, 1.09 mmol, 1.99 equiv), EDC.HCl (210 mg, 1.09 mmol, 2.00 equiv). The resulting solution was stirred overnight at room temperature. The reaction progress was monitored by LCMS. The resulting solution was diluted with 100 mL of dichloromethane. The resulting mixture was washed with 2×50 mL of NH$_4$Cl aq. and 2×50 mL of brine. The mixture was dried over sodium sulfate and concentrated under vacuum. The crude product was purified by Prep-HPLC with the following conditions (1#-Waters 2767-3): Column, SunFire Prep C18, 5 um, 19*150 mm; mobile phase, water with 0.05% TFA and CH$_3$CN (30% CH$_3$CN up to 42% in 6 min); Detector, UV 220&254 nm. This resulted in 87.2 mg (15%) of N1-(4-(butyl(methyl)amino)-2-(4-(3-(trifluoromethyl)benzylcarbamoyl)pyridin-2-yl)phenyl)-N3-methyl-N3-(2-morpholinoethyl)isophthalamide as a yellow solid. LC-MS (ES, m/z): 731 [M+H]$^+$ H-NMR (300 MHz, DMSO, ppm): 11.95 (s, 1H), 9.75 (s, 1H), 9.52 (s, 1H), 8.88 (d, J=5.1 Hz, 1H), 8.27 (s, 1H), 8.10 (d, J=9.3 Hz, 1H), 7.97-7.83 (m, 2H), 7.82 (d, J=5.1 Hz, 1H), 7.70-7.54 (m, 6H), 7.17 (s, 1H), 6.95 (d, J=7.5 Hz, 1H), 4.61 (d, J=5.7 Hz, 2H), 4.02 (s, 2H), 3.90 (s, 2H), 3.65 (s, 4H), 3.45-3.39 (m, 4H), 3.20 (s, 2H), 3.0 (d, J=12.3 Hz, 6H), 1.55-1.50 (m, 2H), 1.35-1.30 (m, 2H), 0.93-0.88 (m, 3H).

Example 128

N1-(2-(4-((3-(trifluoromethyl)benzyl)carbamoyl)pyridin-2-yl)-4-(ethyl(propyl)amino)phenyl)-N3-methyl-N3-(2-morpholinoethyl)isophthalamide

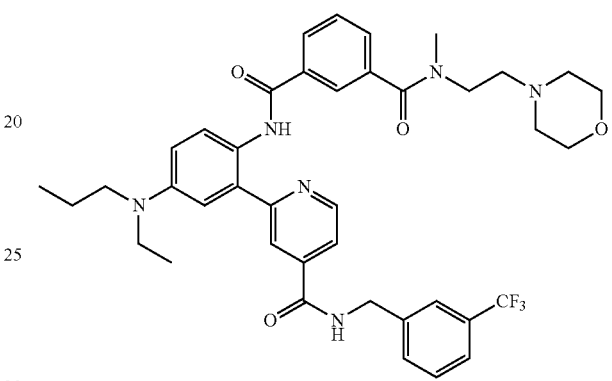

Into a 50-mL round-bottom flask, was placed a solution of N-(3-(trifluoromethyl)benzyl)-2-(2-amino-5-(ethyl(propyl)amino)phenyl)isonicotinamide (150 mg, 0.30 mmol, 1.00 equiv, 90%) in dichloromethane (8 mL), 3-(methyl(2-morpholinoethyl)carbamoyl)benzoic acid (144 mg, 0.44 mmol, 1.50 equiv, 90%), EDC.HCl (126 mg, 0.66 mmol, 2.00 equiv), 4-dimethylaminopyridine (80 mg, 0.66 mmol, 2.00 equiv). The resulting solution was stirred overnight at room temperature. The resulting solution was diluted with 100 mL of ethyl acetate. The resulting mixture was washed with 2×20 mL of NH$_4$Cl aq. and 1×20 mL of sodium bicarbonate (10%). The resulting mixture was washed with 1×20 mL of brine. The mixture was dried over anhydrous sodium sulfate and concentrated under vacuum. The crude product (250 mg) was purified by Prep-HPLC with the following conditions (1#-Waters 2767-3): Column, SunFire Prep C18, 19*150 mm 5 um; mobile phase, water with 0.05% TFA and CH$_3$CN (25% CH$_3$CN up to 39% in 6 min); Detector, Waters2545 UvDector 254&270 nm. 183.7 mg product was obtained. This resulted in 183.7 mg (56%) of N1-(2-(4-((3-(trifluoromethyl)benzyl)carbamoyl)pyridin-2-yl)-4-(ethyl(propyl)amino)phenyl)-N3-methyl-N3-(2-morpholinoethyl)isophthalamide as a yellow solid. LC-MS (ES, m/z) 731 [M+H]$^+$; H-NMR (300 MHz, DMSO, ppm): 9.83 (s, 1H), 9.52 (t, J=18 Hz, 1H), 8.89 (d, J=3 Hz, 1H), 8.26 (s, 1H), 8.13 (s, 1H), 7.99 (m, 2H), 7.82 (d, 1H), 7.54-7.69 (m, 6H), 6.95-7.54 (m, 2H), 4.60 (s, 2H), 3.85-4.02 (m, 4H), 3.64 (m, 4H), 3.36-3.47 (m, 6H), 3.18 (m, 2H), 2.95 (s, 3H), 1.60 (m, 2H), 1.09-1.13 (m, 3H), 0.87-0.92 (m, 3H).

Example 129

N¹-methyl-N³-(4-(methyl(propyl)amino)-2-(4-((3-(trifluoromethyl)benzyl)carbamoyl)pyridin-2-yl)phenyl)-N¹-(2-morpholinoethyl)isophthalamide

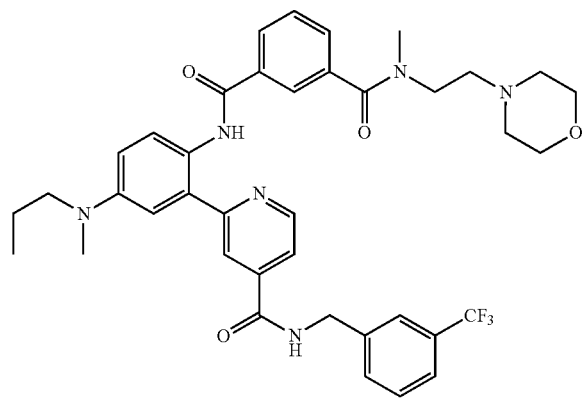 [SMILES: CCCN(C)c1ccc(NC(=O)c2cccc(C(=O)N(C)CCN3CCOCC3)c2)c(-c2cc(C(=O)NCc3cccc(C(F)(F)F)c3)ccn2)c1]

This compound was prepared according to the procedure described for the synthesis of N¹-(4-(diethylamino)-2-(4-((3-(trifluoromethyl)benzyl)carbamoyl)pyridin-2-yl)phenyl)-N³-methyl-N³-(2-morpholinoethyl)isophthalamide 25, using N-methylpropan-1-amine in place of diethylamine. MS (ES, m/z): 717.3 [M+H]⁺.

Example 130

(S)—N1-methyl-N1-(2-morpholinoethyl)-N3-(2-(4-(1,2,3,4-tetrahydronaphthalen-1-ylcarbamoyl)pyridin-2-yl)-4-(trifluoromethyl)phenyl)isophthalamide Scheme 60.

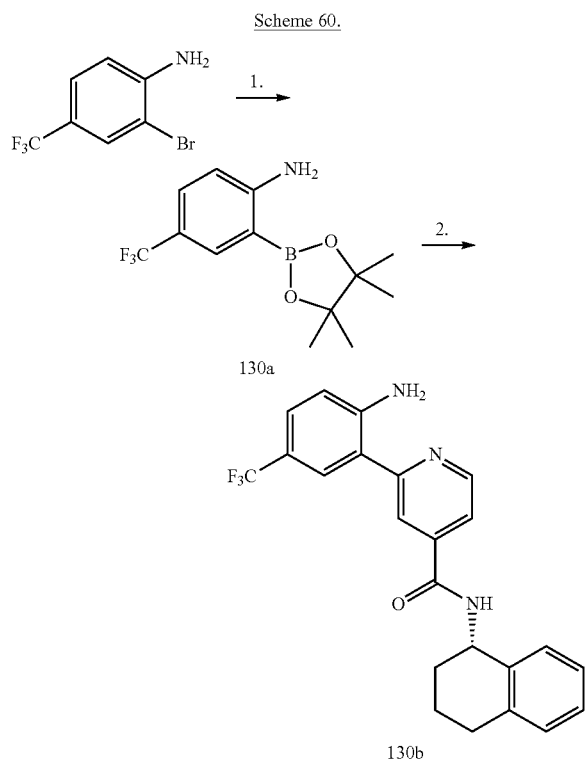

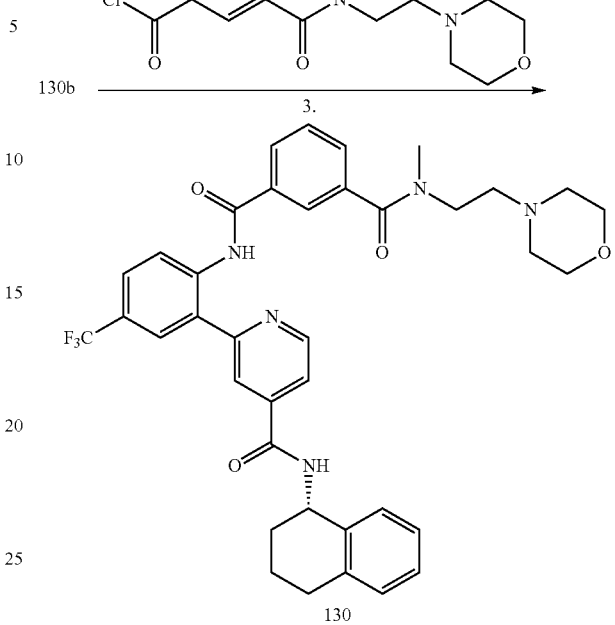

1. PdCl₂(dppf), KOAc, DMSO, 4,4,4',4',5,5,5',5'-octamethyl-2,2'-bi(1,3,2-dioxaborolane) 2. 126c, Pd(PPh₃)₄, Na₂CO₃, H₂O, DME 3. Py, DCM.

Intermediate 130a

Into a 50-mL round-bottom flask purged and maintained with an inert atmosphere of nitrogen, was placed a solution of 2-bromo-4-(trifluoromethyl)benzenamine (1 g, 4.17 mmol, 1.00 equiv) in DMSO (20 mL), 4,4,5,5-tetramethyl-2-(4,4,5,5-tetramethyl-1,3,2-dioxaborolan-2-yl)-1,3,2-dioxaborolane (1.58 g, 6.22 mmol, 1.50 equiv), PdCl₂ (dppf) (91 mg, 0.12 mmol, 0.03 equiv), potassium acetate (1 g, 10.40 mmol, 2.57 equiv). The resulting solution was stirred overnight at 80° C. in an oil bath. The resulting mixture was combined with the solution of the previous batch and then diluted with 100 mL of ethyl acetate. The resulting mixture was washed with 2×100 mL of brine. The mixture was dried over anhydrous sodium sulfate and concentrated under vacuum. The residue was applied onto a silica gel column with ethyl acetate/petroleum ether (1:100). This resulted in 1.2 g of 2-(4,4,5,5-tetramethyl-1,3,2-dioxaborolan-2-yl)-4-(trifluoromethyl)benzenamine as a yellow solid.

Intermediate 130b

Into a 100-mL 3-necked round-bottom flask purged and maintained with an inert atmosphere of nitrogen, was placed a solution of 2-(4,4,5,5-tetramethyl-1,3,2-dioxaborolan-2-yl)-4-(trifluoromethyl)benzenamine (1.2 g, 4.18 mmol, 1.00 equiv) in ethylene glycol dimethyl ether (40 mL), (S)-2-bromo-N-(1,2,3,4-tetrahydronaphthalen-1-yl)isonicotinamide (1.38 g, 4.17 mmol, 1.00 equiv), Pd(PPh₃)₄, (480 mg, 0.42 mmol, 0.10 equiv), a solution of sodium carbonate (2.22 g, 20.94 mmol, 5.00 equiv) in water (20 mL). The resulting solution was stirred for 1 h at 80° C. in an oil bath. The resulting solution was diluted with 100 mL of ethyl acetate.

The resulting mixture was washed with 2×100 mL of brine. The mixture was dried over anhydrous sodium sulfate and concentrated under vacuum. The residue was applied onto a silica gel column with petroleum ether/ethyl acetate (5:1). This resulted in 900 mg (65%) of (S)-2-(2-amino-5-(trifluoromethyl)phenyl)-N-(1,2,3,4-tetrahydronaphthalen-1-yl)isonicotinamide as a yellow solid.

Example 130

Into a 25-mL round-bottom flask, was placed a solution of (S)-2-(2-amino-5-(trifluoromethyl)phenyl)-N-(1,2,3,4-tetrahydronaphthalen-1-yl)isonicotinamide (200 mg, 0.49 mmol, 1.00 equiv) in dichloromethane (6 mL), pyridine (3 mL). This was followed by the addition of a solution of 3-(methyl(2-morpholinoethyl)carbamoyl)benzoyl chloride (230 mg, 0.74 mmol, 1.50 equiv) in dichloromethane (1 mL) dropwise with stirring. The resulting solution was stirred for 3 h at room temperature. The pH value of the solution was adjusted to 7 with 10% hydrochloric acid. The resulting solution was extracted with 2×100 mL of ethyl acetate and the organic layers combined and concentrated under vacuum. The crude product (200 mg) was purified by Prep-HPLC with the following conditions (1#-Waters 2767-3): Column, SunFire Prep C18, 19*150 mm 5 um; mobile phase, water with 0.05% TFA and CH$_3$CN (40% CH$_3$CN up to 54% in 6 min); Detector, Waters2545 UvDector 254&270 nm. 93.7 mg product was obtained. This resulted in 93.7 mg (21%) of (S)—N1-methyl-N1-(2-morpholinoethyl)-N3-(2-(4-(1,2,3,4-tetrahydronaphthalen-1-ylcarbamoyl)pyridin-2-yl)-4-(trifluoromethyl)phenyl)isophthalamide as a light yellow solid. LC-MS (ES, m/z): 686 [M+H]$^+$; H-NMR (300 MHz, DMSO, ppm): 13.29 (s, 1H), 9.28 (d, J=8.7 Hz, 1H), 8.96 (d, J=5.1 Hz, 1H), 8.77 (d, J=8.7 Hz, 1H), 8.46 (s, 1H), 8.34 (s, 1H), 8.10 (m, 2H), 7.97 (m, 2H), 7.78 (m, 2H), 7.18 (m, 4H), 5.29 (d, J=5.7 Hz, 1H), 3.69 (m, 10H), 3.21 (s, 2H), 2.98 (s, 4H), 2.82 (m, 2H), 2.03 (m, 4H).

Example 131

(S)—N$^1$-(4-(diethylamino)-2-(4-((1,2,3,4-tetrahydronaphthalen-1-yl)carbamoyl)pyridin-2-yl)phenyl)-N$^3$-methyl-N$^3$-(2-morpholinoethyl)isophthalamide Scheme 61.

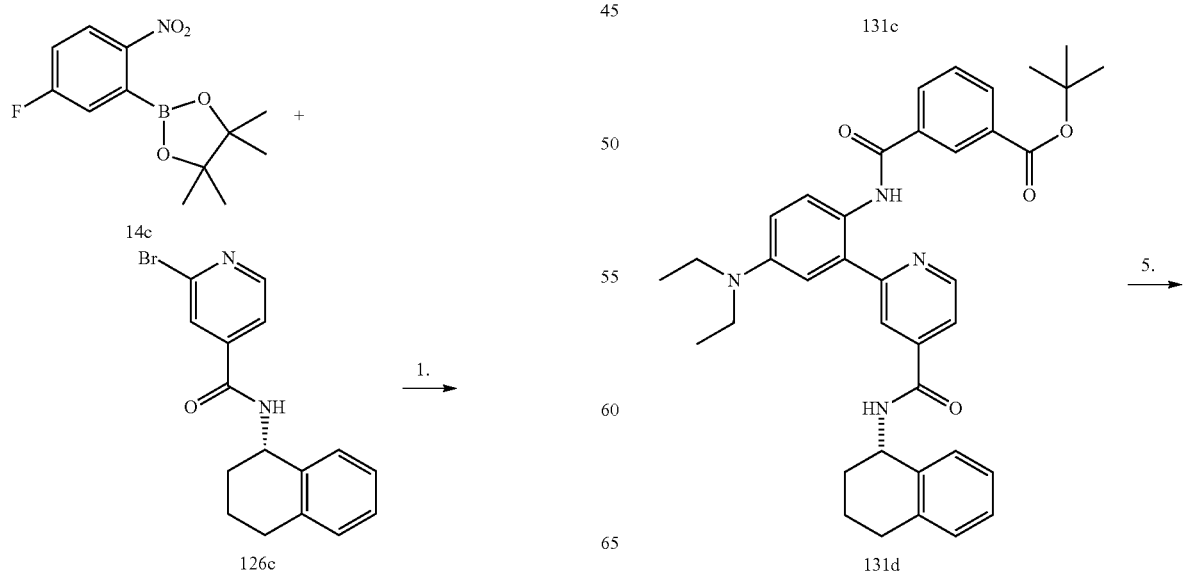

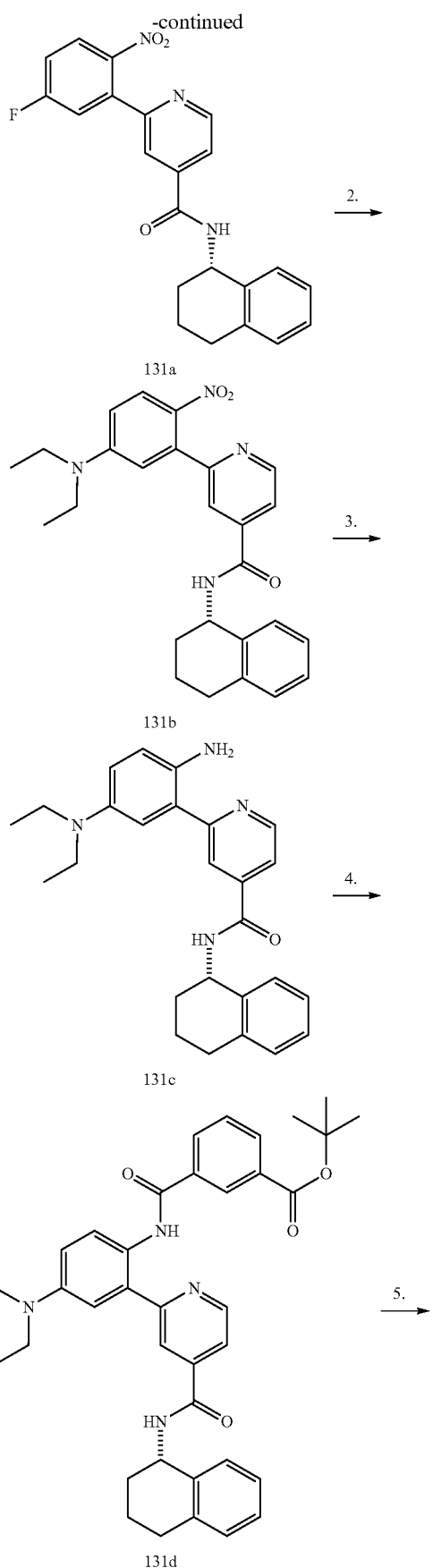

-continued

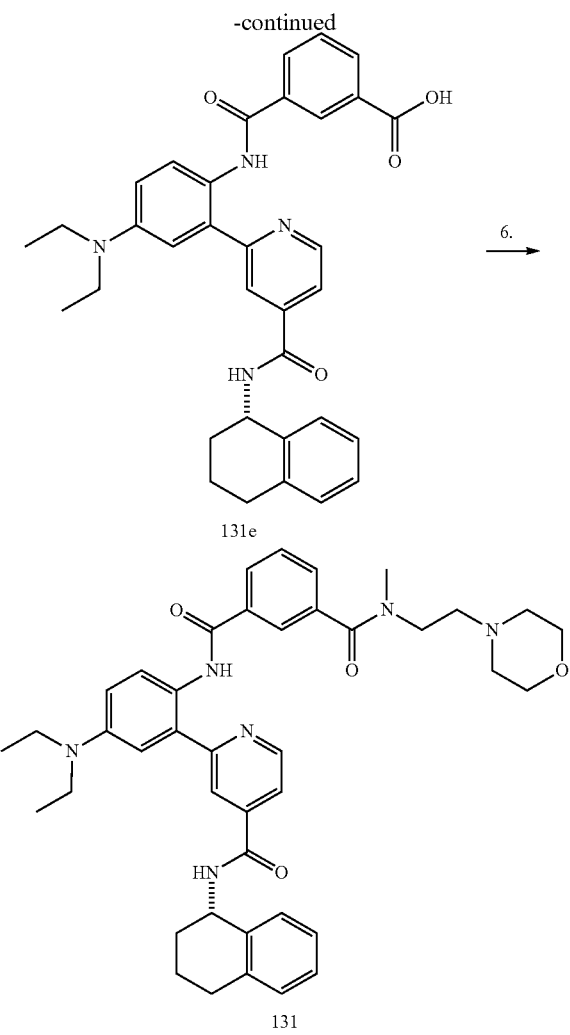

131

Pd(PPh₃)₄, Na₂CO₃, DME, H₂O 2. diethylamine, K₂CO₃, DMF; 3. Pd/C, H₂, MeOH; 4. 3-(tert-butoxycarbonyl)benzoic acid, HATU, DIEA, DMF; 5. 4M HCl in dioxane; 6. N-methyl-2-morpholinoethanamine, HATU, DIEA, DMF.

Intermediate 131a

Into a 1000-mL 3-necked round-bottom flask purged and maintained with an inert atmosphere of nitrogen, was placed a solution of 2-(5-fluoro-2-nitrophenyl)-4,4,5,5-tetramethyl-1,3,2-dioxaborolane (10.7 g, 40.07 mmol, 1.20 equiv) in ethylene glycol dimethyl ether (300 mL), (S)-2-bromo-N-(1,2,3,4-tetrahydronaphthalen-1-yl)isonicotinamide (11.05 g, 33.38 mmol, 1.00 equiv), Pd(PPh₃)₄ (3.86 g, 3.34 mmol, 0.10 equiv), a solution of sodium carbonate (17.69 g, 166.89 mmol, 5.00 equiv) in water (150 mL). The resulting solution was stirred for 18 h at 80° C. in an oil bath. The resulting solution was diluted with 100 mL of water. The resulting solution was extracted with 2×100 mL of ethyl acetate and the organic layers combined and dried over sodium sulfate and concentrated under vacuum. The residue was applied onto a silica gel column with petroleum ether/ethyl acetate (10:1-1:1). This resulted in 5.0014 g (32%) of (S)-2-(5-fluoro-2-nitrophenyl)-N-(1,2,3,4-tetrahydronaphthalen-1-yl)isonicotinamide as a yellow solid. LC-MS (ES, m/z): 392 [M+H]⁺ H-NMR (400 MHz, CDCl₃, ppm): 8.73 (d, J=3.9 Hz, 1H), 8.02-7.98 (m, 1H), 7.83 (s, 1H), 7.60-7.58 (m, 1H), 7.32-7.13 (m, 6H), 6.45 (d, J=9.0 Hz, 1H), 5.42-5.38 (m, 1H), 2.89-2.77 (m, 2H), 2.20-2.13 (m, 1H), 2.01-1.90 (m, 3H).

Intermediate 131b: (S)-2-(5-(diethylamino)-2-nitrophenyl)-N-(1,2,3,4-tetrahydronaphthalen-1-yl)isonicotinamide A mixture of (S)-2-(5-fluoro-2-nitrophenyl)-N-(1,2,3,4-tetrahydronaphthalen-1-yl)isonicotinamide (12.77 mmol, 5 g), diethylamine (25.55 mmol, 1.87 g), and K₂CO₃ (31.93 mmol, 4.41 g) in DMF (30 mL) was stirred at 60° C. overnight. The mixture was diluted with ethyl acetate, and the resulting solution was washed with water (2×), and then with brine. The solution was dried (Na₂SO₄) and the solvent was removed at reduced pressure. The residue was purified by chromatography on silica gel to give a yellow solid. (4.73 g, 83%).

Intermediate 131c: (S)-2-(2-amino-5-(diethylamino)phenyl)-N-(1,2,3,4-tetrahydronaphthalen-1-yl)isonicotinamide A mixture of (S)-2-(5-(diethylamino)-2-nitrophenyl)-N-(1,2,3,4-tetrahydronaphthalen-1-yl)isonicotinamide (4.73 g) and 10% Pd/C (1.3 g) in methanol (20 mL) was stirred under a hydrogen atmosphere for 2 h. The mixture was filtered and concentrated to give a brown solid (4 g, 91%).

Intermediate 131d: (S)-tert-butyl 3-((4-(diethylamino)-2-(4-((1,2,3,4-tetrahydronaphthalen-1-yl)carbamoyl)pyridin-2-yl)phenyl)carbamoyl)benzoate To a mixture of (S)-2-(2-amino-5-(diethylamino)phenyl)-N-(1,2,3,4-tetrahydronaphthalen-1-yl)isonicotinamide (7.1 mmol, 2.94 g), 3-(tert-butoxycarbonyl)benzoic acid (8.52 mmol, 1.89 g) and DIEA (35.5 mmol, 4.59 g) in DMF (16 mL) was added HATU (8.52 mmol, 3.24 g). The mixture was stirred at 60° C. for 1 h. The reaction mixture was diluted with ethyl acetate, washed with water (2×), brine (1×), dried and concentrated. The residue was purified by column to give a yellow solid (4.31 g, 98%).

Intermediate 131e: (S)-3-((4-(diethylamino)-2-(4-((1,2,3,4-tetrahydronaphthalen-1-yl)carbamoyl)pyridin-2-yl)phenyl)carbamoyl)benzoic acid To ((S)-tert-butyl 3-((4-(diethylamino)-2-(4-((1,2,3,4-tetrahydronaphthalen-1-yl)carbamoyl)pyridin-2-yl)phenyl)carbamoyl)benzoate (4.31 g) was added 4M HCl in dioxane (20 mL). The mixture was stirred at room temperature for 5 h, concentrated to give a yellow solid which was used without further purification.

Example 131

(S)—N¹-(4-(diethylamino)-2-(4-((1,2,3,4-tetrahydronaphthalen-1-yl)carbamoyl)pyridin-2-yl)phenyl)-N³-methyl-N³-(2-morpholinoethyl)isophthalamide To a mixture of (S)-3-((4-(diethylamino)-2-(4-((1,2,3,4-tetrahydronaphthalen-1-yl)carbamoyl)pyridin-2-yl)phenyl)carbamoyl)benzoic acid (1.81 mmol, 1.15 g), N-methyl-2-morpholinoethanamine (2.17 mmol, 0.313 g) and DIEA (12.67 mmol, 1.64 g) in DMF (5 mL) was added HATU (2.17 mmol, 0.826 g), and the mixture was stirred at 60° C. for 2 h. The reaction mixture was diluted with ethyl acetate, washed with water (2×), brine (1×), dried and concentrated. The residue was purified by column to give a yellow solid (0.98 g, 79%). MS (ESI, m/z) 689.28 [M+H]+.

Example 132

Scheme 62.

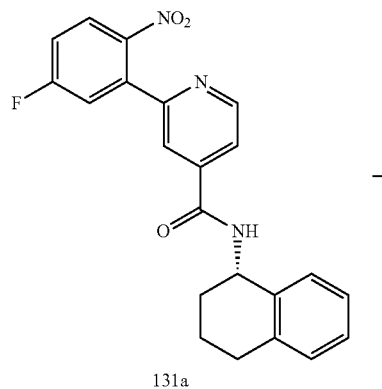

131a

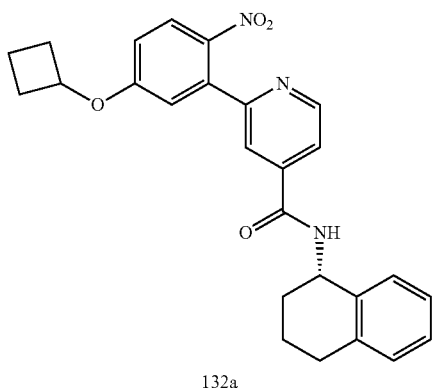

132a

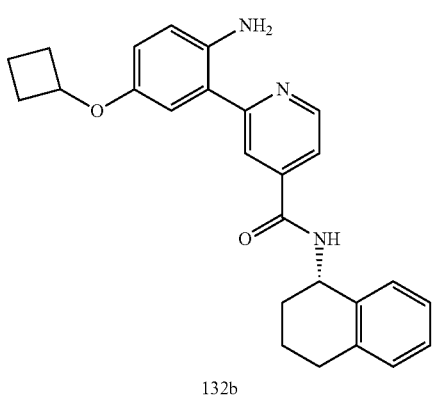

132b

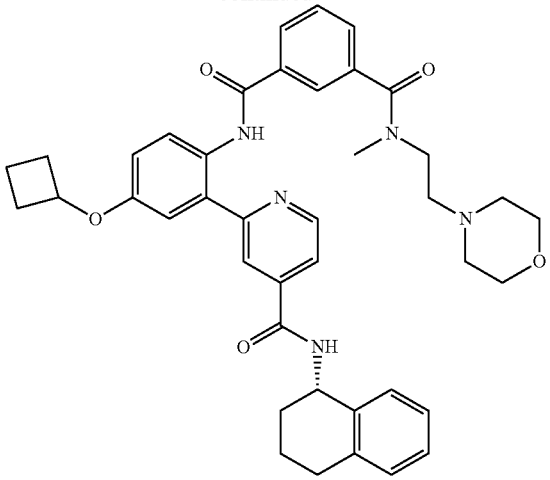

132

1. Cyclobutanol DMF, NaH 2. Pd/C, H₂, MeOH 3. 80e, EDC·HCl, DMAP, DCM.

Intermediate 132a

To a suspension of sodium hydride (100 mg, 4.17 mmol, 2.04 equiv, 100%) in N,N-dimethylformamide (25 mL) under an inert atmosphere of nitrogen, was added cyclobutanol (200 mg, 2.77 mmol, 1.36 equiv, 100%) dropwise with stirring at 0° C. over 5 min. To the resulting solution was added 2-(5-fluoro-2-nitrophenyl)-N—((S)-1,2,3,4-tetrahydronaphthalen-1-yl)isonicotinamide (800 mg, 2.04 mmol, 1.00 equiv, 100%) at 0° C. The resulting solution was stirred for 3 h at room temperature. The reaction was then quenched by the addition of 15 mL of water. The resulting solution was extracted with 3×20 mL of ethyl acetate and the organic layers combined. The resulting mixture was washed with 1×20 mL of brine. The mixture was dried over anhydrous sodium sulfate and concentrated under vacuum. This resulted in 0.92 g (95%) of 2-(5-cyclobutoxy-2-nitrophenyl)-N—((S)-1,2,3,4-tetrahydronaphthalen-1-yl)isonicotinamide as yellow oil.

Intermediate 132b

Into a 100-mL round-bottom flask, was placed a solution of 2-(5-cyclobutoxy-2-nitrophenyl)-N—((S)-1,2,3,4-tetrahydronaphthalen-1-yl)isonicotinamide (920 mg, 2.07 mmol, 1.00 equiv, 100%) in methanol (30 mL), Palladium carbon (800 mg, 10%). Hydrogen gas was introduced to the reaction vessel The resulting solution was stirred overnight at room temperature. The solids were filtered out. The resulting mixture was concentrated under vacuum. The residue was applied onto a silica gel column with ethyl acetate/petroleum ether (1:5). This resulted in 0.42 g (48%) of 2-(2-amino-5-cyclobutoxyphenyl)-N—((S)-1,2,3,4-tetrahydronaphthalen-1-yl) isonicotinamide as light yellow oil. LC-MS (ES, m/z): 414 [M+H]+ H-NMR (300 MHz, CDCl3, ppm): 8.71 (d, J=5.1 Hz, 1H), 7.69 (s, 1H), 7.52 (d, J=1.5 Hz, 1H), 7.51~7.16 (m, 4H), 7.09 (d, J=2.7 Hz, 1H), 6.86~6.76 (m, 2H), 6.47 (d, J=8.1 Hz, 1H), 5.44 (d, J=7.2 Hz, 1H), 4.65~4.60 (m, 1H), 2.91~2.84 (m, 2H), 2.49~2.39 (m, 4H), 2.23~2.14 (m, 5H) 2.06~4.88 (m, 1H).

Example 132

Into a 100-mL round-bottom flask, was placed a solution of 2-(2-amino-5-cyclobutoxyphenyl)-N—((S)-1,2,3,4-tetrahydronaphthalen-1-yl)isonicotinamide (100 mg, 0.24 mmol, 1.00 equiv, 100%) in dichloromethane (20 mL), 3-(methyl(2-morpholinoethyl)carbamoyl)benzoic acid (80 mg, 0.27 mmol, 1.13 equiv, 100%), 4-dimethylaminopyridine (44 mg, 0.36 mmol, 1.49 equiv, 100%), EDCI (69 mg, 0.36 mmol, 1.49 equiv, 100%). The resulting solution was stirred overnight at room temperature. The reaction progress was monitored by LCMS. The resulting mixture was washed with 2×10 mL of water. The mixture was dried over anhydrous sodium sulfate and concentrated under vacuum. The crude product (0.15 g) was purified by Prep-HPLC with the following conditions (1#-Waters 2767-3): Column, SunFire Prep C18, 19*150 mm 5 um; mobile phase, water with 0.05% TFA and $CH_3CN$ (36% $CH_3CN$ up to 52% in 6 min); Detector, Waters2545 UvDector 254&270 nm. 84 mg product was obtained. This resulted in 108.4 mg (65%) of N1-(2-(4-(((S)-1,2,3,4-tetrahydronaphthalen-1-yl)carbamoyl)pyridin-2-yl)-4-cyclobutoxyphenyl)-N3-methyl-N3-(2-morpholinoethyl)isophthalamide as a light yellow solid. LC-MS (ES, m/z): 688 $[M+H]^+$ H-NMR (300 MHz, DMSO, ppm): 12.52 (s, 1H), 9.27 (d, J=8.7 Hz, 1H), 8.89 (d, J=5.1 Hz, 1H), 8.32 (d, J=8.7 Hz, 2H), 8.04~8.00 (m, 2H), 7.89~7.87 (m, 2H), 7.69~7.64 (m, 1H), 7.58 (d, J=3.0 Hz, 1H), 7.22~7.12 (m, 4H), 7.05~7.02 (m, 1H), 5.26 (d, J=6.0 Hz, 1H), 4.78~4.76 (t, 1H), 4.03 (s, 2H), 3.87 (s, 2H), 3.21 (s, 2H), 2.97 (s, 4H), 2.80 (d, J=5.1 Hz, 2H), 2.08 (d. J=7.5 Hz, 4H), 2.04~1.99 (m, 4H).

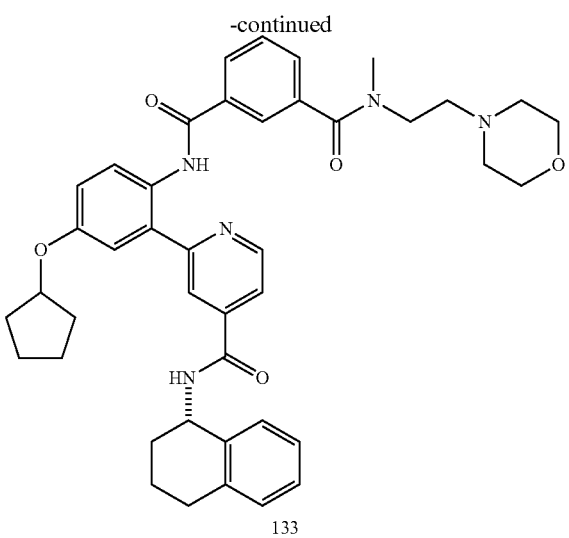

133

1. 3-(methyl(2-morpholinoethyl)carbamoyl)benzoic acid, HATU, DIEA, DMF.

Example 133

(S)—$N^1$-(4-(cyclopentyloxy)-2-(4-((1,2,3,4-tetrahydronaphthalen-1-yl)carbamoyl)pyridin-2-yl)phenyl)-$N^3$-methyl-$N^3$-(2-morpholinoethyl)isophthalamide

Intermediate 133a: (S)-2-(2-amino-5-(cyclopentyloxy)phenyl)-N-(1,2,3,4-tetrahydronaphthalen-1-yl)isonicotinamide This intermediate was prepared according to the procedure described for the synthesis of (S)-2-(2-amino-5-cyclobutoxyphenyl)-N-(1,2,3,4-tetrahydronaphthalen-1-yl)isonicotinamide Example 132, using cyclopentanol in place of cyclobutanol.

Example 133

(S)—$N^1$-(4-(cyclopentyloxy)-2-(4-((1,2,3,4-tetrahydronaphthalen-1-yl)carbamoyl)pyridin-2-yl)phenyl)-$N^3$-methyl-$N^3$-(2-morpholinoethyl)isophthalamide To a mixture of (S)-2-(2-amino-5-(cyclopentyloxy)phenyl)-N-(1,2,3,4-tetrahydronaphthalen-1-yl)isonicotinamide (0.076 mmol, 32 mg), 3-(methyl(2-morpholinoethyl)carbamoyl)benzoic acid (0.083 mmol, 24 mg) and DIEA (0.38 mmol, 49 mg) in DMF (0.25 mL) was added HATU (0.083 mmol, 32 mg). The mixture was stirred at 60° C. overnight and purified by prep. HPLC to give Example 133 as a yellow solid (36 mg, 51%). MS (ES, m/z): 703.3 $[M+H]^+$.

Scheme 63a.

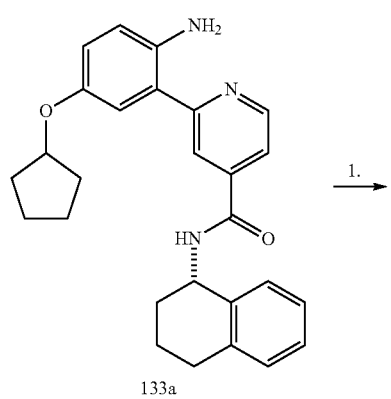

133a

Example 134
2-(3-(3-(4-(piperidin-1-yl)-2-(4-(3-(trifluoromethyl)
benzylcarbamoyl)pyridin-2-yl)phenylcarbamoyl)
benzylthio)phenoxy)acetic acid
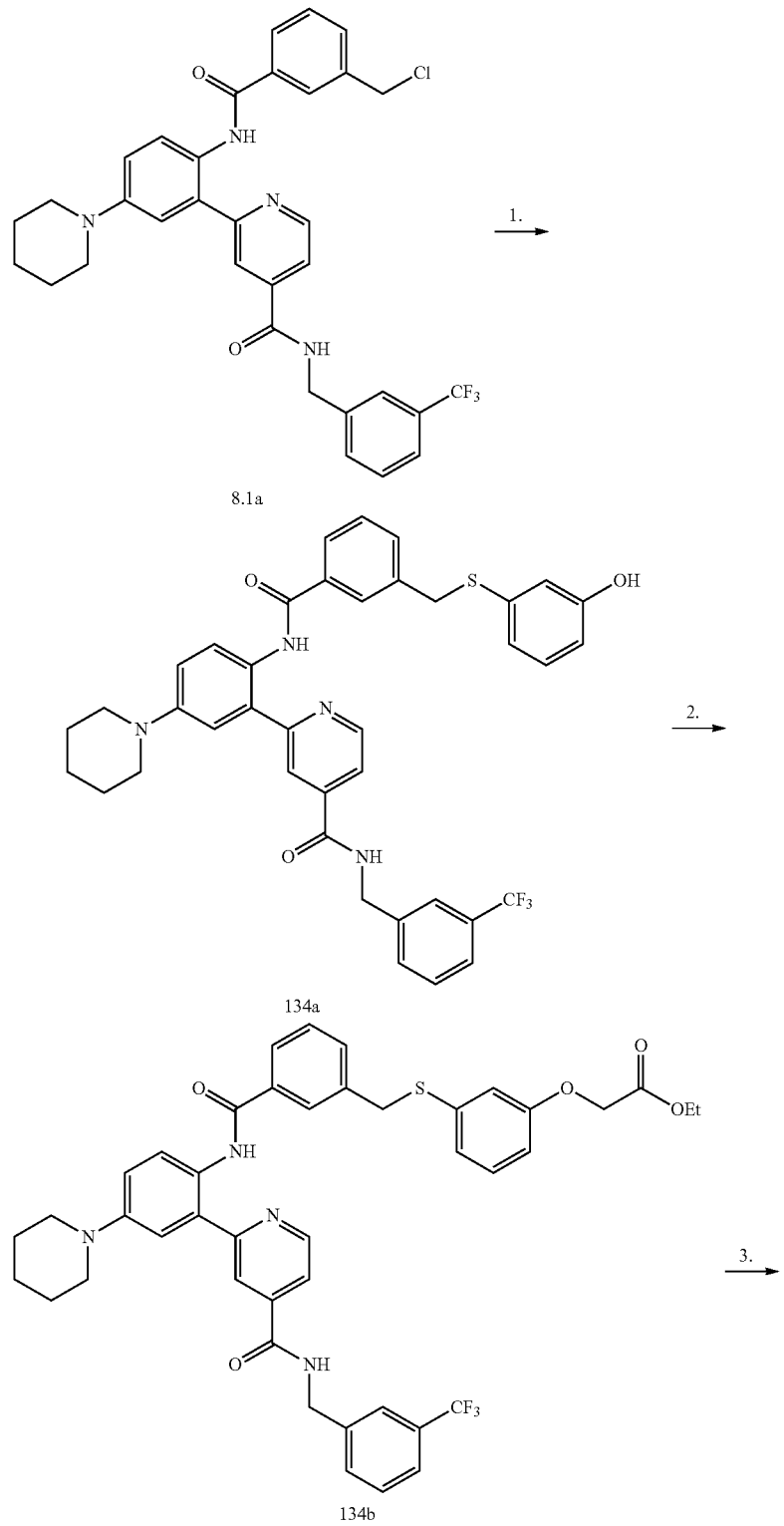
Scheme 63b.

-continued

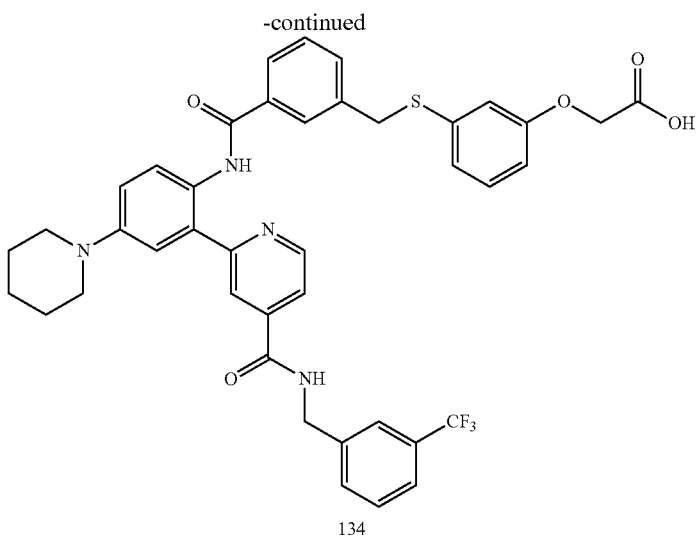

134

1. 3-mercaptophenol, $K_2CO_3$, DMF; 2. ethyl 2-bromoacetate, sodium iodide, $K_2CO_3$, DMF; 3. LiOH.

Intermediate 134a: 2-(2-(3-((3-hydroxyphenylthio)methyl)benzamido)-5-(piperidin-1-yl)phenyl)-N-(3-(trifluoromethyl)benzyl)isonicotinamide A mixture of 8.1a (300 mg, 0.49 mmol), 3-mercaptophenol (66 μL, 0.59 mmol), and $K_2CO_3$ (75 mg, 1.5 mmol) in dry DMF (3 mL) was stirred at for 1 h and then filtered. The filtrate was poured into $H_2O$ (50 mL), forming a yellow precipitate. The solid was filtered, then dissolved in DCM and washed with aqueous HCl, saturated aqueous $NaHCO_3$, and $H_2O$. The solvent was then removed to give 298 mg (87%) of the product 134a as a yellow solid.

Example 134

2-(3-(3-(4-(piperidin-1-yl)-2-(4-(3-(trifluoromethyl)benzylcarbamoyl)pyridin-2-yl)phenylcarbamoyl)benzylthio)phenoxy)acetic acid A mixture of 134a (74 mg, 0.11 mmol), ethyl 2-bromoacetate (21 mg, 0.13 mmol), sodium iodide (1 mg, 0.05 mmol), and $K_2CO_3$ (37 mg, 0.27 mmol) were combined in dry DMF and the suspension heated to 100° C. and stirred for 1 h. The suspension was poured into $H_2O$ (100 mL), resulting in the formation of a yellow precipitate, which was filtered. The solid was dissolved in DCM and washed with aqueous HCl, saturated aqueous $NaHCO_3$, and $H_2O$, then dried over $Na_2SO_4$ and the solvent removed to give intermediate 134b. The residue was dissolved in dioxane (2 mL) and $H_2O$ (1 mL), to which $LiOH.H_2O$ (7 mg, 0.16 mmol) was added the solution stirred for 1 h. The solution was then acidified and purified by reverse-phase HPLC eluting with a water/acetonitrile gradient containing 0.1% TFA. The process resulted in 62 mg (60%) of the product Example 134 as the di-TFA salt. MS (ES, m/z) 755 [M+H]⁺.

Example 135

3-(2-(2-(2-(N-methyl-3-(3-(4-(piperidin-1-yl)-2-(4-(3-(trifluoromethyl)benzylcarbamoyl)pyridin-2-yl)phenylcarbamoyl)benzylthio)benzamido)ethoxy)ethoxy)ethoxy)propanoic acid Scheme 64.

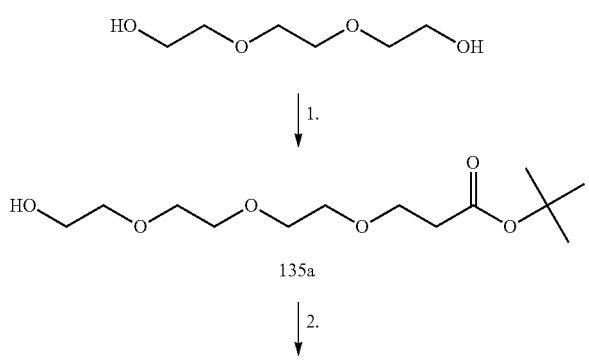

135a

-continued
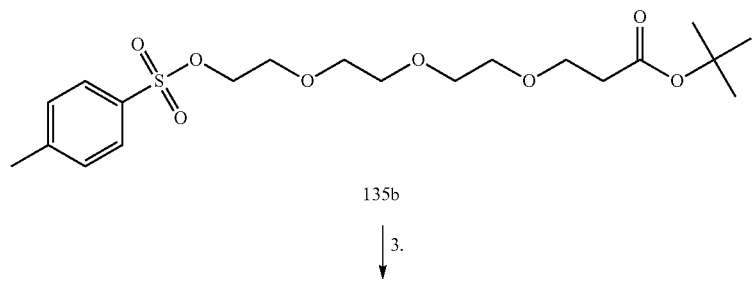
135b
↓ 3.
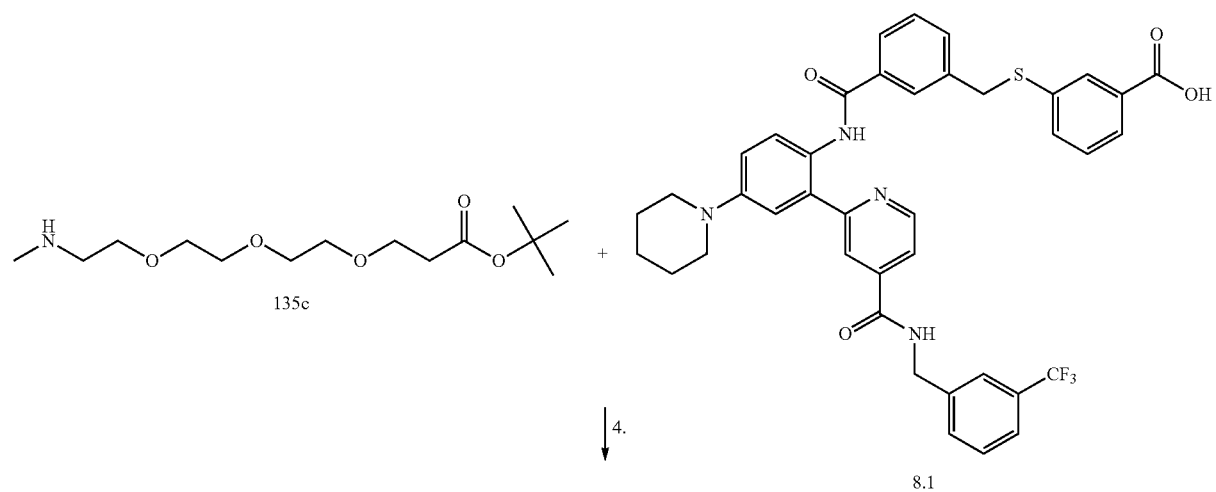
↓ 4.
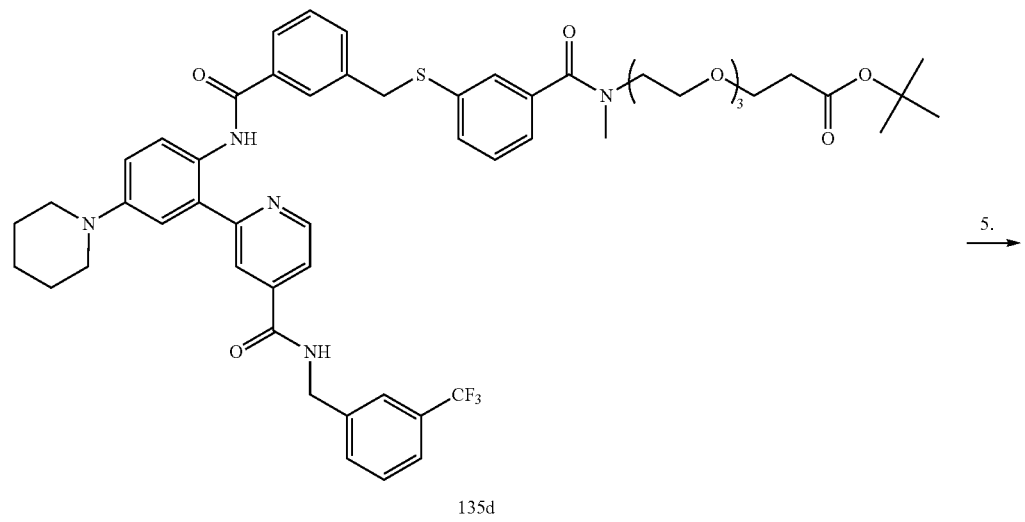
135d
→ 5.

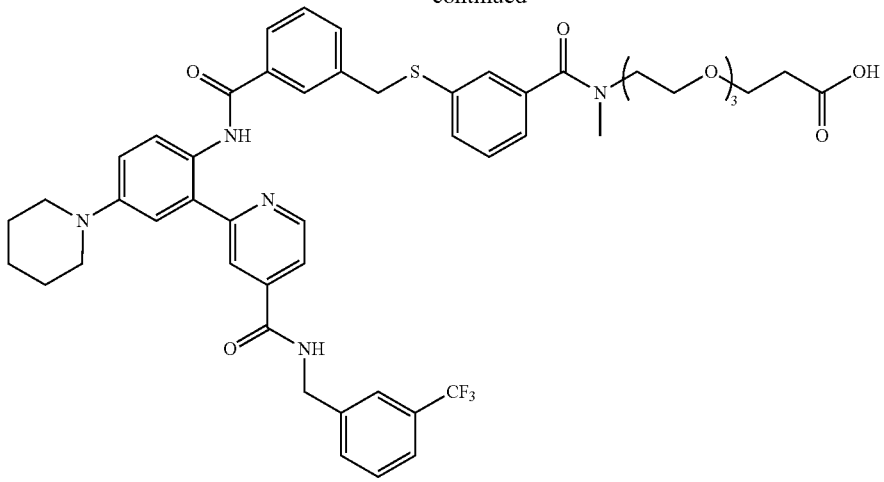

135

1. tert-butyl acrylate, Na, THF 2. 4-methylbenzene-1-sulfonyl chloride, pyridine 3. 2-methoxyethanamine 4. HATU, DIEA, DMF; 5. TFA, DCM.

Into a 1000-mL round-bottom flask, was placed a solution of 2,2'-(2,2'-oxybis(ethane-2,1-diyl)bis,2-diylbis(oxy))diethanol (82 g, 546.05 mmol, 3.50 equiv) in tetrahydrofuran (300 mL), sodium (110 mg, 4.78 mmol, 0.03 equiv). This was followed by the addition of tert-butyl acrylate (20 g, 156.04 mmol, 1.00 equiv) dropwise with stirring at room temperature. The resulting solution was stirred overnight at room temperature. The pH value of the solution was adjusted to 7 with 1M hydrochloric acid. The resulting solution was extracted with 3×100 mL of ethyl acetate and the organic layers combined. The resulting mixture was washed with 3×100 mL of brine. The mixture was dried over anhydrous sodium sulfate and concentrated under vacuum. This resulted in 36.6 g (84%) of tert-butyl 3-(2-(2-(2-hydroxyethoxy)ethoxy)ethoxy)propanoate as yellow oil.

Into a 250-mL round-bottom flask, was placed a solution of tert-butyl 3-(2-(2-(2-hydroxyethoxy)ethoxy)ethoxy)propanoate (10 g, 35.97 mmol, 1.00 equiv) in pyridine (40 mL). This was followed by the addition of 4-methylbenzene-1-sulfonyl chloride (6.8 g, 35.79 mmol, 1.00 equiv), in portions at 0° C. The resulting solution was stirred for 4 h at 0° C. The resulting mixture was concentrated under vacuum. The residue was dissolved in 30 ml of dichloromethane. The resulting mixture was washed with 3×20 mL of 3% hydrochloric acid (aq). The resulting mixture was washed with 20 mL of sodium chloride (aq). The mixture was dried over sodium sulfate and concentrated under vacuum. This resulted in 14 g (90%) of tert-butyl 3-(2-(2-(2-(tosyloxy)ethoxy)ethoxy)ethoxy)propanoate as yellow oil.

Into a 250-mL sealed bottle, was placed a solution of tert-butyl 3-(2-(2-(2-(tosyloxy)ethoxy)ethoxy)ethoxy)propanoate (14 g, 32.41 mmol, 1.00 equiv) in tetrahydrofuran (5 mL), $CH_3NH_2$ (66.9 g, 712.16 mmol, 21.98 equiv, 33% in ethanol). The resulting solution was stirred overnight at 50° C. The resulting mixture was concentrated under vacuum. The residue was dissolved in 150 ml of dichloromethane. The resulting mixture was washed with 2×150 mL of water. The resulting mixture was washed with 1×150 mL of sodium chloride (aq). The mixture was dried over sodium sulfate and concentrated under vacuum. This resulted in 8.2 g (87%) of tert-butyl 3-(2-(2-(2-(methylamino)ethoxy)ethoxy)ethoxy) propanoate as yellow oil.

The following intermediates were prepared as depicted in scheme 64 by substituting appropriate alcohols in place of 135a then displacing the sulfonate in step 3 with amines, amides or potassium thioacetate with or without the addition of a suitable base.

TABLE 7

| Intermediate | Alcohol | Nucleophile | Intermediate |
|---|---|---|---|
| 135c.1 | 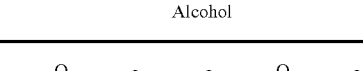 | Methylamine | 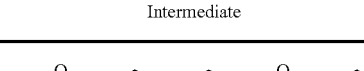 |

TABLE 7-continued

| Intermediate | Alcohol | Nucleophile | Intermediate |
|---|---|---|---|
| 135c.2 | | 2-methoxyethanamine | |
| 135c.3 | | KSAc | |
| 135c.4 | | 2-methoxyethanamine | |
| 135c.5* | | tert-butyl oxopiperazine-1-carboxylate | |
| 135c.6 ** | | NaN₃ | |

*For intermediate 135c.5 the product was obtained after acidic deprotection of the displacement product.
**For intermediate 135c.6 the product was obtained after catalytic hydrogenation of the displacement product.

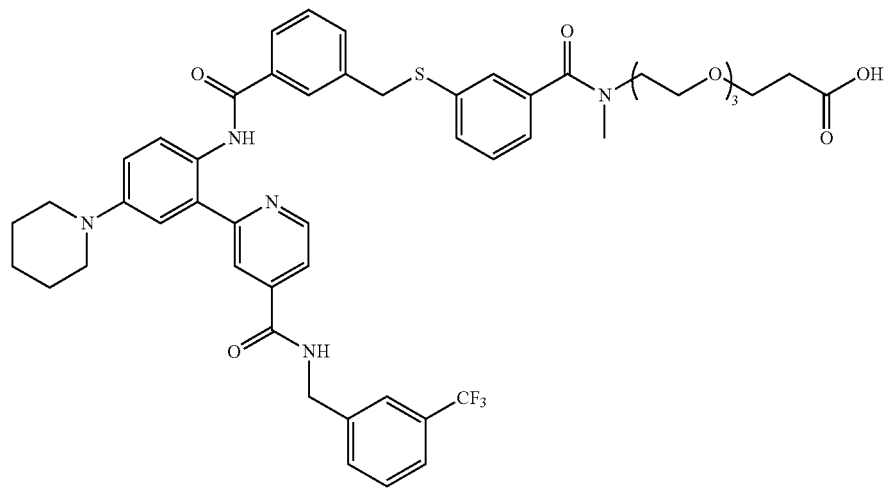

This compound was prepared using the method described for the preparation of Example 10.1, using tert-butyl 3-(2-(2-(2-(methylamino)ethoxy)ethoxy)ethoxy)propanoate 135c in place of tert-butyl 3-(2-(2-(2-aminoethoxy)ethoxy)ethoxy)propanoate. MS (ES, m/z) 942 [M+H]⁺.

Example 136

2-(2-(3-((3-(2-(methyl(2-morpholinoethyl)amino)-2-oxoethyl)phenylthio)methyl)benzamido)-5-(piperidin-1-yl)phenyl)-N-(3-(trifluoromethyl)benzyl)isonicotinamide

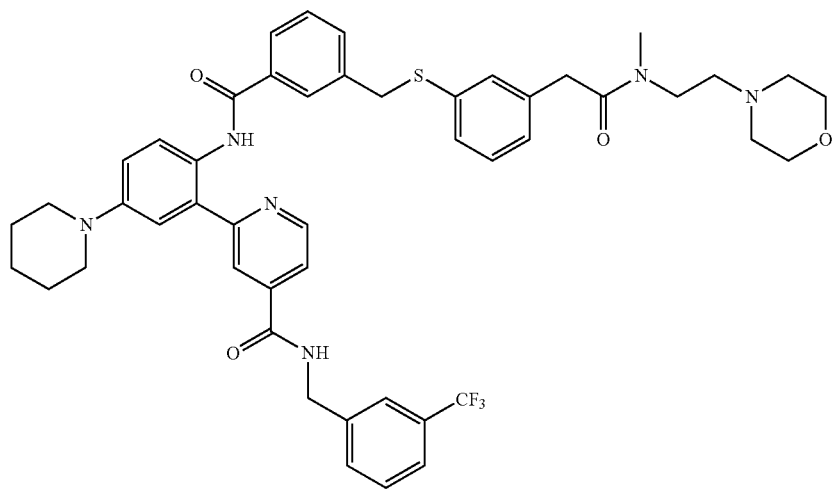 [SMILES: CN(CCN1CCOCC1)C(=O)Cc1cccc(SCc2cccc(C(=O)Nc3ccc(N4CCCCC4)cc3-c3cc(C(=O)NCc4cccc(C(F)(F)F)c4)ccn3)c2)c1]

This compound was prepared using the method described for the preparation of Example 10.1a, using 8.18 in place of 8.1 and N-methyl-2-morpholinoethanamine in place of tert-butyl 3-(2-(2-(2-aminoethoxy)ethoxy)ethoxy)propanoate. MS (ES, m/z) 865 [M+H]⁺.

Examples 137-141

The compounds presented in Table 8 were prepared using the procedure described for the preparation of intermediate 10.1, using 8.18 in place of 8.1.

TABLE 8

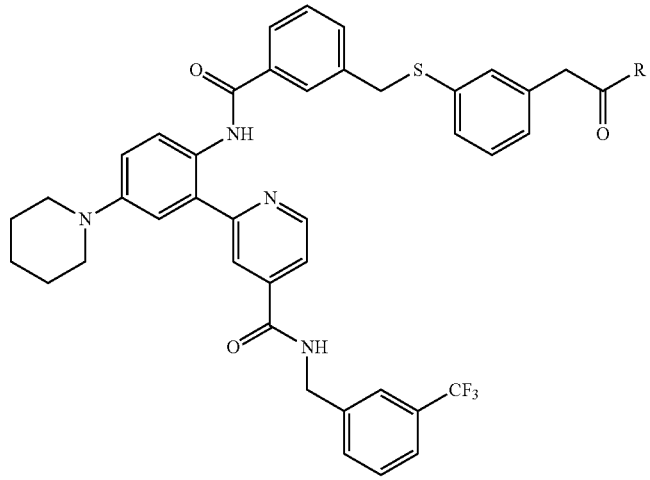

| Example No. | R | Mass Spectrum |
|---|---|---|
| 137 | —NH(CH$_2$CH$_2$O)$_3$CH$_2$CH$_2$COOH | 942 [M + H] |
| 138 | —N(Me)(CH$_2$CH$_2$O)$_3$CH$_2$CH$_2$COOH | 956 [M + H] |
| 139 | —NHCH$_2$COOH | 796 [M + H] |

TABLE 8-continued

| 140 | —NHCH$_2$CH$_2$COOH | 810 [M + H] |
|---|---|---|
| 141 | —NHCH$_2$CH$_2$CH$_2$COOH | 824 [M + H] |

Example 142

1-(3-{[4-(piperidin-1-yl)-2-(4-{[(1S)-1,2,3,4-tetrahydronaphthalen-1-yl]carbamoyl}pyridin-2-yl)phenyl]carbamoyl}phenyl)-5,8,11,14-tetraoxa-2-thiaheptadecan-17-oic acid Scheme 65.

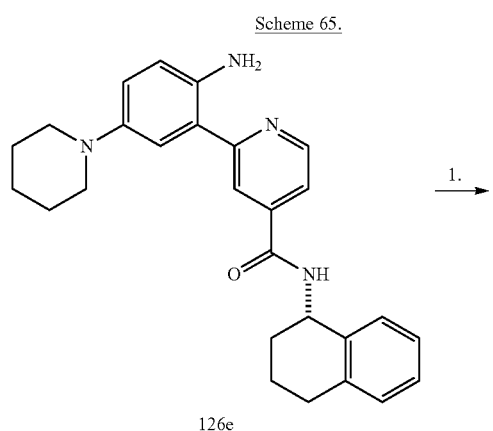

126e

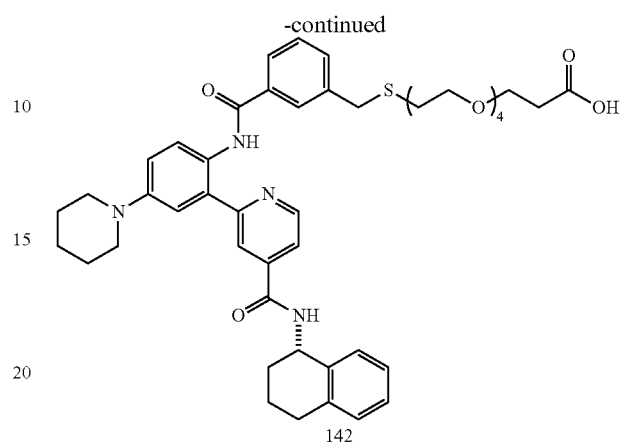

142

1. 3-(chloromethyl)benzoyl chloride, diisopropylethylamine, DCM; 2. 1-mercapto-3,6,9,12-tetraoxapentadecan-15-oic acid, K$_2$CO$_3$, DMF.

Intermediate 142a: (S)-2-(2-(3-(chloromethyl)benzamido)-5-(piperidin-1-yl)phenyl)-N-(1,2,3,4-tetrahydronaphthalen-1-yl)isonicotinamide To a stirring mixture of 126e (4.00 g, 9.38 mmol) and diisopropylethylamine (6.52 mL, 37.5 mmol) in DCM (50 mL) cooled to 0° C. was slowly added dropwise 3-(chloromethyl)benzoyl chloride (1.46 mL, 10.3 mmol). The solution was then allowed to warm to room temperature and stirred for 1 h, at which time it was washed with aqueous HCl, saturated aqueous NaHCO$_3$, and H$_2$O. The organic layer was dried over Na$_2$SO$_4$ and then the solvent removed to give 4.64 g of the product (85%) as a yellow solid.

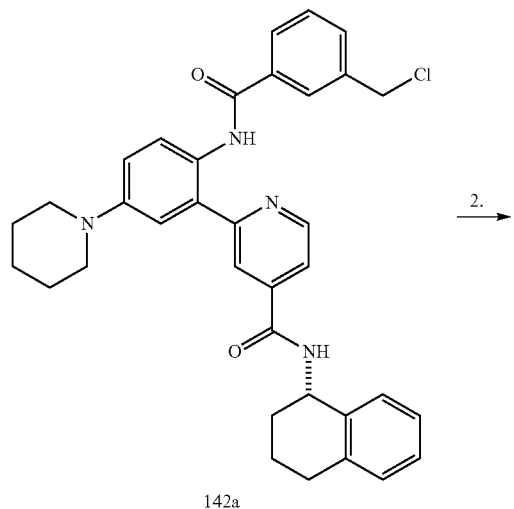

142a

Example 142

(S)-1-(3-(4-(piperidin-1-yl)-2-(4-(1,2,3,4-tetrahydronaphthalen-1-ylcarbamoyl)pyridin-2-yl)phenylcarbamoyl)phenyl)-5,8,11,14-tetraoxa-2-thiaheptadecan-17-oic acid A mixture of 142a (600 mg, 1.04 mmol), 1-mercapto-3,6,9,12-tetraoxapentadecan-15-oic acid (322 mg, 1.14 mmol), and K$_2$CO$_3$ (431 mg, 3.12 mmol) in dry DMF was stirred for 3 h. The mixture was then poured into H$_2$O (150 mL) and the resulting suspension acidified with HCl and filtered. The solid was further purified by reverse-phase HPLC eluting with a water/acetonitrile gradient containing 0.1% TFA. The process resulted in 560 mg (51%) of Example 142 as the di-TFA salt. MS (ES, m/z) 825 [M+H]$^+$.

Example 143

2-(3-(3-(4-(diethylamino)-2-(4-(3-(trifluoromethyl)benzylcarbamoyl)pyridin-2-yl)phenylcarbamoyl)benzylthio)phenyl)acetic acid Scheme 66.

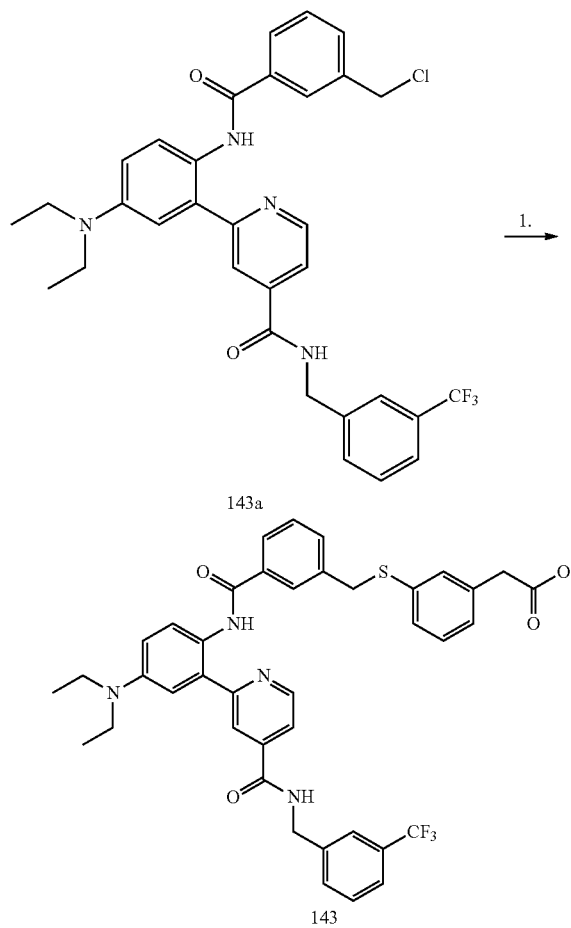

1. 2-(3-mercaptophenyl)acetic acid, K$_2$CO$_3$, DMF.

Intermediate 143a: 2-(2-(3-(chloromethyl)benzamido)-5-(diethylamino)phenyl)-N-(3-(trifluoromethyl)benzyl)isonicotinamide This compound was prepared using the method described for the preparation of Example 142a, using 25b in place of 126e. MS (ES, m/z) 886 [M+H]$^+$.

Example 143

2-(3-(3-(4-(diethylamino)-2-(4-(3-(trifluoromethyl)benzylcarbamoyl)pyridin-2-yl)phenylcarbamoyl)benzylthio)phenyl)acetic acid A mixture of 143a (1.56 g, 2.62 mmol), 2-(3-mercaptophenyl)acetic acid (463 mg, 2.75 mmol), and K$_2$CO$_3$ (1.09 g, 7.86 mmol) in DMF (15 mL) was stirred for 16 h under an atmosphere of N$_2$. The mixture was poured into aqueous HCl and the resulting precipitate was filtered. The solid was dissolved in DCM and washed with H$_2$O and dried over Na$_2$SO$_4$. The solvent was removed, yielding 1.26 g (66%) of the product as a yellow solid. MS (ES, m/z) 727 [M+H]$^+$. 1H NMR (400 MHz, cdcl3) δ 8.70 (d, J=5.2 Hz, 1H), 8.20 (d, J=9.2 Hz, 1H), 8.08 (s, 1H), 7.69 (s, 1H), 7.62 (d, J=7.6 Hz, 2H), 7.61-7.55 (m, 2H), 7.55-7.48 (m, 3H), 7.46-7.40 (m, 1H), 7.34 (t, J=7.6 Hz, 2H), 7.28 (s, 1H), 7.16-7.10 (m, 2H), 7.01-6.94 (m, 1H), 6.78 (dd, J=8.7, 2.6 Hz, 1H), 4.63 (d, J=5.9 Hz, 2H), 4.13 (s, 2H), 3.48 (s, 2H), 3.29 (q, J=7.0 Hz, 4H), 1.10 (t, J=7.1 Hz, 6H).

Example 144

3-(2-(2-(2-(2-(3-(3-(4-(diethylamino)-2-(4-(3-(trifluoromethyl)benzylcarbamoyl)pyridin-2-yl)phenylcarbamoyl)benzylthio)phenyl)-N-methylacetamido)ethoxy)ethoxy)ethoxy)propanoic acid Scheme 67.

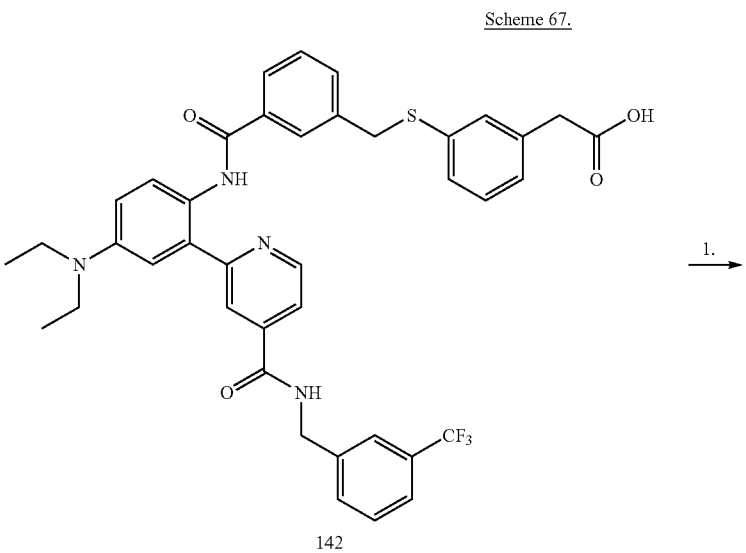

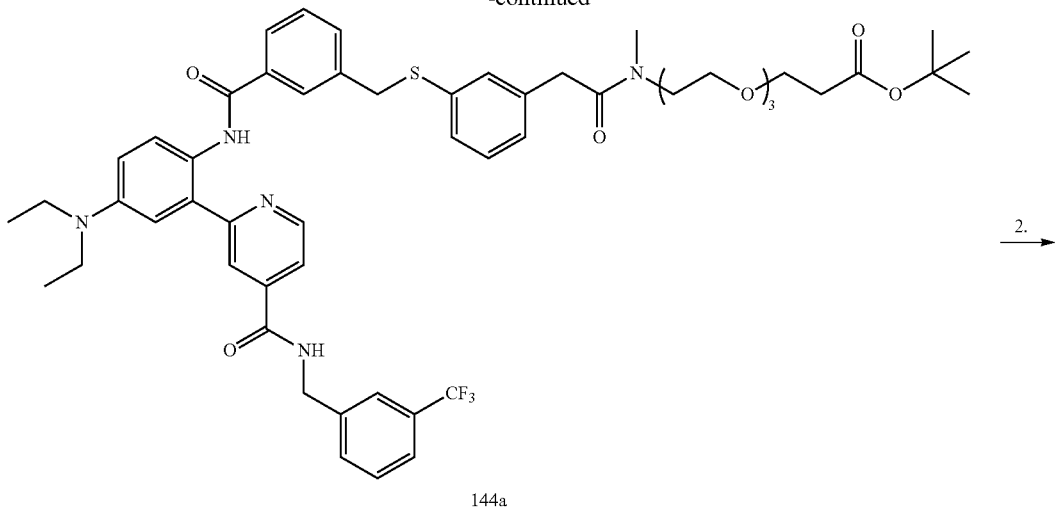

144a

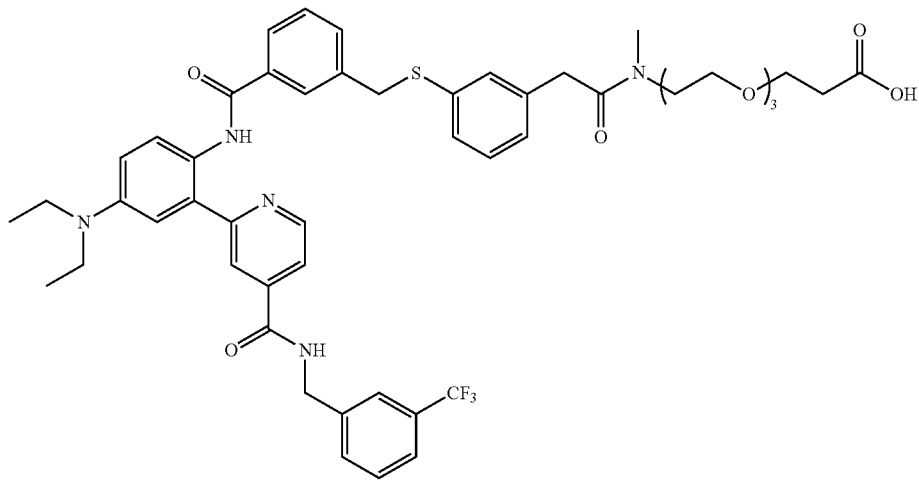

144

1. tert-butyl 3-(2-(2-(2-(methylamino)ethoxy)ethoxy)ethoxy)propanoate, diisopropylethylamine, HATU, DMF; 2. TFA, DCM.

Example 144

3-(2-(2-(2-(2-(3-(3-(4-(diethylamino)-2-(4-(3-(trifluoromethyl)benzylcarbamoyl)pyridin-2-yl)phenylcarbamoyl)benzylthio)phenyl)-N-methylacetamido)ethoxy)ethoxy)ethoxy)propanoic acid To a mixture of 142 (1.72 g, 2.37 mmol), tert-butyl 3-(2-(2-(2-(methylamino)ethoxy)ethoxy)ethoxy)propanoate (827 mg, 2.84 mmol), and diisopropylethylamine (1.65 mL, 9.48 mmol) in dry DMF (5 mL) was added HATU (991 mg, 2.61 mmol) and the solution stirred for 2 h. The solution was then poured into aqueous HCl and the resulting precipitate 144a was filtered. The solid was washed with $H_2O$, then dissolved in EtOAc and washed with saturated aqueous $NaHCO_3$, $H_2O$, and brine, then dried over $Na_2SO_4$ and the solvent removed. The residue was purified by silica gel chromatography, using a gradient of 30% to 100% EtOAc in hexanes as eluent and the solvent removed to furnish intermediate 144a. The purified 144a was dissolved in DCM/TFA (1:1). After 1 h. the solvent was removed with a stream of $N_2$ and the resulting residue dissolved in a mixture of $H_2O$/MeCN (1:1) and lyophilized to give 2.70 g (96%) of Example 144 as this di-TFA salt. MS (ES, m/z) 944 [M+H]$^+$. 1H NMR (400 MHz, dmso) δ 8.97 (s, 1H), 7.90 (s, 3H), 7.80 (s, 2H), 7.72 (s, 2H), 7.68-7.55 (m, 5H), 7.54-7.43 (m, 1H), 7.24-7.18 (m, 4H), 7.04-6.96 (m, 1H), 4.62 (d, J=5.7 Hz, 2H), 4.36 (s, 2H), 3.65 (d, J=14.7 Hz, 2H), 3.59-3.53 (m, 4H), 3.50-3.41 (m, 14H), 2.95 (s, 2H), 2.79 (s, 1H), 2.41 (q, J=5.6 Hz, 2H), 1.10 (t, J=7.0 Hz, 6H).

Example 145
18-(2-(2-hydroxyethoxy)ethyl)-17-oxo-1-(3-(4-(piperidin-1-yl)-2-(4-(3-(trifluoromethyl)benzylcarbamoyl)pyridin-2-yl)phenylcarbamoyl)phenyl)-5,8,11,14-tetraoxa-2-thia-18-azaicosan-20-oic acid
Scheme 68.
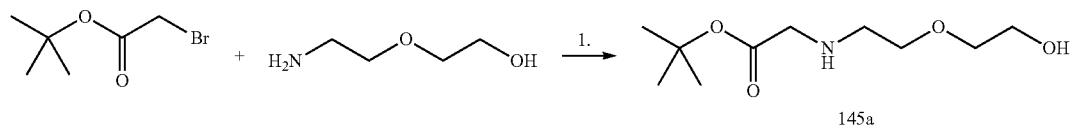
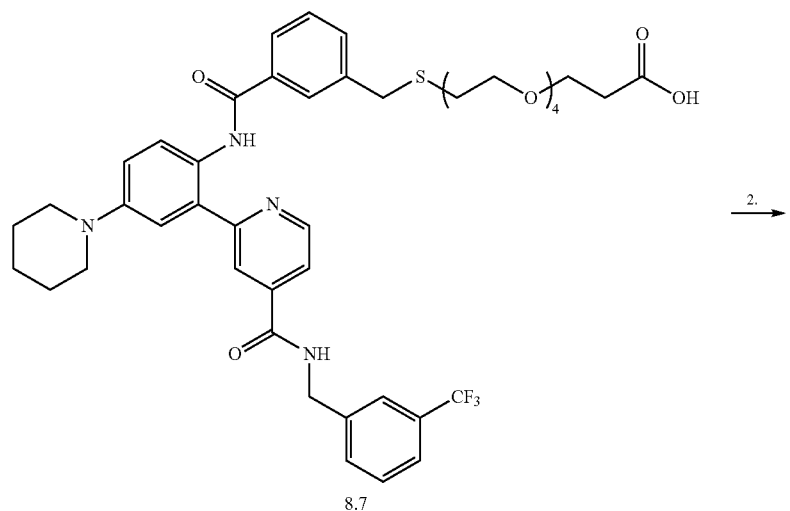
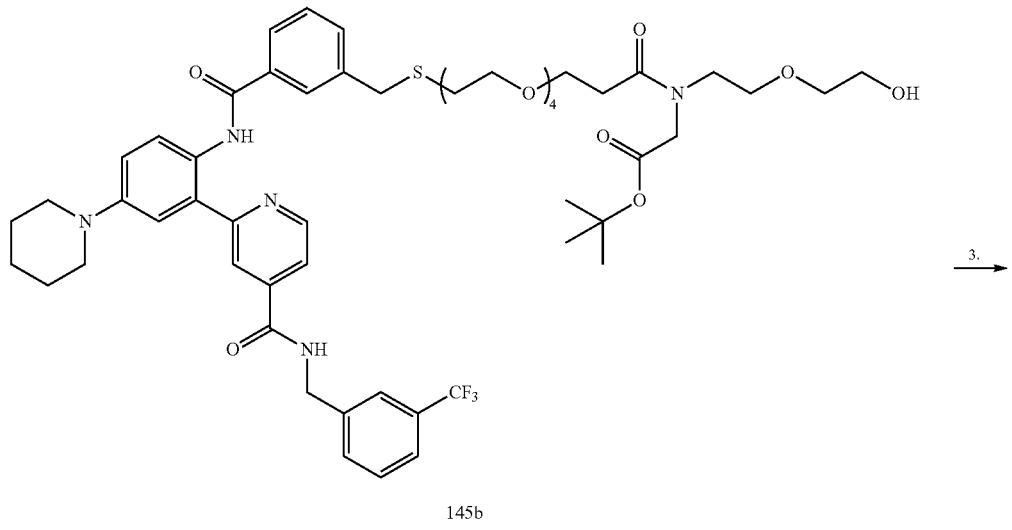

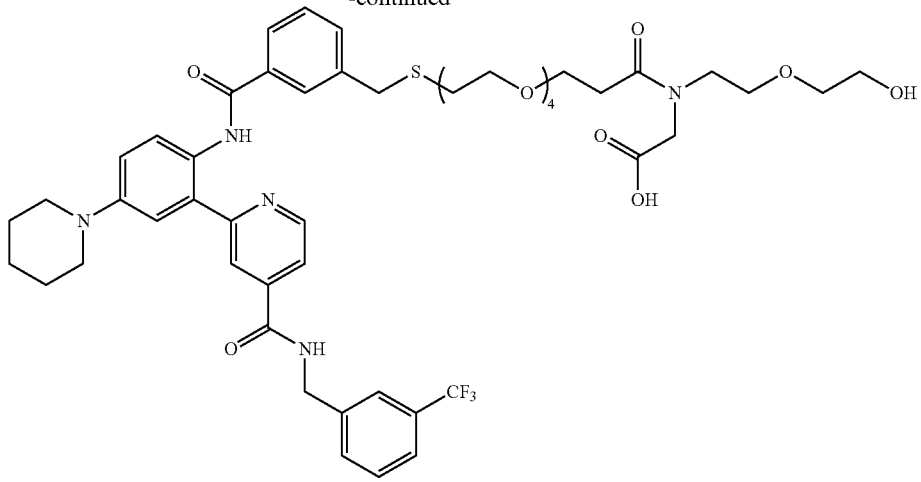

145

1. Triethylamine, THF; 2. 8.7, 145a, diisopropylethylamine, HATU, DMF; 3. TFA, DCM.

Intermediate 145a: tert-butyl 2-(2-(2-hydroxyethoxy)ethylamino)acetate 2-(2-aminoethoxy)ethanol (11 g, 104.62 mmol, 1.00 equiv) was dissolved in THF (300 mL) and cooled to 0° C. To the stirring solution was added dropwise tert-butyl 2-bromoacetate (20 g, 102.54 mmol, 1.00 equiv) and then triethylamine (15.5 g, 153.18 mmol, 1.50 equiv) dropwise The solution was then stirred for 16 h at room temperature. The solvent was removed and the residue then dissolved in DCM and washed twice with brine, then dried over anhydrous sodium sulfate and solvent removed. The residue was applied onto a silica gel column with dichloromethane/methanol (20:1) as eluent. This resulted in 5.25 g (16%) of the product as a yellow oil. MS (ES, m/z) 220 [M+H]$^+$ Example 145

18-(2-(2-hydroxyethoxy)ethyl)-17-oxo-1-(3-(4-(piperidin-1-yl)-2-(4-(3-(trifluoromethyl)benzylcarbamoyl)pyridin-2-yl)phenylcarbamoyl)phenyl)-5,8,11,14-tetraoxa-2-thia-18-azaicosan-20-oic acid To a mixture of 8.7 (25 mg, 0.023 mmol), 145a (6 mg, 0.029 mmol), and diisopropylethylamine (16 µL, 0.092 mmol) was added HATU (10 mg, 0.025 mmol). The solution was stirred for 2 h, the acidified with TFA and purified by reverse-phase HPLC eluting with a water/acetonitrile gradient containing 0.1% TFA and lyophilized to give intermediate 145b. The residue was dissolved in DCM/TFA (1:1). After 1 h, the solvent was removed under a stream of N$_2$ and the resulting residue dissolved in a mixture of H$_2$O/MeCN (1:1) and lyophilized to give 20 mg (82%) of Example 145 as the di-TFA salt. MS (ES, m/z) 998 [M+H]$^+$ Example 146

2-(2-(3-(20-morpholino-17-oxo-5,8,11,14-tetraoxa-2-thia-18-azaicosyl)benzamido)-5-(piperidin-1-yl)phenyl)-N-(3-(trifluoromethyl)benzyl)isonicotinamide

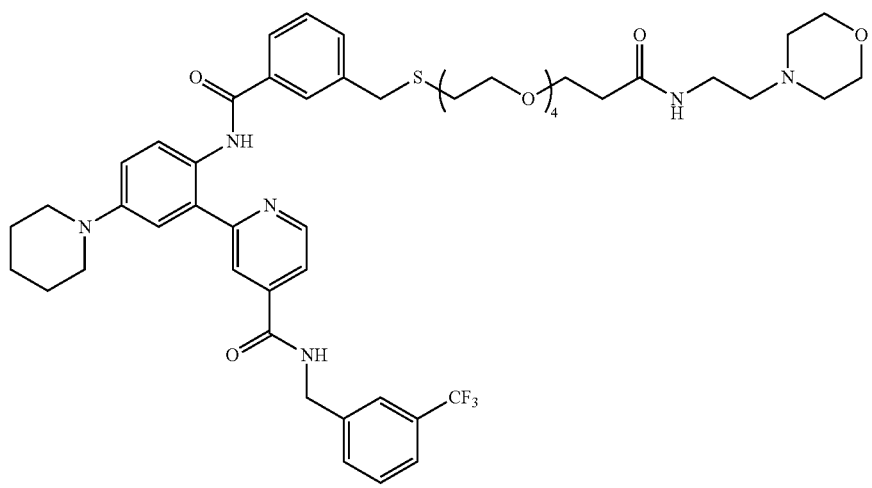

This compound was prepared using the method described for the preparation of Example 145b, using 2-morpholinoethanamine in place of tert-butyl 2-(2-(2-hydroxyethoxy)ethylamino)acetate. MS (ES, m/z) 965 [M+H]$^+$ Example 147

2-(2-(3-(17-(4-(2-(2-hydroxyethoxy)ethyl)piperazin-1-yl)-17-oxo-5,8,11,14-tetraoxa-2-thiaheptadecyl)benzamido)-5-(piperidin-1-yl)phenyl)-N-(3-(trifluoromethyl)benzyl)isonicotinamide

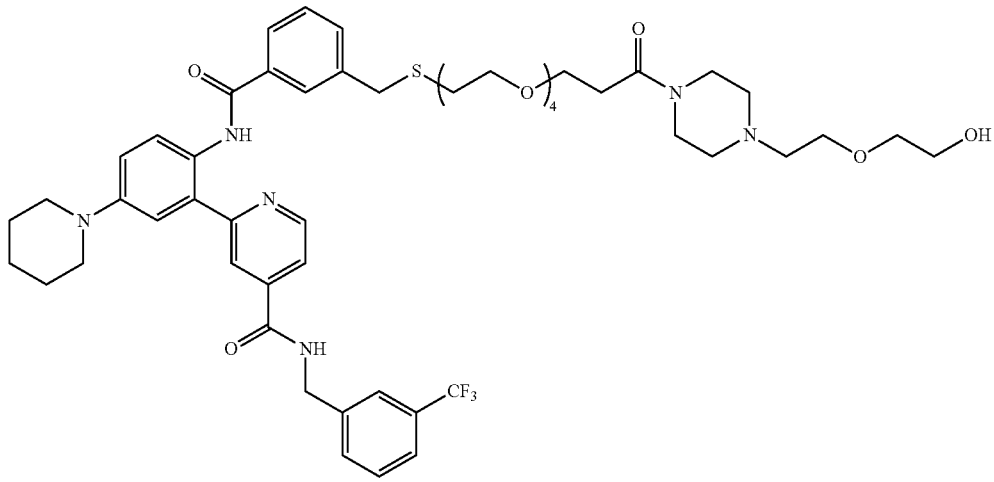

This compound was prepared using the method described for the preparation of Example 145b, using 2-(2-(piperazin-1-yl)ethoxy)ethanol in place of tert-butyl 2-(2-(2-hydroxyethoxy)ethylamino)acetate. MS (ES, m/z) 1009 [M+H]$^+$.

Example 148

2-(2-(3-(27-oxo-2,5,8,11,14,17,20,23,30,33,36,39-dodecaoxa-42-thia-26-azatritetracontan-43-yl)benzamido)-5-(piperidin-1-yl)phenyl)-N-(3-(trifluoromethyl)benzyl)isonicotinamide

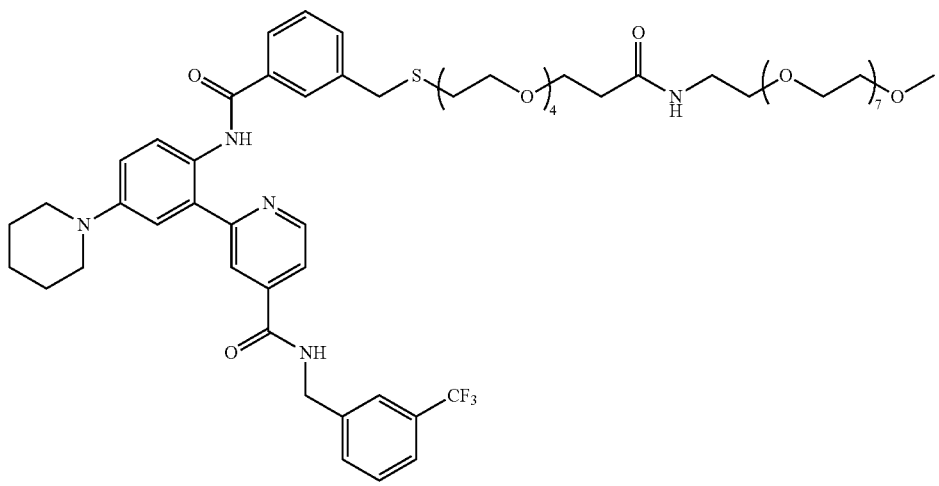

This compound was prepared using the method described for the preparation of Example 145b, using 2,5,8,11,14,17,20,23-octaoxapentacosan-25-amine in place of tert-butyl 2-(2-(2-hydroxyethoxy)ethylamino)acetate. MS (ES, m/z) 1218 [M+H]$^+$.

Example 149

2-(2-(3-(41-hydroxy-17-oxo-5,8,11,14,21,24,27,30,33,36,39-undecaoxa-2-thia-18-azahentetracontyl)benzamido)-5-(piperidin-1-yl)phenyl)-N-(3-(trifluoromethyl)benzyl)isonicotinamide

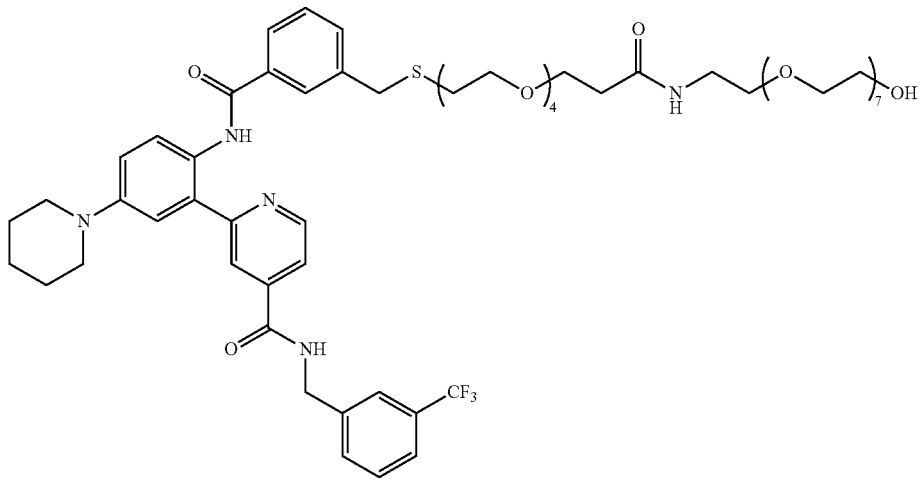

This compound was prepared using the method described for the preparation of Example 145b, using 23-amino-3,6,9,12,15,18,21-heptaoxatricosan-1-ol in place of tert-butyl 2-(2-(2-hydroxyethoxy)ethylamino)acetate. MS (ES, m/z) 1204 [M+H]$^+$.

Example 150

2-(2-(3-(18-methyl-20-morpholino-17-oxo-5,8,11,14-tetraoxa-2-thia-18-azaicosyl)benzamido)-5-(piperidin-1-yl)phenyl)-N-(3-(trifluoromethyl)benzyl)isonicotinamide

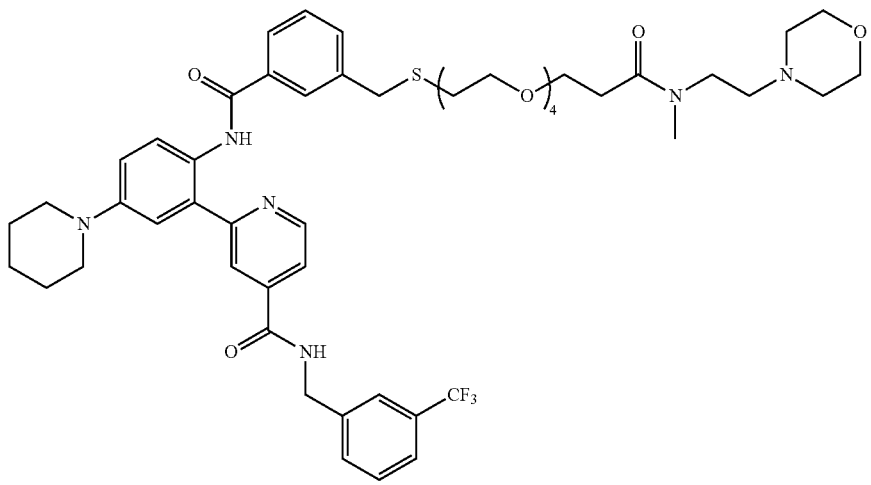

This compound was prepared using the method described for the preparation of Example 145b, using N-methyl-2-morpholinoethanamine in place of tert-butyl 2-(2-(2-hydroxyethoxy)ethylamino)acetate. MS (ES, m/z) 979 [M+H]$^+$ Example 151

2-(2-(3-(20-hydroxy-18-(2-hydroxyethyl)-17-oxo-5,8,11,14-tetraoxa-2-thia-18-azaicosyl)benzamido)-5-(piperidin-1-yl)phenyl)-N-(3-(trifluoromethyl)benzyl)isonicotinamide

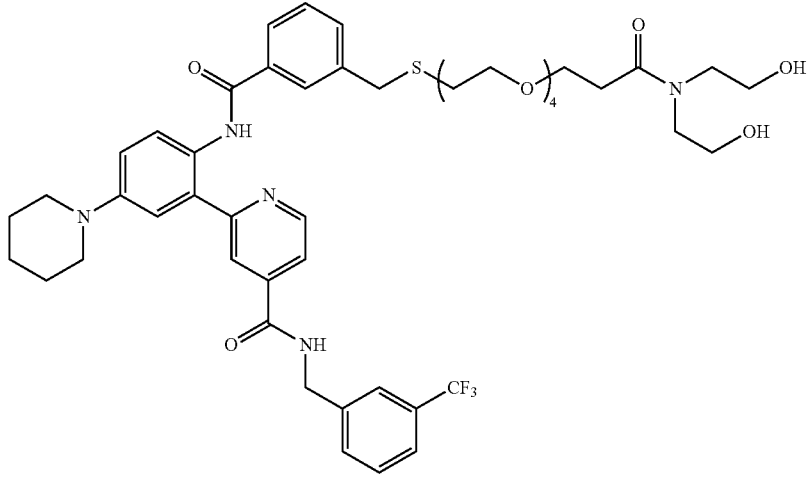

This compound was prepared using the method described for the preparation of Example 145b, using diethanolamine in place of tert-butyl 2-(2-(2-hydroxyethoxy)ethylamino)acetate. MS (ES, m/z) 940 [M+H]$^+$.

Example 152

2-(2-(3-(21-ethyl-18-methyl-17-oxo-5,8,11,14-tetraoxa-2-thia-18,21-diazatricosyl)benzamido)-5-(piperidin-1-yl)phenyl)-N-(3-(trifluoromethyl)benzyl)isonicotinamide

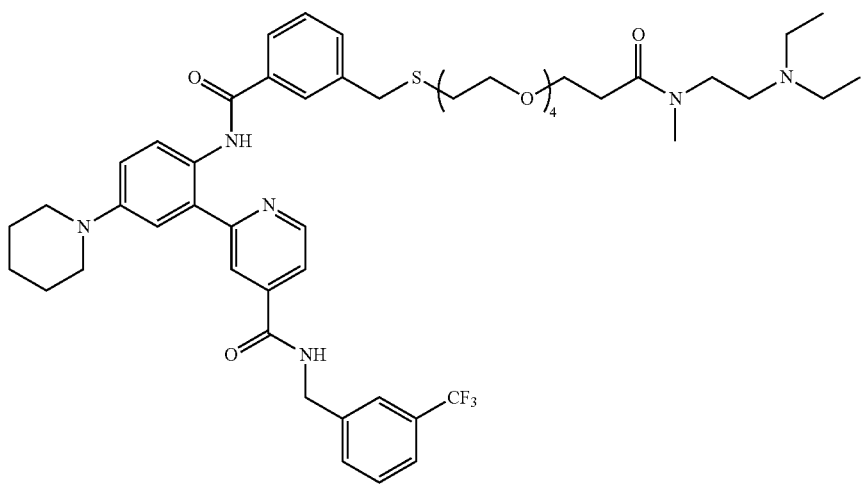

This compound was prepared using the method described for the preparation of Example 145b, using N1,N1-diethyl-N2-methylethane-1,2-diamine in place of tert-butyl 2-(2-(2-hydroxyethoxy)ethylamino)acetate. MS (ES, m/z) 965 [M+H]+.

Example 153

2-(2-(3-(17-(4-acetyl-1,4-diazepan-1-yl)-17-oxo-5,8,11,14-tetraoxa-2-thiaheptadecyl)benzamido)-5-(piperidin-1-yl)phenyl)-N-(3-(trifluoromethyl)benzyl)isonicotinamide

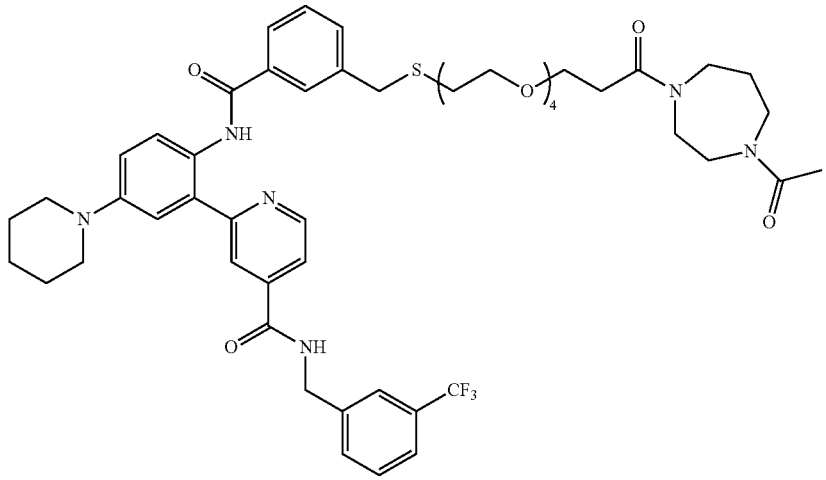

This compound was prepared using the method described for the preparation of Example 145b, using 1-(1,4-diazepan-1-yl)ethanone in place of tert-butyl 2-(2-(2-hydroxyethoxy)ethylamino)acetate. MS (ES, m/z) 977 [M+H]+.

Example 154

2-(2-(3-(17-(4-morpholinopiperidin-1-yl)-17-oxo-5,8,11,14-tetraoxa-2-thiaheptadecyl)benzamido)-5-(piperidin-1-yl)phenyl)-N-(3-(trifluoromethyl)benzyl)isonicotinamide

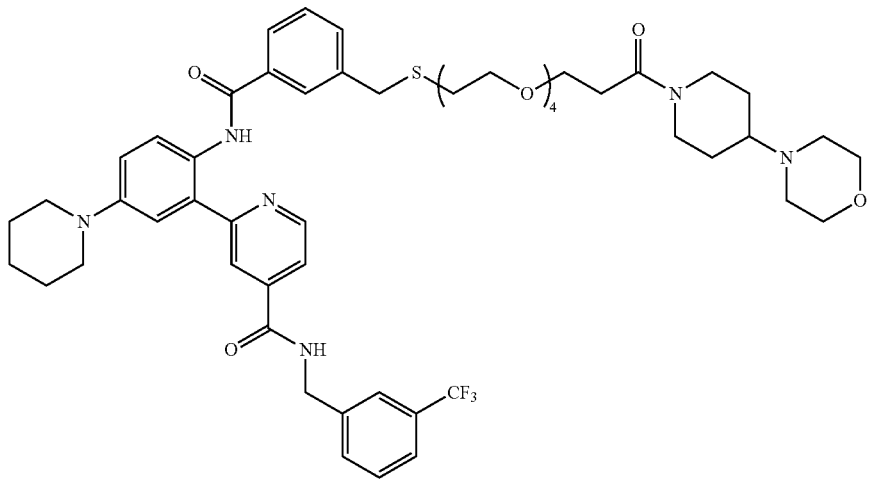

This compound was prepared using the method described for the preparation of Example 145b, using 4-(piperidin-4-yl)morpholine in place of tert-butyl 2-(2-(2-hydroxyethoxy)ethylamino)acetate. MS (ES, m/z) 1005 [M+H]+

Example 155

17-oxo-1-(3-(4-(piperidin-1-yl)-2-(4-(3-(trifluoromethyl)benzylcarbamoyl)pyridin-2-yl)phenylcarbamoyl)phenyl)-5,8,11,14,21,24,27-heptaoxa-2-thia-18-azatriacontan-30-oic acid

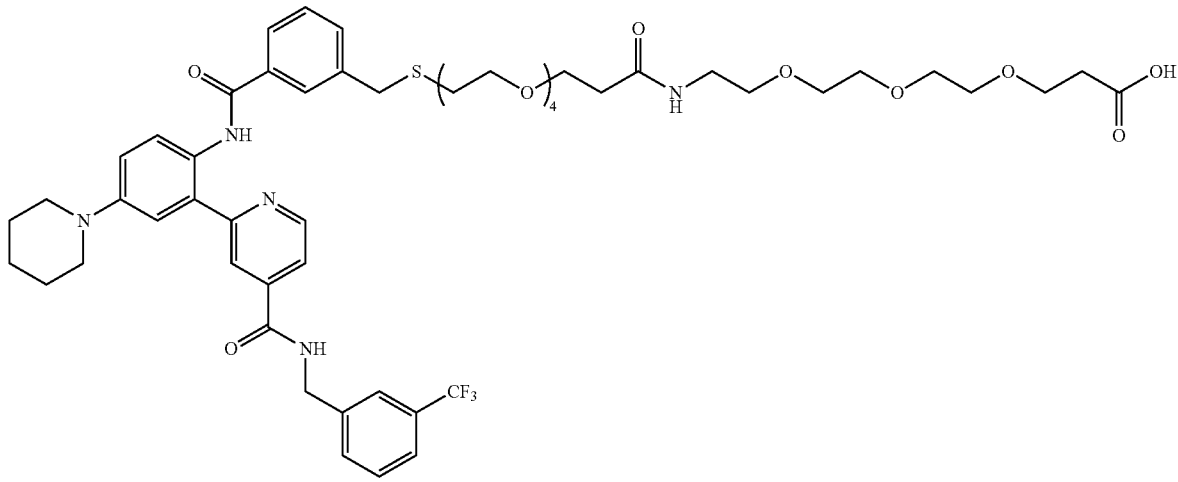

This compound was prepared using the method described for the preparation of Example 145, using tert-butyl 3-(2-(2-(2-aminoethoxy)ethoxy)ethoxy)propanoate in place of tert-butyl 2-(2-(2-hydroxyethoxy)ethylamino)acetate. MS (ES, m/z) 1056 [M+H]+.

Example 157

(S)-1-(3-(4-(diethylamino)-2-(4-(1,2,3,4-tetrahydronaphthalen-1-ylcarbamoyl)pyridin-2-yl)phenylcarbamoyl)phenyl)-5,8,11,14-tetraoxa-2-thiaheptadecan-17-oic acid Scheme 69.

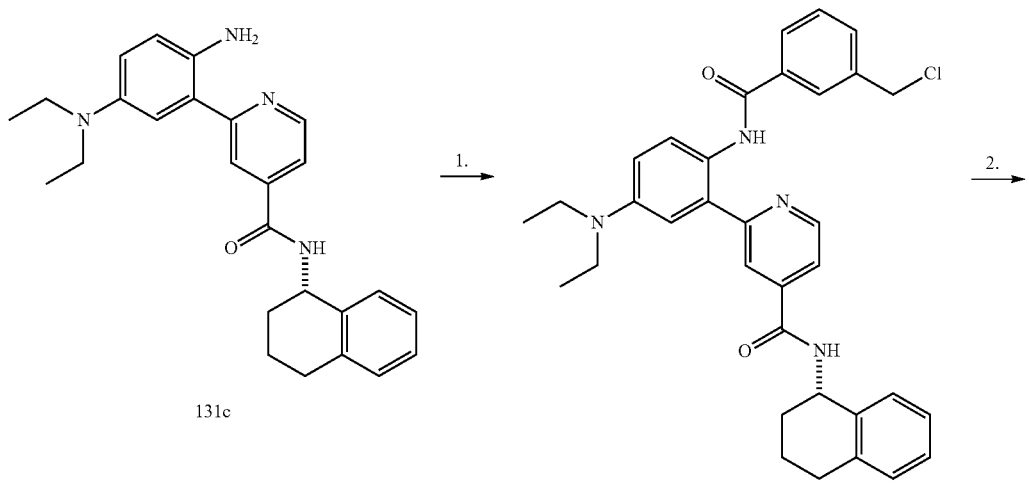

-continued

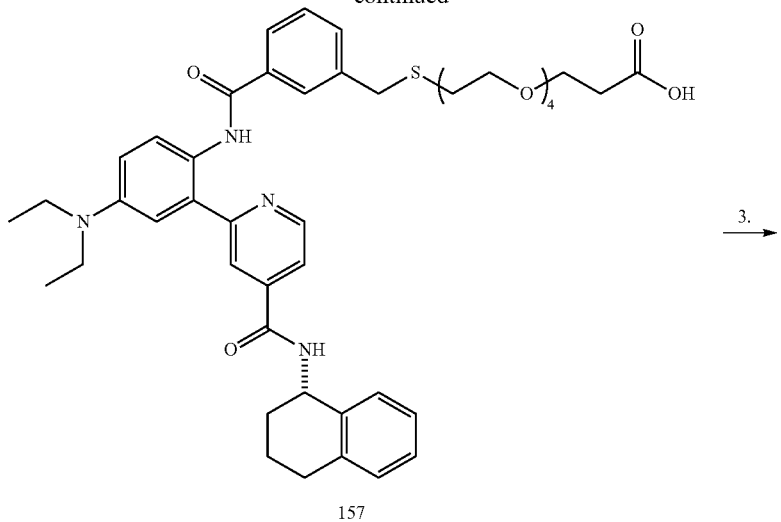

157

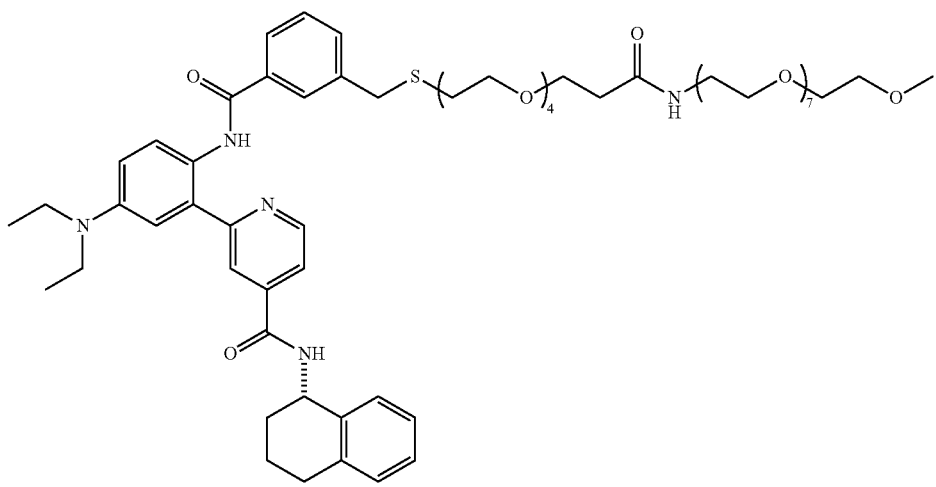

157.1

1. 3-(chloromethyl)benzoyl chloride, diisopropylethylamine, DCM; 2. 1-mercapto-3,6,9,12-tetraoxapentadecan-15-oic acid, $K_2CO_3$, DMF; 3. 2,5,8,11,14,17,20,23-octaoxapentacosan-25-amine, HATU, diisopropylethylamine, DMF.

Intermediate 157a: (S)-2-(2-amino-5-(diethylamino)phenyl)-N-(1,2,3,4-tetrahydronaphthalen-1-yl)isonicotinamide To a stirring mixture of 131c (970 mg, 2.34 mmol) and diisopropylethylamine (1.63 mL, 9.36 mmol) in DCM (25 mL) cooled to 0° C. was slowly added dropwise 3-(chloromethyl)benzoyl chloride (365 µL, 2.57 mmol). The solution was then allowed to warm to room temperature and stirred for 1 h, then the solvent was removed. The resulting residue was dissolved in EtOAc and washed with aqueous HCl, saturated aqueous $NaHCO_3$, and brine, then dried over $Na_2SO_4$. The solvent was removed and the residue purified by silica gel chromatography, using a gradient of 30% to 70% EtOAc in hexanes as eluent and the solvent removed. This gave 1.22 g (92%) of the product as a yellow solid.

Example 157

(S)-1-(3-(4-(diethylamino)-2-(4-(1,2,3,4-tetrahydronaphthalen-1-ylcarbamoyl)pyridin-2-yl)phenylcarbamoyl)phenyl)-5,8,11,14-tetraoxa-2-thiaheptadecan-17-oic acid A stirring mixture of 157a (1.22 g, 2.15 mmol), 1-mercapto-3,6,9,12-tetraoxapentadecan-15-oic acid (668 mg, 2.37 mmol), and $K_2CO_3$ (891 mg, 6.45 mmol) in dry DMF (15 mL) was stirred for 2 h, then poured into $H_2O$ (100 mL). The solution was acidified with aqueous HCl and extracted twice with DCM. The combined organic layers were washed thrice with $H_2O$ and then dried over $Na_2SO_4$. Removal of the solvent gave 1.61 g (92%) of the product Example 157 as a yellow foam. MS (ES, m/z) 813 $[M+H]^+$

Example 157.1

(S)-2-(5-(diethylamino)-2-(3-(27-oxo-2,5,8,11,14,17,20,23,30,33,36,39-dodecaoxa-42-thia-26-azatetracontan-43-yl)benzamido)phenyl)-N-(1,2,3,4-tetrahydronaphthalen-1-yl)isonicotinamide

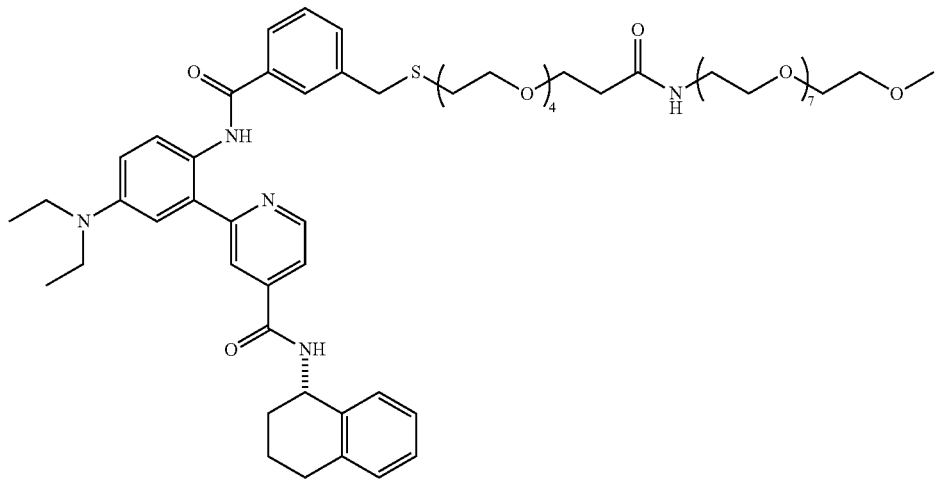

To a mixture of 157 (390 mg, 1.14 mmol), 2,5,8,11,14,17,20,23-octaoxapentacosan-25-amine (482 mg, 1.26 mmol), and diisopropylethylamine (793 µL, 4.56 mmol) was added HATU (479 mg, 1.26 mmol). The solution was stirred for 2 h, the acidified with TFA and purified by reverse-phase HPLC eluting with a water/acetonitrile gradient containing 0.1% TFA and lyophilized to give 1.40 g (87%) of the product Example 157.1 as the di-TFA salt. MS (ES, m/z) 1178 [M+H]$^+$

Example 158

(S)-2-(5-(diethylamino)-2-(3-(20-hydroxy-19,19-bis(hydroxymethyl)-17-oxo-5,8,11,14-tetraoxa-2-thia-18-azaicosyl)benzamido)phenyl)-N-(1,2,3,4-tetrahydronaphthalen-1-yl)isonicotinamide

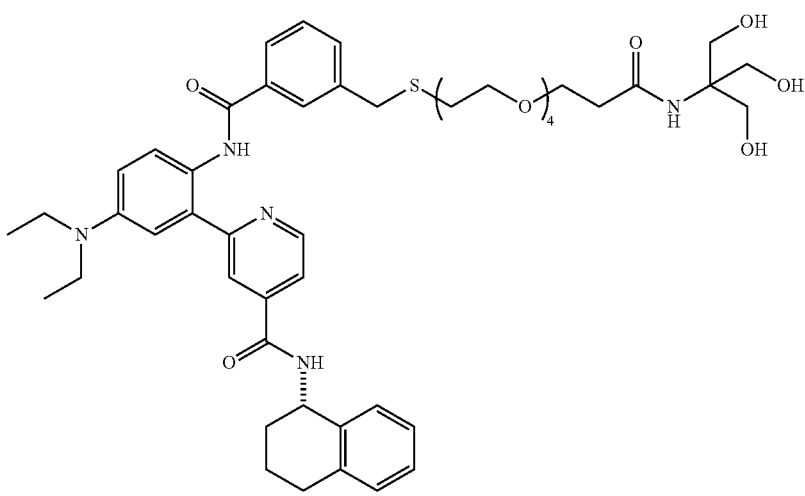

This compound was prepared using the method described for the preparation of Example 157.1, using tris(hydroxymethyl)aminomethane.HCl in place of 2,5,8,11,14,17,20,23-octaoxapentacosan-25-amine. MS (ES, m/z) 916 [M+H]$^+$ Example 159

(S)-2-(5-(diethylamino)-2-(3-(20-hydroxy-19-(hydroxymethyl)-17-oxo-5,8,11,14-tetraoxa-2-thia-18-azaicosyl)benzamido)phenyl)-N-(1,2,3,4-tetrahydronaphthalen-1-yl)isonicotinamide

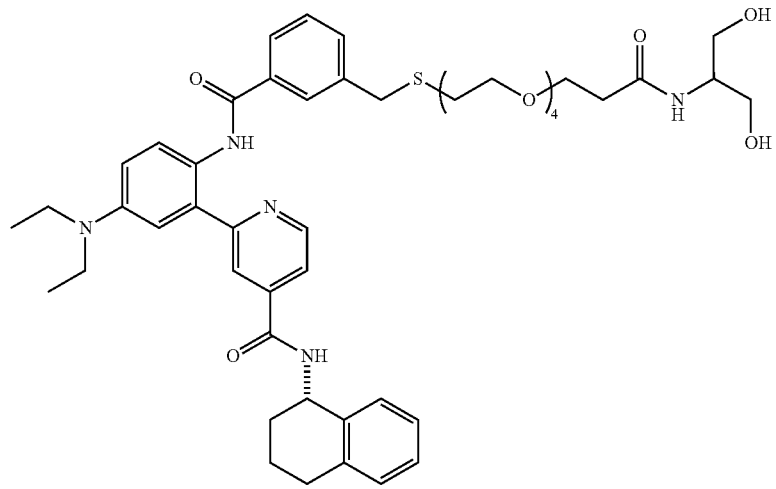

This compound was prepared using the method described for the preparation of Example 157.1, using 2-aminopropane-1,3-diol.HCl in place of 2,5,8,11,14,17,20,23-octaoxapentacosan-25-amine. MS (ES, m/z) 886 [M+H]$^+$ Example 160

(S)-2-(5-(diethylamino)-2-(3-(20-hydroxy-18-(2-hydroxyethyl)-17-oxo-5,8,11,14-tetraoxa-2-thia-18-azaicosyl)benzamido)phenyl)-N-(1,2,3,4-tetrahydronaphthalen-1-yl)isonicotinamide

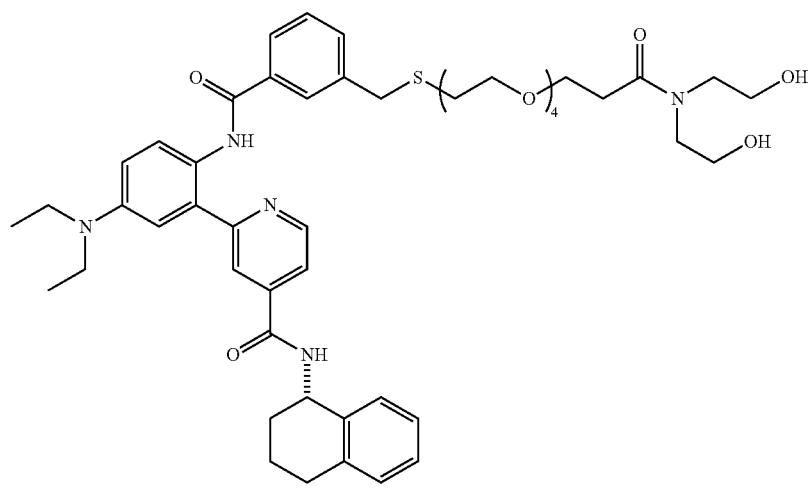

This compound was prepared using the method described for the preparation of Example 157.1, using diethanolamine in place of 2,5,8,11,14,17,20,23-octaoxapentacosan-25-amine. MS (ES, m/z) 900 [M+H]⁺

Example 161

(S)-1-(3-(4-diethylamino-2-(4-(1,2,3,4-tetrahydronaphthalen-1-ylcarbamoyl)pyridin-2-yl)phenylcarbamoyl)phenyl)-5,8,11,14,17,20,23,26-octaoxa-2-thianonacosan-29-oic acid This compound was prepared using the method described for the preparation of Example 157, using 1-mercapto-3,6,9,12,15,18,21,24-octaoxaheptacosan-27-oic acid in place of 1-mercapto-3,6,9,12-tetraoxapentadecan-15-oic acid. MS (ES, m/z) 989 [M+H]⁺

Example 162

1-(3-(4-(diethylamino)-2-(4-(3-(trifluoromethyl)benzylcarbamoyl)pyridin-2-yl)phenylcarbamoyl)phenyl)-5,8,11,14-tetraoxa-2-thiaheptadecan-17-oic acid

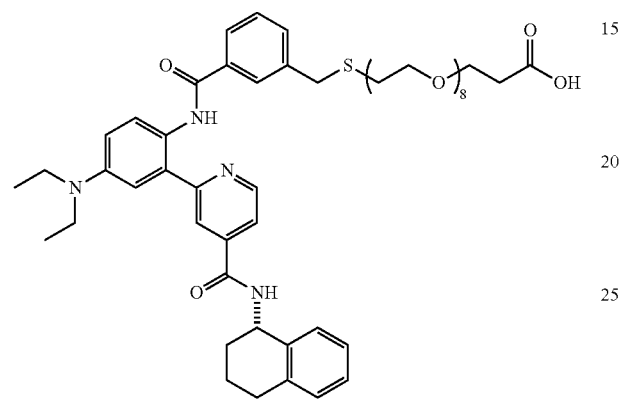

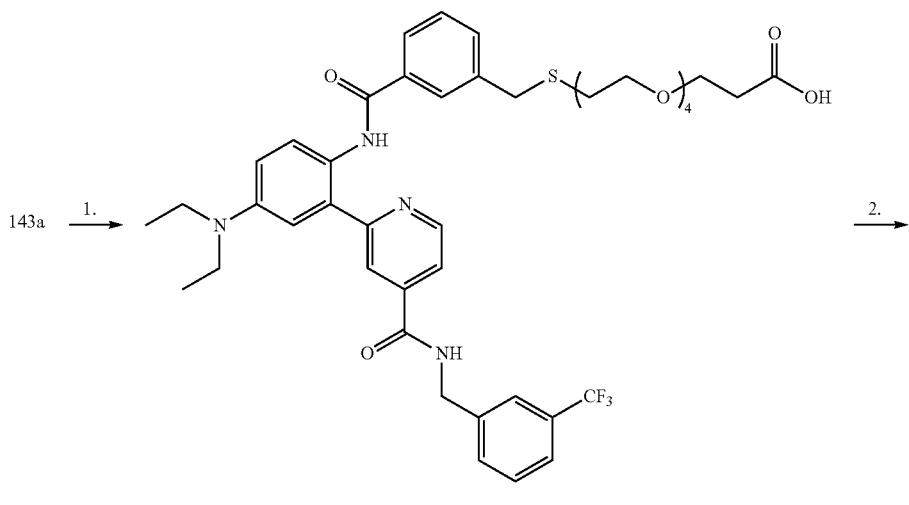

Scheme 70.

162

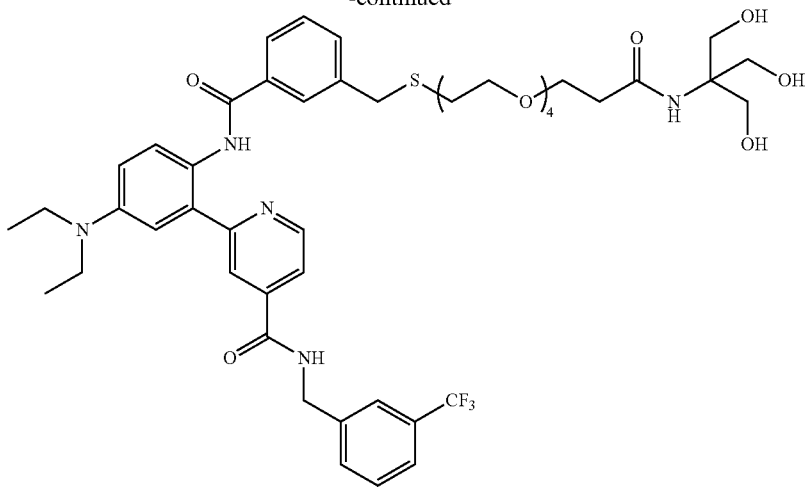

163

1. 1-mercapto-3,6,9,12-tetraoxapentadecan-15-oic acid, K₂CO₃, DMF; 2. tris(hydroxymethyl)aminomethane•HCl, HATU, diisopropylethylamine, DMF

Example 162

1-(3-(4-(diethylamino)-2-(4-(3-(trifluoromethyl)benzylcarbamoyl)pyridin-2-yl)phenylcarbamoyl)phenyl)-5,8,11,14-tetraoxa-2-thiaheptadecan-17-oic acid A mixture of 143a (1.1 g, 1.8 mmol), 1-mercapto-3,6,9,12-tetraoxapentadecan-15-oic acid (0.5 g (1.8 mmol), and K₂CO₃ (250 mg) in DMF (18 mL) was stirred for 16 h. The mixture was acidified with TFA and purified by reverse-phase HPLC eluting with a water/acetonitrile gradient containing 0.1% TFA and lyophilized to give 1.05 g (55%) of the product Example 162 as the di-TFA salt. MS (ES, m/z) 841 [M+H]⁺.

1H NMR (400 MHz, dmso) δ 9.83 (s, 1H), 9.02 (d, J=5.2 Hz, 1H), 8.74-8.58 (m, 1H), 8.52 (s, 1H), 7.92 (d, J=5.0 Hz, 2H), 7.82 (d, J=7.6 Hz, 1H), 7.73 (s, 1H), 7.70-7.48 (m, 7H), 4.62 (d, J=5.9 Hz, 2H), 3.92 (s, 2H), 3.55 (q, J=6.4 Hz, 4H), 3.50-3.43 (m, 16H), 2.59 (t, J=6.6 Hz, 2H), 2.41 (t, J=6.4 Hz, 2H), 1.10 (t, J=7.1 Hz, 6H).

Example 163

2-(5-(diethylamino)-2-(3-(20-hydroxy-19,19-bis(hydroxymethyl)-17-oxo-5,8,11,14-tetraoxa-2-thia-18-azaicosyl)benzamido)phenyl)-N-(3-(trifluoromethyl)benzyl)isonicotinamide

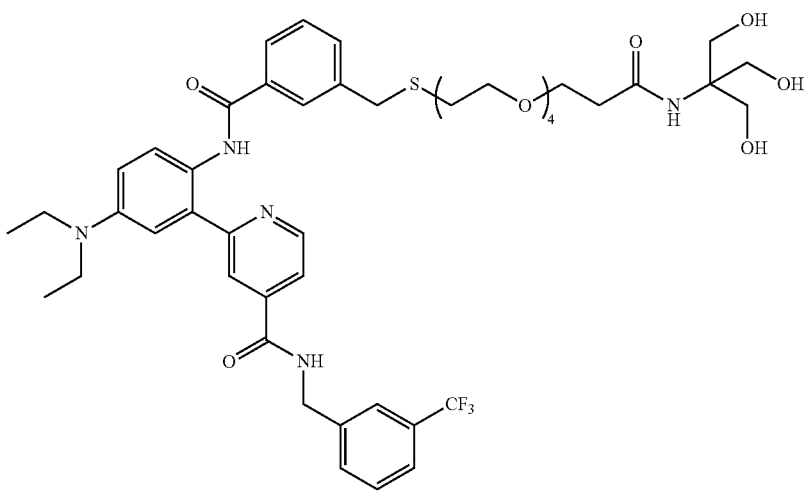

Example 163

2-(5-(diethylamino)-2-(3-(20-hydroxy-19,19-bis(hydroxymethyl)-17-oxo-5,8,11,14-tetraoxa-2-thia-18-azaicosyl)benzamido)phenyl)-N-(3-(trifluoromethyl)benzyl)isonicotinamide To a mixture of Example 162 (1.02 g, 1.12 mmol), tris(hydroxymethyl)aminomethane.HCl (223 mg, 1.40 mmol), and diisopropylethylamine (0.97 mL, 5.6 mmol) in dry DMF (10 mL) was added HATU (468 mg, 1.23 mmol). The solution was stirred for 2 h, the acidified with TFA and purified by reverse-phase HPLC eluting with a water/acetonitrile gradient containing 0.1% TFA and lyophilized to give 880 mg (67%) of the product as the di-TFA salt. MS (ES, m/z) 944 [M+H]$^+$.

Example 164

2-(5-(diethylamino)-2-(3-(20-hydroxy-18-(2-hydroxyethyl)-17-oxo-5,8,11,14-tetraoxa-2-thia-18-azaicosyl)benzamido)phenyl)-N-(3-(trifluoromethyl)benzyl)isonicotinamide

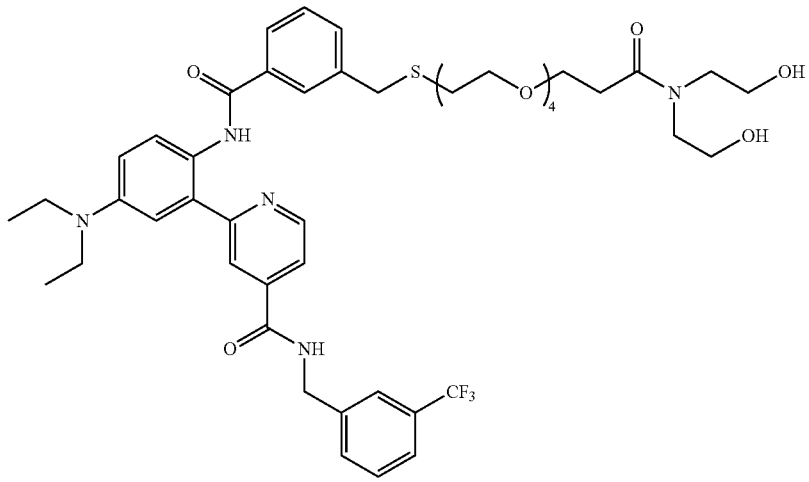

2-(5-(diethylamino)-2-(3-(20-hydroxy-18-(2-hydroxyethyl)-17-oxo-5,8,11,14-tetraoxa-2-thia-18-azaicosyl)benzamido)phenyl)-N-(3-(trifluoromethyl)benzyl)isonicotinamide. This compound was prepared using the method described for the preparation of Example 163, using diethanolamine in place of tris(hydroxymethyl)aminomethane.HCl. MS (ES, m/z) 928 [M+H]$^+$.

Example 165

2-(5-(diethylamino)-2-(3-(27-oxo-2,5,8,11,14,17,20,23,30,33,36,39-dodecaoxa-42-thia-26-azatritetracontan-43-yl)benzamido)phenyl)-N-(3-(trifluoromethyl)benzyl)isonicotinamide

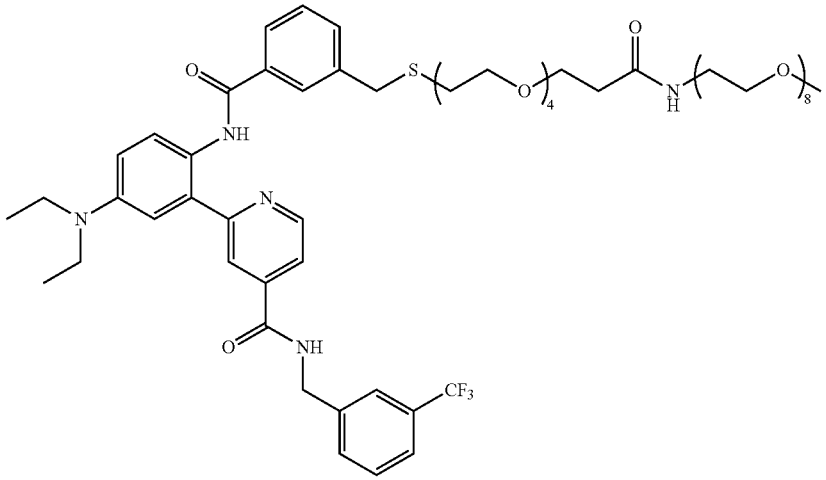

2-(5-(diethylamino)-2-(3-(27-oxo-2,5,8,11,14,17,20,23,30,33,36,39-dodecaoxa-42-thia-26-azatritetracontan-43-yl)benzamido)phenyl)-N-(3-(trifluoromethyl)benzyl)isonicotinamide. This compound was prepared using the method described for the preparation of Example 163, using 2,5,8,11,14,17,20,23-octaoxapentacosan-25-amine in place of tris(hydroxymethyl)aminomethane.HCl. MS (ES, m/z) 1206 [M+H]⁺.

Example 166

1-(3-(4-(diethylamino)-2-(4-(3-(trifluoromethyl)benzylcarbamoyl)pyridin-2-yl)phenylcarbamoyl)phenyl)-5,8,11,14,17,20,23,26-octaoxa-2-thianonacosan-29-oic acid

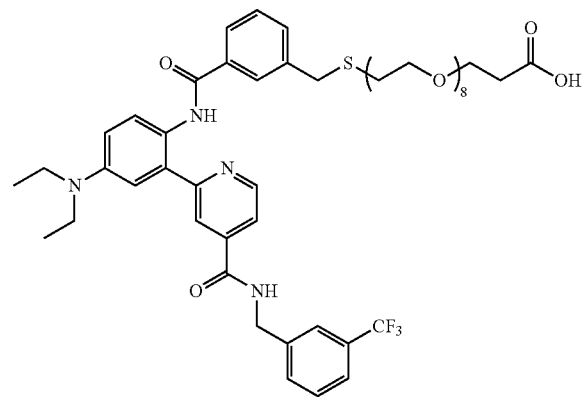

This compound was prepared using the method described for the preparation of Example 162, using 1-mercapto-3,6,9,12,15,18,21,24-octaoxaheptacosan-27-oic acid in place of 1-mercapto-3,6,9,12-tetraoxapentadecan-15-oic. MS (ES, m/z) 1017 [M+H]⁺. 1H NMR (400 MHz, dmso) δ 12.24-12.06 (m, 1H), 11.82 (s, 1H), 9.49 (t, J=5.9 Hz, 1H), 8.95 (d, J=5.1 Hz, 1H), 8.23 (s, 1H), 8.13 (d, J=9.3 Hz, 1H), 7.85-7.77 (m, 2H), 7.75-7.67 (m, 2H), 7.64 (t, J=7.3 Hz, 2H), 7.58 (d, J=8.0 Hz, 1H), 7.53-7.41 (m, 3H), 7.06 (d, J=2.6 Hz, 1H), 6.87 (dd, J=9.2, 3.0 Hz, 1H), 4.61 (d, J=6.0 Hz, 2H), 3.88 (s, 2H), 3.58 (t, J=6.3 Hz, 2H), 3.54 (t, J=6.6 Hz, 2H), 3.50-3.36 (m, 36H), 2.58 (t, J=6.4 Hz, 2H), 2.43 (t, J=6.3 Hz, 2H), 1.13 (t, J=6.9 Hz, 6H).

Example 167

1-(((3-((4-diethylamino-2-[4-(((3-(trifluoromethyl)phenyl]methyl)carbamoyl)pyridin-2-yl)phenyl)carbamoyl)phenyl)methane)sulfonyl)-3,6,9,12-tetraoxapentadecan-15-oic acid

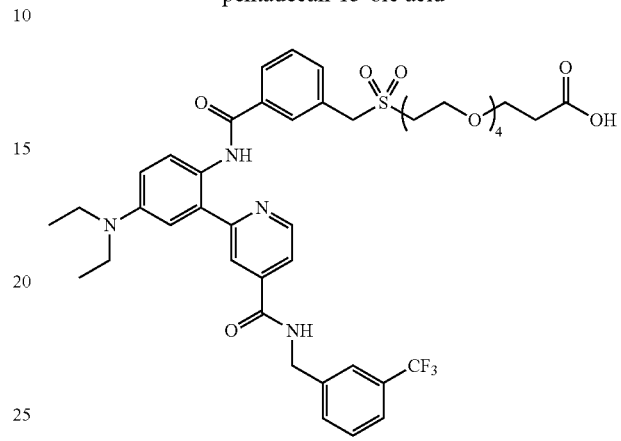

A mixture of Example 162 (25 mg, 0.023 mmol) and Oxone® (71 mg, 0.12 mmol) in THF/MeOH/H₂O (1 mL: 0.5 mL: 0.5 mL) was stirred for 18 h and then filtered and the solid washed with EtOAc. The combined organic layers were washed with H₂O and brine, then dried over Na₂SO₄ and the solvent removed. The resulting residue was dissolved in MeOH, then 10 mol % Pd/C (5 mg) was added and the suspension stirred under an atmosphere of H₂ for 0.5 h. The suspension was filtered through celite and the solvent removed then purified by reverse-phase HPLC eluting with a water/acetonitrile gradient containing 0.1% TFA and lyophilized to give 12 mg (47%) of the product as the di-TFA salt. MS (ES, m/z) 873 [M+H]⁺

Example 168

2-(5-(diethylamino)-2-(3-(19-hydroxy-2,5,8,11,14,17-hexaoxanonadecyl)benzamido)phenyl)-N-(3-(trifluoromethyl)benzyl)isonicotinamide Scheme 71.

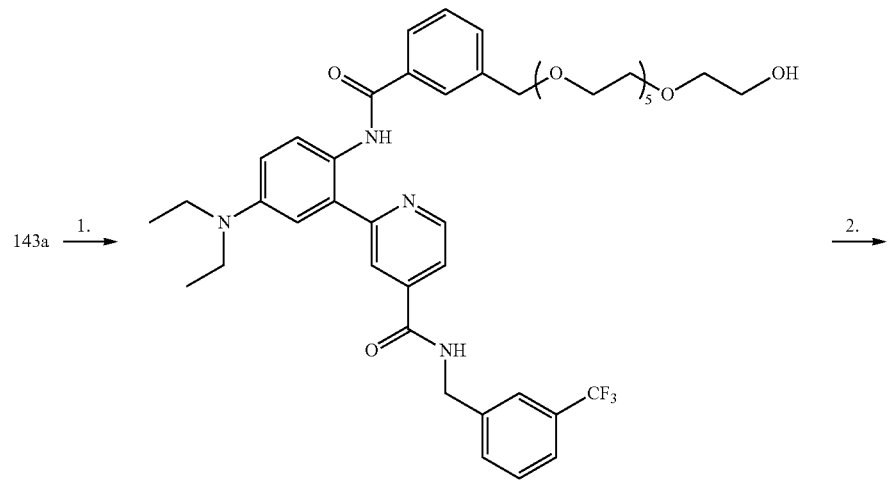

168

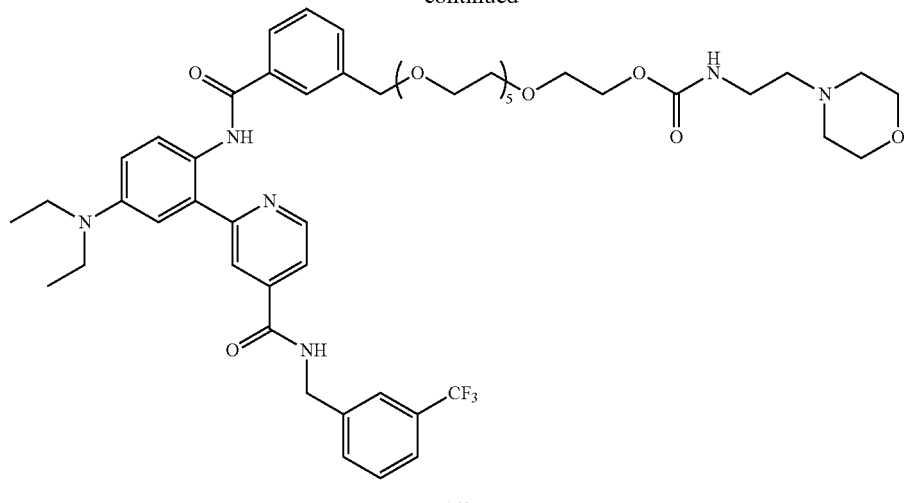

169

1. 3,6,9,12,15-pentaoxaheptadecane-1,17-diol, sodium hydride, THF; 2. 4-nitrophenylchloroformate, diisopropylethylamine, DCM, then 2-morpholinoethanamine.

Example 168

2-(5-(diethylamino)-2-(3-(19-hydroxy-2,5,8,11,14,17-hexaoxanonadecyl)benzamido)phenyl)-N-(3-(trifluoromethyl)benzyl)isonicotinamide To a mixture of 143a (500 mg, 0.840 mmol) and 3,6,9,12,15-pentaoxaheptadecane-1,17-diol (1.06 mL, 4.20 mmol) in dry THF (8 mL) was added a 60% sodium hydride dispersion in mineral oil (101 mg) and the mixture stirred at 50° C. for 1 h. The solution was then diluted with DCM and washed with aqueous HCl and H$_2$O, then dried over Na$_2$SO$_4$ and the solvent removed to give 634 mg (90%) of the product as a yellow oil. MS (ES, m/z) 841 [M+H]$^+$.

Example 169

1-(3-(4-(diethylamino)-2-(4-(3-(trifluoromethyl)benzylcarbamoyl)pyridin-2-yl)phenylcarbamoyl)phenyl)-2,5,8,11,14,17-hexaoxanonadecan-19-yl 2-morpholinoethylcarbamate

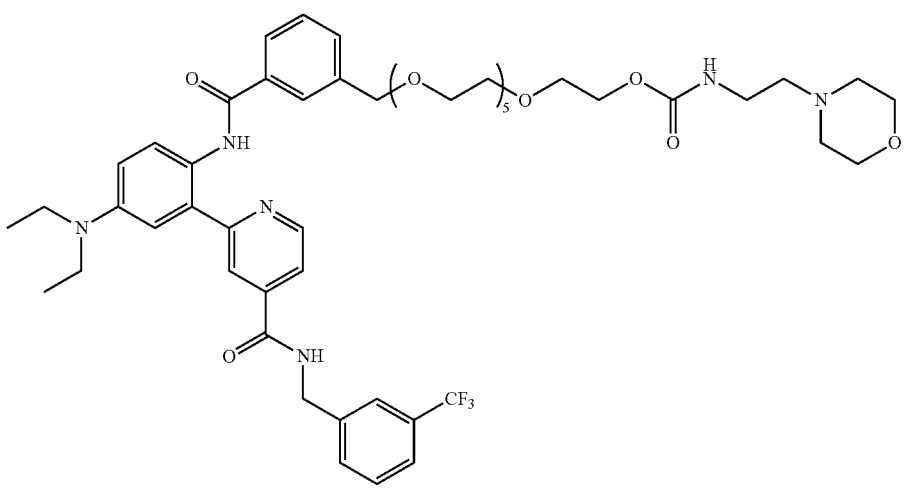

Example 169

1-(3-(4-(diethylamino)-2-(4-(3-(trifluoromethyl) benzylcarbamoyl)pyridin-2-yl)phenylcarbamoyl) phenyl)-2,5,8,11,14,17-hexaoxanonadecan-19-yl 2-morpholinoethylcarbamate To a mixture of Example 168 (50 mg, 0.060 mmol) and diisopropylethylamine (31 μL, 0.18 mmol) in DCM (1 mL) was added 4-nitrophenylchloroformate (52 mg, 0.26 mmol) and the solution stirred for 1 h. 2-Morpholinoethanamine (46 μL, 0.36 mmol) was then added and the solution stirred for 1 h, then the solvent removed and the residue purified by reverse-phase HPLC eluting with a water/acetonitrile gradient containing 0.1% TFA and lyophilized to give 20 mg (25%) of the product as the tri-TFA salt. MS (ES, m/z) 997 [M+H]$^+$.

1H NMR (400 MHz, CDCl$_3$) δ 9.54 (t, J=6.0 Hz, 1H), 9.25 (d, J=2.6 Hz, 1H), 9.17 (d, J=9.1 Hz, 1H), 8.92-8.83 (m, 2H), 8.08 (s, 1H), 8.03 (dd, J=5.1, 1.4 Hz, 1H), 7.98 (dt, J=7.0, 1.9 Hz, 1H), 7.69 (s, 1H), 7.62 (d, J=7.6 Hz, 1H), 7.58-7.46 (m, 3H), 7.46-7.35 (m, 2H), 6.27 (s, 1H), 4.74 (d, J=6.0 Hz, 2H), 4.68 (s, 2H), 4.23-4.12 (m, 2H), 4.02-3.82 (m, 4H), 3.74-3.50 (m, 22H), 3.25 (t, J=5.6 Hz, 2H), 2.93 (t, J=12.0 Hz, 2H), 1.27 (t, J=7.2 Hz, 6H).

Example 170

1-(3-(4-(diethylamino)-2-(4-(3-(trifluormethyl)benzylcarbamoyl)pyridin-2-yl)phenylcarbamoyl)phenyl)-2,5,8,11,14,17-hexaoxanonadecan-19-yl methyl (2-morpholinoethyl)carbamate

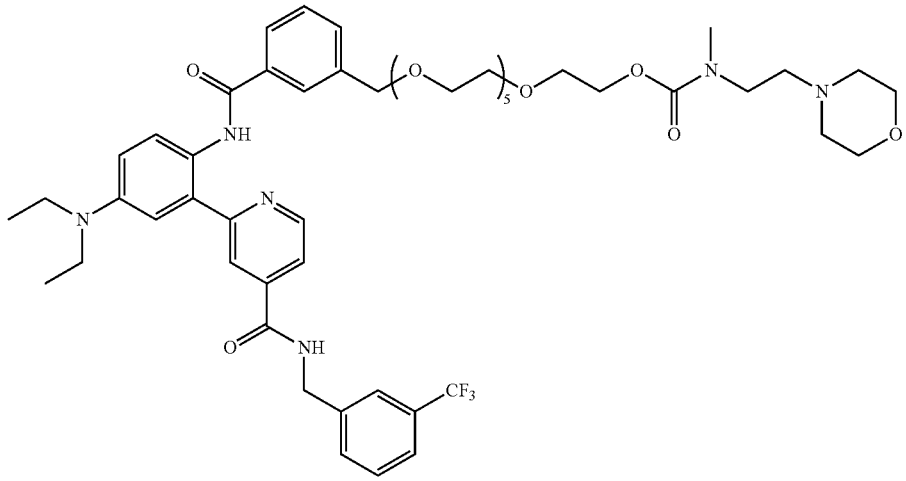

This compound was prepared using the method described for the preparation of Example 169, using N-methyl-2-morpholinoethanamine in place of morpholinoethanamine. MS (ES, m/z) 1011 [M+H]+

Example 171

1-(3-(4-(diethylamino)-2-(4-(3-(trifluoromethyl)benzylcarbamoyl)pyridin-2-yl)phenylcarbamoyl)phenyl)-2,5,8,11,14,17-hexaoxanonadecan-19-yl 4-(2-(2-hydroxyethoxy)ethyl)piperidine-1-carboxylate

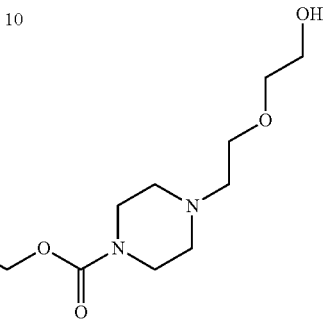
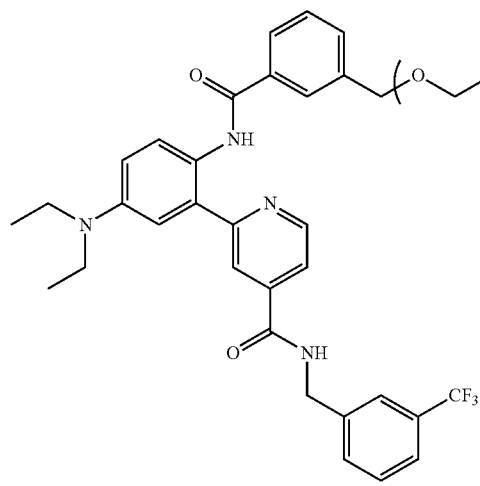

This compound was prepared using the method described for the preparation of Example 169, using 2-(2-(piperidin-4-yl)ethoxy)ethanol in place of morpholinoethanamine. MS (ES, m/z) 1041 [M+H]+

Example 172

1-(3-(4-(diethylamino)-2-(4-(3-(trifluoromethyl)benzylcarbamoyl)pyridin-2-yl)phenylcarbamoyl)phenyl)-2,5,8,11,14,17-hexaoxanonadecan-19-yl bis(2-hydroxyethyl)carbamate

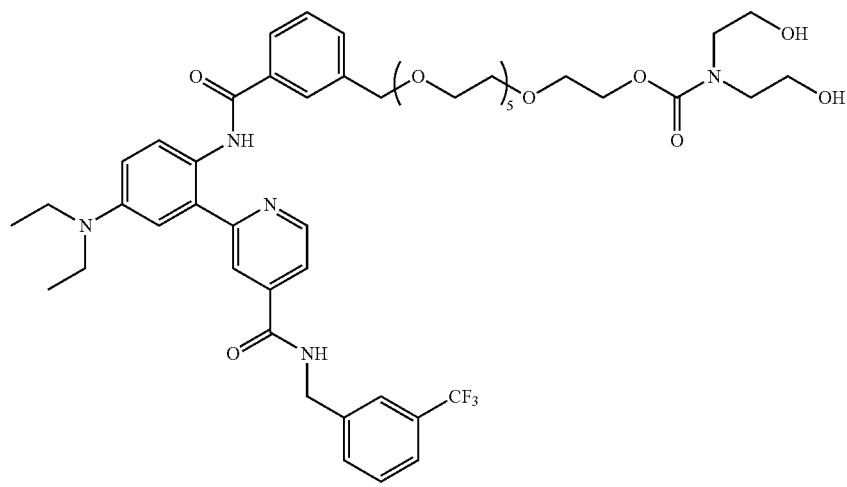

This compound was prepared using the method described for the preparation of Example 169, using diethanolamine in place of morpholinoethanamine. MS (ES, m/z) 972 [M+H]⁺. 1H NMR (400 MHz, cdcl3) δ 9.53 (t, J=5.9 Hz, 1H), 9.33 (d, J=2.6 Hz, 1H), 9.20 (d, J=9.2 Hz, 1H), 8.94 (s, 1H), 8.88 (d, J=5.2 Hz, 1H), 8.13-8.08 (m, 1H), 8.04 (dd, J=5.1, 1.4 Hz, 1H), 8.00 (dt, J=7.3, 1.7 Hz, 1H), 7.71 (s, 1H), 7.63 (d, J=7.5 Hz, 1H), 7.60-7.32 (m, 5H), 4.74 (d, J=6.0 Hz, 2H), 4.69 (s, 2H), 4.29-4.22 (m, 2H), 3.82 (s, 4H), 3.76-3.54 (m, 26H), 3.47 (s, 4H), 1.27 (t, J=7.2 Hz, 6H).

Example 173

2-(2-(3-2,5,8,11,14,17,20,23,26-nonaoxaheptacosyl-benzamido)-5-(diethylamino)phenyl)-N-(3-(trifluoromethyl)benzyl)isonicotinamide

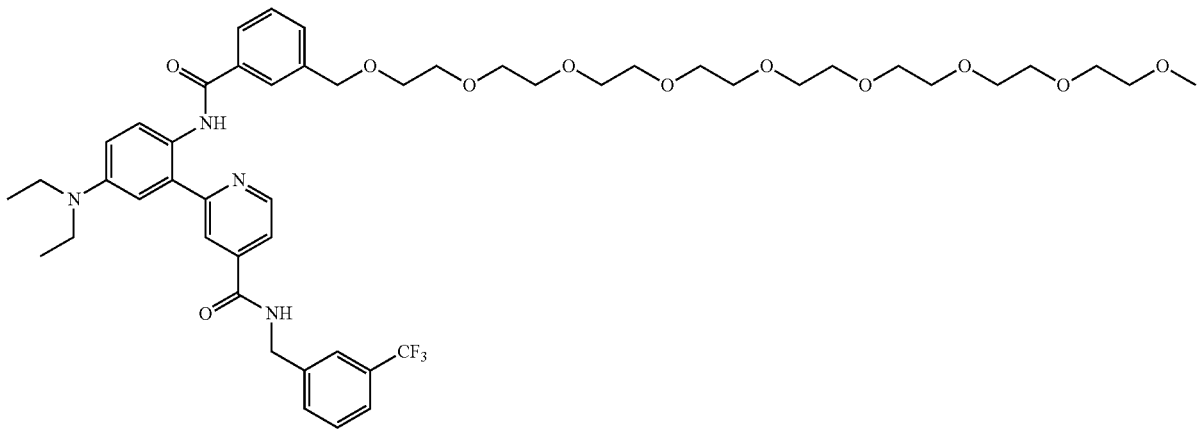 [SMILES: CCN(CC)c1ccc(NC(=O)c2cccc(COCCOCCOCCOCCOCCOCCOCCOCCOC)c2)c(-c2cc(C(=O)NCc3cccc(C(F)(F)F)c3)ccn2)c1]

This compound can be prepared using the method described for the preparation of Example 169, using 2,5,8,11,14,17,20,23-octaoxapentacosan-25-ol in place of 3,6,9,12,15-pentaoxaheptadecane-1,17-diol. MS (ES, m/z) 943 [M+H]⁺

Example 174

1-(3-(4-(diethylamino)-2-(4-(3-(trifluoromethyl)benzylcarbamoyl)pyridin-2-yl)phenylcarbamoyl)phenyl)-2,5,8,11,14,17-hexaoxanonadecan-19-yl 2,5,8,11,14,17,20-heptaoxadocosan-22-ylcarbamate

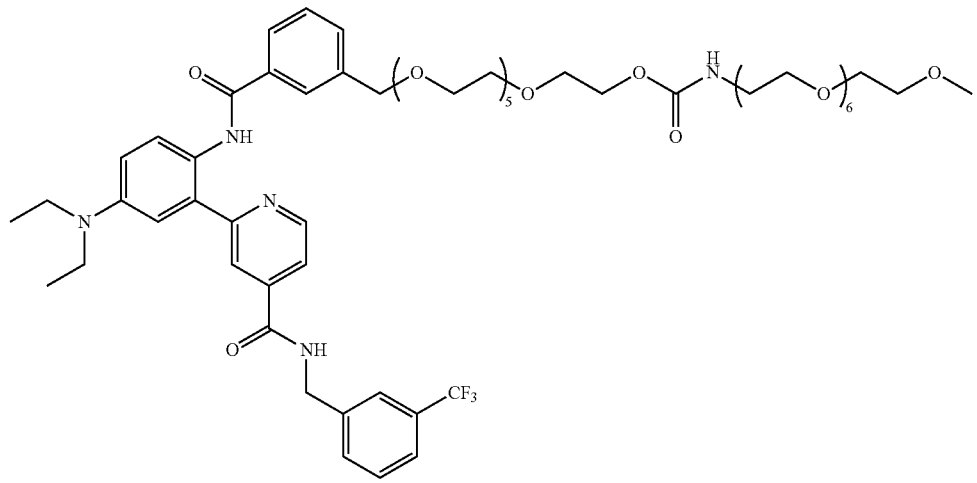

This compound was prepared using the method described for the preparation of Example 169, using 2,5,8,11,14,17,20,23-octaoxapentacosan-25-amine 135c.6 in place of morpholinoethanamine. MS (ES, m/z) 972 [M+H]$^+$
Example 175
1-(3-(4-(diethylamino)-2-(4-(3-(trifluoromethyl)benzylcarbamoyl)pyridin-2-yl)phenylcarbamoyl)phenyl)-2,5,8,11-tetraoxatridecan-13-yl-2,5,8,11,14,17,20-heptaoxadocosan-22-ylcarbamate
Scheme 72.
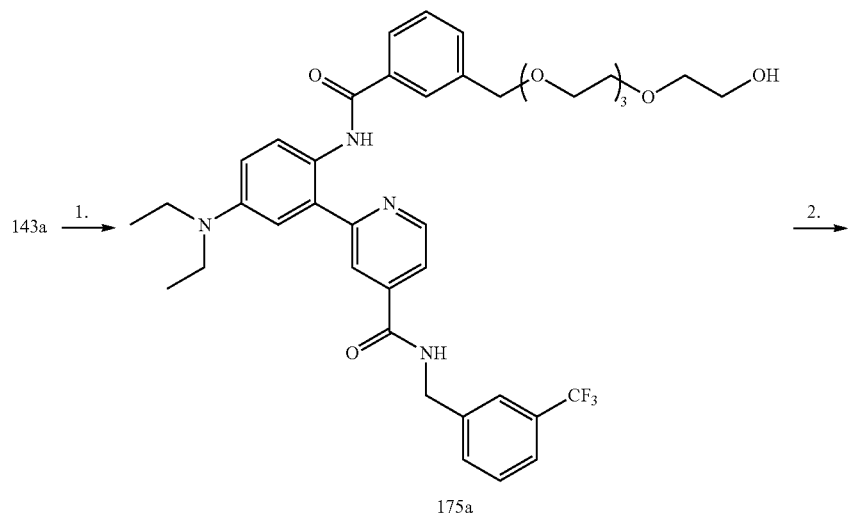
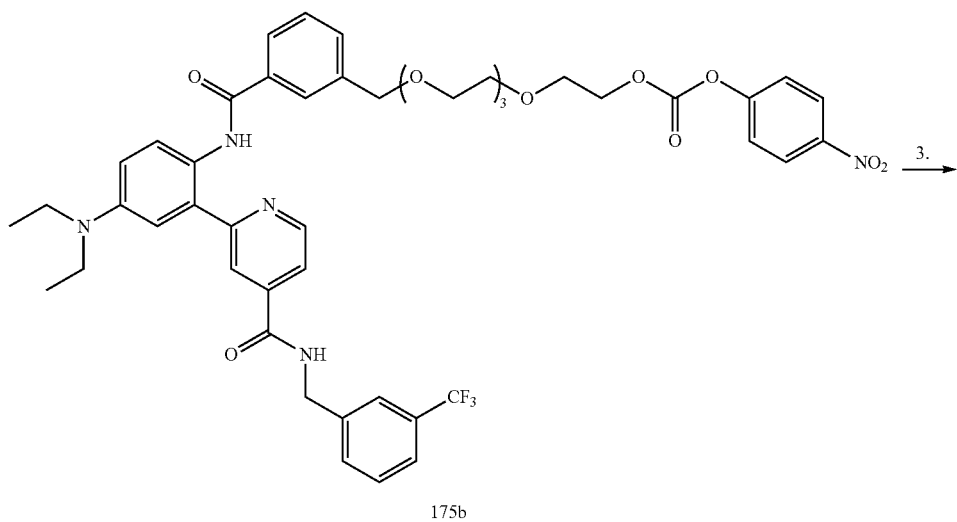

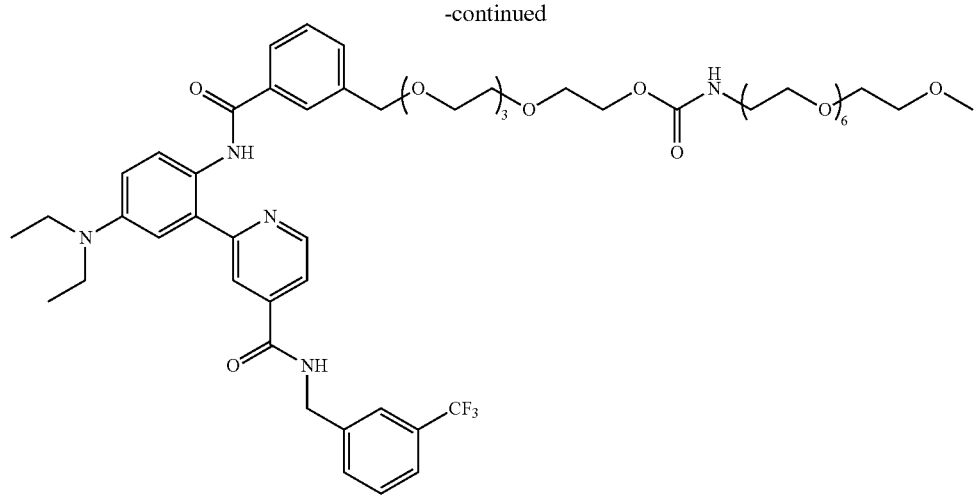

175

1. 2,2'-(2,2'-oxybis(ethane-2,1-diyl)bis(oxy))diethanol, sodium hydride, THF;
2. 4-nitrophenylchloroformate, diisopropylethylamine, DCM;
3. 2,5,8,11,14,17,20,23-octaoxapentacosan-25-amine, DMAP, MeCN.

Intermediate 175a: 2-(5-(diethylamino)-2-(3-(13-hydroxy-2,5,8,11-tetraoxatridecyl)benzamido)phenyl)-N-(3-(trifluoromethyl)benzyl)isonicotinamide This compound was prepared using the method described for the preparation of Example 168, using 2,2'-(2,2'-oxybis(ethane-2,1-diyl)bis(oxy))diethanol in place of 3,6,9,12,15-pentaoxaheptadecane-1,17-diol.

Intermediate 175b: 1-(3-(4-(diethylamino)-2-(4-(3-(trifluoromethyl)benzylcarbamoyl)pyridin-2-yl)phenylcarbamoyl)phenyl)-2,5,8,11-tetraoxatridecan-13-yl 4-nitrophenyl carbonate To a mixture of 175a (196 mg, 0.329 mmol) and diisopropylethylamine (286 μL, 1.65 mmol) was added 4-nitrophenylchloroformate (266 mg, 1.32 mmol) and the mixture stirred for 2 h. The solution was diluted with DCM and washed with $H_2O$, then dried over $Na_2SO_4$ and the solvent removed. The resulting residue was purified by silica gel chromatography, using a gradient of 50% to 100% EtOAc in hexanes as eluent and the solvent removed. This gave 80 mg (26%) of the product as a viscous, yellow oil.

Example 175

1-(3-(4-(diethylamino)-2-(4-(3-(trifluoromethyl)benzylcarbamoyl)pyridin-2-yl)phenylcarbamoyl)phenyl)-2,5,8,11-tetraoxamidecan-13-yl 2,5,8,11,14,17,20-heptaoxadocosan-22-ylcarbamate A mixture of 175b (20 mg, 0.022 mmol), 2,5,8,11,14,17,20,23-octaoxapentacosan-25-amine (15 mg, 0.436 mmol) and catalytic DMAP in MeCN was stirred at 80° C. for 2 h. The solution was acidified with acetic acid and purified by reverse-phase HPLC eluting with a water/acetonitrile gradient containing 0.1% TFA and lyophilized to give 15 mg (51%) of the product as the di-TFA salt. MS (ES, m/z) 1118 [M+H]$^+$ Example 176

1-(3-(4-(diethylamino)-2-(4-(3-(trifluoromethyl)benzylcarbamoyl)pyridin-2-yl)phenylcarbamoyl)phenyl)-2,5,8,11-tetraoxamidecan-13-yl bis(2-hydroxyethyl)carbamate

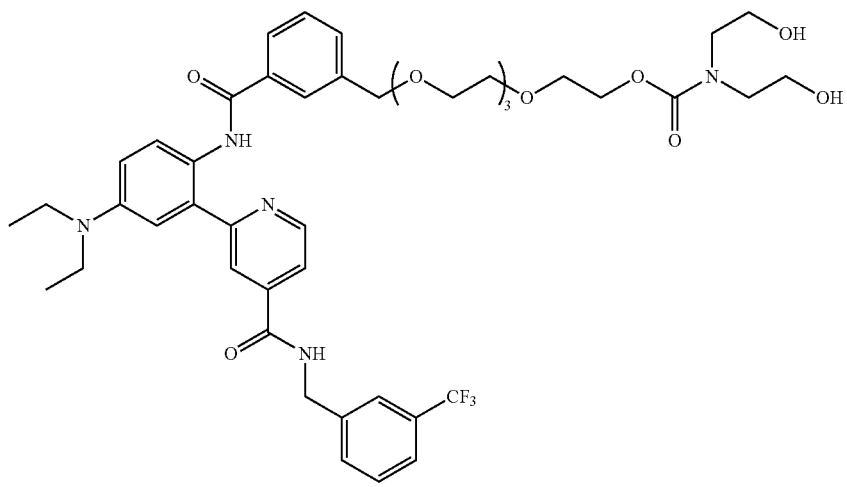

This compound was prepared using the method described for the preparation of Example 175, using diethanolamine in place of 2,5,8,11,14,17,20,23-octaoxapentacosan-25-amine. MS (ES, m/z) 884 [M+H]⁺

Example 177

1-(3-(4-(diethylamino)-2-(4-(3-(trifluoromethyl)benzylcarbamoyl)pyridin-2-yl)phenylcarbamoyl)phenyl)-2,5,8,11-tetraoxamidecan-13-yl-1,3-dihydroxy-2-(hydroxymethyl)propan-2-ylcarbamate

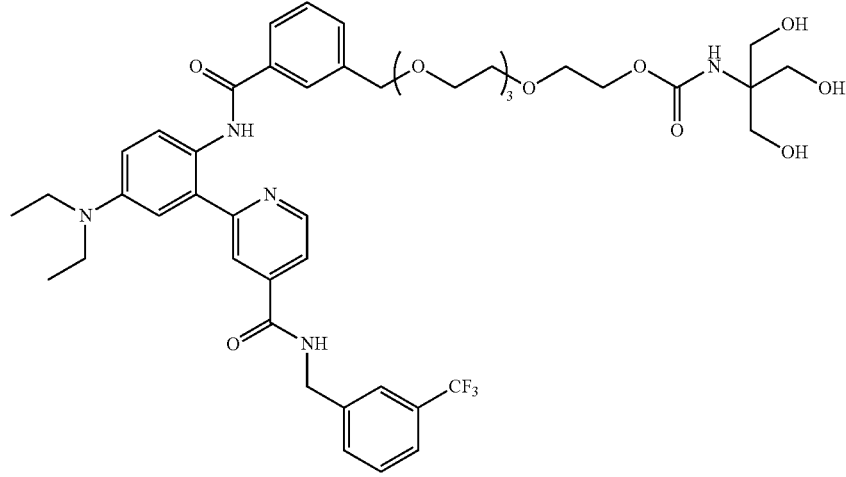

This compound was prepared using the method described for the preparation of Example 175, using tris(hydroxymethyl)aminomethane.HCl in place of 2,5,8,11,14,17,20,23-octaoxapentacosan-25-amine. MS (ES, m/z) 900 [M+H]⁺

Example 178

2-(5-(diethylamino)-2-(3-(22-hydroxy-20-(2-hydroxyethyl)-2,5,8,11,14,17-hexaoxa-20-azadocosyl)benzamido)phenyl)-N-(3-(trifluoromethyl)benzyl)isonicotinamide Scheme 73.

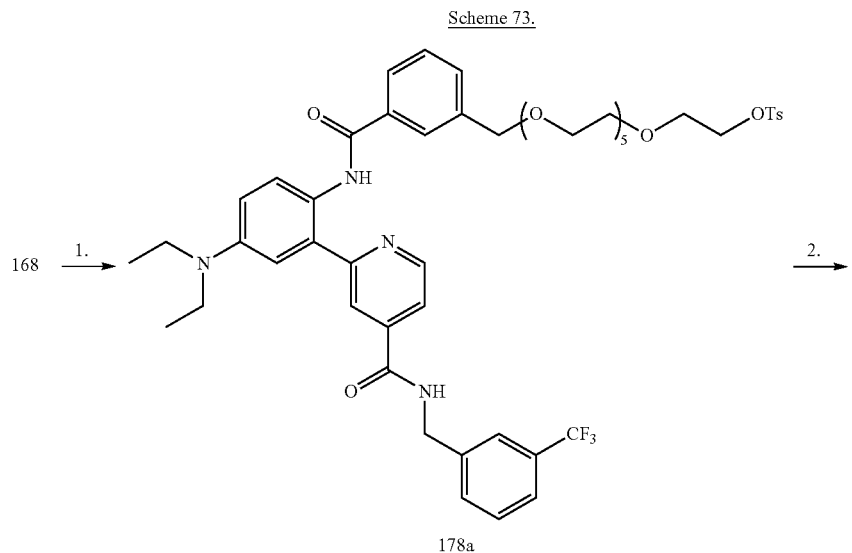

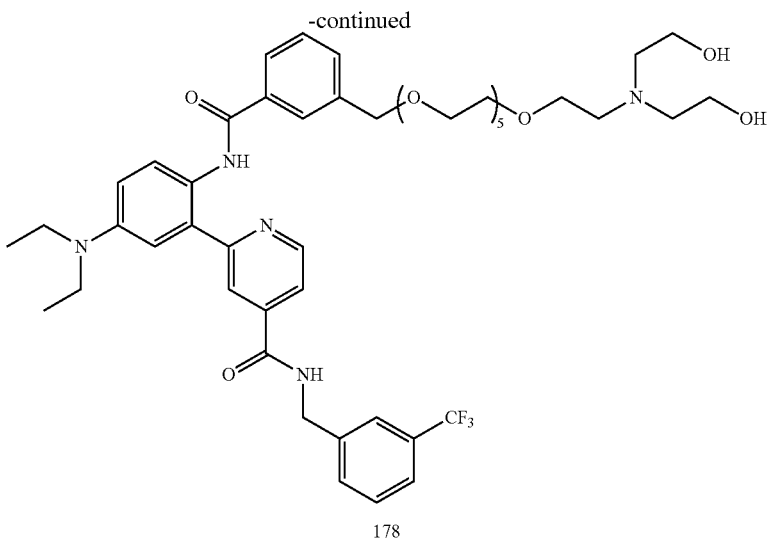

178

1. p-Toluenesulfonyl chloride, triethylamine, DCM;
2. Diethanolamine, MeCN.

Intermediate 178a: 1-(3-(4-(diethylamino)-2-(4-(3-(trifluoromethyl)benzylcarbamoyl)pyridin-2-yl)phenylcarbamoyl)phenyl)-2,5,8,11,14,17-hexaoxanonadecan-19-yl 4-methylbenzenesulfonate To a mixture of Example 168 (500 mg, 0.595 mmol) and triethylamine (167 µL, 1.19 mmol) in DCM (3 mL) was added p-toluenesulfonyl chloride (136 mg, 0.714 mmol) in several portions and the solution stirred for 16 h. The solution was then diluted with DCM and washed with aqueous HCl and $H_2O$, then dried over $Na_2SO_4$ and the solvent removed. The residue was purified by silica gel chromatography, using a gradient of 20% to 100% EtOAc in hexanes as eluent and the solvent removed. This gave 560 mg (95%) of the product as a yellow oil.

Example 178

2-(5-(diethylamino)-2-(3-(22-hydroxy-20-(2-hydroxyethyl)-2,5,8,11,14,17-hexaoxa-20-azadocosyl)benzamido)phenyl)-N-(3-(trifluoromethyl)benzyl)isonicotinamide A mixture of 178a (85 mg, 0.085 mmol) and diethanolamine (18 mg, 0.17 mmol) in MeCN (1 mL) was heated to 80° C. and stirred for 18 h. The solution was diluted with $H_2O$ and purified by reverse-phase HPLC eluting with a water/acetonitrile gradient containing 0.1% TFA and lyophilized to give 43 mg (40%) of the product as the tri-TFA salt. MS (ES, m/z) 928 [M+H]$^+$. 1H NMR (400 MHz, cdcl3) δ 9.56 (t, J=6.0 Hz, 1H), 9.31 (d, J=2.5 Hz, 1H), 9.18 (d, J=9.2 Hz, 1H), 8.94 (s, 1H), 8.87 (d, J=5.1 Hz, 1H), 8.10 (s, 1H), 8.06-7.94 (m, 2H), 7.70 (s, 1H), 7.63 (d, J=7.5 Hz, 1H), 7.58-7.37 (m, 5H), 4.72 (d, J=5.9 Hz, 2H), 4.67 (s, 2H), 4.00-3.90 (m, 4H), 3.86 (d, J=4.8 Hz, 2H), 3.70 (d, J=5.3 Hz, 4H), 3.67-3.39 (m, 22H), 1.26 (t, J=7.2 Hz, 6H).

Example 179

2-(5-(diethylamino)-2-(3-(20-methyl-22-morpholino-2,5,8,11,14,17-hexaoxa-20-azadocosyl)benzamido)phenyl)-N-(3-(trifluoromethyl)benzyl)isonicotinamide

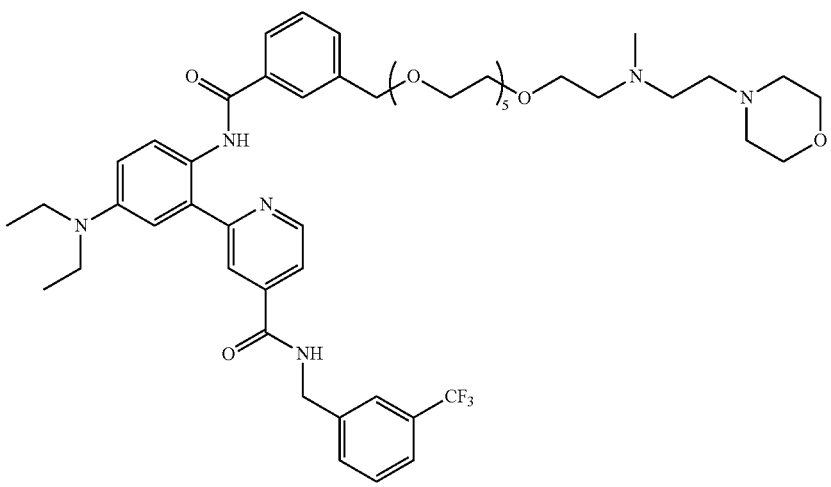

This compound was prepared using the method described for the preparation of Example 178, using N-methyl-2-morpholinoethanamine in place of diethanolamine. MS (ES, m/z) 967 [M+H]$^+$.

Example 180

N-(2-(2-(2-hydroxyethoxy)ethoxy)ethyl)-1-(3-(4-(piperidin-1-yl)-2-(4-(3-(trifluoromethyl)benzylcarbamoyl)pyridin-2-yl)phenylcarbamoyl)benzyl)-1H-indole-4-carboxamide Scheme 74.

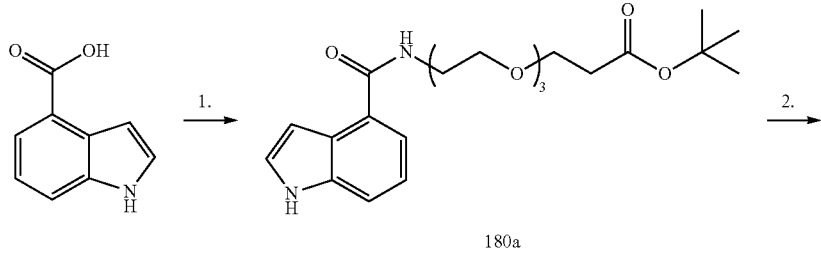

180a

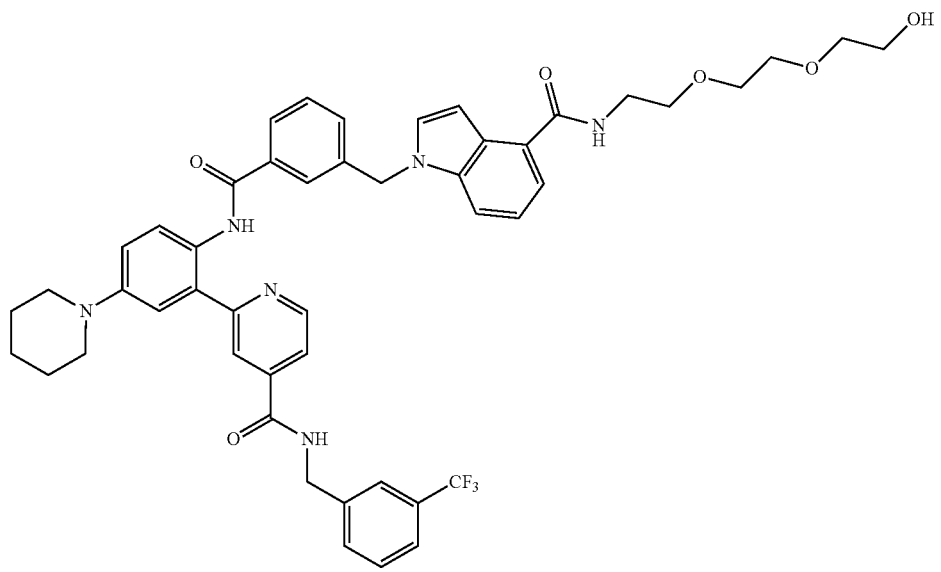

180

1. tert-butyl 3-(2-(2-(2-aminoethoxy)ethoxy)ethoxy)propanoate, HATU, diisopropylethylamine, DMF; 2. 8.1a K$_2$CO$_3$, DMF.

347

Intermediate 180a: tert-butyl 1-(1H-indol-4-yl)-1-oxo-5,8,11-trioxa-2-azatetradecan-14-oate To a mixture of 1H-indole-4-carboxylic acid (322 mg, 2.00 mmol), tert-butyl 3-(2-(2-(2-aminoethoxy)ethoxy)ethoxy) propanoate (554 mg, 2.00 mmol), and diisopropylethylamine (700 µL, 4.00 mmol) in DMF (3 mL) was added HATU (950 mg, 2.50 mmol) and the solutions stirred for 16 h. The solvent was removed and the resulting residue was purified by silica gel chromatography, using a gradient of 70% to 100% EtOAc in hexanes as eluent and the solvent removed. This gave 557 mg (66%) of the product.

348

Example 180

N-(2-(2-(2-hydroxyethoxy)ethoxy)ethyl)-1-(3-(4-(piperidin-1-yl)-2-(4-(3-(trifluoromethyl)benzylcarbamoyl)pyridin-2-yl)phenylcarbamoyl)benzyl)-1H-indole-4-carboxamide A mixture of 180a (524 mg, 1.25 mmol), 8.1a (755 mg, 1.25 mmol), and $K_2CO_3$ (510 mg, 3.70 mmol) in DMF (2 mL) was stirred for 3 days, then purified by reverse-phase HPLC eluting with a water/acetonitrile gradient containing 0.1% TFA and lyophilized to give 16 mg (1%) of the product as the di-TFA salt. MS (ES, m/z) 863 [M+H]$^+$ Example 181

(S)-1-oxo-1-(1-(3-(4-(piperidin-1-yl)-2-(4-(1,2,3,4-tetrahydronaphthalen-1-ylcarbamoyl)pyridin-2-yl) phenylcarbamoyl)benzyl)-1H-indol-4-yl)-5,8,11-trioxa-2-azatetradecan-14-oic acid Scheme 75.

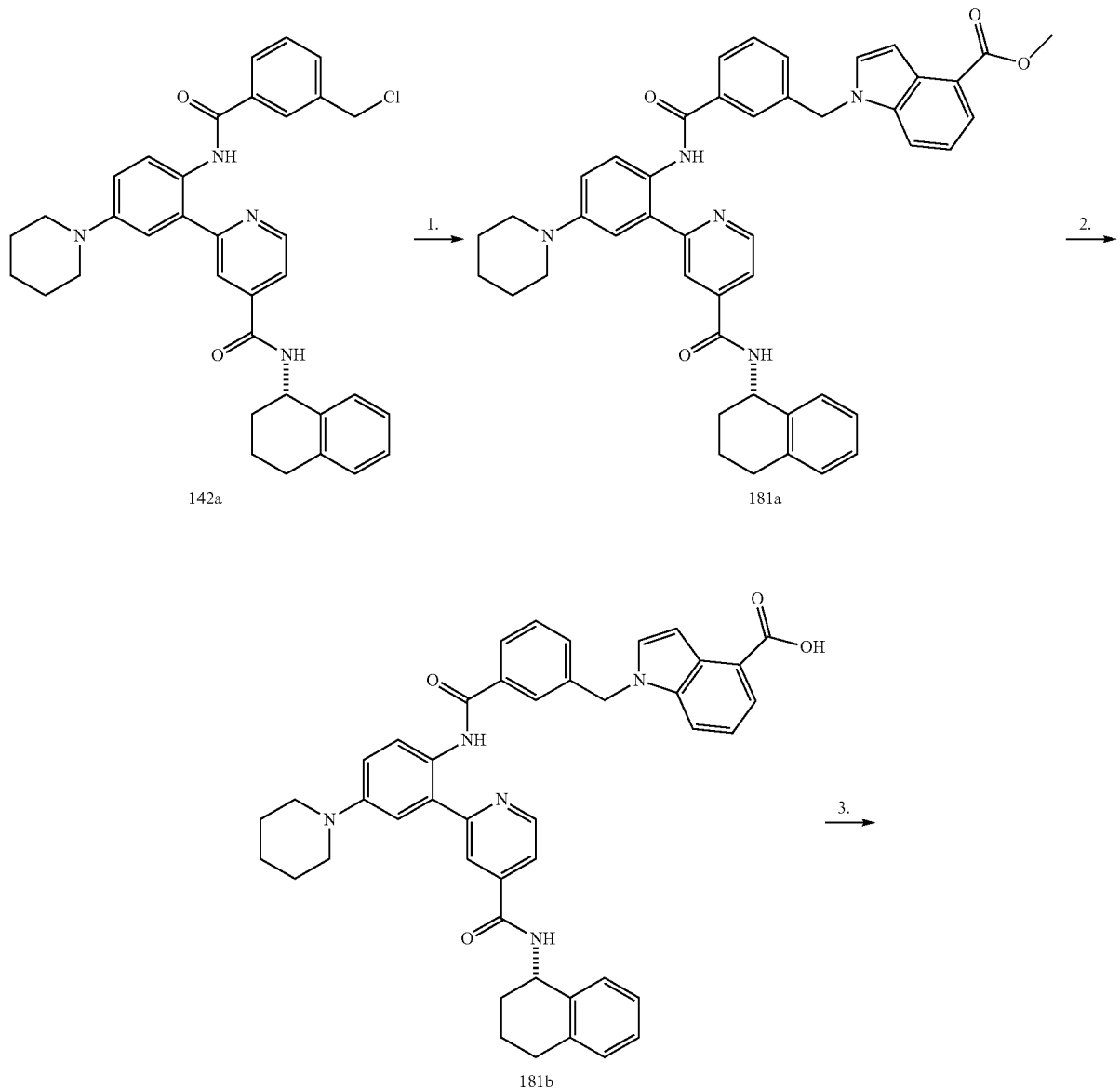

-continued

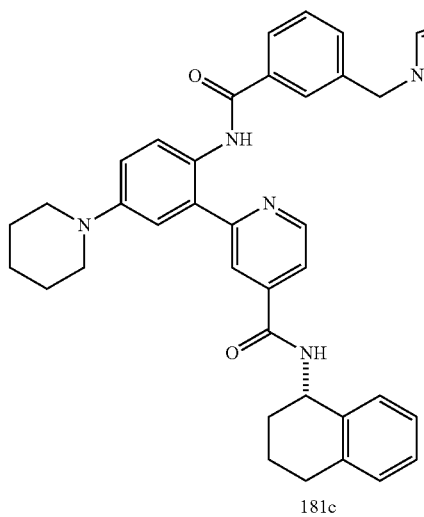
181c

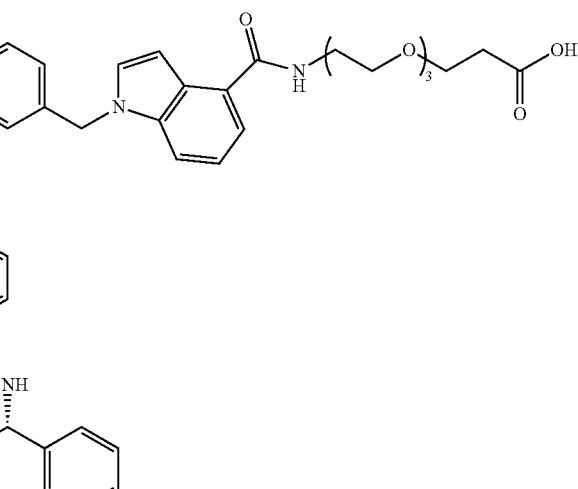
181

1. methyl 1H-indole-4-carboxylate, Cs₂CO₃, DMF;
2. LiOH•H₂O, THF, H₂O;
3. tert-butyl 3-(2-(2-(2-aminoethoxy)ethoxy)ethoxy)propanoate, HATU, diisopropylethylamine, DMF;
4. HCl, dioxane.

Intermediate 181a: (S)-methyl 1-(3-(4-(piperidin-1-yl)-2-(4-(1,2,3,4-tetrahydronaphthalen-1-ylcarbamoyl)pyridin-2-yl)phenylcarbamoyl)benzyl)-1H-indole-4-carboxylate A mixture of 142a (14.9 g, 25.7 mmol), methyl 1H-indole-4-carboxylate (4.5 g, 25.7 mmol), and Cs₂CO₃ (16.7 g, 51.3 mmol) in DMF (50 mL) was stirred for 15 h under an atmosphere of N₂. The suspension was filtered and the solvent removed. The resulting residue was purified by silica gel chromatography to give 16.2 g (88%) of the product.

Intermediate 181b: (S)-1-(3-(4-(piperidin-1-yl)-2-(4-(1,2,3,4-tetrahydronaphthalen-1-ylcarbamoyl)pyridin-2-yl)phenylcarbamoyl)benzyl)-1H-indole-4-carboxylic acid A mixture of 181a (16.0 g, 22.3 mmol) and LiOH.H₂O (1.87 g, 44.5 mmol) in THF/H₂O (176 mL/44 mL) was heated to 60° C. and stirred for 40 h. The solution was concentrated, then DCM added (300 mL) and washed with aqueous HCl, then dried over Na₂SO₄ and the solvent removed to give 15.4 g (98%) of the product.

Intermediate 181c: (S)-tert-butyl 1-oxo-1-(1-(3-(4-(piperidin-1-yl)-2-(4-(1,2,3,4-tetrahydronaphthalen-1-yl carbamoyl)pyridin-2-yl)phenylcarbamoyl)benzyl)-1H-indol-4-yl)-5,8,11-trioxa-2-azatetradecan-14-oate To a mixture of 181b (14.7 g, 20.9 mmol), tert-butyl 3-(2-(2-(2-aminoethoxy)ethoxy)ethoxy)propanoate (6.06 g, 21.8 mmol), and diisopropylethylamine (14.5 mL, 83.4 mmol) in DMF (63 mL) was added HATU (9.93 g, 26.1 mmol), then the solution heated to 50° C. and stirred for 2 h. The solvent was removed and the resulting residue dissolved in EtOAc and washed thrice with H₂O, then dried over Na₂SO₄ and the solvent removed. The resulting residue was purified by silica gel chromatography to give 10 g (50%) of the product.

Example 181

(S)-1-oxo-1-(1-(3-(4-(piperidin-1-yl)-2-(4-(1,2,3,4-tetrahydronaphthalen-1-ylcarbamoyl)pyridin-2-yl)phenylcarbamoyl)benzyl)-1H-indol-4-yl)-5,8,11-trioxa-2-azatetradecan-14-oic acid A mixture of 181c (12.5 g, 13.0 mmol) in a 4M HCl solution of dioxane (120 mL) was stirred at 0° C. for 1 h and then the solvent removed. The resulting residue was dissolved in DCM and washed with $H_2O$, then dried over $Na_2SO_4$. The solvent was removed and the residue was purified by silica gel chromatography, using a gradient of 2% to 4% MeOH in DCM as eluent and the solvent removed. This gave 9.6 g (75%) of the product as the HCl salt. MS (ES, m/z) 907 [M+H]$^+$. $^1$H NMR (400 MHz, dmso) δ 12.14 (s, 1H), 11.95 (s, 1H), 9.16 (d, J=8.6 Hz, 1H), 8.68 (d, J=5.1 Hz, 1H), 8.29-8.18 (m, 2H), 8.14 (d, J=9.0 Hz, 1H), 7.84-7.66 (m, 3H), 7.61 (dd, J=11.5, 5.7 Hz, 2H), 7.51-7.27 (m, 4H), 7.22-7.02 (m, 5H), 6.96-6.84 (m, 1H), 5.58 (s, 2H), 5.29-5.18 (m, 1H), 3.61-3.38 (m, 14H), 3.22-3.11 (m, 4H), 2.85-2.69 (m, 2H), 2.42 (t, J=6.3 Hz, 2H), 2.06-1.88 (m, 2H), 1.87-1.70 (m, 2H), 1.70-1.58 (m, 4H), 1.54 (d, J=5.0 Hz, 2H).

Example 182

(S)-1-(1-(3-(4-(diethylamino)-2-(4-(1,2,3,4-tetrahydronaphthalen-1-ylcarbamoyl)pyridin-2-yl)phenylcarbamoyl)benzyl)-1H-indol-4-yl)-1-oxo-5,8,11-trioxa-2-azatetradecan-14-oic acid

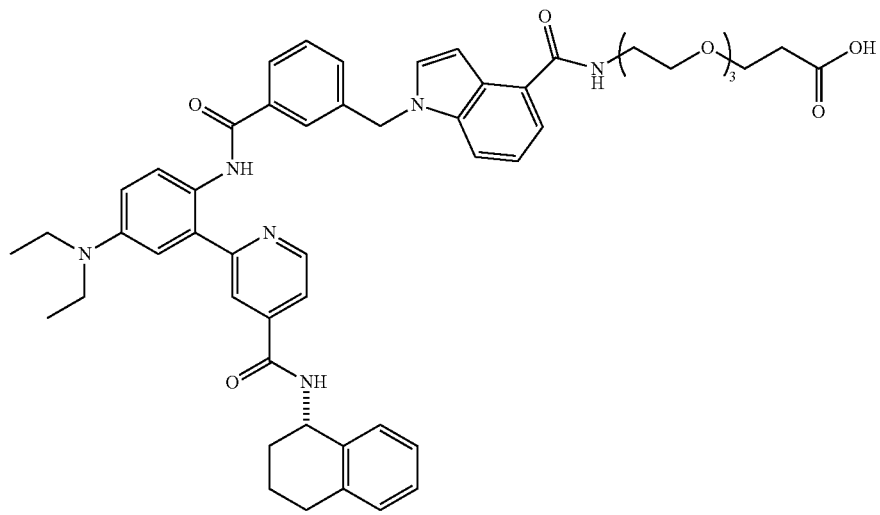

This compound was prepared using the method described for the preparation of Example 181, using 131c in place of 142a. MS (ES, m/z) 895 [M+H]⁺

Example 183

3-((3-(4-(piperidin-1-yl)-2-(4-(3-(trifluoromethyl)benzylcarbamoyl)pyridin-2-yl)phenylcarbamoyl)phenoxy)methyl)benzoic acid

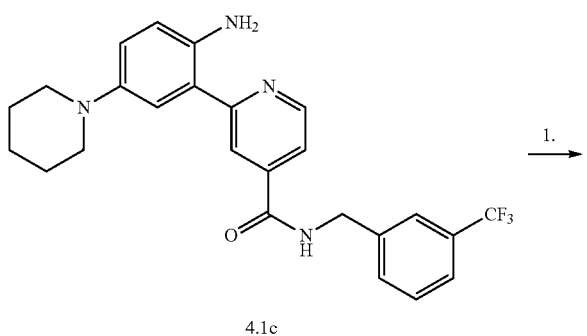

1. 3-Hydroxybenzoic acid, HATU, diisopropylethylamine, DMF; 2. Methyl 3-(bromomethyl)benzoate, K₂CO₃, DMF.

Intermediate 183a: 2-(2-(3-hydroxybenzamido)-5-(piperidin-1-yl)phenyl)-N-(3-(trifluoromethyl)benzyl)isonicotinamide To a mixture of 4.1c (91 mg, 0.20 mmol), 3-hydroxybenzoic acid (28 mg, 0.20 mmol), and diisopropylethylamine (104 □L, 0.60 mmol) in DMF (2 mL) was added HATU (76 mg, 0.20 mmol) and the solution stirred for 18 h. The solvent was removed and the resulting residue purified by reverse-phase HPLC eluting with a water/acetonitrile gradient containing 0.1% TFA and lyophilized to give 34 mg (30%) of the product.

Example 183

3-((3-(4-(piperidin-1-yl)-2-(4-(3-(trifluoromethyl)benzylcarbamoyl)pyridin-2-yl)phenylcarbamoyl)phenoxy)methyl)benzoic acid A mixture of 183a (34 mg, 0.059 mmol), methyl 3-(bromomethyl)benzoate (27 mg, 0.12 mmol), and K₂CO₃ (24 mg, 0.18 mmol) was stirred for 16 h and then filtered. The solvent was removed and resulting residue purified by reverse-phase HPLC eluting with a water/acetonitrile gradient containing 0.1% TFA and lyophilized to give 18 mg (43%) of the product. MS (ES, m/z) 709 [M+H]⁺

Example 184

3-((2-(3-(4-(piperidin-1-yl)-2-(4-(3-(trifluoromethyl)benzylcarbamoyl)pyridin-2-yl)phenylcarbamoyl)phenyl)-1-meth benzoic acid

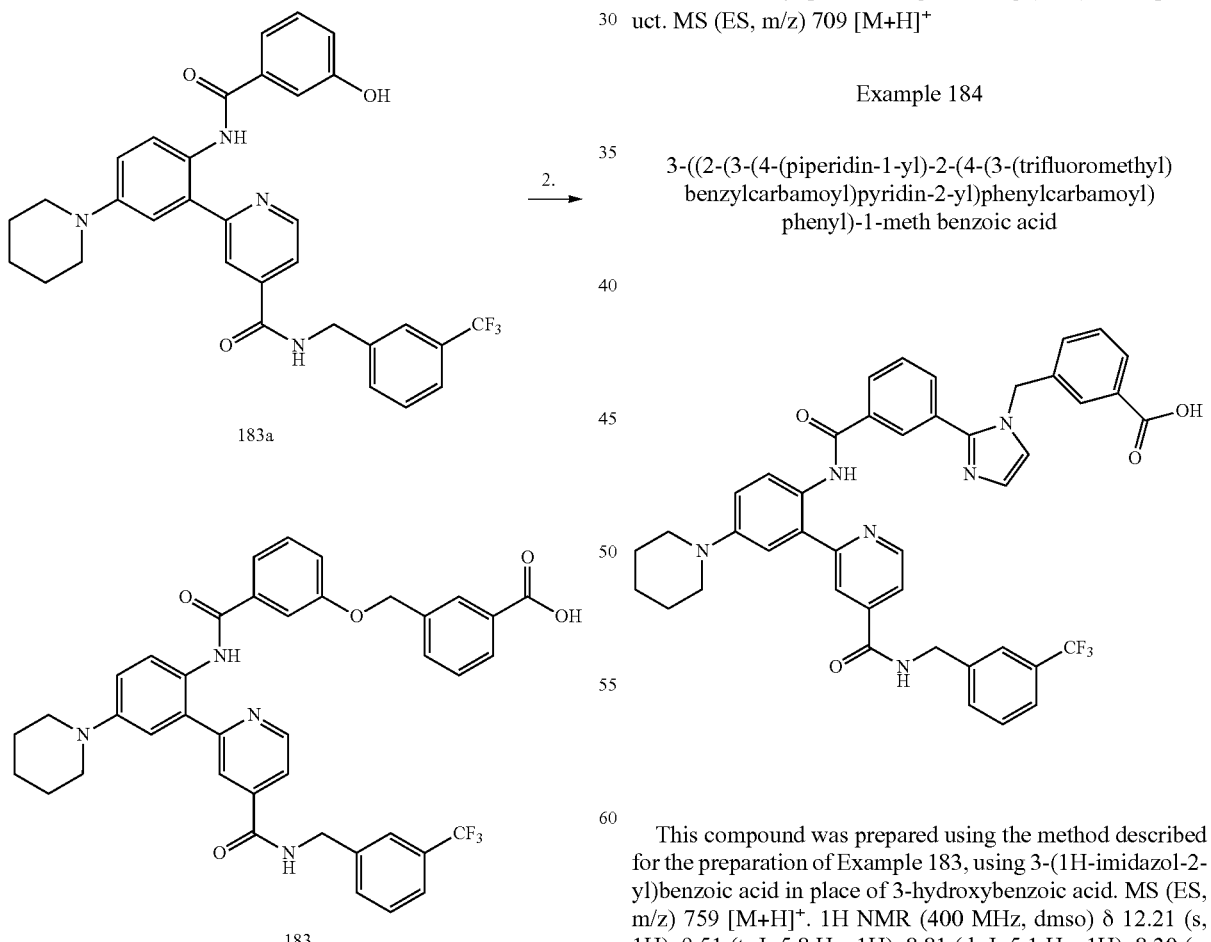

This compound was prepared using the method described for the preparation of Example 183, using 3-(1H-imidazol-2-yl)benzoic acid in place of 3-hydroxybenzoic acid. MS (ES, m/z) 759 [M+H]⁺. 1H NMR (400 MHz, dmso) δ 12.21 (s, 1H), 9.51 (t, J=5.8 Hz, 1H), 8.81 (d, J=5.1 Hz, 1H), 8.30 (s, 1H), 8.23-8.14 (m, 2H), 8.11 (d, J=7.6 Hz, 1H), 7.88-7.71 (m, 7H), 7.66 (s, 1H), 7.55 (dd, J=18.5, 10.9 Hz, 4H), 7.41 (t, J=7.7 Hz, 1H), 7.32 (d, J=7.7 Hz, 2H), 5.51 (s, 2H), 4.57 (d, J=5.8 Hz, 2H), 3.31 (s, 4H), 1.71 (s, 4H), 1.57 (s, 2H).

Example 185

3-((3-(4-(piperidin-1-yl)-2-(4-(3-(trifluoromethyl)benzylcarbamoyl)pyridin-2-yl)phenylcarbamoyl)benzyloxy)methyl)benzoic acid

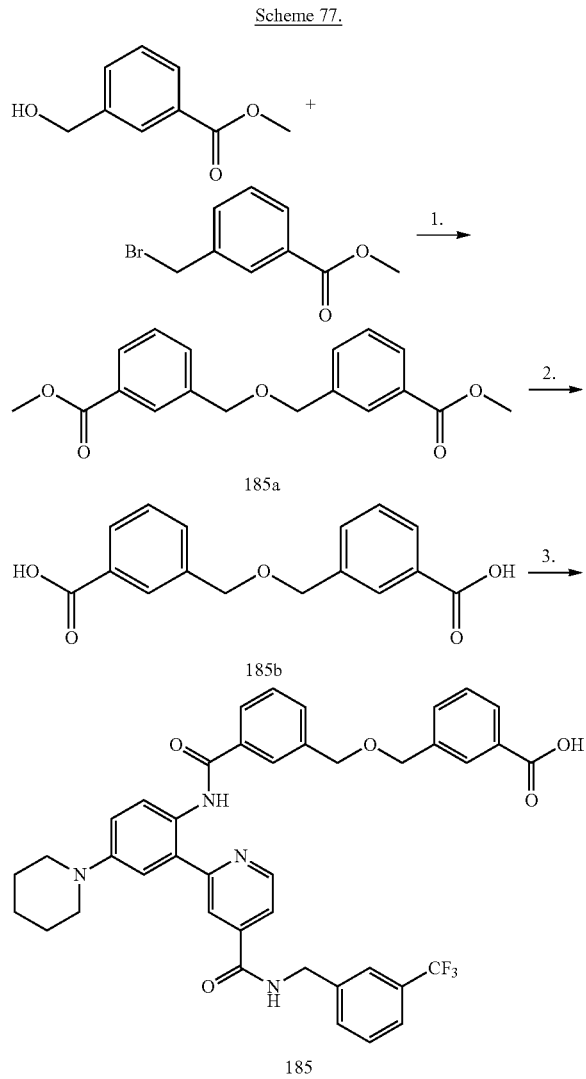

1. Sodium hydride, DMF;
2. NaOH, MeOH, H₂O;
3. 4.1c, HATU, diisopropylethylamine, DMF.

Intermediate 185a: dimethyl 3,3'-oxybis(methylene)dibenzoate

To a mixture of methyl 3-(hydroxymethyl)benzoate (500 mg, 3.01 mmol) in DMF (5 mL) cooled to 0° C. was added a 60% sodium hydride dispersion in mineral oil (180 mg). The mixture was stirred for 0.5 h at 0° C., then methyl 3-(bromomethyl)benzoate (690 mg, 3.01 mmol) was added and the mixture stirred an additional 4 h at room temperature, then diluted with EtOAc. The solution was washed with aqueous HCl, saturated aqueous NaHCO₃, H₂O, and brine, then dried over Na₂CO₃ and the solvent removed. The resulting residue was purified by silica gel chromatography to give 450 mg (48%) of the product 185a.

Intermediate 185b: 3,3'-oxybis(methylene)dibenzoic acid

A mixture of 185a (450 mg, 1.43 mmol) and three pellets of NaOH in MeOH/H₂O (4 mL:4 mL) was stirred for 4 h at 0° C., then diluted with EtOAc. The solution was washed with aqueous HCl, H₂O, and brine, then dried over Na₂CO₃ and the solvent removed to give 370 mg (90%) of the product 185b.

Example 185

3-((3-(4-(piperidin-1-yl)-2-(4-(3-(trifluoromethyl)benzylcarbamoyl)pyridin-2-yl)phenylcarbamoyl)benzyloxy)methyl)benzoic acid To a mixture of 4.1c (190 mg, 0.420 mmol), 185b (370 mg, 1.26 mmol) and diisopropylethylamine (660 µL, 3.80 mmol) in DMF (3 mL) was added HATU (240 mg, 0.630 mmol) and the solution stirred for 16 h. The solvent was removed and the residue purified by reverse-phase HPLC eluting with a water/acetonitrile gradient containing 0.1% TFA and lyophilized to give 25 mg (8%) of the product. MS (ES, m/z) 723 [M+H]⁺

Example 186

3-((3-(4-(piperidin-1-yl)-2-(4-(3-(trifluoromethyl)benzylcarbamoyl)pyridin-2-yl)phenylcarbamoyl)phenylthio)methyl)benzoic acid

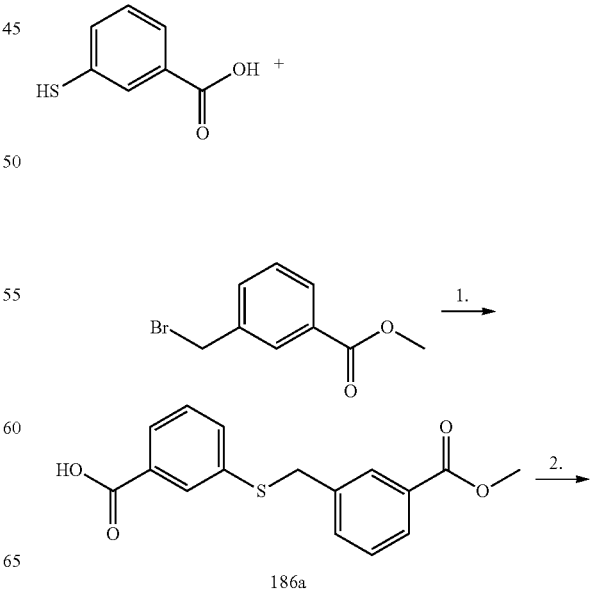

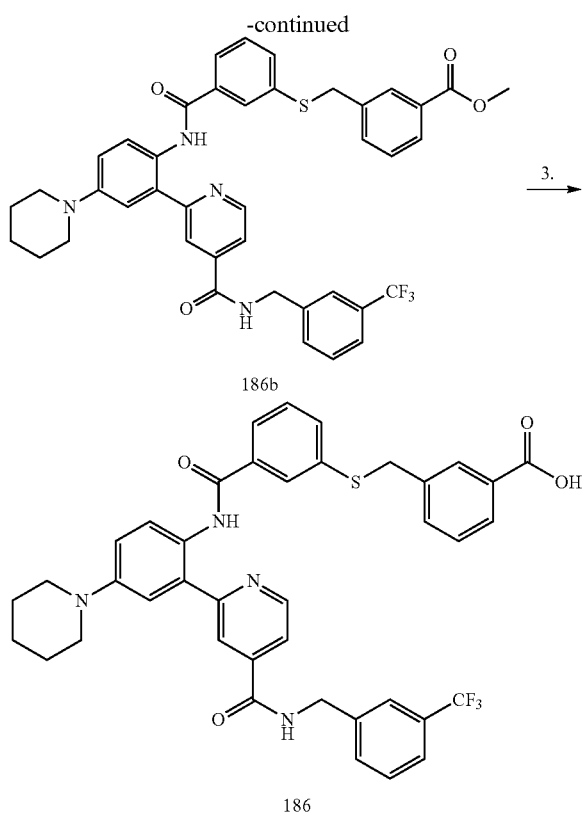

1. $K_2CO_3$, DMF;
2. 4.1c, HATU, diisopropylethylamine, DMF;
3. LiOH·$H_2O$, THF, $H_2O$.

Intermediate 186a:
3-(3-(methoxycarbonyl)benzylthio)benzoic acid

A mixture of 3-mercaptobenzoic acid (154 mg, 1.00 mmol), methyl 3-(bromomethyl)benzoate (229 mg, 1.00 mmol) and $K_2CO_3$ (414 mg, 3.00 mmol) in DMF (1 mL) was stirred for 16 h, then solvent removed. The resulting residue was purified by silica gel chromatography to give 300 mg (90%) of the product.

Intermediate 186b: methyl 3-((3-(4-(piperidin-1-yl)-2-(4-(3-trifluoromethyl)benzylcarbamoyl)pyridin-2-yl)phenylcarbamoyl)phenylthio)methyl)benzoate To a mixture of 186a (300 mg, 0.991 mmol), 4.1c (454 mg, 1.00 mmol), and diisopropylethylamine (521 μL, 3.00 mmol) in DMF (3 mL) was added HATU (570 mg, 1.5 mmol) and then stirred for 18 h. The solvent was removed and the residue purified by silica gel chromatography to give 462 mg (63%) of the product.

Example 186

3-((3-(4-(piperidin-1-yl)-2-(4-(3-(trifluoromethyl)benzylcarbamoyl)pyridin-2-yl)phenylcarbamoyl)phenylthio)methyl)benzoic acid A mixture of 186b (462 mg, 0.625 mmol) and LiOH·$H_2O$ (40 mg, 0.953 mmol) in THF/$H_2O$ (3 mL:1 mL) was stirred for 4 h, then the solution concentrated and purified by reverse-phase HPLC eluting with a water/acetonitrile gradient containing 0.1% TFA and lyophilized to give 30 mg (7%) of the product. MS (ES, m/z) 725 [M+H]$^+$. 1H NMR (400 MHz, dmso) δ 12.34 (s, 1H), 9.55 (t, J=5.9 Hz, 1H), 8.87 (d, J=5.1 Hz, 1H), 8.36 (s, 2H), 7.97 (s, 1H), 7.88 (d, J=5.1 Hz, 2H), 7.83-7.73 (m, 3H), 7.73-7.45 (m, 8H), 7.41 (t, J=7.7 Hz, 1H), 4.62 (d, J=5.7 Hz, 2H), 4.40 (s, 2H), 3.45 (s, 4H), 1.85 (s, 4H), 1.63 (s, 2H).

Example 187

(S)-tert-butyl 1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidine-2-carboxylate Scheme 79.

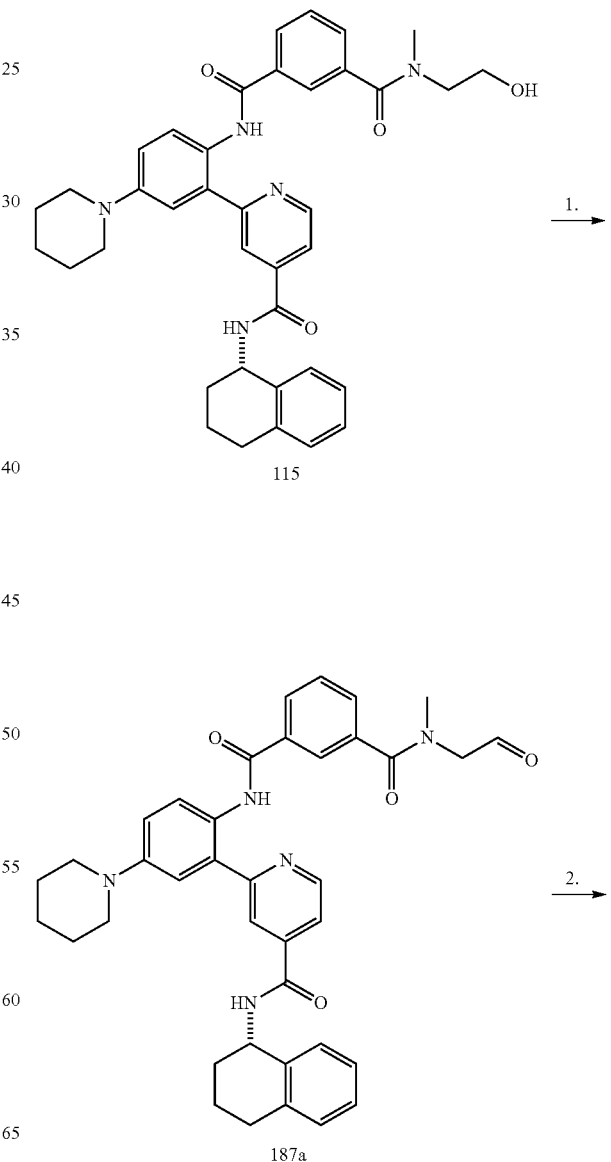

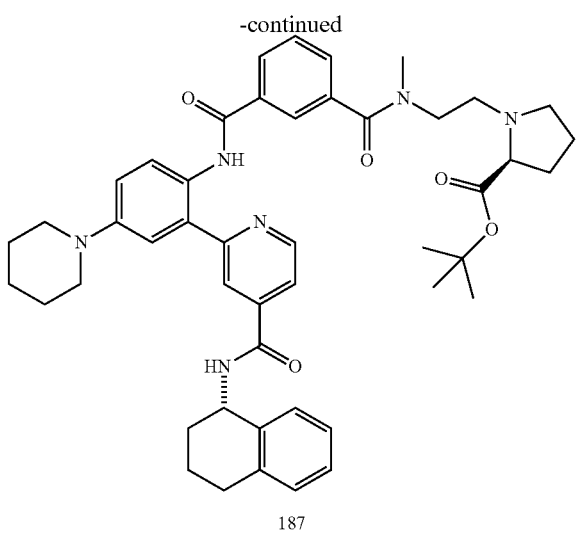

1. DMSO, (CO)₂Cl₂, DCM;
2. L-proline-t-butyl ester, NaCNBH₃, HOAc, EtOH

Intermediate: 187a (S)—N¹-methyl-N¹-(2-oxoethyl)-N³-(4-(piperidin-1-yl)-2-(4-((1,2,3,4-tetrahydronaphthalen-1-yl)carbamoyl)pyridin-2-yl)phenyl)isophthalamide To a solution of DMSO (2.07 mmol, 162 mg) in DCM (1.6 mL) at –78° C. was added a solution of oxalyl chloride (1.04 mmol, 131 mg) in DCM (0.2 mL). The mixture was stirred at –78° C. for 15 minutes. Then a solution of (S)—N¹-(2-hydroxyethyl)-N¹-methyl-N³-(4-(piperidin-1-yl)-2-(4-((1,2,3,4-tetrahydronaphthalen-1-yl)carbamoyl)pyridin-2-yl)phenyl)isophthalamide Example 115 (0.69 mmol, 435 mg) in DCM (0.5 mL) was added. The mixture was stirred at –78° C. for 3 h. Triethylamine (0.5 mL) was added. The mixture was slowly warmed to room temperature. The mixture was diluted with aqueous 10% citric acid and extracted with DCM (3×). The combined organic layers was washed with water (1×), dried, concentrated to give a yellow solid which was used without purification.

Example 187

(S)-tert-butyl 1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidine-2-carboxylate To a solution of L-proline-t-butyl ester (0.096 mmol, 16 mg) in ethanol (0.2 mL) were added (S)—N¹-methyl-N¹-(2-oxoethyl)-N³-(4-(piperidin-1-yl)-2-(4-((1,2,3,4-tetrahydronaphthalen-1-yl)carbamoyl)pyridin-2-yl)phenyl)isophthalamide (0.032 mmol, 20 mg) and HOAc (0.064 mmol, 4 mg). The mixture was stirred at room temperature for 25 minutes, and then sodium cyanoborohydride (0.16 mmol, 10 mg) was added. The mixture was stirred for an additional 20 minutes and quenched with water. The yellow solid was collected via filtration and was purified by prep HPLC to give a yellow solid (12 mg, 37%). MS (ES, m/z): 786.1 [M+H]⁺.

Example 188

1-(3-((4-(diethylamino)-2-(4-((3-(trifluoromethyl)benzyl)carbamoyl)pyridin-2-yl)phenyl)carbamoyl)phenyl)-2-methyl-1-oxo-5,8,11-trioxa-2-azatetradecan-14-oic acid Scheme 80.

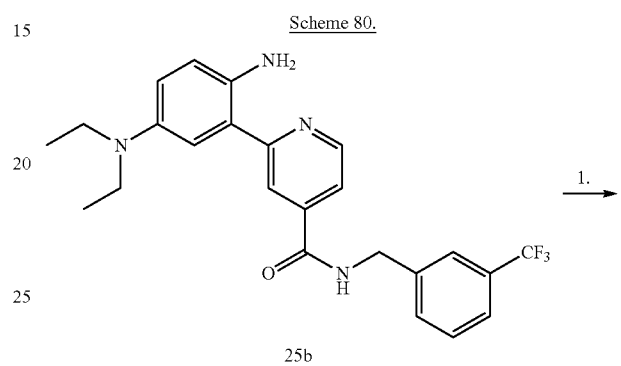

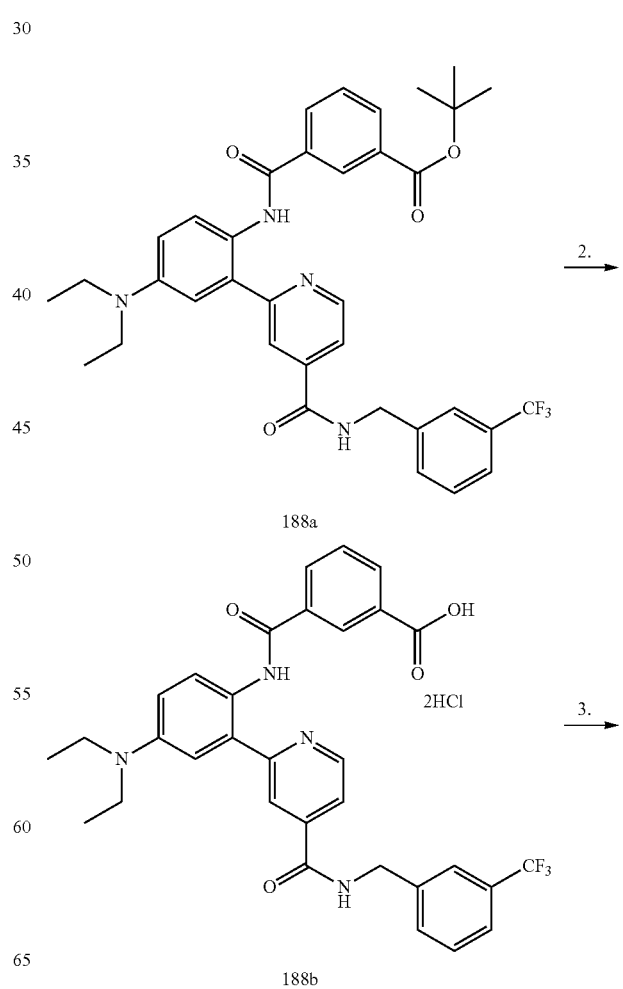

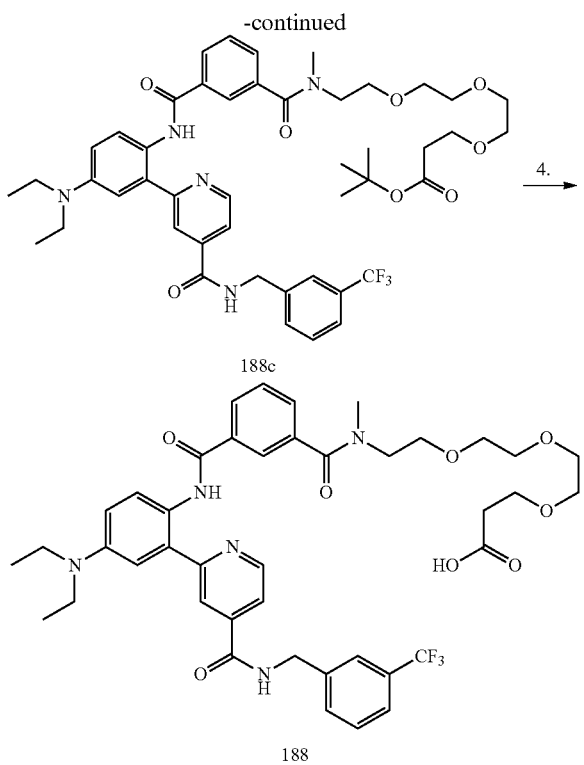

188c 1. 3-(tert-butoxycarbonyl)benzoic acid, HATU, DIEA, DMF;
2. 4M HCl in dioxane;
3. tert-butyl 5,8,11-trioxa-2-azatetradecan-14-oate, HATU, DIEA, DMF;
4. TFA.

Intermediate 188a: tert-butyl 3-((4-(diethylamino)-2-(4-((3-(trifluoromethyl)benzyl)carbamoyl)pyridin-2-yl)phenyl)carbamoyl)benzoate To a mixture of 2-(2-amino-5-(diethylamino)phenyl)-N-(3-(trifluoromethyl)benzyl)isonicotinamide (25a, 6.33 mmol, 2.8 g), 3-(tert-butoxycarbonyl)benzoic acid (7.60 mmol, 1.69 g) and DIEA (31.65 mmol, 4.09 g) in DMF (15 mL) was added HATU (7.6 mmol, 2.89 g). The mixture was stirred at 60° C. for 2 hours. The reaction mixture was diluted with ethyl acetate, washed with water (2×), sat. aqueous NaHCO₃ (1×), brine (1×), dried and concentrated. The residue was purified by column to give a yellow solid (3.9 g, 95%).

Intermediate 188b: 3-((4-(diethylamino)-2-(4-((3-(trifluoromethyl)benzyl)carbamoyl)pyridin-2-yl)phenyl)carbamoyl)benzoic acid To tert-butyl 3-((4-(diethylamino)-2-(4-((3-(trifluoromethyl)benzyl)carbamoyl)pyridin-2-yl)phenyl)carbamoyl)benzoate was added 4M HCl in dioxane (25 mL). The mixture was stirred at room temperature for 3 hours, concentrated to give a light yellow solid which was used without further purification.

Intermediate 188c: tert-butyl 1-(3-((4-(diethylamino)-2-(4-((3-(trifluoromethyl)benzyl)carbamoyl)pyridin-2-yl)phenyl)carbamoyl)phenyl)-2-methyl-1-oxo-5,8,11-trioxa-2-azatetradecan-14-oate To a mixture of 344-(diethylamino)-2-(4-((3-(trifluoromethyl)benzyl)carbamoyl)pyridin-2-yl)phenyl)carbamoyl)benzoic acid (1.81 mmol, 1.2 g), tert-butyl 5,8,11-trioxa-2-azatetradecan-14-oate (1.9 mmol, 554 mg) and DIEA (12.67 mmol, 1.64 g) in DMF (5 mL) was added HATU (2.17 mmol, 826 mg). The mixture was stirred at 60° C. for 1 hour. The reaction mixture was diluted with ethyl acetate, washed with water (2×), sat. aqueous NaHCO₃ (1×), brine (1×), dried and concentrated. The residue was purified by column to give a syrup (1.17 g, 75%).

Example 188

1-(3-((4-(diethylamino)-2-(4-((3-(trifluoromethyl)benzyl)carbamoyl)pyridin-2-yl)phenyl)carbamoyl)phenyl)-2-methyl-1-oxo-5,8,11-trioxa-2-azatetradecan-14-oic acid To a mixture of tert-butyl 1-(3-((4-(diethylamino)-2-(4-((3-(trifluoromethyl)benzyl)carbamoyl)pyridin-2-yl)phenyl)carbamoyl)phenyl)-2-methyl-1-oxo-5,8,11-trioxa-2-azatetradecan-14-oate (1.17 g) in DCM (20 mL) was added TFA (20 mL). The mixture was stirred for 1 hour, concentrated and lyophilized to give a think brown syrup. MS (ES, m/z): 808.3 [M+H]⁺.

Example 189

(S)-2-(5-(diethylamino)-2-(3-(3-((2-methoxyethyl)carbamoyl)piperidine-1-carbonyl)benzamido)phenyl)-N-(3-(trifluoromethyl)benzyl)isonicotinamide

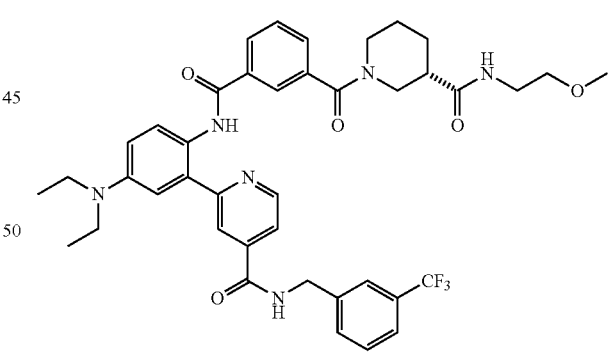

This compound was prepared according to the procedure described for the synthesis of tert-butyl 1-(3-((4-(diethylamino)-2-(4-((3-(trifluoromethyl)benzyl)carbamoyl)pyridin-2-yl)phenyl)carbamoyl)phenyl)-2-methyl-1-oxo-5,8,11-trioxa-2-azatetradecan-14-oate Example 188, using (S)—N-(2-methoxyethyl)piperidine-3-carboxamide 4.14a in place of tert-butyl 5,8,11-trioxa-2-azatetradecan-14-oate. MS (ES, m/z): 759.4 [M+H]⁺.

Example 190 tert-Butyl 2-methyl-1-((S)-1-(2-(N-methyl-3-((4-(piperidin-1-yl)-2-(4-((((S)-1,2,3,4-tetrahydronaphthalen-1-yl)carbamoyl)pyridin-2-yl)phenyl)carbamoyl)benzamido)ethyl)pyrrolidin-2-yl)-1-oxo-5,8,11-trioxa-2-azatetradecan-14-oate Scheme 81.

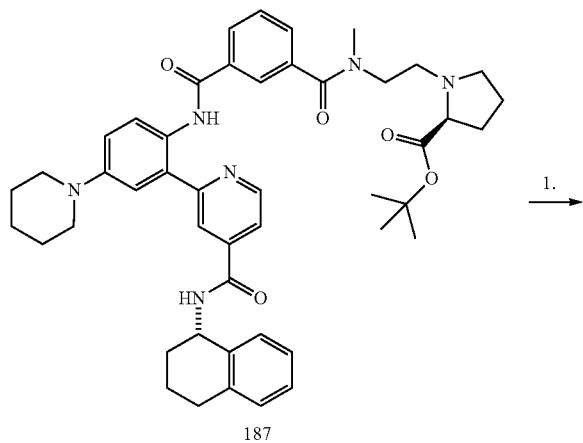

187

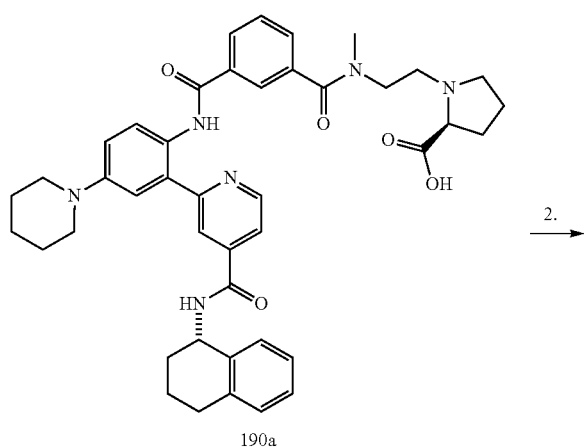

190a

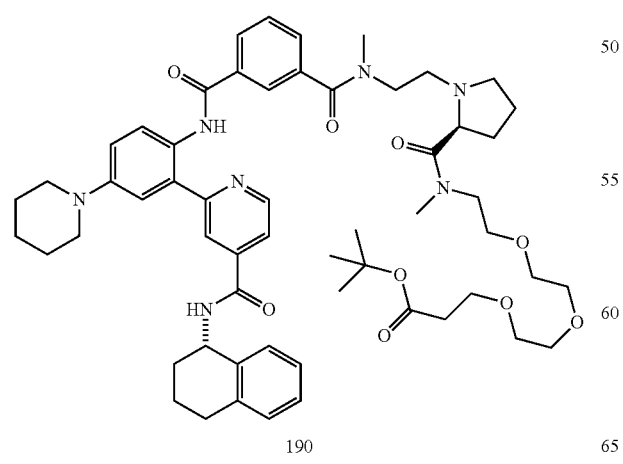

190

1. TFA; 2. tert-butyl 5,8,11-trioxa-2-azatetradecan-14-oate 135c, HATU, DIEA, DMF.

Intermediate 190a: (S)-1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidine-2-carboxylic acid To (S)-tert-butyl 1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidine-2-carboxylate (90 mg) was added TFA (5 mL). The mixture was stirred at room temperature for 6 h, concentrated and purified by column to give a yellow solid (75 mg, 90%).

Example 190 tert-Butyl 2-methyl-1-((S)-1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl) pyrrolidin-2-yl)-1-oxo-5,8,11-trioxa-2-azatetradecan-14-oate To a mixture of (S)-1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidine-2-carboxylic acid (0.035 mmol, 25.7 mg), tert-butyl 5,8,11-trioxa-2-azatetradecan-14-oate 135c (0.042 mmol, 12.4 mg) and DIEA (0.212 mmol, 27 mg) in DMF (0.15 mL) was added HATU (0.042 mmol, 16 mg). The mixture was stirred at 60° C. for 1 h. The reaction mixture was diluted with ethyl acetate, washed with water (2×), brine (1×), dried and concentrated. 23% of the residue was purified by prep. HPLC to give a yellow solid (4 mg, 37%). MS (ES, m/z): 1002.36 [M+H]$^+$.

Example 191

2-Methyl-1-((S)-1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidin-2-yl)-1-oxo-5,8,11-trioxa-2-azatetradecan-14-oic acid

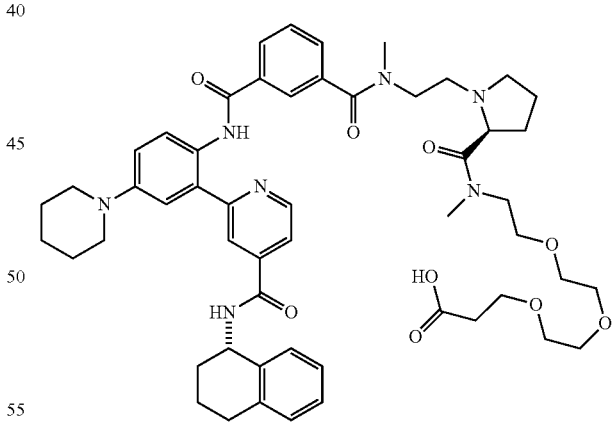

Example 191

2-Methyl-1-((S)-1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidin-2-yl)-1-oxo-5,8,11-trioxa-2-azatetradecan-14-oic acid To tert-Butyl 2-methyl-1-((S)-1-(2-(N-methyl-3-((4-(piperidin-1-yl)-2-(4-(((S)-1,2,3,4-tetrahydronaphthalen-1-yl)

carbamoyl)pyridin-2-yl)phenyl)carbamoyl)benzamido) ethyl) pyrrolidin-2-yl)-1-oxo-5,8,11-trioxa-2-azatetradecan-14-oate (16 mg) was added TFA (2 mL). The mixture was stirred at rt for 30 minutes, concentrated and purified by prep. HPLC to give a yellow solid (17.6 mg, 86%). MS (ES, m/z): 946.34 [M+H]$^+$.

Example 192 tert-butyl 1-((S)-1-(2-(N-methyl-3-((4-(piperidin-1-yl)-2-(4-(((S)-1,2,3,4-tetrahydronaphthalen-1-yl) carbamoyl)pyridin-2-yl)phenyl)carbamoyl)benzamido)ethyl)pyrrolidin-2-yl)-1-oxo-5,8,11-trioxa-2-azatetradecan-14-oate

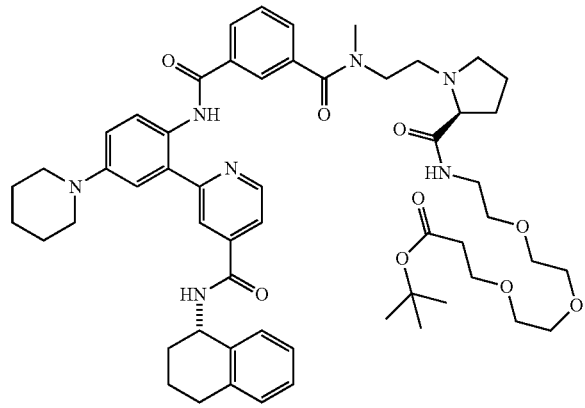

This compound was prepared according to the procedure described for the synthesis of tert-butyl 2-methyl-1-((S)-1-(2-(N-methyl-3-((4-(piperidin-1-yl)-2-(4-(((S)-1,2,3,4-tetrahydronaphthalen-1-yl)carbamoyl)pyridin-2-yl)phenyl) carbamoyl)benzamido)ethyl)pyrrolidin-2-yl)-1-oxo-5,8,11-trioxa-2-azatetradecan-14-oate Example 190, using tert-butyl 3-(2-(2-(2-aminoethoxy)ethoxy)ethoxy)propanoate in place of tert-butyl 5,8,11-trioxa-2-azatetradecan-14-oate. MS (ES, m/z): 988.34 [M+H]$^+$.

Example 193

1-((S)-1-(2-(N-methyl-3-((4-(piperidin-1-yl)-2-(4-(((S)-1,2,3,4-tetrahydronaphthalen-1-yl)carbamoyl) pyridin-2-yl)phenyl)carbamoyl)benzamido)ethyl) pyrrolidin-2-yl)-1-oxo-5,8,11-trioxa-2-azatetradecan-14-oic acid

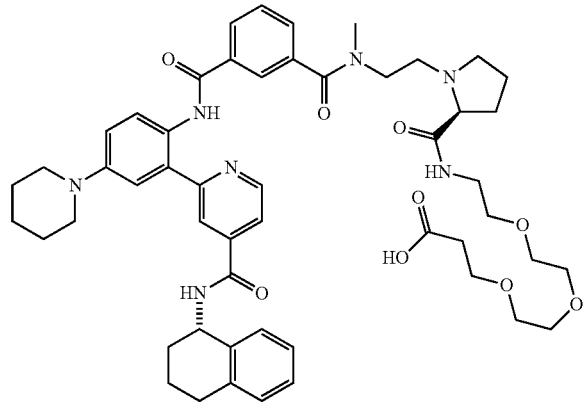

This compound was prepared according to the procedure described for the synthesis of 2-Methyl-1-((S)-1-(2-(N-methyl-3-((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidin-2-yl)-1-oxo-5,8,11-trioxa-2-azatetradecan-14-oic acid Example 191, using tert-butyl 3-(2-(2-(2-aminoethoxy)ethoxy)ethoxy)propanoate in place of tert-butyl 5,8,11-trioxa-2-azatetradecan-14-oate. MS (ES, m/z): 932.38 [M+H]$^+$.

Example 194

(S)—N$^1$-(4-(diethylamino)-2-(4-((1,2,3,4-tetrahydronaphthalen-1-yl)carbamoyl)pyridin-2-yl)phenyl)-N$^3$-(2-hydroxyethyl)-N$^3$-methylisophthalamide

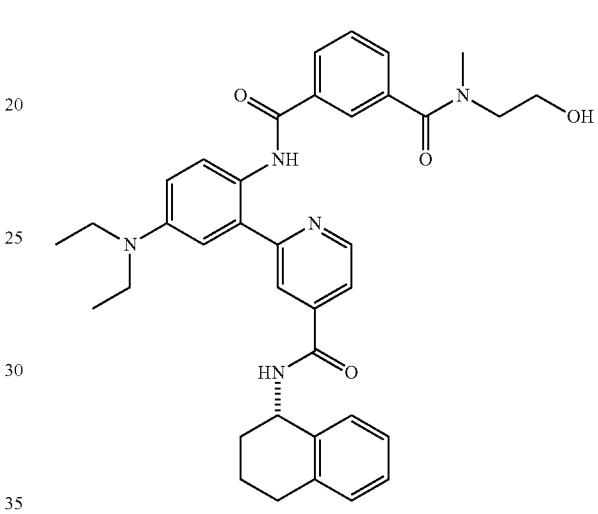

This compound was prepared according to the procedure described for the synthesis of (S)—N$^1$-(4-(diethylamino)-2-(4-((1,2,3,4-tetrahydronaphthalen-1-yl)carbamoyl)pyridin-2-yl)phenyl)-N$^3$-methyl-N$^3$-(2-morpholinoethyl)isophthalamide Example 131, using 2-(methylamino)ethanol in place of N-methyl-2-morpholinoethanamine. MS (ES, m/z): 620.32 [M+H]$^+$.

Example 195

N$^1$-(2-((S)-2-(2,5,8,11,14,17,20,23-octaoxapentacosan-25-ylcarbamoyl)pyrrolidin-1-yl)ethyl)-N$^1$-methyl-N$^3$-(4-(piperidin-1-yl)-2-(4-(((S)-1,2,3,4-tetrahydronaphthalen-1-yl)carbamoyl)pyridin-2-yl)phenyl)isophthalamide

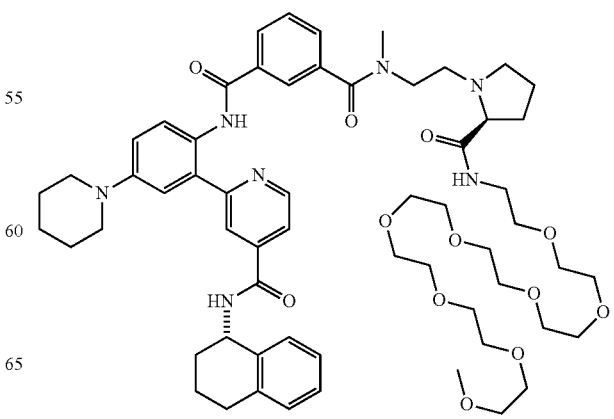

This compound was prepared according to the procedure described for the synthesis of tert-butyl 2-methyl-1-((S)-1-(2-(N-methyl-3 ((4-(piperidin-1-yl)-2-(4-(((S)-1,2,3,4-tetrahydronaphthalen-1-yl)carbamoyl)pyridin-2-yl)phenyl)carbamoyl)benzamido)ethyl)pyrrolidin-2-yl)-1-oxo-5,8,11-trioxa-2-azatetradecan-14-oate Example 190, using 2,5,8,11,14,17,20,23-octaoxapentacosan-25-amine in place of tert-butyl 5,8,11-trioxa-2-azatetradecan-14-oate. MS (ES, m/z): 1094.47 [M+H]$^+$.

Example 196

N$^1$-(2-((S)-2-(2,5,8,11,14,17,20,23-octaoxapentacosan-25-ylcarbamoyl)pyrrolidin-1-yl)ethyl)-N$^3$-(4-(diethylamino)-2-(4-(((S)-1,2,3,4-tetrahydronaphthalen-1-yl)carbamoyl)pyridin-2-yl)phenyl)-N$^1$-methylisophthalamide This compound was prepared according to the procedure described for the synthesis of N$^1$-(2-((S)-2-(2,5,8,11,14,17,20,23-octaoxapentacosan-25-ylcarbamoyl)pyrrolidin-1-yl)ethyl)-N$^1$-methyl-N$^3$-(4-(piperidin-1-yl)-2-(4-(((S)-1,2,3,4-tetrahydronaphthalen-1-yl)carbamoyl)pyridin-2-yl)phenyl)isophthalamide Example 195, using (S) —N$^1$-(4-(diethylamino)-2-(4-((1,2,3,4-tetrahydronaphthalen-1-yl)carbamoyl)pyridin-2-yl)phenyl)-N$^3$-methyl-N$^3$-(2-oxoethyl)isophthalamide in place of (S)—N$^1$-methyl-N$^1$-(2-oxoethyl)-N$^3$-(4-(piperidin-1-yl)-2-(4-(1,2,3,4-tetrahydronaphthalen-1-yl)carbamoyl)pyridin-2-yl)phenyl)isophthalamide. MS (ES, m/z): 1082.52 [M+H]$^+$.

Example 197

(S)—N$^1$-(2-(4-(2,5,8,11,14,17,20,23-octaoxahexacosan-26-oyl)-1,4-diazepan-1-yl)ethyl)-N$^3$-(4-(diethylamino)-2-(4-((1,2,3,4-tetrahydronaphthalen-1-yl)carbamoyl)pyridin-2-yl)phenyl)-N$^1$-methylisophthalamide

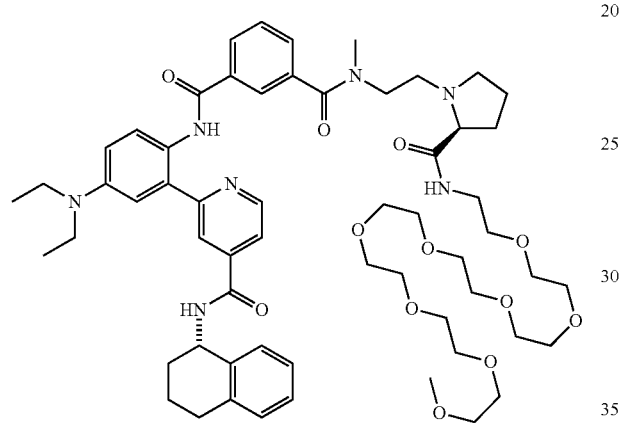

Scheme 82.

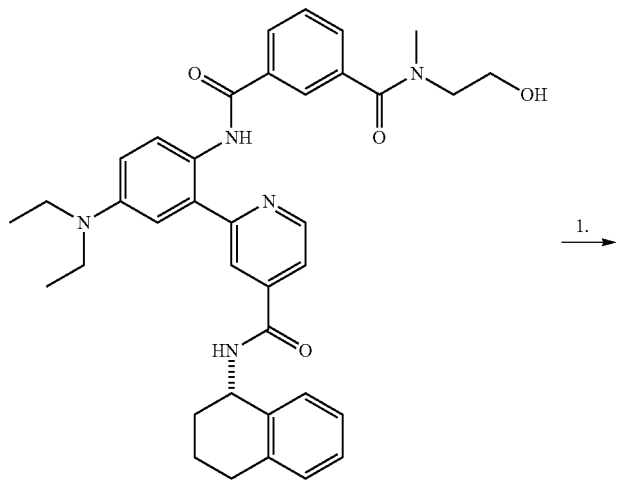

194

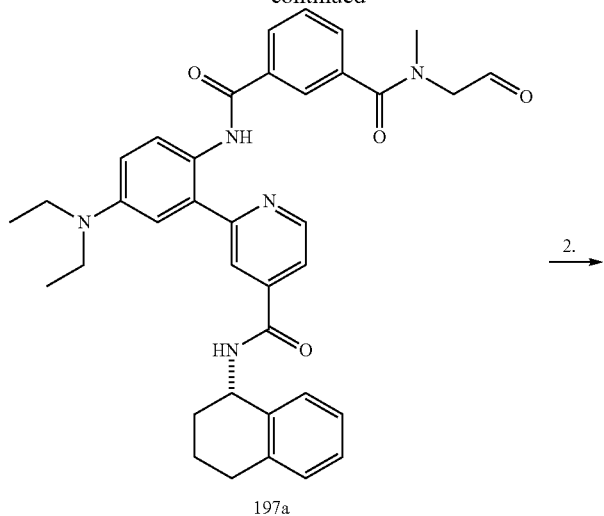
197a
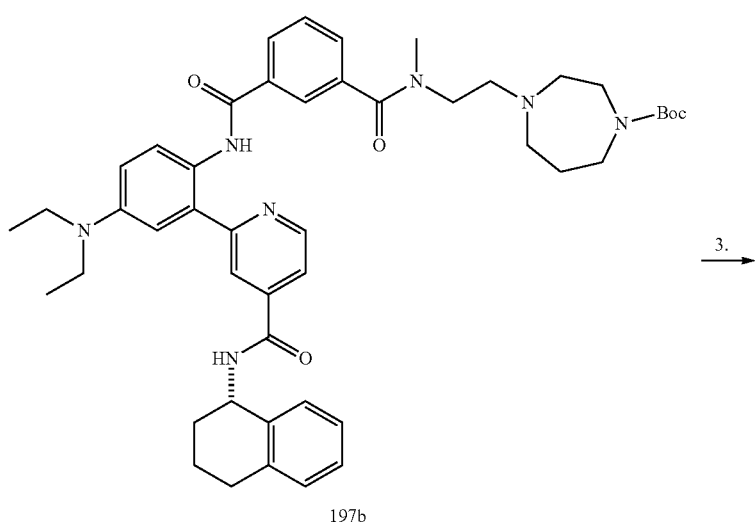
197b
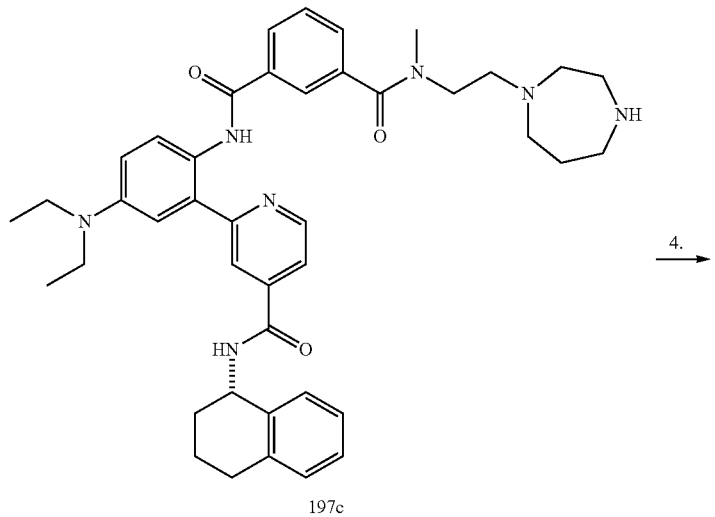
197c

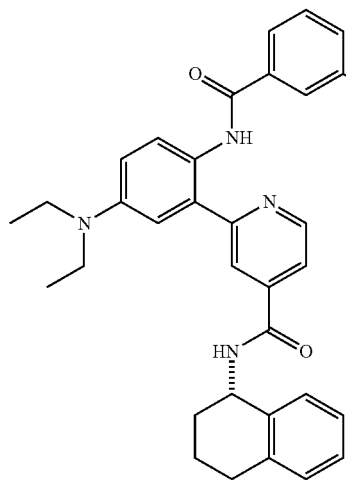
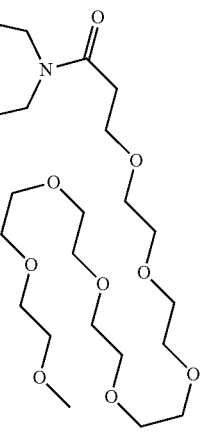

197

1. DMSO, (CO)₂Cl₂, DCM;
2. tert-butyl 1,4-diazepane-1-carboxylate, NaCNBH₃, HOAc, EtOH;
3. 4M HCl in dioxane;
4. m-dPEG₈—NHS ester, TEA, DMF.

Intermediate 197a: (S)—$N^1$-(4-(diethylamino)-2-(4-((1,2,3,4-tetrahydronaphthalen-1-yl)carbamoyl)pyridin-2-yl)phenyl)-$N^3$-methyl-$N^3$-(2-oxoethyl)isophthalamide To a solution of DMSO (4.8 mmol, 375 mg) in DCM (3 mL) at −78° C. was added a solution of oxalyl chloride (2.4 mmol, 305 mg) in DCM (0.4 mL). The mixture was stirred at −78° C. for 15 minutes. Then a solution of (S)—$N^1$-(4-(diethylamino)-2-(4-((1,2,3,4-tetrahydronaphthalen-1-yl)carbamoyl)pyridin-2-yl)phenyl)-$N^3$-(2-hydroxyethyl)-$N^3$-methylisophthalamide Example 194 (1.2 mmol, 742 mg) in DCM (1.7 mL) was added dropwise. The mixture was stirred at −78° C. for 3 h and quenched with triethylamine (0.85 mL). The mixture was stirred at −78° C. for 10 minutes, at 0° C. for 10 minutes, then diluted with water, and extracted with DCM (2×). The combined organic layers was washed with water (1×), dried, and concentrated. The residue was used without further purification.

Intermediate 197b: (S)-tert-butyl 4-(2-(3-((4-(diethylamino)-2-(4-((1,2,3,4-tetrahydronaphthalen-1-yl)carbamoyl)pyridin-2-yl)phenyl)carbamoyl)-N-methylbenzamido)ethyl)-1,4-diazepane-1-carboxylate To a mixture of (S)—$N^1$-(4-(diethylamino)-2-(4-((1,2,3,4-tetrahydronaphthalen-1-yl)carbamoyl)pyridin-2-yl)phenyl)-$N^3$-methyl-$N^3$-(2-oxoethyl)isophthalamide (0.162 mmol, 100 mg) in ethanol (1 mL) were added tert-butyl 1,4-diazepane-1-carboxylate (0.324 mmol, 65 mg) and HOAc (0.324 mmol, 19.4 mg). The mixture was stirred at room temperature for 20 minutes, and then sodium cyanoborohydride (0.81 mmol, 51 mg) was added. The mixture was stirred for an additional 1 h, diluted with ethyl acetate, washed with sat. aqueous NaHCO₃ and brine, dried, concentrated and purified by column to give a product (70 mg, 54%).

Intermediate 197c: (S)—$N^1$-(2-(1,4-diazepan-1-yl)ethyl)-$N^3$-(4-(diethylamino)-2-(4-((1,2,3,4-tetrahydronaphthalen-1-yl)carbamoyl)pyridin-2-yl)phenyl)-$N^1$-methylisophthalamide To (S)-tert-butyl 4-(2-(3-((4-(diethylamino)-2-(4-((1,2,3,4-tetrahydronaphthalen-1-yl)carbamoyl)pyridin-2-yl)phenyl)carbamoyl)-N-methylbenzamido)ethyl)-1,4-diazepane-1-carboxylate was added 4M HCl in dioxane (3 mL). The mixture was stirred at room temperature for 2 h, concentrated to give a light yellow solid which was used without further purification.

Example 197

(S)—$N^1$-(2-(4-(2,5,8,11,14,17,20,23-octaoxahexacosan-26-oyl)-1,4-diazepan-1-yl)ethyl)-$N^3$-(4-(diethylamino)-2-(4-((1,2,3,4-tetrahydronaphthalen-1-yl)carbamoyl)pyridin-2-yl)phenyl)-$N^1$-methylisophthalamide To a mixture of (S)—$N^1$-(2-(1,4-diazepan-1-yl)ethyl)-$N^3$-(4-(diethylamino)-2-(4-((1,2,3,4-tetrahydronaphthalen-1-yl)carbamoyl)pyridin-2-yl)phenyl)-$N^1$-methylisophthalamide (0.024, 20 mg) and m-dPEG₈-NHS ester (0.024 mmol, 12.2 mg) in DMF (0.15 mL) was added triethylamine (0.144 mmol, 14.6 mg). The mixture was stirred at 60° C. for 1 h and purified by prep. HPLC to give a brown gel (6.3 mg, 18%). MS (ES, m/z): 1096.55 [M+H]+.

Example 198

N[1]-(2-(((S)-2-(2,5,8,11,14,17,20-heptaoxadocosan-22-yl(methyl)carbamoyl)pyrrolidin-1-yl)ethyl)-N[1]-methyl-N[3]-(4-(piperidin-1-yl)-2-(4-(((S)-1,2,3,4-tetrahydronaphthalen-1-yl)carbamoyl)pyridin-2-yl)phenyl)isophthalamide

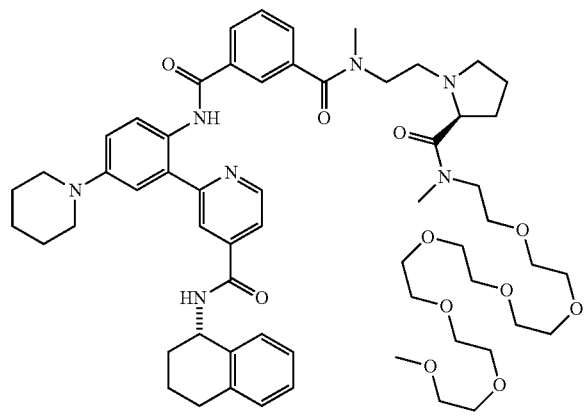

This compound was prepared according to the procedure described for the synthesis of tert-butyl 2-methyl-1-((S)-1-(2-(N-methyl-3-((4-(piperidin-1-yl)-2-(4-(((S)-1,2,3,4-tetrahydronaphthalen-1-yl)carbamoyl)pyridin-2-yl)phenyl carbamoyl)benzamido)ethyl)pyrrolidin-2-yl)-1-oxo-5,8,11-trioxa-2-azatetradecan-14-oate Example 190, using N-methyl-2,5,8,11,14,17,20-heptaoxadocosan-22-amine in place of tert-butyl 5,8,11-trioxa-2-azatetradecan-14-oate. MS (ES, m/z): 1064.42 [M+H]+.

Example 199

(S)-2,5,8,11,14,17,20,23,26,29,32-undecaoxatetratriacontan-34-yl 4-(2-(3-((4-(diethylamino)-2-(4-((1,2,3,4-tetrahydronaphthalen-1-yl)carbamoyl)pyridin-2-yl)phenyl)carbamoyl)-N-methylbenzamido)ethyl)-1,4-diazepane-carboxylate

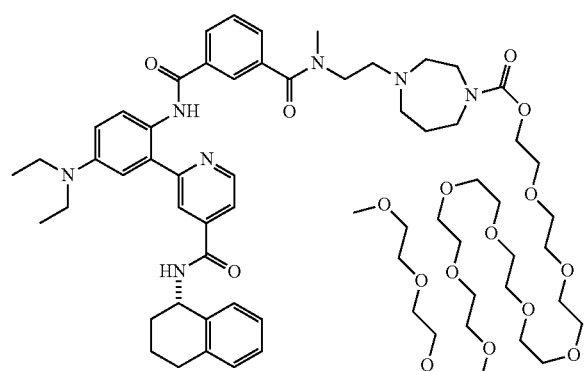

This compound was prepared according to the procedure described for the synthesis of (S)—N[1]-(2-(4-(2,5,8,11,14,17, 20,23-octaoxahexacosan-26-oyl)-1,4-diazepan-1-yl)ethyl)-N[3]-(4-(diethylamino)-2-(4-((1,2,3,4-tetrahydronaphthalen-1-yl)carbamoyl)pyridin-2-yl)phenyl)-N[1]-methylisophthalamide Example 197, using m-dPEG$_{11}$-NHS carbonate in place of m-dPEG$_8$-NHS ester. MS (ES, m/z): 1244.49 [M+H]+.

Example 200

2-(2-(3-(2,5,8,11,14,17,20,23,26-nonaoxaheptacosyl)benzamido)-5-(dipropylamino)phenyl)-N-(3-(trifluoromethyl)benzyl)isonicotinamide

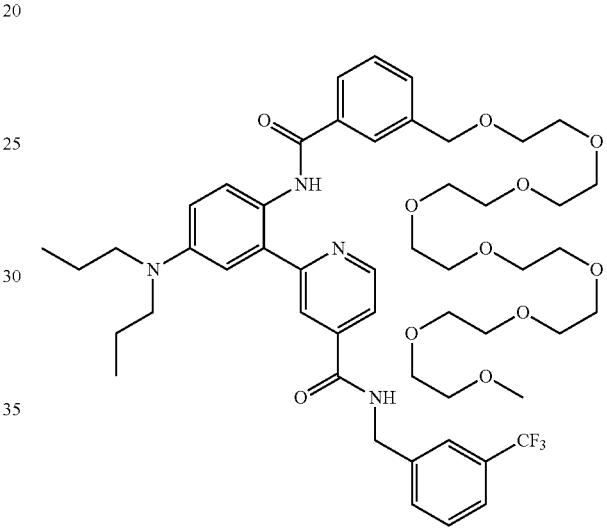

Example 200

2-(2-(3-(2,5,8,11,14,17,20,23,26-nonaoxaheptacosyl)benzamido)-5-(dipropylamino)phenyl)-N-(3-(trifluoromethyl)benzyl)isonicotinamide To a mixture of 2-(2-amino-5-(dipropylamino)phenyl)-N-(3-(trifluoromethyl)benzyl)isonicotinamide (19b, 1.27 mmol, 600 mg), 3-(2,5,8,11,14,17,20,23,26-nonaoxaheptacosyl)benzoic acid (prepared as in Example 185 2,5,9,12,15,18,21,24-octaoxahexacosan-26-ol in place of methyl 3-(hydroxymethyl)benzoate) (1.40 mmol, 729 mg) and DIEA (7.66 mmol, 990 mg) in DMF (4 mL) was added HATU (1.40 mmol, 534 mg). The mixture was stirred at 60° C. for 1 h, diluted with DCM, washed with water (3×), dried, concentrated and purified by column to give a yellow syrup (1.01 g, 82%). MS (ES, m/z): 971.42 [M+H]+.

Example 201

(S)—N¹-(2-(2-(2,5,8,11,14,17,20,23-octaoxapenta-cosan-25-ylcarbamoyl)piperidin-1-yl)ethyl)-N³-(4-(diethylamino)-2-(4-((3-(trifluoromethyl)benzyl)carbamoyl)pyridin-2-yl)phenyl)-N¹-methylisophthalamide Scheme 83.

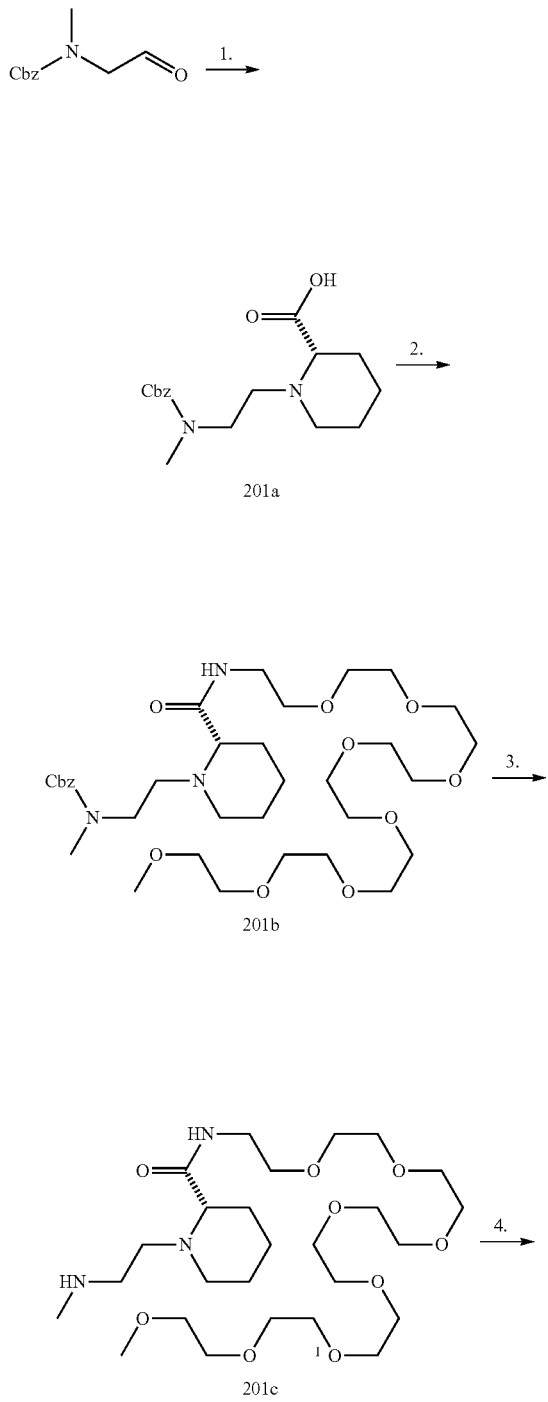

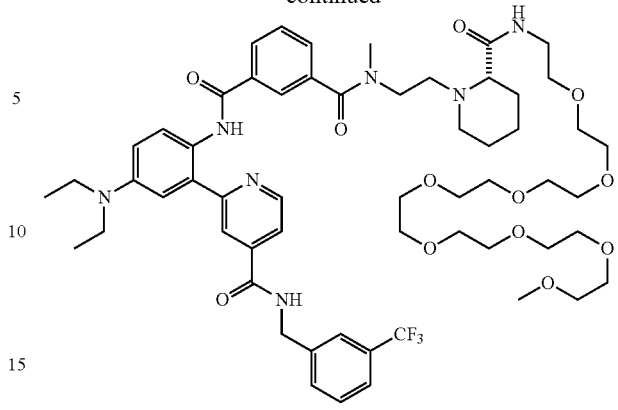

201d 1. (S)-methyl piperidine-2-carboxylate, Na(OAc)₃BH, TEA, DCE;
2. 2,5,8,11,14,17,20,23-octaoxapentacosan-25-amine, HATU, DIEA;
3. Pd/C, H₂, MeOH;
4. 3-((4-(diethylamino)-2-(4-((3-(trifluoromethyl)benzyl)carbamoyl)pyridine-2-yl)phenyl)carbamoyl) benzoic acid, HATU, DIEA, DMF.

Intermediate 201a: (S)-1-(2-(((benzyloxy)carbonyl)(methyl)amino)ethyl)piperidine-2-carboxylic acid To a mixture of benzyl methyl(2-oxoethyl)carbamate (0.47 mmol, 98 mg) and triethylamine (0.47 mmol, 48 mg) in DCE (1.7 mL) was added (S)-methyl piperidine-2-carboxylate (0.47 mmol, 85 mg), followed by addition of sodium triacetoxyborohydride (0.71 mmol, 150 mg). The mixture was stirred at rt for 1 h, concentrated under reduced pressure and purified by column to give a solid product (70 mg, 47%) and a clear syrup ((S)-methyl 1-(2-(((benzyloxy)carbonyl)(methyl)amino)ethyl)piperidine-2-carboxylate, 30 mg).

Intermediate 201b (S)-benzyl (2-(2-(2,5,8,11,14,17,20,23-octaoxapentacosan-25-ylcarbamoyl) piperidin-1-yl)ethyl)(methyl) carbamate To a mixture of (S)-1-(2-(((benzyloxy)carbonyl)(methyl)amino)ethyl)piperidine-2-carboxylic acid (0.145 mmol, 46.4 mg), 2,5,8,11,14,17,20,23-octaoxapentacosan-25-amine (0.145 mmol, 55.6 mg), DIEA (0.725 mmol, 94 mg) in DMF (0.3 mL) was added HATU (0.16 mmol, 61 mg). The mixture was stirred at 60° C. for 1 h. The crude mixture was used in next step without purification.

Intermediate 201c: (S)-1-(2-(methylamino)ethyl)-N-(2,5,8,11,14,17,20,23-octaoxapentacosan-25-yl)piperidine-2-carboxamide To a solution of the above crude mixture ((S)-benzyl (2-(2-(2,5,8,11,14,17,20,23-octaoxapentacosan-25-ylcarbamoyl)piperidin-1-yl)ethyl)(methyl)carbamate) in methanol (2 mL) was added 10% Pd/C (30 mg). The mixture was stirred at rt under hydrogen atmosphere for 1 h. The mixture was filtered and the filtrate was concentrated under high vacuum which was used without further purification.

Example 201

(S)—N¹-(2-(2-(2,5,8,11,14,17,20,23-octaoxapentacosan-25-ylcarbamoyl)piperidin-1-yl)ethyl)-N³-(4-(diethylamino)-2-(4-((3-(trifluoromethyl)benzyl)carbamoyl)pyridin-2-yl)phenyl)-N¹-methylisophthalamide

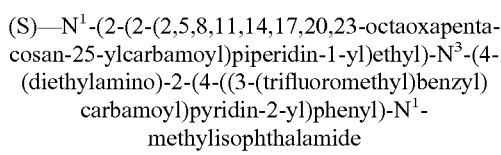

To a mixture of (S)-1-(2-(methylamino) ethyl)-N-(2,5,8,11,14,17,20,23-octaoxapentacosan-25-yl)piperidine-2-carboxamide (0.145 mmol), 3-((4-(diethylamino)-2-(4-((3-(trifluoromethyl)benzyl)carbamoyl)pyridin-2-yl)phenyl)carbamoyl)benzoic acid (0.12 mmol, 80 mg) and DIEA (0.6 mmol, 78 mg) in DMF (0.4 mL) was added HATU (0.145 mmol, 55 mg). The mixture was stirred at 60° C. for 1 h and purified by prep. HPLC to give a yellow solid (91 mg, 52%). MS (ES, to/z): 1124.38 [M+H]⁺.

Example 202

2-(2-(3-(2,5,8,11,14,17,20,23,26-nonaoxaheptacosyl)benzamido)-5-cyclobutoxyphenyl)-N-(3-(trifluoromethyl)benzyl)isonicotinamide

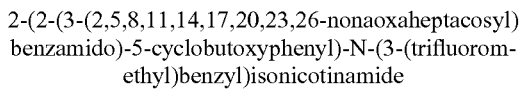

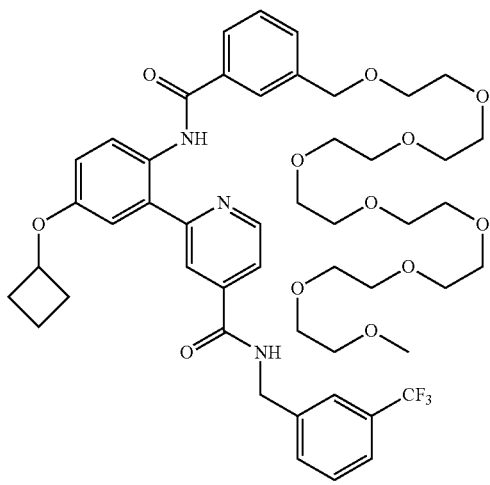 [SMILES: COCCOCCOCCOCCOCCOCCOCCOCCOCc1cccc(C(=O)Nc2ccc(OC3CCC3)cc2-c2cc(C(=O)NCc3cccc(C(F)(F)F)c3)ccn2)c1]

Compound: 2-(2-(3-(2,5,8,11,14,17,20,23,26-nonaoxaheptacosyl)benzamido)-5-cyclobutoxyphenyl)-N-(3-(trifluoromethyl)benzyl)isonicotinamide To a mixture of 2-(2-amino-5-cyclobutoxyphenyl)-N-(3-(trifluoromethyl)benzyl)-isonicotinamide 26b (1.5 mmol, 662 mg), 3-(2,5,8,11,14,17,20,23,26-nonaoxaheptacosyl)benzoic acid (prepared as in Example 185 2,5,9,12,15,18,21,24-octaoxahexacosan-26-ol in place of methyl 3-(hydroxymethyl)benzoate) (1.65 mmol, 857 mg) and DIEA (9.0 mmol, 1.16 g) in DMF (5 mL) was added HATU (1.65 mmol, 627 mg). The mixture was stirred at 60° C. for 1 h, diluted with DCM, washed with water (4×), dried, concentrated and purified by column to give a yellow syrup. To a solution of the syrup in DCM (4 mL) at 0° C. was added 4M HCl in dioxane (0.35 mL) dropwise. The mixture was concentrated and triturated with dry ether to give an orange solid (955 mg, 65%). MS (ES, m/z): 942.56 [M+H]⁺.

Example 203

(S)—N¹-(2-(2-(2,5,8,11,14,17,20,23-octaoxapentacosan-25-ylcarbamoyl)pyrrolidin-1-yl)ethyl)-N³-(4-(diethylamino)-2-(4-((3-(trifluoromethyl)benzyl)carbamoyl)pyridin-2-yl)phenyl)-N¹-methylisophthalamide

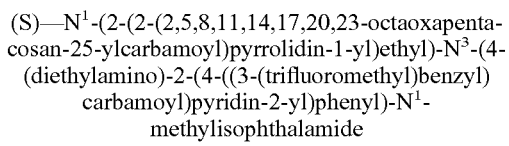

Scheme 84.

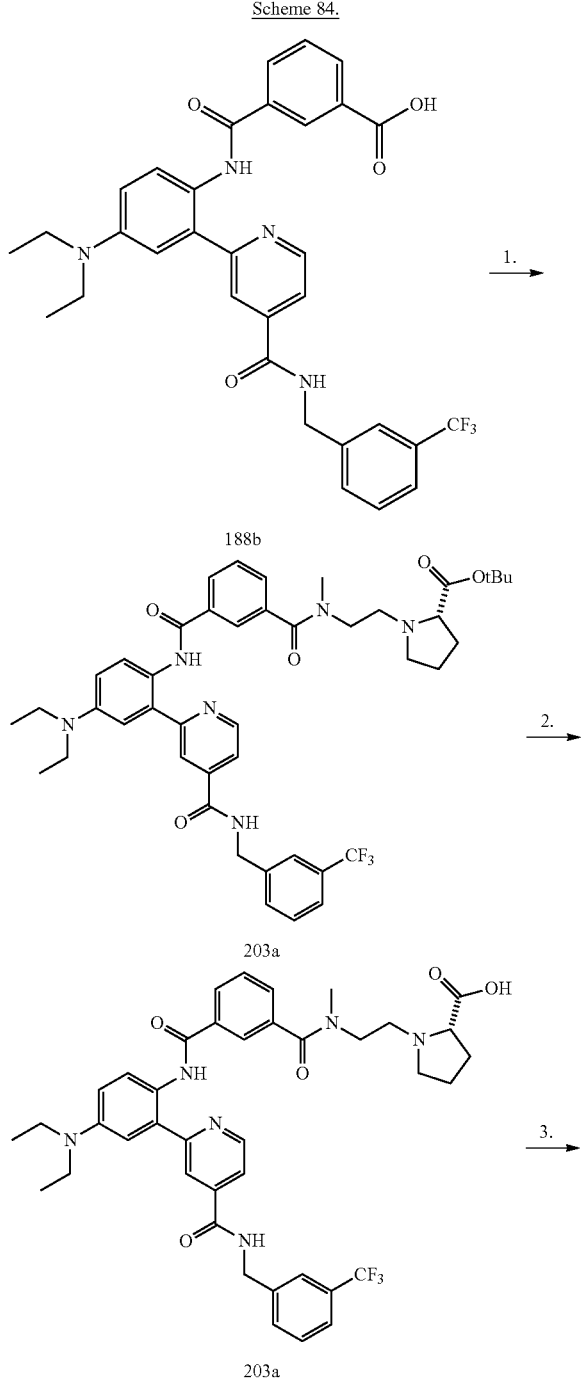 [SMILES: CCN(CC)c1ccc(NC(=O)c2cccc(C(=O)O)c2)c(-c2cc(C(=O)NCc3cccc(C(F)(F)F)c3)ccn2)c1 ; CCN(CC)c1ccc(NC(=O)c2cccc(C(=O)N(C)CCN3CCC[C@H]3C(=O)OC(C)(C)C)c2)c(-c2cc(C(=O)NCc3cccc(C(F)(F)F)c3)ccn2)c1 ; CCN(CC)c1ccc(NC(=O)c2cccc(C(=O)N(C)CCN3CCC[C@H]3C(=O)O)c2)c(-c2cc(C(=O)NCc3cccc(C(F)(F)F)c3)ccn2)c1]

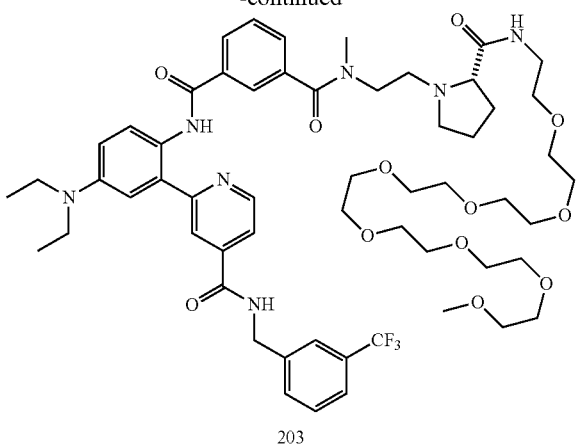

203

1. (S)-tert-butyl 1-(2-(methylamino)ethyl)pyrrolidine-2-carboxylate, HATU, DIEA, DMF;
2. 4M HCl;
3. 2,5,8,11,14,17,20,23-octaoxapentacosan-25-amine, HATU, DIEA, DMF.

Intermediate 203a: (S)-tert-butyl 1-(2-(3-((4-(diethylamino)-2-(4-((3-(trifluoromethyl)benzyl)carbamoyl)pyridin-2-yl)phenyl)carbamoyl)-N-methylbenzamido)ethyl)pyrrolidine-2-carboxylate To a mixture of 2-(2-amino-5-(diethylamino)phenyl)-N-(3-(trifluoromethyl)benzyl)isonicotinamide 188b (2.01 mmol, 1.33 g), 3-(S)-tert-butyl 1-(2-(methylamino)ethyl) pyrrolidine-2-carboxylate (2.41 mmol, 0.551 g) and DIEA (14.08 mmol, 1.82 g) in DMF (6 mL) was added HATU (2.41 mmol, 0.918 g). The mixture was stirred at 60° C. for 1 h. The reaction mixture was diluted with ethyl acetate, washed with water (2×), brine (1×), dried and concentrated. The residue was purified by column to give a yellow solid (1.57 g, 98%).

Intermediate 203b: (S)-1-(2-(3-((4-(diethylamino)-2-(4-((3-(trifluoromethyl)benzyl)carbamoyl)pyridin-2-yl)phenyl)carbamoyl)-N-methylbenzamido)ethyl) pyrrolidine-2-carboxylic acid To a mixture of (S)-tert-butyl 1-(2-(3-((4-(diethylamino)-2-(4-((3-(trifluoromethyl)benzyl)carbamoyl)pyridin-2-yl)phenyl)carbamoyl)-N-methylbenzamido)ethyl)pyrrolidine-2-carboxylate in DCM (3 mL) was added 4M HCl in dioxane (40 mL). The mixture was stirred at room temperature for 3 h and concentrated to give a yellow solid, which was used without further purification.

Example 203

(S)—N$^1$-(2-(2-(2,5,8,11,14,17,20,23-octaoxapentacosan-25-ylcarbamoyl)pyrrolidin-1-yl)ethyl)-N$^3$-(4-(diethylamino)-2-(4-((3-(trifluoromethyl)benzyl)carbamoyl)pyridin-2-yl)phenyl)-N$^1$-methylisophthalamide To a mixture of (S)-1-(2-(3-((4-(diethylamino)-2-(4-((3-(trifluoromethyl)benzyl)carbamoyl)pyridin-2-yl)phenyl)carbamoyl)-N-methylbenzamido)ethyl)pyrrolidine-2-carboxylic acid (1.32 mmol, 1.12 g), 2,5,8,11,14,17,20,23-octaoxapentacosan-25-amine (1.38 mmol, 530 mg) and DIEA (9.21 mmol, 1.19 g) in DMF (4 mL) was added HATU (1.45 mmol, 0.551 g). The mixture was stirred at 60° C. for 1 h and purified by prep. HPLC to give a syrup (1.18 g, 62%). MS (ES, m/z): 1110.42 [M+H]$^+$.

Example 205

(S)-2-(2-(3-(2,5,8,11,14,17,20,23,26-nonaoxaheptacosyl)benzamido)-5-cyclobutoxyphenyl)-N-(1,2,3,4-tetrahydronaphthalen-1-yl)isonicotinamide

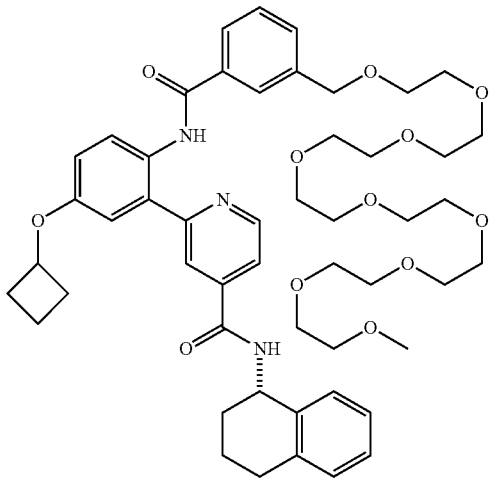

This compound was prepared according to the procedure described for the synthesis of (S)-tert-butyl 16-(3-((4-cyclobutoxy-2-(4-((1,2,3,4-tetrahydronaphthalen-1-yl)carbamoyl)pyridin-2-yl)phenyl)carbamoyl)phenyl)-4,7,10,13-tetraoxahexadecan-1-oate Example 284, using intermediate 3-(2,5,8,11,14,17,20,23,26-nonaoxaheptacosyl)benzoic acid in place of 3-(2,2-dimethyl-4-oxo-3,7,10,13,16-pentaoxanonadecan-19-yl)benzoic acid. MS (ES, m/z): 914.6 [M+H]$^+$.

Example 207
N1-(2-(4-((2-methoxyethyl)carbamoyl)piperazin-1-yl)ethyl)-N3-(2-(4-((3-(trifluoromethyl)benzyl)carbamoyl)pyridin-2-yl)-4-(piperidin-1-yl)phenyl)-N1-methylisophthalamide
Scheme 85a.
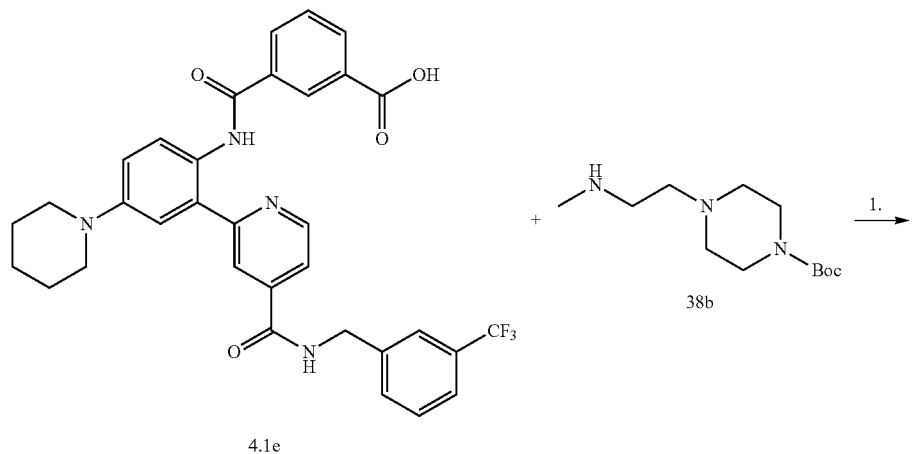
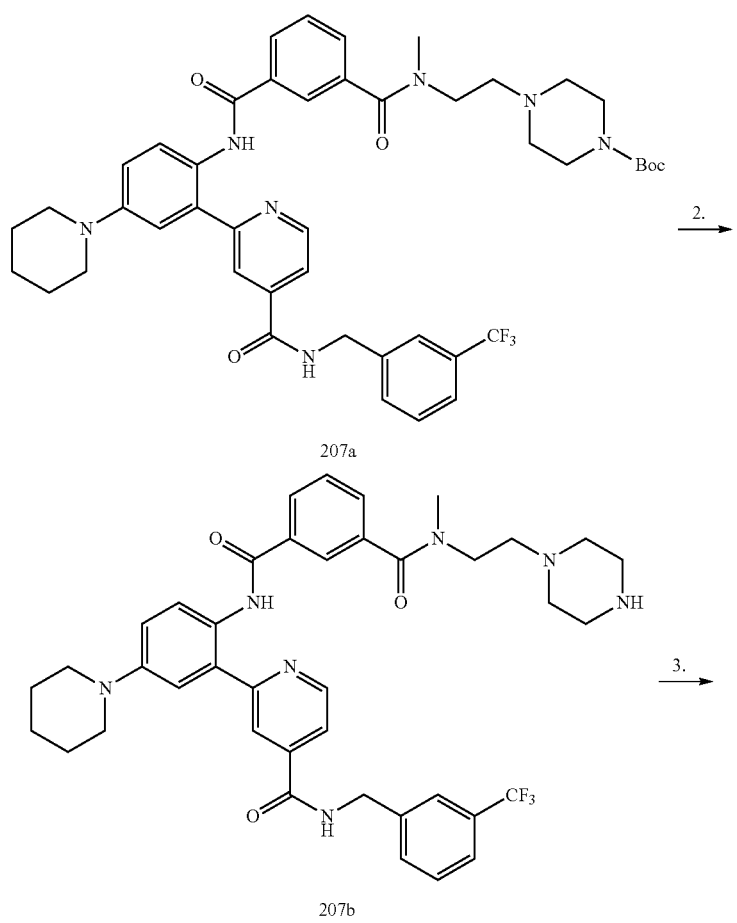

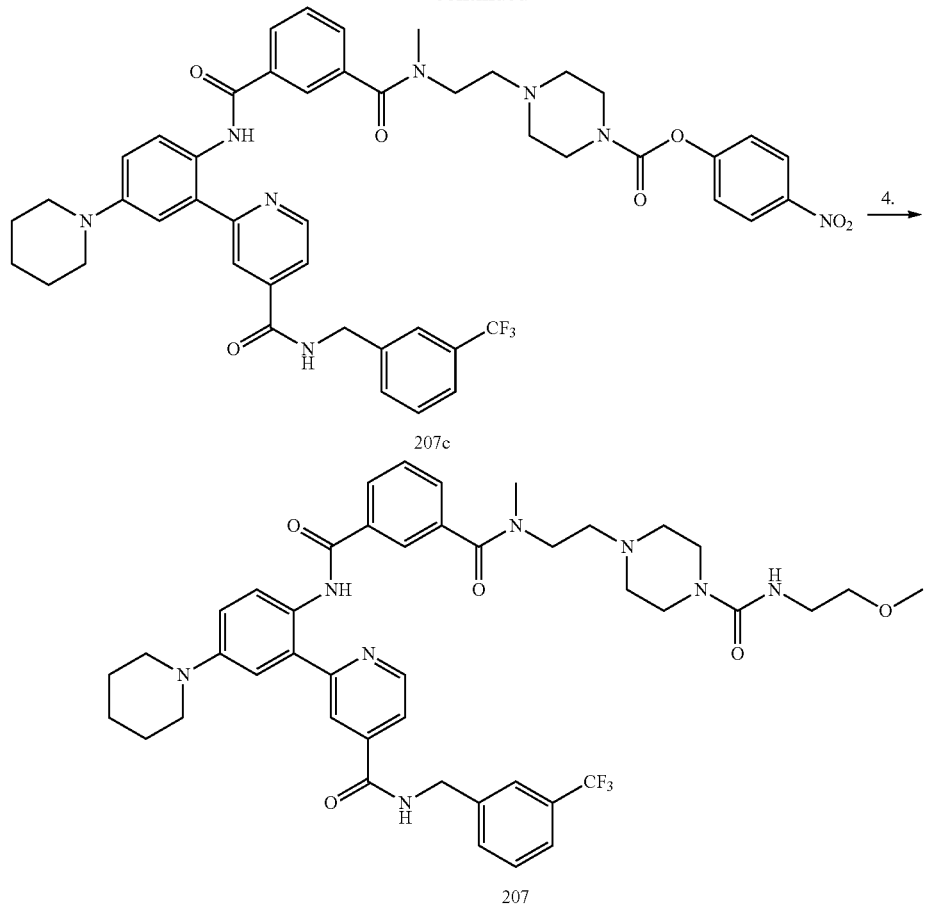

1. EDC·HCl, DMAP, Et₃N
2. TFA/DCM
3. 4-nitrophenyl carbonochloridate, DCM
4. 2-methoxyethanamine.

Intermediate 207a

Into a 100-mL round-bottom flask, was placed a solution of 3-(4-(piperidin-1-yl)-2-(4-(3-(trifluoromethyl)benzylcarbamoyl)pyridin-2-yl)phenylcarbamoyl)benzoic acid (900 mg, 1.49 mmol, 1.00 equiv) in dichloromethane (30 mL), tert-butyl 4-(2-(methylamino)ethyl)piperazine-1-carboxylate (468 mg, 1.92 mmol, 1.30 equiv), EDC.HCl (432 mg, 2.25 mmol, 1.50 equiv), 4-dimethylaminopyridine (279 mg, 2.28 mmol, 1.50 equiv). The resulting solution was stirred for 2 h at 25° C. The resulting solution was diluted with 10 mL of water. The resulting solution was extracted with 2×10 mL of dichloromethane and the organic layers combined. The resulting mixture was washed with 1×5 mL of water and 2×5 mL of brine. The mixture was dried over anhydrous sodium sulfate and concentrated under vacuum. This resulted in 800 mg (65%) of tert-butyl 4-(2-(N-methyl-3-(4-(piperidin-1-yl)-2-(4-(3-(trifluoromethyl)benzylcarbamoyl)pyridin-2-yl)phenylcarbamoyl)benzamido)ethyl)piperazine-1-carboxylate as a light yellow syrup.

Intermediate 207b

Into a 100-mL round-bottom flask, was placed a solution of tert-butyl 4-(2-(N-methyl-3-(4-(piperidin-1-yl)-2-(4-(3-(trifluoromethyl)benzylcarbamoyl)pyridin-2-yl)phenylcarbamoyl)benzamido)ethyl)piperazine-1-carboxylate (800 mg, 0.97 mmol, 1.00 equiv) in dichloromethane (30 mL), trifluoroacetic acid (5 g). The resulting solution was stirred for 3 h at 25° C. The resulting mixture was concentrated under vacuum. This resulted in 550 mg of crude product and 400 mg was added to the next step. The crude product (150 mg) was purified by Prep-HPLC with the following conditions (1#-Waters 2767-3): Column, SunFire Prep C18, 19*150 mm 5 um; mobile phase, water with 0.05% TFA and CH3CN (20% CH3CN up to 38% in 6 min); Detector, Waters2545 UvDector 254&270 nm. 95.2 mg product was obtained. This resulted in 95.2 mg of N1-methyl-N1-(2-(piperazin-1-yl)ethyl)-N3-(4-(piperidin-1-yl)-2-(4-(3-(trifluoromethyl)benzylcarbamoyl)pyridin-2-yl)phenyl)isophthalamide as a light yellow syrup. LC-MS (ES, m/z): 728 [M+H]⁺; H-NMR (300 MHz, CD₃OD, ppm): 8.97 (d, J=5.4 Hz, 1H), 8.82 (d, J=9.0 Hz, 1H), 8.48 (s, 1H), 8.25 (d, J=2.7 Hz, 1H), 8.12~8.09 (m, 2H), 7.90~7.88 (m, 1H), 7.77~7.67 (m, 5H), 7.62~7.53 (m, 2H), 4.72 (s, 2H), 3.83 (s, 2H), 3.72~3.70 (m, 4H), 3.68 (s, 1H), 3.13~2.96 (m, 10H), 2.64~2.52 (m, 2H), 2.07 (d, J=4.8 Hz, 4H), 1.85 (d, J=5.4 Hz, 2H).

Intermediate 207c

N1-(2-(4-((2-methoxyethyl)carbamoyl)piperazin-1-yl)ethyl)-N3-(2-(4-((3-(trifluoromethyl)benzyl)carbamoyl)pyridin-2-yl)-4-(piperidin-1-yl)phenyl)-N1-methylisophthalamide. Into a 50-mL round-bottom flask, was placed a solution of 207b (250 mg, 0.21 mmol, 1.05 equiv) in sodium bicarbonate aq. (10 mL). The mixture was stirred for 20 minutes at room temperature. The resulting solution was extracted with 3×10 mL of ethyl acetate and the organic layers combined. The mixture was dried over anhydrous sodium sulfate and concentrated under vacuum. This resulted in 150 mg of N1-(2-(4-((3-(trifluoromethyl)benzyl)carbamoyl)pyridin-2-yl)-4-(piperidin-1-yl)phenyl)-N3-methyl-N3-(2-(piperazin-1-yl)ethyl)isophthalamide free base used without purification in the next reaction.

Into a 50-mL round-bottom flask, was placed a solution of N1-(2-(4-((3-(trifluoromethyl)benzyl)carbamoyl)pyridin-2-yl)-4-(piperidin-1-yl)phenyl)-N3-methyl-N3-(2-(piperazin-1-yl)ethyl)isophthalamide (100 mg, 0.14 mmol, 1.00 equiv) in dichloromethane (3 mL), triethylamine (42 mg, 0.42 mmol, 3.00 equiv). This was followed by the addition of 4-nitrophenyl carbonochloridate (31 mg, 0.15 mmol, 1.10 equiv) dropwise with stirring at 0° C. The resulting solution was stirred for 40 min at 25° C. The resulting solution was diluted with 3 mL of sodium bicarbonate. The resulting solution was extracted with 2×5 mL of dichloromethane and the organic layers combined. The resulting mixture was washed with 1×5 mL of water and 2×5 mL of Brine. The mixture was dried over anhydrous sodium sulfate and concentrated under vacuum. This resulted in 110 mg (90%) of 4-nitrophenyl 4-(2-(N-methyl-3-(4-(piperidin-1-yl)-2-(4-(3-(trifluoromethyl)benzylcarbamoyl)pyridin-2-yl)phenylcarbamoyl)benzamido)ethyl)piperazine-1-carboxylate as a yellow solid.

Example 207

Into a 50-mL round-bottom flask, was placed 4-nitrophenyl 4-(2-(N-methyl-3-(4-(piperidin-1-yl)-2-(4-(3-(trifluoromethyl)benzylcarbamoyl)pyridin-2-yl)phenylcarbamoyl)benzamido)ethyl)piperazine-1-carboxylate 207c (100 mg, 0.11 mmol, 1.00 equiv), 2-methoxyethanamine (1 ml). The resulting solution was stirred for 4 h at 25° C. The resulting solution was diluted with 5 ml of water. The resulting solution was extracted with 2×5 ml of dichloromethane and the organic layers combined. The mixture was dried over anhydrous sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH3CN (20% CH3CN up to 40% in 6 min); Detector, Waters2545 UvDector 254&270 nm. 72.8 mg product was obtained. This resulted in 72.8 mg (78%) of N1-(2-(4-((2-methoxyethyl)carbamoyl)piperazin-1-yl)ethyl)-N3-(2-(4-((3-(trifluoromethyl)benzyl)carbamoyl)pyridin-2-yl)-4-(piperidin-1-yl)phenyl)-N1-methylisophthalamide as a light yellow solid. LC-MS (ES, m/z): 829 [M+H]$^+$ H-NMR (300 MHz, CD3OD, ppm): 8.96 (d, J=5.1 Hz, 1H), 8.74 (d, J=9.0 Hz, 1H), 8.45 (s, 1H), 8.17~8.15 (m, 3H), 7.88~7.86 (s, 1H), 7.80 (d, J=7.5 Hz, 1H), 7.72~7.64 (m, 4H), 7.62~7.55 (m, 2H), 4.72 (s, 2H), 4.00 (s, 2H), 3.90~3.54 (m, 16H), 3.48~3.33 (m, 5H), 3.11 (s, 3H), 2.03 (d, J=4.8 Hz, 1H), 1.82 (d, J=5.1 Hz, 1H).

Example 208

N-(2-methoxyethyl)-4-(2-(methyl(3-(4-(piperidin-1-yl)-2-(4-(3-(trifluoromethyl)benzylcarbamoyl)pyridin-2-yl)phenylcarbamoyl)benzyl)amino)ethyl)piperazine-1-carboxamide

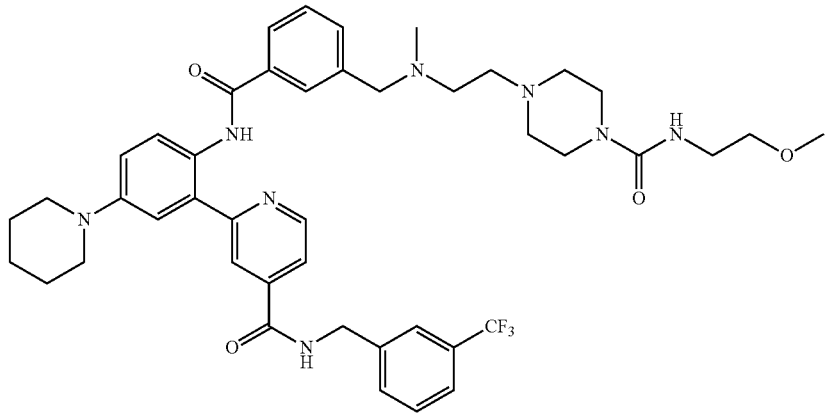 [SMILES: COCCNC(=O)N1CCN(CCN(C)Cc2cccc(C(=O)Nc3ccc(N4CCCCC4)cc3-c3cc(C(=O)NCc4cccc(C(F)(F)F)c4)ccn3)c2)CC1]

This compound was prepared according to the procedure described for the synthesis of N-(2-methoxyethyl)-4-(2-(methyl(3-(4-(piperidin-1-yl)-2-(4-(3-(trifluoromethyl)benzylcarbamoyl)pyridin-2-yl)phenylcarbamoyl)benzyl)amino)ethyl)piperazine-1-carboxamide Example 207 substituting tert-butyl 4-(2-(methyl(3-(4-(piperidin-1-yl)-2-(4-(3-(trifluoromethyl)benzylcarbamoyl)pyridin-2-yl)phenylcarbamoyl)benzyl)amino)ethyl)piperazine-1-carboxylate Example 38 in place of tert-butyl 4-(2-(N-methyl-3-(4-(piperidin-1-yl)-2-(4-(3-(trifluoromethyl)benzylcarbamoyl)pyridin-2-yl)phenylcarbamoyl)benzamido)ethyl)piperazine-1-carboxylate 207a LC-MS (ES, m/z): 815 [M+H]$^+$ H-NMR (300 MHz, DMSO, ppm): 12.30 (s, 1H), 9.55-9.59 (t, J=6.6 Hz, 1H), 8.92-8.94 (d, J=6 Hz, 1H), 8.28-8.34 (sd, J=9 Hz, 2H), 8.11-8.14 (m, 1H), 8.04 (s, 1H), 7.94-7.96 (d, J=6 Hz, 1H), 7.85-7.86 (d, J=3 Hz, 1H), 7.56-7.71 (m, 7H), 7.31 (s, 1H), 6.92-6.95 (m, 1H), 6.73 (s, 1H), 4.63-4.64 (d, J=3 Hz, 2H), 4.28 (s, 2H), 3.46 (s, 3H), 3.31-3.35 (m, 7H), 3.17-3.23 (m, 9H), 2.94 (s, 4H), 2.63 (s, 3H), 1.60-1.74 (m, 6H).

Example 209

N-(2-methoxyethyl)-N-methyl-4-(2-(methyl(3-(4-(piperidin-1-yl)-2-(4-(3-(trifluoromethyl)benzylcarbamoyl)pyridin-2-yl)phenylcarbamoyl)benzyl)amino)ethyl)piperazine-1-carboxamide

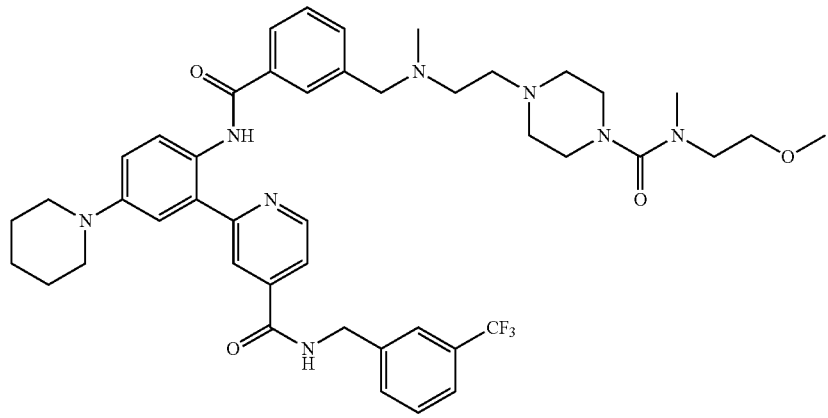 [SMILES: COCCN(C)C(=O)N1CCN(CCN(C)Cc2cccc(C(=O)Nc3ccc(N4CCCCC4)cc3-c3cc(C(=O)NCc4cccc(C(F)(F)F)c4)ccn3)c2)CC1]

This compound was prepared according to the procedure described for the synthesis of N-(2-methoxyethyl)-4-(2-(methyl(3-(4-(piperidin-1-yl)-2-(4-(3-(trifluoromethyl)benzylcarbamoyl)pyridin-2-yl)phenylcarbamoyl)benzyl)amino)ethyl)piperazine-1-carboxamide Example 208 substituting 2-methoxy-N-methylethanamine in place of 2-methoxyethanamine LC-MS (ES, m/z): 829 [M+H]$^+$ H-NMR (300 MHz, DMSO, ppm): 12.31 (s, 1H), 9.56 (t, J=3.6 Hz, 1H), 8.93 (d, J=6 Hz, 1H), 8.31 (d, J=6 Hz, 2H), 8.04 (s, 1H), 7.94 (d, J=9 Hz, 1H), 7.84-7.86 (m, 1H), 7.56-7.71 (m, 7H), 7.30 (d, J=9 Hz, 1H), 4.63 (d, J=3 Hz, 2H), 4.26 (s, 2H), 3.45 (t, J=6.6 Hz, 2H), 3.23-3.32 (m, 16H), 3.17 (s, 1H), 3.00 (s, 4H), 2.80 (s, 3H), 2.63 (s, 3H), 1.60-1.74 (m, 6H).

Example 210

N-(2-methoxyethyl)-N-methyl-4-(2-(methyl((6-(4-(piperidin-1-yl)-2-(4-(3-(trifluoromethyl)benzylcarbamoyl)pyridin-2-yl)phenylcarbamoyl)pyridin-2-yl)methyl)amino)ethyl)piperazine-1-carboxamide

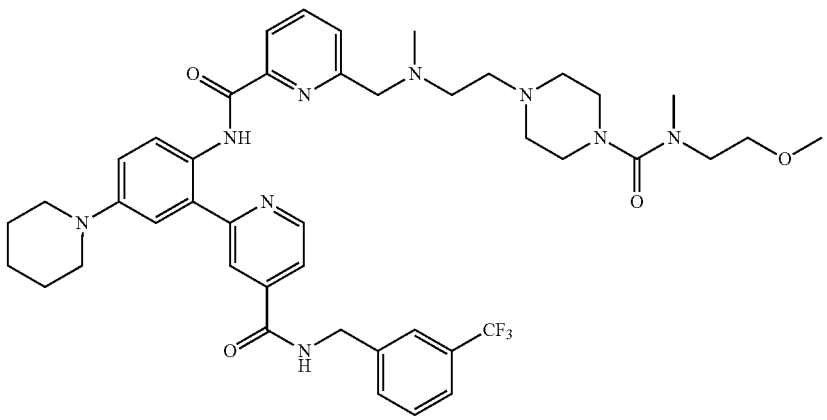 [SMILES: COCCN(C)C(=O)N1CCN(CCN(C)Cc2cccc(C(=O)Nc3ccc(N4CCCCC4)cc3-c3cc(C(=O)NCc4cccc(C(F)(F)F)c4)ccn3)n2)CC1]

This compound was prepared according to the procedure described for the synthesis of N-(2-methoxyethyl)-N-methyl-4-(2-(methyl((6-(4-(piperidin-1-yl)-2-(4-(3-(trifluoromethyl)benzylcarbamoyl)pyridin-2-yl)phenylcarbamoyl)pyridin-2-yl)methyl)amino)ethyl)piperazine-1-carboxamide Example 208 substituting 2-methoxy-N-methylethanamine in place of 2-methoxyethanamine. LC-MS (ES, m/z): 830 [M+H]$^+$ H-NMR (300 MHz, DMSO, ppm): 12.81 (s, 1H), 9.57-9.55 (m, 1H), 9.05-9.03 (m, 1H), 8.50-8.47 (m, 1H), 8.27 (m, 1H), 8.10-8.06 (m, 2H), 7.89-7.87 (m, 1H), 7.79-7.52 (m, 6H), 7.27 (m, 1H), 4.65-4.63 (d, J=5.7 Hz, 3H), 4.09 (m, 3H), 3.43-3.01 (m, 22H), 2.74 (m, 3H), 1.72-1.59 (m, 6H).

Example 211

N1-(2-(4-((2-methoxyethyl)(methyl)carbamoyl)piperazin-1-yl)ethyl)-N1-methyl-N3-(4-(piperidin-1-yl)-2-(4-(3-(trifluoromethyl)benzylcarbamoyl)pyridin-2-yl)phenyl)isophthalamide

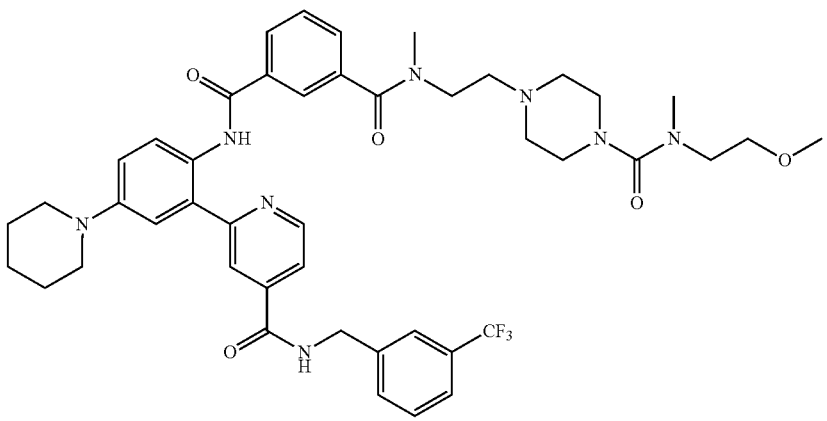 [SMILES: COCCN(C)C(=O)N1CCN(CCN(C)C(=O)c2cccc(C(=O)Nc3ccc(N4CCCCC4)cc3-c3cc(C(=O)NCc4cccc(C(F)(F)F)c4)ccn3)c2)CC1]

This compound was prepared according to the procedure described for the synthesis of N1-(2-(4-((2-methoxyethyl)carbamoyl)piperazin-1-yl)ethyl)-N3-(2-(4-((3-(trifluoromethyl)benzyl)carbamoyl)pyridin-2-yl)-4-(piperidin-1-yl)phenyl)-N1-methylisophthalamide Example 207 substituting methoxy-N-methylethanamine in place of 2-methoxyethanamine. LC-MS (ES, m/z): 843 [M+H]$^+$ H-NMR (300 MHz, CD$_3$OD, ppm): 8.99 (d, J=5.1 Hz, 1H), 8.77 (d, J=9.0 Hz, 1H), 8.46 (s, 1H), 8.19 (m, 3H), 7.90 (m, 1H), 7.81 (d, J=7.8 Hz, 1H), 7.74~7.67 (m, 4H), 7.62~7.53 (m, 2H), 4.72 (s, 2H), 4.00 (s, 2H), 3.90~3.65 (m, 9H), 3.57 (d, J=5.1 Hz, 1H), 3.47 (d, J=4.8 Hz, 1H), 3.34 (s, 3H), 3.12 (s, 3H), 2.97 (s, 3H), 2.04 (d, J=4.8 Hz, 4H), 1.83 (d, J=4.2 Hz, 2H).

Example 212
tert-butyl 3-[2-(2-{2-[(4-{2-[1-(3-{[4-(diethy-
lamino)-2-(4-{[(1S)-1,2,3,4-tetrahydronaphthalen-1-
yl]carbamoyl}pyridin-2-yl)phenyl]
carbamoyl}phenyl)-N-methylformamido]
ethyl}piperazin-1-yl)carbonyl(methyl)amino]
ethoxy}ethoxy)ethoxy]propanoate
Scheme 85b.
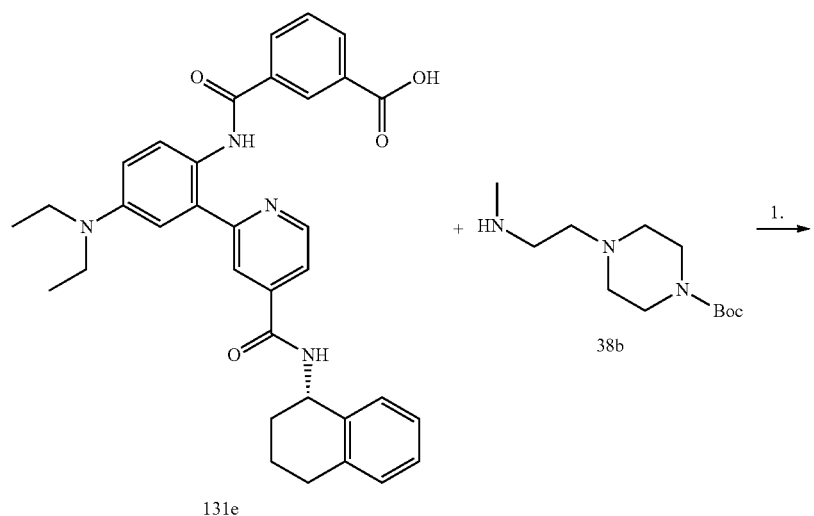
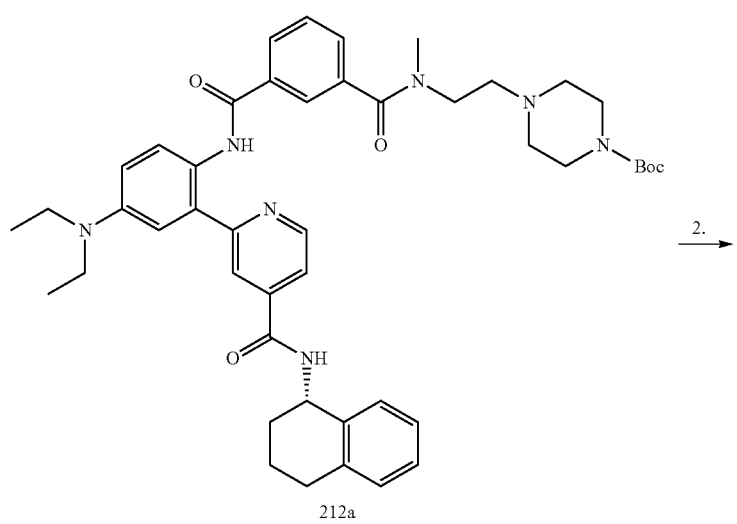

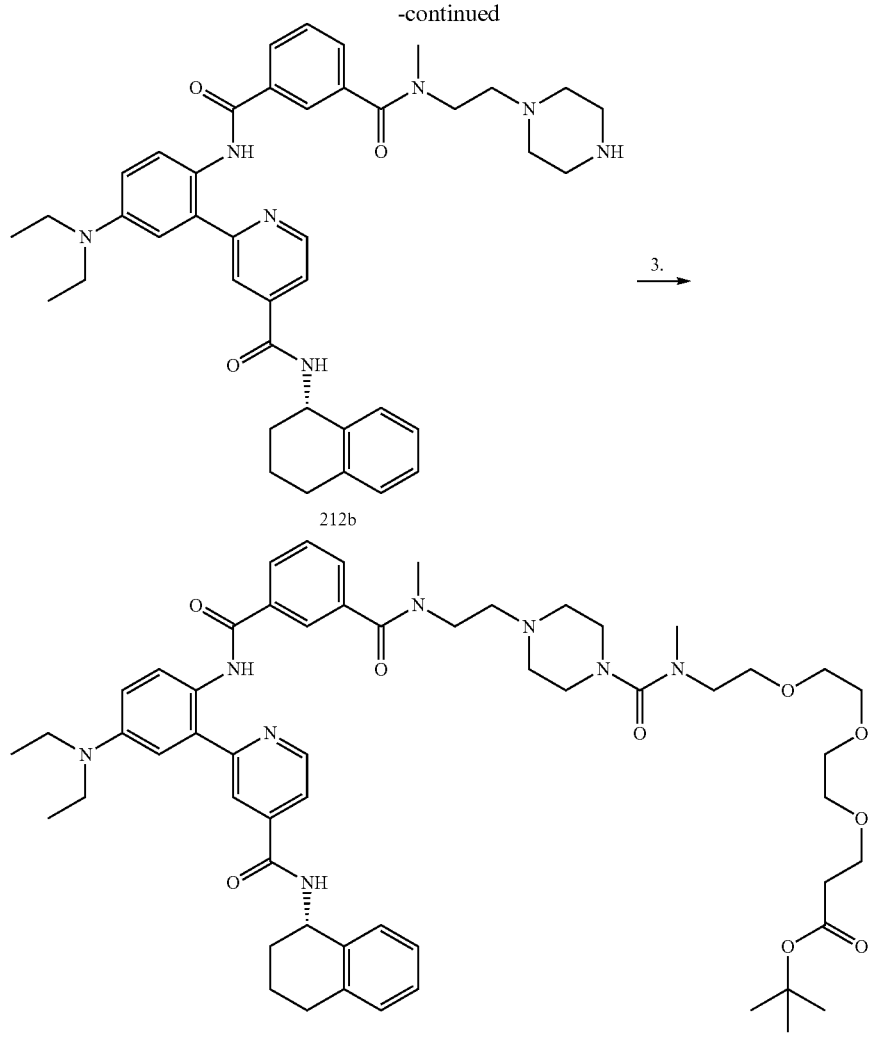

1. EDC·HCl, DMAP, Et₃N
2. TFA/DCM
3.i. triphosgene ii. tert-butyl 5,8,11-trioxa-2-azatetradecan-14-oate 135c.

Intermediate 212a

Into a 100-mL round-bottom flask, was placed a solution of 3-((2-(4-(((S)-1,2,3,4-tetrahydronaphthalen-1-yl)carbamoyl)pyridin-2-yl)-4-(diethylamino)phenyl)carbamoyl)benzoic acid (880 mg, 1.56 mmol, 1.00 equiv) in dichloromethane (10 mL), tert-butyl 4-(2-(methylamino)ethyl)piperazine-1-carboxylate (570 mg, 2.35 mmol, 1.50 equiv), EDC.HCl (0.60 g, 3.14 mmol, 2.00 equiv), 4-dimethylaminopyridine (0.19 g, 1.56 mmol, 1.00 equiv). The resulting solution was stirred overnight at room temperature. The resulting mixture was concentrated under vacuum. The residue was applied onto a silica gel column with ethyl acetate/petroleum ether (1:5-1:1). This resulted in 0.8 g (65%) of tert-butyl 4-(2-(3-(carbamoyl)-N-methylbenzamido)ethyl)piperazine-1-carboxylate as a yellow solid.

Intermediate 212b

Into a 50-mL round-bottom flask, was placed a solution of tert-butyl 4-(2-(3-(carbamoyl)-N-methylbenzamido)ethyl)piperazine-1-carboxylate (800 mg, 1.02 mmol, 1.00 equiv) in dichloromethane (5 mL), trifluoroacetic acid (6 mL). The resulting solution was stirred overnight at room temperature. The resulting mixture was concentrated under vacuum. The resulting solution was diluted with 10 mL of water. The pH value of the solution was adjusted to 8~9 with sodium bicarbonate. The resulting solution was extracted with 3×30 mL of dichloromethane and the organic layers combined. The resulting mixture was washed with 3×30 mL of Brine. The mixture was dried over anhydrous sodium sulfate and concentrated under vacuum. This resulted in 0.65 g (93%) of N1-(2-(4-(((S)-1,2,3,4-tetrahydronaphthalen-1-yl)carbamoyl)pyridin-2-yl)-4-(diethylamino)phenyl)-N3-methyl-N3-(2-(piperazin-1-yl)ethyl)isophthalamide as a yellow solid.

Example 212

Into a 50-mL round-bottom flask, was placed a solution of (S)-4-nitrophenyl 4-(2-(3-(4-(diethylamino)-2-(4-(1,2,3,4-tetrahydronaphthalen-1-ylcarbamoyl)pyridin-2-yl)phenylcarbamoyl)-N-methylbenzamido)ethyl)piperazine-1-carboxylate (400 mg, 0.47 mmol, 1.00 equiv) in dichloromethane (3 mL), triethylamine (2 mL). This was followed by the addition of a solution of bis(trichloromethyl) carbonate (80 mg, 0.27 mmol, 0.50 equiv) in dichloromethane (4 mL) dropwise with stirring at 0° C. The resulting solution was stirred for 0.5 h at room temperature. To this was added triethylamine (2 mL), a solution of tert-butyl 3-(2-(2-(2-(methylamino)ethoxy)ethoxy)ethoxy)propanoate (224 mg, 0.77 mmol, 1.50 equiv) in dichloromethane (3 mL). The resulting solution was stirred for 2 h at room temperature. The reaction progress was monitored by LCMS. The resulting mixture was concentrated under vacuum. The crude product (0.1 g) was purified by Prep-HPLC with the following conditions (1#-Waters 2767-3): Column, SunFire Prep C18, 19*150 mm 5 um; mobile phase, water with 0.05% TFA and CH₃CN (5% CH₃CN up to 30% in 1 min, up to 40% in 5 min); Detector, Waters2545 UvDector 254&270 nm. 21.8 mg product was obtained. This resulted in 21.8 mg (4%) of Example 212 as a yellow solid. LC-MS (ES, m/z): 1006 [M+H]⁺ H-NMR (300 MHz, DMSO, ppm): 9.14 (m, 1H), 8.87 (m, 1H), 8.24 (m, 2H), 7.96 (m, 2H), 7.83 (m, 1H), 7.63 (m, 2H), 7.13 (m, 6H), 5.76 (m, 1H), 3.45 (m, 18H), 2.98 (m, 15H), 2.46 (m, 3H), 1.87 (m, 5H), 1.38 (m, 11H), 1.12 (m, 7H).

Example 213

(S)—N1-(2-(4-2,5,8,11,14,17,20,23-octaoxapentacosane-1,4-diazepan-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide

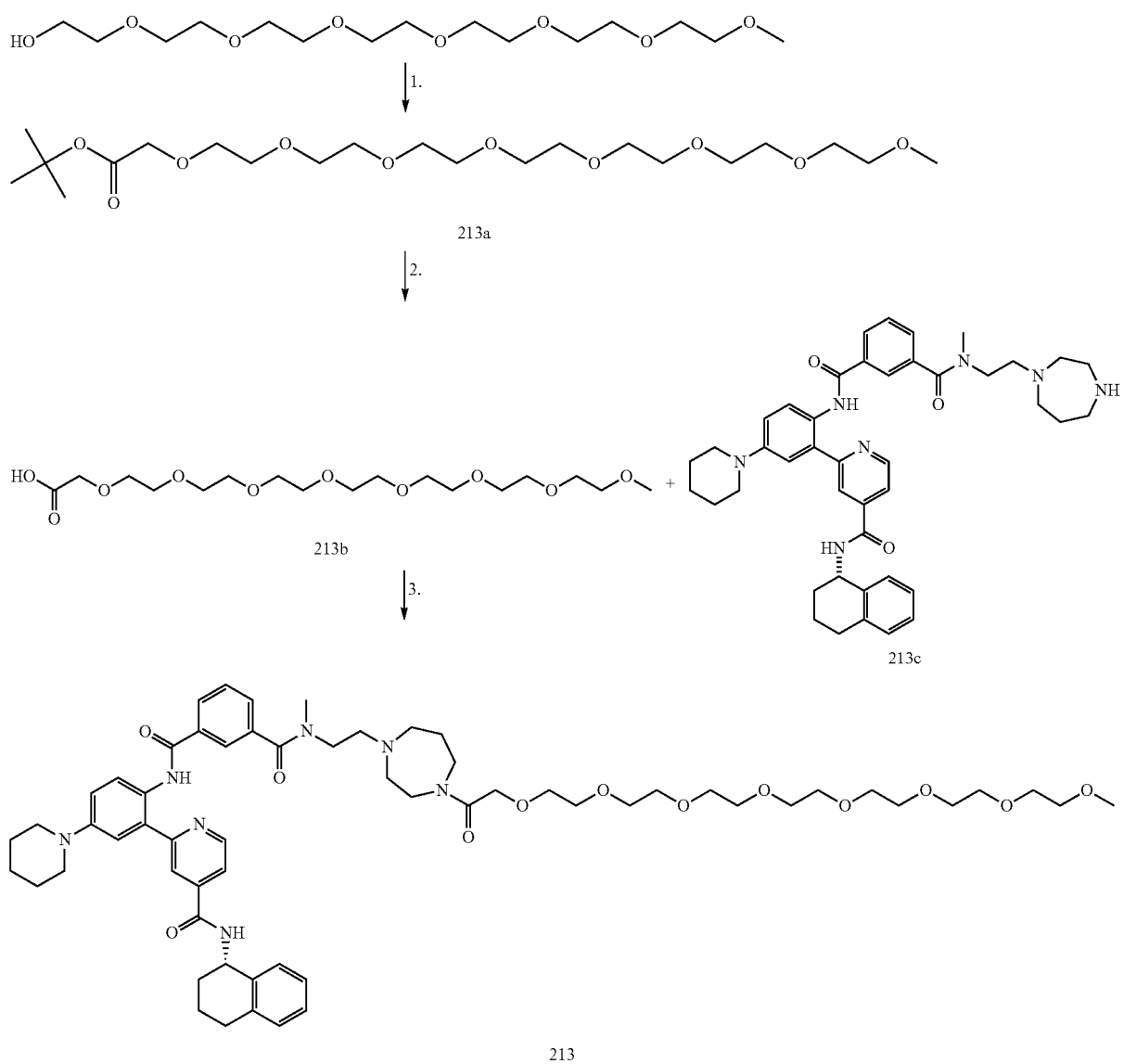

1. NaH, tert-butylbromoacetate
2. HCl/DCM
3. EDC, DMAP, DCM.

Intermediate 213a

Into a 50-mL round-bottom flask, was placed a solution of 2-(2-(2-(2-(2-(2-(2-methoxyethoxy)ethoxy)ethoxy)ethoxy)ethoxy)ethoxy)ethanol (500 mg, 1.47 mmol, 1.00 equiv) in tetrahydrofuran (15 mL). This was followed by the addition of sodium hydride (135 mg, 5.62 mmol, 3.83 equiv) in several batches at 0-5° C. The resulting solution was stirred for 15 min at room temperature. To this was added tert-butyl 2-bromoacetate (345 mg, 1.78 mmol, 1.21 equiv). The resulting solution was allowed to react, with stirring, for an additional 4 h at room temperature. The reaction was then quenched by the addition of 50 mL of water/ice. The resulting solution was extracted with 3×20 mL of ethyl acetate and the organic layers combined. The resulting mixture was washed with 3×20 mL of sodium chloride. The mixture was dried over anhydrous sodium sulfate and concentrated under vacuum. This resulted in 500 mg (75%) of tert-butyl-2-(2-(2-(2-(2-(2-(2-(2-methoxyethoxy)ethoxy)ethoxy)ethoxy)ethoxy)ethoxy)ethoxy) acetate as colourless oil.

Intermediate 213b

Into a 100-mL round-bottom flask, was placed a solution of tert-butyl 2-(2-(2-(2-(2-(2-(2-(2-methoxyethoxy)ethoxy)ethoxy)ethoxy)ethoxy)ethoxy)ethoxy)acetate (500 mg, 1.10 mmol, 1.00 equiv) in dichloromethane (20 mL). The gas of hydrochloric acid was introduced in. The resulting solution was stirred for 3 h at room temperature. The resulting mixture was concentrated under vacuum. This resulted in 400 mg (91%) of 2-(2-(2-(2-(2-(2-(2-(2-methoxyethoxy)ethoxy)ethoxy)ethoxy)ethoxy)ethoxy)ethoxy)acetic acid as yellow oil.

Example 213

(S)—N1-(2-(4-2,5,8,11,14,17,20,23-octaoxapentacosane-1,4-diazepan-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide This compound was prepared according to the procedure described for the synthesis of Example 197 using 2-(2-(2-(2-(2-(2-(2-methoxyethoxy)ethoxy)ethoxy)ethoxy)ethoxy)ethoxy)acetic acid 213b in place of m-dPEG$_8$-NHS ester and 187a in place of 197a LC-MS (ES, m/z): 1094 [M+H]$^+$ H-NMR (300 MHz, CDCl$_3$, ppm): 8.93 (d, J=5.1 Hz, 1H), 8.68-8.65 (m, 1H), 8.41 (s, 1H), 8.16-8.07 (m, 3H), 7.87-7.85 (m, 1H), 7.78-7.65 (m, 3H), 7.25-7.14 (m, 4H), 5.38 (m, 1H), 4.31 (s, 2H), 3.99-3.86 (m, 3H), 3.66-3.51 (m, 39H), 3.37-3.31 (m, 3H), 3.13-3.09 (m, 3H), 2.91-2.84 (m, 2H), 2.32-1.80 (m, 12H).

Example 214

(S)-2,5,8,11,14,17,20-heptaoxadocosan-22-yl 4-(2-(N-methyl-3-(4-(piperidin-1-yl)-2-(4-(1,2,3,4-tetrahydronaphthalen-1-ylcarbamoyl)pyridin-2-yl)phenylcarbamoyl)benzamido)ethyl)-1,4-diazepane-1-carboxylate _Scheme 87._

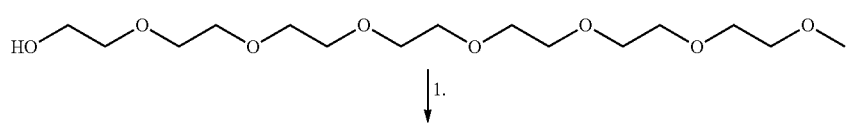

↓ 1.

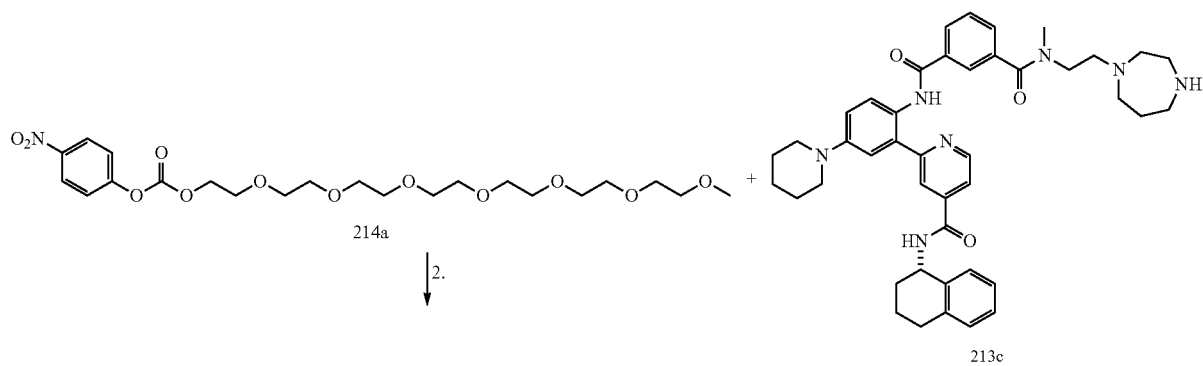

↓ 2.

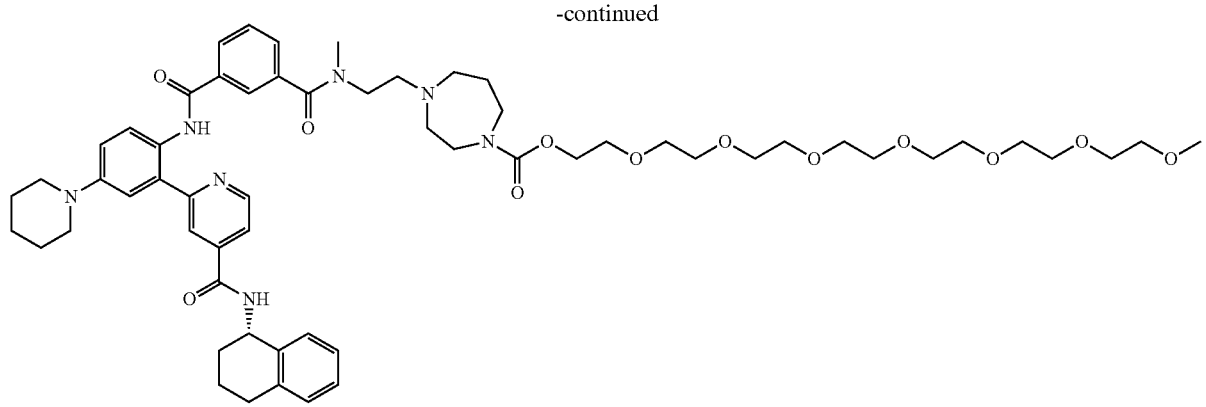

1. 4-nitrophenyl carbonochloridate, TEA, DCM
2. DMAP, CH₃CN.

214

Intermediate 214a

Into a 100-mL round-bottom flask, was placed a solution of 4-nitrophenyl carbonochloridate (200 mg, 1.00 mmol, 1.00 equiv) in dichloromethane (10 mL), 2-(2-(2-(2-(2-(2-(2-methoxyethoxy)ethoxy)ethoxy)ethoxy)ethoxy)ethanol (338 mg, 0.99 mmol, 1.00 equiv), triethylamine (301 mg, 2.98 mmol, 2.99 equiv). The resulting solution was stirred for 3 h at room temperature. The resulting solution was diluted with 10 mL of dichloromethane. The resulting mixture was washed with 2×10 mL of brine. The mixture was dried over anhydrous sodium sulfate and concentrated under vacuum. This resulted in 240 mg (48%) of 2-(2-(2-(2-(2-(2-(2-methoxyethoxy)ethoxy)ethoxy)ethoxy)ethoxy)ethyl 4-nitrophenyl carbonate as yellow oil.

Example 214

Into a 100-mL round-bottom flask, was placed a solution of (S)—N1-(2-(1,4-diazepan-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide (150 mg, 0.21 mmol, 1.00 equiv) in acetonitrile (1 mL), 2-(2-(2-(2-(2-(2-(2-methoxyethoxy)ethoxy)ethoxy)ethoxy)ethoxy)ethoxy)ethyl 4-nitrophenyl carbonate (106 mg, 0.21 mmol, 1.00 equiv), 4-dimethylaminopyridine (39 mg, 0.32 mmol, 1.51 equiv). The resulting solution was stirred overnight at 80° C. in an oil bath. The resulting mixture was washed with 2×20 mL of sat. NH₄Cl. The mixture was dried over sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH₃CN (25% CH₃CN up to 38% in 6 min); Detector, Waters2545 UvDector 254&270 nm. 35.2 mg product was obtained. This resulted in 35.2 mg (12%) of (S)-2,5,8,11,14,17,20-heptaoxadocosan-22-yl 4-(2-(N-methyl-3-(4-(piperidin-1-yl)-2-(4-(1,2,3,4-tetrahydronaphthalen-1-ylcarbamoyl)pyridin-2-yl)phenyl-carbamoyl)benzamido)ethyl)-1,4-diazepane-1-carboxylate as yellow oil. LC-MS (ES, m/z): 1081 [M+H]⁺ H-NMR (400 MHz, CD₃OD, ppm): 8.93~8.92 (d, J=4.8 Hz, 1H), 8.61~8.59 (d, J=8.8 Hz, 1H), 8.38 (s, 1H), 8.15~8.10 (t, 2H), 7.97 (s, 1H), 7.86~7.84 (d, J=5.2 Hz, 1H), 7.79~7.70 (m, 2H), 7.59~7.56 (d, J=9.2 Hz, 1H), 7.28~7.26 (d, J=7.2 Hz, 1H), 7.18~7.14 (m, 3H), 5.39 (s, 1H), 4.27 (s, 2H), 4.00 (s, 3H), 3.80~3.72 (m, 5H), 3.63 (s, 24H), 3.57~3.46 (m, 10H), 3.33 (s, 2H), 3.13 (s, 3H), 2.91~2.86 (m, 2H), 2.24~2.16 (m, 3H), 2.04~1.90 (m, 7H), 1.78 (s, 2H).

Example 215

(S)—N1-methyl-N1-(2-(3-oxopiperazin-1-yl)ethyl)-N3-(4-(piperidin-1-yl)-2-(4-(1,2,3,4-tetrahydronaphthalen-1-ylcarbamoyl)pyridin-2-yl)phenyl)isophthalamide

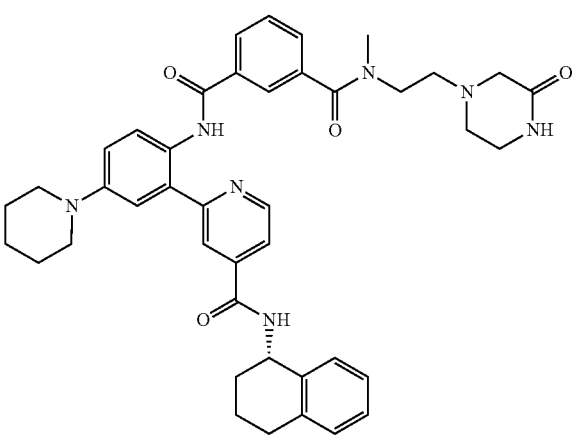 [SMILES: CN(CCN1CCNC(=O)C1)C(=O)c1cccc(C(=O)Nc2ccc(N3CCCCC3)cc2-c2cc(C(=O)N[C@H]3CCCc4ccccc43)ccn2)c1]

This compound was prepared according to the procedure described for the synthesis of Example 187 using piperazin-2-one in place of L-proline-tert-butyl ester. Into a 50-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl) isophthalamide (100 mg, 0.16 mmol, 1.00 equiv) in ethanol (5 mL), piperazin-2-one (20 mg, 0.20 mmol, 1.20 equiv). This was followed by the addition of acetic acid (20 mg, 0.33 mmol, 2.20 equiv). The mixture was allowed to react with stirring for 1 h at room temperature. To this was added NaBH₃CN (22 mg, 0.35 mmol, 2.20 equiv). The resulting solution was stirred overnight at room temperature. The resulting mixture was concentrated under vacuum. The pH value of the solution was adjusted to 7 with sodium bicarbonate (2 mol/L). The resulting solution was extracted with 3×20 mL of dichloromethane and the organic layers combined and dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and CH₃CN (20% CH₃CN up to 40% in 6 min); Detector, Waters2545 UvDector 254&270 nm. 91.4 mg product was obtained. This resulted in 91.4 mg (54%) of (S)—N1-methyl-N1-(2-(3-oxopiperazin-1-yl)ethyl)-N3-(4-(piperidin-1-yl)-2-(4-(1,2,3,4-tetrahydronaphthalen-1-ylcarbamoyl)pyridin-2-yl)phenyl)isophthalamide as a yellow solid. LCMS (ES, m/z): 714 [M+H]⁺ H-NMR (300 MHz, CD₃OD, ppm): 8.94 (m, 1H), 8.70 (m, 1H), 8.40 (s, 2H), 8.12 (m, 3H), 7.85 (m, 1H), 7.72 (m, 3H), 7.17 (m, 3H), 5.39 (s, 1H), 3.94 (m, 3H), 3.56 (m, 7H), 3.09 (m, 3H), 2.86 (m, 3H), 1.95 (m, 8H).

Example 216

(S)—N1-methyl-N1-(2-(4-methyl-3-oxopiperazin-1-yl)ethyl)-N3-(4-(piperidin-1-yl)-2-(4-(1,2,3,4-tetrahydronaphthalen-1-ylcarbamoyl)pyridin-2-yl)phenyl)isophthalamide

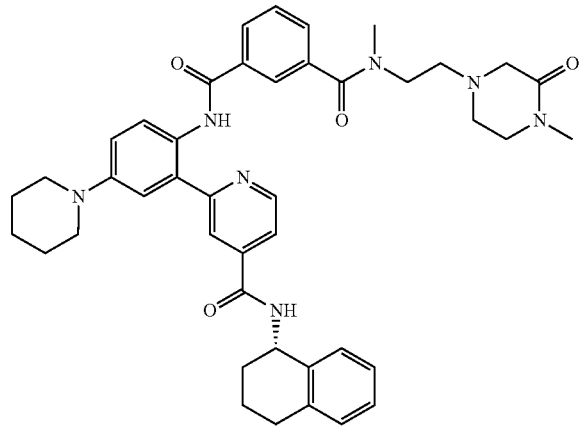 [SMILES: CN1CCN(CCN(C)C(=O)c2cccc(C(=O)Nc3ccc(N4CCCCC4)cc3-c3cc(C(=O)N[C@H]4CCCc5ccccc54)ccn3)c2)CC1=O]

This compound was prepared according to the procedure described for the synthesis of Example 187 using methylpiperazin-2-one in place of L-proline-tert-butyl ester. Into a 50-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl)isophthalamide (100 mg, 0.16 mmol, 1.00 equiv) in ethanol (2 mL). This was followed by the addition of a solution of 1-methylpiperazin-2-one (18 mg, 0.16 mmol, 1.00 equiv) in ethanol (2 mL), two drop of acetic acid. To this was added NaBH₃CN (20 mg, 0.32 mmol, 2.00 equiv). The resulting solution was stirred for 2 h at room temperature. The resulting solution was diluted with 50 mL of ethyl acetate. The resulting mixture was washed with 2×20 mL of brine. The mixture was dried over anhydrous sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH₃CN (22% CH₃CN up to 38% in 6 min); Detector, Waters2545 UvDector 254&270 nm. 70 mg product was obtained. This resulted in 70 mg (61%) of (S)—N1-methyl-N1-(2-(4-methyl-3-oxopiperazin-1-yl)ethyl)-N3-(4-(piperidin-1-yl)-2-(4-(1,2,3,4-tetrahydronaphthalen-1-ylcarbamoyl)pyridin-2-yl)phenyl)isophthalamide as a yellow solid. LC-MS (ES, m/z): 728 [M+H]⁺ H-NMR (300 MHz, DMSO, ppm): 12.25 (s, 1H), 9.18 (d, J=8.4 Hz, 1H), 8.80 (d, J=5.1 Hz, 1H), 8.29 (d, J=13.8 Hz 2H), 7.99 (t, J=6.9 Hz, 2H), 7.86 (d, J=4.8 Hz, 1H), 7.57~7.67 (m, 3H), 7.10~7.28 (m, 5H), 5.25 (d, J=5.4 Hz, 1H), 3.92~3.85 (m, 4H), 3.30~3.54 (m, 10H), 2.78~2.95 (m, 9H), 1.99 (d, J=3.6 Hz, 2H), 1.72~1.80 (m, 6H), 1.60 (s, 2H).

Example 217

(S)—N1-(2-(bis(2-methoxyethyl)amino)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide

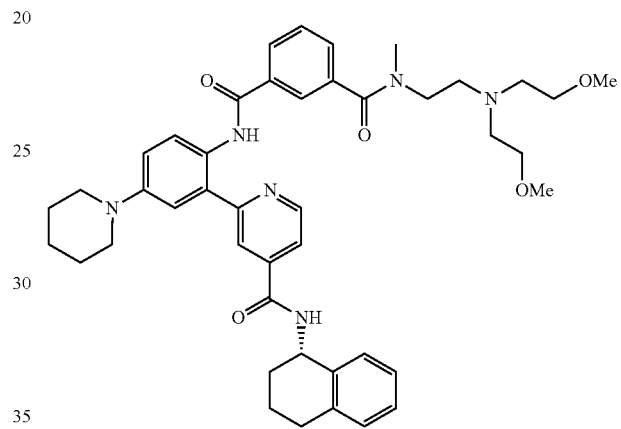

This compound was prepared according to the procedure described for the synthesis of Example 187 using bis(2-methoxyethyl)amine in place of L-proline-tert-butyl ester. Into a 25-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl)isophthalamide (100 mg, 0.16 mmol, 1.00 equiv) in ethanol (1 mL), bis(2-methoxyethyl)amine (25 mg, 0.19 mmol, 1.20 equiv), NaBH₃CN (20 mg, 0.32 mmol, 2.00 equiv), acetic acid (1.0 mg, 0.02 mmol, 0.10 equiv). The resulting solution was stirred for 2 h at 25° C. The reaction was then quenched by the addition of 10 mL of water. The resulting solution was extracted with 2×10 mL of ethyl acetate and the organic layers combined and dried over anhydrous sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH₃CN (25% CH₃CN up to 38% in 6 min); Detector, Waters2545 UvDector 254&270 nm. 47.9 mg product was obtained. This resulted in 47.9 mg (40%) of (S)—N1-(2-(bis(2-methoxyethyl)amino)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide as a yellow solid. LC-MS (ES, m/z): 747 [M+H]⁺ H-NMR (300 MHz, DMSO, ppm): 12.24 (s, 1H), 9.50 (s, 1H), 9.20 (d, J=9 Hz, 1H), 8.89 (d, J=3 Hz, 1H), 8.24-8.32 (m, 2H), 7.99 (d, J=6 Hz, 2H), 7.86 (d, J=6 Hz, 1H), 7.60-7.69 (m, 3H), 7.30 (s, 1H), 7.10-7.24 (m, 4H), 5.25 (t, J=6.9 Hz, 1H), 3.80 (d, J=33 Hz, 5H), 3.63 (s, 6H), 3.33 (s, 12H), 2.97 (s, 4H), 2.74 (s, 2H), 1.96-2.00 (m, 2H), 1.73-1.88 (m, 6H), 1.60 (d, J=6 Hz, 2H).

Example 218

(S)—N1-(2-(4-(dimethylcarbamoyl)piperidin-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide

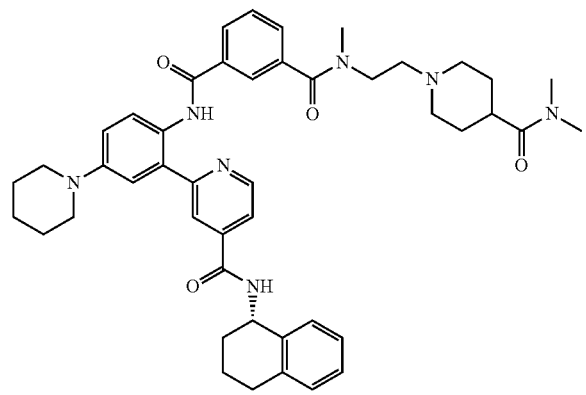 [SMILES: CN(C)C(=O)C1CCN(CCN(C)C(=O)c2cccc(C(=O)Nc3ccc(N4CCCCC4)cc3-c3cc(C(=O)N[C@H]4CCCc5ccccc54)ccn3)c2)CC1]

This compound was prepared according to the procedure described for the synthesis of Example 187 using N,N-dimethylpiperidine-4-carboxamide in place of L-proline-tert-butyl ester. Into a 100-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl)isophthalamide (100 mg, 0.16 mmol, 1.00 equiv) in ethanol (10 mL), N,N-dimethylpiperidine-4-carboxamide (50 mg, 0.32 mmol, 2.02 equiv), acetic acid (22 mg, 0.37 mmol, 2.31 equiv). The resulting solution was stirred for 0.5 h at room temperature. To the above was added NaBH$_3$CN (22 mg, 0.35 mmol, 2.20 equiv). The resulting solution was allowed to react, with stirring, for an additional 4 h at room temperature. The resulting mixture was concentrated under vacuum. The pH value of the solution was adjusted to 8 with sodium bicarbonate.aq. The resulting solution was extracted with 3×20 mL of ethyl acetate and the organic layers combined. The mixture was dried over anhydrous sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH$_3$CN (22% CH$_3$CN up to 38% in 6 min); Detector, Waters2545 UvDector 254&270 nm. 51.5 mg product was obtained. This resulted in 51.5 mg (42%) of (S)—N1-(2-(4-(dimethylcarbamoyl)piperidin-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide as a light yellow solid. LC-MS (ES, m/z): 770 [M+H]$^+$ H-NMR (400 MHz, DMSO, ppm): 12.26 (s, 1H), 9.18~9.16 (m, 2H), 8.90~8.88 (d, J=3.9 Hz, 1H), 8.32~8.25 (m, 2H), 8.02~7.98 (t, 2H), 7.88~7.87 (d, J=3.9 Hz, 1H), 7.71~7.64 (m, 2H), 7.60 (s, 1H), 7.28 (s, 1H), 7.20~7.10 (m, 4H), 5.26 (s, 1H), 3.85 (s, 1H), 3.38~3.30 (m, 8H), 3.04 (s, 5H), 2.96 (s, 5H), 2.83~2.78 (m, 5H), 2.00~1.91 (m, 4H), 1.86~1.72 (m, 9H), 1.60~1.59 (d, J=3.3 Hz, 2H).

Example 219

(S)-tert-butyl 4-(2-(N-methyl-3-(4-(piperidin-1-yl)-2-(4-(1,2,3,4-tetrahydronaphthalen-1-ylcarbamoyl)pyridin-2-yl)phenylcarbamoyl)benzamido)ethyl)-1,4-diazepane-1-carboxylate

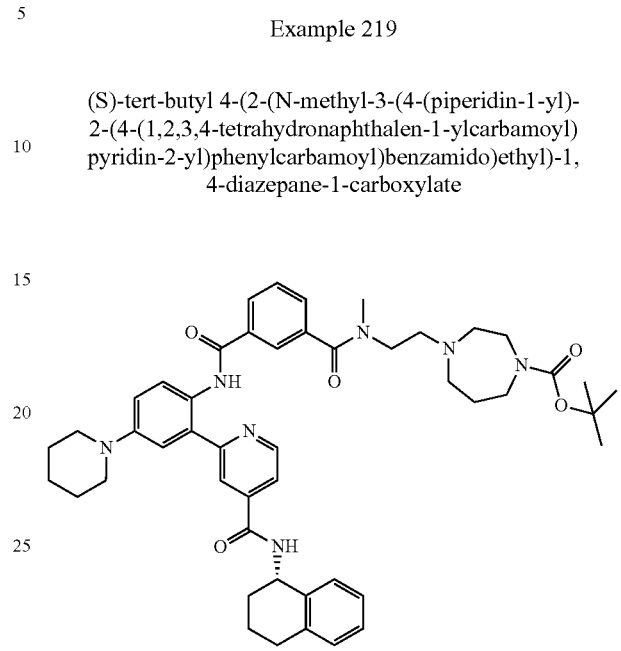

This compound was prepared according to the procedure described for the synthesis of Example 187 using tert-butyl 1,4-diazepane-1-carboxylate in place of L-proline-tert-butyl ester. Into a 50-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl)isophthalamide (100 mg, 0.16 mmol, 1.00 equiv) in ethanol (5 mL), tert-butyl 1,4-diazepane-1-carboxylate (50 mg, 0.25 mmol, 1.57 equiv), acetic acid (20 mg, 0.33 mmol, 2.10 equiv). The resulting solution was stirred for 0.5 h at room temperature. To the above was added NaBH$_3$CN (20 mg, 0.32 mmol, 2.00 equiv). The resulting solution was allowed to react, with stirring, for an additional 3 h at room temperature. The resulting mixture was concentrated under vacuum. The pH value of the solution was adjusted to 8-9 with sodium bicarbonate. The resulting solution was extracted with 3×20 mL of ethyl acetate and the organic layers combined. The mixture was dried over anhydrous sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH$_3$CN (25% CH$_3$CN up to 43% in 6 min); Detector, Waters2545 UvDector 254&270 nm. 60.2 mg product was obtained. This resulted in 60.2 mg (47%) of (S)-tert-butyl 4-(2-(N-methyl-3-(4-(piperidin-1-yl)-2-(4-(1,2,3,4-tetrahydronaphthalen-1-ylcarbamoyl)pyridin-2-yl)phenylcarbamoyl)benzamido)ethyl)-1,4-diazepane-1-carboxylate as a light yellow solid. LC-MS (ES, m/z): 814 [M+H]$^+$ H-NMR (300 MHz, DMSO, ppm): 12.23 (s, 1H), 9.38 (s, 1H), 9.18 (d, J=8.4 Hz, 1H), 8.88 (d, J=5.1 Hz, 1H), 8.31 (s, 1H), 8.23 (d, J=7.8 Hz, 1H), 7.98 (d, J=6.3 Hz, 2H), 7.85 (d, J=5.1 Hz, 1H), 7.68-7.56 (m, 3H), 7.28-7.12 (m, 5H), 5.25 (d, J=6.0 Hz, 1H), 3.82-3.46 (m, 12H), 3.30 (s, 3H), 2.96-2.51 (m, 2H), 2.07-1.99 (m, 4H), 1.83-1.72 (m, 6H), 1.59 (d, J=4.2 Hz, 1H), 1.42 (s, 9H).

Example 220

(S)—N1-methyl-N1-(2-(4-(methylsulfonyl)-1,4-diazepan-1-yl)ethyl)-N3-(4-(piperidin-1-yl)-2-(4-(1,2,3,4-tetrahydronaphthalen-1-ylcarbamoyl)pyridin-2-yl)phenyl)isophthalamide Scheme 88.

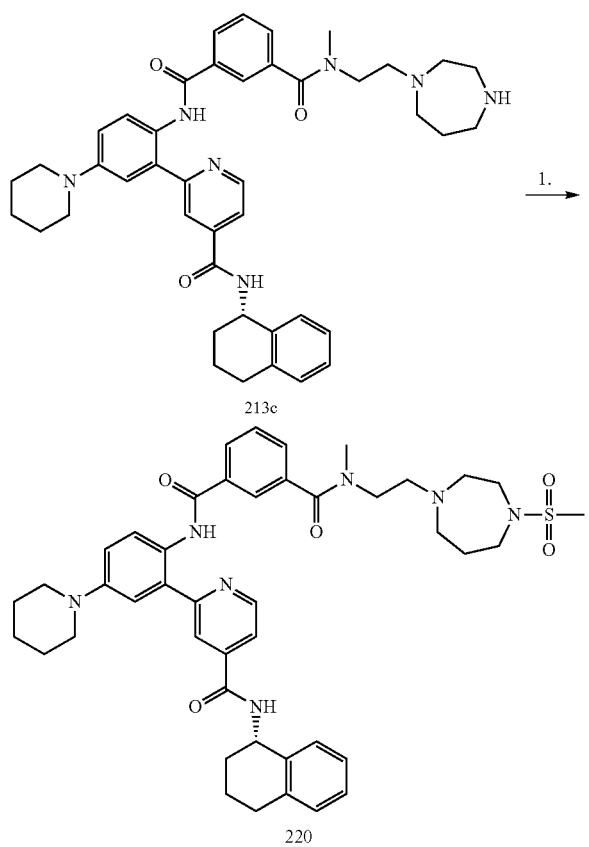

1. Methanesulfonylchloride, TEA, DCM.

Example 220

Into a 50-mL round-bottom flask, was placed a solution of (S)—N1-(2-(1,4-diazepan-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide (150 mg, 0.21 mmol, 1.00 equiv) in dichloromethane (5 mL), methanesulfonyl chloride (40 mg, 0.35 mmol, 1.50 equiv), triethylamine (43 mg, 0.43 mmol, 2.00 equiv). The resulting solution was stirred for 1 h at room temperature. The resulting mixture was washed with 1×20 mL of water. The mixture was dried over anhydrous sodium sulfate and concentrated under vacuum. The crude product (120 mg) was purified by Prep-HPLC with the following conditions (1#-Waters 2767-3): Column, SunFire Prep C18, 19*150 mm 5 um; mobile phase, water with 0.05% TFA and $CH_3CN$ (25% $CH_3CN$ up to 36% in 6 min); Detector, Waters2545 UvDector 300&270 nm. 43.5 mg product was obtained. This resulted in 43.5 mg (18%) of (S)—N1-methyl-N1-(2-(4-(methylsulfonyl)-1,4-diazepan-1-yl)ethyl)-N3-(4-(piperidin-1-yl)-2-(4-(1,2,3,4-tetrahydronaphthalen-1-ylcarbamoyl)pyridin-2-yl)phenyl)isophthalamide as a yellow solid. LCMS (ES, m/z): 792 $[M+H]^+$ H-NMR (300 MHz, $CD_3OD$, ppm): 8.94 (m, 1H), 8.68 (m, 1H), 8.39 (s, 1H), 8.12 (m, 3H), 7.86 (m, 1H), 7.77 (m, 3H), 7.25 (m, 1H), 7.17 (m, 3H), 5.38 (m, 1H), 3.99 (m, 2H), 3.56 (m, 14H), 3.11 (s, 3H), 2.91 (s, 3H), 2.86 (m, 2H), 2.28 (m, 2H), 2.02 (m, 8H), 1.81 (m, 2H).

Example 221

5-{2-[N-methyl-1-(3-{[4-(piperidin-1-yl)-2-(4-{[(1S)-1,2,3,4-tetrahydronaphthalen-1-yl]carbamoyl}pyridin-2-yl)phenyl]carbamoyl}phenyl)formamido]ethyl}-2,8,11,14-tetraoxa-5-azaheptadecan-17-oic acid Scheme 89.

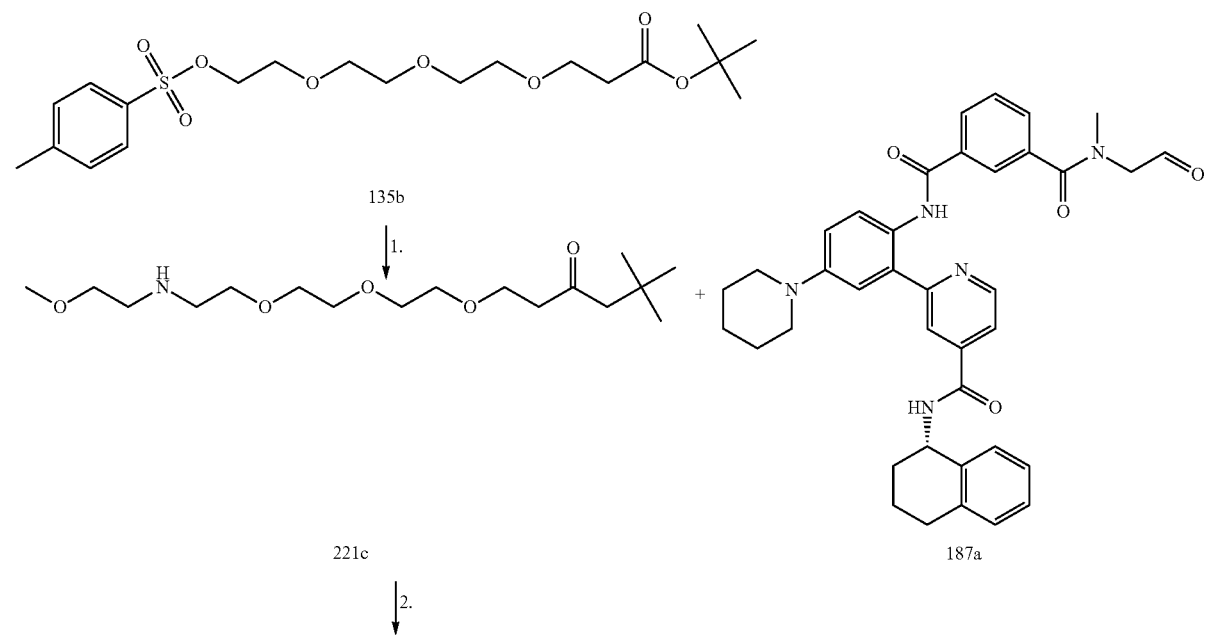

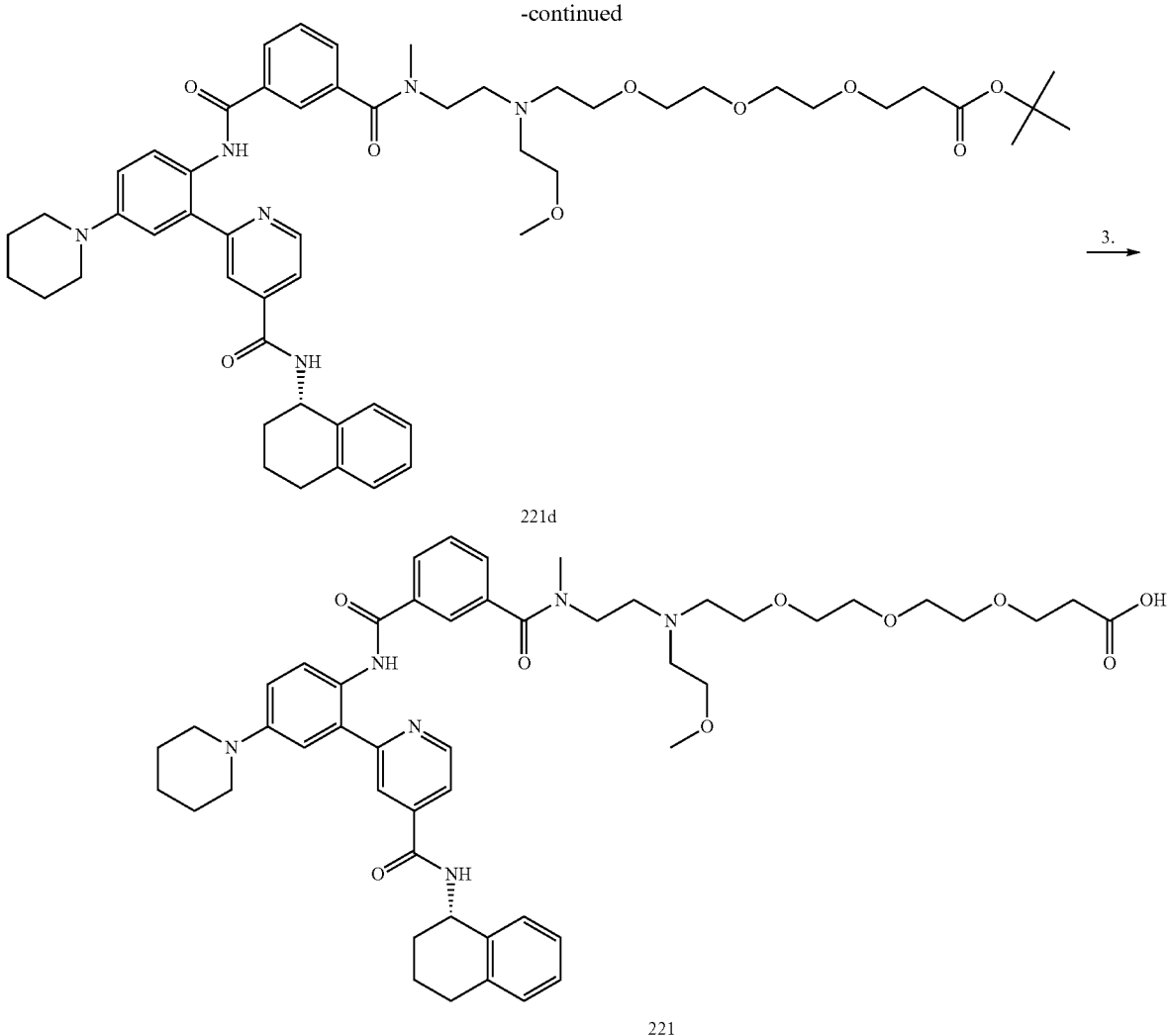

1. 2-methoxyethanamine
2. NaBH₃CN, AcOH, EtOH
3. TFA, DCM.

Intermediate 221c

Into a 50-mL sealed tube, was placed tert-butyl 3-(2-(2-(2-(tosyloxy)ethoxy)ethoxy)ethoxy)propanoate (3 g, 6.94 mmol, 1.00 equiv), 2-methoxyethanamine (30 mL). The resulting solution was stirred overnight at 50° C. The resulting mixture was concentrated under vacuum. The resulting solution was diluted with 200 mL of ethyl acetate. The resulting mixture was washed with 2×200 mL of brine. The mixture was dried over anhydrous sodium sulfate and concentrated under vacuum. This resulted in 2 g (86%) of 221c as light yellow oil.

Intermediate 221d

Into a 50-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl)isophthalamide (200 mg, 0.32 mmol, 1.00 equiv) in ethanol (4 mL), amine 221c (160 mg, 0.48 mmol, 1.50 equiv), acetic acid (34 mg, 0.71 mmol, 2.20 equiv). The mixture was stirred overnight at room temperature. To the above was added NaBH₃CN (44 mg, 0.70 mmol, 2.20 equiv). The resulting solution was stirred for 1 h at room temperature. The reaction was then quenched by the addition of 20 ml of water. The resulting solution was extracted with 2×100 mL of ethyl acetate and the organic layers combined. The resulting mixture was washed with 2×100 mL of brine. The mixture was dried over anhydrous sodium sulfate and concentrated under vacuum. This resulted in 300 mg (100%) 221d as yellow oil.

Example 221

Into a 50-mL round-bottom flask, was placed a solution of 221d (100 mg, 0.11 mmol, 1.00 equiv) in dichloromethane (3 mL), trifluoroacetic acid (1.5 mL). The resulting solution was stirred for 2 h at room temperature. The resulting mixture was concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH₃CN (25% CH₃CN up to 37% in 6 min); Detector, Waters2545 UvDector 254&270 nm. 46.6 mg product was obtained. This resulted in 46.6 mg (39%) Example 221 as a yellow solid. LC-MS (ES, m/z): 893 [M+H]⁺ H-NMR (300 MHz, CD₃OD ppm): 8.94 (d, J=5.1 Hz, 1H), 8.67 (d, J=9 Hz, 1H), 8.40 (s, 1H), 8.15~8.16 (m, 2H), 8.06~8.11 (m, 1H), 7.86~7.87 (m, 1H), 7.78~7.85 (m, 2H), 7.63~7.67 (m, 1H), 7.14~7.28 (m, 4H), 5.39~5.40 (m, 1H), 3.99 (s, 4H), 3.84 (s, 1H), 3.57~3.64 (m, 20H), 3.44 (s, 3H), 3.14 (s, 3H), 2.84~2.91 (m, 2H), 2.52 (t, J=6 Hz, 2H), 2.14~2.17 (m, 1H), 2.03~2.07 (m, 7H), 1.96~2.00 (m, 2H).
Example 222
(S)—N1-(14-azido-3-methyl-6,9,12-trioxa-3-azatetradecyl)-N3-(4-(diethylamino)-2-(4-(1,2,3,4-tetrahydronaphthalen-1-ylcarbamoyl)pyridin-2-yl)phenyl)-N1-methylisophthalamide
Scheme 90.
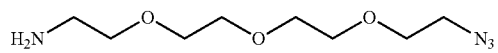
↓ 1.
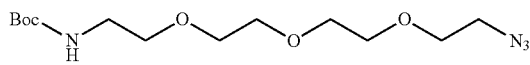
222a
↓ 2.
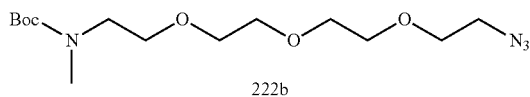
222b
↓ 3.
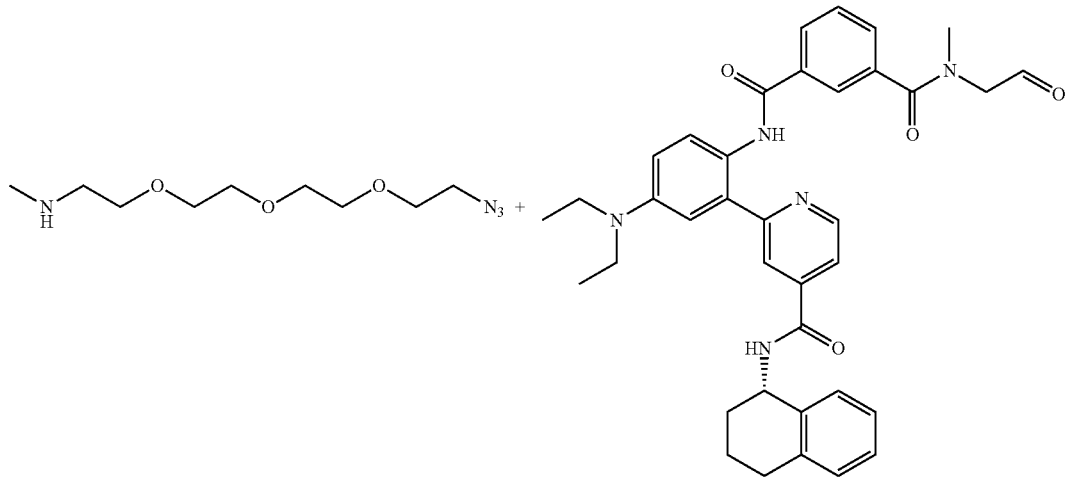
222c        197a
↓ 4.

-continued

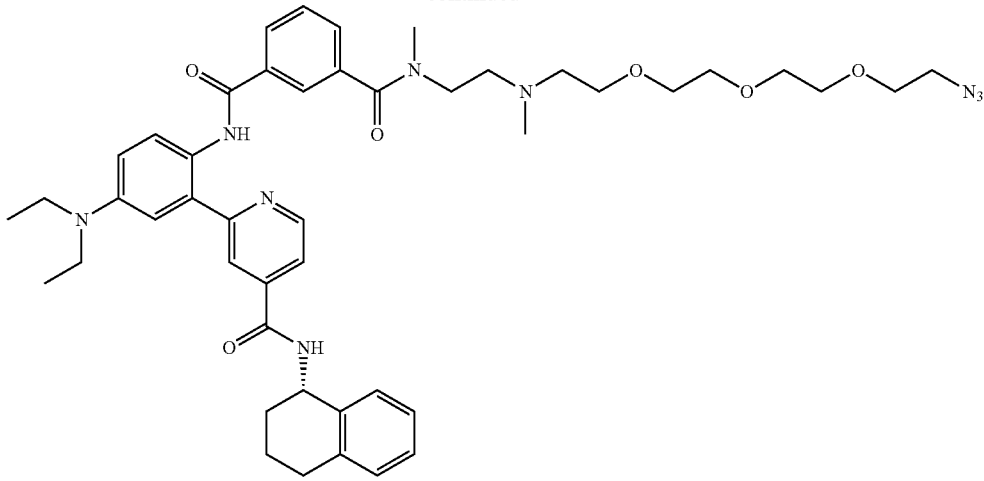

222

1. di-tert-butyl dicarbonate, TEA, THF
2. MeI NaH
3. TFA, DCM
4. NaBH₃CN, AcOH, EtOH.

Intermediate 222a

Into a 250-mL round-bottom flask, was placed a solution of 2-(2-(2-(2-azidoethoxy)ethoxy)ethoxy)ethanamine (3 g, 13.75 mmol, 1.00 equiv) in tetrahydrofuran (100 mL), triethylamine (4.17 g, 41.21 mmol, 3.00 equiv). This was followed by the addition of di-tert-butyl dicarbonate (9 g, 41.24 mmol, 3.00 equiv), in portions at 0° C. The resulting solution was stirred overnight at 25° C. The mixture was concentrated under vacuum. The resulting solution was diluted with 100 mL of dichloromethane. The resulting mixture was washed with 2×100 mL of Brine. The mixture was dried over anhydrous sodium sulfate and concentrated under vacuum. The residue was applied onto a silica gel column with ethyl acetate/petroleum ether (1:1). This resulted in 4 g (91%) of tert-butyl 2-(2-(2-(2-azidoethoxy)ethoxy)ethoxy)ethylcarbamate as colorless oil.

Intermediate 222b

Into a 100-mL 3-necked round-bottom flask, was placed a solution of tert-butyl 2-(2-(2-(2-azidoethoxy)ethoxy)ethoxy)ethylcarbamate (3.0 g, 9.43 mmol, 1.00 equiv) in N,N-dimethylformamide (40 mL). This was followed by the addition of sodium hydride (876 mg, 21.9 mmol, 2.00 equiv, 60%), in portions at 0° C. in 5 min. The resulting solution was stirred for 0.5 h at 0° C. To this was added iodomethane (16.2 g, 114.08 mmol, 10.00 equiv) dropwise with stirring at 0° C. in 20 min. The resulting solution was stirred for 18 h at room temperature. The resulting mixture was concentrated under vacuum. The resulting solution was diluted with 50 mL of dichloromethane. The resulting mixture was washed with 2×20 mL of water. The resulting mixture was washed with 2×20 mL of brine. The mixture was dried over anhydrous sodium sulfate and concentrated under vacuum. This resulted in 2200 mg (70%) of tert-butyl 2-(2-(2-(2-azidoethoxy)ethoxy)ethoxy)ethyl(methyl)carbamate as yellow oil.

Intermediate 222c

Into a 50-mL round-bottom flask, was placed a solution of tert-butyl 2-(2-(2-(2-azidoethoxy)ethoxy)ethoxy)ethyl(methyl)carbamate (2200 mg, 6.63 mmol, 1.00 equiv) in dichloromethane (5 mL). This was followed by the addition of 2,2,2-trifluoroacetic acid (3 mL) dropwise with stirring at 0° C. The resulting solution was stirred for 1 h at 25° C. in an oil bath. The resulting mixture was concentrated under vacuum. The resulting solution was diluted with 5 mL of methanol. The pH value of the solution was adjusted to 12 with sodium hydroxide (0.5 mol/L). The resulting mixture was concentrated under vacuum. The residue was dissolved in 10 mL of dichloromethane. The solids were filtered out. The resulting mixture was concentrated under vacuum. This resulted in 1230 mg (80%) of 2-(2-(2-(2-azidoethoxy)ethoxy)ethoxy)-N-methylethanamine as yellow oil. LC-MS (ES, m/z): 233 [M+H]⁺ H-NMR (300 MHz, CD₃OD, ppm): 3.78-3.74 (m, 2H), 3.70-3.67 (m, 10H), 3.42-3.39 (m, 2H), 3.23-3.20 (m, 2H), 2.74 (s, 3H).

Example 222

Into a 100-mL round-bottom flask, was placed a solution of (S)—N1-(4-(diethylamino)-2-(4-(1,2,3,4-tetrahydronaphthalen-1-ylcarbamoyl)pyridin-2-yl)phenyl)-N3-formyl-N3-(2-oxoethyl)isophthalamide (160 mg, 0.27 mmol, 1.00 equiv) in ethanol (3 mL), 2-(2-(2-(2-azidoethoxy)ethoxy)ethoxy)-N-methylethanamine (90 mg, 0.39 mmol, 1.50 equiv), acetic acid (27 mg, 0.56 mmol, 2.20 equiv). The resulting solution was stirred overnight at room temperature. To the above was added NaBH₃CN (36 mg, 0.57 mmol, 2.20 equiv). The resulting solution was stirred for 2 h at room temperature. The mixture was concentrated under vacuum. The crude product (160 mg) was purified by Prep-HPLC with the following conditions (1#-Waters 2767-3): Column, SunFire Prep C18, 19*150 mm 5 um; mobile phase, water with 0.05% TFA and CH₃CN (hold 30% CH₃CN in 6 min); Detector, Waters2545 UvDector 254&270 nm. 20 mg product was obtained. This resulted in 20 mg (6%) of (S)—N1-(14-azido-3-methyl-6,9,12-trioxa-3-azatetradecyl)-N3-(4-(diethylamino)-2-(4-(1,2,3,4-tetrahydronaphthalen-1-ylcarbamoyl)pyridin-2-yl)phenyl)-N1-methylisophthalamide as a yellow solid. LC-MS (ES, m/z): 834 [M+H]⁺ H-NMR (400 MHz, CD₃OD, ppm): 8.806 (s, 1H), 8.515 (d, J=8.4 Hz, 1H), 8.246 (s, 1H), 7.987~8.032 (m, 2H), 7.734~7.767 (m, 2H), 7.600~7.676 (m, 2H), 7.369 (d, J=8 Hz, 1H), 7.146 (d, J=7.2 Hz, 1H), 7.016~7.067 (m, 3H), 5.258 (t, J=5.6 Hz, 1H), 3.883 (s, 1H), 3.808 (s, 2H), 3.544~3.599 (m, 8H), 3.514 (s, 10H), 3.209~3.244 (m, 8H), 3.000 (d, J=8.8 Hz, 6H), 2.716~2.783 (m, 2H), 1.775~2.039 (m, 4H), 1.558 (d, J=6.8 Hz, 1H), 1.113 (t, J=6.8 Hz, 6H).

Example 223

(S)—N1-(4-(diethylamino)-2-(4-(1,2,3,4-tetrahydronaphthalen-1-ylcarbamoyl)pyridin-2-yl)phenyl)-N3-methyl-N3-(17-methyl-1-morpholino-4-oxo-8,11,14-trioxa-3,5,17-triazanonadecan-19-yl)isophthalamide Scheme 91.

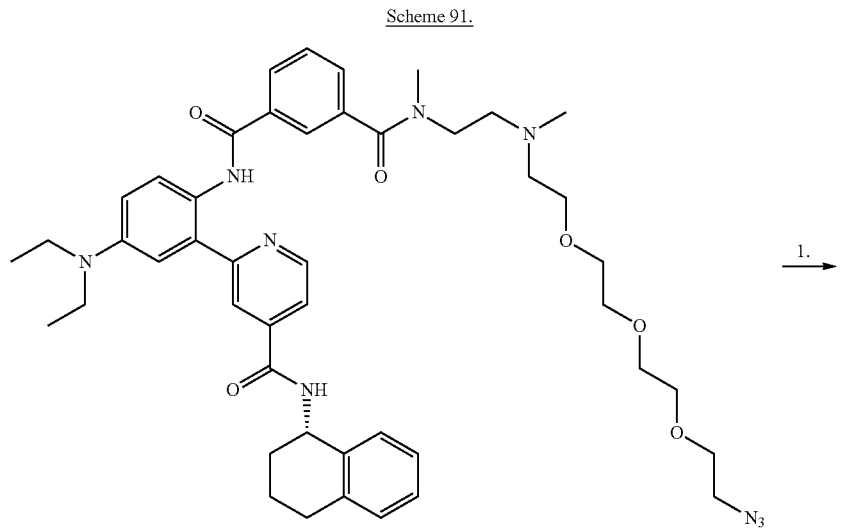

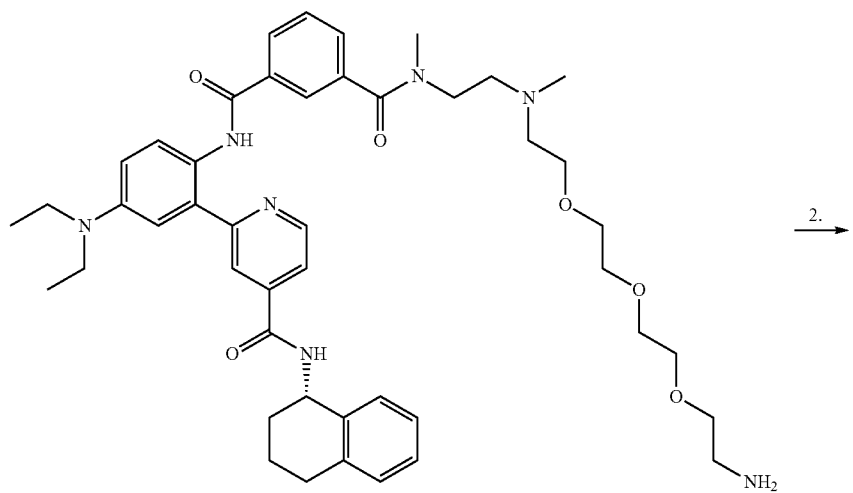

-continued

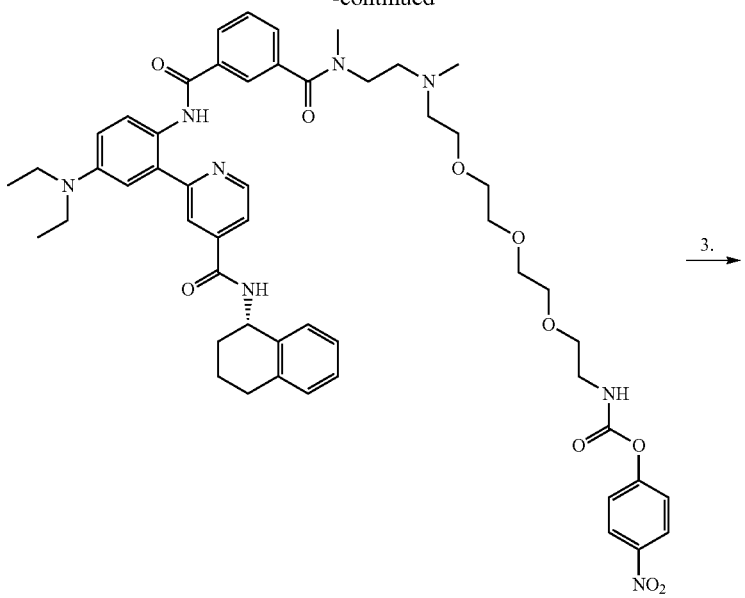

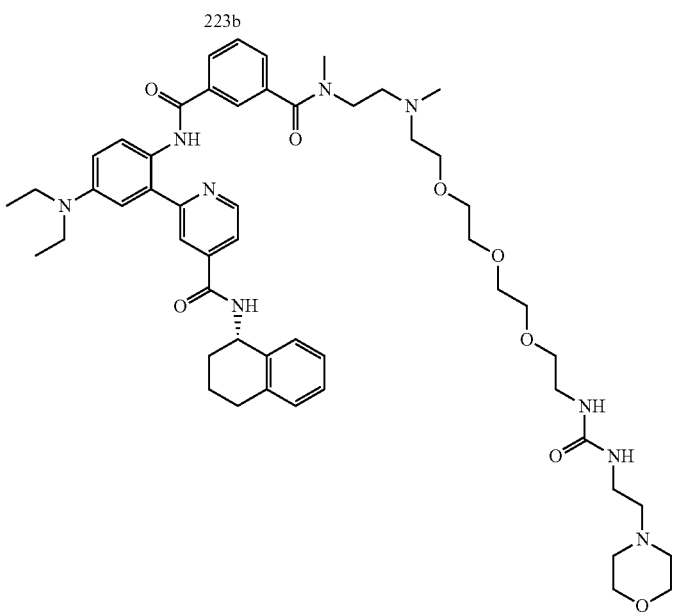

1. PPh₃, H₂O, THF
2.
3. 4-nitrophenyl carbonochloridate, DCM, TEA
4. 2-morpholinoethanamine, DMAP, CH₃CN.

Intermediate 223a

Into a 100-mL round-bottom flask, was placed a solution of (S)—N1-(14-azido-3-methyl-6,9,12-trioxa-3-azatetradecyl)-N3-(4-(diethylamino)-2-(4-(1,2,3,4-tetrahydronaphthalen-1-ylcarbamoyl)pyridin-2-yl)phenyl)-N1-methylisophthalamide (500 mg, 0.60 mmol, 1.00 equiv) in tetrahydrofuran/water (20/2 mL), triphenylphosphine (350 mg, 1.34 mmol, 2.23 equiv). The resulting solution was stirred overnight at 40° C. The resulting mixture was concentrated under vacuum. The residue was applied onto a silica gel column with dichloromethane:methanol (10:1). This resulted in 350 mg (72%) of (S)—N1-(14-amino-3-methyl-6,9,12-trioxa-3-azatetradecyl)-N3-(4-(diethylamino)-2-(4-(1,2,3,4-tetrahydronaphthalen-1-ylcarbamoyl)pyridin-2-yl)phenyl)-N1-methylisophthalamide as a yellow solid.

Intermediate 223b

Into a 100-mL round-bottom flask, was placed a solution of (S)—N1-(14-amino-3-methyl-6,9,12-trioxa-3-azatetradecyl)-N3-(4-(diethylamino)-2-(4-(1,2,3,4-tetrahydronaphthalen-1-ylcarbamoyl)pyridin-2-yl)phenyl)-N1-methylisophthalamide (300 mg, 0.37 mmol, 1.00 equiv) in dichloromethane (30 mL), triethylamine (112.5 mg, 1.11 mmol, 3.00 equiv), 4-nitrophenyl carbonochloridate (74.6 mg, 0.37 mmol, 1.00 equiv). The resulting solution was stirred overnight at room temperature. The resulting mixture was washed with 2×30 mL of brine. The mixture was dried over anhydrous sodium sulfate and concentrated under vacuum. This resulted in 320 mg (89%) of (S)-4-nitrophenyl 1-(3-(4-(diethylamino)-2-(4-(1,2,3,4-tetrahydronaphthalen-1-ylcarbamoyl)pyridin-2-yl)phenylcarbamoyl)phenyl)-2,5-dimethyl-1-oxo-8,11,14-trioxa-2,5-diazahexadecan-16-ylcarbamate as a yellow solid.

Example 223

Into a 25-mL round-bottom flask, was placed a solution of (S)-4-nitrophenyl 1-(3-(4-(diethylamino)-2-(4-(1,2,3,4-tetrahydronaphthalen-1-ylcarbamoyl)pyridin-2-yl)phenylcarbamoyl)phenyl)-2,5-dimethyl-1-oxo-8,11,14-trioxa-2,5-diazahexadecan-16-ylcarbamate (200 mg, 0.21 mmol, 1.00 equiv) in acetonitrile (5 mL). This was followed by the addition of 2-morpholinoethanamine (26 mg, 0.20 mmol, 0.97 equiv) and 4-dimethylaminopyridine (38 mg, 0.31 mmol, 1.51 equiv). The resulting solution was stirred for 4 h at 80° C. in an oil bath. The resulting mixture was concentrated under vacuum. The crude product (200 mg) was purified by Prep-HPLC with the following conditions (1#-PreP-HPLC-001 (SHIMADZU)): Column, SunFire Prep C18, 19*150 mm 5 um; mobile phase, CH3CN and water with 0.05% TFA (20% CH3CN up to 35% in 6 min, up to 100% in 1 min, down to 20% in 0.7 min); Detector, Waters2545 UvDector 254&220 nm. This resulted in 80.3 mg (28%) of (S)—N1-(4-(diethylamino)-2-(4-(1,2,3,4-tetrahydronaphthalen-1-ylcarbamoyl)pyridin-2-yl)phenyl)-N3-methyl-N3-(17-methyl-1-morpholino-4-oxo-8,11,14-trioxa-3,5,17-triazanonadecan-19-yl)isophthalamide as yellow oil. LC-MS (ES, m/z): 965 [M+H]+ H-NMR (300 MHz, CD3OD, ppm): 8.899 (d, J=5.1 Hz, 1H), 8.304 (s, 1H), 8.080~8.109 (m, 2H), 7.815~7.837 (m, 1H), 7.707~7.755 (m, 3H), 7.188~7.196 (m, 2H), 7.130~7.175 (m, 3H), 5.348~5.389 (m, 1H), 3.916~3.993 (m, 6H), 3.500~3.715 (m, 22H), 3.209~3.482 (m, 2H), 3.110 (d, J=6.3 Hz, 6H), 2.837~2.911 (m, 3H), 2.131~2.200 (m, 1H), 1.204~1.251 (m, 6H).

Example 224

(S)—N1-(1-amino-14-methyl-1-oxo-5,8,11-trioxa-2,14-diazahexadecan-16-yl)-N3-(4-(diethylamino)-2-(4-(1,2,3,4-tetrahydronaphthalen-1-ylcarbamoyl)pyridin-2-yl)phenyl)-N1-methylisophthalamide

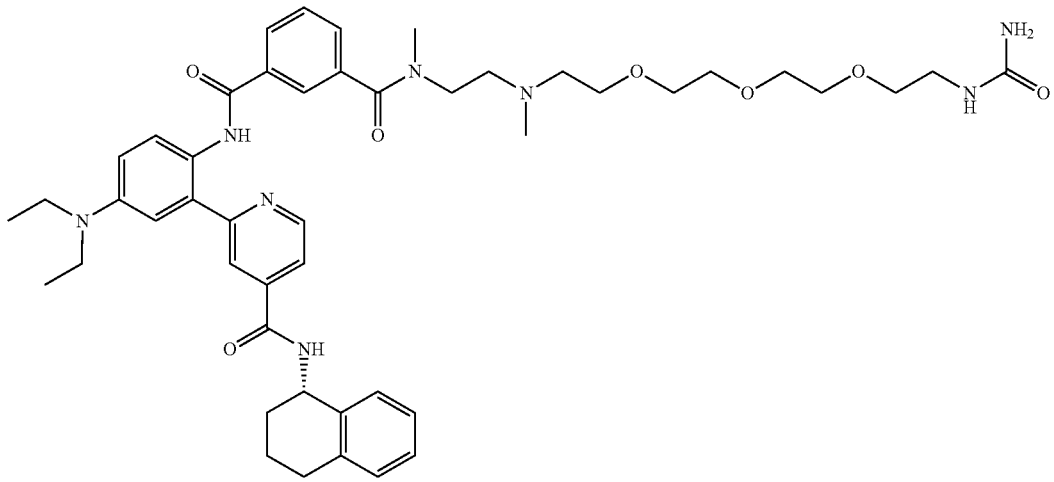 [SMILES: CCN(CC)c1ccc(NC(=O)c2cccc(C(=O)N(C)CCN(C)CCOCCOCCOCCNC(N)=O)c2)c(-c2cc(C(=O)N[C@H]3CCCc4ccccc43)ccn2)c1]

This compound was prepared according to the procedure described for the synthesis of (S)—N1-(4-(diethylamino)-2-(4-(1,2,3,4-tetrahydronaphthalen-1-ylcarbamoyl)pyridin-2-yl)phenyl)-N3-methyl-N3-(17-methyl-1-morpholino-4-oxo-8,11,14-trioxa-3,5,17-triazanonadecan-19-yl) isophthalamide Example 223 substituting ammonia in methanol in place of 2-morpholinoethanamine. Into a 100-mL round-bottom flask, was placed a solution of (S)-4-nitrophenyl 1-(3-(4-(diethylamino)-2-(4-(1,2,3,4-tetrahydronaphthalen-1-ylcarbamoyl)pyridin-2-yl) phenylcarbamoyl)phenyl)-2,5-dimethyl-1-oxo-8,11,14-trioxa-2,5-diazahexadecan-16-ylcarbamate (100 mg, 0.10 mmol, 1.00 equiv) in NMP (5 mL), methanol (saturated with NH3) (5 mL). The resulting solution was stirred for 3 h at room temperature. The resulting mixture was washed with 2×30 mL of water. The resulting mixture was concentrated under vacuum. The crude product (100 mg) was purified by Prep-HPLC with the following conditions (1#-PreP-HPLC-001 (SHIMADZU)): Column, SunFire Prep C18, 19*150 mm 5 um; mobile phase, water with 0.05% TFA and CH3CN (22% CH3CN up to 38% in 6 min, up to 100% in 1 min, down to 22% in 0.7 min); Detector, Waters2545 UvDector 254&220 nm. This resulted in 26 mg (21%) of (S)—N1-(1- amino-14-methyl-1-oxo-5,8,11-trioxa-2,14-diazahexadecan-16-yl)-N3-(4-(diethylamino)-2-(4-(1,2,3,4-tetrahydronaphthalen-1-ylcarbamoyl)pyridin-2-yl)phenyl)-N1-methylisophthalamide as yellow oil. LC-MS (ES, m/z): 851 [M+H]$^+$ H-NMR (300 MHz, CD$_3$OD, ppm): 8.96~8.94 (d, J=5.1 Hz, 1H), 8.71~8.68 (m, 1H), 8.38 (s, 1H), 8.16~8.12 (m, 2H), 7.88 (s, 1H), 7.87~7.86 (m, 1H), 7.78~7.73 (m, 2H), 7.58~7.54 (m, 1H), 7.25~7.15 (m, 4H), 5.39 (s, 1H), 3.93 (s, 5H), 3.76~3.61 (m, 12H), 3.57~3.48 (m, 3H), 3.27~3.23 (m, 2H), 3.13~3.09 (m, 5H), 2.91~2.84 (m, 3H), 2.05~1.91 (m, 5H), 1.31~1.22 (m, 6H).

Example 225

(S)—N1-(4-(diethylamino)-2-(4-(1,2,3,4-tetrahydronaphthalen-1-ylcarbamoyl)pyridin-2-yl)phenyl)-N3-(1-hydroxy-3-(2-hydroxyethyl)-17-methyl-4-oxo-8,11,14-trioxa-3,5,17-triazanonadecan-19-yl)-N3-methylisophthalamide

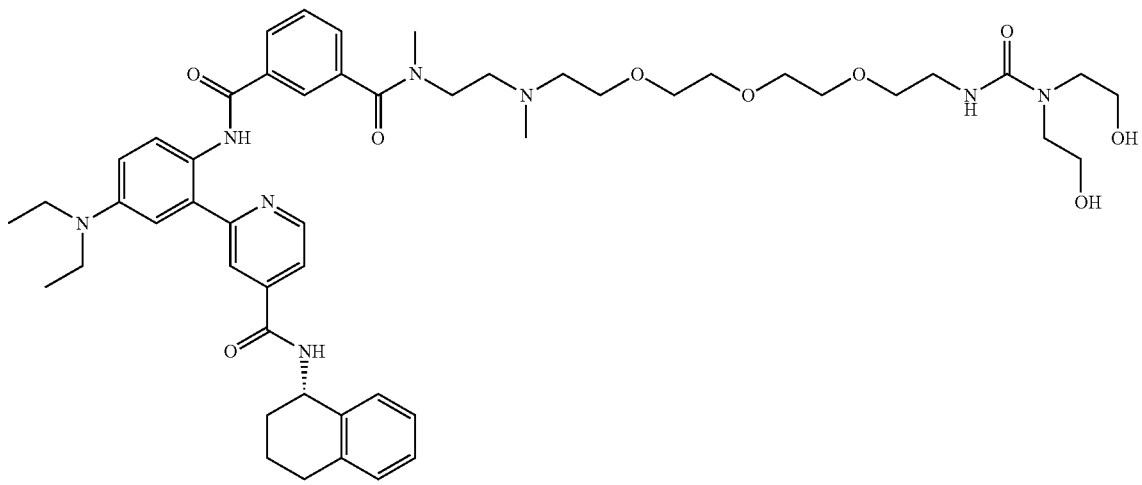 [SMILES: CCN(CC)c1ccc(NC(=O)c2cccc(C(=O)N(C)CCN(C)CCOCCOCCOCCNC(=O)N(CCO)CCO)c2)c(-c2cc(C(=O)N[C@H]3CCCc4ccccc43)ccn2)c1]

This compound was prepared according to the procedure described for the synthesis of (S)—N1-(4-(diethylamino)-2-(4-(1,2,3,4-tetrahydronaphthalen-1-ylcarbamoyl)pyridin-2-yl)phenyl)-N3-methyl-N3-(17-methyl-1-morpholino-4-oxo-8,11,14-trioxa-3,5,17-triazanonadecan-19-yl) isophthalamide Example 223 substituting 2,2'-azanediyldiethanol in place of 2-morpholinoethanamine. Into a 100-mL round-bottom flask, was placed a solution of (S)-4-nitrophenyl 1-(3-(4-(diethylamino)-2-(4-(1,2,3,4-tetrahydronaphthalen-1-ylcarbamoyl)pyridin-2-yl)phenylcarbamoyl)phenyl)-2,5-dimethyl-1-oxo-8,11,14-trioxa-2,5-diazahexadecan-16-ylcarbamate (150 mg, 0.15 mmol, 1.00 equiv) in acetonitrile (10 mL), 2,2'-azanediyldiethanol (20 mg, 0.19 mmol, 1.24 equiv), 4-dimethylaminopyridine (28 mg, 0.23 mmol, 1.49 equiv). The resulting solution was stirred for 4 h at 80° C. in an oil bath. The resulting mixture was concentrated under vacuum. The residue was dissolved in 20 mL of dichloromethane. The resulting mixture was washed with 2×30 mL of NH$_4$Cl (aq). The mixture was dried over sodium sulfate and concentrated under vacuum. The crude product (150 mg) was purified by Prep-HPLC with the following conditions (1#-PreP-HPLC-001 (SHIMADZU)): Column, SunFire Prep C18, 19*150 mm 5 um; mobile phase, CH$_3$CN and water with 0.05% TFA (22% CH$_3$CN to 38% in 6 min, up to 100% in 1 min, down to 22% in 0.7 min); Detector, Waters2545 UvDector 254&220 nm. This resulted in 11.7 mg (6%) of (S)—N1-(4-(diethylamino)-2-(4-(1,2,3,4-tetrahydronaphthalen-1-ylcarbamoyl)pyridin-2-yl)phenyl)-N3-(1-hydroxy-3-(2-hydroxyethyl)-17-methyl-4-oxo-8,11,14-trioxa-3,5,17-triazanonadecan-19-yl)-N3-methylisophthalamide as yellow oil. LC-MS (ES, m/z): 939 [M+H]$^+$ H-NMR (300 MHz, CD$_3$OD, ppm) 8.96~8.94 (d, J=5.1 Hz, 1H), 8.74~8.72 (m, 1H), 8.39 (s, 1H), 8.17~8.12 (m, 2H), 7.89~7.87 (m, 2H), 7.78~7.73 (m, 2H), 7.61~7.56 (m, 1H), 7.25 (s, 1H), 7.18~7.16 (m, 3H), 5.41~5.37 (m, 1H), 4.05~3.92 (m, 4H), 3.80~3.39 (m, 26H), 3.13~3.10 (m, 6H), 2.94~2.9 (m, 3H), 2.19~1.86 (m, 4H), 1.26~1.22 (m, 6H).

Example 226
3-N-[4-(diethylamino)-2-(4-{[(1S)-1,2,3,4-tetrahydronaphthalen-1-yl]carbamoyl}pyridin-2-yl)phenyl]-1-N-(1-methanesulfonamido-12-methyl-3,6,9-trioxa-12-azatetradecan-14-yl)-1-N-methylbenzene-1,3-dicarboxamide
Scheme 92.
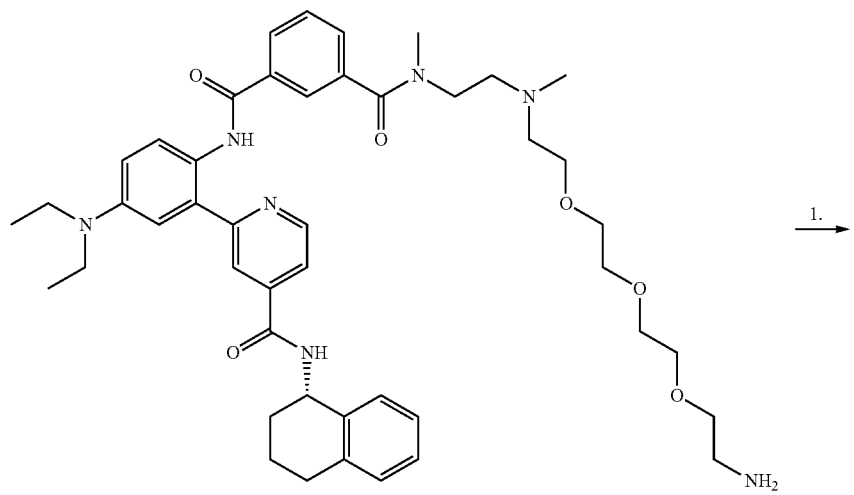
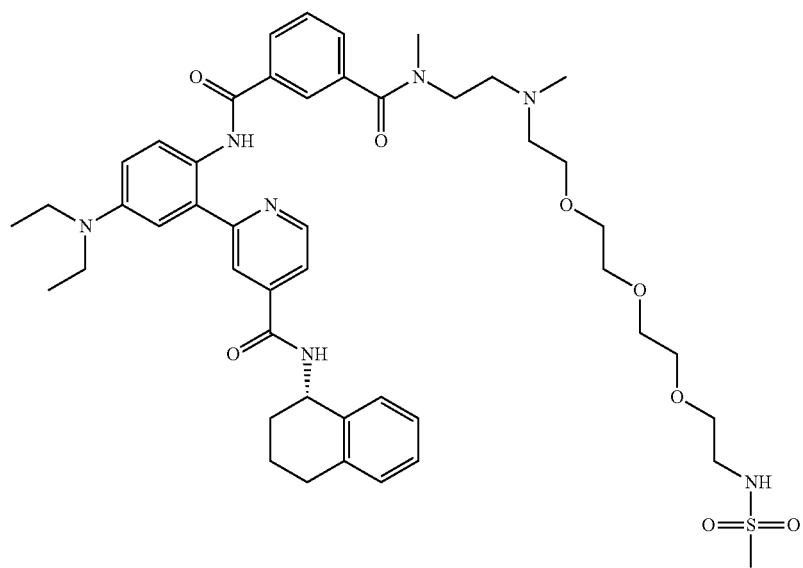
1. Methanesulfonylcholoride, TEA, DCM.

Example 266

Into a 50-mL round-bottom flask, was placed a solution of (S)—N1-(14-amino-3-methyl-6,9,12-trioxa-3-azatetradecyl)-N3-(4-(diethylamino)-2-(4-(1,2,3,4-tetrahydronaphthalen-1-ylcarbamoyl)pyridin-2-yl)phenyl)-N1-methylisophthalamide (40 mg, 0.05 mmol, 1.00 equiv) in dichloromethane (2 mL), methanesulfonyl chloride (8.5 mg, 0.07 mmol, 1.50 equiv), triethylamine (10 mg, 0.10 mmol, 2.00 equiv). The resulting solution was stirred for 1 h at room temperature. The resulting solution was diluted with 10 mL of dichloromethane. The resulting mixture was washed with 1×20 mL of water and 1×20 mL of brine. The mixture was dried over sodium sulfate and concentrated under vacuum. The crude product (50 mg) was purified by Prep-HPLC with the following conditions (1#-PreP-HPLC-001 (SHIMADZU)): Column, SunFire Prep C18, 19*150 mm 5 um; mobile phase, $CH_3CN$ and water with 0.05% TFA (22% $CH_3CN$ up to 38% in 6 min, up to 100% in 1 min, down to 22% in 0.7 min); Detector, Waters2545 UvDector. This resulted in 29 mg (48%) of 3-N-[4-(diethylamino)-2-(4-{[(1S)-1,2,3,4-tetrahydronaphthalen-1-yl]carbamoyl}pyridin-2-yl)phenyl]-1-N-(1-methanesulfonamido-12-methyl-3,6,9-trioxa-12-azatetradecan-14-yl)-1-N-methylbenzene-1,3-dicarboxamide, Example 226 as brown oil. LC-MS (ES, m/z): 886 $[M+H]^+$ H-NMR (300 MHz, $CD_3OD$, ppm): 8.94~8.92 (d, J=5.1 Hz, 1H), 8.60 (s, 1H), 8.35 (s, 1H), 8.15~8.10 (m, 2H), 7.86~7.70 (m, 4H), 7.41 (s, 1H), 7.27~7.25 (m, 1H), 7.20~7.16 (m, 3H), 5.40~5.36 (m, 1H), 3.94 (s, 5H), 3.73~3.62 (m, 12H), 3.58~3.54 (m, 3H), 3.24~3.21 (t, 3H), 3.21~3.08 (m, 6H), 2.95 (s, 3H), 2.91~2.86 (m, 2H), 2.21~1.85 (m, 5H), 1.26~1.21 (t, 6H).

Example 227

(S)—N1-(2-(4-2,5,8,11,14,17,20,23-octaoxapentacosanepiperazin-1-yl)ethyl)-N3-(4-(diethylamino)-2-(4-(1,2,3,4-tetrahydronaphthalen-1-ylcarbamoyl)pyridin-2-yl)phenyl)-N1-methylisophthalamide This compound was prepared according to the scheme for the synthesis of Example 213 substituting 212b in place of 213c. Into a 50-mL round bottom flask, was placed a solution of N1-(2-(4-(((S)-1,2,3,4-tetrahydronaphthalen-1-yl)carbamoyl)pyridin-2-yl)-4-(diethylamino)phenyl)-N3-methyl-N3-(2-(piperazin-1-yl)ethyl)isophthalamide (100 mg, 0.15 mmol, 1.00 equiv) in dichloromethane (10 mL), EDC.HCl (43 mg, 0.22 mmol, 1.50 equiv), 4-dimethylaminopyridine (35.5 mg, 0.29 mmol, 2.00 equiv), 2-(2-(2-(2-(2-(2-(2-(2-methoxyethoxy)ethoxy)ethoxy)ethoxy)ethoxy)ethoxy)ethoxy)acetic acid 213b (70 mg, 0.18 mmol, 1.21 equiv). The resulting solution was stirred for 2 h at room temperature. The resulting mixture was washed with 5×20 mL of $NH_4Cl$. The mixture was dried over anhydrous sodium sulfate and concentrated under vacuum. The crude product (100 mg) was purified by Prep-HPLC with the following conditions (1#-Waters 2767-3): Column, Xbridge Prep C18, 5 um, 19*100 mm; mobile phase, water with 0.05% TFA and $CH_3CN$ (5% $CH_3CN$ up to 48% in 1 min, up to 59% in 5 min); Detector, Waters2545 UV Detector 254&270 nm. 58 mg product was obtained. This resulted in 58 mg (37%) of (S)—N1-(2-(4-2,5,8,11,14,17,20,23-octaoxapentacosanepiperazin-1-yl)ethyl)-N3-(4-(diethylamino)-2-(4-(1,2,3,4-tetrahydronaphthalen-1-ylcarbamoyl)pyridin-2-yl)phenyl)-N1-methylisophthalamide as yellow oil. LC-MS (ES, m/z): 1068 $[M+H]^+$ H-NMR (400 MHz, $CD_3OD$, ppm): 8.94 (s, 1H), 8.38 (m, 1H), 8.17 (s, 1H), 8.13 (m, 2H), 7.95 (m, 1H), 7.87-7.79 (m, 3H), 7.74 (m, 1H), 7.27-7.14 (m, 4H), 5.40 (t,

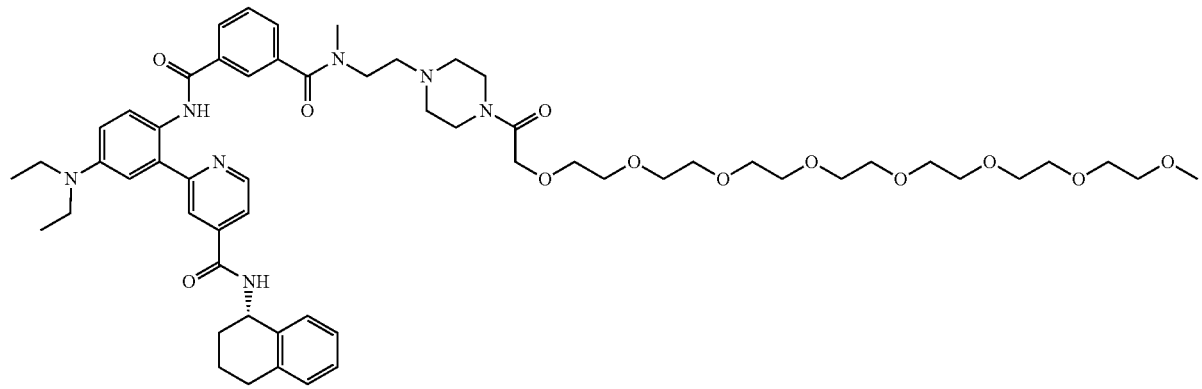 [SMILES: CCN(CC)c1ccc(NC(=O)c2cccc(C(=O)N(C)CCN3CCN(C(=O)COCCOCCOCCOCCOCCOCCOCCOC)CC3)c2)c(-c2cc(C(=O)N[C@H]3CCCc4ccccc43)ccn2)c1]

1H), 4.30-4.0 (m, 7H), 3.7-3.6 (m, 46H), 3.35 (m, 4H), 3.13 (s, 3H), 2.87 (m, 2H), 2.16-1.92 (m, 4H), 1.30-1.22 (m, 6H).

Example 228

(S)—N1-(2-(4-2,5,8,11,14,17,20,23-octaoxapentacosanepiperazin-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide Scheme 93.

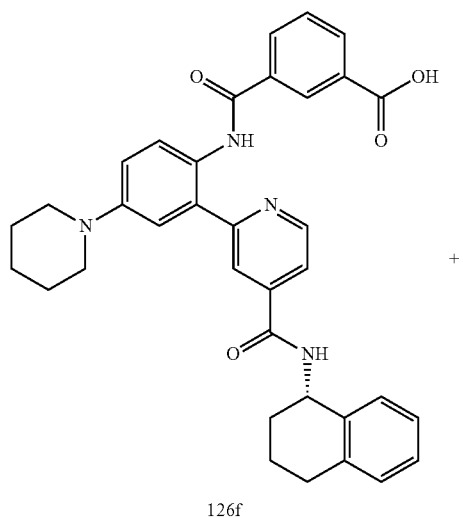

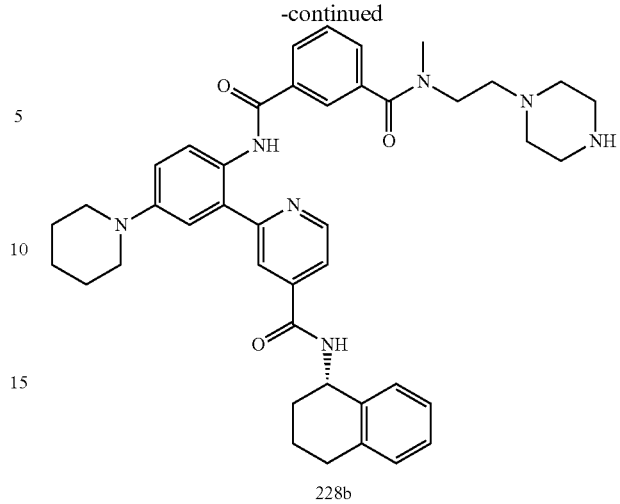

1. EDC•HCl, DMAP, Et₃N
2. HCl/DCM.

Intermediate 228a

Into a 100-mL round-bottom flask, was placed a solution of 3-((2-(4-(((S)-1,2,3,4-tetrahydronaphthalen-1-yl)carbamoyl)pyridin-2-yl)-4-(piperidin-1-yl)phenyl)carbamoyl)benzoic acid (2 g, 3.48 mmol, 1.00 equiv) in dichloromethane (20 mL), EDCHCl (1 g, 5.22 mmol, 1.50 equiv), 4-dimethylaminopyridine (640 mg, 5.25 mmol, 1.51 equiv), tert-butyl 4-(2-(methylamino)ethyl)piperazine-1-carboxylate (1.02 g, 4.20 mmol, 1.21 equiv). The resulting solution was stirred for 3 h at room temperature. The resulting mixture was washed with 3×20 mL of NH₄Cl (aq). The mixture was dried over sodium sulfate and concentrated under vacuum. This resulted in 1.5 g (54%) of tert-butyl 4-(2-(3-(carbamoyl)-N-methylbenzamido)ethyl)piperazine-1-carboxylate as a yellow solid.

Intermediate 228b

Into a 50-mL round-bottom flask, was placed a solution of tert-butyl 4-(2-(3-(carbamoyl)-N-methylbenzamido)ethyl)piperazine-1-carboxylate (1.4 g, 1.75 mmol, 1.00 equiv) in dichloromethane (15 mL). To the above hydrogen chloride (g) was introduced in. The resulting solution was stirred for 3 h at room temperature. The resulting mixture was concentrated under vacuum. This resulted in 1.3 g (88%) of N1-(2-(4-(((S)-1,2,3,4-tetrahydronaphthalen-1-yl)carbamoyl)pyridin-2-yl)-4-(piperidin-1-yl)phenyl)-N3-methyl-N3-(2-(piperazin-1-yl)ethyl)isophthalamide (4HCl salt) as a yellow solid.

This compound was prepared according to the procedure described for the synthesis of Example 227 substituting 228b in place of 212b. Into a 50-mL round bottom flask, was placed a solution of N1-(2-(4-(((S)-1,2,3,4-tetrahydronaphthalen-1-yl)carbamoyl)pyridin-2-yl)-4-(piperidin-1-yl)phenyl)-N3-methyl-N3-(2-(piperazin-1-yl)ethyl)isophthalamide (100 mg, 0.14 mmol, 1.00 equiv) in dichloromethane (12 mL), EDC.HCl (40 mg, 0.20 mmol, 1.49 equiv), 4-dimethylaminopyridine (50 mg, 0.41 mmol, 3.01 equiv), 2-(2-(2-(2-(2-(2-(2-methoxyethoxy)ethoxy)ethoxy)ethoxy)ethoxy)ethoxy)acetic acid 213b (65 mg, 0.16 mmol, 1.20 equiv). The resulting solution was stirred for 2 h at room temperature. The resulting mixture was washed with 5×20 mL of NH₄Cl. The mixture was dried over anhydrous sodium sulfate and concentrated under vacuum. The crude product (100 mg) was purified by Prep-HPLC with the following conditions (1#-Waters 2767-3): Column, Xbridge Prep C18, 5 um, 19*100 mm; mobile phase, water with 0.05% TFA and CH₃CN (5% CH3CN up to 48% in 1 min, up to 59% in 5 min); Detector, Waters2545 UvDector 254&270 nm. 22.5 mg product was obtained. This resulted in 22.5 mg (15%) of Example 228 as yellow oil. LC-MS (ES, m/z): 1081 [M+H]⁺ H-NMR (300 MHz, CD₃OD, ppm): 8.82 (s, 1H), 8.24 (m, 2H), 8.00 (s, 2H), 7.77 (m, 1H), 7.64 (m, 2H), 7.43 (s, 1H), 7.24 (m, 1H), 7.15-7.07 (m, 4H), 5.34 (m, 1H), 4.23-4.07 (m, 2H), 3.74-3.50 (m, 32H), 3.33 (m, 4H), 3.18-3.02 (m, 7H), 2.83-2.58 (m, 6H), 2.19 (m, 3H), 2.01-1.60 (m, 3H), 1.60-1.58 (m, 6H), 1.30 (m, 1H).

Example 229 tert-butyl 3-[2-(2-{2-[methyl(4-{2-[N-methyl-1-(3-{[4-(piperidin-1-yl)-2-(4-{[(1S)-1,2,3,4-tetrahydronaphthalen-1-yl]carbamoyl}pyridin-2-yl)phenyl]carbamoyl}phenyl)formamido]ethyl}piperazin-1-yl)carbonylamino]ethoxy}ethoxy)ethoxy]propanoate

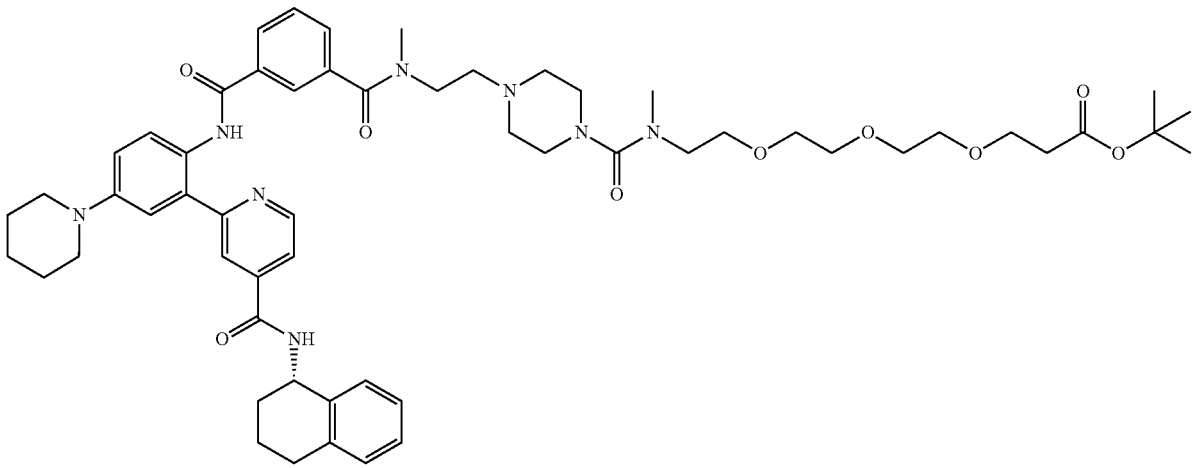 [SMILES: CN(CCN1CCN(C(=O)N(C)CCOCCOCCOCCC(=O)OC(C)(C)C)CC1)C(=O)c1cccc(C(=O)Nc2ccc(N3CCCCC3)cc2-c2cc(C(=O)N[C@H]3CCCc4ccccc43)ccn2)c1]

This compound was prepared according to the procedure described for the synthesis of Example 207 substituting 228b in place of 207b. Into a 100-mL round-bottom flask, was placed a solution of 4-nitrophenyl 4-(2-(3-(carbamoyl)-N-methylbenzamido)ethyl)piperazine-1-carboxylate (1.34 g, 1.55 mmol, 1.00 equiv) in acetonitrile (1 mL), tert-butyl 3-(2-(2-(2-(methylamino)ethoxy)ethoxy)ethoxy)propanoate 135c (900 mg, 3.09 mmol, 1.99 equiv), 4-dimethylaminopyridine (189 mg, 1.55 mmol, 1.00 equiv). The resulting solution was heated to reflux overnight. The resulting mixture was concentrated under vacuum. The residue was dissolved in 30 mL of dichloromethane. The resulting mixture was washed with 3×30 mL of NH₄Cl (aq) and 5×30 mL of water. The mixture was dried over anhydrous sodium sulfate and concentrated under vacuum. This resulted in 1.4 g of crude product and 1.3 g was added to the next step. The crude product (100 mg) was purified by Prep-HPLC with the following conditions (1#-Waters 2767-3): Column, SunFire Prep C18, 19*150 mm 5 um; mobile phase, water with 0.05% TFA and CH₃CN (31% CH₃CN up to 46% in 5 min); Detector, Waters2545 UvDector 254&270 nm. 50.2 mg product was obtained. This resulted in 1.3 g (82%) of tert-butyl 3-(2-(2-(2-(1-(2-(3-(carbamoyl)-N-methylbenzamido)ethyl)-N-methylpiperazine-4-carboxamido)ethoxy)ethoxy)ethoxy)propanoate as yellow oil. LC-MS (ES, m/z): 1039 [M+Na]⁺. H-NMR (300 MHz, CD₃OD, ppm): 8.964-8.947 (m, 1H), 8.821-8.791 (d, J=9.0 Hz, 1H), 8.418 (s, 1H), 8.192 (s, 1H), 8.145-8.088 (s, 2H), 7.885-7.880 (m, 1H), 7.867-7.862 (m, 1H), 7.786-7.662 (m, 2H), 7.225 (m, 1H), 7.177-7.158 (m, 3H), 5.425-5.320 (m, 1H), 4.009 (s, 2H), 3.866-3.848 (m, 1H), 3.736-3.433 (m, 30H), 3.124 (s, 3H), 2.987-2.972 (m, 3H), 2.909-2.862 (m, 2H), 2.519-2.450 (m, 3H), 2.068-1.809 (m, 10H), 1.473-1.448 (m, 13H).

Example 230

(S)-2,5,8,11,14,17,20-heptaoxadocosan-22-yl-4-(2-(3-(4-(diethylamino)-2-(4-(1,2,3,4-tetrahydronaphthalen-1-ylcarbamoyl)pyridin-2-yl)phenylcarbamoyl)-N-methylbenzamido)ethyl)piperazine-1-carboxylate

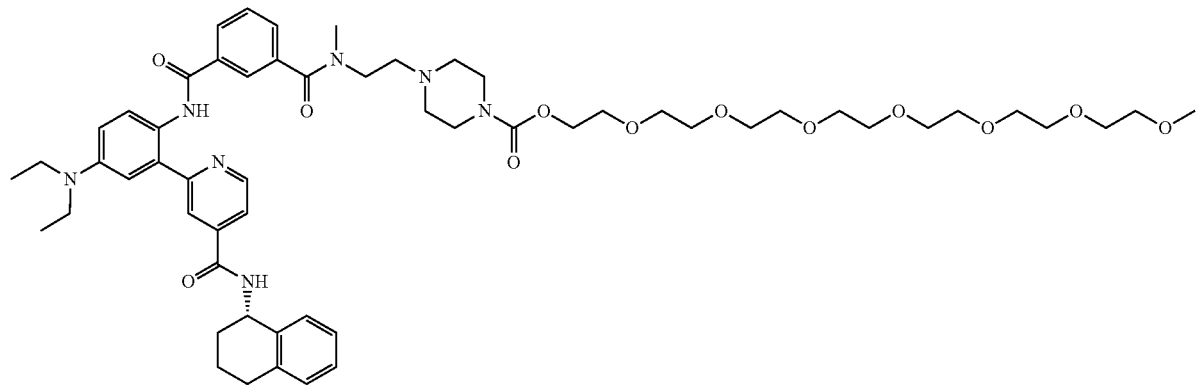 [SMILES: CCN(CC)c1ccc(NC(=O)c2cccc(C(=O)N(C)CCN3CCN(C(=O)OCCOCCOCCOCCOCCOCCOCCOC)CC3)c2)c(-c2cc(C(=O)N[C@H]3CCCc4ccccc43)ccn2)c1]

This compound was prepared according to the procedure described for the synthesis of Example 214 substituting 212b in place of 213c. Into a 8-mL sealed tube, was placed a solution of (S)—N1-(4-(diethylamino)-2-(4-(1,2,3,4-tetrahydronaphthalen-1-ylcarbamoyl)pyridin-2-yl)phenyl)-N3-methyl-N3-(2-(piperazin-1-yl)ethyl)isophthalamide (150 mg, 0.22 mmol, 1.00 equiv) in acetonitrile (5 mL), 2,5,8,11,14,17,20-heptaoxadocosan-22-yl 4-nitrophenyl carbonate (165 mg, 0.33 mmol, 1.50 equiv), 4-dimethylaminopyridine (53 mg, 0.43 mmol, 2.00 equiv). The resulting solution was stirred for 5 h at 90° C. in an oil bath. The resulting mixture was concentrated under vacuum. The resulting solution was diluted with 10 ml of water. The resulting solution was extracted with 3×30 mL of dichloromethane and the organic layers combined. The resulting mixture was washed with 3×30 mL of $NH_4Cl$ aq. The mixture was dried over anhydrous sodium sulfate and concentrated under vacuum. The crude product (100 mg) was purified by Prep-HPLC with the following conditions (1#-UV1-SHIMADZU-SPD-20A): Column, SunFire Prep C18, 19*150 mm 5 um; mobile phase, water with 0.05% TFA and $CH_3CN$ (30% $CH_3CN$ up to 50% in 6 min); Detector, Waters2545 UvDector 254&220 nm. 85.6 mg product was obtained. This resulted in 85.6 mg (28%) of (S)-2,5,8,11,14,17,20-heptaoxadocosan-22-yl 4-(2-(3-(4-(diethylamino)-2-(4-(1,2,3,4-tetrahydronaphthalen-1-ylcarbamoyl)pyridin-2-yl)phenylcarbamoyl)-N-methylbenzamido)ethyl)piperazine-1-carboxylate as a yellow solid. LC-MS (ES, m/z): 1055 $[M+H]^+$ H-NMR (300 MHz, $CD_3OD$, ppm): 8.92 (d, J=5.1 Hz, 1H), 8.60 (s, 1H), 8.35 (s, 1H), 8.13 (t, J=7.5 Hz, 2H), 7.69-7.85 (m, 4H), 7.44-7.46 (m, 1H), 7.26 (d, J=6.6 Hz, 1H), 7.14-7.19 (m, 3H), 5.38 (s, 1H), 4.26-4.86 (m, 3H), 3.99 (s, 2H), 3.63-3.74 (m, 31H), 3.52-3.61 (m, 6H), 3.31-3.34 (m, 5H), 3.09-3.12 (m, 3H), 2.84-2.91 (m, 2H), 1.90-1.97 (m, 4H), 1.21-1.26 (m, 6H).

Example 231
3-N-[4-(diethylamino)-2-(4-{[(1S)-1,2,3,4-tetrahydronaphthalen-1-yl]carbamoyl}pyridin-2-yl)phenyl]-1-N-(2-{4-[(2-{2-[2-(3-{4-[2-(2-hydroxyethoxy)ethyl]piperazin-1-yl}-3-oxopropoxy)ethoxy]ethoxy}ethyl)(methyl)carbamoyl]piperazin-1-yl}ethyl)-1-N-methylbenzene-1,3-dicarboxamide
Scheme 94.
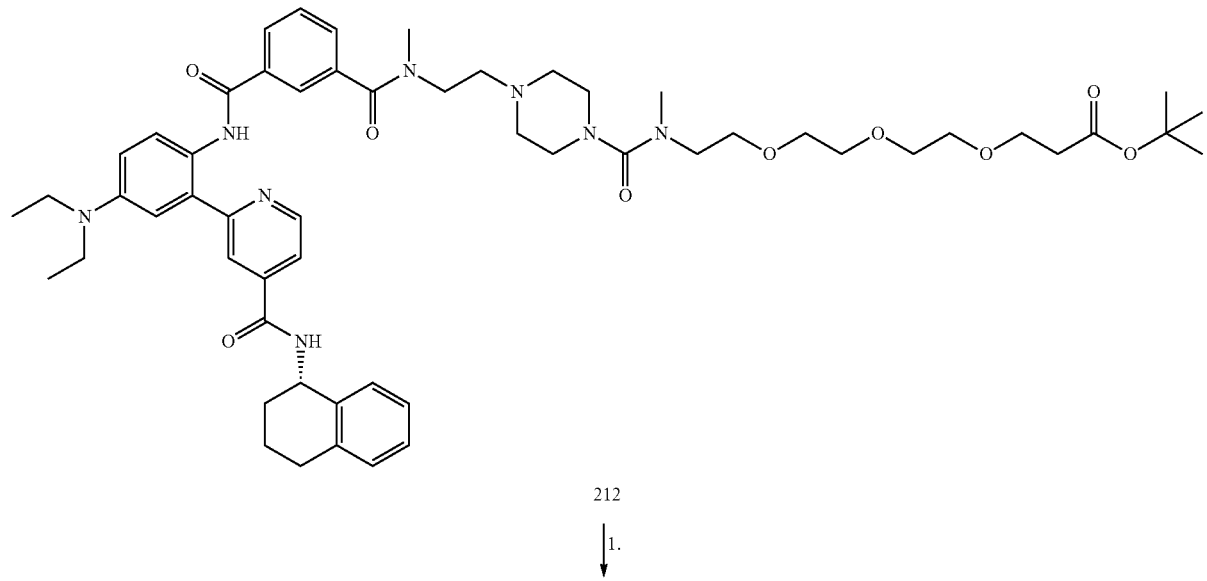
212
↓ 1.
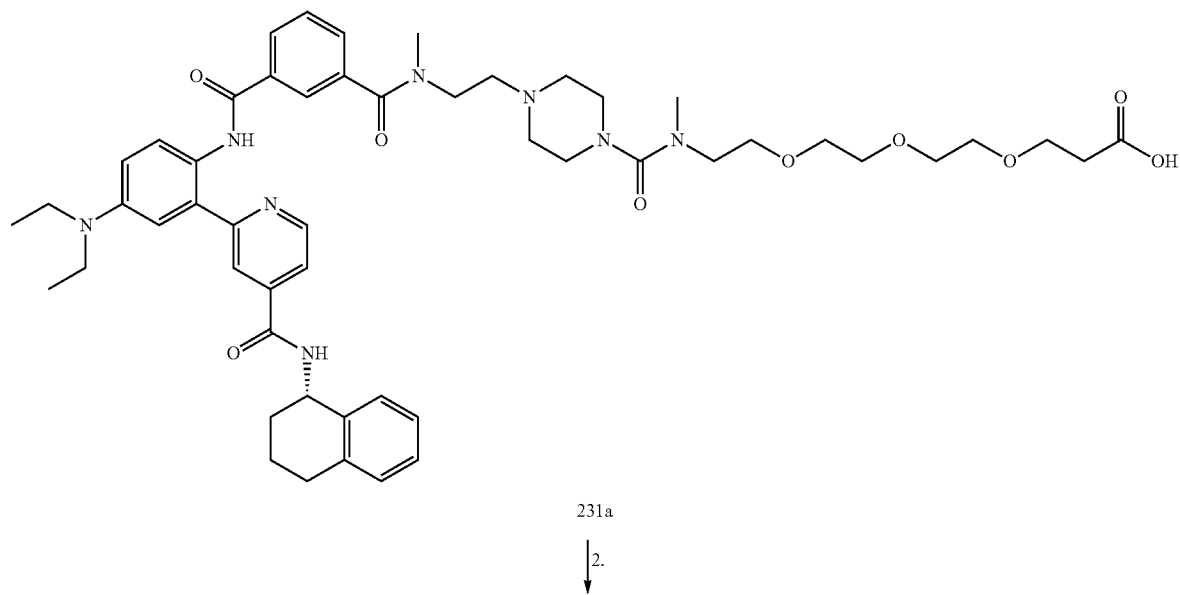
231a
↓ 2.

-continued

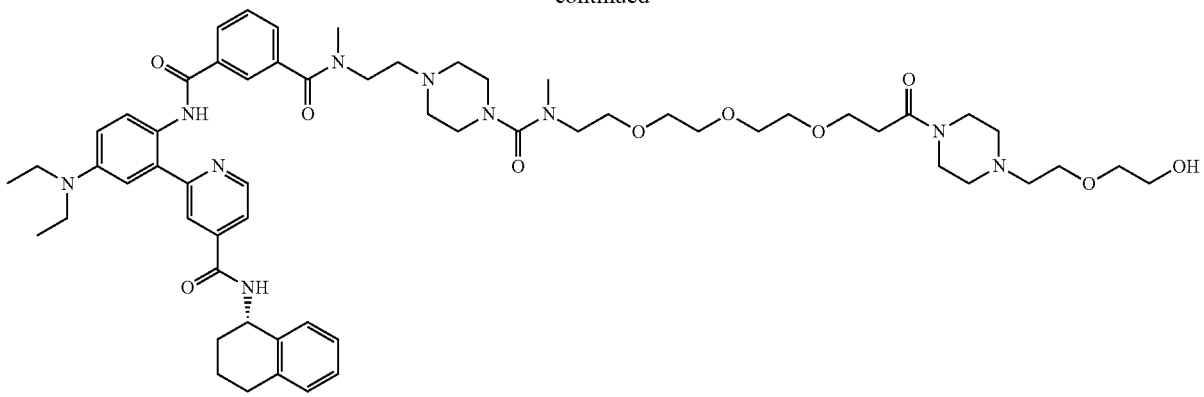

231

1. TFA/DCM
2. EDC·HCl, DMAP, 2-(2-(piperazin-1-yl)ethoxy)ethanol
2. HCl/DCM.

Intermediate 231a

Into a 50-mL round-bottom flask, was placed a solution of (S)-tert-butyl 1-(4-(2-(3-(4-(diethylamino)-2-(4-(1,2,3,4-tetrahydronaphthalen-1-ylcarbamoyl)pyridin-2-yl)phenylcarbamoyl)-N-methylbenzamido)ethyl)piperazin-1-yl)-2-methyl-1-oxo-5,8,11-trioxa-2-azatetradecan-14-oate (200 mg, 0.20 mmol, 1.00 equiv) in dichloromethane (10 mL), trifluoroacetic acid (2 mL). The resulting solution was stirred for 2 h at room temperature. The reaction progress was monitored by LCMS. The resulting mixture was concentrated under vacuum. The crude product (0.1 g) was purified by Prep-HPLC with the following conditions (1#-Waters 2767-3): Column, SunFire Prep C18, 19*150 mm 5 um; mobile phase, water with 0.05% TFA and $CH_3CN$ (23% $CH_3CN$ up to 35% in 6 min); Detector, Waters2545 UvDector 254&270 nm. 20 mg product was obtained. This resulted in 18.1 mg (7%) of Example 231a as a yellow solid. LC-MS (ES, m/z): 950 [M+H]+ H-NMR (300 MHz, DMSO, ppm): 11.88 (s, 1H), 9.56 (s, 1H), 9.15 (m, 1H), 8.87 (m, 1H), 8.25 (m, 2H), 8.12 (m, 2H), 7.97 (m, 1H), 7.83 (m, 2H), 7.67 (m, 5H), 5.23 (m, 1H), 2.37-2.73 (m, 32H), 2.45 (m, 3H), 1.81 (m, 5H), 1.23 (m, 6H).

Example 231

Into a 50-mL sealed tube, was placed a solution of (S)-1-(4-(2-(3-(4-(diethylamino)-2-(4-(1,2,3,4-tetrahydronaphthalen-1-ylcarbamoyl)pyridin-2-yl)phenylcarbamoyl)-N-methylbenzamido)ethyl)piperazin-1-yl)-2-methyl-1-oxo-5,8,11-trioxa-2-azatetradecan-14-oic acid (1000 mg, 0.32 mmol, 1.00 equiv, 30%) in dichloromethane (20 mL), 2-(2-(piperazin-1-yl)ethoxy)ethanol (110 mg, 0.63 mmol, 2.00 equiv), EDC.HCl (120 mg, 0.63 mmol, 2.00 equiv), 4-dimethylaminopyridine (38 mg, 0.31 mmol, 1.00 equiv). The resulting solution was stirred for two days at room temperature. The resulting solution was diluted with 30 mL of dichloromethane. The resulting mixture was washed with 4×50 mL of $NH_4Cl$ aq. The resulting mixture was concentrated under vacuum. The crude product (100 mg) was purified by Prep-HPLC with the following conditions (1#-Waters 2767-3): Column, SunFire Prep C18, 5 um, 19*150 mm; mobile phase, water with 0.05% TFA and $CH_3CN$ (25% $CH_3CN$ up to 40% in 6 min); Detector, UV 220&254 nm. This resulted in 9.8 mg (2%) of Example 231 as a yellow solid. LC-MS (ES, m/z): 1106 [M+H]+ H-NMR (300 MHz, $CD_3OD$, ppm): 8.94-8.95 (d, J=3 Hz, 1H), 8.70-8.72 (d, 1H), 8.38 (s, 1H), 8.11-8.16 (m, 2H), 7.71-7.94 (m, 4H), 7.49-7.51 (d, 1H), 7.19-7.27 (m, 1H), 7.12-7.17 (m, 3H), 5.36-5.40 (m, 1H), 5.45 (m, 1H), 3.82-3.86 (m, 2H), 3.55-3.78 (m, 28H), 3.39-3.41 (m, 7H), 3.11 (s, 3H), 2.97 (s, 3H), 2.83-2.90 (m, 2H), 2.69-2.71 (m, 2H), 1.87-2.23 (m, 4H), 1.21-1.25 (t, 6H).

Example 232

3-N-[4-(diethylamino)-2-(4-{[(1S)-1,2,3,4-tetrahydronaphthalen-1-yl]carbamoyl}pyridin-2-yl)phenyl]-1-N-methyl-1-N-(2-{4-[methyl(2-{2-[2-(2-{methyl[(2S,3R,4R,5R)-2,3,4,5,6-pentahydroxyhexyl]carbamoyl}ethoxy)ethoxy]ethoxy}ethyl)carbamoyl]piperazin-1-yl}ethyl)benzene-1,3-dicarboxamide

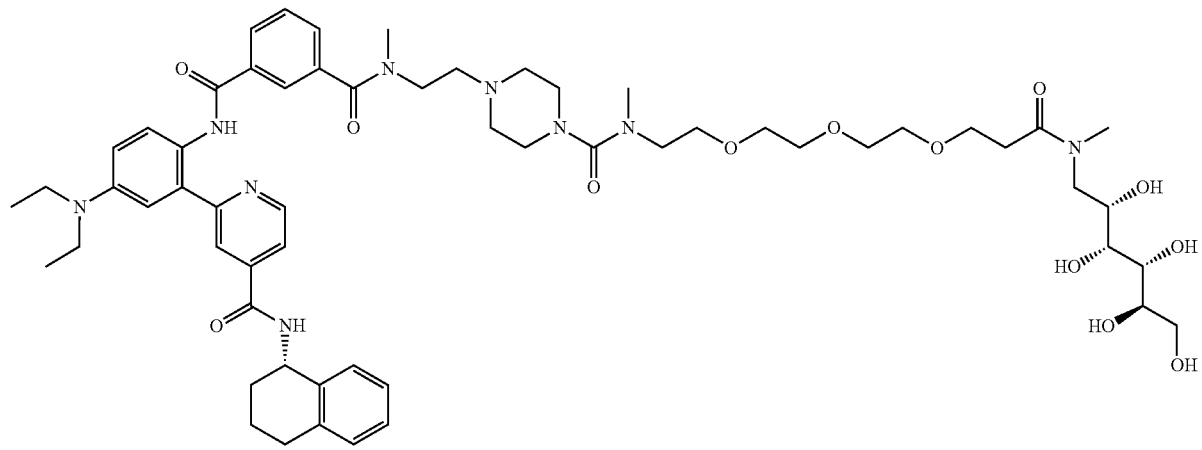 [SMILES: CCN(CC)c1ccc(NC(=O)c2cccc(C(=O)N(C)CCN3CCN(C(=O)N(C)CCOCCOCCOCCC(=O)N(C)C[C@H](O)[C@@H](O)[C@H](O)[C@H](O)CO)CC3)c2)c(-c2cc(C(=O)N[C@H]3CCCc4ccccc43)ccn2)c1]

This compound was prepared according to the procedure described for the synthesis of Example 231 substituting (2R,3R,4R,5S)-6-(methylamino)hexane-1,2,3,4,5-pentaol in place of 2-(2-(piperazin-1-yl)ethoxy)ethanol. Into a 8-mL sealed tube, was placed a solution of (S)-1-(4-(2-(3-(4-(diethylamino)-2-(4-(1,2,3,4-tetrahydronaphthalen-1-ylcarbamoyl)pyridin-2-yl)phenylcarbamoyl)-N-methylbenzamido)ethyl)piperazin-1-yl)-2-methyl-1-oxo-5,8,11-trioxa-2-azatetradecan-14-oic acid (100 mg, 0.11 mmol, 1.00 equiv) in dichloromethane (5 mL), (2R,3R,4R,5S)-6-(methylamino)hexane-1,2,3,4,5-pentaol (30 mg, 0.15 mmol, 1.50 equiv), EDC.HCl (40 mg, 0.21 mmol, 2.00 equiv), 4-dimethylaminopyridine (20 mg, 0.16 mmol, 1.50 equiv). The resulting solution was stirred overnight at room temperature. The resulting mixture was concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH$_3$CN (22% CH$_3$CN up to 34% in 6 min); Detector, Waters2545 UvDector 254&220 nm. 7.1 mg product was obtained. This resulted in 7.1 mg (5%) of Example 232 as a Pale-yellow solid. LC-MS (ES, m/z): 1127 [M+H]$^+$ H-NMR (300 MHz, CD$_3$OD, ppm): 8.94 (d, J=5.1 Hz, 1H), 8.61 (s, 1H), 8.36 (s, 1H), 8.10-8.16 (m, 2H), 7.86 (dd, J=5.1 Hz, 2H), 7.69-7.80 (m, 2H), 7.46-7.49 (m, 1H), 7.14-7.27 (m, 4H), 5.38 (t, J=6.0 Hz, 1H), 4.00 (d, J=6.3 Hz, 3H), 3.41-3.81 (m, 37H), 3.09-3.14 (m, 5H), 2.67-2.97 (m, 10H), 1.91-1.98 (m, 4H), 1.21-1.26 (m, 6H).

Example 233

(S)-1-oxo-1-(3-(3-(4-(piperidin-1-yl)-2-(4-(1,2,3,4-tetrahydronaphthalen-1-ylcarbamoyl)pyridin-2-yl)phenylcarbamoyl)benzylthio)phenyl)-5,8,11-trioxa-2-azatetradecan-14-oic acid

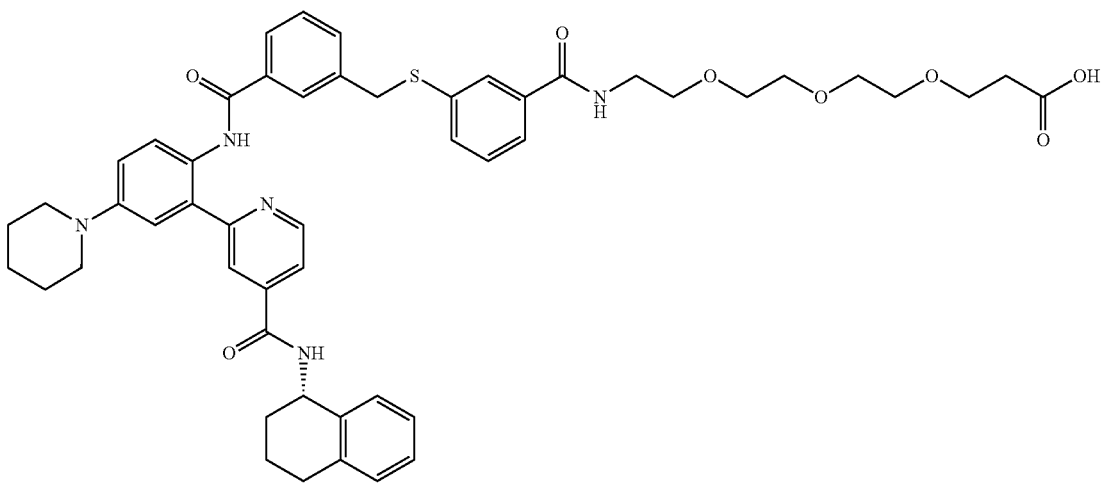 [SMILES: O=C(O)CCOCCOCCOCCNC(=O)c1cccc(SCc2cccc(C(=O)Nc3ccc(N4CCCCC4)cc3-c3cc(C(=O)N[C@H]4CCCc5ccccc54)ccn3)c2)c1]

This compound was prepared according to the procedure described for the synthesis of Example 10.1 substituting 142a in place of 4.1c. LC-MS (ES, m/z): 900 [M+H]⁺. H-NMR (300 MHz, CD₃OD, ppm): 8.911-8.895 (s, 1H), 8.821-8.791 (d, J=9.0 Hz, 1H), 8.422 (s, 1H), 8.203-8.195 (s, 1H), 7.950 (s, 1H), 7.839-7.811 (m, 3H), 7.756-7.725 (m, 1H), 7.624-7.470 (m, 4H), 7.365-7.314 (m, 1H), 7.246 (s, 1H), 7.143 (s, 3H), 5.377 (s, 1H), 4.326 (s, 2H), 3.715-3.465 (m, 18H), 2.843 (m, 2H), 2.504-2.463 (m, 2H), 2.078-1.836 (s, 4H).

This compound was prepared according to the procedure described for the synthesis of Example 143 substituting 142a in place of 143a. LC-MS (ES, m/z): 711.88 [M−2HCl+H]⁺ H-NMR (300 MHz, DMSO, ppm): 12.69 (s, 1H), 9.28 (s, 1H), 8.95 (d, J=5.1 Hz, 1H), 8.50 (d, J=18.6 Hz, 1H), 7.94-7.90 (m, 2H), 7.78 (d, J=7.8 Hz, 2H), 7.60 (d, J=7.5 Hz, 1H), 7.52-7.46 (m, 1H), 7.24-7.05 (m, 8H), 5.26 (d, J=4.8 Hz, 1H), 4.37 (s, 1H), 2.75 (d, J=13.5 Hz, 1H), 1.98-1.67 (m, 2H).

Example 234

(S)-2-(3-(3-(4-(piperidin-1-yl)-2-(4-(1,2,3,4-tetrahydronaphthalen-1-ylcarbamoyl)pyridin-2-yl)phenyl-carbamoyl)benzylthio)phenyl)acetic acid

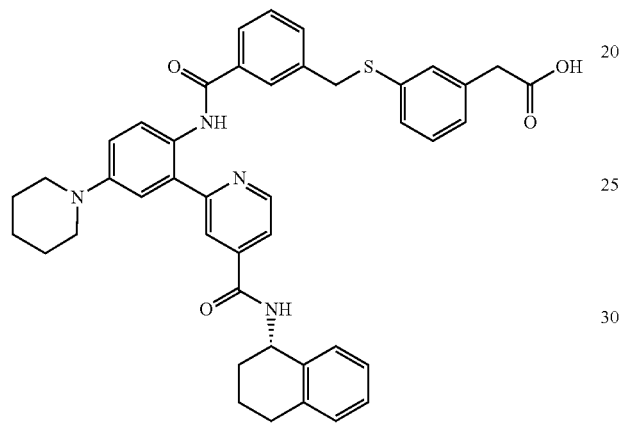

Example 235

(S)-3-methyl-2-oxo-1-(3-(3-(4-(piperidin-1-yl)-2-(4-(1,2,3,4-tetrahydronaphthalen-1-ylcarbamoyl)pyridin-2-yl)phenylcarbamoyl)benzylthio)phenyl)-6,9,12-trioxa-3-azapentadecan-15-oic acid

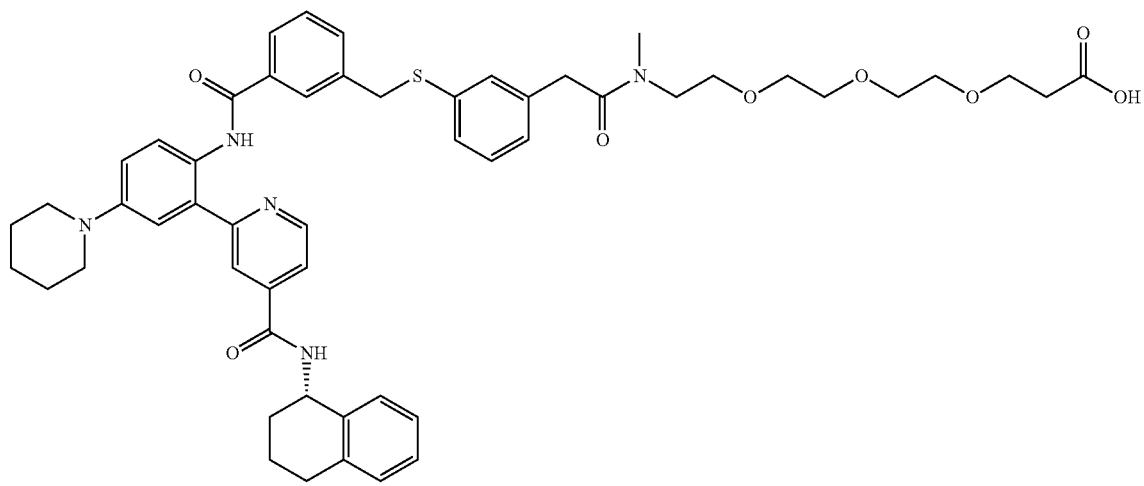 [SMILES: CN(CCOCCOCCOCCC(=O)O)C(=O)Cc1cccc(SCc2cccc(C(=O)Nc3ccc(N4CCCCC4)cc3-c3cc(C(=O)N[C@H]4CCCc5ccccc54)ccn3)c2)c1]

This compound was prepared according to the procedure described for the synthesis of Example 144 substituting 142a in place of 143a. LC-MS (ES, m/z): 928 [M−2HCl+H]+ H-NMR (300 MHz, CDCl$_3$, ppm): 13.64 (s, 1H), 8.99 (s, 2H), 8.84 (s, 1H), 8.50 (s, 1H), 7.95 (d, J=20.7 Hz, 4H), 7.48~7.62 (m, 3H), 7.33 (s, 1H), 7.14~7.28 (m, 6H), 5.49 (s, 1H), 4.21 (s, 2H), 3.47~3.74 (m, 20H), 2.78~3.11 (m, 5H), 2.35~2.71 (m, 4H), 1.80~2.30 (m, 7H).

Example 236

(S)-2-(2-(3-((3-(15-(4-(2-(2-hydroxyethoxy)ethyl) piperazin-1-yl)-3-methyl-2,15-dioxo-6,9,12-trioxa-3-azapentadecyl)phenylthio)methyl)benzamido)-5-(piperidin-1-yl)phenyl)-N-(1,2,3,4-tetrahydronaphthalen-1-yl)isonicotinamide mL of brine. The mixture was dried over sodium sulfate and concentrated under vacuum. The crude product (100 mg) was purified by Prep-HPLC with the following conditions (1#-Waters 2767-3): Column, SunFire Prep C18, 19*150 mm 5 um; mobile phase, water with 0.05% TFA and CH$_3$CN (30% CH$_3$CN up to 42% in 6 min); Detector, Waters2545 UvDector 254&270 nm. 20 mg product was obtained. This resulted in 20 mg (14%) of (S)-2-(2-(3-((3-(15-(4-(2-(2-hydroxyethoxy)ethyl)piperazin-1-yl)-3-methyl-2,15-dioxo-6,9,12-trioxa-3-azapentadecyl)phenylthio)methyl)benzamido)-5-(piperidin-1-yl)phenyl)-N-(1,2,3,4-tetrahydronaphthalen-1-yl) isonicotinamide as a yellow solid. LC-MS (ES, m/z): 1084 [M+H]+ H-NMR (300 MHz, DMSO, ppm): 12.19 (s, 1H), 9.65 (s, 1H), 9.19 (d, J=8.4 Hz, 1H), 8.91 (d, J=15.1 Hz, 1H), 8.28 (d, J=12.9 Hz, 2H), 7.90 (s, 1H), 7.85 (d, J=4.8 Hz, 1H), 7.75 (d, J=7.5 Hz, 1H), 7.44~7.57 (m, 8H), 7.10~7.22 (m, 8H), 7.01 (d, J=2.4 Hz, 1H), 5.25 (d, J=6.6 Hz, 1H), 4.34 (s,

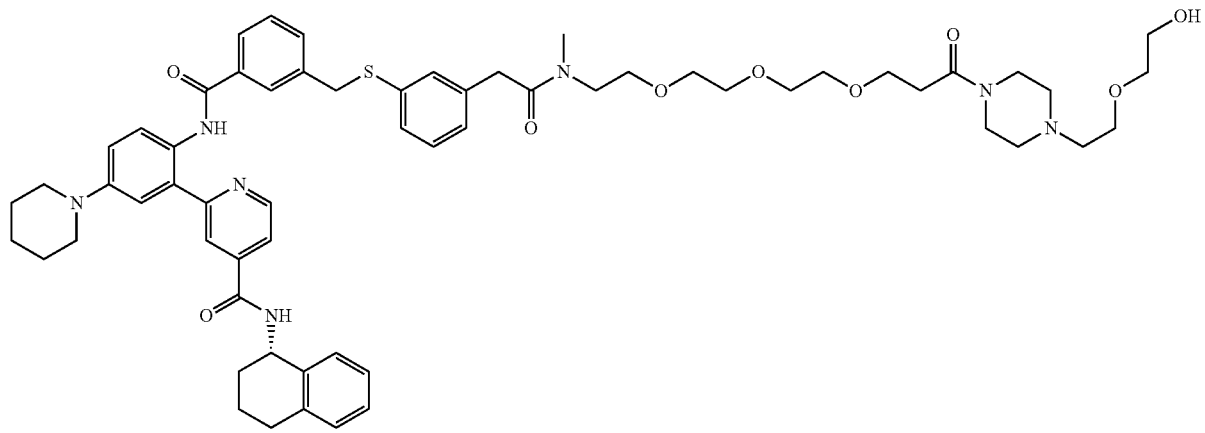 [SMILES: CN(CCOCCOCCOCCC(=O)N1CCN(CCOCCO)CC1)C(=O)Cc1cccc(SCc2cccc(C(=O)Nc3ccc(N4CCCCC4)cc3-c3cc(C(=O)N[C@H]4CCCc5ccccc54)ccn3)c2)c1]

This compound was prepared according to the procedure described for the synthesis of Example 231 substituting Example 235 in place of 231a. A solution of (S)-3-methyl-2-oxo-1-(3-(3-(4-(piperidin-1-yl)-2-(4-(1,2,3,4-tetrahydronaphthalen-1-ylcarbamoyl)pyridin-2-yl)phenylcarbamoyl)benzylthio)phenyl)-6,9,12-trioxa-3-azapentadecan-15-oic acid (120 mg, 0.13 mmol, 1.00 equiv) in dichloromethane (5 mL), 2-(2-(piperazin-1-yl)ethoxy)ethanol (33.7 mg, 0.19 mmol, 1.50 equiv), N-(3-dimethylaminopropyl)-N$_i$-ethyl-carbodiimide hydrochloride (49.7 mg, 0.26 mmol, 2.00 equiv). The resulting solution was stirred overnight at room temperature. The resulting solution was diluted with 50 mL of ethyl acetate. The resulting mixture was washed with 2×20

1H), 4.05 (s, 1H), 3.50~3.80 (m, 8H), 3.30~3.40 (m, 8H), 1.95 (s, 2H), 1.80 (s, 2H), 1.90~2.10 (m, 2H), 1.50~1.80 (m, 8H).

Example 237

(S)-1-(3-(4-chloro-2-(4-(1,2,3,4-tetrahydronaphthalen-1-ylcarbamoyl)pyridin-2-yl)phenylcarbamoyl)phenyl)-2-methyl-1-oxo-5,8,11-trioxa-2-azatetradecan-14-oic acid Scheme 95.

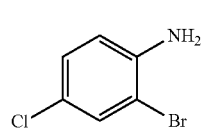

1.→

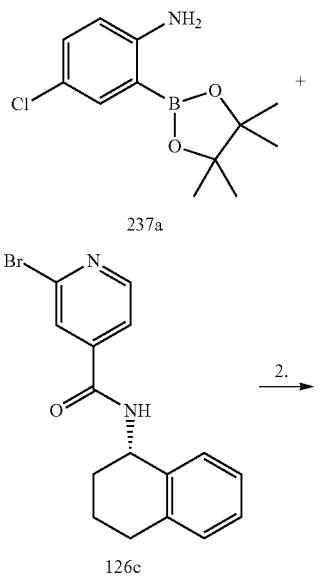

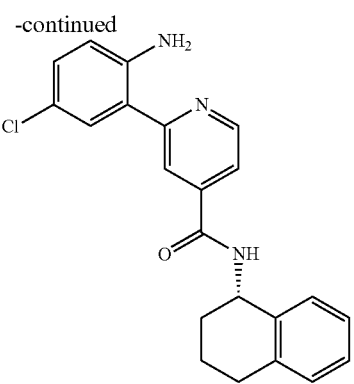

1. Pd(dppf)Cl₂/KOAc/DMSO, 4,4,4',4',5,5,5',5'-octamethyl-2,2'-bi(1,3,2-dioxaborolane)
2. Pd(dppf)Cl₂/Na₂CO₃/H₂O/Dioxane.

Intermediate 237a

Into a 100-mL three-necked round-bottom flask purged and maintained with an inert atmosphere of nitrogen, was placed a solution of 2-bromo-4-chlorobenzenamine (10 g, 48.43 mmol, 1.00 equiv) in DMSO (30 mL), 4,4,5,5-tetramethyl-2-(4,4,5,5-tetramethyl-1,3,2-dioxaborolan-2-yl)-1,3,2-dioxaborolane (18.5 g, 72.86 mmol, 1.50 equiv), potassium acetate (12.2 g, 124.36 mmol, 2.57 equiv), Pd(dppf)Cl₂ (1.1 g, 1.50 mmol, 0.03 equiv). The resulting solution was stirred overnight at 80° C. in an oil bath. The resulting mixture was concentrated under vacuum. The residue was applied onto a silica gel column with ethyl acetate/petroleum ether (1:50). This resulted in 5 g (41%) of 4-chloro-2-(4,4,5,5-tetramethyl-1,3,2-dioxaborolan-2-yl)benzenamine as a white solid. LC-MS (ES, m/z): 254 [M+H]⁺ H-NMR (400 MHz, CDCl₃, ppm): 1.51 (s, 12H), 6.53 (d, J=6.6 Hz, 1H), 7.15 (m, 1H), 7.73 (m, 1H).

Intermediate 237b

Into a 500-mL round-bottom flask purged and maintained with an inert atmosphere of nitrogen, was placed a solution of 4-chloro-2-(4,4,5,5-tetramethyl-1,3,2-dioxaborolan-2-yl)benzenamine (5.75 g, 22.72 mmol, 1.25 equiv) in dioxane (240 mL), (S)-2-bromo-N-(1,2,3,4-tetrahydronaphthalen-1-yl)isonicotinamide (6 g, 18.18 mmol, 1.00 equiv), Pd(dppf)Cl₂ (1.81 g, 2.47 mmol, 0.14 equiv), a solution of sodium carbonate (9.6 g, 90.57 mmol, 4.98 equiv) in water (96 mL). The resulting solution was stirred overnight at 80° C. in an oil bath. The resulting mixture was concentrated under vacuum. The resulting mixture was diluted with 50 mL of water. The resulting solution was extracted with 2×100 mL of ethyl acetate and the organic layers combined. The mixture was dried over anhydrous sodium sulfate and concentrated under vacuum. The residue was applied onto a silica gel column with ethyl acetate/petroleum ether (1:5~1:2). This resulted in 3.5 g (48%) of (S)-2-(2-amino-5-chlorophenyl)-N-(1,2,3,4-tetrahydronaphthalen-1-yl)isonicotinamide as a yellow solid. LC-MS (ES, m/z): 378 [M+H]⁺ H-NMR (300 MHz, CDCl₃, ppm): 8.72 (d, J=5.1 Hz, 1H), 7.96 (s, 1H), 7.56~7.51 (m, 2H), 7.36 (d, J=8.1 Hz, 1H), 7.23~7.12 (m, 4H), 6.72 (d, J=8.7 Hz, 1H), 6.48 (d, J=8.1 Hz, 1H), 6.3~5.65 (m, 2H), 5.45~5.41 (m, 1H), 2.94~2.80 (m, 2H), 2.23~2.19 (m, 1H), 2.05~1.91 (m, 3H).

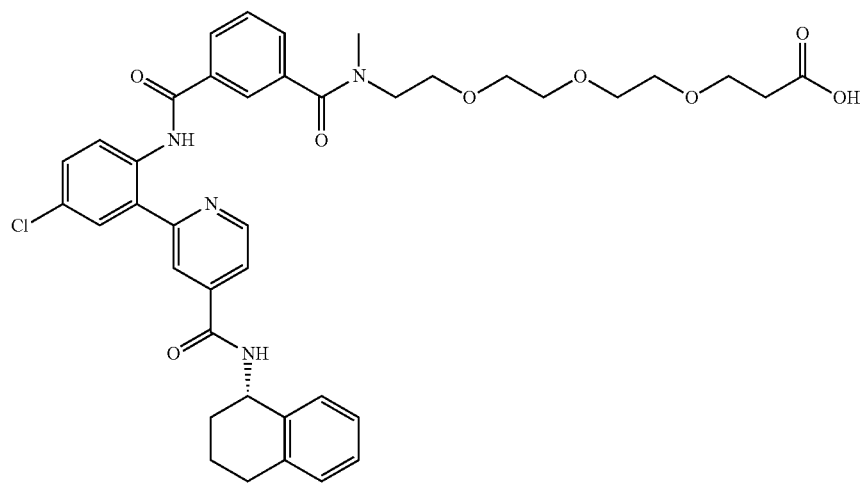 [SMILES: CN(CCOCCOCCOCCC(=O)O)C(=O)c1cccc(C(=O)Nc2ccc(Cl)cc2-c2cc(C(=O)N[C@H]3CCCc4ccccc43)ccn2)c1]

Example 237

This compound was prepared according to the procedure described for the synthesis of Example 188 substituting 237b in place of 25b. LC-MS (ES, m/z): 743 [M−HCl+H]⁺ H-NMR (300 MHz, CDCl₃, ppm): 13.15 (s, 1H), 0.86 (s, 1H), 8.66 (d, J=8.1 Hz, 1H), 8.24 (s, 1H), 8.07 (m, 2H), 7.828 (s, 1H), 7.821 (s, 1H), 7.75~7.56 (m, 2H), 7.54 (d, J=21.3 Hz, 1H), 7.47~7.43 (m, 1H), 7.22~7.14 (m, 3H), 7.02~6.92 (m, 1H), 5.46~5.44 (m, 1H), 3.81~3.58 (m, 16H), 3.17~3.10 (m, 3H), 2.86~2.85 (m, 2H), 2.51~2.47 (t, 2H), 2.20~2.03 (m, 2H), 2.01~1.91 (m, 3H).

Example 238

3-{2-[2-(2-{1-[3-({4-chloro-2-[4-({[3-(trifluoromethyl)phenyl]methyl}carbamoyl)pyridin-2-yl]phenyl}carbamoyl)phenyl]-N-methylformamido}ethoxy)ethoxy]ethoxy}propanoic acid

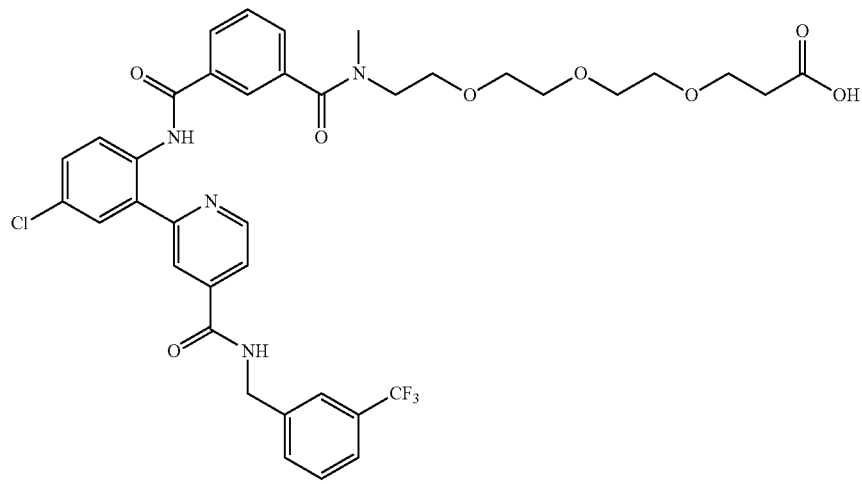 [SMILES: CN(CCOCCOCCOCCC(=O)O)C(=O)c1cccc(C(=O)Nc2ccc(Cl)cc2-c2cc(C(=O)NCc3cccc(C(F)(F)F)c3)ccn2)c1]

This compound was prepared according to the procedure described for the synthesis of Example 188 substituting 21b in place of 25b. LC-MS (ES, m/z): 771.30 [M+H]⁺

Example 239

(S)-1-(3-(3-(4-chloro-2-(4-(1,2,3,4-tetrahydronaphthalen-1-ylcarbamoyl)pyridin-2-yl)phenylcarbamoyl)benzylthio)phenyl)-3-methyl-2-oxo-6,9,12-trioxa-3-azapentadecan-15-oic acid

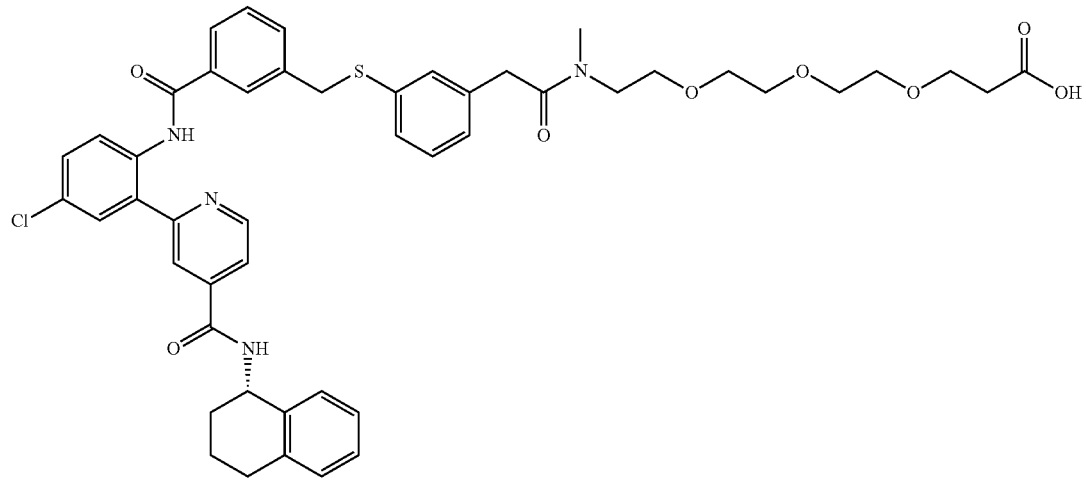 [SMILES: CN(CCOCCOCCOCCC(=O)O)C(=O)Cc1cccc(SCc2cccc(C(=O)Nc3ccc(Cl)cc3-c3cc(C(=O)N[C@H]4CCCc5ccccc54)ccn3)c2)c1]

This compound was prepared according to the procedure described for the synthesis of Example 144 substituting 237b in place of the aniline starting material 4c. (LC-MS (ES, m/z): 879 [M−HCl+H]⁺ H-NMR (300 MHz, DMSO, ppm): 12.94 (s, 1H), 12.08 (s, 1H), 9.26 (d, J=8.4 Hz, 1H), 8.96 (d, J=5.1 Hz, 1H), 8.60 (d, J=8.7 Hz, 1H), 8.412 (s, 1H), 8.09 (s, 1H), 8.08~7.91 (m, 2H), 7.91 (d, J=7.5 Hz, 1H), 7.61~7.48 (m, 3H), 7.22~7.13 (m, 2H), 7.01 (d, J=5.1 Hz, 1H), 5.27 (s, 1H), 4.36 (s, 2H), 3.66~3.48 (m, 7H), 3.45~3.32 (m, 15H), 3.29 (s, 2H), 2.84~2.80 (m, 4H), 2.44~2.38 (m, 3H), 2.02~1.80 (m, 4H).

Example 240 tert-butyl 2-methyl-1-((S)-1-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)piperidin-2-yl)-1-oxo-5,8,11-trioxa-2-azatetradecan-14-oate Scheme 96.

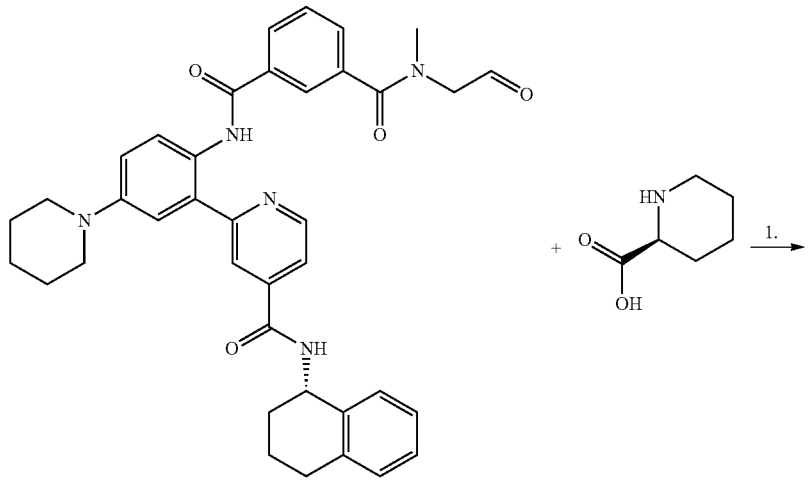

187a

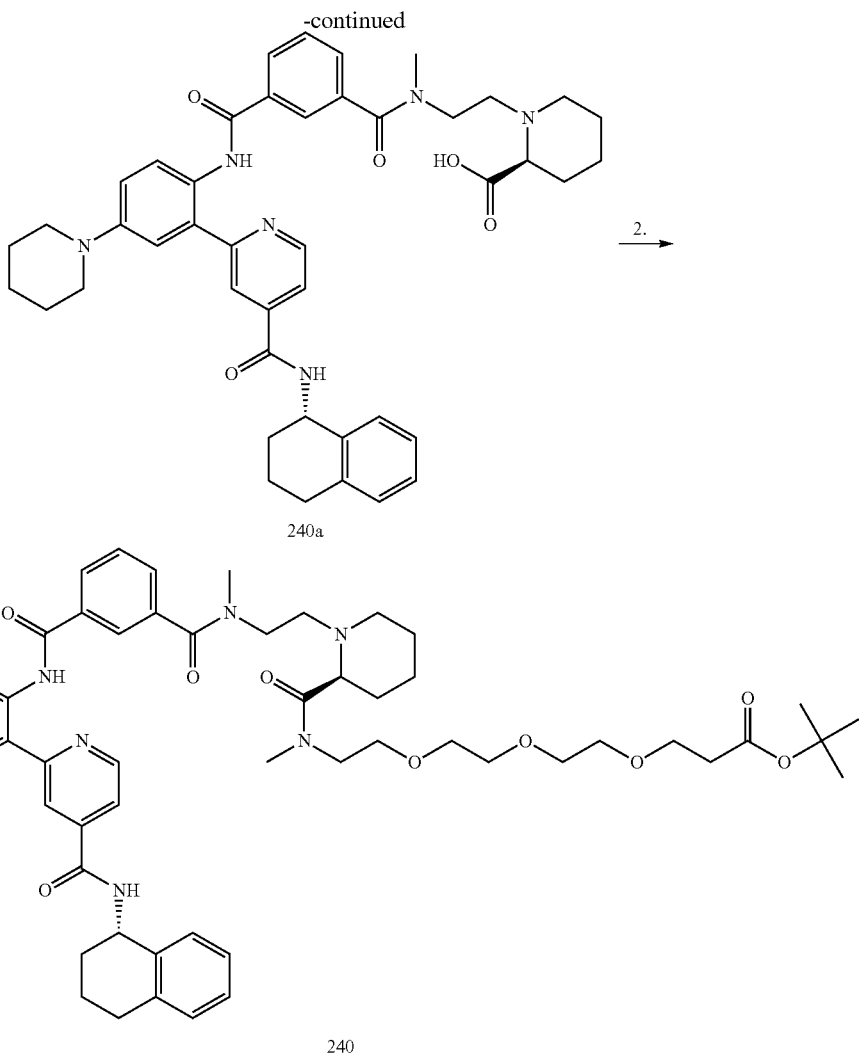

1. NaBH₃CN, EtOH, AcOH
2. tert-butyl 3-(2-(2-(2-(methylamino)ethoxy)ethoxy)ethoxy)propanoate 135c, EDC•HCl, DMAP, DCM.

Intermediate 240a

Into a 100-mL round-bottom flask, was placed a solution of (S)—N1-methyl-N1-(2-oxoethyl)-N3-(4-(piperidin-1-yl)-2-(4-(1,2,3,4-tetrahydronaphthalen-1-ylcarbamoyl)pyridin-2-yl)phenyl)isophthalamide (350 mg, 0.56 mmol, 1.00 equiv) in ethanol (20 mL), (S)-piperidine-2-carboxylic acid (216 mg, 1.67 mmol, 2.00 equiv). This was followed by the addition of acetic acid (2 mL). The mixture was stirred for overnight at room temperature. To this was added NaBH₃CN (77 mg, 1.22 mmol, 2.20 equiv). The resulting solution was stirred for 2 h at room temperature. The resulting mixture was concentrated under vacuum. The residue was dissolved in 50 mL of ethyl acetate. The resulting mixture was washed with 1×20 mL of water. The mixture was dried over sodium sulfate and concentrated under vacuum. The residue was applied onto a silica gel column with methanol:dichloromethane (1:5). This resulted in 300 mg (73%) of (S)-1-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)piperidine-2-carboxylic acid as a yellow solid.

Example 240

Into a 50-mL round-bottom flask, was placed a solution of (S)-1-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)piperidine-2-carboxylic acid (140 mg, 0.19 mmol, 1.00 equiv) in dichloromethane (3 mL), EDC.HCl (73 mg, 0.38 mmol, 2.00 equiv), 4-dimethylaminopyridine (47 mg, 0.38 mmol, 2.00 equiv), tert-butyl 3-(2-(2-(2-(methylamino)ethoxy)ethoxy)ethoxy)propanoate 135c (110 mg, 0.38 mmol, 2.00 equiv). The resulting mixture was stirred overnight at room temperature. The resulting mixture was washed with NH₄Cl aq. The mixture was dried over anhydrous sodium sulfate and concentrated under vacuum. The crude product (140 mg) was purified by Prep-HPLC with the following conditions (1#-Waters 2767-3): Column, Xbridge Prep C18, 5 um, 19*100 mm; mobile phase, water with 0.03% NH₃H₂O and CH₃CN (65% CH₃CN up to 78% in 6 min); Detector, Waters2545 UvDector 254&270 nm. 49.3 mg product was obtained. This resulted in 49.3 mg (26%) of tert-butyl 2-methyl-1-((S)-1-(2-(N-methyl-3-(4-(piperidin- 1-yl)-2-(4-((S)-1,2,3,4-tetrahydronaphthalen-1-ylcarbamoyl)pyridin-2-yl)phenylcarbamoyl)benzamido)ethyl)piperidin-2-yl)-1-oxo-5,8,11-trioxa-2-azatetradecan-14-oate as a yellow solid. LC-MS (ES, m/z): 1016 [M+H]+ H-NMR (300 MHz, CD3OD, ppm): 8.84 (s, 1H), 8.29-8.22 (m, 2H), 8.03-8.01 (m, 2H), 7.79-7.78 (m, 1H), 7.66-7.64 (m, 2H), 7.47 (s, 1H), 7.28-7.26 (m, 1H), 7.18-7.12 (m, 4H), 5.36-5.35 (m, 1H), 3.67-3.53 (m, 16H), 3.26-3.22 (m, 5H), 3.12-3.03 (m, 4H), 2.90-2.80 (m, 5H), 2.70-2.60 (m, 1H), 2.46-2.42 (m, 2H), 2.30-2.20 (m, 1H), 2.19-2.10 (m, 1H), 2.05-1.85 (m, 3H), 1.77-1.76 (m, 5H), 1.65-1.63 (m, 4H), 1.44-1.42 (m, 11H).

Example 241 tert-butyl 3-{2-[2-(2-{1-[(2S,4R)-4-hydroxy-1-{2-[N-methyl-1-(3-{[4-(piperidin-1-yl)-2-(4-{[(1S)-1,2,3,4-tetrahydronaphthalen-1-yl]carbamoyl}pyridin-2-yl)phenyl]carbamoyl}phenyl)formamido]ethyl}pyrrolidin-2-yl]-N-methylformamido}ethoxy)ethoxy]ethoxy}propanoate

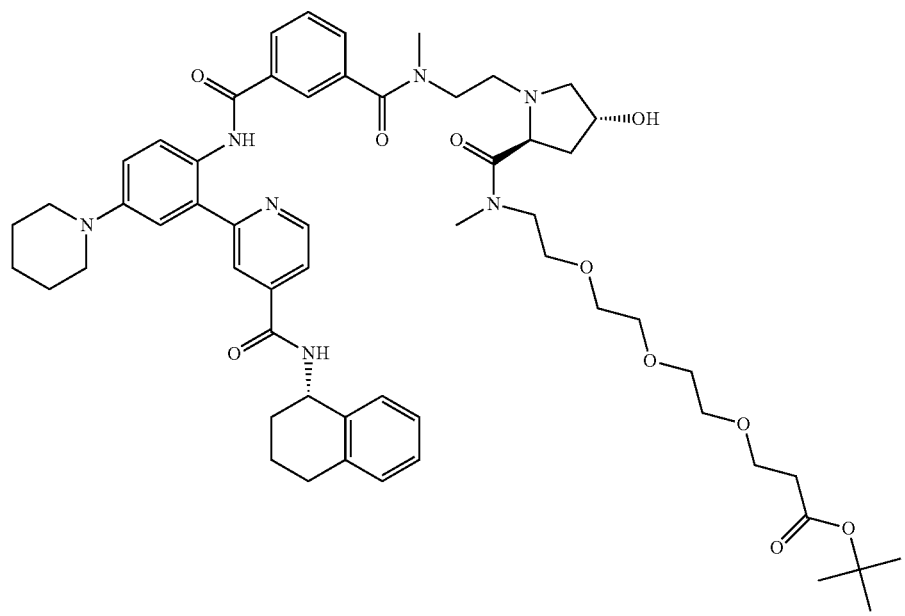 [SMILES: CN(CCN1C[C@H](O)C[C@H]1C(=O)N(C)CCOCCOCCOCCC(=O)OC(C)(C)C)C(=O)c1cccc(C(=O)Nc2ccc(N3CCCCC3)cc2-c2cc(C(=O)N[C@H]3CCCc4ccccc43)ccn2)c1]

451

This compound was prepared according to the procedure described for the synthesis of Example 240 substituting (2S, 4R)-4-hydroxypyrrolidine-2-carboxylic acid in place of (S)-piperidine-2-carboxylic acid LC-MS (ES, m/z): 1018 [M+H]+ H-NMR (300 MHz, DMSO, ppm): 12.25~12.09 (m, 1H), 9.19~9.16 (d, J=8.4 Hz, 1H), 8.86 (s, 1H), 8.28 (s, 1H), 8.19~8.18 (m, 1H), 7.92~7.84 (m, 3H), 7.62 (s, 2H), 7.38 (s, 1H), 7.19~7.10 (m, 6H), 5.24 (s, 1H), 3.58~3.51 (m, 4H), 3.45 (s, 12H), 3.22~3.18 (m, 5H), 3.00~2.72 (m, 10H), 2.41~2.27 (m, 3H), 1.99~1.78 (m, 7H), 1.66~1.56 (m, 7H), 1.33 (s, J=3.3 Hz, 10H), 1.25 (s, 2H).

452

Example 242 tert-butyl 2-methyl-1-((S)-4-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)morpholin-3-yl)-1-oxo-5,8,11-trioxa-2-azatetradecan-14-oate

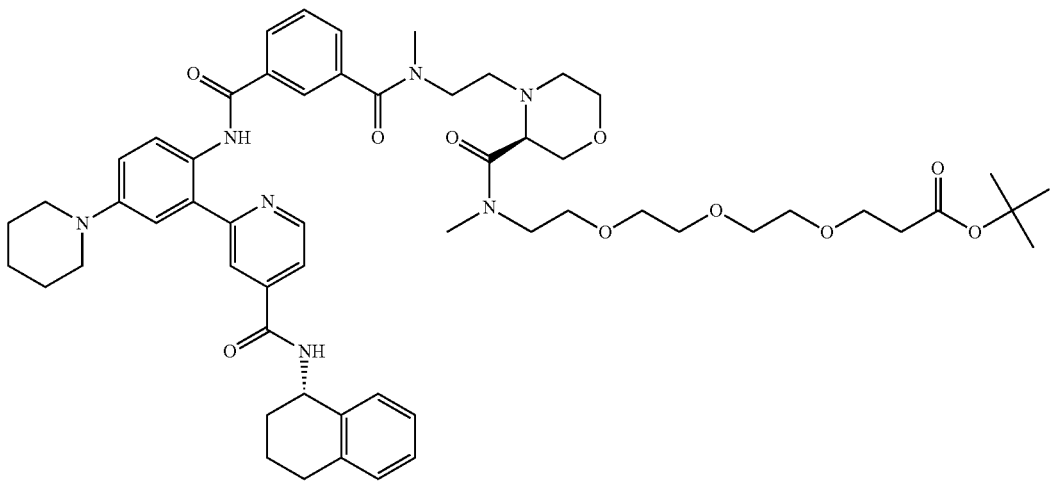

This compound was prepared according to the procedure described for the synthesis of Example 240 substituting (S)-morpholine-3-carboxylic acid in place of (S)-piperidine-2-carboxylic acid. LC-MS (ES, m/z): 1018 [M+H]+ H-NMR (300 MHz, CD3OD, ppm): 8.93~8.91 (d, J=5.4 Hz, 1H), 8.58-8.55 (d, J=8.7 Hz, 1H), 8.36 (s, 1H), 8.23 (s, 1H), 8.13~8.11 (d, J=6.9 Hz, 1H), 7.90~7.83 (m, 3H), 7.75~7.70 (m, 1H), 7.54~7.52 (d, J=6.6 Hz, 1H), 7.28~7.26 (d, J=7.8 Hz, 1H), 7.20~7.14 (m, 3H), 5.40~5.37 (m, 1H), 4.51~4.45 (m, 2H), 4.25~4.21 (m, 1H), 4.09~4.04 (m, 1H), 3.88 (s, 1H), 3.69~3.54 (m, 23H), 3.53~3.52 (m, 2H), 3.15~3.12 (m, 1H), 3.10~3.08 (m, 4H), 3.00 (s, 2H), 2.89~2.86 (m, 3H), 2.49~2.45 (m, 2H), 2.00 (s, 1H), 1.95~1.94 (m, 8H), 1.78~1.76 (m, 2H), 1.44 (s, 9H).

Example 243

2-methyl-1-((S)-4-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)morpholin-3-yl)-1-oxo-5,8,11-trioxa-2-azatetradecan-14-oic acid

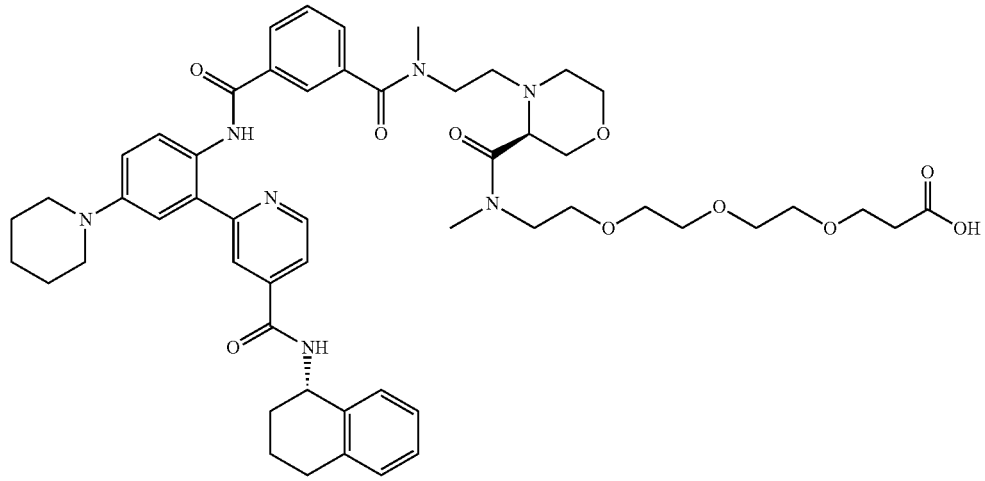

A solution of tert-butyl 2-methyl-1-((S)-4-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)morpholin-3-yl)-1-oxo-5,8,11-trioxa-2-azatetradecan-14-oate Example 242 (100 mg, 0.10 mmol, 1.00 equiv) in dichloromethane (4 mL), trifluoroacetic acid (2 mL). The resulting solution was stirred for 1 h at room temperature. The resulting mixture was concentrated under vacuum. The crude product (80 mg) was purified by Prep-HPLC with the following conditions (1#-Waters 2767-3): Column, SunFire Prep C18, 19*150 mm 5 um; mobile phase, water with 0.05% TFA and CH$_3$CN (5% CH$_3$CN up to 28% in 1 min, up to 38% in 6 min); Detector, Waters2545 UvDector 254&270 nm. 8.4 mg product was obtained. This resulted in 8.4 mg (7%) of 2-methyl-1-((S)-4-(2-(N-methyl-3-(4-(piperidin-1-yl)-2-(4-((S)-1,2,3,4-tetrahydronaphthalen-1-ylcarbamoyl)pyridin-2-yl)phenylcarbamoyl)benzamido)ethyl)morpholin-3-yl)-1-oxo-5,8,11-trioxa-2-azatetradecan-14-oic acid as a yellow solid. LC-MS (ES, m/z): 962 [M+H]$^+$ H-NMR (300 MHz, CD$_3$OD, ppm): 8.93 (d, J=5.1 Hz, 1H), 8.65 (d, J=9.3 Hz, 1H), 8.39 (s, 1H), 8.24 (s, 1H), 8.14-8.11 (m, 1H), 8.03-8.02 (m, 1H), 7.86-7.84 (m, 2H), 7.76-7.72 (m, 1H), 7.64-7.61 (m, 1H), 7.28-7.25 (m, 1H), 7.18-7.14 (m, 3H), 5.39 (m, 1H), 4.50-4.45 (m, 2H), 4.30-4.20 (m, 1H), 4.09-4.05 (m, 1H), 3.86-3.43 (m, 25H), 3.21 (s, 1H), 3.10-3.08 (m, 3H), 3.00 (s, 1H), 2.91-2.84 (m, 2H), 2.57-2.51 (m, 2H), 2.04-1.79 (m, 10H).

Example 244

(S)-tert-butyl 1-(2-(N-methyl-3-(4-(piperidin-1-yl)-2-(4-(1,2,3,4-tetrahydronaphthalen-1-ylcarbamoyl)pyridin-2-yl)phenylcarbamoyl)benzamido)ethyl)piperidine-4-carboxylate

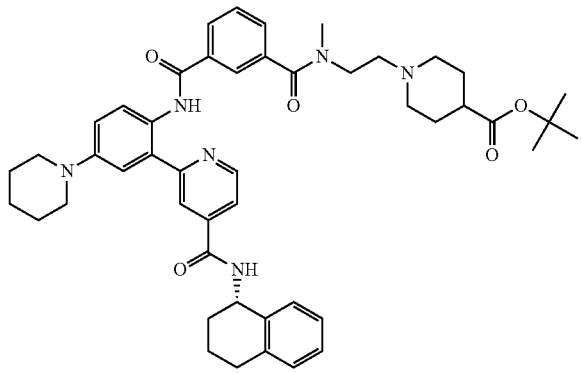

This compound was prepared according to the procedure described for the synthesis of Example 187 substituting tert-butyl piperidine-4-carboxylate in place of L-proline-t-butyl ester. LC-MS (ES, m/z): 799 [M+H]$^+$ H-NMR (300 MHz, DMSO, ppm): 12.19 (s, 1H), 9.19~9.17 (d, J=7.8 Hz, 1H), 9.03 (s, 1H), 8.89~8.87 (d, J=5.1 Hz, 1H), 8.30 (s, 1H), 8.23~8.20 (d, J=9.3 Hz, 1H), 8.00~7.97 (d, J=9.0 Hz, 2H), 7.86~7.84 (d, J=4.8 Hz, 1H), 7.68~7.63 (m, 2H), 7.49 (s, 1H), 7.20~7.13 (m, 5H), 5.25 (s, 1H), 3.84 (s, 3H), 3.39 (s, 3H), 3.31~3.26 (m, 5H), 2.96 (s, 6H), 2.78~2.73 (m, 2H), 2.12~1.98 (m, 5H), 1.84~1.59 (m, 11H), 1.44~1.40 (m, 10H).

Example 245

(S)-2-(2-(3-(3-methyl-3-(2-morpholinoethyl)ureido) benzamido)-5-(piperidin-1-yl)phenyl)-N-(1,2,3,4-tetrahydronaphthalen-1-yl)isonicotinamide

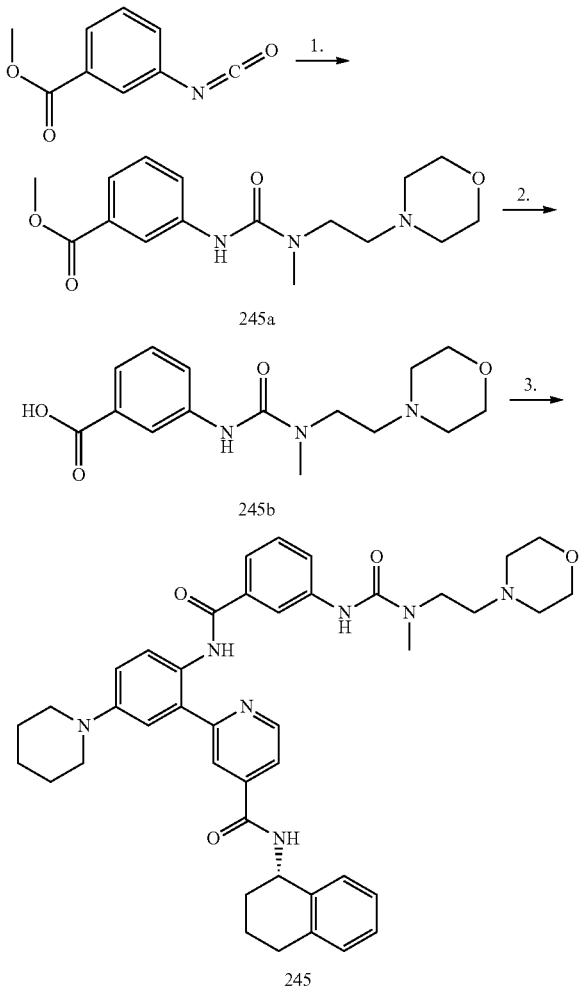

1. N-methyl-2-morpholinoethanamine, TEA, DCM
2. Aq. NaOH, TFH
3. EDC·HCl, DMAP, DCM.

Intermediate 245a

Into a 25-mL round-bottom flask, was placed a solution of N-methyl-2-morpholinoethanamine (162.8 mg, 1.13 mmol, 1.00 equiv) in dichloromethane (5 mL), triethylamine (114.1 mg, 1.13 mmol, 1.00 equiv). This was followed by the addition of methyl 3-isocyanatobenzoate (200 mg, 1.13 mmol, 1.00 equiv), in portions. The resulting solution was stirred for 0.5 h at room temperature. The residue was applied onto a silica gel column with dichloromethane/methanol (500:1-100:1). This resulted in 333 mg (92%) of methyl 3-(3-methyl-3-(2-morpholinoethyl)ureido)benzoate as a yellow semi-solid.

Intermediate 245b

Into a 50-mL round-bottom flask, was placed a solution of methyl 3-(3-methyl-3-(2-morpholinoethyl)ureido)benzoate (479 mg, 1.49 mmol, 1.00 equiv) in tetrahydrofuran (6 mL), a solution of sodium hydroxide (477.6 mg, 11.94 mmol, 8.00 equiv) in water (3 mL). The resulting solution was stirred for 4 h at room temperature. The reaction progress was monitored by TLC,LCMS (dichloromethane/methanol=2:1). The resulting mixture was concentrated under vacuum. The pH value of the solution was adjusted to 6-7 with hydrogen chloride (2 mol/L). The resulting solution was extracted with 2×20 mL of ethyl acetate and the organic layers combined. The resulting mixture was washed with 2×20 mL of sodium chloride (aq). The mixture was dried over anhydrous sodium sulfate and concentrated under vacuum. The residue was applied onto a silica gel column with dichloromethane/methanol (400:1-20:1). This resulted in 600 mg (92%) of 3-(3-methyl-3-(2-morpholinoethyl)ureido)benzoic acid as a light yellow solid.

Example 245

Into a 50-mL round-bottom flask, was placed 2-(2-amino-5-(piperidin-1-yl)phenyl)-N—((S)-1,2,3,4-tetrahydronaphthalen-1-yl)isonicotinamide (200 mg, 0.47 mmol, 1.00 equiv), 3-(3-methyl-3-(2-morpholinoethyl)ureido)benzoic acid (143 mg, 0.47 mmol, 0.99 equiv), EDC.HCl (135 mg, 0.70 mmol, 1.50 equiv), 4-dimethylaminopyridine (86 mg, 0.70 mmol, 1.50 equiv), dichloromethane (5 mL). The resulting solution was stirred for 2 h at room temperature. The reaction progress was monitored by LCMS/TLC (dichloromethane/methanol=10:1). The resulting solution was diluted with 20 mL of water. The resulting solution was extracted with 3×20 mL of dichloromethane and the organic layers combined. The resulting mixture was washed with 2×20 mL of NH₄Cl (aq). The mixture was dried over anhydrous sodium sulfate. The crude product was purified by Prep-HPLC with the following conditions (1#-Waters 2767-3): Column, SunFire Prep C18, 19*150 mm 5 um; mobile phase, water with 0.05% TFA and CH₃CN (24% CH₃CN up to 34% in 6 min); Detector, Waters2545 UvDector 254&270 nm. This resulted in 95.8 mg (19%) of Example 245 as a white solid. LC-MS (ES, m/z): 716 [M+H]⁺ H-NMR (300 MHz, CD₃OD, ppm): 8.95-8.93 (d, J=5.1 Hz, 1H), 8.71-8.68 (d, J=9 Hz, 1H), 3.39 (s, 1H), 8.20-8.11 (m, 1H), 7.86-7.84 (m, 1H), 7.72-7.64 (m, 1H), 7.53-7.48 (m, 2H), 7.27-7.25 (d, J=6.9 Hz, 1H), 7.17-7.13 (m, 4H), 5.38 (s, 1H), 4.00 (s, 2H), 3.83-3.80 (m, 4H), 3.69-3.65 (t, J=5.4 Hz, 6H), 3.44-3.40 (m, 2H), 3.18 (s, 4H), 2.87-2.85 (d, J=6.6 Hz, 2H), 2.04-1.81 (m, 10H).

Example 246

(S)—N1-(2-(4-(2-(2-hydroxyethoxy)ethyl)piperazin-1-yl)-2-oxoethyl)-N1-methyl-N3-(4-(piperidin-1-yl)-2-(4-(1,2,3,4-tetrahydronaphthalen-1-ylcarbamoyl)pyridin-2-yl)phenyl)isophthalamide

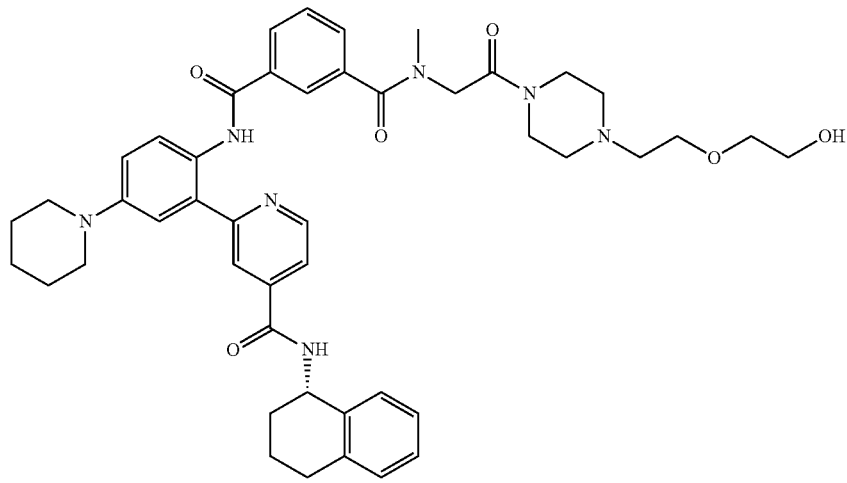

Into a 100-mL round-bottom flask, was placed a solution of (S)-2-(N-methyl-3-(4-(piperidin-1-yl)-2-(4-(1,2,3,4-tetrahydronaphthalen-1-ylcarbamoyl)pyridin-2-yl)phenylcarbamoyl)benzamido)acetic acid (200 mg, 0.31 mmol, 1.00 equiv) in dichloromethane (10 mL), EDC.HCl (113 mg, 0.59 mmol, 1.90 equiv), 4-dimethylaminopyridine (80 mg, 0.65 mmol, 2.11 equiv), 2-(2-(piperazin-1-yl)ethoxy)ethanol (103 mg, 0.59 mmol, 1.91 equiv). The resulting solution was stirred overnight at room temperature. The resulting solution was diluted with 30 mL of dichloromethane. The resulting mixture was washed with 2×30 mL of NH$_4$Cl.aq. The mixture was dried over anhydrous sodium sulfate and concentrated under vacuum. The crude product (200 mg) was purified by Prep-HPLC with the following conditions (1#-Waters 2767-3): Column, SunFire Prep C18, 19*150 mm 5 um; mobile phase, water with 0.05% TFA and CH$_3$CN (23% CH$_3$CN up to 34% in 6 min); Detector, Waters2545 UvDector 254&270 nm. 57.6 mg product was obtained. This resulted in 57.6 mg (23%) of (S)—N1-(2-(4-(2-(2-hydroxyethoxy)ethyl)piperazin-1-yl)-2-oxoethyl)-N1-methyl-N3-(4-(piperidin-1-yl)-2-(4-(1,2,3,4-tetrahydronaphthalen-1-ylcarbamoyl)pyridin-2-yl)phenyl)isophthalamide as a yellow solid. LC-MS (ES, m/z): 802 [M+H]$^+$ H-NMR (300 MHz, DMSO, ppm): 12.38 (s, 1H), 9.94 (s, 1H), 9.21~9.19 (d, J=8.4 Hz, 1H), 8.95~8.90 (m, 1H), 8.00~7.95 (m, 2H), 7.87~7.84 (m, 3H), 7.67~7.54 (m, 3H), 7.30~7.13 (m, 5H), 5.27~5.25 (m, 1H), 3.79~3.69 (m, 3H), 3.57~3.11 (m, 16H), 3.00~2.92 (m, 4H), 2.78 (s, 2H), 2.00 (s, 2H), 1.85~1.79 (m, 6H), 1.55 (s, 2H).

Example 247

3-(2-(2-(2-(3-(3-((3OS)-3-((2-(4-(((S)-1,2,3,4-tetrahydronaphthalen-1-yl)carbamoyl)pyridin-2-yl)-4-(piperidin-1-yl)phenyl)carbamoyl)benzylthio)phenyl)propoxy)ethoxy)ethoxy)ethoxy)propanoic acid Scheme 98.

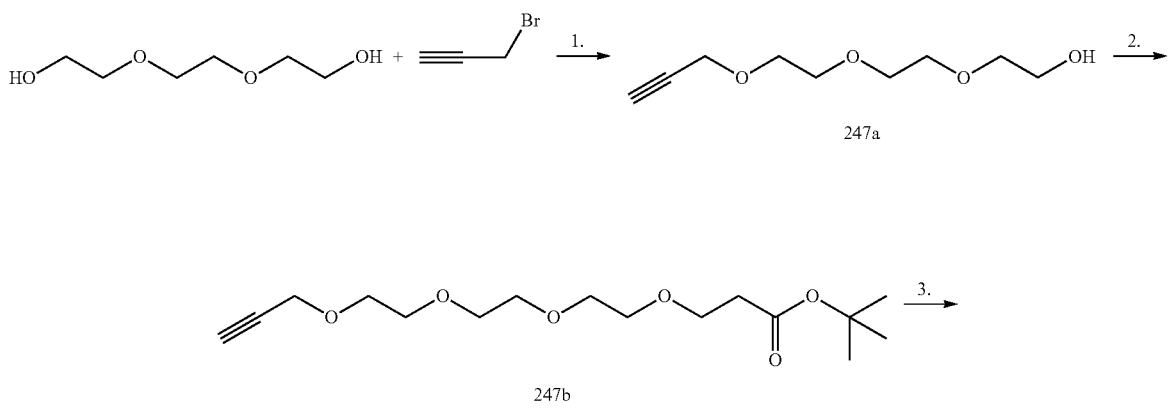

459    460
-continued
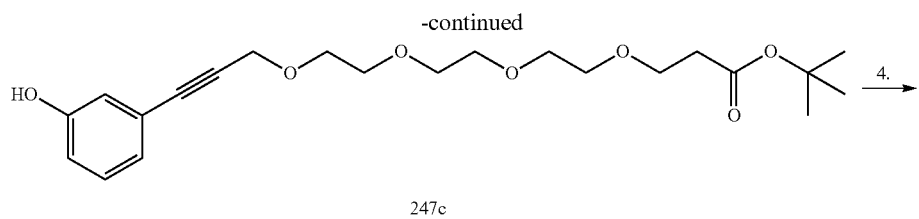
247c
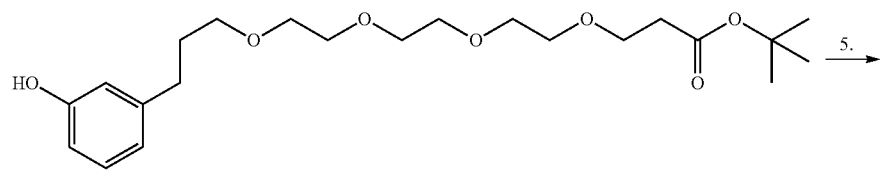
247d
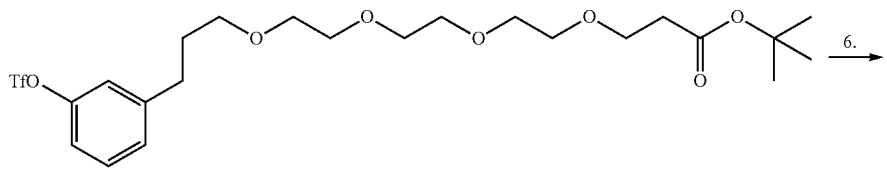
247e
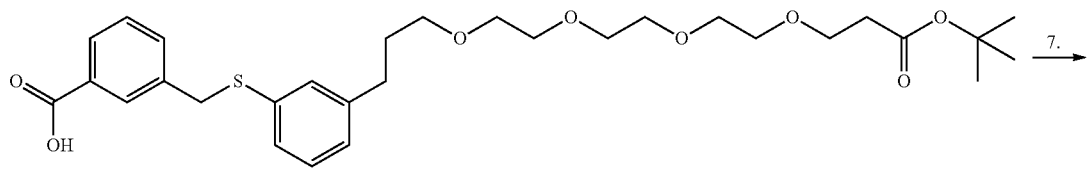
247f
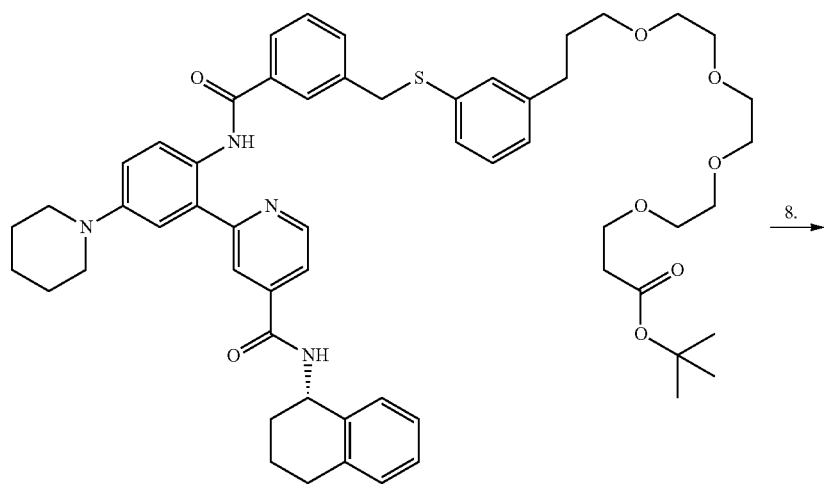
247g

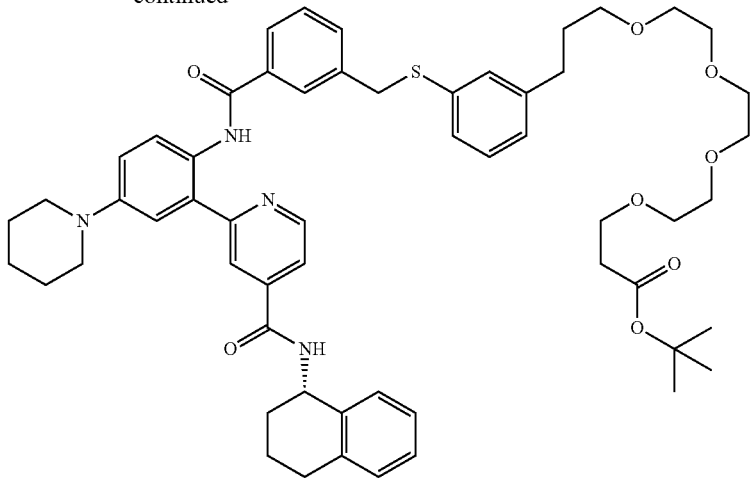

247

1. Na, THF
2. Na, tert-butyl acrylate, THF
3. 3-iodophenol, copper(I)iodide, Pd(PPh₃)₂Cl₂, triethylamine
4. Pd/C, H₂, MeOH
5. trifluoromethanesulfonyl trifluoromethanesulfonate, TEA, DCM
6. 3-(mercaptomethyl)benzoic acid, K₂CO₃, Pd₂(dba)₃, Xantphos, xylene
7. 126e, EDC•HCl, DMAP, DCM.
8. HCl/DCM.

Intermediate 247a

Into a 1-L round-bottom flask, was placed a solution of Triethylene glycol (56.76 g, 378.40 mmol, 0.90 equiv) in tetrahydrofuran (400 mL). This was followed by the addition of sodium hydride (10 g, 416.67 mmol, 1.00 equiv), in portions at 0-5° C. in 10 min. To this was added a solution of 3-bromoprop-1-yne (50 g, 420.17 mmol, 1.00 equiv) in toluene (50 mL) dropwise with stirring at room temperature. The resulting solution was stirred for 2 h at room temperature. The reaction progress was monitored by LCMS. The solids were filtered out. The resulting mixture was concentrated under vacuum. The residue was applied onto a silica gel column with petroleum ether/ethyl acetate (10:1-1:1). This resulted in 30.1 g (37%) of 2-(2-(2-(prop-2-ynyloxy)ethoxy)ethoxy) ethanol as yellow oil.

Intermediate 247b

Into a 1000-mL round-bottom flask, was placed a solution of 2-(2-(2-(prop-2-ynyloxy)ethoxy)ethoxy)ethanol (22.5 g, 119.68 mmol, 1.00 equiv) in tetrahydrofuran (200 mL), sodium (83 mg, 3.61 mmol, 0.03 equiv). This was followed by the addition of a solution of tert-butyl acrylate (15.3 g, 119.53 mmol, 1.00 equiv) in tetrahydrofuran (100 mL) dropwise with stirring. The resulting solution was stirred for 3 h at room temperature. The reaction progress was monitored by LCMS. The pH value of the solution was adjusted to 7-8 with 1N hydrochloric acid. The resulting solution was diluted with 300 mL of water. The resulting solution was extracted with 3×200 ml of ethyl acetate and the organic layers combined. The resulting mixture was washed with 1×200 mL of water. The resulting mixture was washed with 1×200 mL of sodium chloride (aq). The resulting mixture was concentrated under vacuum. This resulted in 31.3 g (79%) of tert-butyl 3-(2-(2-(2-(prop-2-ynyloxy)ethoxy)ethoxy)ethoxy)propanoate as yellow oil.

Intermediate 247c

Into a 1000-mL round-bottom flask purged and maintained with an inert atmosphere of nitrogen, was placed a solution of 3-iodophenol (7 g, 31.82 mmol, 1.01 equiv) in tetrahydrofuran (200 mL), copper(I) iodide (600 mg, 3.16 mmol, 0.10 equiv), Pd(PPh₃)₂Cl₂ (2.22 g, 3.16 mmol, 0.10 equiv), triethylamine (6.4 g, 63.37 mmol, 2.00 equiv). This was followed by the addition of tert-butyl 3-(2-(2-(2-(prop-2-ynyloxy)ethoxy)ethoxy)ethoxy)propanoate (10 g, 31.65 mmol, 1.00 equiv) dropwise with stirring at 0-5° C. in 20 min. The resulting solution was stirred for 2 h at room temperature. The reaction progress was monitored by TLC/LCMS (1:1 ethyl acetate/petroleum ether). The reaction was then quenched by the addition of 200 ml of water. The resulting solution was extracted with 3×200 ml of ethyl acetate and the organic layers combined. The resulting mixture was washed with 1×100 mL of water. The resulting mixture was washed with 3×100 mL of sodium chloride (aq). The resulting mixture was concentrated under vacuum. The residue was applied onto a silica gel column with petroleum ether/ethyl acetate (10:1-1: 2). This resulted in 7 g (43%) of tert-butyl 3-(2-(2-(2-(3-(3-hydroxyphenyl)prop-2-ynyloxy)ethoxy)ethoxy)ethoxy)propanoate as a brown oil.

Intermediate 247d

Into a 250-mL round-bottom flask, was placed a solution of tert-butyl 3-(2-(2-(2-(3-(3-hydroxyphenyl)prop-2-ynyloxy) ethoxy)ethoxy)ethoxy)propanoate (5 g, 12.25 mmol, 1.00 equiv) in methanol/dichloromethane (20/20 mL). This was followed by the addition of Palladium carbon (5 g, 47.17 mmol, 3.85 equiv) and hydrogen gas The resulting solution was stirred overnight at 35° C. in an oil bath. The reaction progress was monitored by LCMS. The solids were filtered out. The resulting mixture was concentrated under vacuum.

This resulted in 4.5 g (86%) of tert-butyl 3-(2-(2-(2-(3-(3-hydroxyphenyl)propoxy)ethoxy)ethoxy)ethoxy)propanoate as yellow oil.

Intermediate 247e

Into a 1000-mL round-bottom flask, was placed a solution of tert-butyl 3-(2-(2-(2-(3-(3-hydroxyphenyl)propoxy) ethoxy)ethoxy)ethoxy)propanoate (6 g, 14.53 mmol, 1.00 equiv) in dichloromethane (100 mL), triethylamine (9 g, 89.11 mmol, 6.13 equiv). This was followed by the addition of a solution of (trifluoromethane)sulfonyl trifluoromethanesulfonate (12 g, 42.54 mmol, 2.93 equiv) in dichloromethane (50 mL) dropwise with stirring at 0-5° C. in 5 min. The resulting solution was stirred for 1 h at 0-5° C. in a water/ice bath. The reaction progress was monitored by LCMS. The reaction was then quenched by the addition of 100 ml of water. The resulting solution was extracted with 3×100 mL of ethyl acetate and the organic layers combined. The resulting mixture was washed with 4×100 mL of sodium chloride (aq). The resulting mixture was concentrated under vacuum. This resulted in 10 g (crude) of tert-butyl 3-(2-(2-(2-(3-(3-(trifluoromethylsulfonyloxy)phenyl)propoxy)ethoxy)ethoxy) ethoxy) propanoate as a brown oil.

Intermediate 247f

Into a 50-mL 3-necked round-bottom flask purged and maintained with an inert atmosphere of nitrogen, was placed a solution of 3-(mercaptomethyl)benzoic acid (2.5 g, 0.015 mol, 1.01 equiv) in xylene (12.5 mL), potassium carbonate (1.01 g, 0.9 mmol, 0.50 equiv). The resulting solution was stirred for 30 min at 25° C. Into another 250-mL 3-necked round-bottom flask purged and maintained with an inert atmosphere of nitrogen, was added a solution of tert-butyl 3-(2-(2-(2-(3-(3-(trifluoromethylsulfonyloxy)phenyl)propoxy)ethoxy)ethoxy)ethoxy)propanoate (8 g, 0.015 mol, 1.00 equiv) in xylene (40 mL), Pd$_2$(dba)$_3$ (1 g), Xantphos (1 g). The resulting solution was stirred for 20 min at 25° C. and then added to the above reacting solution. The resulting solution was stirred overnight at 135° C. in an oil bath. The reaction progress was monitored by LCMS. The resulting mixture was concentrated under vacuum. The pH value of the solution was adjusted to 5~6 with 1N hydrochloric acid. The resulting solution was extracted with 3×50 ml of ethyl acetate and the organic layers combined and concentrated under vacuum. The residue was applied onto a silica gel column with petroleum ether/ethyl acetate (10:1-1:1). This resulted in 2.6 g (28%) of 3-((3-(3-(2-(2-(2-(3-tert-butoxy-3-oxopropoxy)ethoxy)ethoxy)ethoxy)propyl)phenylthio)methyl)benzoic acid as a brown solid. LC-MS (ES, m/z): 561 [M−H]⁻. H-NMR (300 MHz, CDCl$_3$, ppm): 7.965-7.940 (d, J=7.5 Hz, 1H), 7.882 (s, 1H), 7.561-7.535 (d, J=7.8 Hz, 1H), 7.418-7.366 (m, 1H), 7.177-7.161 (d, J=4.8 Hz, 2H), 7.052 (s, 1H), 7.026-6.997 (m, 1H), 4.117 (s, 2H), 3.748-3.566 (m, 15H), 3.428-3.383 (t, J=6.6 Hz, 2H), 2.607-2.495 (m, 4H), 1.859-1.763 (m, 2H), 1.454 (s, 9H).

Intermediate 247g

Into a 100-mL round-bottom flask, was placed a solution of 2-(2-amino-5-(piperidin-1-yl)phenyl)-N—((S)-1,2,3,4-tetrahydronaphthalen-1-yl)isonicotinamide (909.6 mg, 2.14 mmol, 1.00 equiv) in dichloromethane (15 mL), 3-((3-(3-(2-(2-(2-(3-tert-butoxy-3-oxopropoxy)ethoxy)ethoxy)ethoxy) propyl)phenylthio)methyl)benzoic acid (1.2 g, 2.14 mmol, 1.00 equiv), EDC.HCl (614.0 mg, 3.20 mmol, 1.50 equiv), 4-dimethylaminopyridine (390.7 mg, 3.20 mmol, 1.50 equiv). The resulting solution was stirred overnight at room temperature. The reaction progress was monitored by LCMS/TLC (petroleum ether:ethyl acetate=1:1). The resulting solution was diluted with 20 mL of NH$_4$Cl aq. The resulting solution was extracted with 2×20 mL of dichloromethane and the organic layers combined. The resulting mixture was washed with 2×20 mL of brine. The mixture was dried over anhydrous sodium sulfate. The solids were filtered out. The resulting mixture was concentrated under vacuum. The residue was applied onto a silica gel column with petroleum ether/ethyl acetate (20:1~4:1). This resulted in 1.6 g (70%) of tert-butyl 3-(2-(2-(2-(3-(3-((22S)-3-((2-(4-(((S)-1,2,3,4-tetrahydronaphthalen-1-yl)carbamoyl)pyridin-2-yl)-4-(piperidin-1-yl)phenyl)carbamoyl)benzylthio)phenyl)propoxy) ethoxy)ethoxy)ethoxy)propanoate as brown oil.

Example 247

Into a 250-mL round-bottom flask, was placed a solution of tert-butyl 3-(2-(2-(2-(3-(3-((30 S)-3-((2-(4-(((S)-1,2,3,4-tetrahydronaphthalen-1-yl)carbamoyl)pyridin-2-yl)-4-(piperidin-1-yl)phenyl)carbamoyl)benzylthio)phenyl)propoxy) ethoxy)ethoxy)ethoxy)propanoate (1.2 g, 1.24 mmol, 1.00 equiv) in dichloromethane (20 mL), trifluoroacetic acid (20 mL). The resulting solution was stirred for 2 h at room temperature. The reaction progress was monitored by LCMS. The resulting mixture was concentrated under vacuum. The pH value of the solution was adjusted to 5~6 with sat. sodium carbonate. The resulting solution was extracted with 3×10 mL of dichloromethane and the organic layers combined and concentrated under vacuum. The residue was dissolved in 20 mL of acetonitrile, 20 mL of water, 1 mL of hydrochloric acid and lyophilized. This resulted in 0.67 g (50%) of 3-(2-(2-(2-(3-(3-((30S)-3-((2-(4-(((S)-1,2,3,4-tetrahydronaphthalen-1-yl)carbamoyl)pyridin-2-yl)-4-(piperidin-1-yl)phenyl)carbamoyl)benzylthio)phenyl)propoxy)ethoxy)ethoxy)ethoxy) propanoic acid dihydrochloride as a brown semi-solid. LC-MS (ES, m/z): 915[M−2HCl+H]⁺. H-NMR (300 MHz, CD$_3$OD, ppm): 8.969-8.951 (d, J=5.4 Hz, 1H), 8.798-8.768 (m, 1H), 8.481 (s, 1H), 8.296-8.287 (m, 2H), 7.918-7.901 (m, 4H), 7.867-7.837 (m, 2H), 7.517-7.469 (m, 1H), 7.255-7.110 (m, 6H), 7.031-7.009 (m, 1H), 5.393 (m, 1H), 4.250 (s, 2H), 3.793-3.757 (m, 4H), 3.694-3.600 (m, 2H), 3.589-3.546 (m, 10H), 3.490-3.460 (m, 2H), 3.351-3.314 (m, 2H), 2.886-2.857 (m, 2H), 2.596-2.492 (m, 4H), 2.128 (s, 5H), 2.026-1.999 (d, 2H), 1.874 (s, 3H), 1.756-1.730 (m, 2H).

Example 248

3-[2-(2-{2-[N-methyl-1-(3-{[4-(piperidin-1-yl)-2-[4-({[3-(trifluoromethyl)phenyl]methyl}carbamoyl)pyridin-2-yl]phenyl]carbamoyl}phenyl)formamido]ethoxy}ethoxy)ethoxy]propanoic acid

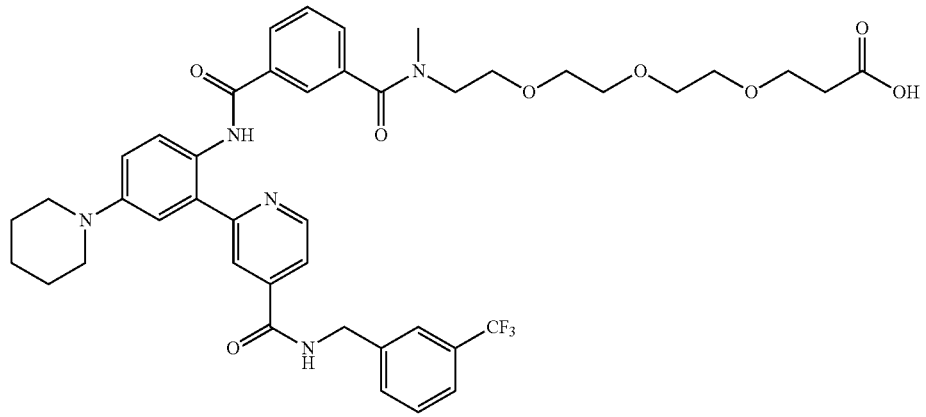 [SMILES: CN(CCOCCOCCOCCC(=O)O)C(=O)c1cccc(C(=O)Nc2ccc(N3CCCCC3)cc2-c2cc(C(=O)NCc3cccc(C(F)(F)F)c3)ccn2)c1]

This compound was prepared according to the procedure described for the synthesis of Example 188 substituting 4.1e in place of 25b. LC-MS (ES, m/z): 820 [M+H]$^+$. H-NMR (300 MHz, CDCl$_3$, ppm): 8.976-8.959 (d, 1H), 8.830-8.800 (d, J=9.0 Hz, 1H), 8.457 (s, 1H), 8.161-8.095 (d, 3H), 7.903-7.881 (m, 1H), 7.727-7.567 (m, 7H), 4.724 (s, 2H), 3.826 (s, 2H), 3.709-3.492 (m, 16H), 3.177-3.096 (m, 3H), 2.513-2.444 (m, 3H), 2.059-2.043 (s, 4H), 1.846-1.828 (s, 2H).

Example 249

3-[2-(2-{2-[N-methyl-1-(3-{[4-(piperidin-1-yl)-2-(4-{[(1S)-1,2,3,4-tetrahydronaphthalen-1-yl]carbamoyl}pyridin-2-yl)phenyl]carbamoyl}phenyl)formamido]ethoxy}ethoxy)ethoxy]propanoic acid

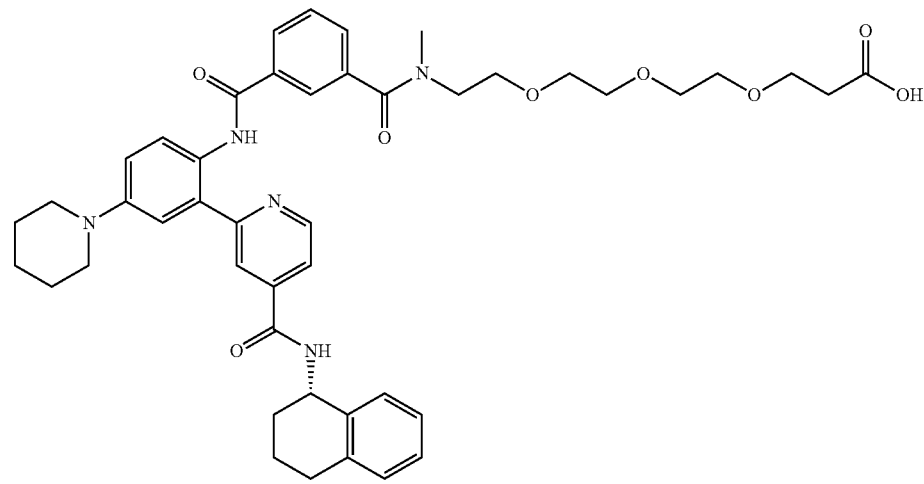 [SMILES: CN(CCOCCOCCOCCC(=O)O)C(=O)c1cccc(C(=O)Nc2ccc(N3CCCCC3)cc2-c2cc(C(=O)N[C@H]3CCCc4ccccc43)ccn2)c1]

467

This compound was prepared according to the procedure described for the synthesis of Example 188 substituting 126e in place of 25b. LC-MS (ES, m/z): 792[M-2HCl+H]+ H-NMR (400 MHz, CDCl₃, ppm): 12.90 (s, 1H), 11.725~11.778 (m, 1H), 8.677~8.861 (m, 3H), 7.888~8.222 (m, 5H), 7.445~7.658 (m, 2H), 7.245~7.262 (m, 1H), 7.062~7.147 (m, 3H), 5.412 (s, 1H), 3.394~3.748 (m, 18H), 2.740~3.072 (m, 5H), 2.246~2.875 (m, 4H), 2.043~2.104 (m, 5H), 1.853~1.992 (m, 3H), 1.230~1.929 (m, 2H).

468

Example 250

1-N-(2-{2-[2-(3-{4-[2-(2-hydroxyethoxy)ethyl]piperazin-1-yl}-3-oxopropoxy)ethoxy]ethoxy}ethyl)-1-N-methyl-3-N-[4-(piperidin-1-yl)-2-(4-{[(1S)-1,2,3,4-tetrahydronaphthalen-1-yl]carbamoyl}pyridin-2-yl)phenyl]benzene-1,3-dicarboxamide

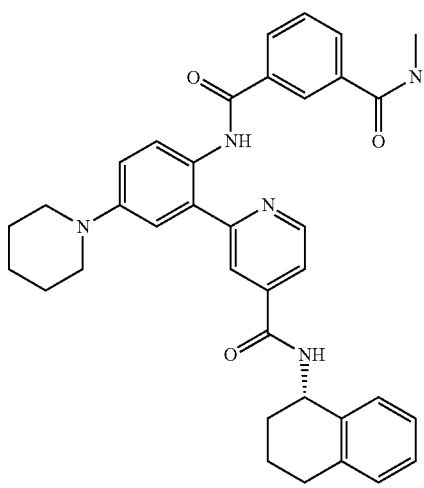

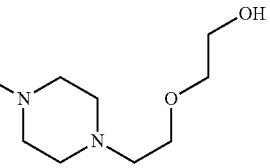

This compound was prepared according to the procedure described for the synthesis of Example 231 substituting Example 249 in place of 231a. LC-MS (ES, m/z): 948 [M+H]+ H-NMR (300 MHz, CD₃OD, ppm): 8.914~8.931 (m, 1H), 8.676 (d, J=9 Hz, 1H), 8.398 (s, 1H), 8.033~8.084 (m, 3H), 7.851~7.872 (m, 1H), 7.615~7.771 (m, 3H), 7.263~7.286 (m, 1H), 7.136~7.220 (m, 3H), 8.369~5.410 (m, 1H), 3.824 (s, 4H), 3.538~3.736 (m, 23H), 3.338~3.398 (m, 3H), 3.090~3.171 (m, 4H), 2.865~2.888 (m, 2H), 2.650 (s, 2H), 1.989~2.007 (m, 1H), 1.795~1.922 (m, 9H).

Example 251

16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid Scheme 99.

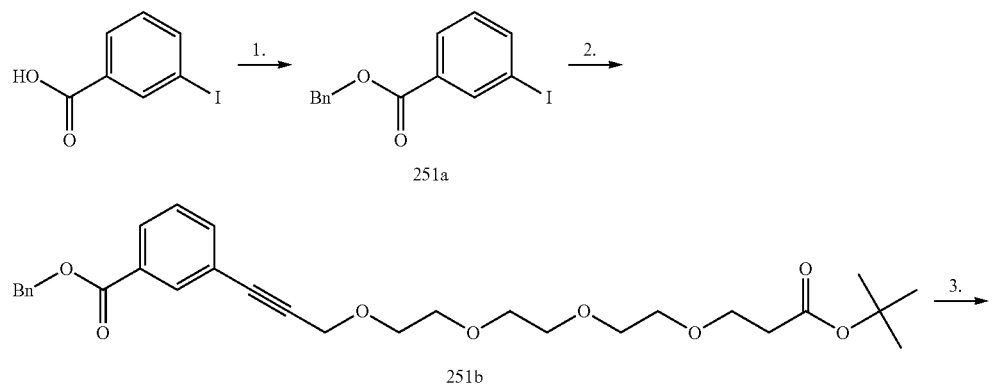

-continued

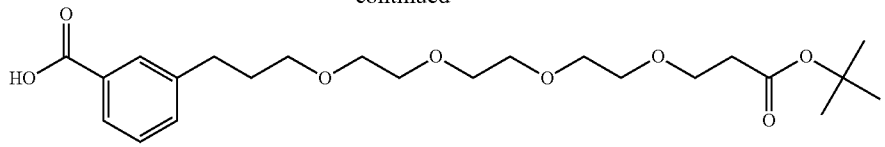

251c 1. 1. Benzyl bromide, K$_2$CO$_3$
2. copper(I)iodide, Pd(PPh$_3$)$_2$Cl$_2$, triethylamine, 247b
3. Pd/C, H$_2$, MeOH.

Intermediate 251a

Into a 500-mL round-bottom flask, was placed a solution of 3-iodobenzoic acid (9.92 g, 40.00 mmol, 1.00 equiv) in DMF (100 mL), 1-(bromomethyl)benzene (6.84 g, 40.00 mmol, 1.00 equiv), potassium carbonate (11.04 g, 80.00 mmol, 2.00 equiv). The resulting solution was stirred for 2 h at room temperature. The solids were filtered out and the filtrate was concentrated under vacuum. The residue was diluted with 50 mL of water and extracted with 2×50 mL of ethyl acetate. The combined organic layers were washed with 2×50 mL of sodium chloride, dried over anhydrous sodium sulfate and concentrated under vacuum to give 13.1 g (97%) of benzyl 3-iodobenzoate as light brown oil Intermediate 251b Into a 250-mL three-bottom flask purged and maintained with an inert atmosphere of nitrogen, was placed a solution of benzyl 3-iodobenzoate (10.7 g, 31.66 mmol, 1.00 equiv) in THF (100 mL), tert-butyl 3-(2-(2-(2-(prop-2-ynyloxy)ethoxy)ethoxy)ethoxy)propanoate (10 g, 31.65 mmol, 1.00 equiv), copper(I) iodide (601 mg, 3.16 mmol, 0.10 equiv), Pd(PPh$_3$)$_2$Cl$_2$ (2.222 g, 3.17 mmol, 0.10 equiv), triethylamine (6.39 g, 63.27 mmol, 2.00 equiv). The resulting solution was stirred for 3 h at room temperature. The resulting mixture was concentrated under vacuum and the residue was diluted with 50 mL of water. The resulting solution was extracted with 3×50 mL of ethyl acetate and the organic layers combined. The resulting mixture was washed with 3×50 mL of brine. The mixture was dried over anhydrous sodium sulfate. The solids were filtered out. The resulting mixture was concentrated under vacuum. The residue was applied onto a silica gel column with petroleum ether/ethyl acetate (20:1~2:1). This resulted in 10.7 g (64%) of benzyl 3-(3-(2-(2-(2-(3-tert-butoxy-3-oxopropoxy)ethoxy)ethoxy)ethoxy)prop-1-ynyl)benzoate as brown oil.

Intermediate 251c

Into a 100-mL round-bottom flask, was placed a solution of benzyl 3-(3-(2-(2-(2-(3-tert-butoxy-3-oxopropoxy)ethoxy)ethoxy)ethoxy)prop-1-ynyl)benzoate (5.8 g, 11.03 mmol, 1.00 equiv) in methanol (50 mL) followed by Palladium on carbon (2.8 g). The mixture was stirred under one atmosphere of hydrogen for 24 h at 35° C. The solids were filtered out and the filtrate was concentrated under vacuum. The residue was applied onto a silica gel column with petroleum ether/ethylacetate (10:1-1:1). This resulted in 2.8 g (58%) of 3-(3-(2-(2-(2-(3-tert-butoxy-3-oxopropoxy)ethoxy)ethoxy)ethoxy)propyl)benzoic acid as light yellow oil. LC-MS (ES, m/z): 463 [M+Na]$^+$ H-NMR (300 MHz, CDCl3, ppm): 7.96 (m, 2H), 7.42 (m, 2H), 3.75-3.59 (m, 14H), 3.48 (t, J=6.3 Hz, 2H), 2.78 (t, J=7.2 Hz, 2H), 2.52 (t, J=6.6 Hz, 2H), 1.99-1.90 (m, 2H), 1.45 (s, 9H).

Scheme 100.

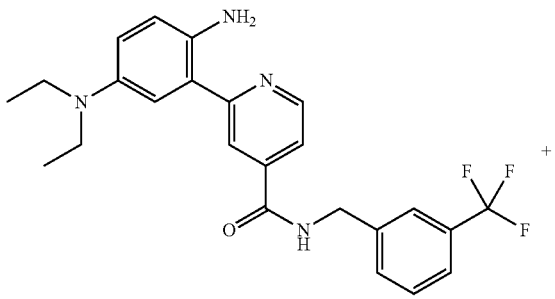

25b

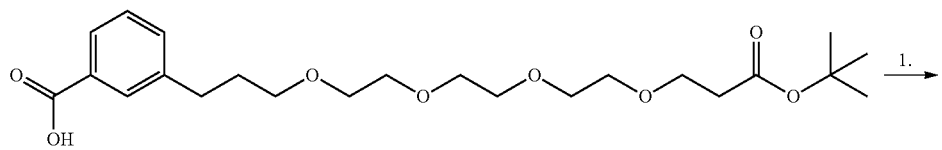

251c

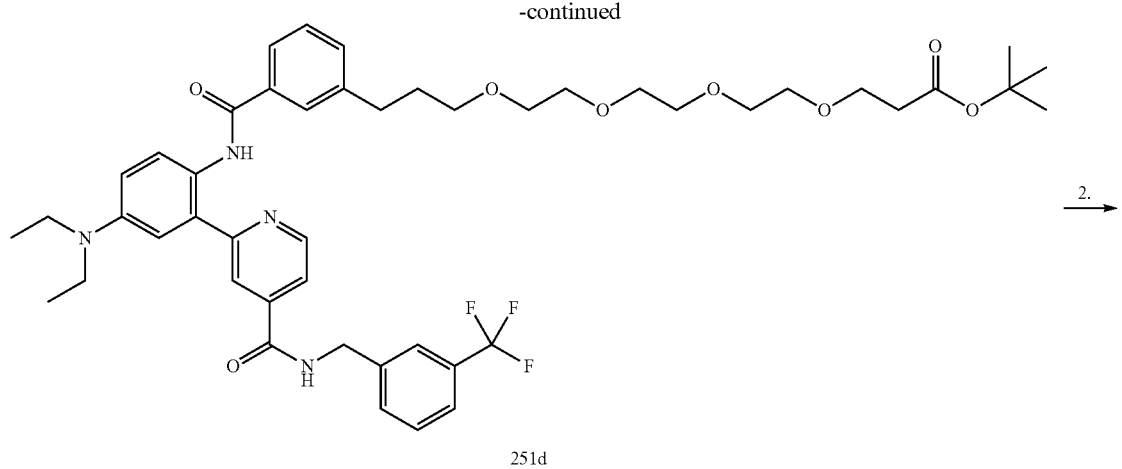

251d

↓ 2.

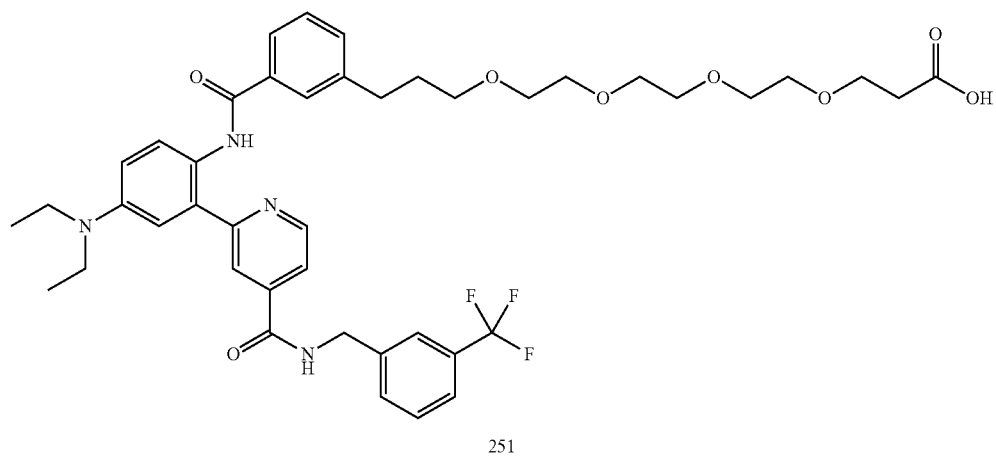

251

1. HATU, DIPEA, DMF;
2. TFA, DCM.

Intermediate 251d: tert-butyl 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oate To a solution of 2-(2-amino-5-(diethylamino)phenyl)-N-(3-(trifluoromethyl)benzyl)isonicotinamide (1.77 g, 4.0 mmol), 3-(2,2-dimethyl-4-oxo-3,7,10,13,16-pentaoxanonadecan-19-yl)benzoic acid (1.70 g, 3.86 mmol) and DIPEA (1.47 g, 11.4 mmol) in DMF (20 ml) was added HATU (1.56 g, 4.10 mmol). The reaction mixture was stirred for 30 minutes, at which time additional 2-(2-amino-5-(diethylamino)phenyl)-N-(3-(trifluoromethyl)benzyl)isonicotinamide (0.06 g, 0.14 mmol) was added. After stirring an additional 25 minutes, the reaction mixture was concentrated under vacuum. The residue was dissolved in DCM (200 mL), washed with water (4×50 mL), dried (Na$_2$SO$_4$) and concentrated to dryness. Purification by flash chromatography on silica gel (50% to 100% EtOAc in hexanes) gave the title compound (2.58 g) as an oil.

Example 251

TFA salt: 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid tert-Butyl 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oate (2.58 g, 2.67 mmol) was dissolved in DCM (5 mL) and TFA (5 mL) was added dropwise. The resulting solution was stirred for 20 minutes and then concentrated at reduced pressure. The residue was dissolved in 50% ACN/water (6 mL) and freeze-dried. Toluene (10 mL) was added and the mixture concentrated under reduced pressure. ACN (100 mL) was added to the mixture, concentrated under reduced pressure and died under vacuum to give a TFA salt of the title compound (3.18 g) as an orange oil. MS (ES, m/z): 809.4 [M+H]$^+$.

Example 251

HCl salt: 16-(3-(4-diethylamino-2-(4-(3-(trifluoromethyl)benzylcarbamoyl)pyridin-2-yl)phenylcarbamoyl)phenyl)-4,7,10,13-tetraoxahexadecan-1-oic acid To tert-butyl 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oate (1.31 g, 1.51 mmol) was added 4N HCl in dioxane (5.68 mL, 22.7 mmol). After stirring for 1 hour, the solvent was removed under a stream of nitrogen. Dioxane (5 mL) was added and then removed under a stream of nitrogen. The residue was then dried under vacuum. The resulting oil was combined with the product of another run (0.17 mmol), dissolved in 50% ACN/water (20 mL) and freeze-dried to give a HCl salt of the title compound (1.41 g) as a light pink solid. $^1$H NMR (400 MHz, CD$_3$OD, ppm) δ 9.52 (m, 0.3H), 8.96 (d, J=5.3 Hz, 1H), 8.79 (d, J=9.0 Hz, 1H), 8.44 (s, 1H), 5.15 (d, J=2.7 Hz, 1H), 7.93 (dd, J$_{AB}$=5.3 Hz, J$_{AC}$=1.6 Hz, 1H), 7.80-7.77 (m, 2H), 7.69 (d, J=2.6 Hz, 1H), 7.68-7.64 (m, 2H), 7.56-7.50 (m, 2H), 7.48-7.46 (m, 2H), 4.68 (s, 2H), 3.77 (quar, J=7.2 Hz, 4H), 3.67-3.47 (m, 16H), 2.80 (dd, J$_{AB}$=9.5 Hz, J$_{AC}$=7.4, 2H), 2.47 (t, J=6.2 Hz, 2H), 1.94-1.90 (m, 2H), 1.22 (t, J=7.2 Hz, 6H). MS (ES, m/z): 809.5 [M+H]$^+$.

Example 251

Na salt: 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid A hydrochloride salt of 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid (4.20 g, 4.76 mmol) was partitioned between EtOAc (70 mL) and water (50 mL). The pH was adjusted to 5.5 with 1N NaOH (7.5 mL), the layers were separated and the aqueous layer was extracted with EtOAc (2×50 mL). The combined organic layers were washed with water (25 mL) and brine (25 mL), then dried (Na$_2$SO$_4$ and concentrated to give the free base of the title compound as a yellow oil (3.96 g). The free base was dissolved in ACN (25 mL) and water (15 mL). 1N NaOH (4.75 mL) was added and the resulting solution was freeze-dried to give the sodium salt of the title compound as a yellow powder. $^1$H NMR (400 MHz, CD$_3$OD, ppm) δ 8.80 (d, J=5.3 Hz, 1H), 8.16 (s, 1H), 8.00 (d, J=9.0 Hz, 1H), 7.74 (dd, J$_{AB}$=5.0 Hz, J$_{AC}$=1.5 Hz, 1H), 7.69-7.65 (m, 3H), 7.61 (d, J=7.5 Hz, 1H), 7.53 (d, J=9.2 Hz, 1H), 7.50-7.48 (m, 1H), 7.39-7.37 (m, 2H), 7.07 (d, J=6.0 Hz, 1H), 6.87 (dd, J$_{AB}$=9.2 Hz, J$_{AC}$=2.9 Hz, 1H), 4.65 (s, 2H), 3.65 (t, J=6.9 Hz, 2H), 3.62-3.52 (m, 12H), 3.50-3.41 (m, 6H), 2.76 (t, J=7.3 Hz, 2H), 2.39 (t, J=6.8 Hz, 2H), 1.94-1.87 (m, 2H), 1.18 (t, J=7.0 Hz, 6H). MS (ES, m/z): 809.4 [M+H]$^+$.

Example 252

3-(2-(2-(2-(3-(3-((2-(4-(((S)-1,2,3,4-tetrahydronaphthalen-1-yl)carbamoyl)pyridin-2-yl)-4-(piperidin-1-yl)phenyl)carbamoyl)phenyl)propoxy)ethoxy)ethoxy)ethoxy)propanoic acid

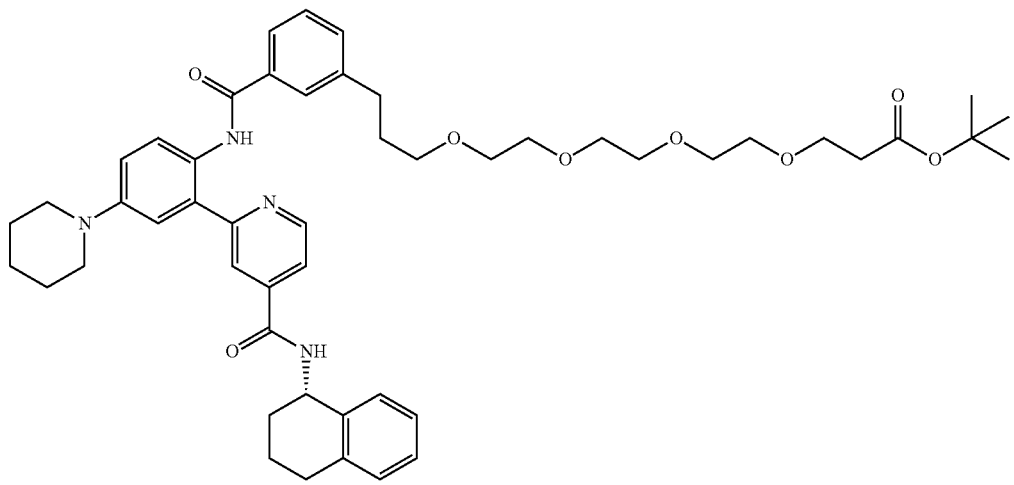 [SMILES: CC(C)(C)OC(=O)CCOCCOCCOCCOCCCc1cccc(C(=O)Nc2ccc(N3CCCCC3)cc2-c2cc(C(=O)N[C@H]3CCCc4ccccc43)ccn2)c1]

This compound was prepared according to the procedure described for the synthesis of Example 251 substituting 126e in place of 25b. Into a 50-mL round-bottom flask, was placed a solution of 3-(3-(2-(2-(2-(3-tert-butoxy-3-oxopropoxy)ethoxy)ethoxy)ethoxy)propyl)benzoic acid (1.308 g, 2.97 mmol, 1.00 equiv) in dichloromethane (15 mL), 2-(2-amino-5-(piperidin-1-yl)phenyl)-N—((S)-1,2,3,4-tetrahydronaphthalen-1-yl)isonicotinamide (1.26 g, 2.96 mmol, 0.99 equiv), EDC.HCl (854.8 mg, 4.46 mmol, 1.50 equiv), 4-dimethylaminopyridine (544 mg, 4.46 mmol, 1.50 equiv). The resulting solution was stirred overnight at room temperature. The reaction progress was monitored by LCMS/TLC (DCM:MeOH=10:1). The resulting mixture was washed with 2×20 mL of NH$_4$Cl aq. The resulting mixture was washed with 2×20 mL of Brine. The resulting mixture was concentrated under vacuum. The residue was applied onto a silica gel column with ethyl acetate/petroleum ether (1:10~1:1). This resulted in 2.0 g (79%) of tert-butyl 3-(2-(2-(2-(3-(3-((2-(4-(((S)-1,2,3,4-tetrahydronaphthalen-1-yl)carbamoyl)pyridin-2-yl)-4-(piperidin-1-yl)phenyl)carbamoyl)phenyl)propoxy)ethoxy)ethoxy)ethoxy)propanoate as yellow oil.

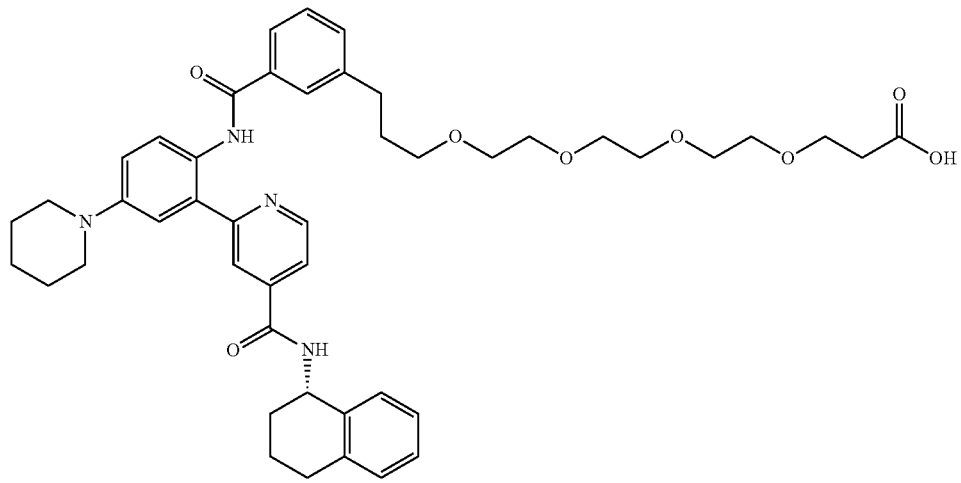 [SMILES: O=C(O)CCOCCOCCOCCOCCCc1cccc(C(=O)Nc2ccc(N3CCCCC3)cc2-c2cc(C(=O)N[C@H]3CCCc4ccccc43)ccn2)c1]

Example 252

Into a 100-mL round-bottom flask was placed a solution of tert-butyl 3-(2-(2-(2-(3-(3-((2-(4-(((S)-1,2,3,4-tetrahydronaphthalen-1-yl)carbamoyl)pyridin-2-yl)-4-(piperidin-1-yl)phenyl)carbamoyl)phenyl)propoxy)ethoxy)ethoxy)ethoxy)propanoate (2.3 g, 2.71 mmol, 1.00 equiv) in dichloromethane (20 mL), trifluoroacetic acid (20 mL). The resulting solution was stirred for 2 h at room temperature. The resulting mixture was concentrated under vacuum. The resulting solution was diluted with 20 mL of dichloromethane. The gas of HCl was introduced in. The mixture was stirred for 0.5 h, then concentrated under vacuum. This resulted in 1.60 g (68%) of 3-(2-(2-(2-(3-(3-((2-(4-(((S)-1,2,3,4-tetrahydronaphthalen-1-yl)carbamoyl)pyridin-2-yl)-4-(piperidin-1-yl)phenyl)carbamoyl)phenyl)propoxy)ethoxy)ethoxy)ethoxy)propanoic acid (HCl salt) as a yellow solid.

LC-MS (ES, m/z): 793 [M−2HCl+H]$^+$ H-NMR (300 MHz, CD3OD, ppm): 9.03 (d, J=5.7 Hz, 1H), 8.58 (s, 1H), 8.35 (s, 1H), 8.12 (m, 1H), 8.08 (m, 2H), 7.70 (m, 2H), 7.46 (m, 2H), 7.15 (m, 4H), 5.33 (t, J=6.0 Hz, 1H), 3.80-3.47 (m, 20H), 2.81-2.76 (m, 4H), 2.56-2.52 (t, J=6.0 Hz, 2H), 2.16 (m, 5H), 1.94-1.87 (m, 7H).

Example 253

Example A.2

(S)-16-(3-(4-(chloro)-2-(4-(1,2,3,4-tetrahydronaphthalen-1-ylcarbamoyl)pyridin-2-yl)phenylcarbamoyl)phenyl)-4,7,10,13-tetraoxahexadecan-1-oic acid

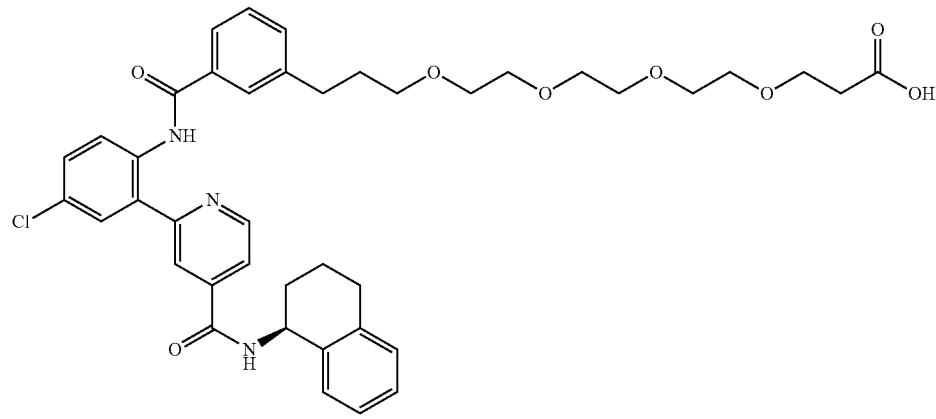 [SMILES: O=C(O)CCOCCOCCOCCOCCCc1cccc(C(=O)Nc2ccc(Cl)cc2-c2cc(C(=O)N[C@H]3CCCc4ccccc43)ccn2)c1]

Scheme 101. 1. HATU, DIPEA, DMAP, DMF, 65° C.; 2. TFA, DCM.

(S)-tert-butyl 16-(3-(4-chloro-2-(4-(1,2,3,4-tetrahydronaphthalen-1-ylcarbamoyl)pyridin-2-yl)phenylcarbamoyl)phenyl)-4,7,10,13-tetraoxahexadecan-1-oate. To a solution of (S)-2-(2-amino-5-chlorophenyl)-N-(1,2,3,4-tetrahydronaphthalen-1-yl)isonicotinamide 237b (1.02 g, 2.7 mmol), 3-(2,2-dimethyl-4-oxo-3,7,10,13,16-pentaoxanonadecan-19-yl)benzoic acid 251c (1.19 g, 2.7 mmol), DIPEA (1.04 g, 8.1 mmol) and DMAP (190 mg, 1.55 mmol) in DMF (20 ml) was added HATU (1.13 g, 2.97 mmol). The reaction mixture was heated at 65° C. for 24 hours, then cooled and concentrated. The residue was combined with another run (0.28 mmol scale), dissolved in DCM (150 mL), washed with water (4×50 mL), dried (Na$_2$SO$_4$) and concentrated to dryness. Purification by flash chromatography on silica gel (10% to 30% EtOAc in DCM) gave the title compound (1.44 g).

(S)-16-(3-(4-(chloro)-2-(4-(1,2,3,4-tetrahydronaphthalen-1-ylcarbamoyl)pyridin-2-yl)phenylcarbamoyl)phenyl)-4,7,10,13-tetraoxahexadecan-1-oic acid. Following the procedures described in Example 251, using (S)-tert-butyl 16-(3-(4-chloro-2-(4-(1,2,3,4-tetrahydronaphthalen-1-ylcarbamoyl)pyridin-2-yl)phenylcarbamoyl)phenyl)-4,7,10,13-tetraoxahexadecan-1-oate gave a HCl salt of the title compound. MS (ES, m/z): 744.2 [M+H]$^+$.

Example 254

2-(2-(3-((S)-3-(2-methoxyethylcarbamoyl)piperidine-1-carbonyl)benzamido)-5-(piperidin-1-yl)phenyl)-N—((S)-1,2,3,4-tetrahydronaphthalen-1-yl)isonicotinamide

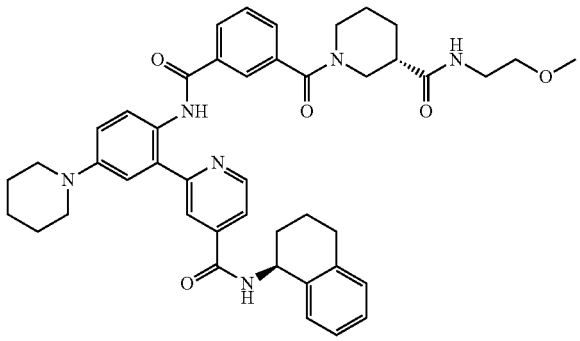 [SMILES: COCCNC(=O)[C@H]1CCCN(C(=O)c2cccc(C(=O)Nc3ccc(N4CCCCC4)cc3-c3cc(C(=O)N[C@H]4CCCc5ccccc54)ccn3)c2)C1]

This compound was prepared using the method described for the preparation of Example 4.14 using (S)-3-(4-(piperidin-1-yl)-2-(4-(1,2,3,4-tetrahydronaphthalen-1-ylcarbamoyl)pyridin-2-yl)phenylcarbamoyl)benzoic acid 126g in place of 4.1e. Purification by reverse-phase HPLC eluting with a water/ACN gradient containing 0.1% TFA gave a TFA salt of the title compound. MS (ES, m/z): 743.7 [M+H]$^+$.

Example 255

2-(2-(3-((S)-3-(2,5,8,11,14,17,20-heptaoxadocosan-22-yl(methyl)carbamoyl)piperidine-1-carbonyl)benzamido)-5-(piperidin-1-yl)phenyl)-N—((S)-1,2,3,4-tetrahydronaphthalen-1-yl)isonicotinamide

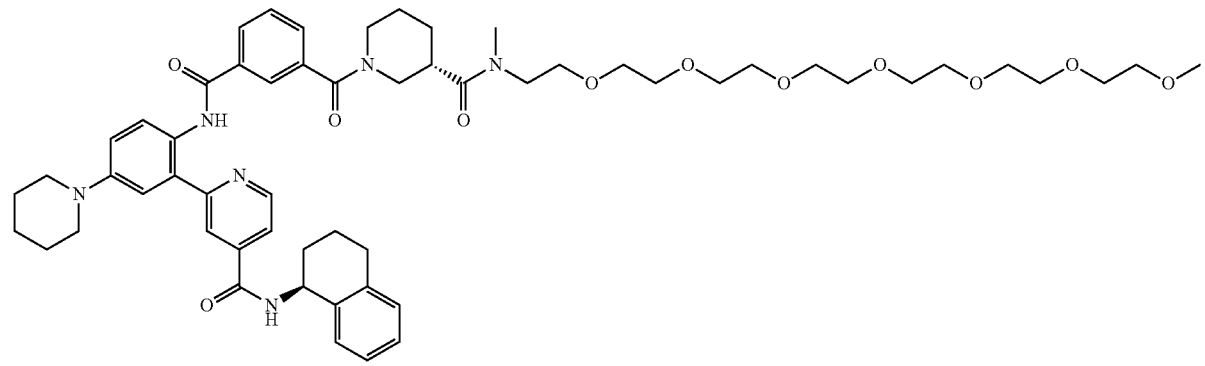 [SMILES: COCCOCCOCCOCCOCCOCCOCCN(C)C(=O)[C@H]1CCCN(C(=O)c2cccc(C(=O)Nc3ccc(N4CCCCC4)cc3-c3cc(C(=O)N[C@H]4CCCc5ccccc54)ccn3)c2)C1]

This compound was prepared using the method described for the preparation of Example 4.14 using (S)-3-(4-(piperidin-1-yl)-2-(4-(1,2,3,4-tetrahydronaphthalen-1-ylcarbamoyl)pyridin-2-yl)phenylcarbamoyl)benzoic acid 126g in place of 4.1e and N-methyl-2,5,8,11,14,17,20-heptaoxadocosan-22-amine 135c.1 in place of 2-methoxyethanamine. Purification by reverse-phase HPLC eluting with a water/ACN gradient containing 0.1% TFA gave a TFA salt of the title compound. MS (ES, m/z): 1021.5 [M+H]$^+$.

Example 256

2-(2-(3-((S)-3-(2,5,8,11,14,17,20-heptaoxadocosan-22-ylcarbamoyl)piperidine-1-carbonyl)benzamido)-5-(piperidin-1-yl)phenyl)-N—((S)-1,2,3,4-tetrahydronaphthalen-1-yl)isonicotinamide

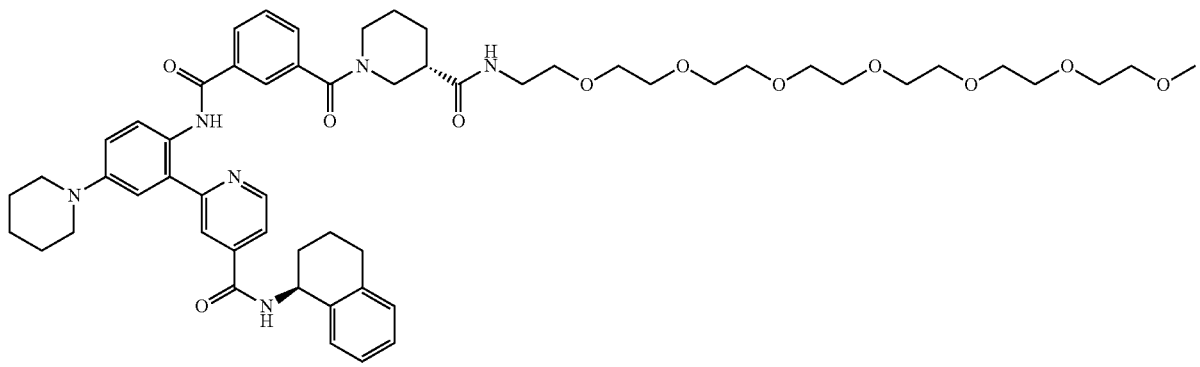 [SMILES: COCCOCCOCCOCCOCCOCCOCCNC(=O)[C@H]1CCCN(C(=O)c2cccc(C(=O)Nc3ccc(N4CCCCC4)cc3-c3cc(C(=O)N[C@H]4CCCc5ccccc54)ccn3)c2)C1]

This compound was prepared using the method described for the preparation of Example 4.14 using (S)-3-(4-(piperidin-1-yl)-2-(4-(1,2,3,4-tetrahydronaphthalen-1-ylcarbamoyl)pyridin-2-yl)phenylcarbamoyl)benzoic acid 126g in place of 4.1e and 2,5,8,11,14,17,20-heptaoxadocosan-22-amine 135c.6 in place of 2-methoxyethanamine. Purification by reverse-phase HPLC eluting with a water/ACN gradient containing 0.1% TFA gave a TFA salt of the title compound. MS (ES, m/z): 1007.5 [M+H]$^+$.

Example 257

(S)-2-(2-(3-(16-(3-(2,5,8,11,14,17,20-heptaoxadocosan-22-yl(methyl)carbamoyl)piperidin-1-yl)-16-oxo-4,7,10,13-tetraoxahexadecyl)benzamido)-5-(diethylamino)phenyl)-N-(3-(trifluoromethyl)benzyl)isonicotinamide Scheme 102.

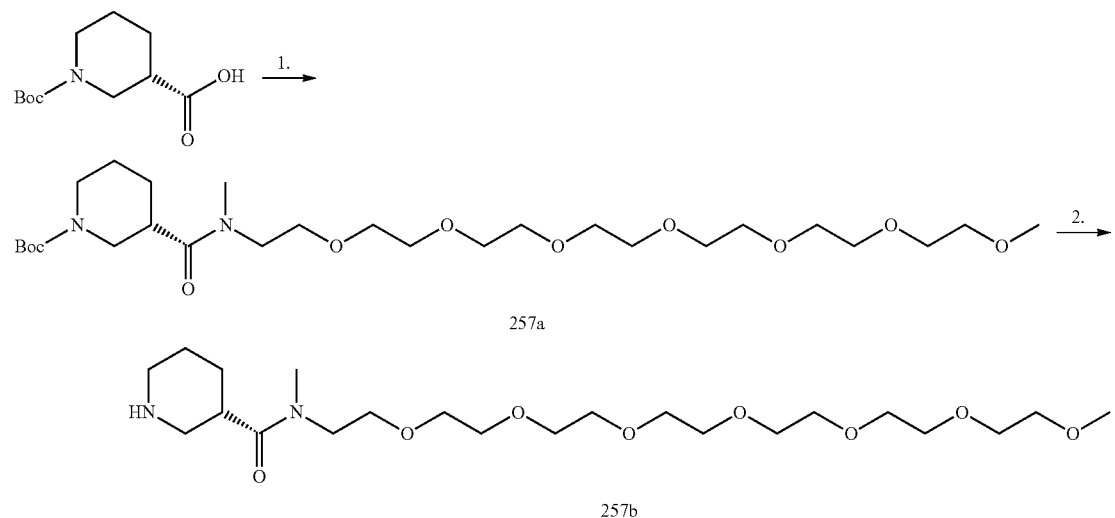

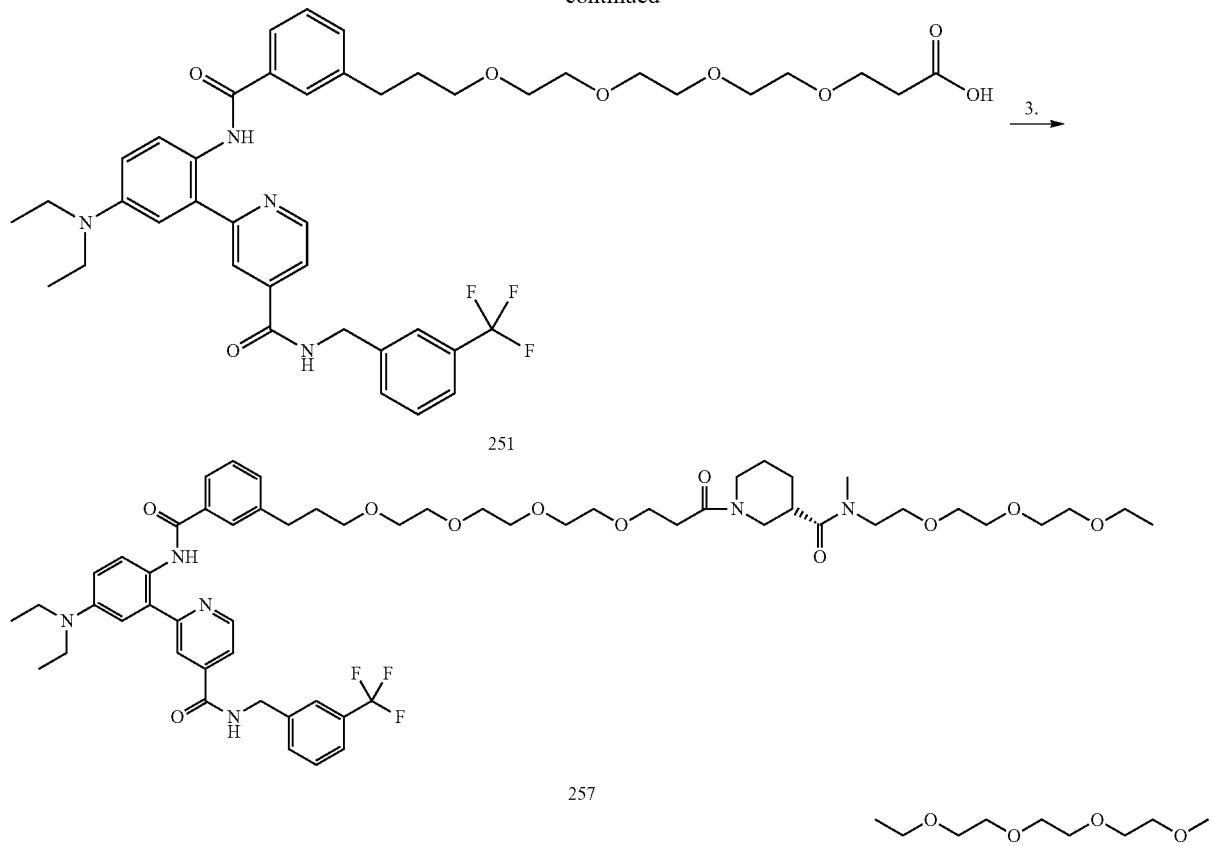

1. HATU, DIPEA, 135c. 1, DMF;
2. TFA, DCM
3. HATU, DIPEA, 257b, DMF.

Intermediate 257a

To a solution of Boc-(S)-nipecotic acid (137 mg, 0.60 mmol), N-methyl-2,5,8,11,14,17,20-heptaoxadocosan-22-amine 135c.1 (310 mg, 0.88 mmol) and DIPEA (335 mg, 2.6 mmol) in DMF (3 mL) was added HATU (285 mg, 0.75 mmol). The reaction was stirred for 1 hour and then the DMF was removed under vacuum. The residue was added to saturated aqueous NaHCO$_3$ (10 mL) and extracted with DCM (3×20 mL). The combined organic layers were dried (Na$_2$SO$_4$) and concentrated to give (S)-tert-butyl 3-(2,5,8,11,14,17,20-heptaoxadocosan-22-yl(methyl)carbamoyl)piperidine-1-carboxylate (720 mg).

Intermediate 257b

Trifluoroacetic acid (2 mL) was added to a solution of (S)-tert-butyl 3-(2,5,8,11,14,17,20-heptaoxadocosan-22-yl(methyl)carbamoyl)piperidine-1-carboxylate (720 mg) in DCM (2 mL) and stirred at RT for 30 minutes. The solvents were removed under vacuum to give a TFA salt of (S)—N-(2,5,8,11,14,17,20-heptaoxadocosan-22-yl)-N-methylpiperidine-3-carboxamide (760 mg).

Example 257

(S)-2-(2-(3-(16-(3-(2,5,8,11,14,17,20-heptaoxadocosan-22-yl(methyl)carbamoyl)piperidin-1-yl)-16-oxo-4,7,10,13-tetraoxahexadecyl)benzamido)-5-(diethylamino)phenyl)-N-(3-(trifluoromethyl)benzyl)isonicotinamide To a solution of 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid Example 251 in place of 4.1e and 2,5,8,11,14,17,20-heptaoxadocosan-22-amine in place of 2-methoxyethanamine. To a solution of 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid (50 mg, 0.062 mmol), intermediate 257b (50 mg, 0.086 mmol) and DIPEA (31 uL, 0.18 mmol) in DMF (1.0 mL) was added HATU (27 mg, 0.070 mmol). The reaction was stirred for 90 minutes and then the DMF was removed under vacuum. Purification by reverse-phase HPLC eluting with a water/ACN gradient containing 0.1% TFA gave a TFA salt of the title compound (65 mg). MS (ES, m/z): 1255.5 [M+H]$^+$.

Example 258

2-(2-(3-(16-(4-(2,5,8,11,14,17,20-heptaoxadocosan-22-yl)-3-oxopiperazin-1-yl)-16-oxo-4,7,10,13-tetraoxahexadecyl)benzamido)-5-(diethylamino)phenyl)-N-(3-(trifluoromethyl)benzyl)isonicotinamide

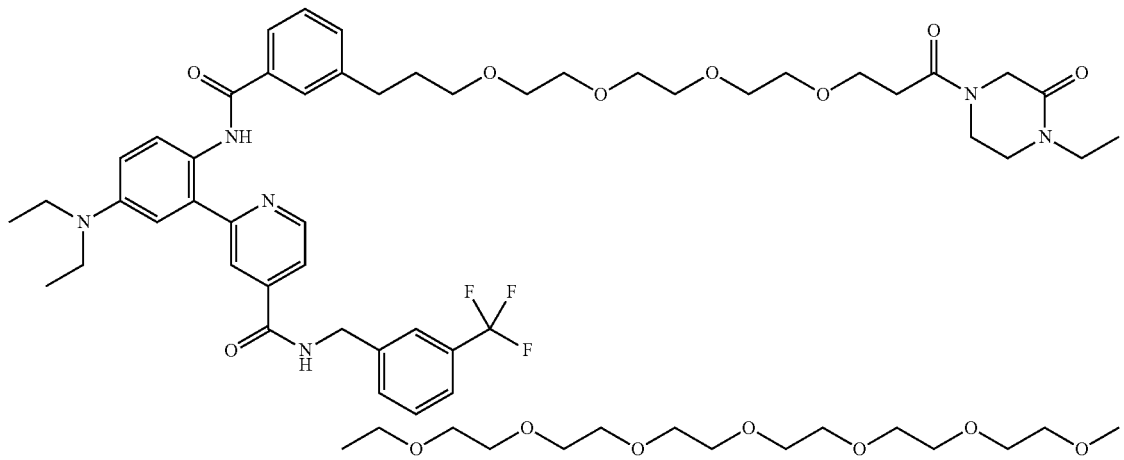

This compound was prepared using the same method described for the preparation of Example 257 using a TFA salt of 1-(2,5,8,11,14,17,20-heptaoxadocosan-22-yl)piperazin-2-one 135c.5 in place of intermediate 257b. $^1$H NMR (400 MHz, CD$_3$OD, ppm) δ 9.44 (t, J=6.0 Hz, 0.4H), 8.92 (d, j=5.0 Hz, 1H), 8.74 (d, J=8.6 Hz, 1H), 8.39 (s, 1H), 7.99 (br s, 1H), 7.87 (dd, J$_{AB}$=5.1 Hz, J$_{AC}$=1.2 Hz, 1H), 7.80-7.76 (m, 2H), 7.69 (s, 1H), 7.64 (d, J=7.6 Hz, 1H), 7.58-7.50 (m, 3H), 7.46 (d, J=5.0 Hz), 4.68 (s, 2H), 4.18 (s, 0.8H), 4.09 (s, 1.2H), 3.76-3.66 (m, 8H), 3.63-3.45 (m, 44H), 3.31 (s, 3H), 2.80 (t (J=7.4 Hz, 2H), 2.64-2.54 (m, 2H), 1.95-1.87 (m, 2H), 1.20 (t, J=7.2 Hz, 6H). MS (ES, m/z): 1213.5 [M+H]$^+$.

Example 259

2-(5-(diethylamino)-2-(3-(23-methyl-24-oxo-2,5,8,11,14,17,20,27,30,33,36-undecaoxa-23-azanonatriacontan-39-yl)benzamido)phenyl)-N-(3-(trifluoromethyl)benzyl)isonicotinamide

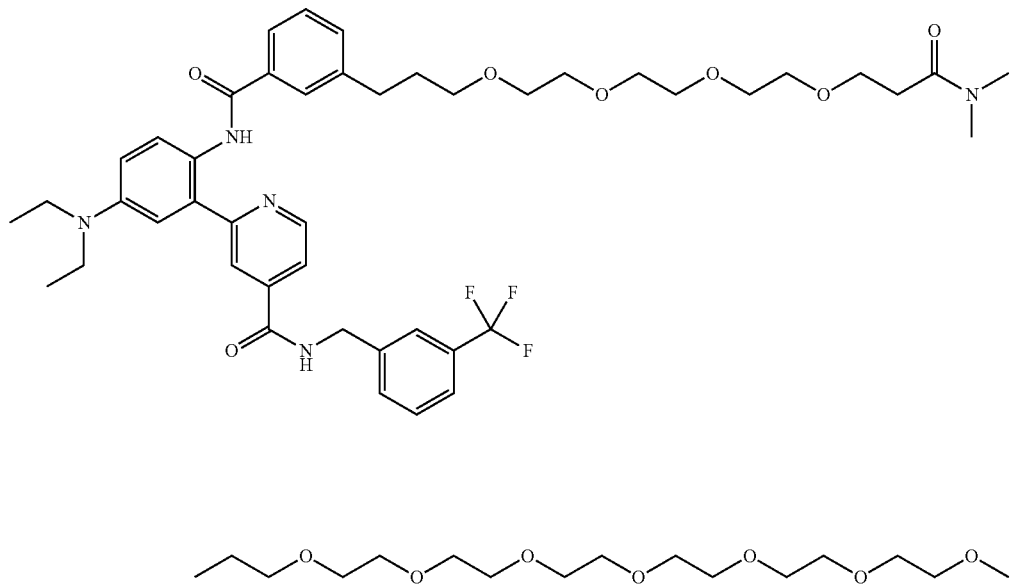

This compound was prepared using the same method described for the preparation of Example 257 using a N-methyl-2,5,8,11,14,17,20-heptaoxadocosan-22-amine 135c.1 in place of a TFA salt of (S)—N-(2,5,8,11,14,17,20-heptaoxadocosan-22-yl)-N-methylpiperidine-3-carboxamide. MS (ES, m/z): 1144.4 [M+H]+.

Example 260

2-(5-(diethylamino)-2-(3-(24-oxo-2,5,8,11,14,17,20,27,30,33,36-undecaoxa-23-azanonatriacontan-39-yl)benzamido)phenyl)-N-(3-(trifluoromethyl)benzyl)isonicotinamide

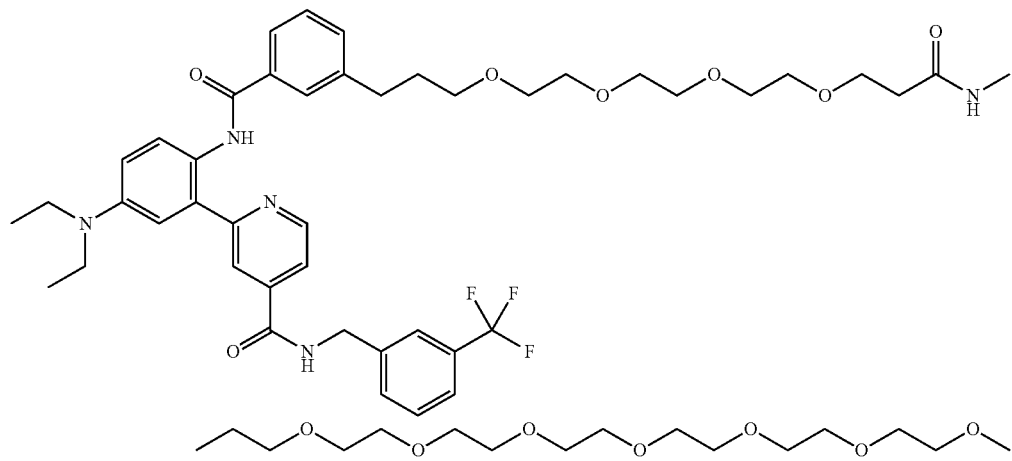

This compound was prepared using the same method described for the preparation of Example 257 using 2,5,8,11,14,17,20-heptaoxadocosan-22-amine 135c.6 in place of a TFA salt of (S)—N-(2,5,8,11,14,17,20-heptaoxadocosan-22-yl)-N-methylpiperidine-3-carboxamide. MS (ES, m/z): 1130.5 [M+H]+.

Example 261

(S)-2-(2-(3-(2,5,8,11,14,17,20,23,26-nonaoxanonacosan-29-yl)benzamido)-5-(diethylamino)phenyl)-N-(1,2,3,4-tetrahydronaphthalen-1-yl)isonicotinamide Scheme 103.

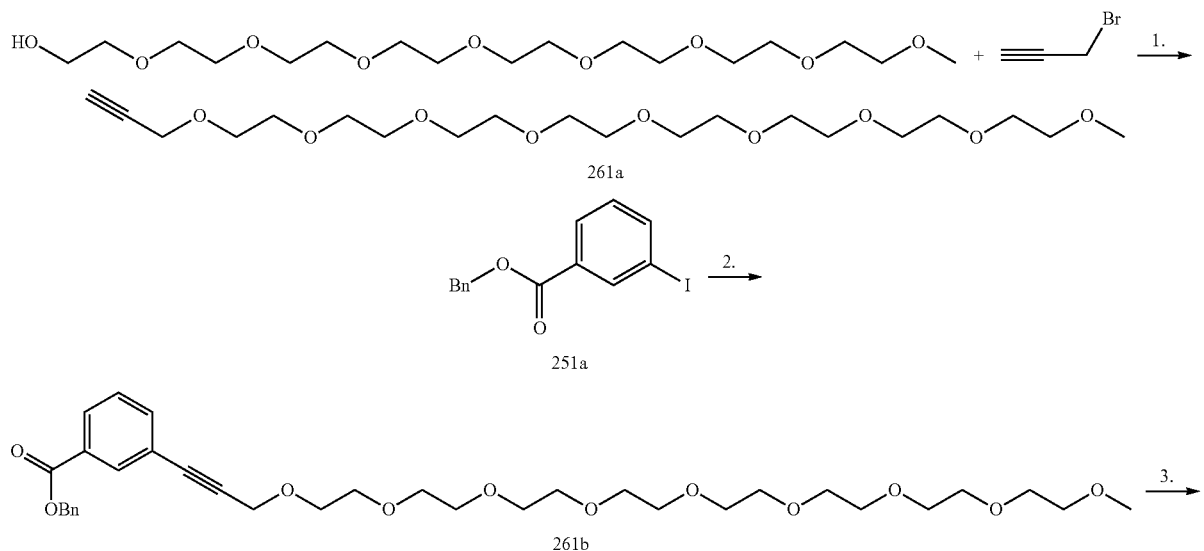

-continued

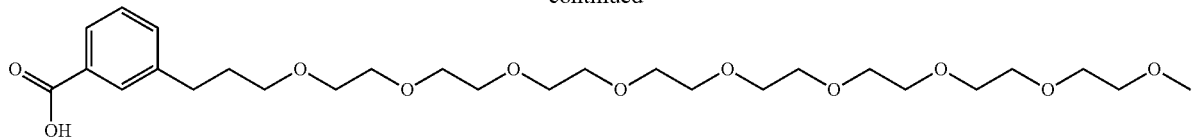

261c

1. Na, THF
2. copper(I)iodide, Pd(PPh3)2Cl2, triethylamine
3. Pd/C, H2, MeOH.

Intermediate 261a

Into a 500-mL round-bottom flask, was placed a solution of 2-(2-(2-(2-(2-(2-(2-(2-methoxyethoxy)ethoxy)ethoxy)ethoxy)ethoxy)ethoxy)ethoxy)ethanol (15 g, 39.06 mmol, 1.00 equiv) in tetrahydrofuran (150 mL). This was followed by the addition of sodium hydride (1.9 g, 79.17 mmol, 1.01 equiv), in portions at 0-5° C. in 5 min. To this was added a solution of 3-bromoprop-1-yne (9.3 g, 78.81 mmol, 2.02 equiv) in toluene (20 mL) dropwise with stirring at 0-5° C. in 5 min. The resulting solution was stirred for 1 h at 0-5° C. in a water/ice bath. The reaction progress was monitored by LCMS/TLC (ethyl acetate/petroleum ether=1:1). The solids were filtered out. The resulting mixture was concentrated under vacuum. This resulted in 15.9 g (96%) of 3-(2-(2-(2-(2-(2-(2-(2-(2-methoxyethoxy)ethoxy)ethoxy)ethoxy)ethoxy)ethoxy)ethoxy)prop-1-yne as brown oil

Intermediate 261b

Into a 250-mL round-bottom flask purged and maintained with an inert atmosphere of nitrogen, was placed a solution of 3-(2-(2-(2-(2-(2-(2-(2-(2-methoxyethoxy)ethoxy)ethoxy)ethoxy)ethoxy)ethoxy)ethoxy)ethoxy)prop-1-yne (12.7 g, 30.09 mmol, 1.00 equiv) in tetrahydrofuran (150 mL), benzyl 3-iodobenzoate (15.9 g, 47.04 mmol, 1.56 equiv), CuI (720 mg, 3.79 mmol, 0.13 equiv), Pd(PPh3)2Cl2 (2.65 g, 3.77 mmol, 0.13 equiv), triethylamine (7.6 g, 75.25 mmol, 2.50 equiv). The resulting solution was stirred for 2 h at room temperature. The reaction progress was monitored by LCMS/TLC (ethyl acetate/petroleum ether=4:1). The resulting mixture was concentrated under vacuum. The resulting solution was diluted with 200 mL of water. The resulting solution was extracted with 3×150 of ethyl acetate and the organic layers combined. The resulting mixture was washed with 3×100 mL of sodium chloride (aq). The resulting mixture was concentrated under vacuum. The residue was applied onto a silica gel column with ethyl acetate/petroleum ether (1:2-ethyl acetate). This resulted in 12.8 g (65%) of benzyl 3-(3-(2-(2-(2-(2-(2-(2-(2-(2-methoxyethoxy)ethoxy)ethoxy)ethoxy)ethoxy)ethoxy)ethoxy)ethoxy)prop-1-ynyl)benzoate as brown oil.

Intermediate 261c

Into a 1000-mL round-bottom flask, was placed a solution of benzyl 3-(3-(2-(2-(2-(2-(2-(2-(2-(2-methoxyethoxy)ethoxy)ethoxy)ethoxy)ethoxy)ethoxy)ethoxy)ethoxy)prop-1-ynyl)benzoate (23 g, 36.39 mmol, 1.00 equiv) in methanol (200 mL), Palladium carbon (20 g). Hydrogen gas was introduced to the reaction vessel The resulting solution was stirred overnight at room temperature. The reaction progress was monitored by LCMS/TLC (ethyl acetate/petroleum ether=4:1). The solids were filtered out. The resulting mixture was concentrated under vacuum. This resulted in 17.2 g (80%) of 3-(3-(2-(2-(2-(2-(2-(2-(2-(2-methoxyethoxy)ethoxy)ethoxy)ethoxy)ethoxy)ethoxy)ethoxy)ethoxy)propyl)benzoic acid as brown oil. LC-MS (ES, m/z): 547 [M+H]$^+$. H-NMR (300 MHz, CDCl$_3$, ppm): 7.948-7.920 (m, 2H), 7.425-7.280 (m, 2H), 5.763 (s, 2H), 3.673-3.390 (m, 38H), 2.801-2.750 (1, J=7.8 Hz, 2H), 1.985-1.893 (m, 2H)

Scheme 104.

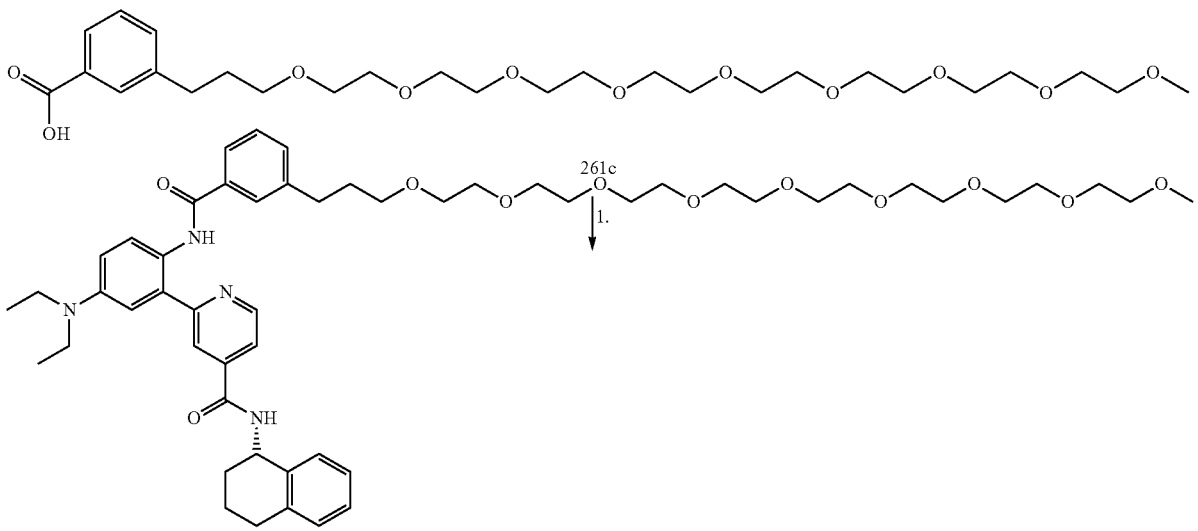

1. A) (COCl)2, DMF, DCM
b) 4. 131c TEA, DCM.

261

Example 261

(S)-2-(2-(3-(2,5,8,11,14,17,20,23,26-nonaoxanonacosan-29-yl)benzamido)-5-(diethylamino)phenyl)-N-(1,2,3,4-tetrahydronaphthalen-1-yl)isonicotinamide To a solution of 261c (10.9 g, 20.0 mmol, 1.5 eq) in DCM (100 mL) under $N_2$ was added oxalyl dichloride (3.04 g, 23.9 mmol, 1.8 eq) and DMF (catalytic). After 1 hour, the solvent was removed and the crude acid chloride dissolved in dry DCM (30 mL). The resulting solution was added dropwise to a solution of 131c (5.5 g, 13.3 mmol, 1 eq) and TEA (5.4 g, 53.2 mmol, 4 eq) in dry DCM (66 mL) at 0° C. The reaction mixture was allowed to come to room temperature under an atmosphere of $N_2$. After 1 hour, the resulting solution was diluted with DCM (40 mL), washed with water (3×75 mL) and brine, and dried over $Na_2SO_4$ to give 10.4 g of (S)-2-(2-(3-(2,5,8,11,14,17,20,23,26-nonaoxanonacosan-29-yl)benzamido)-5-(diethylamino)phenyl)-N-(1,2,3,4-tetrahydronaphthalen-1-yl)isonicotinamide (98% purity) as a yellow oil. MS (ES, m/z) 943.5 [M+H]$^+$; $^1$H NMR (400 MHz, d$_6$DMSO) δ 11.57 (s, 1H), 9.13 (d, J=8.6 Hz, 1H), 8.85 (d, J=5.1 Hz, 1H), 8.21 (s, 1H), 8.04 (d, J=9.0 Hz, 1H), 7.81 (dd, J=5.1, 1.5 Hz, 1H), 7.70-7.63 (m, 2H), 7.46-7.37 (m, 2H), 7.22-7.02 (m, 5H), 6.85 (dd, f=9.1, 2.9 Hz, 1H), 5.28-5.19 (m, 1H), 3.55-3.45 (m, 32H), 3.44-3.35 (m, 8H), 3.31 (s, 3H), 3.22 (s, 3H), 2.81-2.74 (m, 2H), 2.74-2.66 (m, 2H), 2.04-1.91 (m, 2H), 1.88-1.71 (m, 4H), 1.12 (t, J=7.0 Hz, 6H).

Example 262

2-(2-(3-(16-(4-(3-(2,5,8,11,14,17,20,23,26-nonaoxanonacosan-29-yl)benzoyl)piperazin-1-yl)-16-oxo-4,7,10,13-tetraoxahexadecyl)benzamido)-5-(diethylamino)phenyl)-N-(3-(trifluoromethyl)benzyl)isonicotinamide Scheme 105.

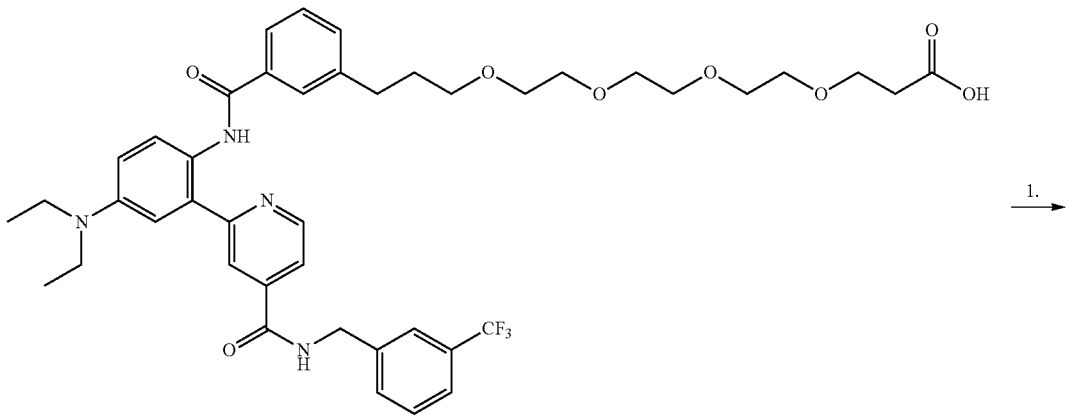

251

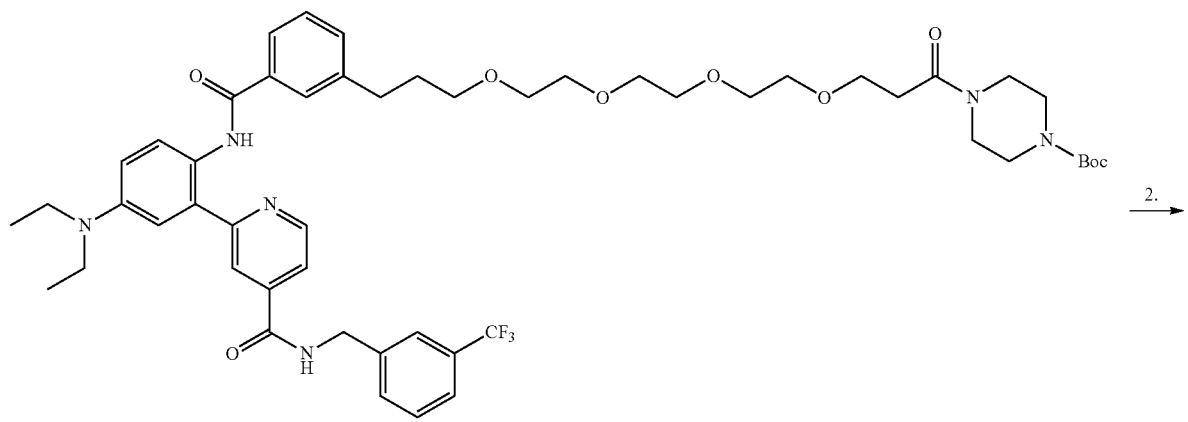

262a

-continued

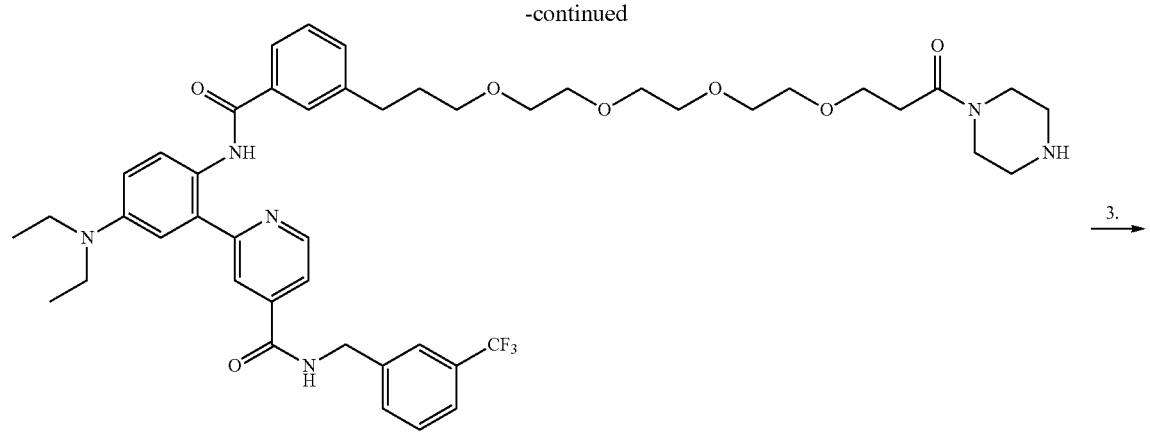

262b

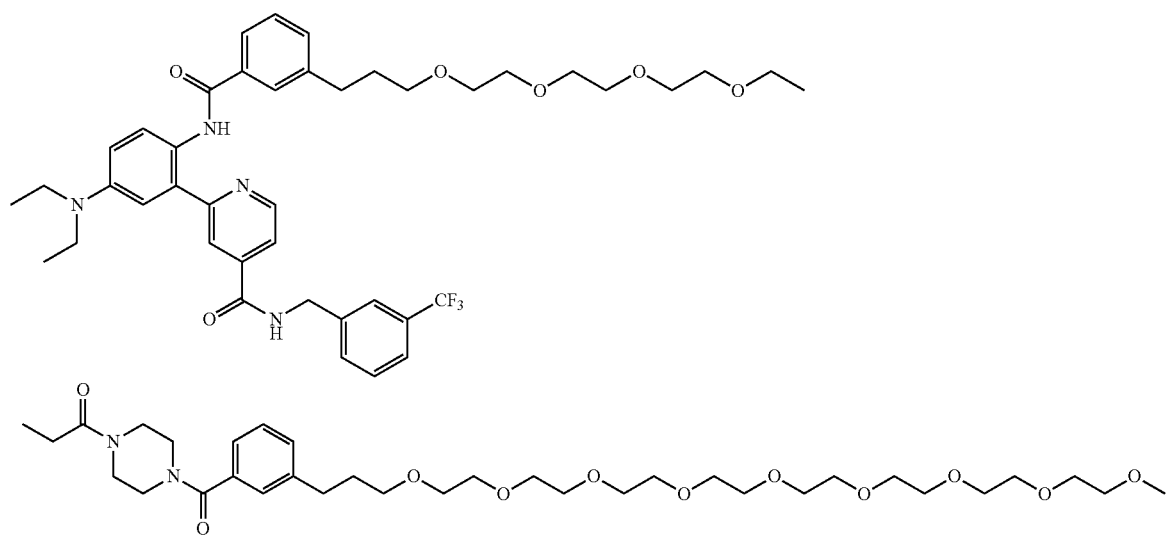

262

1. tert-butyl piperazine-1-carboxylate, HATU, DIPEA, DMF;
2. TFA, DCM;
3. 261c HATU, DIPEA, DMF.

Intermediate 262b: 2-(5-(diethylamino)-2-(3-(16-oxo-16-(piperazin-1-yl)-4,7,10,13-tetraoxahexadecyl)benzamido)phenyl)-N-(3-(trifluoromethyl)benzyl)isonicotinamide To a mixture of 16-(3-(4-(diethyl amino)-2-(4-(3-(trifluoromethyl)benzylcarbamoyl)pyridin-2-yl)phenylcarbamoyl)phenyl)-4,7,10,13-tetraoxahexadecan-1-oic acid (292 mg, 0.36 mmol), tert-butyl piperazine-1-carboxylate (75 mg, 0.40 mmol) and DIPEA (142 mg, 1.1 mmol) in DMF (3 mL) was added HATU (160 mg, 0.42 mmol). After 30 minutes, the solvent was removed under vacuum and the residue was dissolved in DCM (50 mL). This was washed with water (4×25 mL), dried (Na$_2$SO$_4$) and concentrated. The resulting oil was dissolved in DCM (2 mL) and TFA (2 mL) was added dropwise. After 30 minutes, the solvents were removed under vacuum. The residue was dissolved in 50% ACN/water (30 mL) and freeze dried to give the title compound (560 mg) as a TFA salt.

Example 262

2-(2-(3-(16-(4-(3-(2,5,8,11,14,17,20,23,26-nonaoxanonacosan-29-yl)benzoyl)piperazin-1-yl)-16-oxo-4,7,10,13-tetraoxahexadecyl)benzamido)-5-(diethylamino)phenyl)-N-(3-(trifluoromethyl)benzyl)isonicotinamide To a solution of a TFA salt of 2-(5-(diethylamino)-2-(3-(16-oxo-16-(piperazin-1-yl)-4,7,10,13-tetraoxahexadecyl)benzamido)phenyl)-N-(3-(trifluoromethyl)benzyl)isonicotinamide (50 mg, 0.041 mmol), 3-(2,5,8,11,14,17,20,23,26-nonaoxanonacosan-29-yl)benzoic acid 261c (22 mg, 0.041 mmol) and DIPEA (26 mg, 0.20 mmol) in DMF (1.0 mL) was added HATU (27 mg, 0.070 mmol). The reaction was stirred for 90 minutes and then the DMF was removed under vacuum. Purification by reverse-phase HPLC eluting with a water/ACN gradient containing 0.1% TFA gave a TFA salt of the title compound (33 mg). MS (ES, m/z): 1405.6 [M+H]$^+$.

Example 263
2-(5-(diethylamino)-2-(3-(16-(4-(4-(2-(2-(2-methoxyethoxy)ethoxy)ethoxy)phenyl)piperazin-1-yl)-16-oxo-4,7,10,13-tetraoxahexadecyl)benzamido)phenyl)-N-(3-(trifluoromethyl)benzyl)isonicotinamide
Scheme 106.
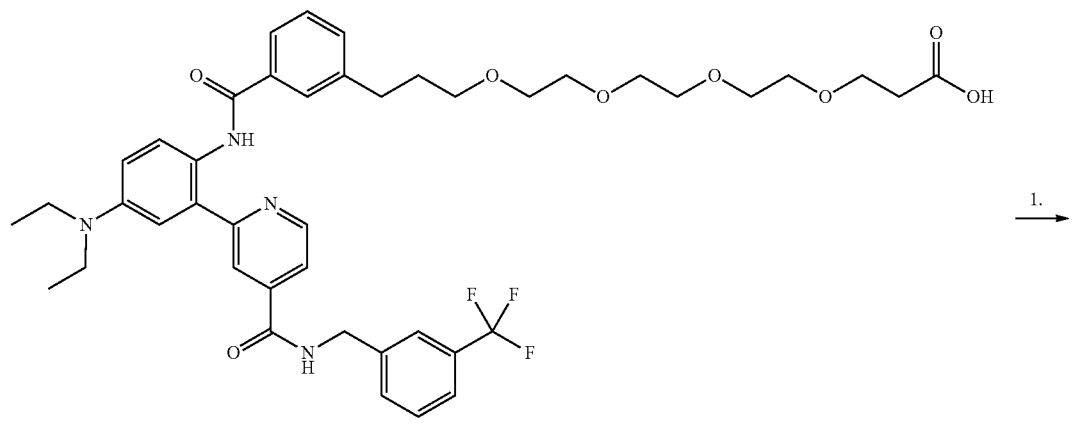
251
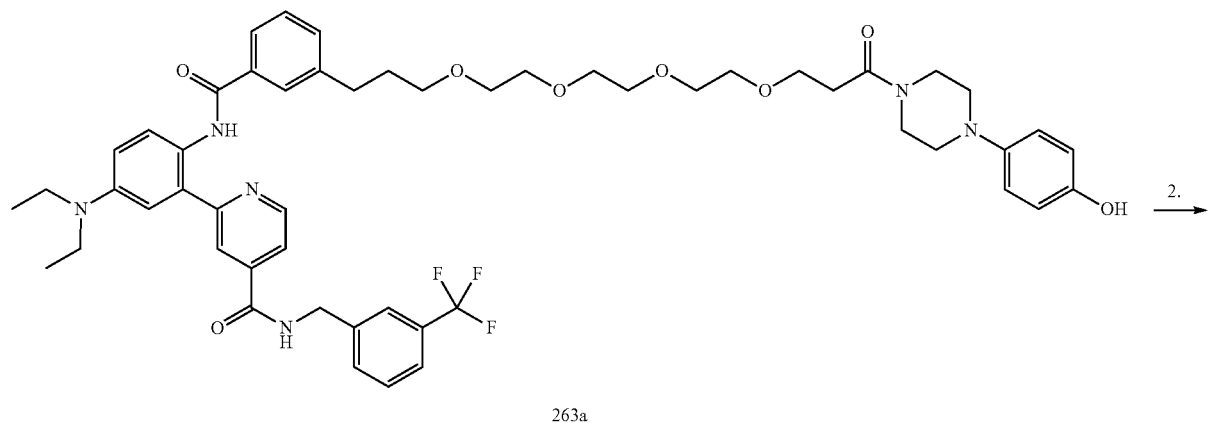
263a
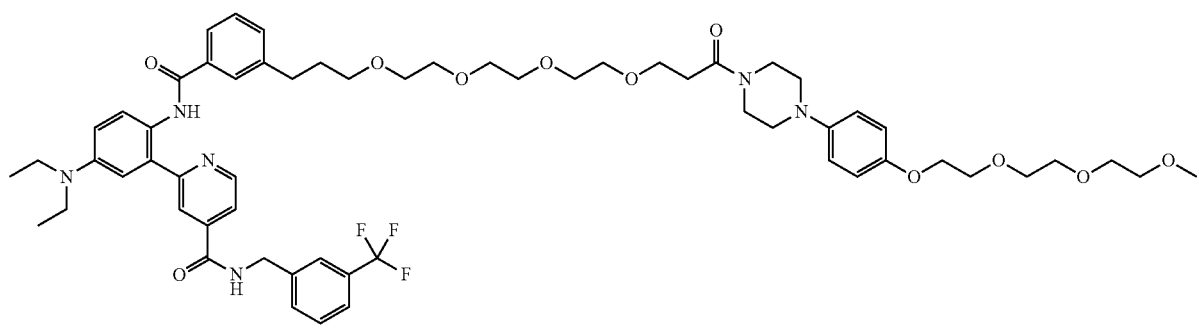
263
1. 4-(piperazin-1-yl)phenol, HATU, DIPEA, DMF; 2. 2-(2-(2-methoxyethoxy)ethoxy)ethyl 4-methylbenzendsulfonate, K$_2$CO$_3$, DMF.

Intermediate 263a: 2-(5-(diethylamino)-2-(3-(16-(4-(4-hydroxyphenyl)piperazin-1-yl)-16-oxo-4,7,10,13-tetraoxahexadecyl)benzamido)phenyl)-N-(3-(trifluoromethyl)benzyl)isonicotinamide To a solution of 16-(3-(4-(diethylamino)-2-(4-(3-(trifluoromethyl)benzylcarbamoyl)pyridin-2-yl)phenylcarbamoyl)phenyl)-4,7,10,13-tetraoxahexadecan-1-oic acid (300 mg, 0.37 mmol), 4-(piperazin-1-yl)phenol (71 mg, 0.40 mmol) and DIPEA (142 mg, 1.1 mmol) in DMF (3 mL) was added HATU (160 mg, 0.42 mmol). After 30 minutes, the solvent was removed under vacuum and the residue was dissolved in DCM (50 mL). This was washed with water (4×25 mL), dried (Na$_2$SO$_4$) and concentrated to give the title compound (379 mg).

Example 263

2-(5-(diethylamino)-2-(3-(16-(4-(4-(2-(2-(2-methoxyethoxy)ethoxy)ethyoxy)phenyl)piperazin-1-yl)-16-oxo-4,7,10,13-tetraoxahexadecyl)benzamido)phenyl)-N-(3-(trifluoromethyl)benzyl) isonicotinamide Finely ground K$_2$CO$_3$ (54 mg, 039 mmol) was added to a solution of 2-(5-(diethylamino)-2-(3-(16-(4-(4-hydroxyphenyl)piperazin-1-yl)-16-oxo-4,7,10,13-tetraoxahexadecyl)benzamido)phenyl)-N-(3-(trifluoromethyl)benzyl)isonicotinamide (125 mg, 0.13 mmol) and 2-(2-(2-methoxyethoxy)ethoxy)ethyl 4-methylbenzenesulfonate (50 mg, 0.16 mmol) in DMF (0.30 mL), and was heated at 70° C. for 3 hours with stirring. The reaction mixture was cooled to room temperature and another portion of 2-(2-(2-methoxyethoxy)ethoxy)ethyl 4-methylbenzenesulfonate (75 mg, 0.34 mmol) was added. The mixture was stirred for 3 days at room temperature and then 5 hours at 70° C. Water (10 mL) was added to the cooled reaction mixture and extracted with DCM (3×10 mL). The combined organic layers were dried (Na$_2$SO$_4$) and concentrated. Purification by reverse-phase HPLC eluting with a water/ACN gradient containing 0.1% TFA gave a TFA salt of the title compound (80 mg). $^1$H NMR (400 MHz, CD$_3$OD, ppm) δ 9.44 (t, J=5.0 Hz, 0.6H), 8.93 (dd, J$_{AB}$=5.3 Hz, J$_{AC}$=0.6 Hz, 1H), 8.84 (d, J=9.0 Hz, 1H), 8.40 (s, 1H), 8.09 (d, J=2.5 Hz, 1H), 7.88 (dd, J$_{AB}$=5.1 Hz. J$_{AC}$=0.5 Hz, 1H), 7.80 (m, 2H), 7.69 (s, 1H), 7.65-7.52 (m, 4H), 7.47 (dd, J$_{AB}$=4.1 Hz, J$_{AC}$=1.2 Hz, 2H), 7.09 (d, J=9.0 Hz, 2H), 6.88 (d, J=9.2 Hz), 4.69 (d, J=4.3 Hz 2H), 4.04 (m, 2H), 3.78-3.68 (m, 12H), 3.66-3.63 (m, 2H), 3.62-3.52 (m, 16H), 3.51-3.45 (m, 4H), 3.31 (s, 3H), 3.22 (t, J=4.1 Hz, 2H), 3.16 (t, J=4.1 Hz, 2H), 2.80 (t, J=7.4 Hz, 2H), 2.64 (t, J=6.3 Hz, 2H), 1.91 (m, 2H), 1.20 (t, J=7.1 Hz, 6H). MS (ES, m/z): 1115.4 [M+H]$^+$.

Example 264

1-(3-(3-(4-chloro-2-(4-(3-(trifluoromethyl)benzylcarbamoyl)pyridin-2-yl)phenylcarbamoyl)benzylthio)phenyl)-1-oxo-5,8,11-trioxa-2-azatetradecan-14-oic acid

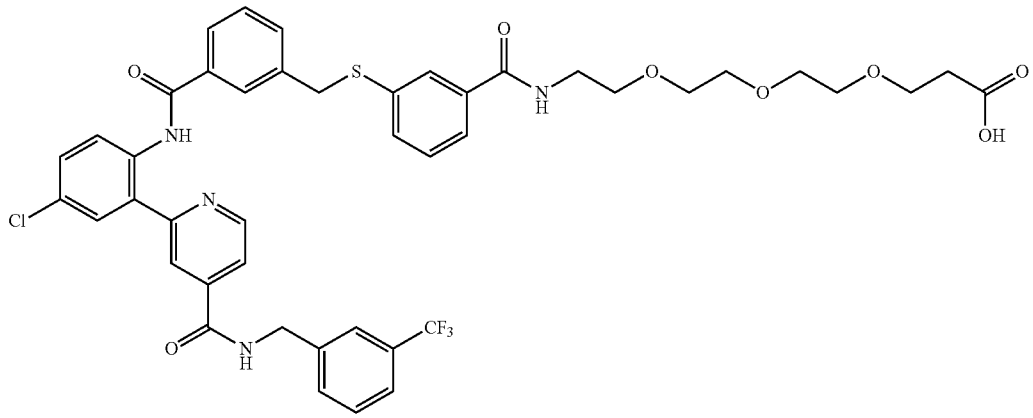 [SMILES: O=C(O)CCOCCOCCOCCNC(=O)c1cccc(SCc2cccc(C(=O)Nc3ccc(Cl)cc3-c3cc(C(=O)NCc4cccc(C(F)(F)F)c4)ccn3)c2)c1]

497

This compound was prepared using the method described for the preparation of Example 10.1 using 3-(3-(4-chloro-2-(4-(3-(trifluoromethyl)benzylcarbamoyl)pyridin-2-yl)phenylcarbamoyl)benzylthio)benzoic acid (Example 8.25) in place of 3-(3-(4-(piperidin-1-yl)-2-(4-(3-(trifluoromethyl) benzylcarbamoyl)pyridin-2-yl)phenylcarbamoyl)benzylthio)benzoic acid (8.1) to give a TFA salt of the title compound. MS (ES, m/z): 879.3 [M+H]$^+$.

498

Example 265

2-(2-(3-(2,5,8,11,14,17,20,23-octaoxa-26-thiaheptacosan-27-yl)benzamido)-5-(diethylamino)phenyl)-N-(3-(trifluoromethyl)benzyl)isonicotinamide Scheme 107.

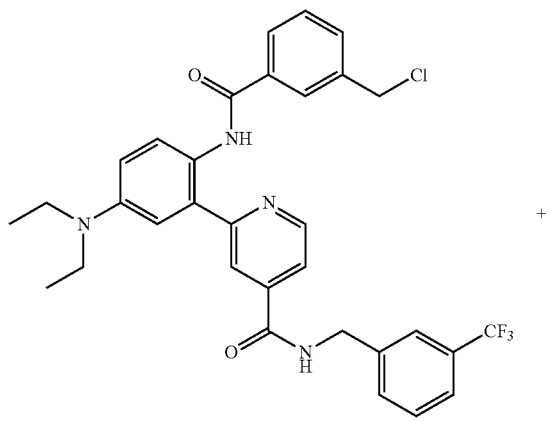

143a

+

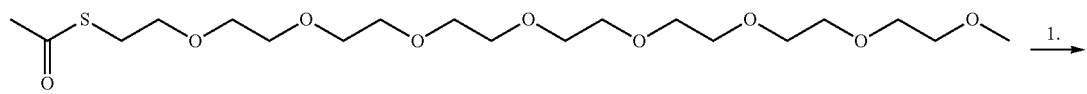

135c.3

1.

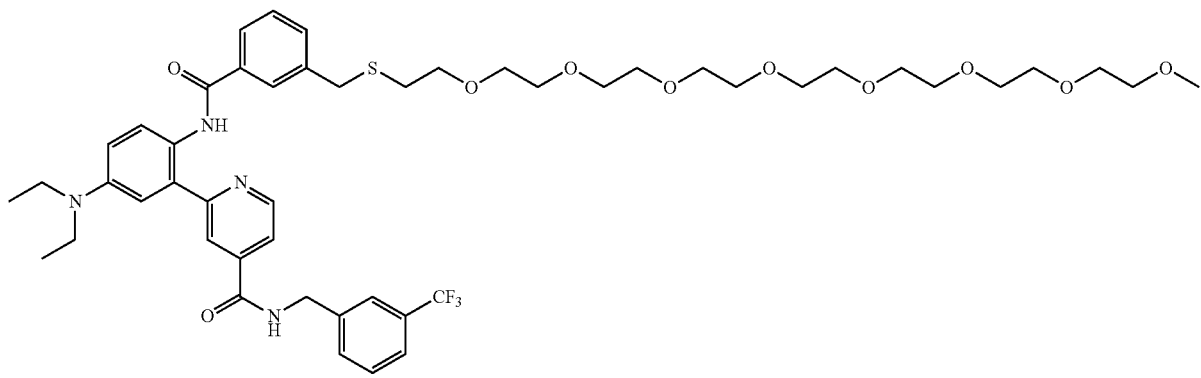

265

1. MeONa, DMF.

Example 265

2-(2-(3-(2,5,8,11,14,17,20,23-octaoxa-26-thiaheptacosan-27-yl)benzamido)-5-(diethylamino)phenyl)-N-(3-(trifluoromethyl)benzyl)isonicotinamide To a solution of 2-(2-(3-(chloromethyl)benzamido)-5-(diethylamino)phenyl)-N-(3-(trifluoromethyl)benzyl)isonicotinamide 143a (715 mg, 1.2 mmol) and S-2,5,8,11,14,17,20,23-octaoxapentacosan-25-yl ethanethioate 135c.3 (590 mg, 1.33 mmol) in DMF (10 mL) was added 4.3 M NaOMe in MeOH (0.37 mL, 1.6 mmol) and stirred at room temperature for 15 minutes. The reaction mixture was added to water (35 mL) and extracted with DCM (3×50 mL). The combined organic layers were washed with water (25 mL), dried (Na2SO4) and concentrated at reduced pressure. The residue was purified by flash chromatography on silica gel (1% to 5% MeOH in DCM). The purified product was dissolved in 50% ACN/water and TFA (410 mg, 3.6 mmol) was added. Lyophylization gave a TFA salt of the title compound (1.34 g) as a light yellow oil. MS (ES, m/z): 959.4 [M+H]$^+$.

Example 266

2-(5-(diethylamino)-2-(3-(1-hydroxy-3,6,9,12-tetraoxapentadec-14-yn-15-yl)benzamido)phenyl)-N-(3-(trifluoromethyl)benzyl)isonicotinamide Scheme 108.

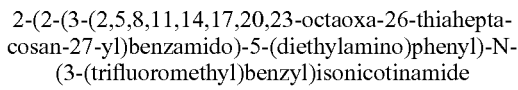
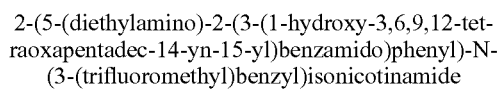

1. NaH, propargyl bromide, THF;
2. 3-Iodobenzoic acid, HATU, DIPEA, DMF;
3., Pd(PPh3)2Cl2, CuI, Et3N, THF.

Intermediate 266a.0

To a suspension of sodium hydride (60% in oil, 740 mg, 18.5 mmol) in THF (50 mL) at 0° C. was added tetraethylene glycol (4.0 g, 20.6 mmol). After stirring for 15 minutes, propargyl bromide (80% in toluene, 2.00 mL, 18.0 mmol) was added slowly. The reaction was allowed to warm to RT and stirred 16 hours. Solids were removed by filtration and rinsed with MTBE (3×20 mL). The combined filtrates were concentrated and purified by flash chromatography on silica gel (EtOAc) to give 3,6,9,12-tetraoxapentadec-14-yn-1-ol (2.14 g).

Intermediate 266a: 2-(5-(diethylamino)-2-(3-iodobenzamido)phenyl)-N-(3-(trifluoromethyl)benzyl)isonicotinamide To a solution of 2-(2-amino-5-(diethylamino)phenyl)-N-(3-(trifluoromethyl)benzyl)isonicotinamide (440 mg, 1.0 mmol), 3-iodobenzoic acid (248 mg, 1.0 mmol) and DIPEA (387 mg, 3.0 mmol) in DMF (5 mL) was added HATU (418 mg, 1.1 mmol). After one hour, the reaction mixture was added to EtOAc (150 mL) washed with water (5×50 mL) and saturated aqueous NaCl (25 mL), dried (Na$_2$SO$_4$) and concentrated. The residue was triturated with DCM (3 mL) to give a solid (718 mg) which was dried under vacuum.

Example 266

2-(5-(diethylamino)-2-(3-(1-hydroxy-3,6,9,12-tetraoxapentadec-14-yn-15-yl)benzamido)phenyl)-N-(3-(trifluoromethyl)benzyl)isonicotinamide To a slurry of 2-(5-(diethylamino)-2-(3-iodobenzamido)phenyl)-N-(3-(trifluoromethyl)benzyl)isonicotinamide (385 mg, 0.57 mmol), 3,6,9,12-tetraoxapentadec-14-yn-1-ol (175 mg, 0.75 mmol), Et$_3$N (3 mL) and THF (2 mL) was added bis(triphenylphosphine)palladium(II)dichloride (12 mg, 0.017 mmol) and CuI (10 mg, 0.053 mmol) and purged well with nitrogen. The reaction mixture was stirred for 13 hours, then concentrated under vacuum and combined with the crude product from another run (0.15 mmol scale). Purification by flash chromatography on silica gel eluting (1% to 5% MeOH in DCM) gave the title compound (349 mg). $^1$H NMR (400 MHz, CDCl$_3$, ppm) δ 12.51 (s, 1H), 8.83 (d, J=5.3 Hz, 1H), 8.42 (d, J=9.0 Hz, 1H), 8.21 (s, 1H), 7.99 (t, J=1.6 Hz, 1H), 7.94 (d, J=8.0 Hz, 1H), 7.75-7.68 (m, 2H), 7.65 (s, 1H), 7.60 (d, J=7.3 Hz, 1H), 7.58-7.54 (m, 2H), 7.48 (t, J=7.6 Hz, 1H), 7.42 (t, J=7.9 Hz, 1H), 6.98 (d, J=2.6 Hz, 1H), 6.76 (d, J=8.8 Hz, 1H), 4.76 (d, J=5.9 Hz, 2H), 4.48 (s, 2H), 3.82-3.80 (m, 2H), 3.72-3.70 (m, 2H), 3.67-3.63 (m, 4H), 3.60 (s, 4H), 3.53-3.51 (m, 2H), 3.32 (quar, J=7.2 Hz, 4H), 2.90 (s, 1H), 1.13 (t, J=6.8 Hz, 6H). MS (ES, m/z): 777.4 [M+H]$^+$.

Example 267

2-(5-(diethylamino)-2-(3-(1-hydroxy-3,6,9,12-tetraoxapentadecan-15-yl)benzamido)phenyl)-N-(3-(trifluoromethyl)benzyl)isonicotinamide Scheme 109a.

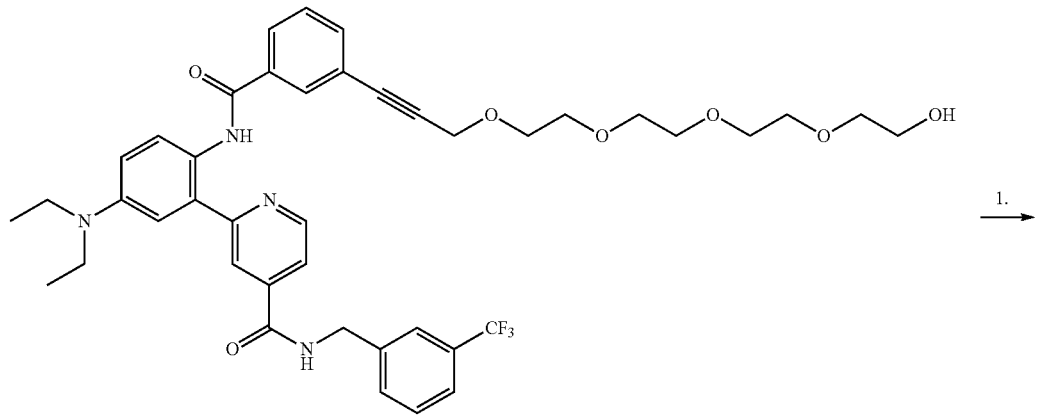

266

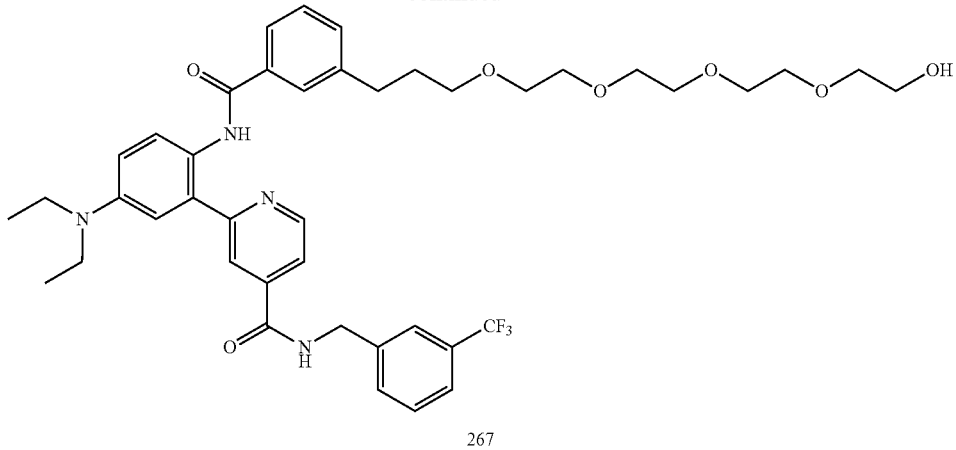

267

1. H₂, Pd/C.

Example 267

2-(5-(diethylamino)-2-(3-(1-hydroxy-3,6,9,12-tetraoxapentadecan-15-yl)benzamido)phenyl)-N-(3-(trifluoromethyl)benzyl)isonicotinamide A mixture of 2-(5-(diethylamino)-2-(3-(1-hydroxy-3,6,9,12-tetraoxapentadec-14-yn-15-yl)benzamido)phenyl)-N-(3-(trifluoromethyl)benzyl)isonicotinamide (107 mg, 0.014 mmol) and 10% palladium on carbon (water content 50%, 40 mg) in methanol (3 mL) was stirred under one atmosphere of H₂ for 1 hour. The mixture was filtered and concentrated under vacuum to give the title compound (92 mg). ¹H NMR (400 MHz, CDCl₃, ppm) δ 12.13 (s, 1H), 8.81 (d, J=5.2 Hz, 1H), 8.39 J=9.0 Hz, 1H), 8.15 (s, 1H), 7.78 (d, J=7.7 Hz, 1H), 7.71 (s, 1H), 7.69 (dd, $J_{AB}$=5.1 Hz, $J_{AC}$=1.4 Hz, 1H), 7.64 (s, 1H), 7.63-7.54 (m, 3H), 7.47 (t, J=7.5 Hz, 1H), 7.37 (t, J=7.6 Hz, 1H), 7.32 (d, J=7.9 Hz, 1H), 6.95 (d, J=2.8 Hz, 1H), 7.67 (dd, $J_{AB}$=9.0 Hz, $J_{AC}$=2.3 Hz, 1H), 4.74 (d, j=6.1 Hz, 2H), 3.66-3.56 (m, 14H), 3.53-3.51 (m, 2H), 3.48 (t, J=6.5 Hz, 2H), 3.32 (quar, J=7.0 Hz, 4H), 2.96 (br s, 1H), 2.77 (t, J=7.2 Hz, 2H), 1.98-1.91 (m, 2H), 1.13 (t, J=6.9 Hz, 6H). MS (ES, m/z): 781.4 [M+H]⁺.

Example 268

2-(2-(3-(2,5,8,11,14,17,20,23,26-nonaoxanonacos-28-yn-29-yl)benzamido)-5-(diethylamino)phenyl)-N-(3-(trifluoromethyl)benzyl)isonicotinamide

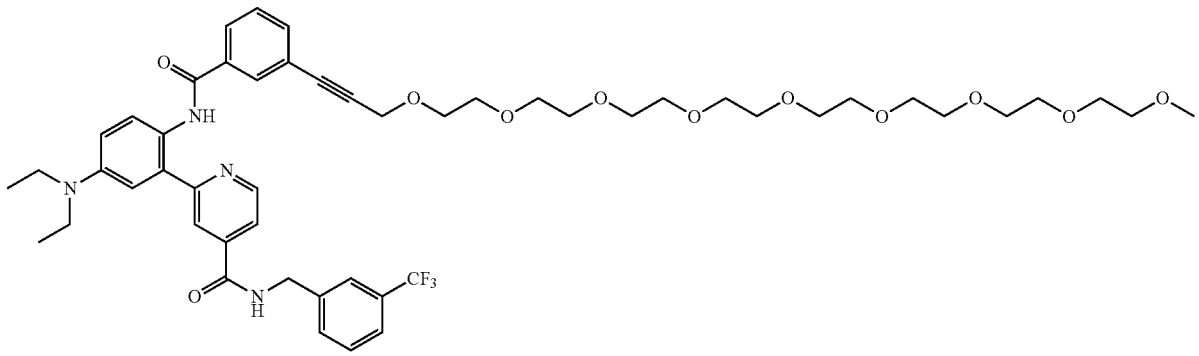 [SMILES: CCN(CC)c1ccc(NC(=O)c2cccc(C#CCOCCOCCOCCOCCOCCOCCOCCOCCOC)c2)c(-c2cc(C(=O)NCc3cccc(C(F)(F)F)c3)ccn2)c1]

Example 268

This compound was prepared using the method described for the preparation of Example 266 using 2,5,8,11,14,17,20,23,26-nonaoxanonacos-28-yne 261a in place of 3,6,9,12-tetraoxapentadec-14-yn-1-ol. Purification by flash chromatography on silica gel (1% to 4% MeOH in DCM) gave the title compound. $^1$H NMR (400 MHz, CDCl$_3$, ppm) δ 12.57 (s, 1H), 8.82 (d, J=5.3 Hz, 1H), 8.41 (d, J=9.0 Hz, 1H), 8.22 (s, 1H), 7.99 (t, J=1.5 Hz, 1H), 7.93 (dt, J$_{AB}$=8.3 Hz, J$_{AC}$=1.8 Hz, 1H), 7.75-7.80 (m, 2H), 7.66 (s, 1H), 7.62 (d, J=8.3 Hz, 1H), 7.57-7.54 (m, 2H), 7.49 (d, J=7.6 Hz, 1H), 7.43 (t, J=7.8 Hz), 9.99 (d, J=3.0 Hz, 1H), 6.75 (dd, J$_{AB}$=8.5 Hz, J$_{AC}$=2.9 Hz, 1H), 4.75 (d, J=5.9 Hz, 2H), 4.47 (s, 2H), 3.81-3.78 (m, 2H), 3.72-3.69 (m, 2H), 3.65-3.50 (m, 26H), 3.35 (s, 3H), 3.31 (quar, J=7.0 Hz, 4H), 1.12 (t, J=7.0 Hz, 6H). MS (ES, m/z): 967.4 [M+H]$^+$.

Example 269

2-(2-(3-(2,5,8,11,14,17,20,23,26-nonaoxanonacosan-29-yl)benzamido)-5-(diethylamino)phenyl)-N-(3-(trifluoromethyl)benzyl)isonicotinamide

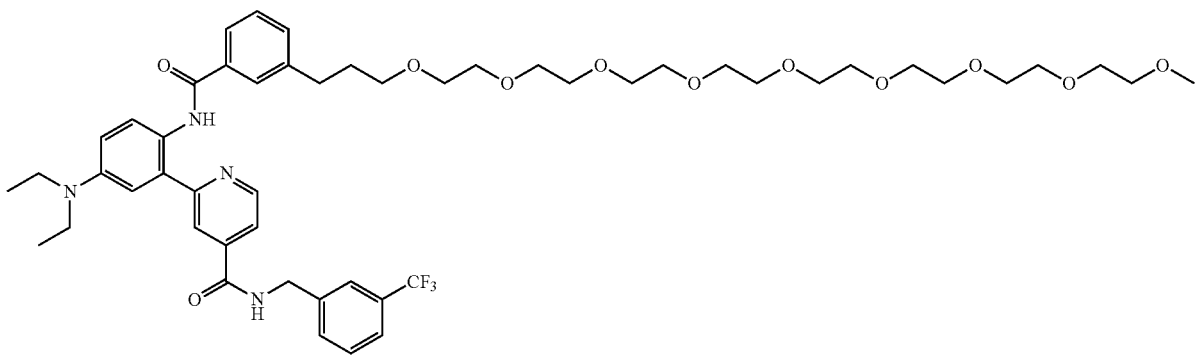 [SMILES: CCN(CC)c1ccc(NC(=O)c2cccc(CCCOCCOCCOCCOCCOCCOCCOCCOCCOC)c2)c(-c2cc(C(=O)NCc3cccc(C(F)(F)F)c3)ccn2)c1]

Example 269

This compound was prepared using the method described for the preparation of Example 269 using 2-(2-(3-(2,5,8,11,14,17,20,23,26-nonaoxanonacos-28-yn-29-yl)benzamido)-5-(diethylamino)phenyl)-N-(3-(trifluoromethyl)benzyl)isonicotinamide (Example 267) in place of 2-(5-(diethylamino)-2-(3-(1-hydroxy-3,6,9,12-tetraoxapentadec-14-yn-15-yl)benzamido)phenyl)-N-(3-(trifluoromethyl)benzyl)isonicotinamide. $^1$H NMR (400 MHz, CDCl$_3$, ppm) δ 12.30 (s, 1H), 8.81 (m, 1H), 8.46 (s, 1H), 8.21 (s, 1H), 7.79 (d, J=7.4 Hz, 1H), 7.76-7.68 (m, 3H), 7.65 (s, 1H), 7.61 (d, J=7.6 Hz, 1H), 7.55 (d, J=7.6 Hz, 1H), 7.49-7.45 (t, J=7.8 Hz, 1H), 7.38 (t, J=7.4 Hz, 1H), 7.33 (d, J=7.9 Hz, 1H), 7.12 (s, 1H), 6.83 (s, 1H), 4.74 (d, J=6.0 Hz, 2H), 3.65-3.45 (m, 34H), 3.40-3.30 (m, 4H), 3.35 (s, 3H), 2.78 (t, J=7.2 Hz, 2H), 1.96-1.92 (m, 2H), 1.15 (s, J=7.0 Hz, 6H). MS (ES, m/z): 971.5 [M+H]$^+$.

Example 270

2-(2-(3-(1-amino-3,6,9,12-tetraoxapentadecan-15-yl)benzamido)-5-(diethylamino)phenyl)-N-(3-(trifluoromethyl)benzyl)isonicotinamide Scheme 109b.

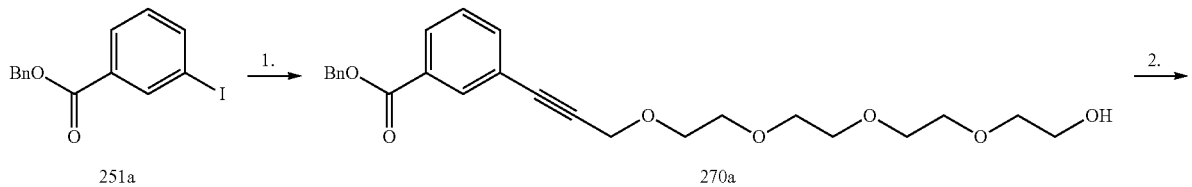

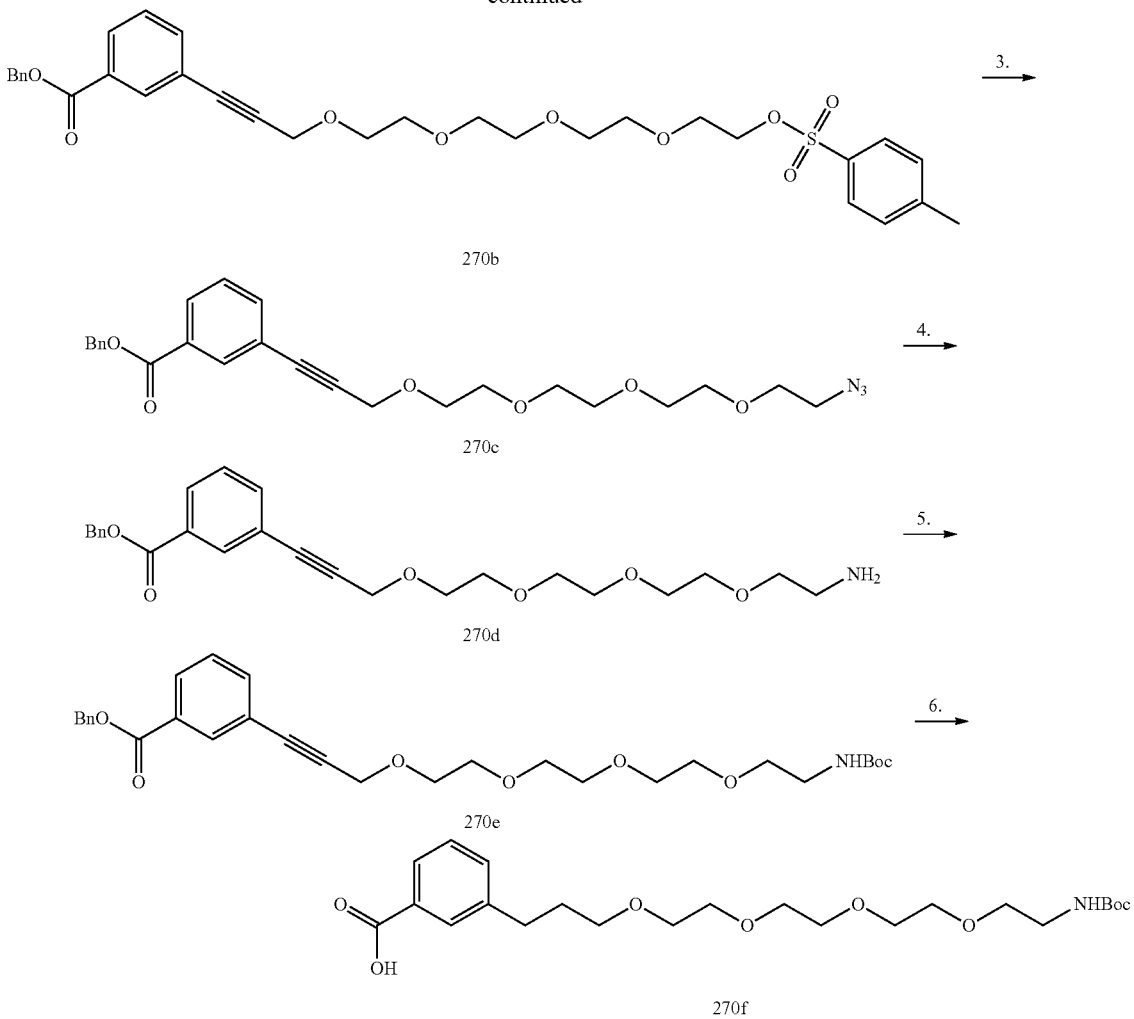

1. Copper(I)iodide, Pd(PPh₃)₂Cl₂, triethylamine, 266a.0
3. methylbenzene-1-sulfonyl chloride, TEA, DCM
4. NaN₃  5. PPh₃, H₂O, THF
5. di-tert-butyl dicarbonate
6. Pd/C, H₂.

Intermediate 270a: benzyl 3-(3-(2-(2-(2-(2-hydroxyethoxy)ethoxy)ethoxy)ethoxy)prop-1-ynyl)benzoate Into a 500-mL round-bottom flask purged and maintained with an inert atmosphere of nitrogen, was placed a solution of benzyl 3-iodobenzoate (25.68 g, 66.19 mmol, 1.00 equiv) in tetrahydrofuran (300 mL), 2-(2-(2-(2-(prop-2-ynyloxy)ethoxy)ethoxy)ethoxy)ethanol (15.36 g, 66.21 mmol, 1.00 equiv), copper(I) iodide (1.26 g, 6.63 mmol, 0.10 equiv), Pd(PPh₃)₂Cl₂ (4.65 g, 6.62 mmol, 0.10 equiv), triethylamine (13.4 g, 132.67 mmol, 2.00 equiv). The resulting solution was stirred for 3 h at room temperature. The resulting mixture was concentrated under vacuum. The residue was applied onto a silica gel column with petroleum ether/ethyl acetate (1:1). This resulted in 20 g (68%) of benzyl 3-(3-(2-(2-(2-(2-hydroxyethoxy)ethoxy)ethoxy)ethoxy)prop-1-ynyl)benzoate as a brown oil.

Intermediate 270b: benzyl 3-(1-(tosyloxy)-3,6,9,12-tetraoxapentadec-14-yn-15-yl)benzoate Into a 500-mL 3 neck round-bottom flask purged and maintained with an inert atmosphere of nitrogen, was placed a solution of benzyl 3-(1-hydroxy-3,6,9,12-tetraoxapentadec-14-yn-15-yl)benzoate (25.2 g, 56.88 mmol, 1.00 equiv) in dichloromethane (300 mL), triethylamine (17.2 g, 170.30 mmol, 3.00 equiv). This was followed by the addition of a solution of 4-methylbenzene-1-sulfonyl chloride (16.3 g, 85.34 mmol, 1.50 equiv) in dichloromethane (100 mL) dropwise with stirring at 0° C. The resulting solution was stirred overnight at room temperature. The resulting mixture was concentrated under vacuum. The residue was applied onto a silica gel column with petroleum ether/ethyl acetate (5:1-1:1). This resulted in 31 g (91%) of benzyl 341-(tosyloxy)-3,6,9,12-tetraoxapentadec-14-yn-15-yl)benzoate as a brown oil.

Intermediate 270c: benzyl 3-(1-azido-3,6,9,12-tetraoxapentadec-14-yn-15-yl)benzoate Into a 1000-mL round-bottom flask, was placed a solution of benzyl 3-(1-(tosyloxy)-3,6,9,12-tetraoxapentadec-14-yn-15-yl)benzoate (35.4 g, 59.30 mmol, 1.00 equiv) in N,N-dimethylformamide (400 mL), sodium bicarbonate (10 g, 119.05 mmol, 2.00 equiv), sodium azide (11 g, 169.23 mmol, 3.00 equiv). The resulting solution was stirred overnight at 80° C. The resulting solution was diluted with 200 mL of water. The resulting solution was extracted with 3×100 mL of ethyl acetate and the organic layers combined. The resulting mixture was washed with 3×100 mL of NaHCO$_3$ aq. The mixture was dried over anhydrous sodium sulfate and concentrated under vacuum. This resulted in 25 g (90%) of benzyl 3-(1-azido-3,6,9,12-tetraoxapentadec-14-yn-15-yl)benzoate as brown oil.

Intermediate 270d: benzyl 3-(1-amino-3,6,9,12-tetraoxapentadec-14-yn-15-yl)benzoate Into a 500-mL round-bottom flask, was placed a solution of benzyl 3-(1-azido-3,6,9,12-tetraoxapentadec-14-yn-15-yl) benzoate (23 g, 49.15 mmol, 1.00 equiv) in tetrahydrofuran (200 mL), water (20 mL), triphenylphosphine (25.7 g, 98.09 mmol, 2.00 equiv). The resulting solution was stirred for 3 h at room temperature. The resulting mixture was concentrated under vacuum. The residue was applied onto a silica gel column with dichloromethane:methanol (100:1-50:1). This resulted in 15 g (69%) of benzyl 3-(1-amino-3,6,9,12-tetraoxapentadec-14-yn-15-yl)benzoate as pale-yellow oil.

Intermediate 270e: benzyl 3-(2,2-dimethyl-4-oxo-3,8,11,14,17-pentaoxa-5-azaicos-19-yn-20-yl)benzoate Into a 500-mL round-bottom flask, was placed a solution of benzyl 3-(1-amino-3,6,9,12-tetraoxapentadec-14-yn-15-yl) benzoate (15 g, 33.94 mmol, 1.00 equiv) in dichloromethane (200 mL), triethylamine (6.85 g, 67.82 mmol, 2.00 equiv). This was followed by the addition of a solution of di-tert-butyl dicarbonate (13.7 g, 62.84 mmol, 2.00 equiv) in dichloromethane (50 mL) dropwise with stirring at 0° C. The resulting solution was stirred for 5 h at room temperature. The resulting mixture was concentrated under vacuum. The residue was applied onto a silica gel column with petroleum ether/ethyl acetate (5:1-1:1). This resulted in 16 g (87%) of benzyl dimethyl-4-oxo-3,8,11,14,17-pentaoxa-5-azaicos-19-yn-20-yl)benzoate as pale-yellow oil.

Intermediate 270f: 3-(2,2-dimethyl-4-oxo-3,8,11,14,17-pentaoxa-5-azaicosan-20-yl)benzoic acid Into a 500-mL round-bottom flask, was placed a solution of benzyl 3-(2,2-dimethyl-4-oxo-3,8,11,14,17-pentaoxa-5-azaicos-19-yn-20-yl)benzoate (16 g, 29.52 mmol, 1.00 equiv) in methanol (200 mL), Palladium carbon (10 g). Hydrogen gas was introduced into the reaction vessel. The resulting solution was stirred for 3 h at room temperature. The solids were filtered out. The resulting mixture was concentrated under vacuum. The residue was applied onto a silica gel column with ethyl acetate/petroleum ether (1:5-1:1). This resulted in 7 g (52%) of 3-(2,2-dimethyl-4-oxo-3,8,11,14,17-pentaoxa-5-azaicosan-20-yl)benzoic acid as pale-yellow oil. LC-MS (ES, m/z): 456 [M+H]$^+$ H-NMR (300 MHz, DMSO, ppm): 7.76 (dd, J=6.0 Hz, 2H), 7.37-7.47 (m, 2H), 6.73 (s, 1H), 3.35-3.52 (m, 16), 3.05 (dd, J=11.7 Hz, 2H), 2.69 (t, J=7.5 Hz, 2H), 1.76-1.85 (m, 2H), 1.36 (s, 9H).

Scheme 110.

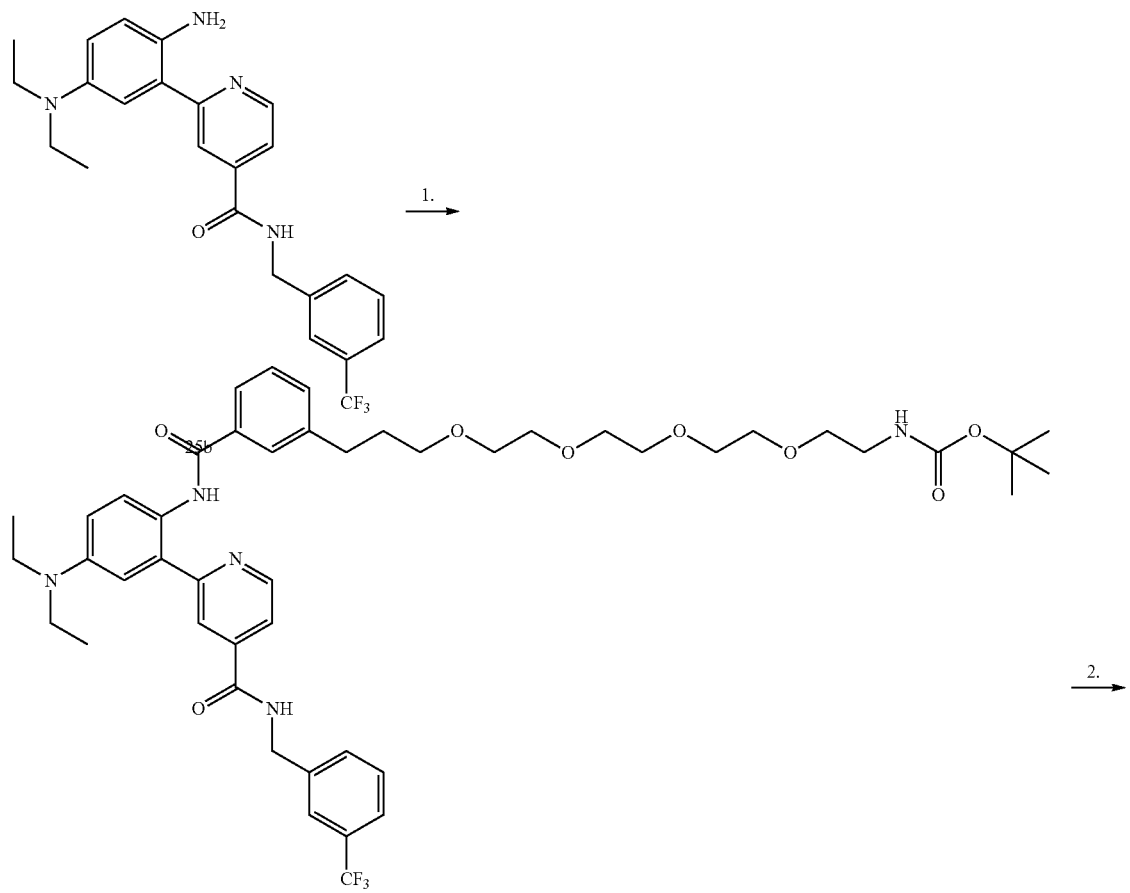

270g

-continued

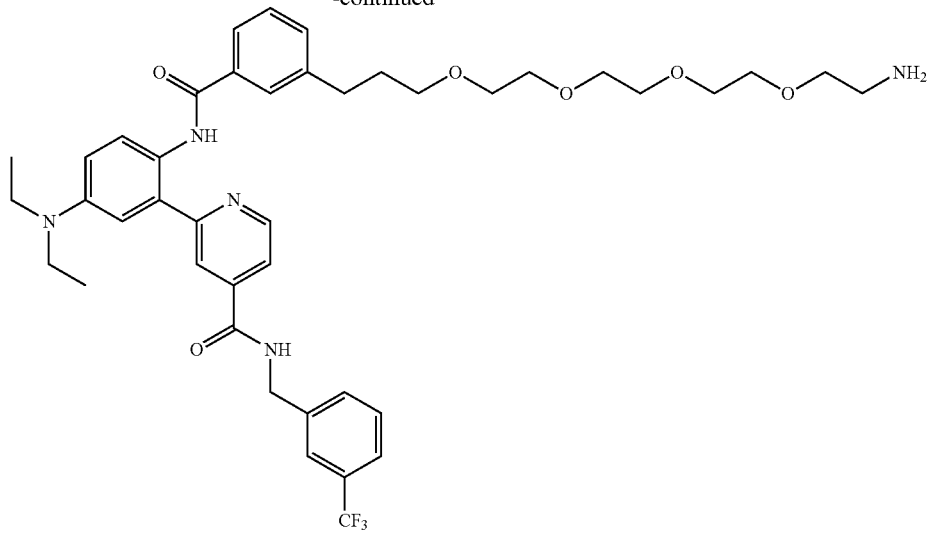

270

1. HATU, DIEA, DMF
2. TFA, DCM.

Intermediate 270g: tert-butyl 15-(3-(4-(diethylamino)-2-(4-(3-(trifluoromethyl)benzylcarbamoyl)pyridin-2-yl)phenylcarbamoyl)phenyl)-3,6,9,12-tetraoxapentadecylcarbamate To a solution of 25b (1.81 g, 4.1 mmol, 1.0 eq) and 270f (1.96 g, 4.3 mmol, 1.05 eq) in DMF (20 mL) was added DIEA (2.2 g, 16.4 mmol, 4.0 eq) and HATU (1.71 g, 4.51 mmol, 1.1 equiv). After 40 minutes the solvent was removed and the residue diluted with EtOAc (200 mL). The resulting solution was washed with water (4×75 mL), brine, and dried over Na$_2$SO$_4$. Purification on SiO$_2$ (220 g, 0-100% EtOAc) gave 3.45 g (95%) of the product as a yellow oil.

Example 270

2-(2-(3-(1-amino-3,6,9,12-tetraoxapentadecan-15-yl)benzamido)-5-(diethylamino)phenyl)-N-(3-(trifluoromethyl)benzyl)isonicotinamide To a solution of compound 270g (3.45 g, 3.9 mmol) in dichloromethane (15 mL) was added TFA (5 mL). The reaction was stirred overnight, diluted with dichloromethane (10 mL) and partitioned with water (25 mL). NaOH was added to bring the resulting solution to pH 6 and obtain 2.69 g of 2-(2-(3-(1-amino-3,6,9,12-tetraoxapentadecan-15-yl)benzamido)-5-(diethylamino)phenyl)-N-(3-(trifluoromethyl)benzyl)isonicotinamide as the free base. MS (ES, m/z) 780.4 [M+H]$^+$.

Example 271

2-(2-(3-(1-(3-(2,5,8,11,14,17,20,23,26-nonaoxanonacosan-29-yl)phenyl)-1-oxo-5,8,11,14-tetraoxa-2-azaheptadecan-17-yl)benzamido)-5-(diethylamino)phenyl)-N-(3-(trifluoromethyl)benzyl)isonicotinamide

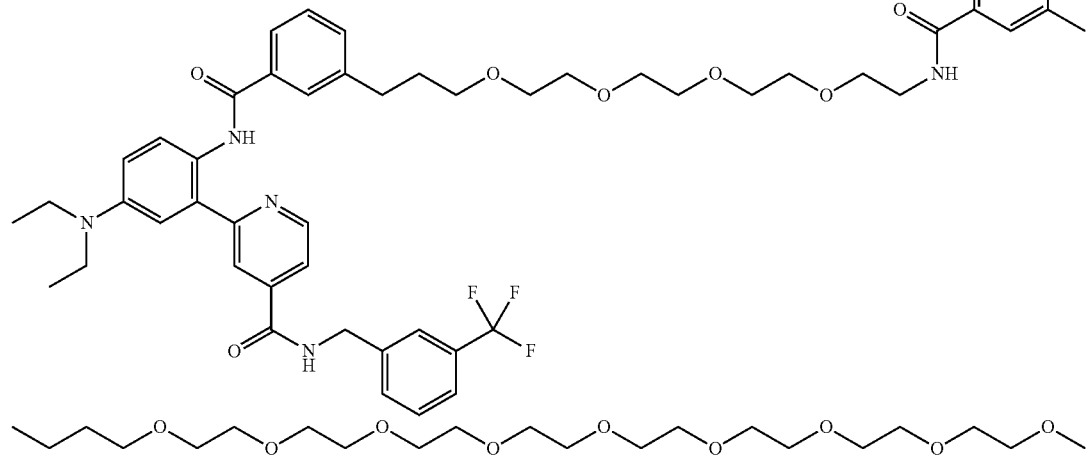

Example 271

This compound was prepared using the method described for the preparation of Example 262 substituting Example 270 in place of 262b in the reaction sequence. Purification by reverse-phase HPLC eluting with a water/ACN gradient containing 0.1% TFA gave a TFA salt of the title compound. MS (ES, m/z): 1308.6 [M+H]$^+$.

Example 272

2-(2-(3-(1-(4-(2,5,8,11,14,17,20-heptaoxadocosan-22-yl(2-methoxyethyl)carbamoyl)phenylsulfonamido)-3,6,9,12-tetraoxapentadecan-15-yl)benzamido)-5-(diethylamino)phenyl)-N-(3-(trifluoromethyl)benzyl)isonicotinamide Scheme 111.

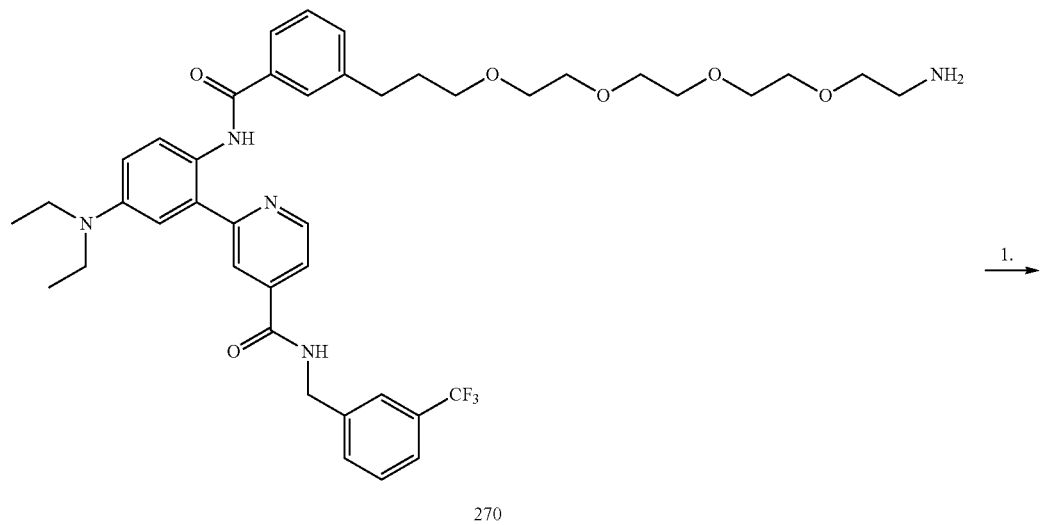

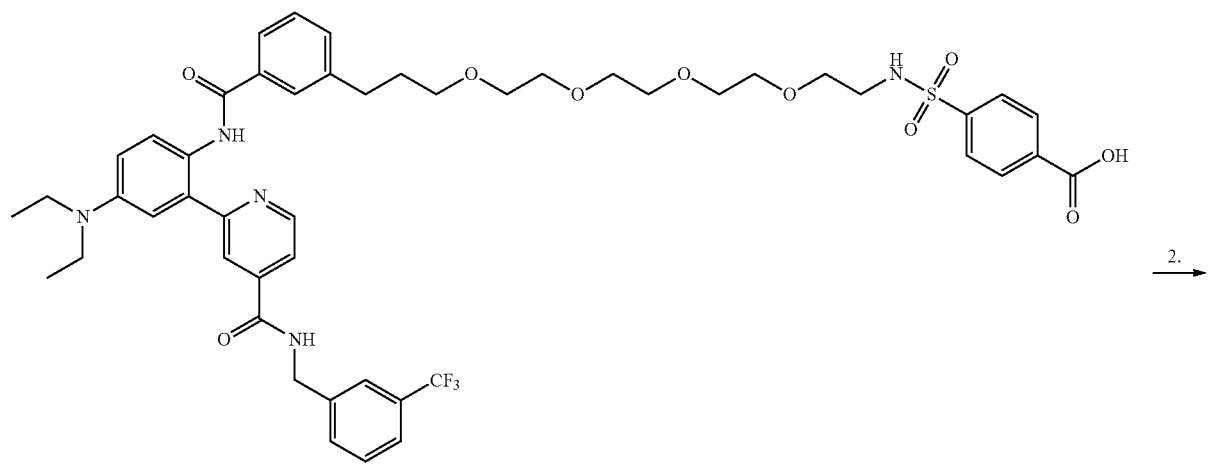

-continued

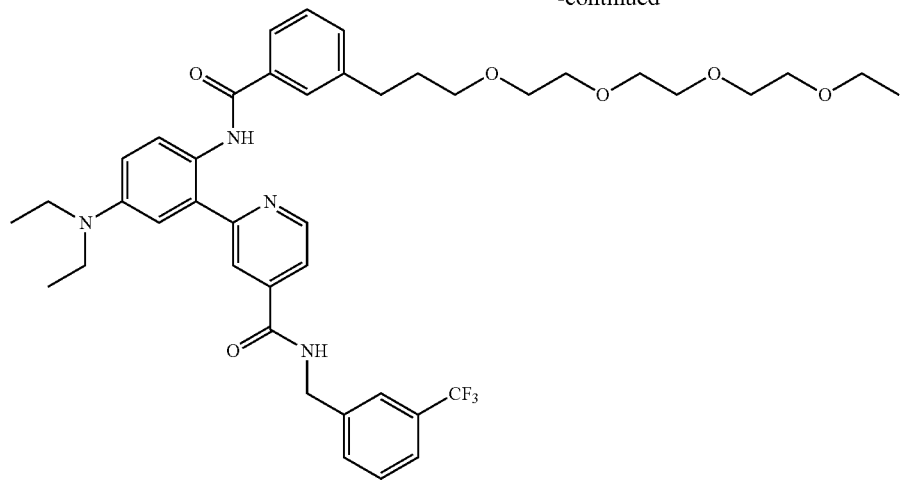

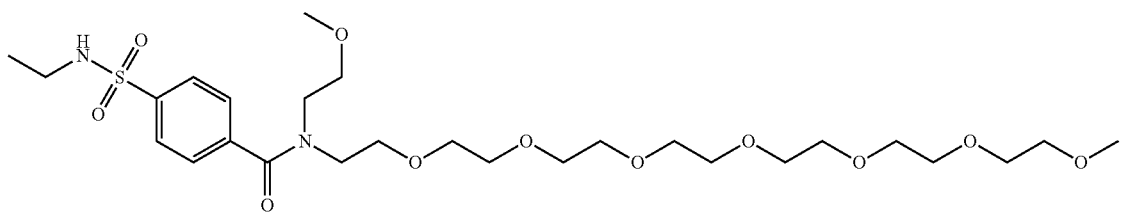

272b

1. TEA, DCM, 0° C.
2. HATU, DIEA, DMF.

Intermediate 272a: 4-(N-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecyl)sulfamoyl)benzoic acid A solution of Example 270 (200 mg, 0.25 mmol, 1.0 eq) and triethylamine (50.5, 0.50 mmol, 2.0 eq) in dichloromethane (5 mL) under $N_2$ was cooled to 0° C. 4-(chlorosulfonyl)benzoic acid (55.15 mg, 0.25 mmol, 1.0 eq) was added and the reaction warmed to room temperature and monitored by LCMS. After 2 hours, the resulting solution was diluted with dichloromethane (20 mL) and washed with water (2×20 mL). The organic layer was acidified to pH 5 with 1N HCl and washed with water (20 mL), brine, and dried over $Na_2SO_4$. Removing the solvent resulted in 172 mg of 4-(N-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecyl)sulfamoyl)benzoic acid as an oil.

Example 272

2-(2-(3-(1-(4-(2,5,8,11,14,17,20-heptaoxadocosan-22-yl(2-methoxyethyl)carbamoyl)phenylsulfonamido)-3,6,9,12-tetraoxapentadecan-15-yl)benzamido)-5-(diethylamino)phenyl)-N-(3-(trifluoromethyl)benzyl)isonicotinamide To a solution of 272a (50 mg, 0.0518 mmol, 1.0 eq) in dimethylformamide (0.26 mL) was added N-(2-methoxyethyl)-2,5,8,11,14,17,20-heptaoxadocosan-22-amine 135c.2 (18.3 mg, 0.0518 mmol, 1.0 eq), DIEA (33.4 mg, 0.259 mmol, 5.0 eq) and HATU (21.7 mg, 0.0569 mmol, 1.1 eq). The resulting solution was stirred for 1 hour at which LCMS indicated complete conversion. The reaction mixture was diluted with acetonitrile/water (1:1, 2 mL), acidified with TFA, and purified by reverse phase HPLC eluting with a water/$CH_3CN$ gradient containing 0.05% TFA. The product was obtained as 26.5 mg as an oil. MS (ES, m/z) 1343.4 $[M+H]^+$; $^1H$ NMR (400 MHz, $CD_3OD$) δ 8.98 (dd, J=5.4, 0.7 Hz, 1H), 8.62 (d, J=8.9 Hz, 1H), 8.49 (dd, J=1.5, 0.8 Hz, 1H), 8.17 (d, J=2.7 Hz, 1H), 8.01 (dd, J=5.4, 1.6 Hz, 1H), 7.86 (d, J=8.4 Hz, 2H), 7.79-7.71 (m, 3H), 7.69 (s, 1H), 7.64 (d, J=7.4 Hz, 1H), 7.62-7.48 (m, 4H), 7.48-7.40 (m, 2H), 4.68 (s, 2H), 3.85-3.68 (m, 7H), 3.68-3.54 (m, 31H), 3.54-3.33 (m, 18H), 3.22 (s, 1H), 3.00 (t, J=5.4 Hz, 2H), 2.83-2.73 (m, 2H), 1.90 (tt, J=12.7, 6.3 Hz, 2H), 1.22 (t, J=7.2 Hz, 6H).

Example 273
2-(5-(diethylamino)-2-(3-(23-methyl-24-oxo-2,5,8,11,14,17,20,28,31,34,37-undecaoxa-23,25-diazatetracontan-40-yl)benzamido)phenyl)-N-(3-(trifluoromethyl)benzyl)isonicotinamide
Scheme 112.
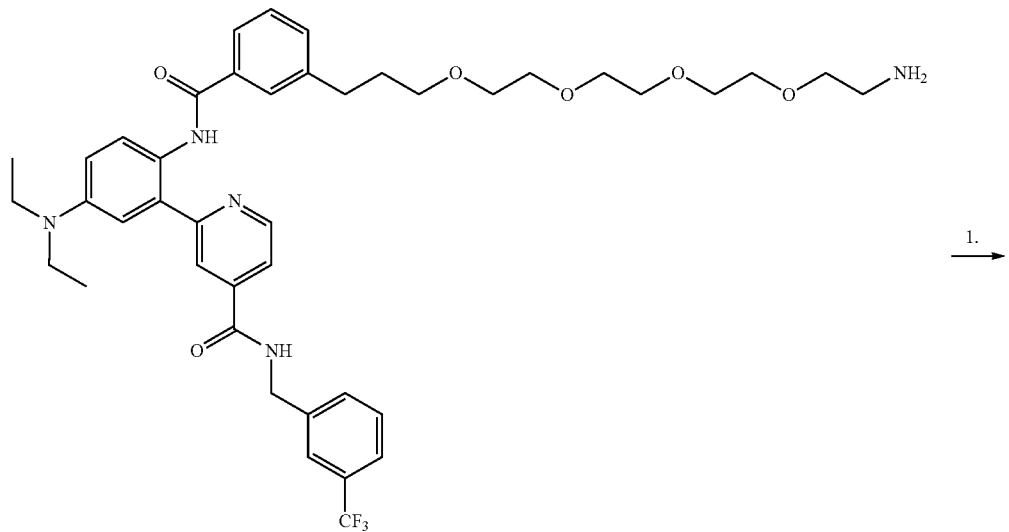
270
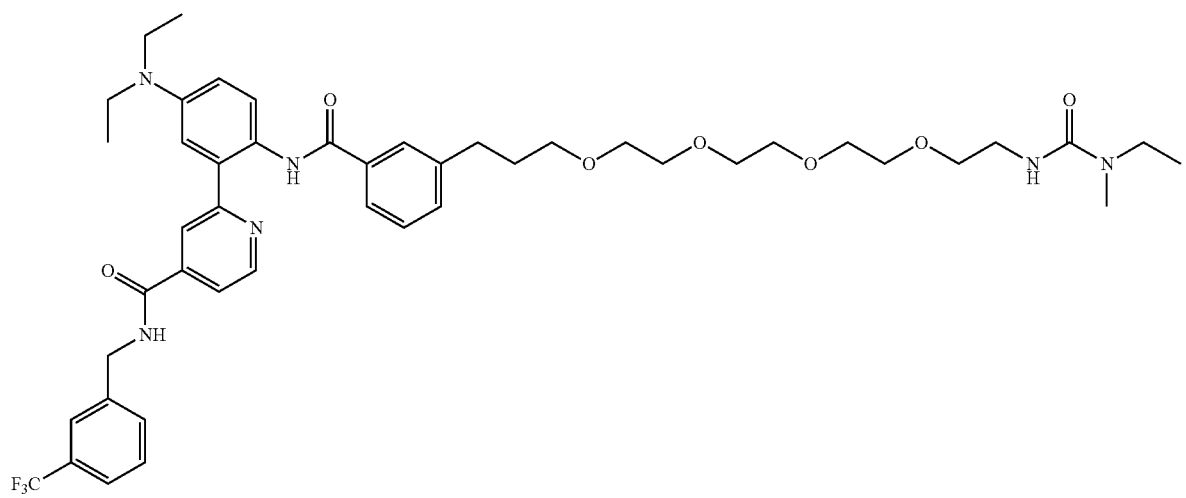
273
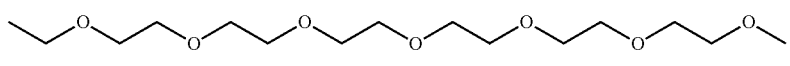
1. a) triphosgene, TEA, DCM b) N-methyl-2,5,8,11,14,17,20-heptaoxadocosan-22-amine (135c.1).

To a solution of triphosgene (2.0 mg, 0.0069 mmol, 0.3 eq) in dry DCM (0.25 mL) was added TEA (5.0 mg, 0.05 mmol, 2.0 eq) and Example 270 (20 mg, 0.025 mmol, 1.0 eq). After 15 minutes, a solution of N-methyl-2,5,8,11,14,17,20-heptaoxadocosan-22-amine (135c.1) in DCM (0.25 mL) was added and the reaction stirred at room temperature. After 30 minutes the solvent was removed and the crude residue diluted with acetonitrile/water (1:1, 2 mL). The resulting solution was purified by reverse phase HPLC eluting with a water/CH$_3$CN gradient containing 0.05% TFA to give 13.6 mg of the title compound as an oil. MS (ES, m/z) 1159.4 [M+H]$^+$.

Example 274

2-(5-(diethylamino)-2-(3-(1-hydroxy-3-(2-hydroxyethyl)-4-oxo-8,11,14,17-tetraoxa-3,5-diazaicosan-20-yl)benzamido)phenyl)-N-(3-(trifluoromethyl)benzyl)isonicotinamide

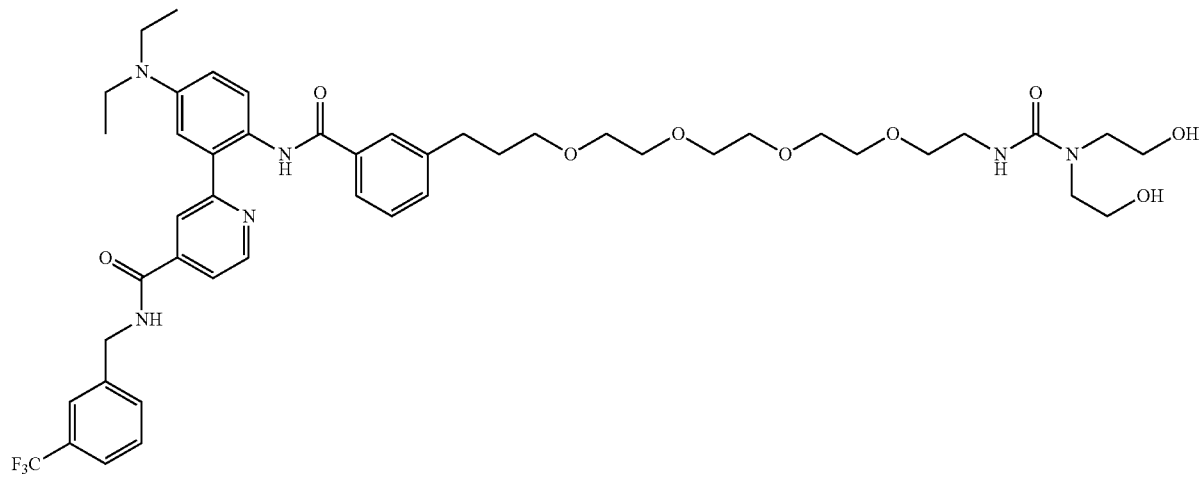 [SMILES: CCN(CC)c1ccc(NC(=O)c2cccc(CCCOCCOCCOCCOCCNC(=O)N(CCO)CCO)c2)c(-c2cc(C(=O)NCc3cccc(C(F)(F)F)c3)ccn2)c1]

A solution of Intermediate 270 (20 mg, 0.25 mmol, 1.0 eq) in dichloromethane (0.25 mL) was added dropwise to a solution of CDI (4.5 mg, 0.028 mmol, 1.1 eq) in dichloromethane (0.25 mL). After 50 minutes the solvent was removed and the residue dissolved in acetonitrile (0.5 mL). 2,2'-azanediyldiethanol (2.89 mg, 0.0275 mmol, 1.1 eq) and DMAP (1 mg) was added and the reaction heated to 50° C. After 45 minutes the reaction was removed from heat, diluted with acetonitrile/water (1:1, 1.5 mL), and purified by reverse phase HPLC eluting with a water/CH$_3$CN gradient containing 0.05% TFA to give 13.0 mg of the title compound as an oil. MS (ES, m/z) 911.3 [M+H]$^+$.

Examples 275-283
The compounds listed in Table 9 were prepared by the procedures described in Example 257 from acids Examples 251, 302 and 303 substituting appropriate amines in the coupling. Mass spectral data (ES, positive ion mode) is provided for each compound.
TABLE 9
| Example | Starting Acid (Example #) | Structure | Mass Spectrum |
|---|---|---|---|
| 275 | 303 | 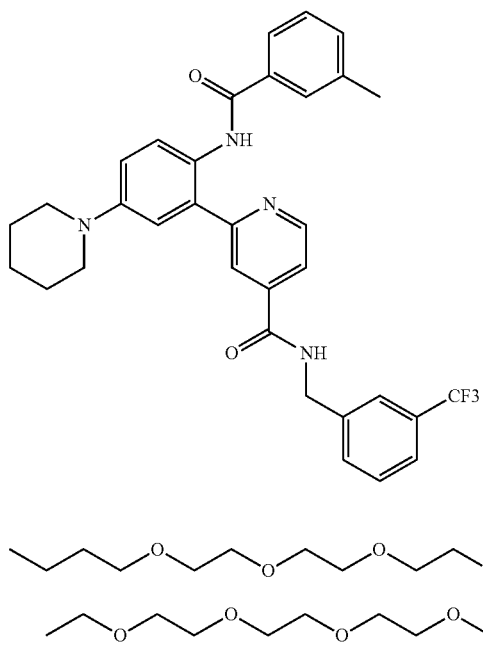 | 1186.5 [M + H] |
| 276 | 303 | 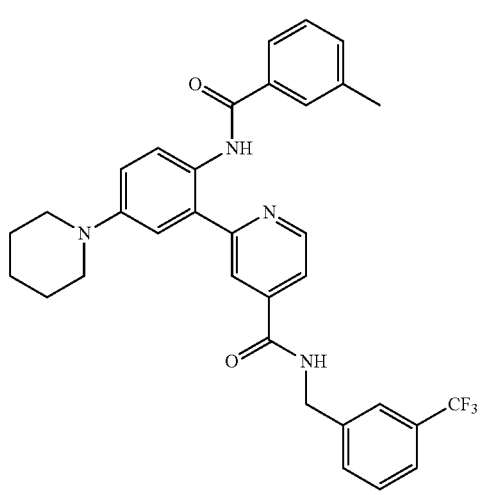 | 1156.5 [M + H] |

TABLE 9-continued

| Example | Starting Acid (Example #) | Structure | Mass Spectrum |
|---|---|---|---|
| 277 | 303 | 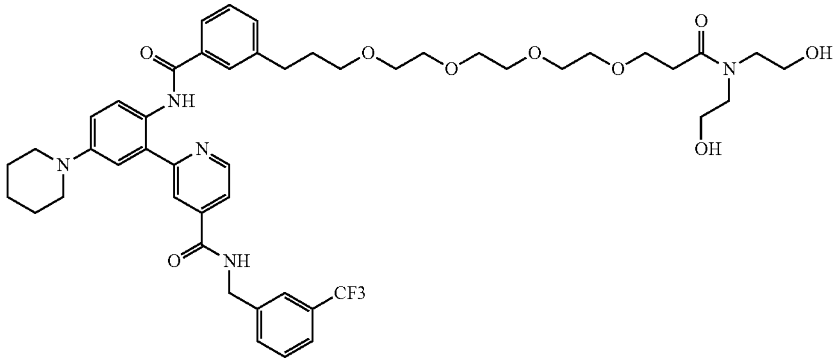 [SMILES: O=C(NCc1cccc(C(F)(F)F)c1)c1ccnc(-c2cc(N3CCCCC3)ccc2NC(=O)c2cccc(CCCOCCOCCOCCOCCC(=O)N(CCO)CCO)c2)c1] | 908.5 [M + H] |
| 278 | 303 | 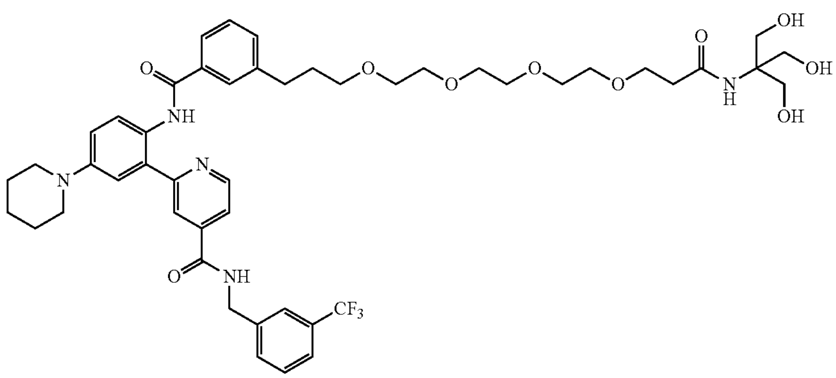 [SMILES: O=C(CCOCCOCCOCCOCCCc1cccc(C(=O)Nc2ccc(N3CCCCC3)cc2-c2cc(C(=O)NCc3cccc(C(F)(F)F)c3)ccn2)c1)NC(CO)(CO)CO] | 924.3 [M + H] |
| 279 | 302 | 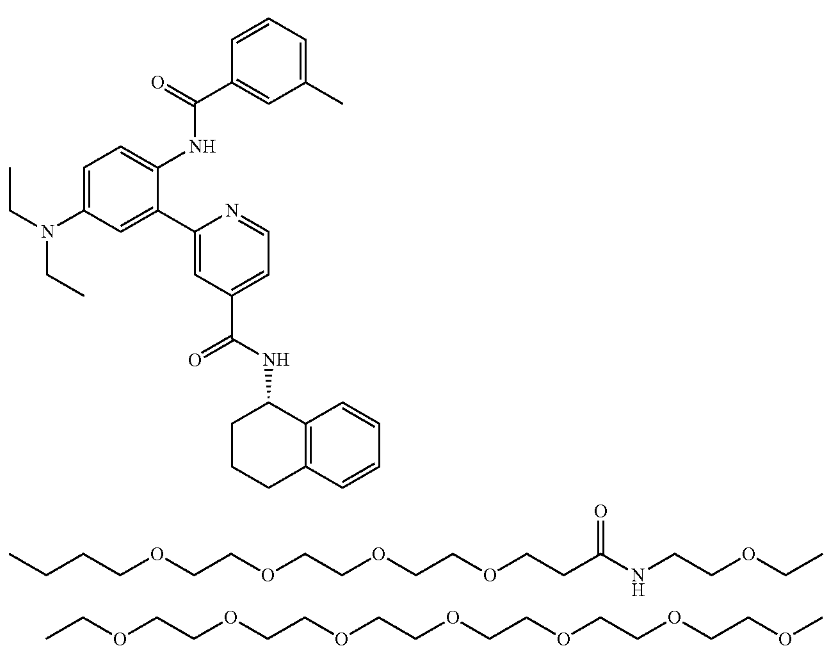 | 1146.5 [M + H] |

TABLE 9-continued
| Example | Starting Acid (Example #) | Structure | Mass Spectrum |
|---|---|---|---|
| 280 | 302 | 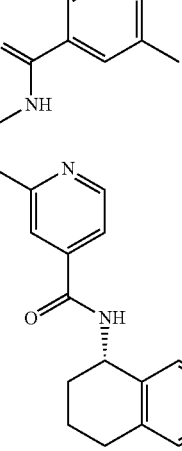 | 1116.5 [M + H] |
| 281 | 251 | 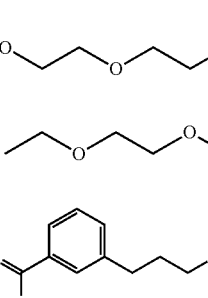 | 912.4 [M + H] |
| 282 | 302 | 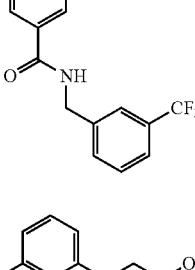 | 868.5 [M + H] |

TABLE 9-continued

| Example | Starting Acid (Example #) | Structure | Mass Spectrum |
|---|---|---|---|
| 283 | 302 | 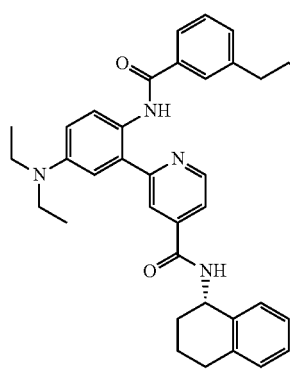 | 884.4 [M + H] |

Example 284

(S)-tert-butyl 16-(3-((4-cyclobutoxy-2-(4-((1,2,3,4-tetrahydronaphthalen-1-yl)carbamoyl)pyridin-2-yl)phenyl)carbamoyl)phenyl)-4,7,10,13-tetraoxahexadecan-1-oate Scheme 113.

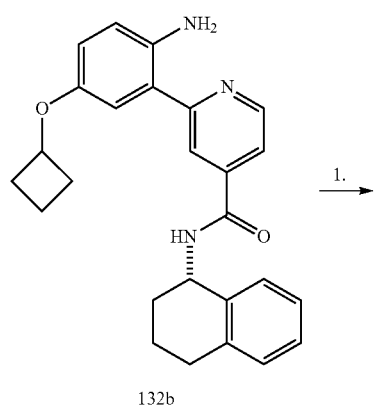

132b

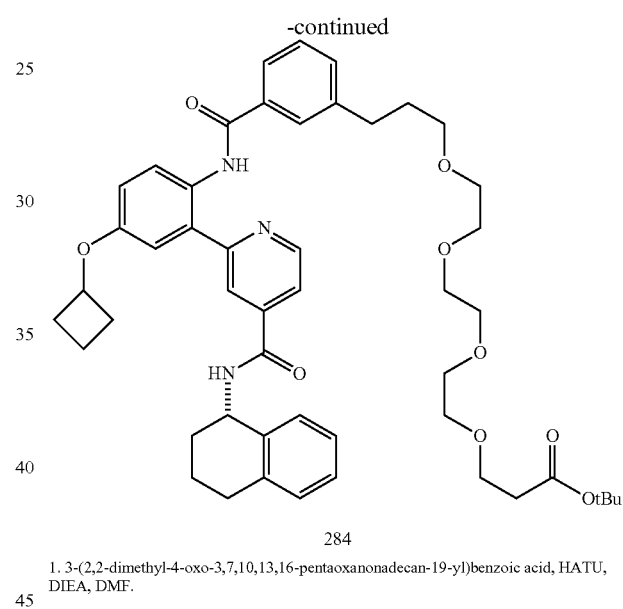

284

1. 3-(2,2-dimethyl-4-oxo-3,7,10,13,16-pentaoxanonadecan-19-yl)benzoic acid, HATU, DIEA, DMF.

Example 284

(S)-tert-butyl 16-(3-((4-cyclobutoxy-2-(4-((1,2,3,4-tetrahydronaphthalen-1-yl)carbamoyl)pyridin-2-yl)phenyl)carbamoyl)phenyl)-4,7,10,13-tetraoxahexadecan-1-oate To a mixture of (S)-2-(2-amino-5-cyclobutoxyphenyl)-N-(1,2,3,4-tetrahydronaphthalen-1-yl)isonicotinamide 132b (0.048 mmol, 20 mg), 3-(2,2-dimethyl-4-oxo-3,7,10,13,16-pentaoxanonadecan-19-yl)benzoic acid (0.053 mmol, 24 mg) and DIEA (0.29 mmol, 38 mg) in DMF (0.16 mL) was added HATU (0.053 mmol, 20 mg). The mixture was stirred at 60°

Example 285

(S)-16-(3-((4-cyclobutoxy-2-(4-((1,2,3,4-tetrahydronaphthalen-1-yl)carbamoyl)pyridin-2-yl)phenyl)carbamoyl)phenyl)-4,7,10,13-tetraoxahexadecan-1-oic acid

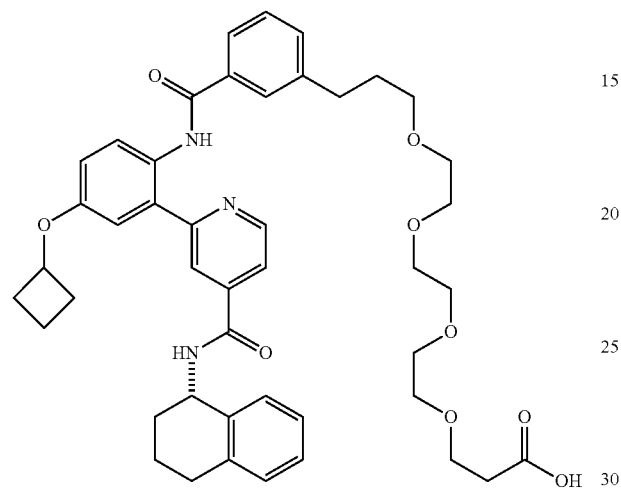

Example 285

(S)-16-(3-((4-cyclobutoxy-2-(4-((1,2,3,4-tetrahydronaphthalen-1-yl)carbamoyl)pyridin-2-yl)phenyl)carbamoyl)phenyl)-4,7,10,13-tetraoxahexadecan-1-oic acid To (S)-tert-butyl 16-(3-((4-cyclobutoxy-2-(4-((1,2,3,4-tetrahydronaphthalen-1-yl)carbamoyl)pyridin-2-yl)phenyl)carbamoyl)phenyl)-4,7,10,13-tetraoxahexadecan-1-oate Example 284 was added trifluoracetic acid (1 mL). The mixture was stirred for 5 minutes, concentrated and purified by prep. TLC to give a yellow syrup (7.2 mg, 64%). MS (ES, m/z): 780.5 [M+H]$^+$.

Example 286

(S)-2-(2-(3-(2,5,8,11,14,17,20,23-octaoxa-26-thiaheptacosan-27-yl)benzamido)-5-(diethylamino)phenyl)-N-(1,2,3,4-tetrahydronaphthalen-1-yl)isonicotinamide

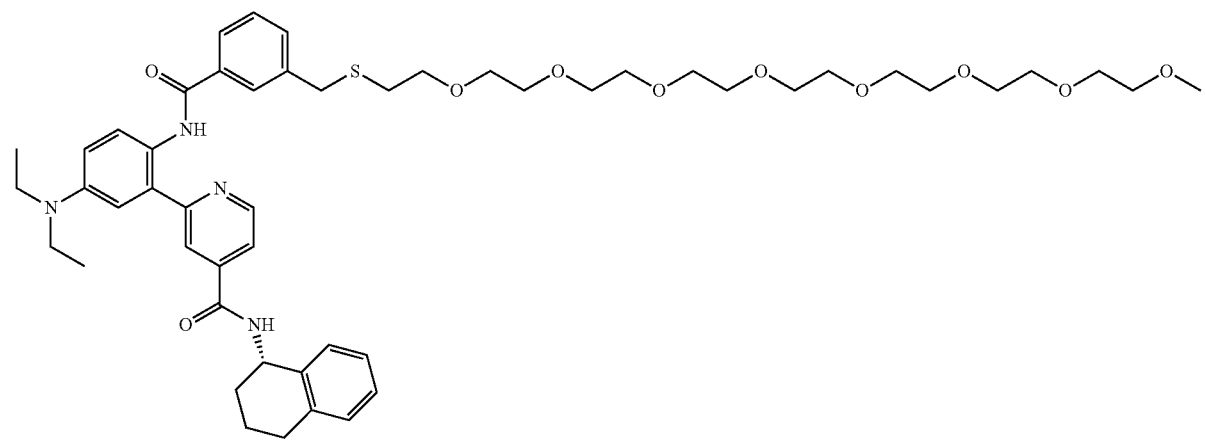 [SMILES: CCN(CC)c1ccc(NC(=O)c2cccc(CSCCOCCOCCOCCOCCOCCOCCOCCOC)c2)c(-c2cc(C(=O)N[C@H]3CCCc4ccccc43)ccn2)c1]

531

Example 286

(S)-2-(2-(3-(2,5,8,11,14,17,20,23-octaoxa-26-thia-heptacosan-27-yl)benzamido)-5-(diethylamino)phenyl)-N-(1,2,3,4-tetrahydronaphthalen-1-yl)isonicotinamide This compound was prepared from Compound 131c according to the procedure described in Example 265 using S-2,5,8,11,14,17,20,23-octaoxapentacosan-25-yl ethanethioate as the protected thiol. MS (ES, m/z) 931.5 [M+H]$^+$.

Example 287

2-(2-(3-(1-(4-(2,5,8,11,14,17,20-heptaoxadocosan-22-yl(methyl)carbamoyl)phenylsulfonamido)-3,6,9,12-tetraoxapentadecan-15-yl)benzamido)-5-(diethylamino)phenyl)-N-(3-(trifluoromethyl)benzyl)isonicotinamide

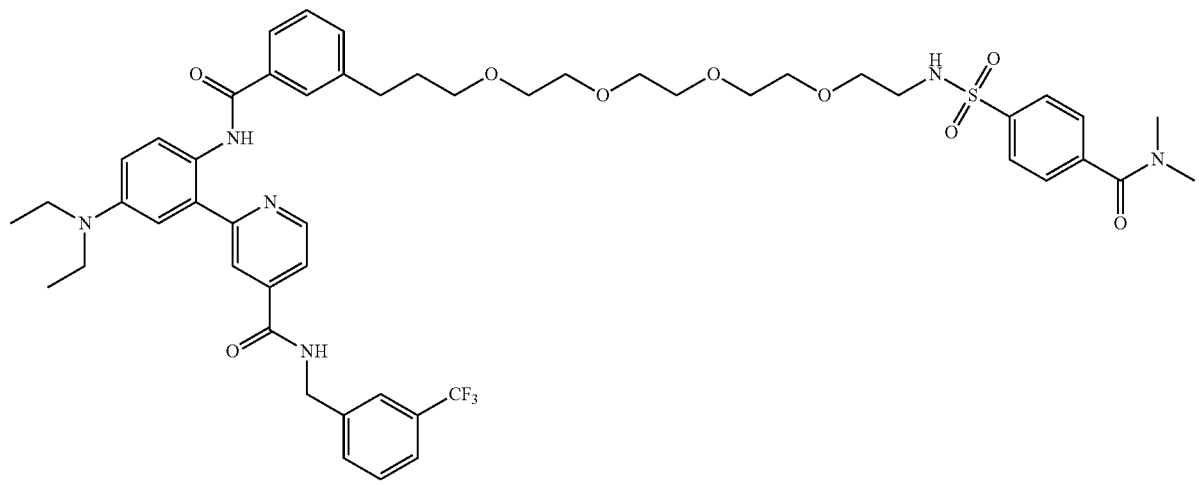

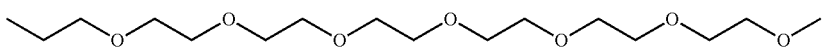

533

This compound was prepared from 4-(N-(15-(3-(4-(di-ethylamino)-2-(4-(3-(trifluoromethyl)benzylcarbamoyl)pyridin-2-yl)phenylcarbamoyl)phenyl)-3,6,9,12-tetraoxapentadecyl)sulfamoyl)benzoic acid 272a by following the procedure described in Example 272 using N-methyl-2,5,8,11,14,17,20-heptaoxadocosan-22-amine 135c.1 as the amine component in this coupling. MS (ES, m/z) 1299.5 [M+H]$^+$.

534

Example 288

2-(2-(3-(1-(4-(4-(2,5,8,11,14,17,20-heptaoxadocosan-22-yl)-3-oxopiperazine-1-carbonyl)phenylsulfonamido)-3,6,9,12-tetraoxapentadecan-15-yl)benzamido)-5-(diethylamino)phenyl)-N-(3-(trifluoromethyl)benzyl)isonicotinamide

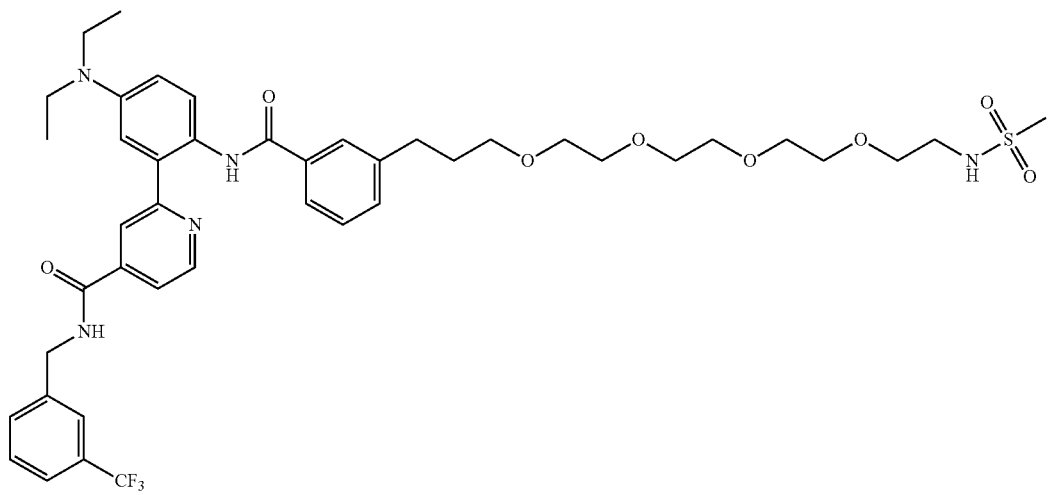

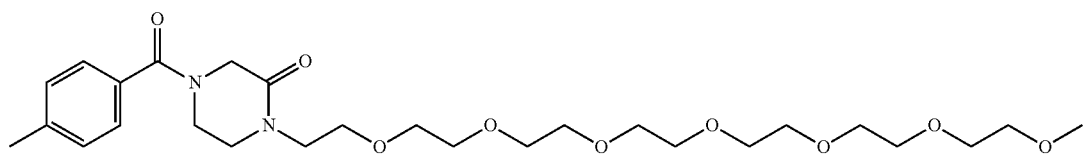

535

This compound was prepared from 4-(N-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecyl)sulfamoyl)benzoic acid 272a by following the procedure described in Example 272 using 1-(2,5,8,11,14,17,20-heptaoxadocosan-22-yl)piperazin-2-one 135c.5 as the amine component in this coupling. MS (ES, m/z) 1368.4 [M+H]+.

536

Example 289

3-(N-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecyl)sulfamoyl) benzoic acid

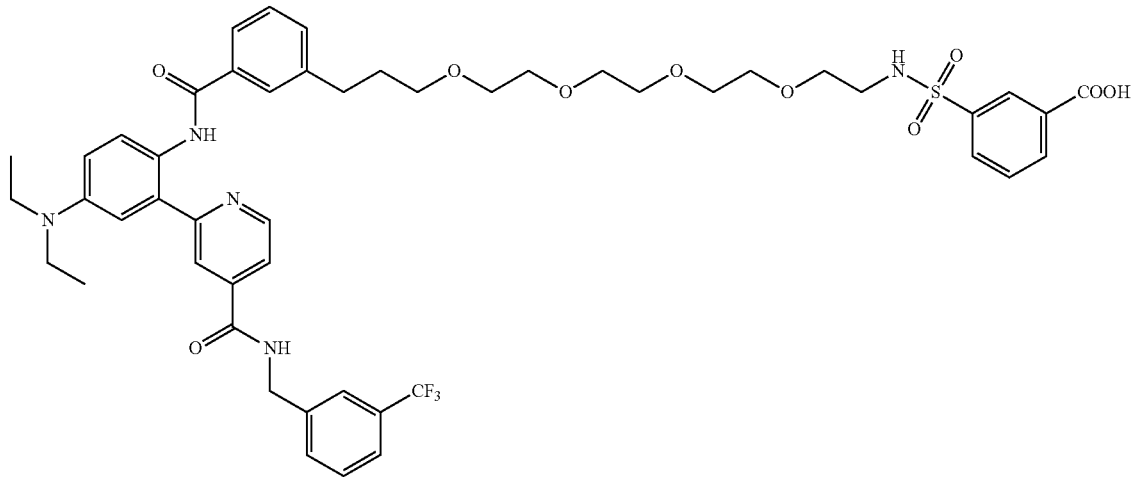 [SMILES: CCN(CC)c1ccc(NC(=O)c2cccc(CCCOCCOCCOCCOCCNS(=O)(=O)c3cccc(C(=O)O)c3)c2)c(-c2cc(C(=O)NCc3cccc(C(F)(F)F)c3)ccn2)c1]

This compound was prepared from Intermediate 270 according to the procedure described in Example 272 using 3-(chlorosulfonyl)benzoic acid as the sulfonyl chloride. MS (ES, m/z) 964.6 [M+H]+.

Example 290

4-(4-(16-(3-(4-(diethylamino)-2-(4-(3-(trifluoromethyl)benzylcarbamoyl)pyridin-2-yl)phenylcarbamoyl)phenyl)-4,7,10,13-tetraoxahexadecane)piperazin-1-ylsulfonyl)benzoic acid Scheme 114.

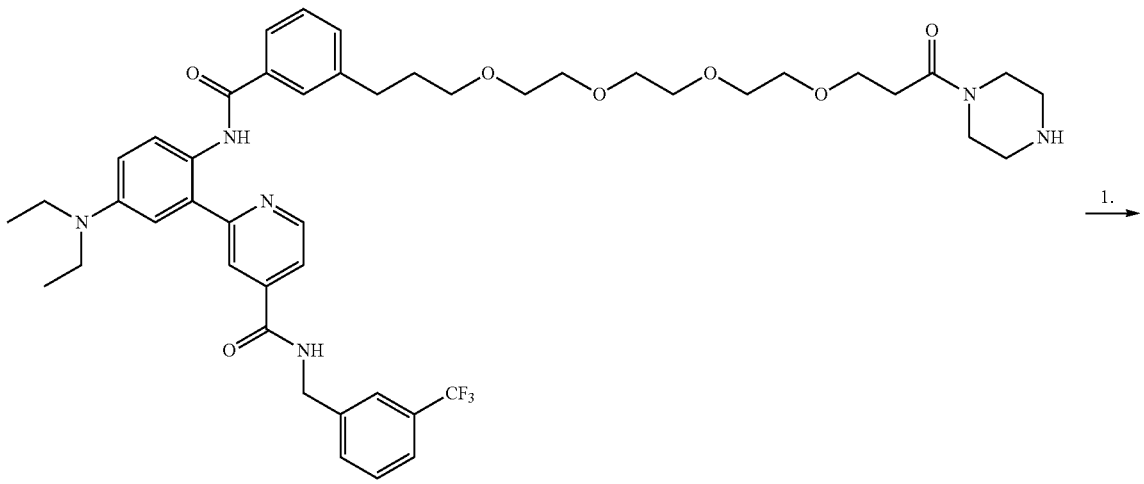

262b

-continued

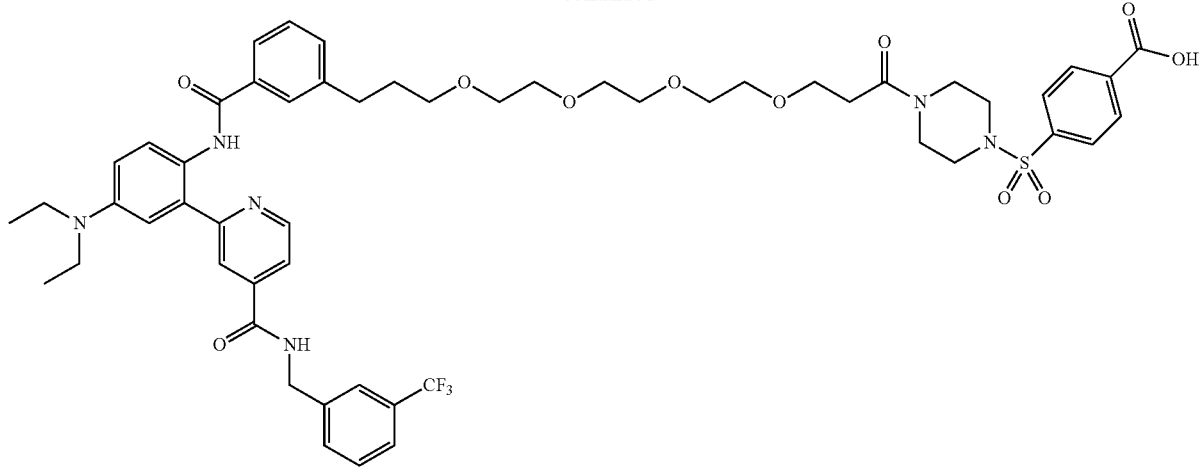

290

1. DIEA, DMF.

Example 290

4-(4-(16-(3-(4-(diethylamino)-2-(4-(3-(trifluoromethyl)benzylcarbamoyl)pyridin-2-yl)phenylcarbamoyl)phenyl)-4,7,10,13-tetraoxahexadecane)piperazin-1-ylsulfonyl)benzoic acid To a solution of 2-(5-(diethylamino)-2-(3-(16-oxo-16-(piperazin-1-yl)-4,7,10,13-tetraoxahexadecyl)benzamido)phenyl)-N-(3-(trifluoromethyl)benzyl)isonicotinamide 262b (50 mg, 0.0505 mmol, 1.0 eq) in DMF (1 mL) was added TEA (19.5 mg, 0.152 mmol, 3.0 eq) and finally 4-(chlorosulfonyl)benzoic acid (11.1 mg, 0.0505 mmol, 1.0 eq). After 2 hours, the resulting solution was diluted with acetonitrile/water solution (1:1, 2 mL), acidified with TFA and purified by reverse phase HPLC eluting with a water/CH$_3$CN gradient containing 0.05% TFA. The product was obtained as 15.8 mg of an oil. MS (ES, m/z) 1061.5 [M+H]$^+$.

Example 291

2-(5-(diethylamino)-2-(3-(16-oxo-16-(4-tosylpiperazin-1-yl)-4,7,10,13-tetraoxahexadecyl)benzamido)phenyl)-N-(3-(trifluoromethyl)benzyl)isonicotinamide

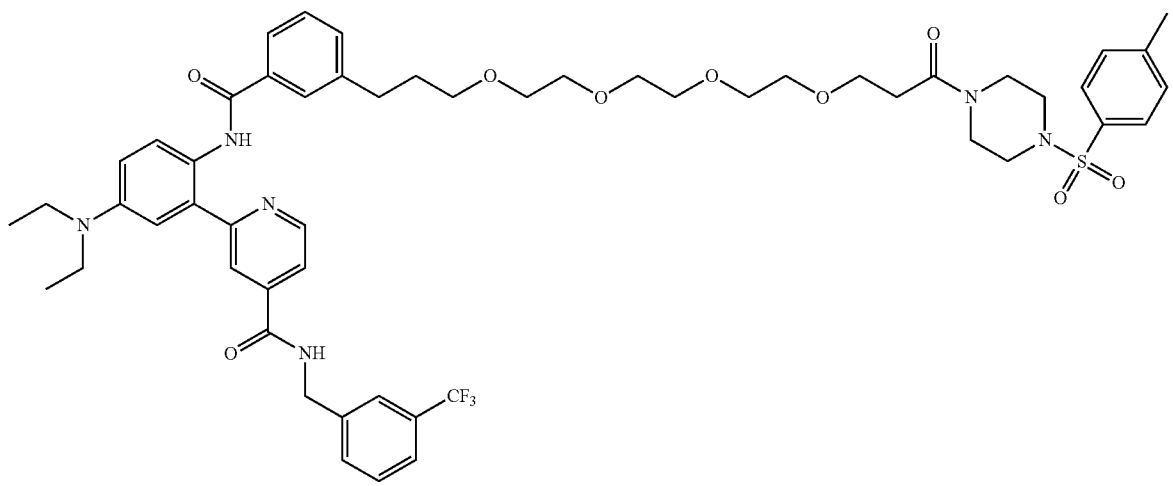 [SMILES: CCN(CC)c1ccc(NC(=O)c2cccc(CCCOCCOCCOCCOCCC(=O)N3CCN(S(=O)(=O)c4ccc(C)cc4)CC3)c2)c(-c2cc(C(=O)NCc3cccc(C(F)(F)F)c3)ccn2)c1]

This compound was prepared from 262b according to the procedure described in Example 290 using 4-methylbenzene-1-sulfonyl chloride as the sulfonyl chloride. MS (ES, m/z) 1031.4 [M+H]⁺.

Example 292

2-(5-(diethylamino)-2-(3-(16-(4-(isopropylsulfonyl)piperazin-1-yl)-16-oxo-4,7,10,13-tetraoxahexadecyl)benzamido)phenyl)-N-(3-(trifluoromethyl)benzyl)isonicotinamide

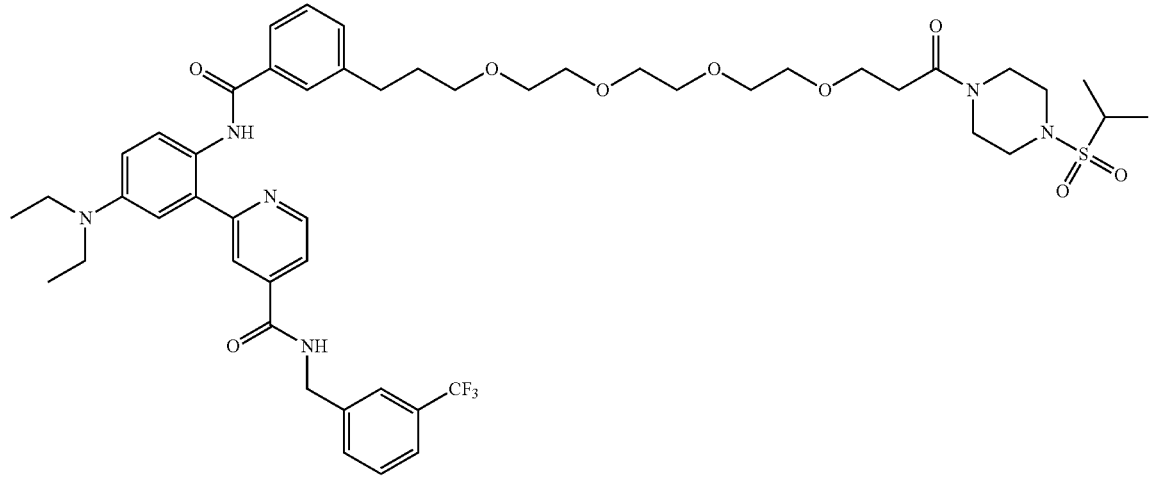 [SMILES: CCN(CC)c1ccc(NC(=O)c2cccc(CCCOCCOCCOCCOCCC(=O)N3CCN(S(=O)(=O)C(C)C)CC3)c2)c(-c2cc(C(=O)NCc3cccc(C(F)(F)F)c3)ccn2)c1]

This compound was prepared from 262b according to the procedure described in Example 290 using propane-2-sulfonyl chloride as the sulfonyl chloride. MS (ES, m/z) 983.9 [M+H]⁺.

Example 293

16-(3-(4-(16-(3-(4-(diethylamino)-2-(4-(3-(trifluoromethyl)benzylcarbamoyl)pyridin-2-yl)phenylcarbamoyl)phenyl)-4,7,10,13-tetraoxahexadecane)piperazine-1-carbonyl)phenyl)-4,7,10,13-tetraoxahexadecan-1-oic acid

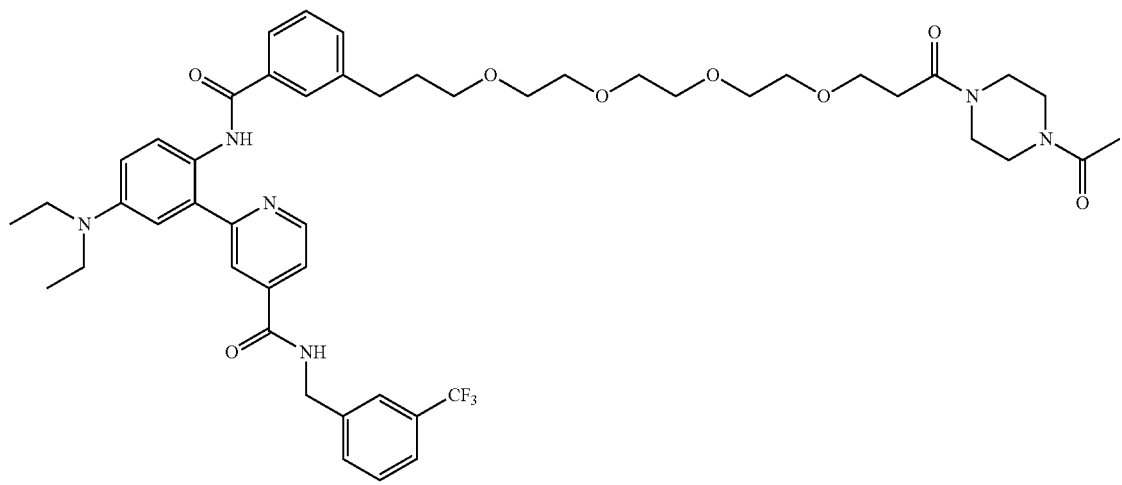

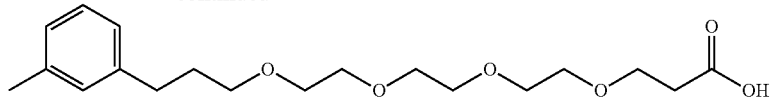

To a solution of 2-(5-(diethylamino)-2-(3-(16-oxo-16-(piperazin-1-yl)-4,7,10,13-tetraoxahexadecyl)benzamido)phenyl)-N-(3-(trifluoromethyl)benzyl)isonicotinamide 262b (56.1 mg, 0.072 mmol, 1.0 eq) and 4-(2,2-dimethyl-4-oxo-3,7,10,13,16-pentaoxanonadecan-19-yl)benzoic acid 251c (31.7 mg, 0.72 mmol, 1.0 eq) in DMF (0.5 mL) was added DIEA (46.5 mg, 0.36 mmol, 5.0 eq) and HATU (30.1 mg, 0.0792 mmol, 1.1 eq). After 4 hours the resulting solution was diluted with EtOAc (10 mL) and washed with water (3×5 mL) and brine, and dried over Na$_2$SO$_4$. The solvent was removed and the resulting crude material diluted with dichloromethane (2 mL). TFA (0.5 mL) was added and the reaction stirred for 30 minutes to remove the ester. The solvent was removed and the resulting residue diluted with acetonitrile/water (1:1, 2 mL) and purified by reverse phase HPLC eluting with a water/CH$_3$CN gradient containing 0.05% TFA. The product was obtained as 55.2 mg of an oil. MS (ES, m/z) 1243.5 [M+H]$^+$.

Example 294

3-(4-(N-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecyl)sulfamoyl)phenyl)propanoic acid

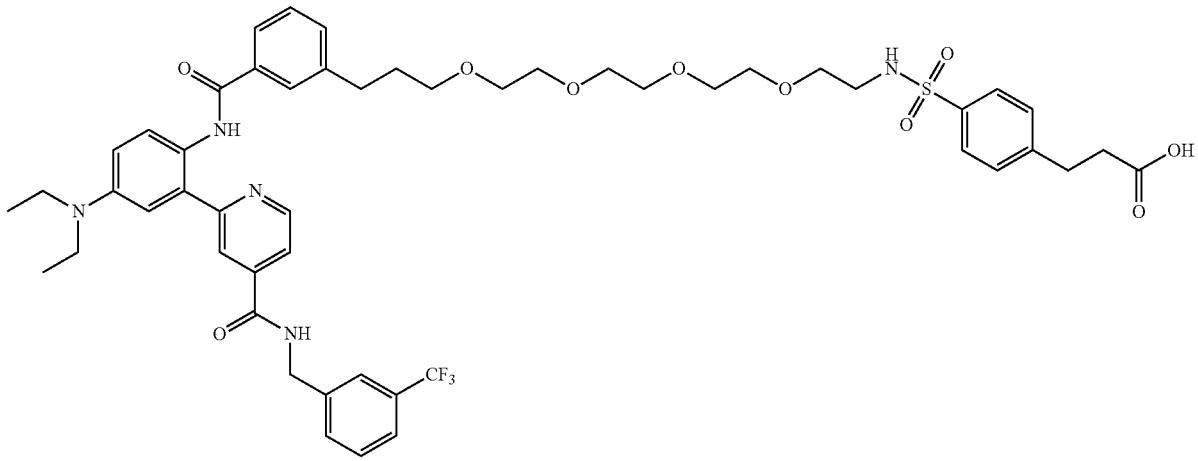 [SMILES: CCN(CC)c1ccc(NC(=O)c2cccc(CCCOCCOCCOCCOCCNS(=O)(=O)c3ccc(CCC(=O)O)cc3)c2)c(-c2cc(C(=O)NCc3cccc(C(F)(F)F)c3)ccn2)c1]

Example 294

3-(4-(N-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecyl)sulfamoyl)phenyl)propanoic acid This compound was prepared from Example 270 according to the procedure described in Example 272 using 3-(4-(chlorosulfonyl)phenyl)propanoic acid as the sulfonyl chloride. MS (ES, m/z) 992.9 [M+H]$^+$; $^1$H NMR (400 MHz, CD$_3$OD) δ 9.42 (t, J=5.9 Hz, 1H), 8.92 (d, J=5.2 Hz, 1H), 8.80 (d, J=9.2 Hz, 1H), 8.39 (s, 1H), 8.04 (s, 1H), 7.87 (dd, J=5.2, 1.5 Hz, 1H), 7.83-7.75 (m, 2H), 7.71-7.66 (m, 3H), 7.64 (d, J=7.5 Hz, 1H), 7.60-7.48 (m, 3H), 7.46 (d, J=5.0 Hz, 2H), 7.35 (d, J=8.5 Hz, 2H), 4.68 (s, 2H), 3.72 (q, J=7.1 Hz, 4H), 3.65-3.53 (m, 9H), 3.52-3.46 (m, 5H), 3.42-3.37 (m, 2H), 3.36-3.31 (m, 2H), 2.98-2.89 (m, 4H), 2.83-2.75 (m, 2H), 2.59 (t, J=7.5 Hz, 2H), 1.91 (dq, J=12.8, 6.3 Hz, 2H), 1.20 (t, J=7.2 Hz, 6H).

Example 295

2-(5-(diethylamino)-2-(3-(1-(4-(23-(2-methoxyethyl)-24-oxo-2,5,8,11,14,17,20-heptaoxa-23-azahexacosan-26-yl)phenylsulfonamido)-3,6,9,12-tetraoxapentadecan-15-yl)benzamido)phenyl)-N-(3-(trifluoromethyl)benzyl)isonicotinamide

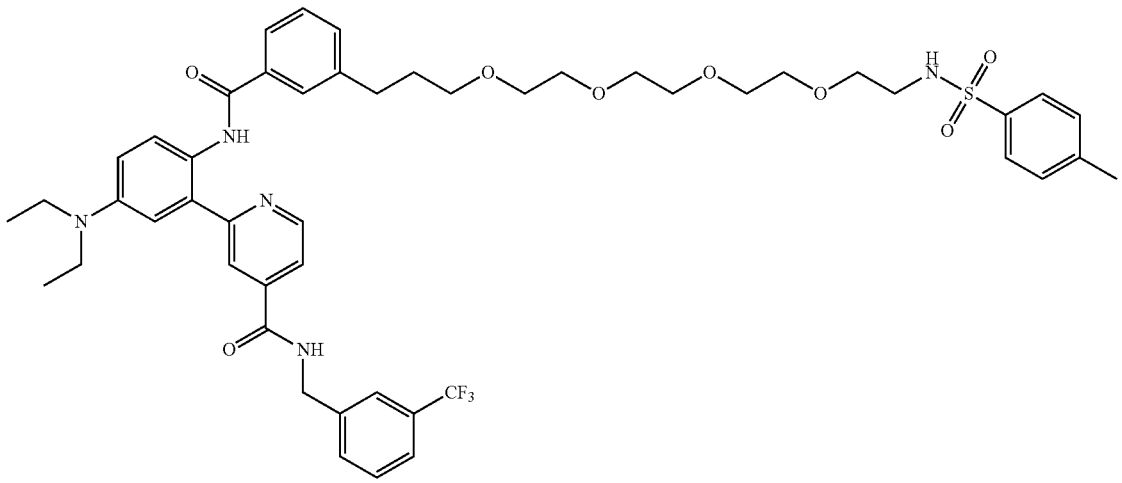

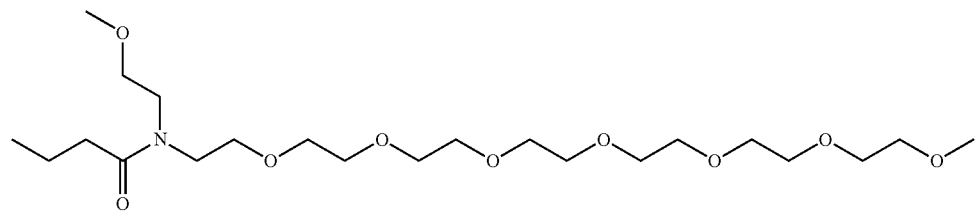

This compound was prepared from compound Example 294 according to the procedure described in Example 272 using N-(2-methoxyethyl)-2,5,8,11,14,17,20-heptaoxadocosan-22-amine as the amine component in this coupling. MS (ES, m/z) 1371.6 [M+H]+.

Example 296

2-(5-(diethylamino)-2-(3-(1-(4-(24-oxo-2,5,8,11,14,17,20-heptaoxa-23-azahexacosan-26-yl)phenylsulfonamido)-3,6,9,12-tetraoxapentadecan-15-yl)benzamido)phenyl)-N-(3-trifluoromethyl)benzyl) isonicotinamide

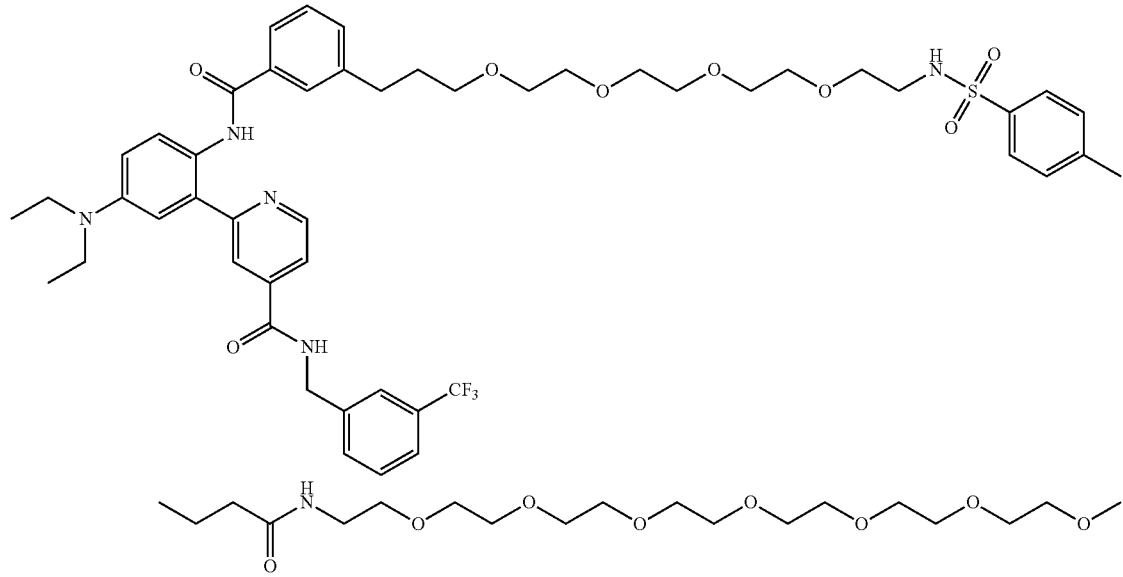

This compound was prepared from compound Example 294 according to the procedure described in Example 272 using 2,5,8,11,14,17,20-heptaoxadocosan-22-amine as the amine component in this coupling. MS (ES, m/z) 1313.6 [M+H]+.

Example 297

16-(4-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecylcarbamoyl)phenyl)-4,7,10,13-tetraoxahexadecan-1-oic acid

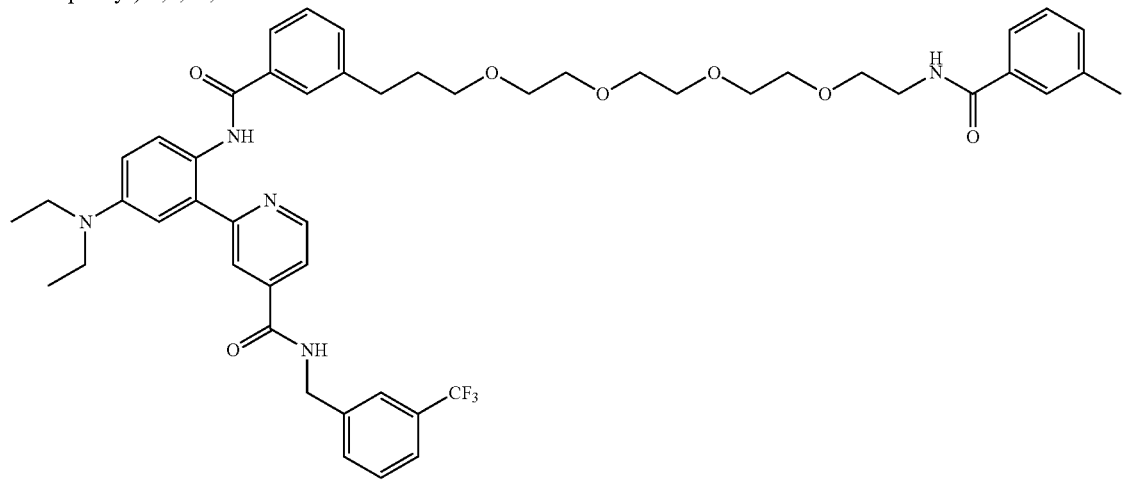

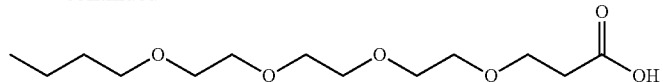

Example 297

16-(4-(15-(3-(4-(diethylamino)-2-(4-(3-(trifluoromethyl)benzylcarbamoyl)pyridin-2-yl)phenylcarbamoyl)phenyl)-3,6,9,12-tetraoxapentadecylcarbamoyl)phenyl)-4,7,10,13-tetraoxahexadecan-1-oic acid This compound was prepared from Example 270 the procedure described in Example 293 using 4-(2,2-dimethyl-4-oxo-3,7,10,13,16-pentaoxanonadecan-19-yl)benzoic acid as the acid component in the coupling. MS (ES, m/z) 1146.6 [M+H]$^+$.

Example 298

31-(3-(4-(diethylamino)-2-(4-(3-(trifluoromethyl)benzylcarbamoyl)pyridin-2-yl)phenylcarbamoyl)phenyl)-4,7,10,13,16,19,22,25,28-nonaoxahentriacontan-1-oic acid

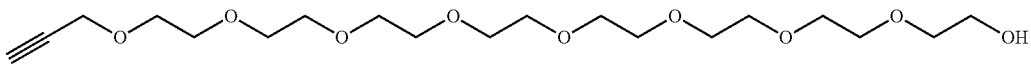 [SMILES: C#CCOCCOCCOCCOCCOCCOCCOCCOCCO]

Intermediate 298a:
3,6,9,12,15,18,21,24-octaoxaheptacos-26-yn-1-ol

Into a 500-mL round-bottom flask, was placed a solution of 3,6,9,12,15,18,21-heptaoxatricosane-1,23-diol (6.7 g, 18.11 mmol, 1.00 equiv) in tetrahydrofuran (200 mL). This was followed by the addition of sodium hydride (724 mg, 18.10 mmol, 1.00 equiv, 60%) in several batches at 0-5° C. in 30 min. The resulting solution was stirred for 30 min at 0° C. To this was added a solution of 3-bromoprop-1-yne (2.24 g, 18.82 mmol, 1.04 equiv) in tetrahydrofuran (100 mL) dropwise with stirring at 0-5° C. in 1 h. The reaction progress was monitored by LCMS. The resulting solution was allowed to react, with stirring, for an additional 1 h at room temperature. The solids were filtered out. The residue was applied onto a silica gel column with dichloromethane:methanol (50:1). This resulted in 3 g (40%) of intermediate 298a as light yellow oil.

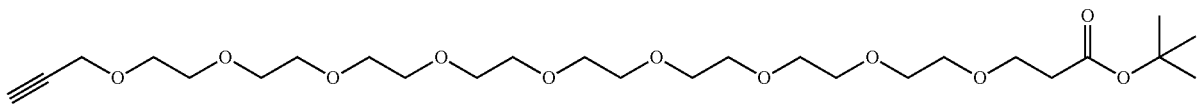 [SMILES: C#CCOCCOCCOCCOCCOCCOCCOCCOCCOCCC(=O)OC(C)(C)C]

Intermediate 298b: tert-butyl 3-(2-(2-(2-(2-(2-(2-(2-(2-(prop-2-ynyloxy)ethoxy)ethoxy)ethoxy)ethoxy)ethoxy)ethoxy)ethoxy)propanoate Into a 500-mL round-bottom flask, was placed a solution of 2-(2-(2-(2-(2-(2-(2-(2-(prop-2-ynyloxy)ethoxy)ethoxy)ethoxy)ethoxy)ethoxy)ethoxy)ethoxy)ethanol (22.3 g, 54.66 mmol, 1.00 equiv) in tetrahydrofuran (100 mL), Na (75 mg, 3.26 mmol, 0.06 equiv). This was followed by the addition of a solution of tert-butyl acrylate (8.4 g, 65.62 mmol, 1.20 equiv) in tetrahydrofuran (100 mL) dropwise with stirring. The resulting solution was stirred overnight at room temperature. The pH value of the solution was adjusted to 7 with hydrogen chloride (1 mol/L). The resulting mixture was concentrated under vacuum. The residue was applied onto a silica gel column with dichloromethane/methanol (200:1). This resulted in 14.5 g (49%) of intermediate 298b as yellow oil.

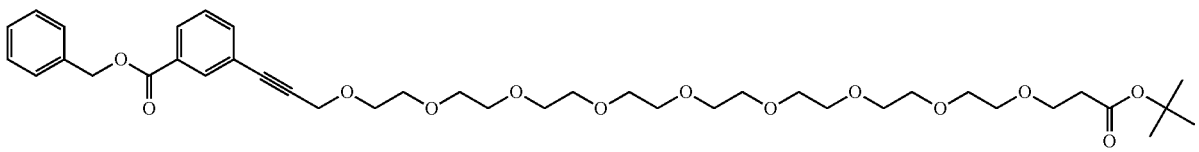 [SMILES: CC(C)(C)OC(=O)CCOCCOCCOCCOCCOCCOCCOCCOCCOCC#Cc1cccc(C(=O)OCc2ccccc2)c1]

Intermediate 298c

Into a 250-mL round-bottom flask purged and maintained with an inert atmosphere of nitrogen, was placed a solution of tert-butyl 3-(2-(2-(2-(2-(2-(2-(2-(2-(prop-2-ynyloxy)ethoxy)ethoxy)ethoxy)ethoxy)ethoxy)ethoxy)ethoxy)propanoate (10.1 g, 18.84 mmol, 1.00 equiv) in tetrahydrofuran (200 mL), benzyl 3-iodobenzoate (7 g, 20.71 mmol, 1.00 equiv), copper(I) iodide (358 mg, 1.88 mmol, 0.10 equiv), $Pd(PPh_3)Cl_2$ (1.32 g, 1.88 mmol, 0.10 equiv), triethylamine (3.8 g, 37.62 mmol, 2.00 equiv). The resulting solution was stirred for 3 h at room temperature. The resulting mixture was concentrated under vacuum. The residue was dissolved in 100 mL of ethyl acetate. The solids were filtered out. The filtrate was washed with 3×100 mL of brine. The mixture was dried over anhydrous sodium sulfate and concentrated under vacuum. The residue was applied onto a silica gel column with dichloromethane/methanol (100:1). This resulted in 6.4 g (46%) of intermediate 298c as red oil.

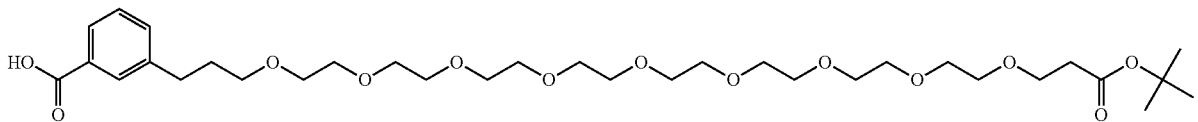 [SMILES: CC(C)(C)OC(=O)CCOCCOCCOCCOCCOCCOCCOCCOCCOCCCc1cccc(C(=O)O)c1]

Intermediate 298d: 3-(2,2-dimethyl-4-oxo-3,7,10,13,16,19,22,25,28,31-decaoxatetratriacontan-34-yl)benzoic acid Into a 250 mL round bottom flask, was placed a solution of intermediate 298c (6.4 g, 8.58 mmol, 1.00 equiv) in methanol (100 mL), Palladium carbon (6.5 g, 60.19 mmol, 7.02 equiv). Hydrogen gas was introduced into the reaction vessel. The resulting solution was stirred overnight at room temperature. The solids were filtered out. The resulting mixture was concentrated under vacuum. This resulted in 5.6 g (99%) of intermediate 298d as dark green oil. LC-MS (ES, m/z): 683 [M+Na]⁺ H-NMR (300 MHz, CDCl₃, ppm): 7.93 (m, 2H), 7.38 (m, 2H), 3.75-3.60 (m, 36H), 3.48 (t, 2H), 3.13 (m, 4H), 2.79 (t, 2H), 2.53 (t, 2H), 1.95 (m, 2H), 1.47 (s, 9H).

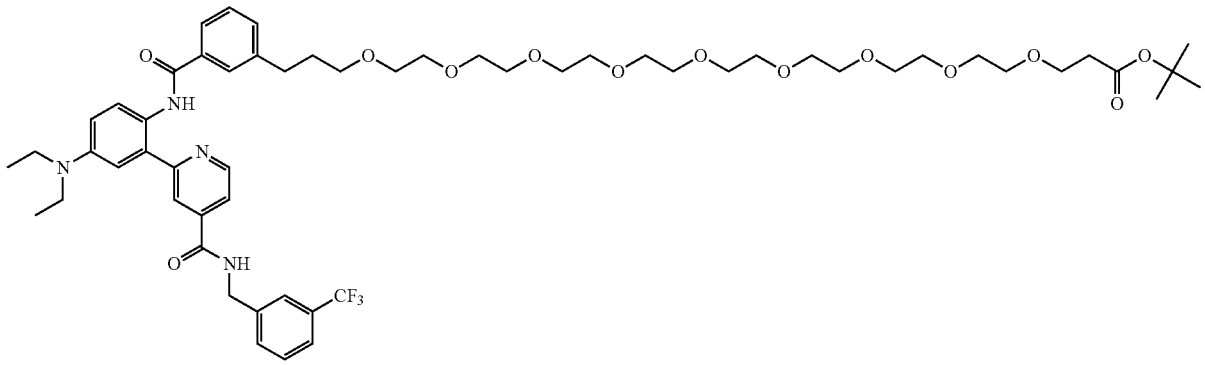 [SMILES: CCN(CC)c1ccc(NC(=O)c2cccc(CCCOCCOCCOCCOCCOCCOCCOCCOCCOCCC(=O)OC(C)(C)C)c2)c(-c2cc(C(=O)NCc3cccc(C(F)(F)F)c3)ccn2)c1]

Intermediate 298e: tert-butyl 31-(3-(4-(diethylamino)-2-(4-(3-(trifluoromethyl)benzylcarbamoyl)pyridin-2-yl)phenylcarbamoyl)phenyl)-4,7,10,13,16,19,22,25,28-nonaoxahentriacontan-1-oate To a solution of 2-(2-amino-5-(diethylamino)phenyl)-N-(3-(trifluoromethyl)benzyl)isonicotinamide 25b 1.4 g, 3.16 mmol, 1.1 eq) and 3-(2,2-dimethyl-4-oxo-3,7,10,13,16,19,22,25,28,31-decaoxatetratriacontan-34-yl)benzoic acid (1.95 g, 2.95 mmol, 1.0 eq) in DMF (15 mL) was added DIEA (1.63 g, 12.64 mmol, 4.3 eq) and HATU (1.32 g, 3.48 mmol, 1.2 eq). After 1 hour the solvent was removed and the resulting residue diluted with EtOAc (150 mL), washed with water (4×75 mL) and brine, and dried over Na₂SO₄. The crude reaction mixture was purified by flash column chromatography (80 g SiO₂, 0 to 4% MeOH in DCM) to give 2.28 g of intermediate 298e as a yellow oil.

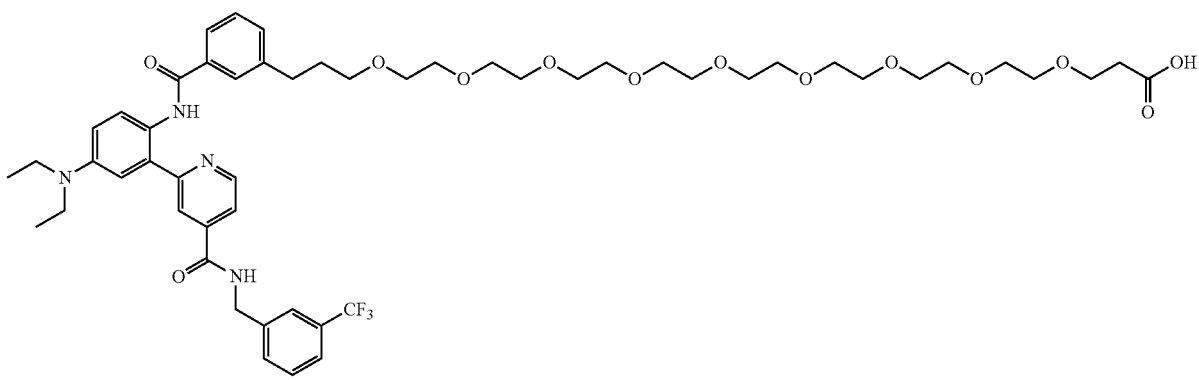 [SMILES: CCN(CC)c1ccc(NC(=O)c2cccc(CCCOCCOCCOCCOCCOCCOCCOCCOCCOCCC(=O)O)c2)c(-c2cc(C(=O)NCc3cccc(C(F)(F)F)c3)ccn2)c1]

Example 298

31-(3-(4-(diethylamino)-2-(4-(3-(trifluoromethyl)benzylcarbamoyl)pyridin-2-yl)phenylcarbamoyl)phenyl)-4,7,10,13,16,19,22,25,28-nonaoxahentriacontan-1-oic acid Intermediate 298e (2.28 g, 2.1 mmol) was dissolved in dichloromethane (10 mL) and TFA (5 mL) was added. The reaction was stirred at room temperature for one hour at which point solvent was removed. The TFA salt was dissolved in EtOAc (15 mL) and partitioned with water (10 mL). The pH was adjusted to 5.5 with 1N HCl and the organic layer diluted with EtOAc (75 mL), washed with water (50 mL). The aqueous layer was extracted with additional EtOAc (3×50 mL) until no color remained. The combined organic layers were washed with brine and dried over $Na_2SO_4$ to give 1.99 g of the free base. This was dissolved in acetonitrile (5 mL) and water (2 mL), NaOH was added (1 eq), and the resulting solution lyophilized to give the 1.81 g of Example 298 as a yellow powder. MS (ES, m/z) 1029.6 [M+H]$^+$. $^1$H NMR (400 MHz, CD$_3$OD) δ 8.99 (dd, J=5.5, 0.7 Hz, 1H), 8.54-8.49 (m, 2H), 8.20 (d, J=2.7 Hz, 1H), 8.07 (dd, J=5.5, 1.6 Hz, 1H), 7.79 (dd, J=8.9, 2.7 Hz, 1H), 7.76-7.70 (m, 2H), 7.69 (s, 1H), 7.64 (d, J=7.5 Hz, 1H), 7.57 (d, J=7.9 Hz, 1H), 7.53 (d, J=7.6 Hz, 1H), 7.46-7.41 (m, 2H), 4.67 (s, 2H), 3.77 (q, J=7.2 Hz, 4H), 3.68 (t, J=6.3 Hz, 2H), 3.63-3.53 (m, 31H), 3.47 (t, J=6.2 Hz, 2H), 3.29 (dt, J=3.3, 1.7 Hz, 8H), 2.81-2.74 (m, 2H), 2.50 (t, J=6.3 Hz, 2H), 1.23 (t, J=7.2 Hz, 6H).

Example 299

22-(3-(4-(diethylamino)-2-(4-(3-(trifluoromethyl)benzylcarbamoyl)pyridin-2-yl)phenylcarbamoyl)phenyl)-4,7,10,13,16,19-hexaoxadocosan-1-oic acid Intermediate 299a:
3,6,9,12,15-pentaoxaoctadec-17-yn-1-ol Into a 1000-mL 3-necked round-bottom flask, was placed a solution of 3,6,9,12-tetraoxatetradecane-1,14-diol (60 g, 251.78 mmol, 0.90 equiv) in tetrahydrofuran (300 mL). This was followed by the addition of sodium hydride (6.7 g, 0.66 equiv, 60%) at 0-10° C. The mixture was stirred for 0.5 h at 0-10° C. To this was added a solution of 3-bromoprop-1-yne (33.32 g, 280.00 mmol, 1.00 equiv) in tetrahydrofuran (100 mL) dropwise with stirring in 1.5 h. The resulting solution was stirred for 2 h at 0~10° C. The solids were filtered out. The resulting mixture was concentrated under vacuum. The residue was applied onto a silica gel column with ethyl acetate/petroleum ether (4:1~2:1). This resulted in 32.1 g (41%) of intermediate 299a as light yellow oil.

Intermediate 299b

Into a 1000-mL round-bottom flask purged and maintained with an inert atmosphere of nitrogen, was placed a solution of 3,6,9,12,15-pentaoxaoctadec-17-yn-1-ol (62.2 g, 225.12 mmol, 1.00 equiv) in tetrahydrofuran (500 mL), sodium (155.3 mg, 6.75 mmol, 0.03 equiv). The mixture was stirred for 30 minutes at room temperature. This was followed by the addition of a solution of tert-butyl acrylate (28.8 g, 224.65 mmol, 1.00 equiv) in tetrahydrofuran (100 mL) dropwise with stirring. The resulting solution was stirred overnight at room temperature. The pH value of the solution was adjusted to 7 with hydrogen chloride (1.2N mol/l). The resulting mixture was concentrated under vacuum. The residue was dissolved in 500 ml of ethyl acetate. The mixture was dried over anhydrous sodium sulfate and concentrated under vacuum. The residue was applied onto a silica gel column with petroleum ether/ethyl acetate (8:1~1:1). This resulted in 44 g (48%) of intermediate 299b as light yellow oil.

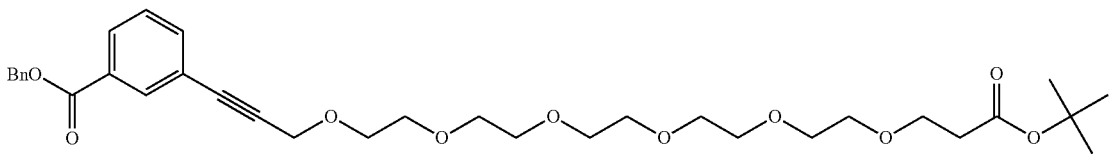 [SMILES: CC(C)(C)OC(=O)CCOCCOCCOCCOCCOCCOCC#Cc1cccc(C(=O)OCc2ccccc2)c1]

Intermediate 299c: tert-butyl 22-(3-(benzyloxycarbonyl)phenyl)-4,7,10,13,16,19-hexaoxadocos-21-yn-1-oate Into a 500-mL round-bottom flask purged and maintained with an inert atmosphere of nitrogen, was placed a solution of tert-butyl 4,7,10,13,16,19-hexaoxadocos-21-yn-1-oate (37.48 g, 92.66 mmol, 1.00 equiv) in tetrahydrofuran (200 mL), benzyl 3-iodobenzoate (34.5 g, 102.04 mmol, 1.10 equiv), copper(I) iodide (1.77 g, 9.29 mmol, 0.10 equiv), Pd(PPh$_3$)$_2$Cl$_2$ (6.50 g, 9.26 mmol, 0.10 equiv), triethylamine (18.72 g, 185.35 mmol, 2.00 equiv). The resulting solution was stirred for 4 h at room temperature. The resulting mixture was concentrated under vacuum. The residue was dissolved in 200 ml of ethyl acetate. The solids were filtered out. The resulting mixture was concentrated under vacuum. The residue was applied onto a silica gel column with petroleum ether/ethyl acetate (2:1~1:2). This resulted in 19.2 g (34%) of intermediate 299c as brown oil.

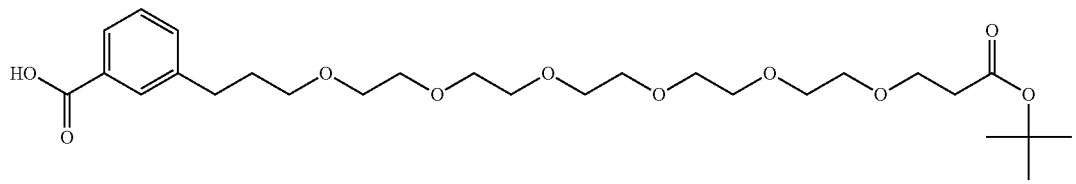 [SMILES: CC(C)(C)OC(=O)CCOCCOCCOCCOCCOCCOCCCc1cccc(C(=O)O)c1]

Intermediate 299d 3-(2,2-dimethyl-4-oxo-3,7,10,13,16,19,22-heptaoxapentacosan-25-yl)benzoic acid. Into a 250-mL round-bottom flask, was placed a solution of tert-butyl 22-(3-(benzyloxycarbonyl)phenyl)-4,7,10,13,16,19-hexaoxadocos-21-yn-1-oate (12.5 g, 20.36 mmol, 1.00 equiv) in methanol (200 mL), Palladium on carbon (25 g). Hydrogen gas was introduced into the reaction vessel. The resulting solution was stirred for 5 h at room temperature. The solids were filtered out. The resulting mixture was concentrated under vacuum. The crude product was washed with 2×30 mL of n-hexane. This resulted in 9.8 g (87%) of intermediate 299d as brown oil. LC-MS (ES, m/z): 551 [M+Na]$^+$ H-NMR (400 MHz, CDCl$_3$, ppm): 7.93~7.90 (m, 2H), 7.37~7.31 (m, 2H), 4.68 (s, 2H), 3.72~3.56 (m, 22H), 3.48~3.42 (m, H), 2.75 (tri, Jl=5.4 Hz, Jr=5.7 Hz, 2H), 2.50 (tri, Jl=4.8 Hz, Jr=5.1 Hz, 2H), 1.94~1.87 (m, 2H), 1.43~1.38 (m, 9H).

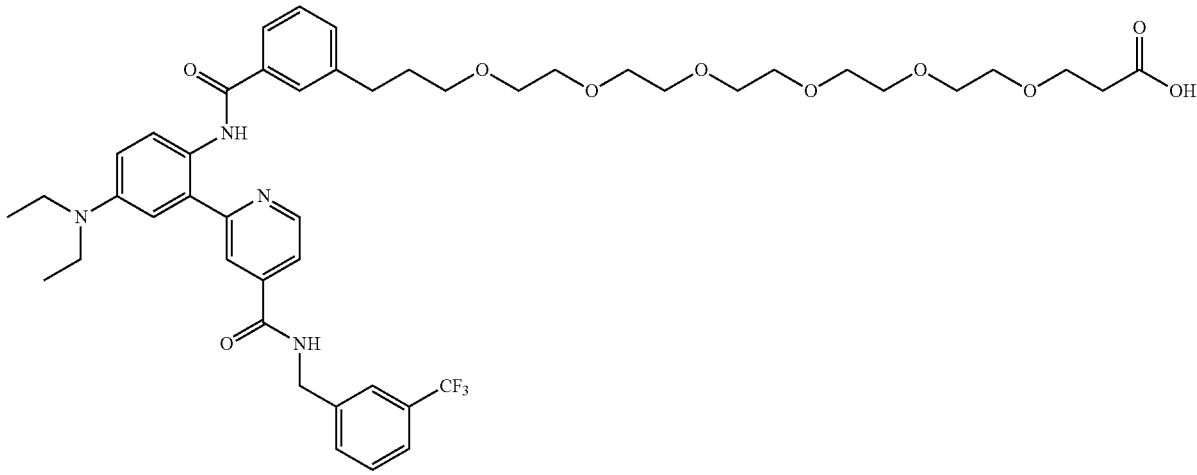 [SMILES: CCN(CC)c1ccc(NC(=O)c2cccc(CCCOCCOCCOCCOCCOCCOCCC(=O)O)c2)c(-c2cc(C(=O)NCc3cccc(C(F)(F)F)c3)ccn2)c1]

Example 299

22-(3-(4-(diethylamino)-2-(4-(3-(trifluoromethyl)benzylcarbamoyl)pyridin-2-yl)phenylcarbamoyl)phenyl)-4,7,10,13,16,19-hexaoxadocosan-1-oic acid This compound was prepared from 2-(2-amino-5-(diethylamino)phenyl)-N-(3-(trifluoromethyl)benzyl)isonicotinamide 25b using the procedures described in Example 251 using 3-(2,2-dimethyl-4-oxo-3,7,10,13,16,19,22-heptaoxapentacosan-25-yl)benzoic acid 299d as the protected acid component in the coupling. MS (ES, m/z) 897.9 [M+H]$^+$; $^1$H NMR (400 MHz, d$_6$ DMSO) δ 11.77 (s, 1H), 10.60 (t, J=5.9 Hz, 1H), 8.78 (d, J=5.2 Hz, 1H), 8.50 (s, 1H), 7.81 (d, J=5.1 Hz, 1H), 7.76 (s, 2H), 7.73 (s, 1H), 7.68 (s, 1H), 7.65-7.58 (m, 3H), 7.58-7.53 (m, 2H), 7.49 (t, J=7.9 Hz, 1H), 7.36-7.26 (m, 2H), 6.99 (d, J=3.0 Hz, 1H), 6.79 (dd, J=9.0, 3.0 Hz, 1H), 4.57 (d, J=6.0 Hz, 2H), 3.56-3.30 (m, 43H), 2.68-2.58 (m, 2H), 2.07 (t, J=7.5 Hz, 2H), 1.77 (p, J=6.1 Hz, 2H), 1.09 (t, J=7.0 Hz, 6H).

Example 300

19-(3-(4-(diethylamino)-2-(4-(3-(trifluoromethyl)benzylcarbamoyl)pyridin-2-yl)phenylcarbamoyl)phenyl)-4,7,10,13,16-pentaoxanonadecan-1-oic acid

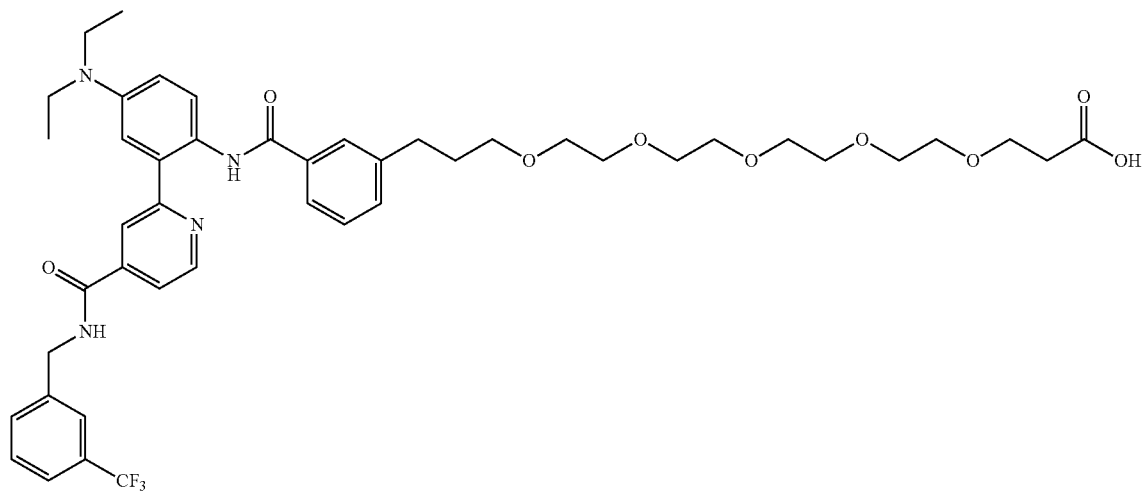 [SMILES: CCN(CC)c1ccc(NC(=O)c2cccc(CCCOCCOCCOCCOCCOCCC(=O)O)c2)c(-c2cc(C(=O)NCc3cccc(C(F)(F)F)c3)ccn2)c1]

This compound was prepared according to the procedure described for the synthesis of Example 251 substituting 2,2'-(2,2'-oxybis(ethane-2,1-diyl)bis(oxy))diethanol for triethylene glycol as a starting material. MS (ES, m/z) 853.6 [M+H]$^+$. $^1$H NMR (400 MHz, d$_6$DMSO) δ 11.81 (s, 1H), 10.76 (s, 1H), 8.77 (d, J=5.1 Hz, 1H), 8.55 (s, 1H), 7.82 (d, J=5.0 Hz, 1H), 7.78 (s, 1H), 7.72-7.66 (m, 2H), 7.64-7.52 (m, 4H), 7.48 (t, J=7.7 Hz, 1H), 7.35-7.24 (m, 2H), 6.98 (d, J=3.0 Hz, 1H), 6.78 (dd, J=8.8, 3.0 Hz, 1H), 4.57 (d, J=5.7 Hz, 3H), 3.57-3.30 (m, 37H), 2.67-2.57 (m, 3H), 2.08 (t, J=7.5 Hz, 2H), 1.82-1.71 (m, 2H), 1.09 (t, J=7.0 Hz, 7H).

Example 302

(S)-16-(3-(4-(diethylamino)-2-(4-(1,2,3,4-tetrahydronaphthalen-1-ylcarbamoyl)pyridin-2-yl)phenylcarbamoyl)phenyl)-4,7,10,13-tetraoxahexadecan-1-oic acid

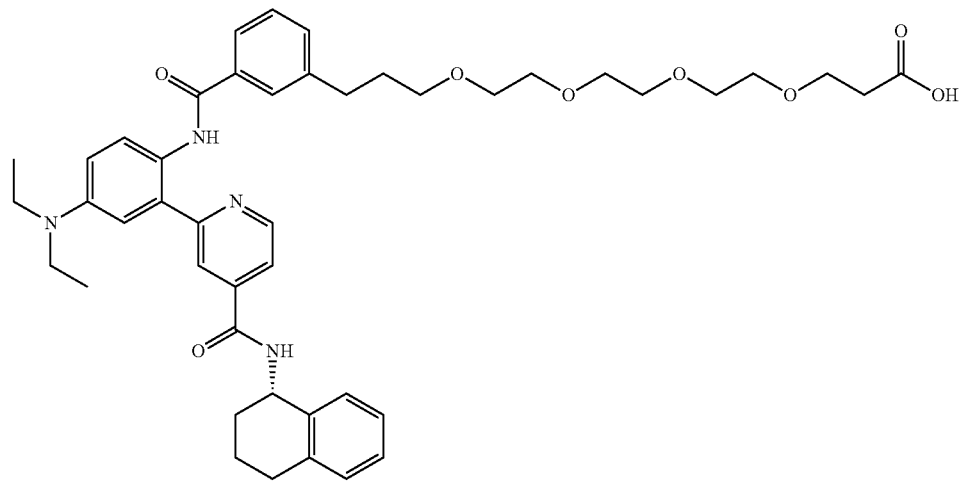 [SMILES: CCN(CC)c1ccc(NC(=O)c2cccc(CCCOCCOCCOCCOCCC(=O)O)c2)c(-c2cc(C(=O)N[C@H]3CCCc4ccccc43)ccn2)c1]

Example 302

(S)-16-(3-(4-(diethylamino)-2-(4-(1,2,3,4-tetrahydronaphthalen-1-ylcarbamoyl)pyridin-2-yl)phenylcarbamoyl)phenyl)-4,7,10,13-tetraoxahexadecan-1-oic acid This compound was prepared according to the procedure described for the synthesis of Example 251 substituting 131c in place of 25b. MS (ES, m/z) 781.4 [M+H]$^+$.

Example 303

16-(3-(4-(piperidin-1-yl)-2-(4-(3-(trifluoromethyl)benzylcarbamoyl)pyridin-2-yl)phenylcarbamoyl)phenyl)-4,7,10,13-tetraoxahexadecan-1-oic acid

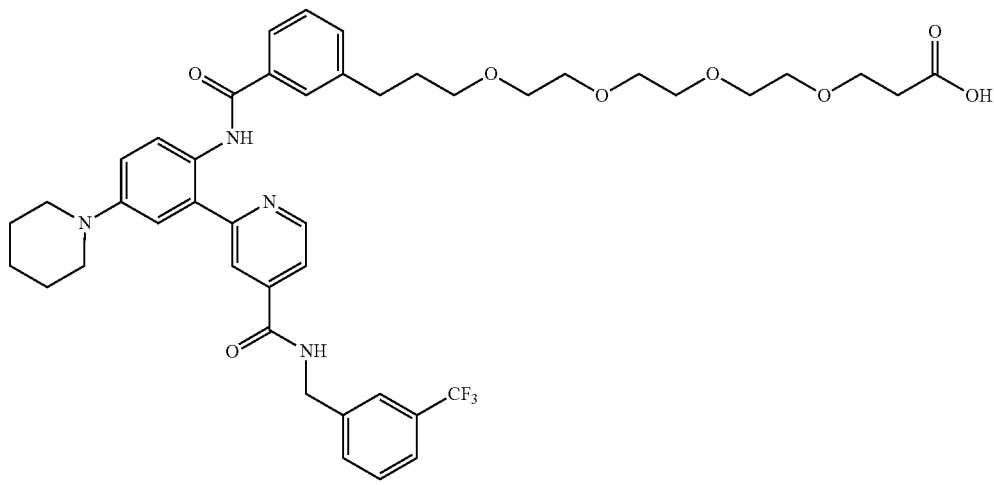 [SMILES: O=C(O)CCOCCOCCOCCOCCCc1cccc(C(=O)Nc2ccc(N3CCCCC3)cc2-c2cc(C(=O)NCc3cccc(C(F)(F)F)c3)ccn2)c1]

Example 303

16-(3-(4-(piperidin-1-yl)-2-(4-(3-(trifluoromethyl)benzylcarbamoyl)pyridin-2-yl)phenylcarbamoyl)phenyl)-4,7,10,13-tetraoxahexadecan-1-oic acid This compound was prepared according to the procedure described for the synthesis of Example 251 substituting 4.1c in place of 25b. MS (ES, m/z) 821.5 [M+H]$^+$.

Example 304

(S)-22-(3-(4-(diethylamino)-2-(4-(1,2,3,4-tetrahydronaphthalen-1-ylcarbamoyl)pyridin-2-yl)phenylcarbamoyl)phenyl)-4,7,10,13,16,19-hexaoxadocosan-1-oic-acid

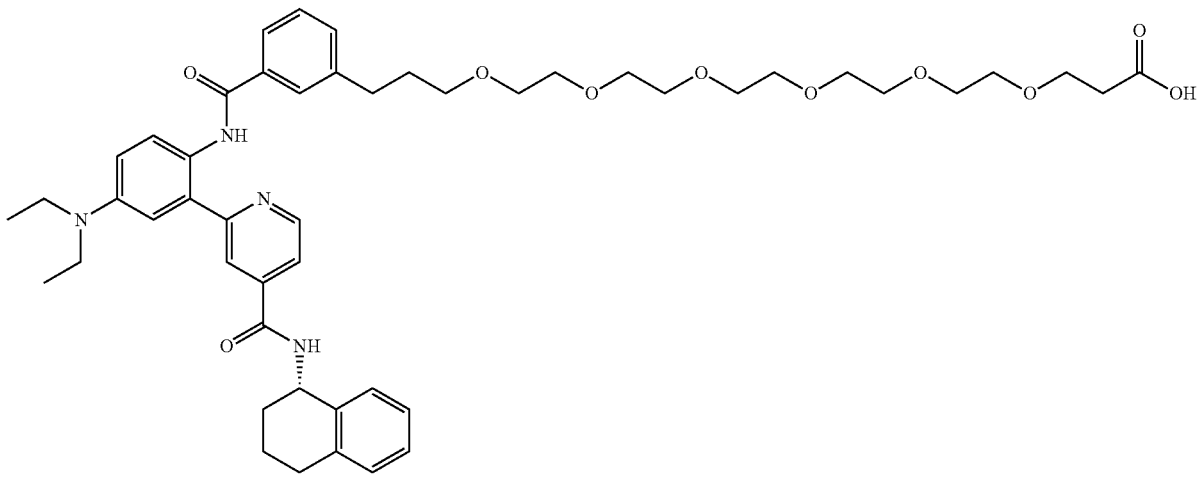 [SMILES: CCN(CC)c1ccc(NC(=O)c2cccc(CCCOCCOCCOCCOCCOCCOCCC(=O)O)c2)c(-c2cc(C(=O)N[C@H]3CCCc4ccccc43)ccn2)c1]

This compound was prepared from 131c according to the procedures described in Example 251 using 3-(2,2-dimethyl-4-oxo-3,7,10,13,16,19,22-heptaoxapentacosan-25-yl)benzoic acid 299d as the protected acid component. MS (ES, m/z) 869.6 [M+H]$^+$; $^1$H NMR (400 MHz, d$_6$ DMSO) δ 11.63 (s, 1H), 9.38 (d, J=8.3 Hz, 1H), 8.79 (d, J=5.2 Hz, 1H), 8.29 (s, 1H), 7.88 (d, J=9.0 Hz, 1H), 7.79 (d, J=6.3 Hz, 1H), 7.69 (s, 1H), 7.65-7.58 (m, 1H), 7.39-7.31 (m, 2H), 7.17-6.97 (m, 6H), 6.79 (dd, J=10.2, 1.5 Hz, 1H), 5.23-5.12 (m, 1H), 3.53-3.31 (m, 36H), 2.78-2.70 (m, 2H), 2.68-2.59 (m, 3H), 2.03-1.87 (m, 5H), 1.84-1.73 (m, 4H), 1.09 (t, J=6.9 Hz, 6H).

Example 306

(S)-19-(3-(4-(diethylamino)-2-(4-(1,2,3,4-tetrahydronaphthalen-1-ylcarbamoyl)pyridin-2-yl)phenylcarbamoyl)phenyl)-4,7,10,13,16-pentaoxanonadecan-1-oic acid

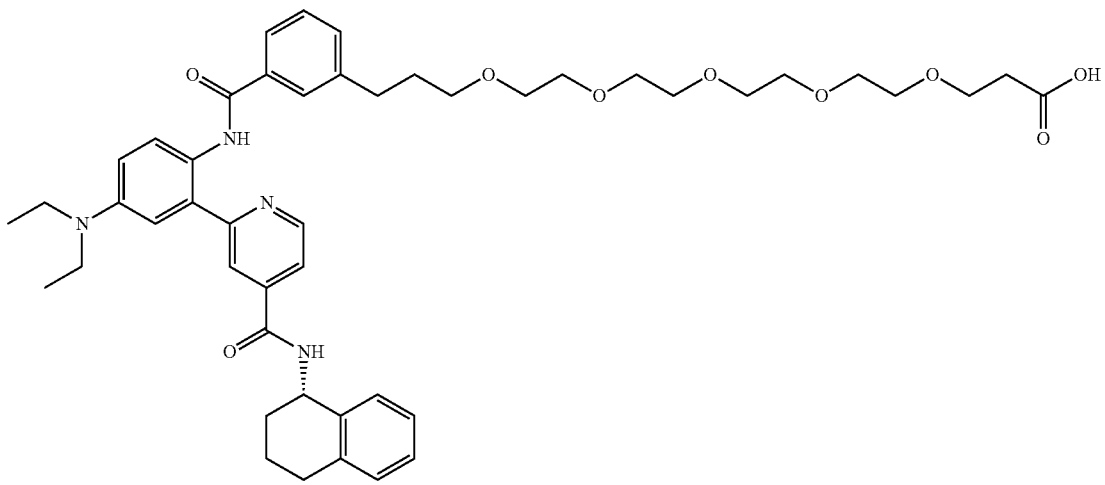 [SMILES: CCN(CC)c1ccc(NC(=O)c2cccc(CCCOCCOCCOCCOCCOCCC(=O)O)c2)c(-c2cc(C(=O)N[C@H]3CCCc4ccccc43)ccn2)c1]

This compound was prepared from 131c according to the procedures described in Example 251 and Example 300 using 3-(2,2-dimethyl-4-oxo-3,7,10,13,16,19-hexaoxadocosan-22-yl)benzoic acid as the protected acid component. MS (ES, m/z) 825.9 [M+H]$^+$.

Examples 320-326

The compounds listed in table 10 were prepared by the procedures described in Examples 262 and 272 from amine 270 and 270.1. Mass spectral data (ES, positive ion mode) is provided for each compound.

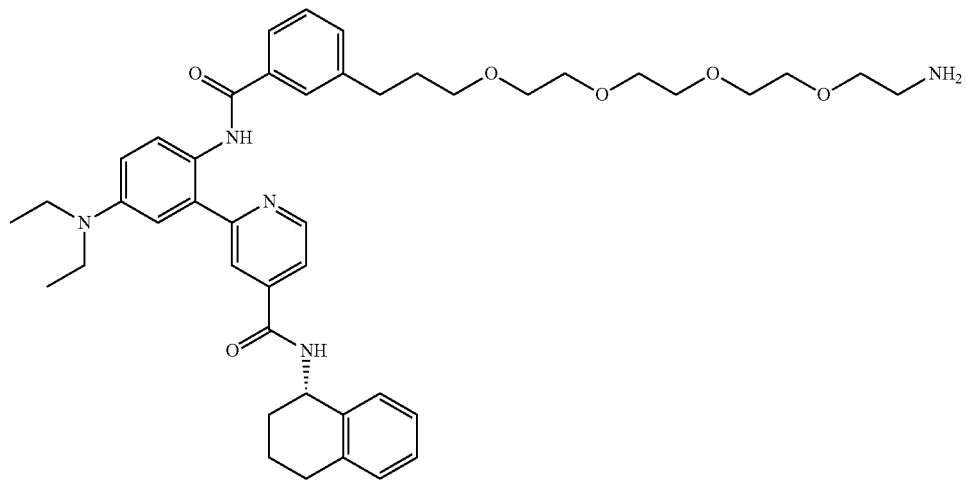 [SMILES: CCN(CC)c1ccc(NC(=O)c2cccc(CCCOCCOCCOCCOCCN)c2)c(-c2cc(C(=O)N[C@H]3CCCc4ccccc43)ccn2)c1]

Intermediate 270.1: (S)-2-(2-(3-(1-amino-3,6,9,12-tetraoxapentadecan-15-yl)benzamido)-5-(diethylamino)phenyl)-N-(1,2,3,4-tetrahydronaphthalen-1-yl)isonicotinamide This compound was prepared from (S)-2-(2-amino-5-(diethylamino)phenyl)-N-(1,2,3,4-tetrahydronaphthalen-1-yl)isonicotinamide 131c according to the procedures described in Example 270 using 270f as the protected acid. MS (ES, m/z) 752.4 [M+H]⁺.

TABLE 10

| Example | Method from Example | Structure | Mass Spectrum |
|---|---|---|---|
| 320 | 272 | 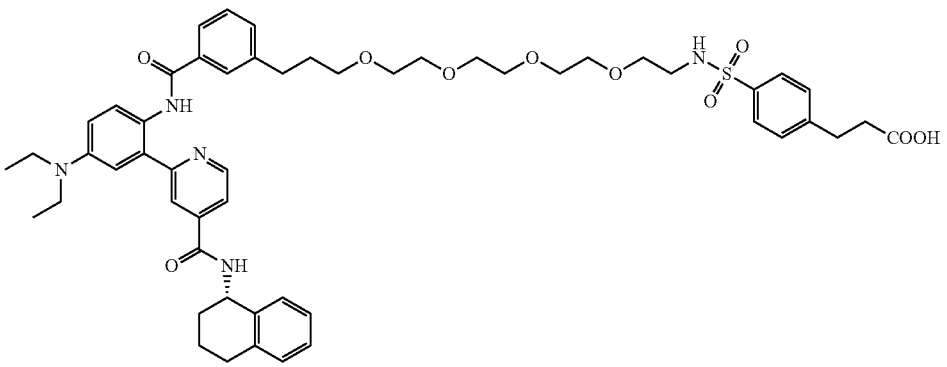 [SMILES: CCN(CC)c1ccc(NC(=O)c2cccc(CCCOCCOCCOCCOCCNS(=O)(=O)c3ccc(CCC(=O)O)cc3)c2)c(-c2cc(C(=O)N[C@H]3CCCc4ccccc43)ccn2)c1] | 964.6 [M + H] |
| 321 | 272 | 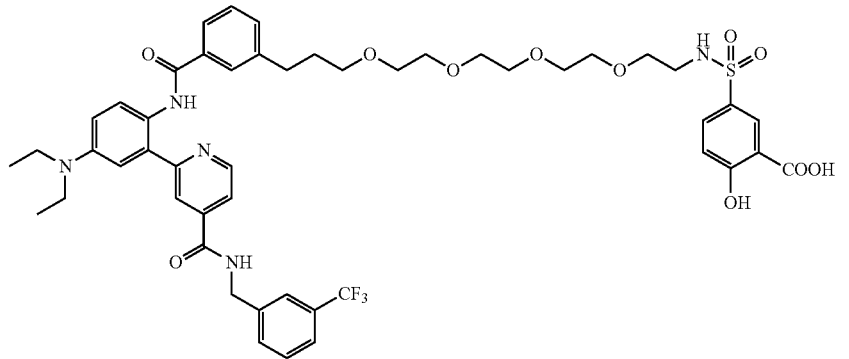 | 952.5 [M + H] |
| 322 | 262 | 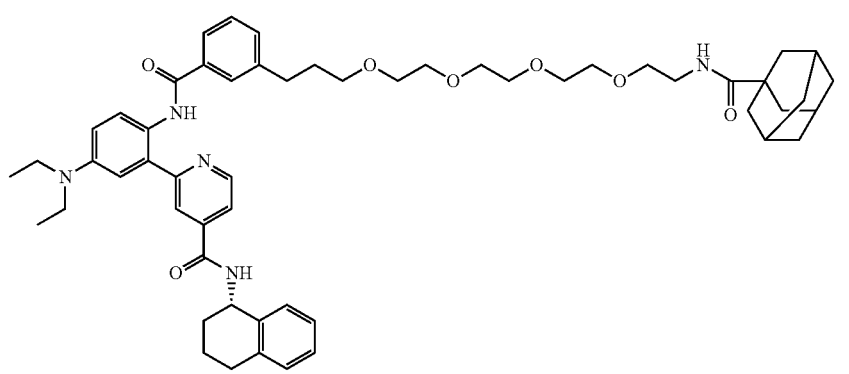 [SMILES: CCN(CC)c1ccc(NC(=O)c2cccc(CCCOCCOCCOCCOCCNC(=O)C34CC5CC(CC(C5)C3)C4)c2)c(-c2cc(C(=O)N[C@H]3CCCc4ccccc43)ccn2)c1] | 914.6 [M + H] |

TABLE 10-continued

| Example | Method from Example | Structure | Mass Spectrum |
|---------|---------------------|-----------|---------------|
| 323 | 262 | 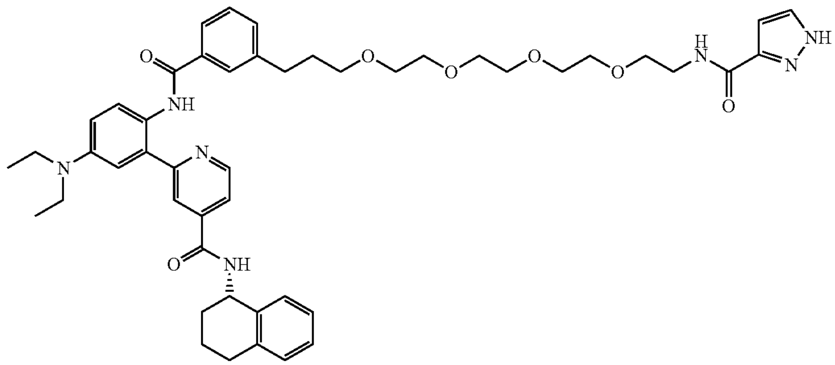 | 846.5 [M + H] |
| 324 | 262 | 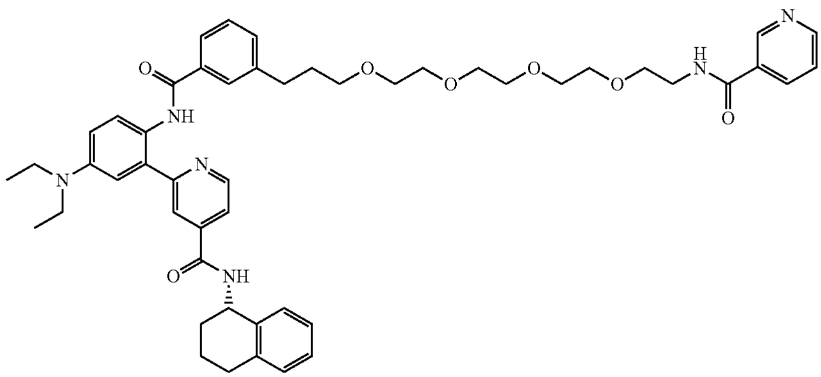 | 857.4 [M + H] |
| 325 | 262 | 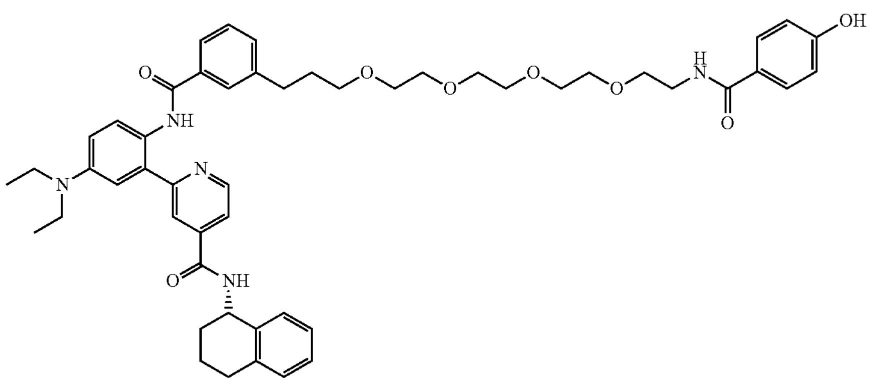 | 872.5 [M + H] |
| 326 | 262 | 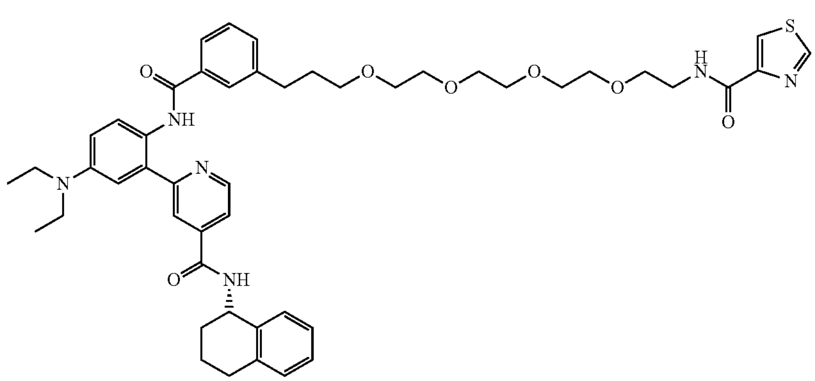 | 863.5 [M + H] |

Example 327

(S)—N1-(2-(4-(2,5,8,11,14,17,20-heptaoxadocosan-22-yl)-3-oxopiperazin-1-yl)ethyl)-N3-(4-(diethylamino)-2-(4-(1,2,3,4-tetrahydronaphthalen-1-ylcarbamoyl)pyridin-2-yl)phenyl)-N1-methylisophthalamide

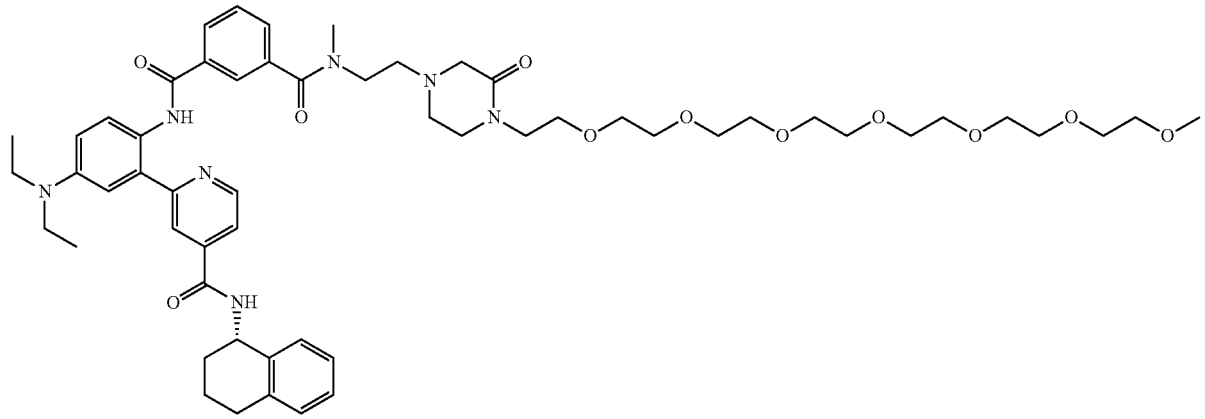 [SMILES: CCN(CC)c1ccc(NC(=O)c2cccc(C(=O)N(C)CCN3CCN(CCOCCOCCOCCOCCOCCOCCOC)C(=O)C3)c2)c(-c2cc(C(=O)N[C@H]3CCCc4ccccc43)ccn2)c1]

(S)—N1-(2-(4-(2,5,8,11,14,17,20-heptaoxadocosan-22-yl)-3-oxopiperazin-1-yl)ethyl)-N3-(4-(diethylamino)-2-(4-(1,2,3,4-tetrahydronaphthalen-1-ylcarbamoyl)pyridin-2-yl)phenyl)-N1-methylisophthalamide: This compound was prepared from 197a according to the procedure described in Example 197 using 1-(2,5,8,11,14,17,20-heptaoxadocosan-22-yl)piperazin-2-one 135c.5 as the amine. MS (ES, m/z) 1024.4 [M+H]$^+$.

Example 328

(S)—N1-(4-(diethylamino)-2-(4-(1,2,3,4-tetrahydronaphthalen-1-ylcarbamoyl)pyridin-2-yl)phenyl)-N3-(23-(2-methoxyethyl)-2,5,8,11,14,17,20-heptaoxa-23-azapentacosan-25-yl)-N3-methylisophthalamide

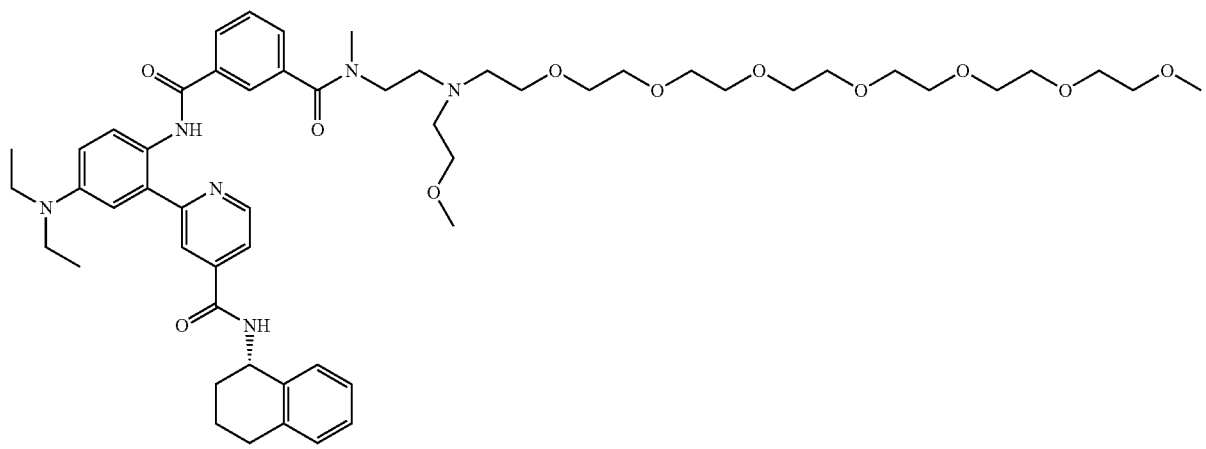 [SMILES: CCN(CC)c1ccc(NC(=O)c2cccc(C(=O)N(C)CCN(CCOC)CCOCCOCCOCCOCCOCCOCCOC)c2)c(-c2cc(C(=O)N[C@H]3CCCc4ccccc43)ccn2)c1]

Example 328

(S)—N1-(4-(diethylamino)-2-(4-(1,2,3,4-tetrahydronaphthalen-1-ylcarbamoyl)pyridin-2-yl)phenyl)-N3-(23-(2-methoxyethyl)-2,5,8,11,14,17,20-heptaoxa-23-azapentacosan-25-yl)-N3-methylisophthalamide This compound was prepared from 197a according to the procedure described in Example 197 using N-(2-methoxyethyl)-2,5,8,11,14,17,20-heptaoxadocosan-22-amine as the amine. MS (ES, m/z) 999.4 [M+H]⁺.

Example 329 tert-butyl 3-methyl-1-[N-methyl-1-(3-{[4-(piperidin-1-yl)-2-(4-{[(1S)-1,2,3,4-tetrahydronaphthalen-1-yl]carbamoyl}pyridin-2-yl)phenyl]carbamoyl}phenyl)formamido]-6,9,12-trioxa-3-azapentadecan-15-oate

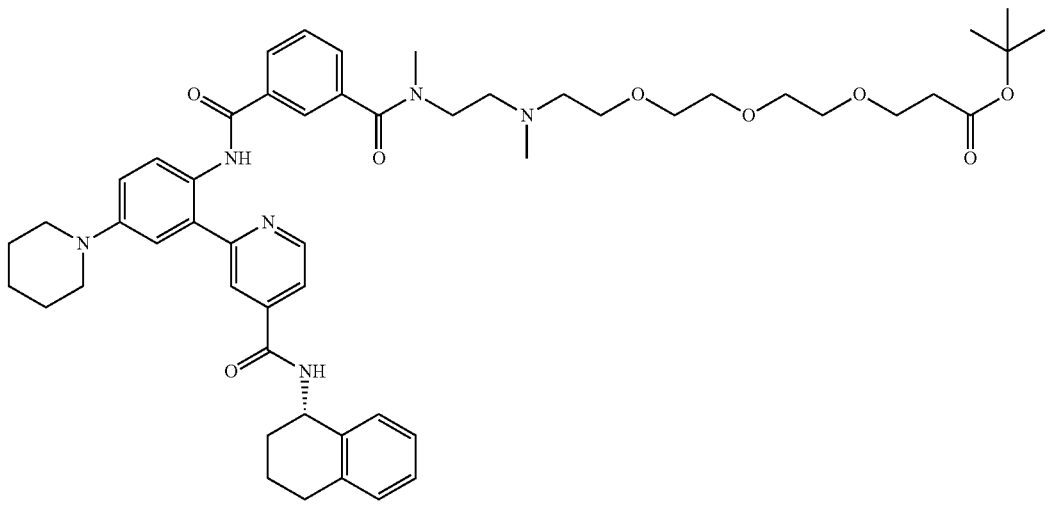 [SMILES: CN(CCOCCOCCOCCC(=O)OC(C)(C)C)CCN(C)C(=O)c1cccc(C(=O)Nc2ccc(N3CCCCC3)cc2-c2cc(C(=O)N[C@H]3CCCc4ccccc43)ccn2)c1]

Example 329

This compound was prepared from intermediate 187a according to the procedure described in Example 197 using tert-butyl 5,8,11-trioxa-2-azatetradecan-14-oate as the amine. MS (ES, m/z) 905.3 [M+H]⁺.

Example 330

2-(2-(2-(3-(3-(4-(diethylamino)-2-(4-(3-(trifluoromethyl)benzylcarbamoyl)pyridin-2-yl)phenylcarbamoyl)phenyl)propoxy)ethoxy)ethoxy)-N,N,N-triethylethanaminium Scheme 115.

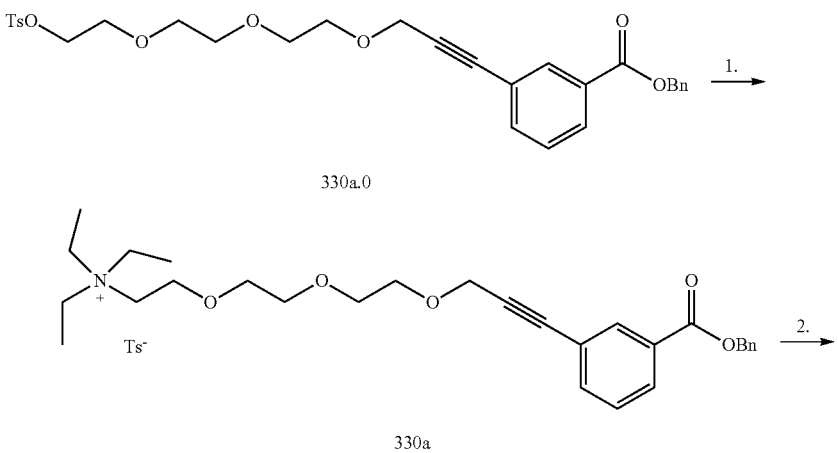

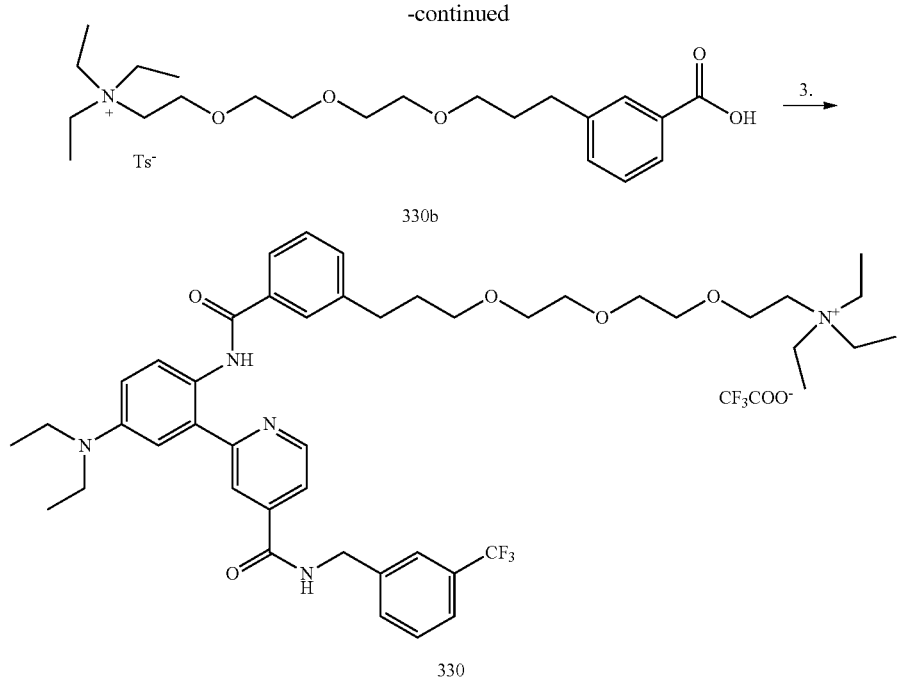

1. Triethylamine, butanone, ethanol
2. H₂, Pd/C, MeOH
3. EDC•HCl, DMAP, DCM.

Intermediate 330a.0. Benzyl 3-(3-(2-(2-(2-(tosyloxy)ethoxy)ethoxy)ethoxy)prop-1-ynyl)benzoate This compound was prepared in a manner analogous to that described in Example 270b from benzyl 3-iodobenzoate by substituting 2-(2-(2-(2-(prop-2-ynyloxy)ethoxy)ethoxy)ethoxy)ethanol for the alkyne.

Intermediate 330a

Into a 100-mL round-bottom flask, was placed a solution of benzyl 3-(3-(2-(2-(2-(tosyloxy)ethoxy)ethoxy)ethoxy)prop-1-ynyl)benzoate (300 mg, 0.54 mmol, 1.00 equiv) in butanone (5 mL), a solution of triethylamine (2 mL) in ethanol (2 mL). The resulting solution was stirred overnight at 80° C. in an oil bath. The resulting mixture was concentrated under vacuum. This resulted in 250 mg (96%) of 2-(2-(2-(3-(3-(benzyloxycarbonyl)phenyl)prop-2-ynyloxy)ethoxy)ethoxy)-N,N,N-triethylethanaminium as brown oil.

Intermediate 330b

Into a 100-mL round-bottom flask, was placed a solution of 2-(2-(2-(3-(3-(benzyloxycarbonyl)phenyl)prop-2-ynyloxy)ethoxy)ethoxy)-N,N,N-triethylethanaminium (250 mg, 0.52 mmol, 1.00 equiv) in methanol (20 mL), Palladium carbon (250 mg). Hydrogen gas was introduced into the reaction vessel. The resulting solution was stirred overnight at room temperature. The solids were filtered out. The resulting mixture was concentrated under vacuum. This resulted in 200 mg (97%) of 2-(2-(2-(3-(3-carboxyphenyl)propoxy)ethoxy)ethoxy)-N,N,N-triethylethanaminium as brown oil.

Example 330

Into a 100-mL round-bottom flask, was placed a solution of 2-(2-(2-(3-(3-carboxyphenyl)propoxy)ethoxy)ethoxy)-N,N,N-triethylethanaminium (107 mg, 0.27 mmol, 1.19 equiv) in dichloromethane (20 mL), EDC.HCl (65 mg, 0.34 mmol, 1.50 equiv), 4-dimethylaminopyridine (42 mg, 0.34 mmol, 1.52 equiv), 2-(2-amino-5-(diethylamino)phenyl)-N-(3-(trifluoromethyl)benzyl)isonicotinamide (100 mg, 0.23 mmol, 1.00 equiv). The resulting solution was stirred overnight at room temperature. The resulting solution was diluted with 30 mL of dichloromethane. The resulting mixture was washed with 2×100 mL of NH₄Cl (aq). The mixture was dried over sodium sulfate and concentrated under vacuum. The crude product (150 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH3CN (27% CH3CN up to 45% in 6 min, up to 100% in 1 min, down to 27% in 0.7 min); Detector, Waters2545 UvDector 254&220 nm. This resulted in 28.1 mg (15%) of 2-(2-(2-(3-(3-(4-(diethylamino)-2-(4-(3-(trifluoromethyl)benzylcarbamoyl)pyridin-2-yl)phenylcarbamoyl)phenyl)propoxy)ethoxy)ethoxy)-N,N,N-triethylethanaminium as yellow oil. LC-MS (ES, m/z): 820 [M+H]⁺ H-NMR (400 MHz, CD3OD, ppm): 8.95 (s, 1H), 8.82 (d, J=9.2 Hz, 1H), 8.46 (s, 1H), 8.14 (s, 1H), 7.92~7.91 (m, 1H), 7.85~7.83 (m, 2H), 7.72~7.67 (m, 2H), 7.62~7.51 (m, 5H), 4.72 (s, 2H), 3.86 (s, 2H), 3.78~3.72 (m, 4H), 3.66~3.60 (m, 8H), 3.55~3.47 (m, 4H), 3.43~3.37 (m, 6H), 2.85~2.83 (m, 2H), 1.99~1.95 (m, 2H), 1.30~1.23 (m, 14H).

Example 331

1-(2-(2-(2-(3-(4-(4-(diethylamino)-2-(4-(3-(trifluoromethyl)benzylcarbamoyl)pyridin-2-yl)phenylcarbamoyl)phenyl)propoxy)ethoxy)ethoxy)ethyl)-1-azonia-bicyclo[2.2.2]octane Scheme 116.

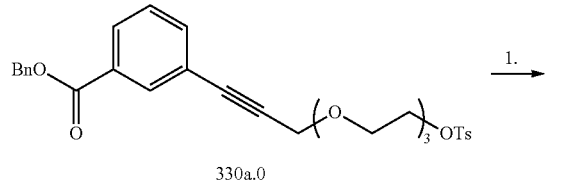

330a.0

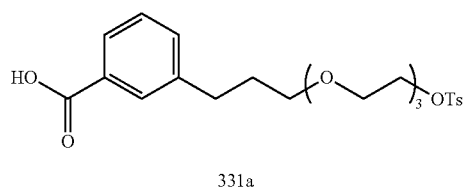

331a

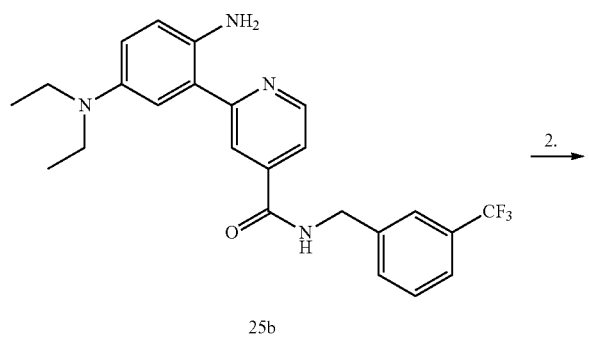

25b

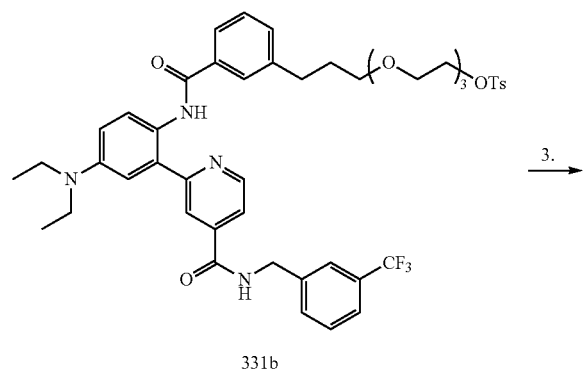

331b

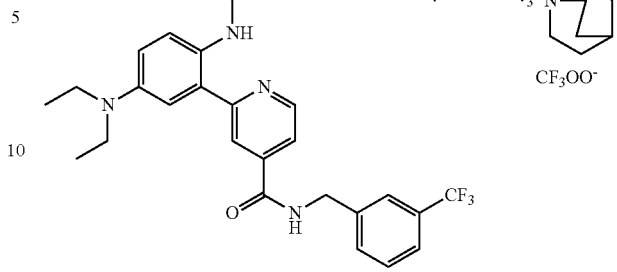

331

1. H₂, Pd/C, MeOH
2. 331a, EDC•HCl, DMAP, DCM
3. quinuclidine, butanone.

Intermediate 331a

Into a 50-mL round-bottom flask, was placed a solution of benzyl 3-(3-(2-(2-(2-(tosyloxy)ethoxy)ethoxy)ethoxy)prop-1-ynyl)benzoate (300 mg, 0.54 mmol, 1.00 equiv) in methanol (3 mL), Palladium carbon (1.0 g). Hydrogen gas was introduced into the reaction vessel. The resulting solution was stirred for 2 days at 25° C. The reaction progress was monitored by LCMS,TLC (ethyl acetate/petroleum ether=1:1). The solids were filtered out. The resulting mixture was concentrated under vacuum. This resulted in 0.2 g (79%) of 3-(3-(2-(2-(2-(tosyloxy)ethoxy)ethoxy)ethoxy)propyl)benzoic acid as a yellow crude solid.

Intermediate 331b

Into a 50-mL round-bottom flask purged and maintained with an inert atmosphere of nitrogen, was placed 2-(2-amino-5-(diethylamino)phenyl)-N-(3-(trifluoromethyl)benzyl) isonicotinamide (150 mg, 0.34 mmol, 1.00 equiv), 3-(3-(2-(2-(2-(tosyloxy)ethoxy)ethoxy)ethoxy)propyl)benzoic acid (190 mg, 0.41 mmol, 1.20 equiv), EDCl (97.6 mg, 0.51 mmol, 1.50 equiv), 4-dimethylaminopyridine (62.2 mg, 0.51 mmol, 1.50 equiv), dichloromethane (2 mL). The resulting solution was stirred overnight at 25° C. The resulting mixture was washed with 2×2 mL of brine. The mixture was dried over anhydrous sodium sulfate and concentrated under vacuum. The residue was applied onto a silica gel column with ethyl acetate/petroleum ether (1:2). This resulted in 200 mg (66%) of 2-(2-(2-(3-(3-(4-(diethylamino)-2-(4-(3-(trifluoromethyl) benzylcarbamoyl)pyridin-2-yl)phenylcarbamoyl)phenyl) propoxy)ethoxy)ethoxy)ethyl 4-methylbenzenesulfonate as yellow oil.

Example 331

Into a 25-mL round-bottom flask, was placed a solution of 2-(2-(2-(3-(4-(4-(diethylamino)-2-(4-(3-(trifluoromethyl) benzylcarbamoyl)pyridin-2-yl)phenylcarbamoyl)phenyl) propoxy)ethoxy)ethoxy)ethyl 4-methylbenzenesulfonate (200 mg, 0.22 mmol, 1.00 equiv) in butanone (2 mL), quinuclidine (5 g, 44.97 mmol, 200.00 equiv). The resulting solution was stirred overnight at 25° C. The resulting mixture was concentrated under vacuum. The crude product (200 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (27% CH$_3$CN up to 47% in 6 min, up to 100% in 1 min, down to 27% in 0.7 min); Detector, Waters2545 UvDector 254&220 nm. This resulted in 97.4 mg (52%) of 1-(2-(2-(2-(3-(4-(4-(diethylamino)-2-(4-(3-(trifluoromethyl)benzyl-carbamoyl)pyridin-2-yl)phenylcarbamoyl)phenyl)propoxy)ethoxy)ethoxy)ethyl)-1-azonia-bicyclo[2.2.2]octane as a yellow semi-solid. LC-MS (ESI, m/z): 831 [M+H]$^+$ H-NMR (300 MHz, CD$_3$OD, ppm): δ 8.97 (d, J=3 Hz, 1H), 8.84 (d, J=9 Hz, 1H), 8.45 (s, 1H), 8.16 (s, 1H), 7.91-7.93 (m, 1H), 7.83-7.86 (m, 2H), 7.56-7.73 (m, 5H), 7.51-7.53 (m, 2H), 4.73 (s, 2H), 3.89 (s, 2H), 3.73-3.80 (m, 4H), 3.61-3.66 (m, 8H), 3.49-3.56 (m, 8H), 3.34-3.36 (m, 2H), 2.85 (t, J=9 Hz, 2H), 2.12-2.14 (m, 1H), 1.94-2.01 (m, 8H), 1.25 (t, J=7.2 Hz, 6H).

Example 332

N-(3-(trifluoromethyl)benzyl)-2-(5-(diethylamino)-2-(3-(3-(2-(2-(2-(2-(3-hydroxy-2,2-bis(hydroxymethyl)propoxy)ethoxy)ethoxy)ethoxy)ethoxy)propyl)benzamido)phenyl)isonicotinamide

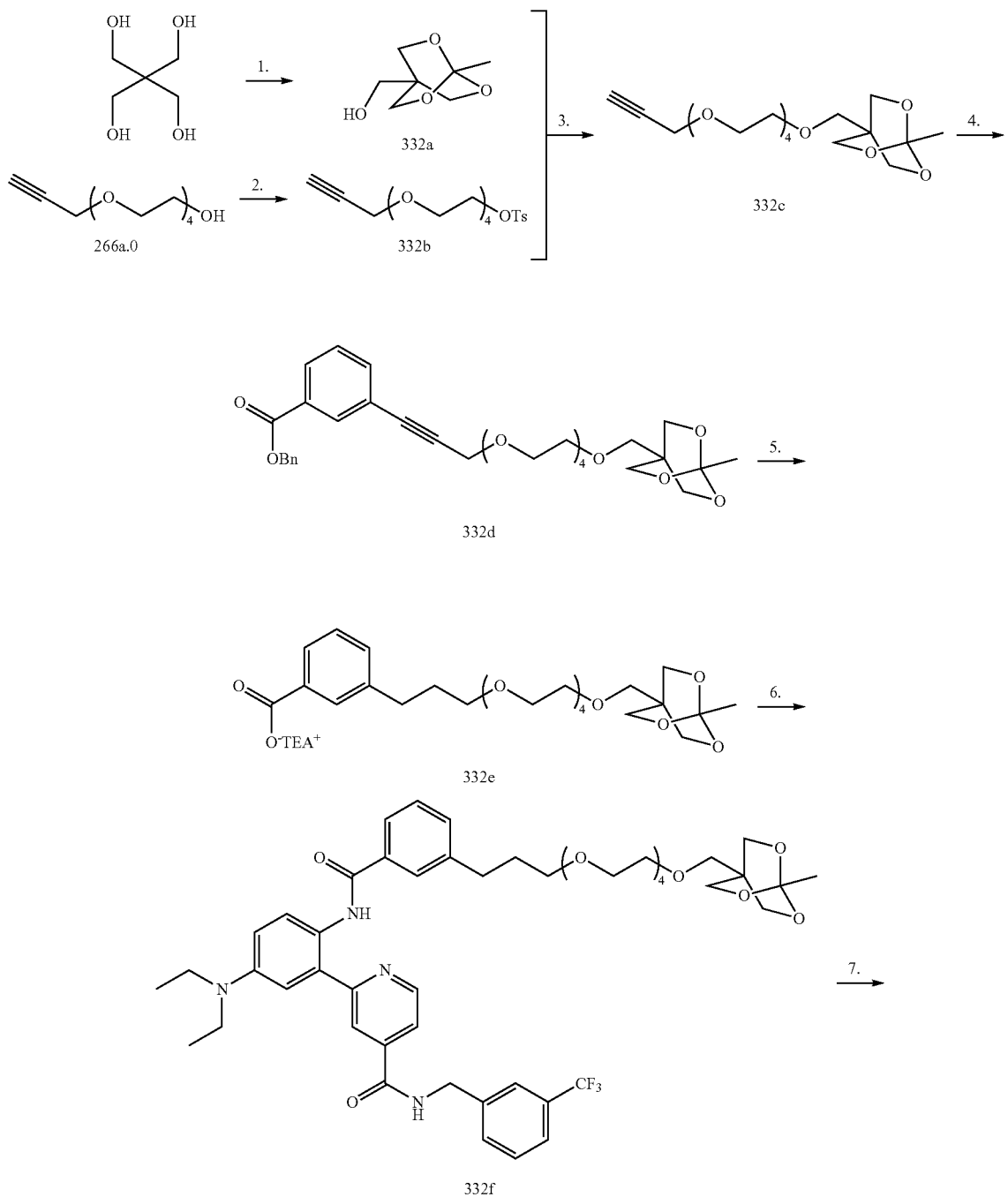
Scheme 117.

-continued

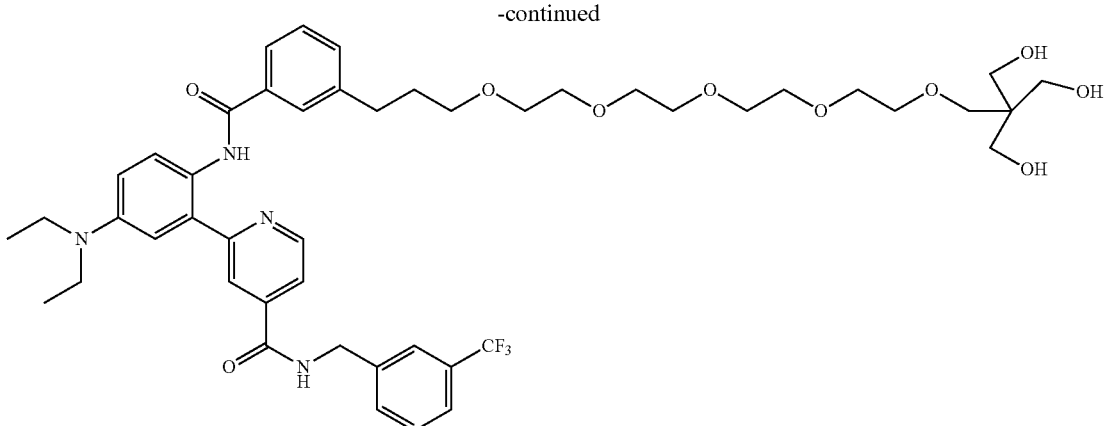

332

1. 1,1,1-triethoxyethane, methylbenzenesulfonic acid
2. 4-methylbenzene-1-sulfonyl chloride, pyridine
3. NaH, DMF
4. Pd(PPh$_3$)$_2$Cl$_2$, CuI, TEA, THF
5. H$_2$, Pd/C, TEA, MeOH
6. EDC·HCl, DMAP, DCM 7. HCl, MeOH.

Intermediate 332a

Into a 100-mL round-bottom flask, was placed 2,2-bis(hydroxymethyl)propane-1,3-diol (15 g, 110.29 mmol, 1.00 equiv), 1,1,1-triethoxyethane (20.2 mL, 1.00 equiv), 4-methylbenzenesulfonic acid (947 mg, 5.51 mmol, 0.05 equiv). The resulting solution was stirred for 0.5 h at 100° C. in an oil bath. The temperature was increased to 130° C. and the mixture was stirred for 0.5 h. The solids were filtered out. The resulting mixture was concentrated under vacuum. The residue was applied onto a Al$_2$O$_3$ column with ethyl acetate/petroleum ether (1:10~1:1). This resulted in 2 g (10%) of (1-methyl-2,6,7-trioxa-bicyclo[2.2.2]octan-4-yl)methanol as a white solid.

Intermediate 332b

Into a 100-mL 3-necked round-bottom flask, was placed a solution of 266a.0 (2 g, 8.19 mmol, 1.00 equiv, 95%) in dichloromethane (10 mL), pyridine (15 mL). This was followed by the addition of 4-methylbenzene-1-sulfonyl chloride (3.27 g, 17.21 mmol, 2.00 equiv), in portions at 0-10° C. The resulting solution was stirred overnight at room temperature. The resulting solution was diluted with 200 mL of ethyl acetate. The resulting mixture was washed with 1×30 mL of water and 2×30 mL of 10% hydrogen chloride. The resulting mixture was washed with 1×30 mL of sodium bicarbonate and 1×30 mL of brine. The mixture was dried over anhydrous sodium sulfate and concentrated under vacuum. The residue was applied onto a silica gel column with ethyl acetate/petroleum ether (1:1). This resulted in 1.2 g (32%) of 2-(2-(2-(2-(prop-2-ynyloxy)ethoxy)ethoxy)ethoxy)ethyl 4-methylbenzenesulfonate as light brown oil.

Intermediate 332c

Into a 50-mL 3-necked round-bottom flask, was placed a solution of (1-methyl-2,6,7-trioxa-bicyclo[2.2.2]octan-4-yl)methanol (750 mg, 3.75 mmol, 1.50 equiv, 80%) in N,N-dimethylformamide (10 mL). This was followed by the addition of sodium hydride (150 mg, 6.25 mmol, 2.00 equiv), in portions at 0-5° C. To this was added 2-(2-(2-(2-(prop-2-ynyloxy)ethoxy)ethoxy)ethoxy)ethyl 4-methylbenzenesulfonate (1.2 g, 2.64 mmol, 1.00 equiv, 85%). The resulting solution was stirred overnight at room temperature. The resulting solution was diluted with 150 mL of ethyl acetate. The resulting mixture was washed with 3×20 mL of Brine. The mixture was dried over sodium sulfate and concentrated under vacuum. The residue was applied onto a silica gel column with ethyl acetate/petroleum ether (1:2). This resulted in 690 mg (63%) of 1-methyl-4-((2-(2-(2-(2-(prop-2-ynyloxy)ethoxy)ethoxy)ethoxy)ethoxy)methyl)-2,6,7-trioxa-bicyclo[2.2.2]octane as brown oil.

Intermediate 332d

Into a 50-mL round-bottom flask purged and maintained with an inert atmosphere of nitrogen, was placed a solution of 1-methyl-4-((2-(2-(2-(2-(prop-2-ynyloxy)ethoxy)ethoxy)ethoxy)ethoxy)methyl)-2,6,7-trioxa-bicyclo[2.2.2]octane (690 mg, 1.66 mmol, 1.00 equiv, 90%) in tetrahydrofuran (10 mL), benzyl 3-iodobenzoate (623 mg, 1.75 mmol, 1.00 equiv, 95%), Pd(PPh$_3$)$_2$Cl$_2$ (130 mg, 0.19 mmol, 0.10 equiv), copper (I) iodide (35 mg, 0.18 mmol, 0.10 equiv), triethylamine (373 mg, 3.69 mmol, 2.00 equiv). The resulting solution was stirred for 4 h at room temperature. The resulting solution was diluted with 150 mL of ethyl acetate. The resulting mixture was washed with 3×30 mL of Brine. The mixture was dried over anhydrous sodium sulfate and concentrated under vacuum. The residue was applied onto a Al$_2$O$_3$ column with ethyl acetate/petroleum ether (1:2). This resulted in 270 mg (25%) of benzyl 3-(3-(2-(2-(2-(2-((1-methyl-2,6,7-trioxa-bicyclo[2.2.2]octan-4-yl)methoxy)ethoxy)ethoxy)ethoxy)ethoxy)prop-1-ynyl)benzoate as a brown oil.

Intermediate 332e

Into a 50-mL round-bottom flask, was placed a solution of benzyl 3-(3-(2-(2-(2-(2-((1-methyl-2,6,7-trioxa-bicyclo[2.2.2]octan-4-yl)methoxy)ethoxy)ethoxy)ethoxy)ethoxy)

prop-1-ynyl)benzoate (270 mg, 0.42 mmol, 1.00 equiv, 90%) in methanol (5 mL), Palladium carbon (270 mg), triethylamine (3 drops). Hydrogen gas was introduced into the reaction vessel. The resulting solution was stirred overnight at room temperature. The solids were filtered out. The resulting mixture was concentrated under vacuum. This resulted in 200 mg (86%) of 3-(3-(2-(2-(2-(2-((1-methyl-2,6,7-trioxa-bicyclo[2.2.2]octan-4-yl)methoxy)ethoxy)ethoxy)ethoxy)ethoxy)propyl)benzoic acid as brown oil.

Intermediate 332f

Into a 50-mL round-bottom flask, was placed a solution of N-(3-(trifluoromethyl)benzyl)-2-(2-amino-5-(diethylamino)phenyl)isonicotinamide (190 mg, 0.39 mmol, 1.00 equiv, 90%) in dichloromethane (8 mL), 3-(3-(2-(2-(2-(2-((1-methyl-2,6,7-trioxa-bicyclo[2.2.2]octan-4-yl)methoxy)ethoxy)ethoxy)ethoxy)ethoxy)propyl)benzoic acid (200 mg, 0.32 mmol, 1.00 equiv, 80%), EDC.HCl (154 mg, 0.80 mmol, 2.00 equiv), 4-dimethylaminopyridine (98 mg, 0.80 mmol, 2.00 equiv). The resulting solution was stirred for 4 h at room temperature. The resulting solution was diluted with 200 mL of ethyl acetate. The resulting mixture was washed with 3×20 mL of Brine. The mixture was dried over anhydrous sodium sulfate and concentrated under vacuum. The residue was applied onto a silica gel column with dichloromethane/methanol (100:1). This resulted in 260 mg (51%) of intermediate 232f as brown oil.

Example 332

Into a 50-mL round-bottom flask, was placed a solution of N-(3-(trifluoromethyl)benzyl)-2-(5-(diethylamino)-2-(3-(3-(2-(2-(2-(2-((1-methyl-2,6,7-trioxa-bicyclo[2.2.2]octan-4-yl)methoxy)ethoxy)ethoxy)ethoxy)ethoxy)propyl)benzamido)phenyl)isonicotinamide (250 mg, 0.19 mmol, 1.00 equiv, 70%) in methanol (8 mL), hydrogen chloride (12M) (1 mL). The resulting solution was stirred for 4 h at room temperature. The pH value of the solution was adjusted to 5-6 with sodium carbonate. The resulting mixture was concentrated under vacuum. The resulting solution was diluted with 20 mL of methanol. The solids were filtered out. The resulting mixture was concentrated under vacuum. The crude product (200 mg) was purified by Prep-HPLC with the following conditions (1#-Pre-HPLC-001 (SHIMADZU)): Column, SunFire Prep C18, 19*150 mm 5 um; mobile phase, water with 0.05% TFA and CH$_3$CN (30% CH$_3$CN up to 48% in 6 min, up to 100% in 1 min, down to 30% in 0.7 min); Detector, Waters2545 UvDector 254&220 nm. This resulted in 137.4 mg (79%) of N-(3-(trifluoromethyl)benzyl)-2-(5-(diethylamino)-2-(3-(3-(2-(2-(2-(2-(3-hydroxy-2,2-bis(hydroxymethyl)propoxy)ethoxy)ethoxy)ethoxy)ethoxy)propyl)benzamido)phenyl)isonicotinamide as brown oil. LC-MS (ES, m/z): 899 [M+H]$^+$ H-NMR (300 MHz, CD$_3$OD, ppm): 8.97 (d, J=3 Hz, 1H), 8.82 (d, J=9 Hz, 1H), 8.43 (s, 1H), 8.06 (s, 1H), 7.91-7.93 (m, 1H), 7.82-7.84 (m, 2H), 7.56-7.72 (m, 5H), 7.50-7.52 (m, 2H), 4.72 (s, 2H), 3.73-3.80 (m, 4H), 3.59-3.65 (m, 22H), 3.45 (s, 2H), 2.82-2.87 (m, 2H), 1.93-1.99 (m, 2H), 1.22-1.27 (m, 6H).

Example 333

(S)—N$^1$-Methyl-N$^1$-(23-methyl-2,5,8,11,14,17,20-heptaoxa-23-azapentacosan-25-yl)-N3-(4-(piperidin-1-yl)-2-(4-(1,2,3,4-tetrahydronaphthalen-1-ylcarbamoyl)pyridin-2-yl)phenyl)isophthalamide

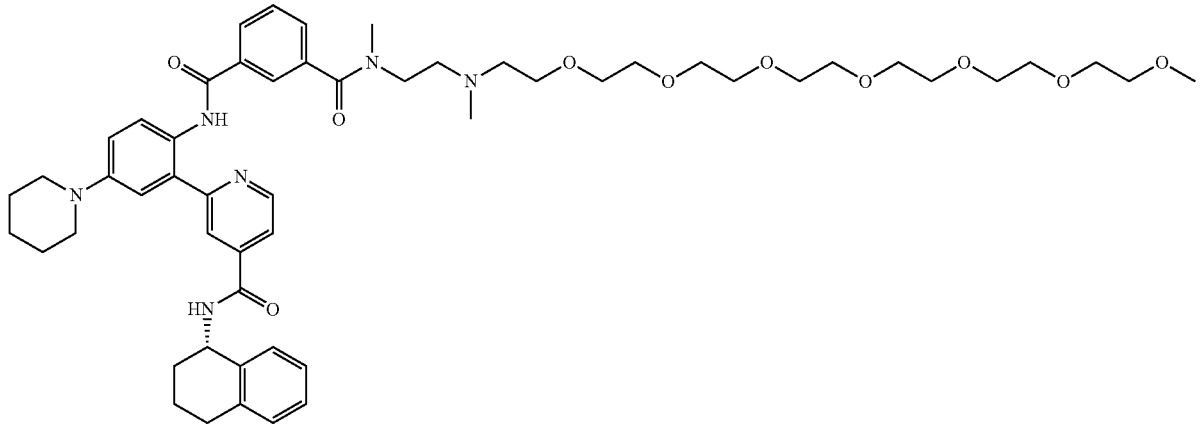 [SMILES: COCCOCCOCCOCCOCCOCCOCCN(C)CCN(C)C(=O)c1cccc(C(=O)Nc2ccc(N3CCCCC3)cc2-c2cc(C(=O)N[C@H]3CCCc4ccccc43)ccn2)c1]

(S)—N$^1$-Methyl-N$^1$-(23-methyl-2,5,8,11,14,17,20-heptaoxa-23-azapentacosan-25-yl)-N3-(4-(piperidin-1-yl)-2-(4-(1,2,3,4-tetrahydronaphthalen-1-ylcarbamoyl)pyridin-2-yl)phenyl)isophthalamide Sodium cyanoborohydride (0.75 g, 11.9 mmol) was added portionwise to (S)—N$^1$-methyl-N$^1$-(2-oxoethyl)-N$^3$-(4-(piperidin-1-yl)-2-(4-(1,2,3,4-tetrahydronaphthalen-1-ylcarbamoyl)pyridin-2-yl)phenyl)isophthalamide 187a (1.5 g, 2.38 mmol), N-methyl-2,5,8,11,14,17,20-heptaoxadocosan-22-amine 135c.1 (2.52 g, 7.14 mmol) and acetic acid (0.41 mL, 7.14 mmol) in ethanol (15 mL) and the mixture stirred overnight at room temperature. The reaction was diluted with ethyl acetate, washed with saturated aqueous sodium bicarbonate and brine, dried (MgSO$_4$). The residue was purified by PTLC (10% MeOH/20% ethyl acetate/dichloromethane) to give product as an orange oil (0.85 g, 37%); MS (ES, m/z): 969 [M+H]$^+$; NMR (400 MHz, CDCl$_3$, ppm): δ 12.8 (s, 1H);

8.80 (s, 1H); 8.55 (d, J=8.8 Hz, 1H); 8.10 (s, 1H); 7.98-8.02 (m, 2H); 7.47-7.55 (m, 3H); 7.06-7.24 (m, 5H); 6.69 (m, 1H); 5.41 (m, 1H).

Example 334

(S)—$N^1$-(2-(4-(2,5,8,11,14,17,20-Heptaoxa-docosan-22-yl(methyl)carbamoyl)piperidin-1-yl)ethyl)-N1-methyl-N3-(4-(piperidin-1-yl)-2-(4-(1,2,3,4-tetrahydronaphthalen-1-ylcarbamoyl)pyridin-2-yl)phenyl)isophthalamide

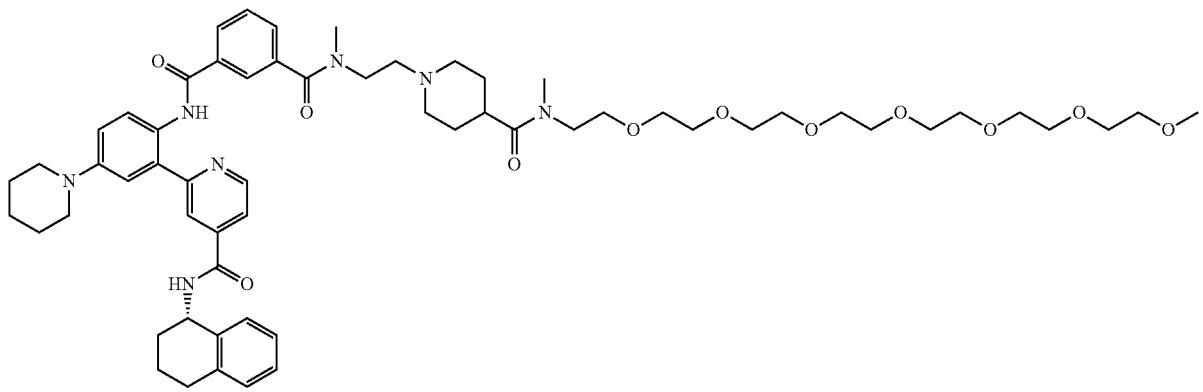 [SMILES: COCCOCCOCCOCCOCCOCCOCCN(C)C(=O)C1CCN(CCN(C)C(=O)c2cccc(C(=O)Nc3ccc(N4CCCCC4)cc3-c3cc(C(=O)N[C@H]4CCCc5ccccc54)ccn3)c2)CC1]

Example 334

DIEA (0.068 mL, 0.392 mmol) was added to (S)-1-(2-(N-methyl-3-(4-(piperidin-1-yl)-2-(4-(1,2,3,4-tetrahydronaphthalen-1-ylcarbamoyl)pyridin-2-yl)phenylcarbamoyl)benzamido)ethyl)piperidine-4-carboxylic acid (prepared from Example 244 by acidic hydrolysis) (58.1 mg, 0.0783 mmol), N-methyl-2,5,8,11,14,17,20-heptaoxadocosan-22-amine 135c.1 (35.9 mg, 0.102 mmol), and HATU (38.7 mg, 0.102 mmol) in DMF (2 mL) and the mixture stirred for 2 hours at room temperature. The reaction was diluted with water and extracted with ethyl acetate. The extract was washed with water and brine, dried (MgSO$_4$), and evaporated. The residue was purified by PTLC (10% methanol/20% ethyl acetate/dichloromethane) to give product as an orange foam (1.2 g, 73%); MS (ES, m/z): 1080 [M+H]$^+$; NMR (400 MHz, DMSO-d$_6$, ppm): δ 12.05 (m, 1H); 9.16 (d, J=8.8 Hz, 1H); 8.85 (d, J=4.8 Hz, 1H); 8.27 (s, 1H); 8.16 (d, J=8.8 Hz, 1H); 7.95 (m, 1H); 7.85 (d, J=4.8 Hz, 1H); 7.60 (m, 2H); 7.40 (s, 1H); 7.09-7.20 (m, 4H); 5.20-5.30 (m, 1H); 3.40-3.65 (m, 21H); 3.18-3.24 (m, 5H); 2.75-3.20 (m, 7H); 1.99 (m, 2H); 1.80 (m, 2H); 1.65 (m, 4H); 1.56 (m, 2H); 1.23-1.28 (m, 6H).

Example 335

$N^1$-(4-(Diethylamino)-2-(4-(3-(trifluoromethyl)benzylcarbamoyl)pyridin-2-yl)phenyl)-$N^3$-(23-(2-methoxyethyl)-2,5,8,11,14,17,20-heptaoxa-23-azapentacosan-25-yl)-$N^3$-methylisophthalamide, trifluoroacetate Scheme 118.

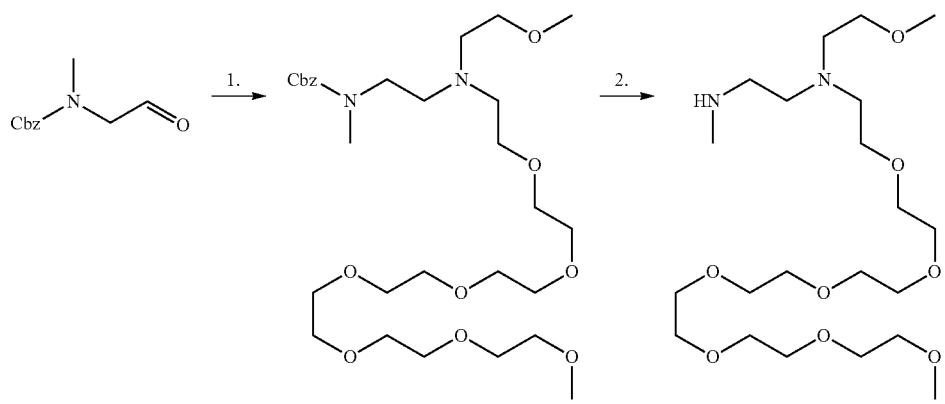

335a        335b

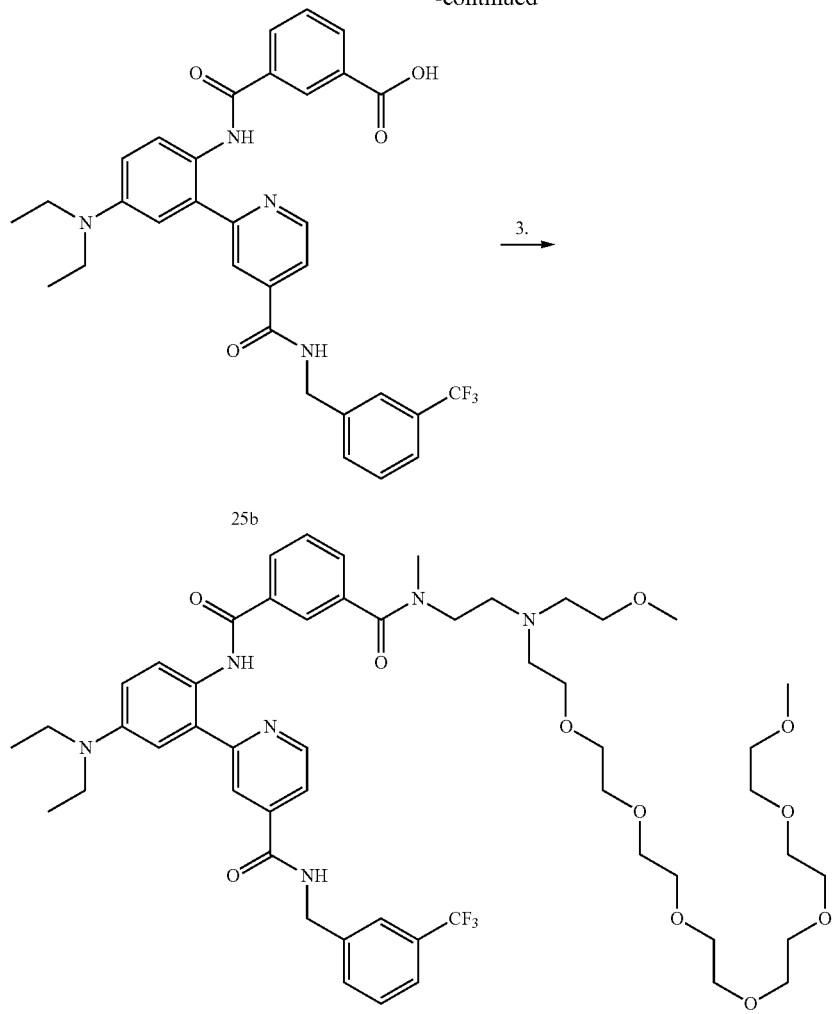

1. Na(OAc)₃BH, Acetic acid, THF N-(2-methoxyethyl)-2,5,8,11,14,17,20-heptaoxadocosan-22-amine
2. Pd/C, H₂, MeOH;
3. HATU, DIEA, DMF.

Intermediate 335a: Benzyl 23-(2-methoxyethyl)-2,5,8,11,14,17,20-heptaoxa-23-azapentacosan-25-yl(methyl)carbamate Sodium triacetoxyborohydride (2.21 g, 10.4 mmol) was added portionwise at room temperature to benzyl methyl(2-oxoethyl)carbamate (1.66 g, 8.03 mmol), N-(2-methoxyethyl)-2,5,8,11,14,17,20-heptaoxadocosan-22-amine 135c.2 (3.19 g, 8.03 mmol), and acetic acid (0.92 mL, 16.1 mmol) in THF (50 mL). The mixture was stirred for 2 hours, diluted with ethyl acetate, washed with saturated aqueous sodium bicarbonate and brine, dried (MgSO₄) and evaporated. The residue was purified by PTLC (10% methanol/20% ethyl acetate/dichloromethane) to give product as an oil (2.58 g, 55%); MS for $C_{29}H_{52}N_2O_{10}$ m/z 589 (M+H)⁺.

Intermediate 335b: N¹-(2,5,8,11,14,17,20-Heptaoxadocosan-22-yl)-N¹-(2-methoxyethyl)-N²-methylethane-1,2-diamine Benzyl 23-(2-methoxyethyl)-2,5,8,11,14,17,20-heptaoxa-23-azapentacosan-25-yl(methyl)carbamate 335a (2.58 g, 4.38 mmol) and palladium on carbon (10%, wet, 0.6 g) in methanol (30 mL) were stirred under a hydrogen atmosphere (balloon) for 2 hours. The mixture was filtered through celite and evaporated to give product as an oil (1.9 g, 99%); MS (ES, m/z): 455 [M+H]⁺.

Example 335

DIEA (1.40 mL, 8.05 mmol) was added to a mixture of the 3-(4-(diethylamino)-2-(4-(3-(trifluoromethyl)benzylcarbamoyl)pyridin-2-yl)phenylcarbamoyl)benzoic acid 25b (1.07 g), N¹-(2,5,8,11,14,17,20-heptaoxadocosan-22-yl)-N¹-(2-methoxyethyl)-N²-methylethane-1,2-diamine 335b (1.07 g, 1.61 mmol) and HATU (0.80 g, 2.09 mmol) in DMF (8 mL) and the reaction stirred for 2 hours at room temperature. The reaction was diluted with water and extracted with ethyl acetate. The extract was washed with water and brine, dried (MgSO₄), and evaporated. The residue was purified by PTLC (10% methanol/20% ethyl acetate/dichloromethane) to give the title compound as an orange oil (1.2 g, 73%); MS (ES, m/z): 1029 [M+H]⁺; NMR (400 MHz, DMSO-d₆, ppm): δ 9.52 (m, 2H); 8.90 (d, J=5.2 Hz, 1H); 8.25 (s, 1H); 7.98 (m, 2H); 7.84 (m, 2H); 7.54-7.70 (m, 6H); 4.62 (d, J=5.6 Hz, 2H); 3.80-3.88 (m, 4H); 3.74 (m, 2H); 3.60 (m, 2H); 3.42-3.56 (m, XH); 3.38-3.41 (m, 2H); 3.32 (m, 2H); 3.22 (s, 3H); 1.12 (t, J=6.8 Hz, 6H).

Example 336 tert-Butyl 3-[2-[2-[2-[2-[[3-[[4-(diethylamino)-2-[5-[[3-(trifluoromethyl)phenyl]methylcarbamoyl]-2-pyridyl]phenyl]carbamoyl]benzoyl]-methyl-amino]ethyl-(2-methoxyethyl)amino]ethoxy]ethoxy]ethoxy]propanoate

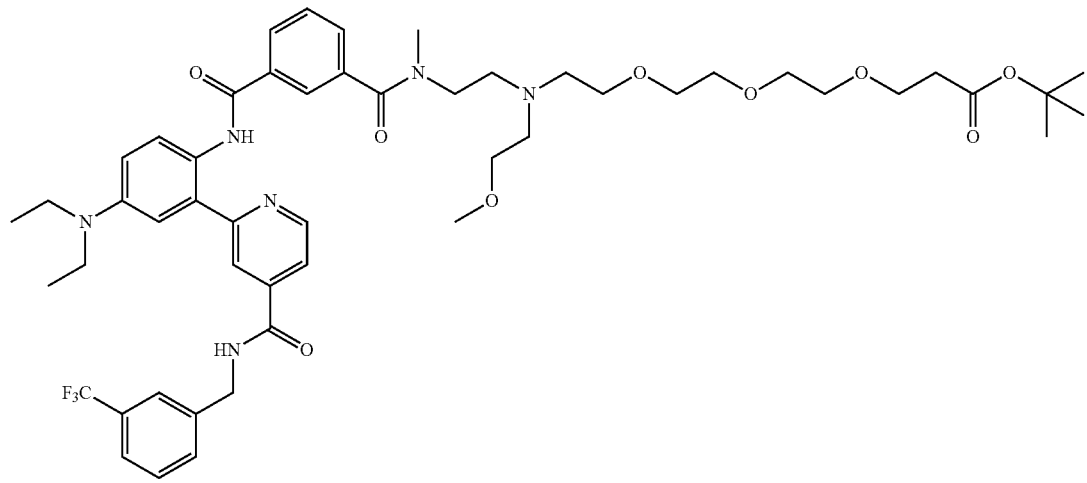 [SMILES: CCN(CC)c1ccc(NC(=O)c2cccc(C(=O)N(C)CCN(CCOC)CCOCCOCCOCCC(=O)OC(C)(C)C)c2)c(-c2cc(C(=O)NCc3cccc(C(F)(F)F)c3)ccn2)c1]

Example 336 was prepared as described in Example 335 substituting tert-butyl 2,8,11,14-tetraoxa-5-azaheptadecan-17-oate 135c.4 in place of N-(2-methoxyethyl)-2,5,8,11,14,17,20-heptaoxadocosan-22-amine to prepare tert-butyl 5-(2-methoxyethyl)-8,11,14-trioxa-2,5-diazaheptadecan-17-oate DIEA (2.04 mL, 11.7 mmol) was added to a mixture of the 3-(4-(diethylamino)-2-(4-(3-(trifluoromethyl)benzylcarbamoyl)pyridin-2-yl)phenylcarbamoyl)benzoic acid 25b (2.34 mmol), tert-butyl 5-(2-methoxyethyl)-8,11,14-trioxa-2,5-diazaheptadecan-17-oate (0.92 g, 2.34 mmol) and HATU (1.15 g, 3.04 mmol) in DMF (15 mL) and the reaction stirred for 2 hours at room temperature. The reaction was diluted with water and extracted with ethyl acetate. The extract was washed with water and brine, dried (MgSO$_4$), and evaporated. The residue was purified by PTLC (10% methanol/20% ethyl acetate/dichloromethane) to give product as an orange oil (2.13 g, 94%); MS (ES, m/z): 967 [M+H]$^+$; NMR (400 MHz, DMSO-d$_6$, ppm): δ 11.8 (m, 1H); 9.49 (m, 1H); 8.87 (d, J=5.2 Hz, 1H); 8.23 (s, 1H); 8.03 (s, 1H); 7.95 (m, 1H); 7.79 (m, 1H); 7.69 (s, 1H); 7.55-7.65 (m, 5H); 7.06 (d, J=2.8 Hz, 1H); 6.86 (dd, J=2.8 and 9.2 Hz, 1H); 4.60 (d, J=5.6 Hz, 2H); 3.83 (m, 2H); 3.52 (m, 2H); 3.36-3.60 (m, 20H); 3.06 (m, 2H); 3.01 (m, 2H); 2.95 (m, 2H); 2.88 (m, 3H); 2.73 (s, 3H); 2.38 (m, 2H); 1.37 (s, 9H); 1.13 (t, J=6.8 Hz, 6H).

Example 337

N$^1$-(4-(Diethylamino)-2-(4-(3-(trifluoromethyl)benzylcarbamoyl)pyridin-2-yl)phenyl)-N3-(3-(2-methoxyethyl)-17,17-dimethyl-15-oxo-6,9,12-trioxa-3,16-diazaoctadecyl)-N$^3$-methylisophthalamide Scheme 119.

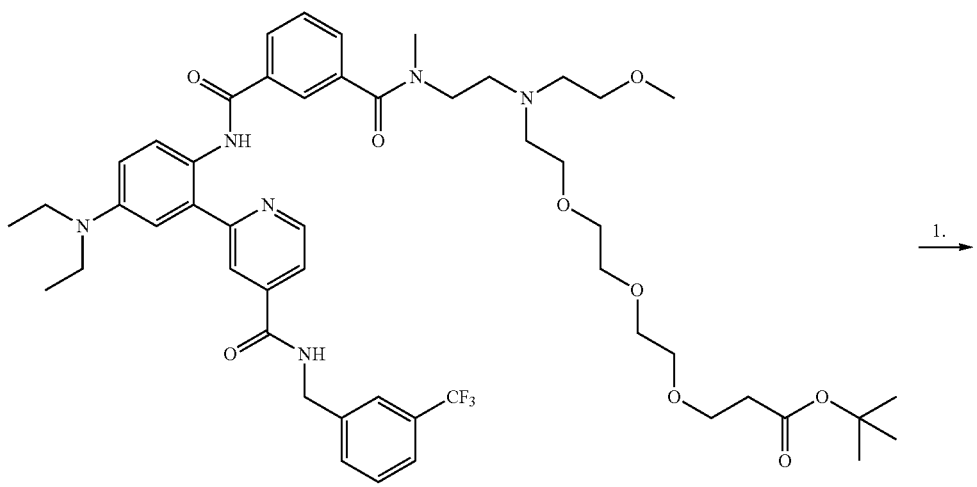

1.

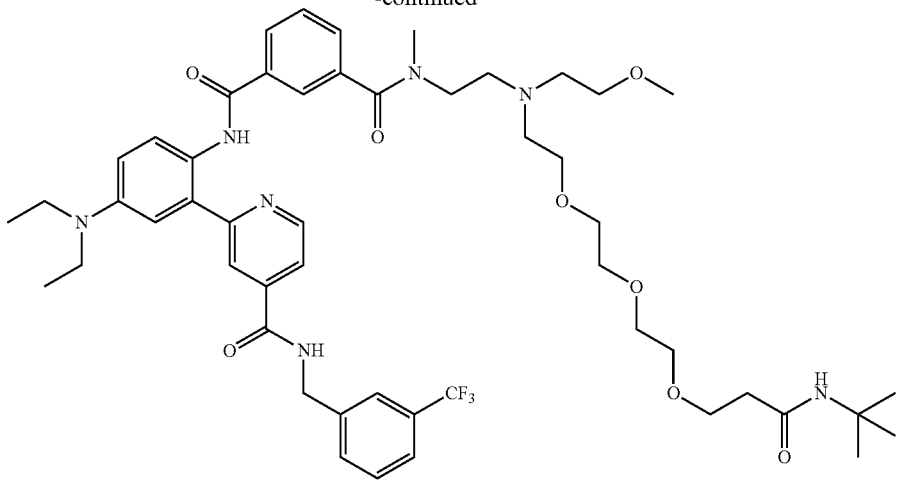

337

1. a. 4M HCl/Dioxane; b. HATU, DIEA, tert-butylamine DMF.

tert-Butyl 3-[2-[2-[2-[2-[[3-[[4-(diethylamino)-2-[5-[[3-(trifluoromethyl)phenyl]methylcarbamoyl]-2-pyridyl]phenyl]carbamoyl]benzoyl]-methyl-amino]ethyl-(2-methoxyethyl)amino]ethoxy]ethoxy]ethoxy]propanoate (0.101 g, 0.105 mmol) Example 336 and hydrochloric acid (4N in dioxane, 3 mL) were stirred for 4 hours at room temperature and then evaporated to give the carboxylic acid, 3-[2-[2-[2-[2-[[3-[[4-(diethylamino)-2-[5-[[3-(trifluoromethyl)phenyl]methylcarbamoyl]-2-pyridyl]phenyl]carbamoyl]benzoyl]-methyl-amino]ethyl-(2-methoxyethyl)amino]ethoxy]ethoxy]ethoxy]propanoic acid, as a white solid. DIEA (0.091 mL, 0.525 mmol) was added to a mixture of the acid, tert-butylamine (7.65 mg, 0.105 mmol) and HATU (48 mg, 0.126 mmol) in DMF (1 mL) and the reaction stirred for 2 hours at room temperature. The reaction was diluted with water and extracted with ethyl acetate. The extract was washed with water and brine, dried (MgSO$_4$), and evaporated. The residue was purified by PTLC (10% methanol/20% ethyl acetate/dichloromethane) to give product as an orange foam (30 mg, 30%); MS (ES, m/z): 966 [M+H]$^+$; NMR (400 MHz, DMSO-d$_6$, ppm): δ 11.8 (m, 1H); 9.53 (m, 1H); 8.85 (d, J=5.2 Hz, 1H); 8.23 (m, 1H); 8.06 (m, 1H); 7.91 (m, 1H); 7.86 (s, 1H); 7.81 (m, 1H); 7.70 (m, 1H); 7.54-7.66 (m, 5H); 7.37 (m, 1H); 7.06 (d, J=2.8 Hz, 1H); 6.86 (dd, J=2.8 and 9.2 Hz, 1H); 4.61 (d, J=6.0 Hz, 2H); 3.36-3.56 (m, 15H); 3.22 (m, 3H); 3.14 (m, 1H); 3.06 (m, 2H); 3.01 (m, 2H); 2.92 (m, 2H); 2.72 (m, 2H); 2.60 (m, 1H); 2.40 (m, 2H); 2.23 (m, 2H); 1.21 (s, 9H); 1.12 (t, J=6.8 Hz, 6H).

Example 338

N$^1$-(4-(Diethylamino)-2-(4-(3-(trifluoromethyl)benzylcarbamoyl)pyridin-2-yl)phenyl)-N$^3$-(3-(2-methoxyethyl)-16-methyl-18-morpholino-15-oxo-6,9,12-trioxa-3,16-diazaoctadecyl)-N$^3$-methylisophthalamide

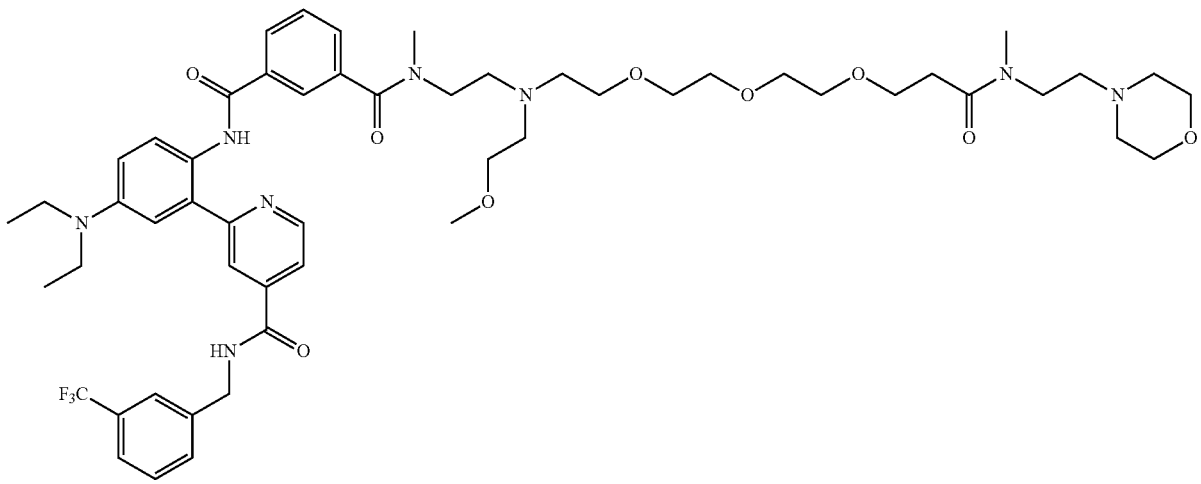 [SMILES: CCN(CC)c1ccc(NC(=O)c2cccc(C(=O)N(C)CCN(CCOC)CCOCCOCCOCCC(=O)N(C)CCN3CCOCC3)c2)c(-c2cc(C(=O)NCc3cccc(C(F)(F)F)c3)ccn2)c1]

Example 338 was prepared as described in Example 337 substituting N-methyl-2-morpholinoethanamine in place of tert-butylamine. MS (ES, m/z): 1035 [M+H]$^+$; NMR (400 MHz, DMSO-d$_6$, ppm): δ 11.8 (m, 1H); 9.49 (m, 1H); 8.86 (d, J=5.2 Hz, 1H); 8.23 (s, 1H); 8.05 (m, 1H); 7.91 (m, 1H); 7.86 (m, 1H); 7.80 (m, 1H); 7.70 (m, 1H); 7.55-7.66 (m, 4H); 7.06 (d, J=2.8 Hz, 1H); 6.86 (dd, J=2.8 and 9.2 Hz, 1H); 4.61 (d, J=6 Hz, 2H); 3.30-3.3.64 (m, 25H); 3.23 (m, 4H); 3.14 (m, 2H); 3.11 (m, 1H); 3.01 (m, 1H); 2.90-2.94 (m, 4H); 2.79 (s, 3H); 2.71 (m, 2H); 2.60 (m, 1H); 2.38 (m, 6H); 1.13 (t, J=6.8 Hz, 6H).

Example 339

(S)-tert-Butyl 1-(3-(4-(diethylamino)-2-(4-(1,2,3,4-tetrahydronaphthalen-1-ylcarbamoyl)pyridin-2-yl)phenylcarbamoyl)phenyl)-2,5-dimethyl-1-oxo-8,11,14-trioxa-2,5-diazahexadecan-16-ylcarbamate Scheme 120.

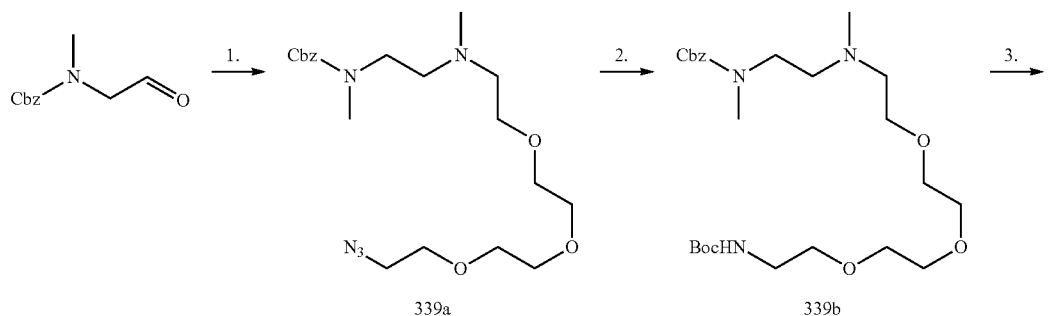

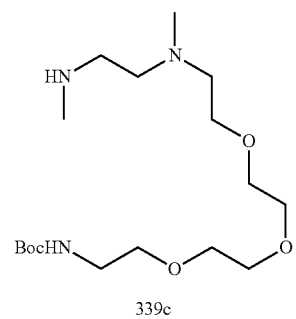

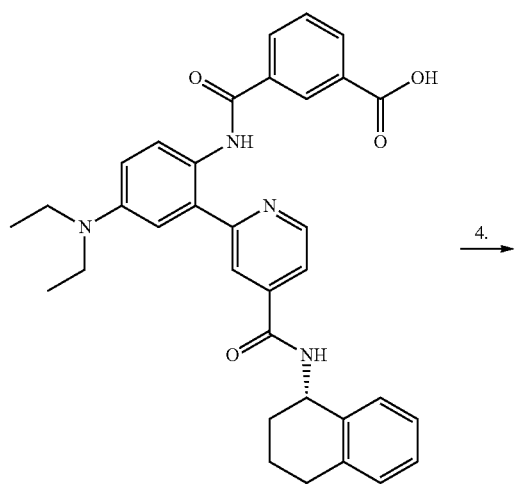

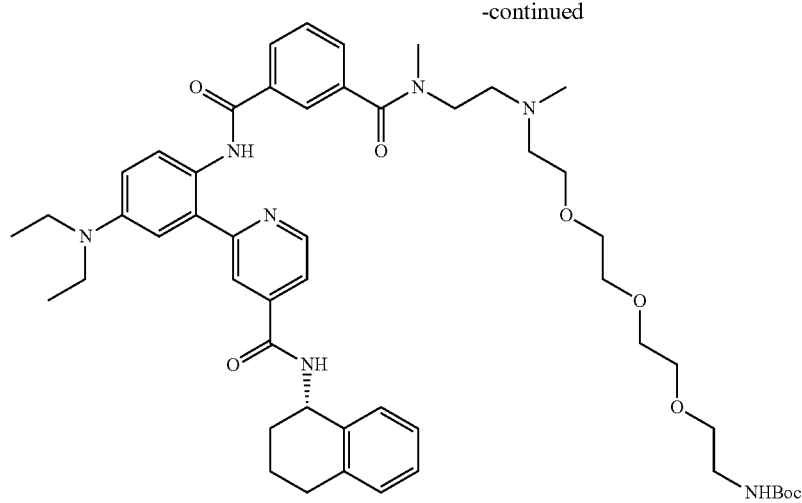

1. Na(OAc)₃BH, Acetic acid, THF 222c;
2. a. PPh₃, H₂O, THF; b. di-tert-butyl dicarbonate, DCM, DIEA
3. Pd/C, H₂, MeOH;
4. HATU, DIEA, DMF.

Intermediate 339a: Benzyl 14-azido-3-methyl-6,9,12-trioxa-3-azatetradecyl(methyl)carbamate Sodium triacetoxyborohydride (3.55 g, 16.8 mmol) was added portionwise at room temperature to benzyl methyl(2-oxoethyl)carbamate (2.68 g, 12.9 mmol), 2-(2-(2-(2-azidoethoxy)ethoxy)ethoxy)-N-methylethanamine 222c (3.00 g, 12.9 mmol), and acetic acid (2 equiv.) in THF (20 mL). The mixture was stirred for 2 hours, diluted with ethyl acetate, washed with saturated aqueous sodium bicarbonate and brine, dried (Mg₂SO₄) and evaporated. The residue was purified by Combiflash purification system (ethyl acetate/dichloromethane) to give product as an oil (3.19 g, 58%); MS (ES, m/z): 424 [M+H]⁺.

Intermediate 339b: tert-Butyl N-[2-[2-[2-[2-[2-(benzyloxycarbonylamino)ethyl-(2-methoxyethyl)amino]ethoxy]ethoxy]ethoxy]ethyl]carbamate Triphenylphosphine (1.80 g, 6.89 mmol) was added to benzyl 14-azido-3-methyl-6,9,12-trioxa-3-azatetradecyl(methyl)carbamate (2.92 g, 6.89 mmol) in THF (30 mL) and the mixture stirred for 5 hours at room temperature. Water (0.25 mL) was added, the mixture stirred at 50° C. overnight, and then evaporated under vacuum. The residue was dissolved in DCM (30 mL) and DIEA (1.80 mL, 10.3 mmol), and di-tert-butyl dicarbonate (1.65 g, 7.58 mmol) in DCM (3 mL) added dropwise at 0° C. The mixture was allowed to warm to room temperature, washed with water and brine, dried (Mg₂SO₄) and evaporated. The residue was purified by Combiflash purification system (ethyl acetate/dichloromethane) to give product as an oil (2.99 g, 87%); MS (ES, m/z): 498 [M+H]⁺.

Intermediate 339c: tert-Butyl 5-methyl-8,11,14-trioxa-2,5-diazahexadecan-16-ylcarbamate tert-Butyl N-[2-[2-[2-[2-[2-(benzyloxycarbonylamino)ethyl-(2-methoxyethyl)amino]-ethoxy]ethoxy]ethoxy]ethyl]carbamate (2.99 g,) and palladium on carbon (10%, wet, 0.6 g) in methanol (30 mL) were stirred under a hydrogen atmosphere (balloon) for 2 hours. The mixture was filtered through celite and evaporated to give product as an oil (2.18 g, quantitative).

Example 339

(S)-tert-Butyl 3-(4-(diethylamino)-2-(4-(1,2,3,4-tetrahydronaphthalen-1-ylcarbamoyl)pyridin-2-yl)phenylcarbamoyl)benzoate (1.48 g, 2.39 mmol) and hydrochloric acid (4M in dioxane, 10 mL) were stirred at room temperature for 4 hours and then evaporated to dryness to give product as a white solid. DIEA (2.08 mL, 11.9 mmol) was added to (S)-3-(4-(diethylamino)-2-(4-(1,2,3,4-tetrahydronaphthalen-1-ylcarbamoyl)pyridin-2-yl)phenylcarbamoyl)benzoic acid (1.48 g, 2.39 mmol), tert-butyl 5-methyl-8,11,14-trioxa-2,5-diazahexadecan-16-ylcarbamate (0.87 g, 2.39 mmol) and HATU (1.09 g, 2.87 mmol) in DMF (15 mL) and the mixture stirred for 2 hours at room temperature. The mixture was diluted with water and extracted with ethyl acetate. The extract was washed with water and brine, dried (Mg₂SO₄) and evaporated. The residue was purified by PTLC (10% methanol/20% ethyl acetate/dichloromethane) to give product as a yellow oil ( ); MS (ES, m/z): 909 [M+H]⁺; NMR (400 MHz, DMSO-d₆, ppm): δ 9.13 (d, J=8.4 Hz, 1H); 8.83 (d, J=5.2 Hz, 1H); 8.21 (s, 1H); 8.03 (m, 1H); 7.90-7.92 (m, 1H); 7.86 (s, 1H); 7.81 (d, J=4.4 Hz, 1H); 7.58-7.61 (m, 2H); 7.09-7.19 (m, 4H); 7.06 (d, J=2.8 Hz, 1H); 6.85 (dd, J=2.8 and 9.2 Hz, 1H); 6.72 (m, 1H); 5.23 (m, 1H); 3.33-3.57 (m, 19H); 2.96-3.08 (m, 4H); 2.91 (m, 1H); 2.72-2.80 (m, 2H); 2.24-2.38 (m, 2H); 1.92-2.02 (m, 2H); 1.90 (m, 1H); 1.72-1.84 (m, 2H); 1.35 (s, 9H); 1.12 (t, J=7.2 Hz, 6H).

Example 340
N[1]-[2-[2-[2-[2-[2-(Adamantane-1-carbonylamino)ethoxy]ethoxy]ethoxy]ethyl-methyl-amino]ethyl]N[3]-[4-(diethylamino)-2-[5-[[3-(trifluoromethyl)phenyl]methylcarbamoyl]-2-pyridyl]phenyl]-N[1]-methyl-benzene-1,3-dicarboxamide
Scheme 121.
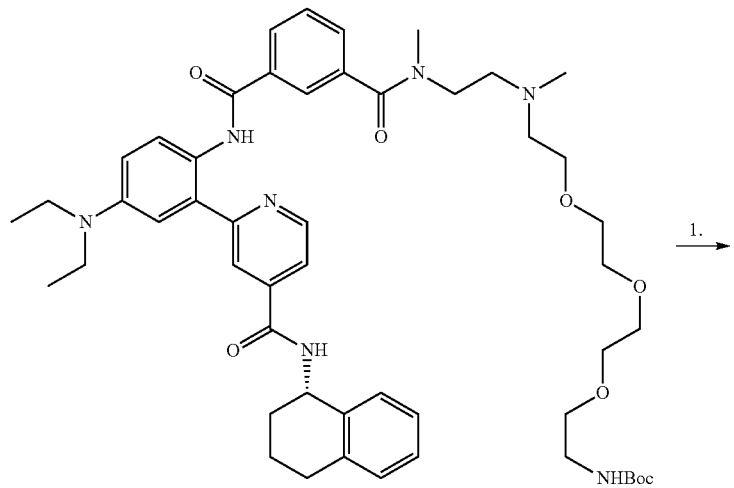
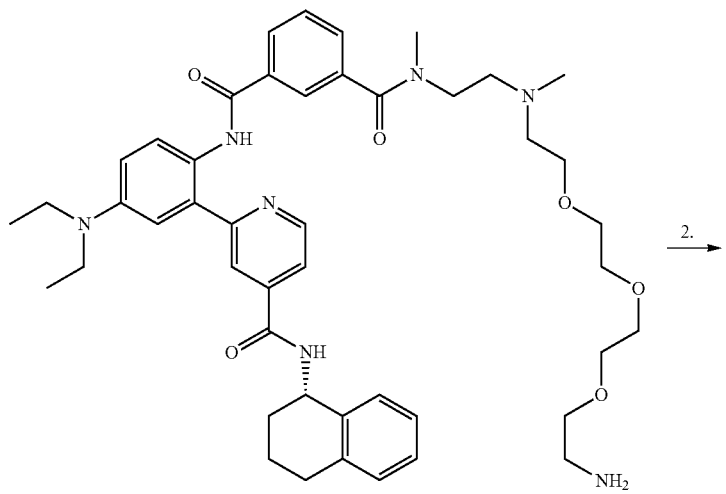

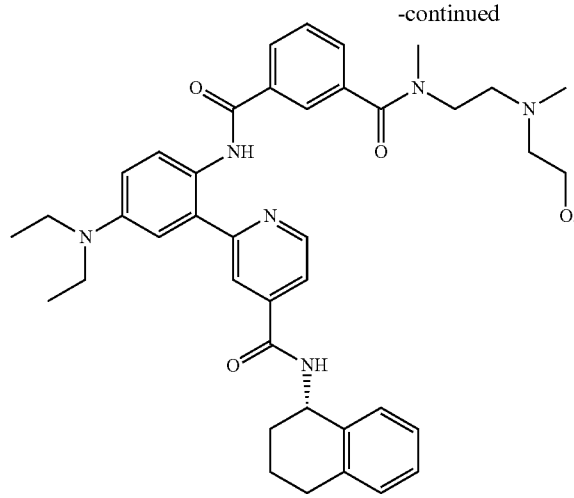

340

1. 4M HCl, Dioxane
2. 1-adamantanecarboxylic acid HATU, DIEA, DMF.

Intermediate 340a (S)-tert-Butyl 1-(3-(4-(diethylamino)-2-(4-(1,2,3,4-tetrahydronaphthalen-1-ylcarbamoyl)pyridin-2-yl)phenylcarbamoyl)phenyl)-2,5-dimethyl-1-oxo-8,11,14-trioxa-2,5-diazahexadecan-16-ylcarbamate Example 339 (1.08 g, 1.23 mmol) and hydrochloric acid in dioxane (4N, 20 mL) were stirred for 4 hours at room temperature and then evaporated to dryness to give the intermediate (S)—$N^1$-(14-amino-3-methyl-6,9,12-trioxa-3-azatetradecyl)-$N^3$-(4-(diethylamino)-2-(4-(1,2,3,4-tetrahydronaphthalen-1-ylcarbamoyl)pyridin-2-yl)phenyl)-$N^1$-methylisophthalamide tetrahydrochloride 340a as a foam (1.2 g, quantitative); MS (ES, m/z): 808 [M+H]$^+$.

Example 340

DIEA (0.12 mL, 0.666 mmol) was added to (S)—$N^1$-(14-amino-3-methyl-6,9,12-trioxa-3-azatetradecyl)-$N^3$-(4-(diethylamino)-2-(4-(1,2,3,4-tetrahydronaphthalen-1-ylcarbamoyl)pyridin-2-yl)phenyl)-$N^1$-methylisophthalamide tetrahydrochloride 340a (0.106 g, 0.111 mmol), 1-adamantanecarboxylic acid (20.1 mg, 0.111 mmol) and HATU (51 mg, 0.133 mmol) in DMF (2 mL) and the mixture stirred for 2 hours at room temperature. The reaction was diluted with ethyl acetate, washed with water and brine, dried (MgSO$_4$) and evaporated. The residue was purified by PTLC (10% methanol/20% ethyl acetate/dichloromethane) to give product as a yellow foam (0.076 g, 70%); MS (ES, m/z): 972 [M+H]$^+$; NMR (400 MHz, DMSO-d$_6$, ppm): δ 11.8 (m, 1H); 9.13 (d, J=8.8 Hz, 1H); 8.83 (d, J=5.2 Hz, 1H); 8.21 (s, 1H); 8.03 (m, 1H); 7.95 (s, 1H); 7.91 (m, 1H); 7.86 (m, 1H); 7.81 (d, J=4.8 Hz, 1H); 7.58 (m, 2H); 7.29 (t, J=5.2 Hz, 1H); 7.09-7.19 (m, 4H); 7.05 (m, 1H); 6.85 (dd, J=2.8 and 9.2 Hz, 1H); 5.22 (m, 1H); 3.30-3.52 (m, 16H); 3.25 (m, 2H); 2.88-3.05 (m, 6H); 2.70-2.83 (2H); 2.33 (m, 2H); 1.70-2.04 (m, 15); 1.56-1.68 (m, 6H); 1.12 (t, J=6.8 Hz, 6H).

Example 341

(S)—$N^1$-(4-(Diethylamino)-2-(4-(1,2,3,4-tetrahydronaphthalen-1-ylcarbamoyl)pyridin-2-yl)phenyl)-$N^3$-methyl-$N^3$-(3-methyl-16-oxo-6,9,12-trioxa-3,15-diazaheptadecyl)isophthalamide

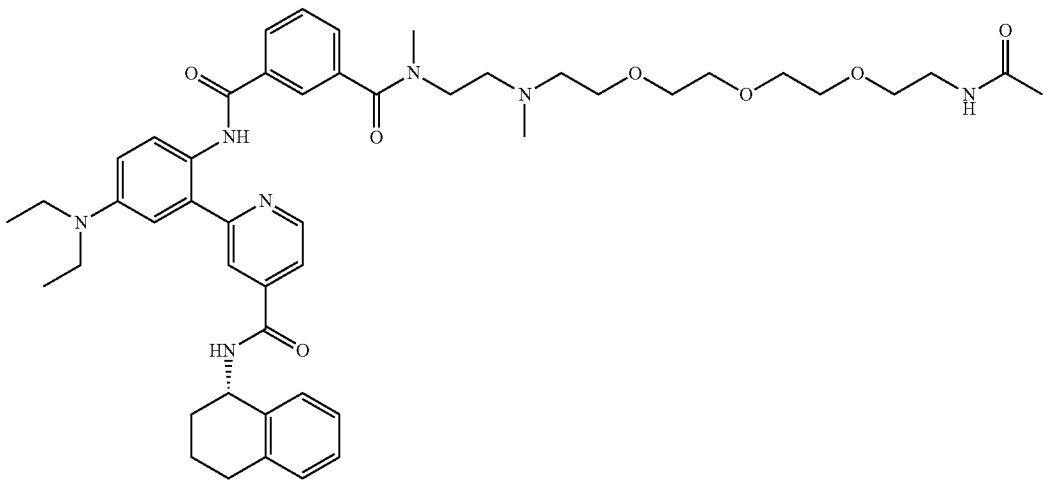 [SMILES: CCN(CC)c1ccc(NC(=O)c2cccc(C(=O)N(C)CCN(C)CCOCCOCCOCCNC(C)=O)c2)c(-c2cc(C(=O)N[C@H]3CCCc4ccccc43)ccn2)c1]

Example 341

DIEA (0.12 mL, 0.66 mmol) was added to (S)—$N^1$-(14-amino-3-methyl-6,9,12-trioxa-3-azatetradecyl)-$N^3$-(4-(diethylamino)-2-(4-(1,2,3,4-tetrahydronaphthalen-1-ylcarbamoyl)pyridin-2-yl)phenyl)-$N^1$-methylisophthalamide tetrahydrochloride 340a (0.105 g, 0.11 mmol) and acetic anhydride (0.0125 mL, 0.132 mmol) in DCM (5 mL) and the mixture stirred for 2 hours at room temperature. The reaction was diluted with DCM, washed with water and brine, dried (MgSO$_4$) and evaporated. The residue was purified by PTLC (10% methanol/20% ethyl acetate/dichloromethane) to give product as a yellow foam (0.089 g, 95%); MS (ES, m/z): 852 [M+H]$^+$; NMR (400 MHz, DMSO-d$_6$, ppm): δ 11.4 (m, 1H); 9.13 (d, J=8.8 Hz, 1H); 8.83 (d, J=5.6 Hz, 1H); 8.21 (s, 1H); 8.02 (m, 1H); 7.91 (m, 1H); 7.85 (m, 1H); 7.81 (d, J=4.4 Hz, 1H); 7.58-7.59 (m, 2H); 7.09-7.19 (m, 4H); 7.06 (d, J=3.2 Hz, 1H); 6.85 (dd, J=3.2 and 9.2 Hz, 1H); 5.23 (m, 1H); 3.24-3.56 (m, 18H); 3.15 (q, J=5.6 Hz, 2H); 3.00 (m, 2H); 2.91 (m, 2H); 2.76-2.79 (m, 2H); 2.63 (m, 1H); 2.57 (m, 1H); 2.46 (m, 1H); 2.33 (m, 1H); 2.29 (m, 2H); 1.93-2.04 (m, 2H); 1.89 (m, 1H); 1.70-1.84 (m, 2H); 1.77 (s, 3H); 1.12 (t, J=6.8 Hz, 6H).

Example 342

(S)—$N^1$-(4-(Diethylamino)-2-(4-(1,2,3,4-tetrahydronaphthalen-1-ylcarbamoyl)pyridin-2-yl)phenyl)-$N^3$-methyl-$N^3$-(14-methyl-1-oxo-1-(pyridin-3-yl)-5,8,11-trioxa-2,14-diazahexadecan-16-yl)isophthalamide

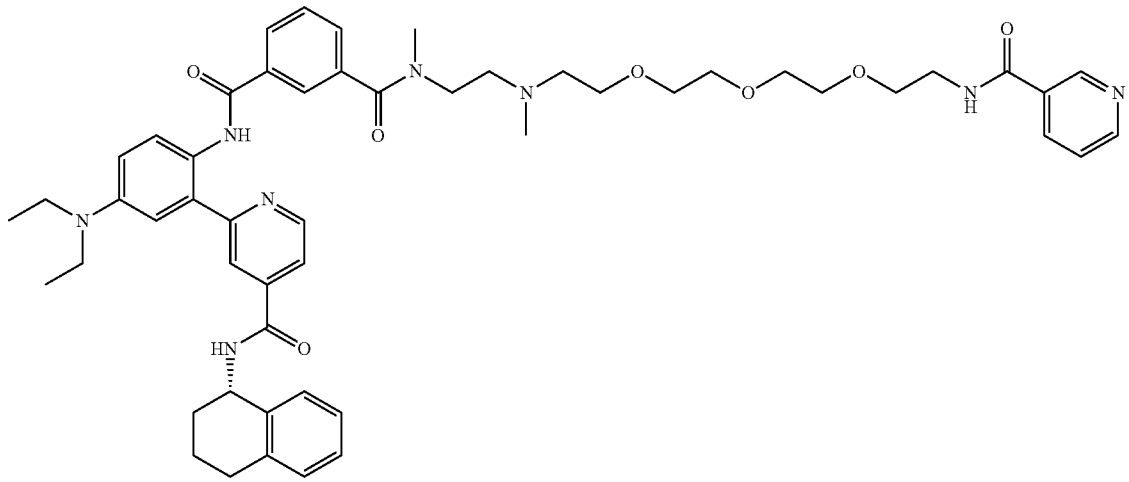 [SMILES: CCN(CC)c1ccc(NC(=O)c2cccc(C(=O)N(C)CCN(C)CCOCCOCCOCCNC(=O)c3cccnc3)c2)c(-c2cc(C(=O)N[C@H]3CCCc4ccccc43)ccn2)c1]

Example 342

DIEA (0.11 mL, 0.654 mmol) was added to (S)—N$^1$-(14-amino-3-methyl-6,9,12-trioxa-3-azatetradecyl)-N$^3$-(4-(diethylamino)-2-(4-(1,2,3,4-tetrahydronaphthalen-1-ylcarbamoyl)pyridin-2-yl)phenyl)-N$^1$-methylisophthalamide tetrahydrochloride 340a (0.104 g, 0.109 mmol), nicotinic acid (13.4 mg, 0.109 mmol) and HATU (49 mg, 0.131 mmol) in DMF (2 mL) and the mixture stirred for 2 hours at room temperature. The reaction was diluted with ethyl acetate, washed with water and brine, dried (MgSO$_4$) and evaporated. The residue was purified by PTLC (10% methanol/20% ethyl acetate/dichloromethane) to give product as a yellow foam (0.079 g, 80%); MS (ES, m/z): 915 [M+H]$^+$; NMR (400 MHz, DMSO-d$_6$, ppm): δ 11.7 (m, 1H); 9.13 (d, J=8.4 Hz, 1H); 8.98 (m, 1H); 8.83 (d, J=4.4 Hz, 1H); 8.68-8.70 (m, 2H); 8.21 (s, 1H); 8.15-8.18 (m, 1H); 8.02 (m, 1H); 7.92 (m, 1H); 7.86 (m, 1H); 7.80 (d, J=4.8 Hz, 1H); 7.59 (m, 2H); 7.47-7.50 (m, 1H); 7.11-7.19 (m, 4H); 7.06 (d, J=2.8 Hz, 1H); 6.85 (dd, J=2.8 and 9.2 Hz, 1H); 5.22 (m, 1H); 3.32-3.64 (m, 18H); 3.14 (m, 1H); 3.00 (m, 2H); 2.92 (m, 2H); 2.77 (m, 2H); 2.32 (m, 1H); 1.70-2.04 (m, 5H); 1.12 (t, J=6.8 Hz, 6H).

Example 343

(S)—N$^1$-(4-(Diethylamino)-2-(4-(1,2,3,4-tetrahydronaphthalen-1-ylcarbamoyl)pyridin-2-yl)phenyl)-N$^3$-methyl-N$^3$-(14-methyl-1-oxo-1-(tetrahydro-2H-pyran-4-yl)-5,8,11-trioxa-2,14-diazahexadecan-16-yl)isophthalamide

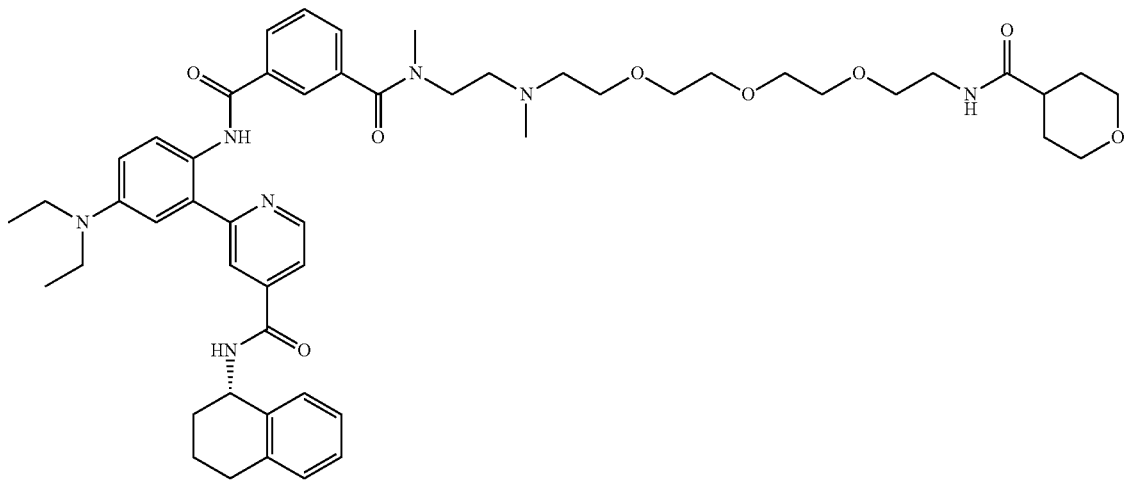 [SMILES: CCN(CC)c1ccc(NC(=O)c2cccc(C(=O)N(C)CCN(C)CCOCCOCCOCCNC(=O)C3CCOCC3)c2)c(-c2cc(C(=O)N[C@H]3CCCc4ccccc43)ccn2)c1]

Example 343

DIEA (0.11 mL, 0.654 mmol) was added to (S)—N$^1$-(14-amino-3-methyl-6,9,12-trioxa-3-azatetradecyl)-N$^3$-(4-(diethylamino)-2-(4-(1,2,3,4-tetrahydronaphthalen-1-ylcarbamoyl)pyridin-2-yl)phenyl)-N$^1$-methylisophthalamide tetrahydrochloride 340a (0.101 g, 0.106 mmol), tetrahydropyran-4-yl-carboxylic acid (13.8 mg, 0.106 mmol) and HATU (48 mg, 0.127 mmol) in DMF (2 mL) and the mixture stirred for 2 hours at room temperature. The reaction was diluted with ethyl acetate, washed with water and brine, dried (MgSO$_4$) and evaporated. The residue was purified by PTLC (10% methanol/20% ethyl acetate/dichloromethane) to give product as a yellow foam (0.071 g, 73%); MS (ES, m/z): 921 [M+H]$^+$; NMR (400 MHz, DMSO-d$_6$, ppm): δ 11.7 (m, 1H); 9.13 (d, J=8.4 Hz, 1H); 8.83 (d, J=5.2 Hz, 1H); 8.21 (s, 1H); 8.02 (m, 1H); 7.92 (m, 1H); 7.87 (m, 1H); 7.76-7.84 (m, 1H); 7.60 (m, 1H); 7.08-7.20 (m, 4H); 7.06 (d, J=2.8 Hz, 1H); 6.84 (dd, J=2.8 and 9.2 Hz, 1H); 5.22 (m, 1H); 3.80-3.84 (m, 2H); 3.20-3.66 (m, 17H); 3.12-3.20 (m, 2H); 3.00 (m, 3H); 2.93 (m, 2H); 2.72-2.82 (m, 2H); 2.26-2.38 (m, 2H); 1.98 (m, 2H); 1.79 (m, 2H); 1.51-1.56 (m, 4H); 1.12 (t, J=6.8 Hz, 6H).

Example 344

(S)—N$^1$-(4-(Diethylamino)-2-(4-(1,2,3,4-tetrahydronaphthalen-1-ylcarbamoyl)pyridin-2-yl)phenyl)-N$^3$-methyl-N$^3$-(14-methyl-1-oxo-1-(thiazol-4-yl)-5,8,11-trioxa-2,14-diazahexadecan-16-yl) isophthalamide

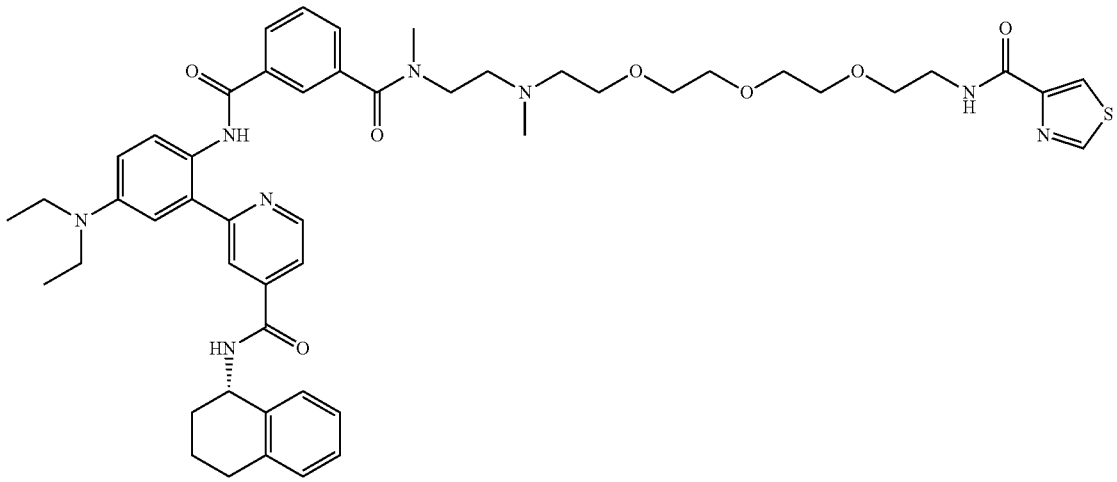 [SMILES: CCN(CC)c1ccc(NC(=O)c2cccc(C(=O)N(C)CCN(C)CCOCCOCCOCCNC(=O)c3cscn3)c2)c(-c2cc(C(=O)N[C@H]3CCCc4ccccc43)ccn2)c1]

Example 344

DIEA (0.11 mL, 0.654 mmol) was added to (S)—N$^1$-(14-amino-3-methyl-6,9,12-trioxa-3-azatetradecyl)-N$^3$-(4-(diethyl amino)-2-(4-(1,2,3,4-tetrahydronaphthalen-1-ylcarbamoyl)pyridin-2-yl)phenyl)-N$^1$-methylisophthalamide tetrahydrochloride 340a (0.101 g, 0.106 mmol), thiazole-5-carboxylic acid (14.2 mg, 0.110 mmol) and HATU (50 mg, 0.132 mmol) in DMF (2 mL) and the mixture stirred for 2 hours at room temperature. The reaction was diluted with ethyl acetate, washed with water and brine, dried (MgSO$_4$) and evaporated. The residue was purified by PTLC (10% methanol/20% ethyl acetate/dichloromethane) to give product as a yellow foam (0.073 g, 75%); MS (ES, m/z): 921 [M+H]$^+$; NMR (400 MHz, DMSO-d$_6$, ppm): δ 11.7 (m, 1H); 9.19 (s, 1H); 9.13 (d, J=8.4 Hz, 1H); 8.83 (d, J=4.4 Hz, 1H); 8.80 (m, 1H); 8.46 (s, 1H); 8.21 (s, 1H); 8.03 (m, 1H); 7.90 (m, 2H); 7.81 (d, J=4.8 Hz, 1H); 7.60 (m, 2H); 7.08-7.20 (m, 4H), 7.05 (d, J=2.8 Hz, 1H); 6.85 (dd, J=2.8 and 9.2 Hz, 1H); 5.22 (m, 1H); 3.20-3.66 (m, 20H); 3.13 (m, 2H); 3.00 (m, 2H); 2.93 (m, 2H); 2.76 (m, 2H); 1.97 (m, 2H); 1.78 (m, 2H); 1.12 (t, J=6.8 Hz, 6H).

Example 345

(S)—N$^1$-(4-(Diethylamino)-2-(4-(1,2,3,4-tetrahydronaphthalen-1-ylcarbamoyl)pyridin-2-yl)phenyl)-N$^3$-(1-(4-hydroxyphenyl)-14-methyl-1-oxo-5,8,11-trioxa-2,14-diazahexadecan-16-yl)-N$^3$-methylisophthalamide

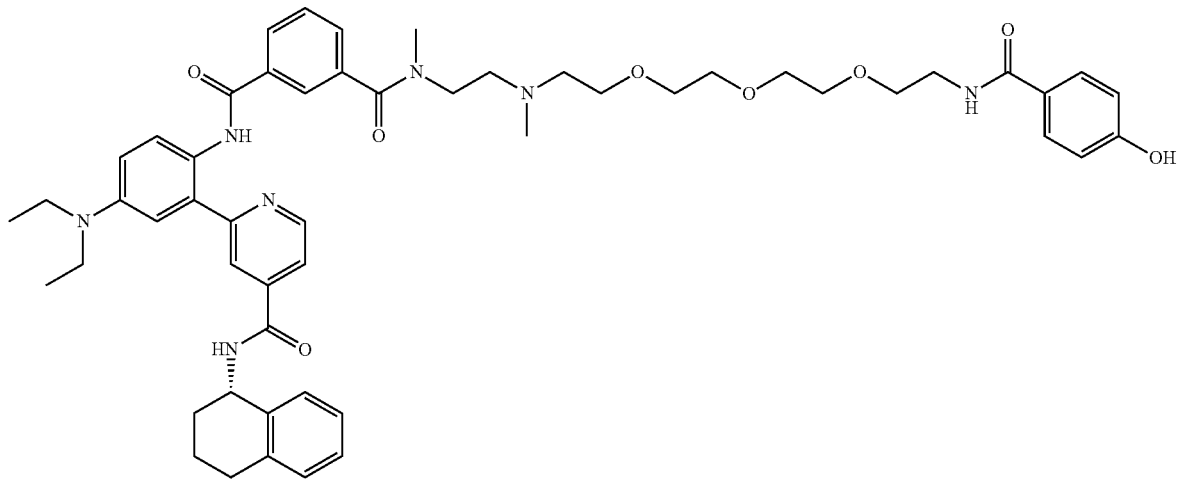 [SMILES: CCN(CC)c1ccc(NC(=O)c2cccc(C(=O)N(C)CCN(C)CCOCCOCCOCCNC(=O)c3ccc(O)cc3)c2)c(-c2cc(C(=O)N[C@H]3CCCc4ccccc43)ccn2)c1]

Example 345

DIEA (0.11 mL, 0.654 mmol) was added to (S)—$N^1$-(14-amino-3-methyl-6,9,12-trioxa-3-azatetradecyl)-$N^3$-(4-(diethylamino)-2-(4-(1,2,3,4-tetrahydronaphthalen-1-ylcarbamoyl)pyridin-2-yl)phenyl)-$N^1$-methylisophthalamide tetrahydrochloride 340a (0.101 g, 0.106 mmol), 4-acetoxybenzoic acid (19.1 mg, 0.106 mmol) and HATU (48 mg, 0.127 mmol) in DMF (2 mL) and the mixture stirred for 2 hours at room temperature. The reaction was diluted with ethyl acetate, washed with water and brine, dried (MgSO$_4$) and evaporated. The residue was purified by PTLC (10% methanol/20% ethyl acetate/dichloromethane) to give the intermediate (S)-4-(1-(3-(4-(diethylamino)-2-(4-(1,2,3,4-tetrahydronaphthalen-1-ylcarbamoyl)pyridin-2-yl)phenylcarbamoyl)phenyl)-2,5-dimethyl-1-oxo-8,11,14-trioxa-2,5-diazahexadecan-16-ylcarbamoyl)phenyl acetate as a yellow foam (0.082 g, 75%); MS (ES, m/z): 972 [M+H]$^+$. Ammonia in methanol (2M, 4 mL) was added and the mixture stirred overnight at room temperature. The reaction was evaporated and the residue purified by PTLC (10% methanol/20% ethyl acetate/dichloromethane) to give product as a yellow foam (0.065 g, 83%); MS (ES, m/z): 928 [M+H]$^+$; NMR (400 MHz, DMSO-d$_6$, ppm): δ 11.7 (m, 1H); 9.93 (s, 1H); 9.13 (d, J=8.4 Hz, 1H); 8.83 (d, J=5.2 Hz, 1H); 8.21 (m, 2H); 7.96-8.06 (m, 1H); 7.84-7.94 (m, 2H); 7.80 (d, J=4.8 Hz, 1H); 7.70 (dd, J=2.0 and 6.8 Hz, 2H); 7.60 (m, 2H); 7.09-7.19 (m, 4H); 7.06 (d, J=3.2 Hz, 1H); 6.85 (dd, J=2.8 and 8.8 Hz, 1H); 6.77 (m, 2H); 5.23 (m, 1H); 3.35-3.60 (m, 25H); 2.99 (m, 3H); 2.92 (m, 2H); 2.33 (m, 1H); 1.90-2.04 (m, 3H); 1.70-1.86 (m, 2H); 1.12 (t, J=6.8 Hz, 6H).

Example 346

$N^1$-(4-(diethylamino)-2-(4-(3-(trifluoromethyl)benzylcarbamoyl)pyridin-2-yl)phenyl)-$N^3$-methyl-$N^3$-(3,17,17-trimethyl-16-oxo-6,9,12-trioxa-3,15-diazaoctadecyl)isophthalamide

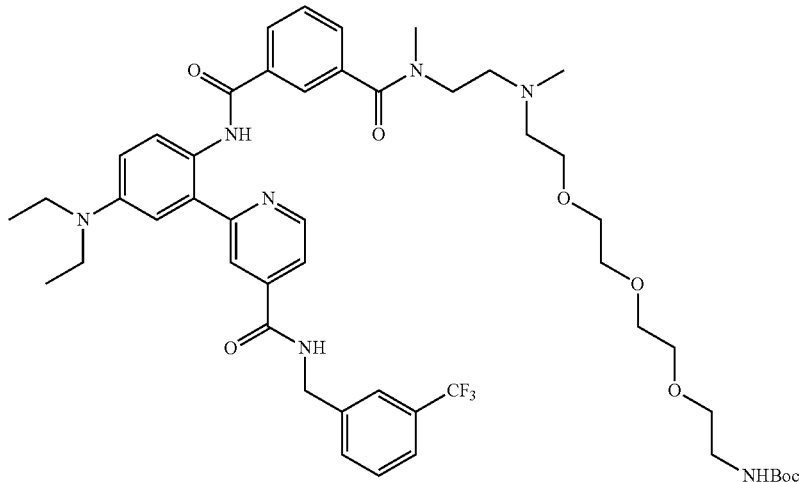 [SMILES: CCN(CC)c1ccc(NC(=O)c2cccc(C(=O)N(C)CCN(C)CCOCCOCCOCCNC(=O)OC(C)(C)C)c2)c(-c2cc(C(=O)NCc3cccc(C(F)(F)F)c3)ccn2)c1]

Example 346

The compound was prepared as described in Examples 339 substituting 25b in place of 131c. DIEA (1.47 mL, 8.45 mmol) was added to 3-(4-(diethylamino)-2-(4-(3-(trifluoromethyl)benzylcarbamoyl)pyridin-2-yl)phenylcarbamoyl)benzoic acid, dihydrochloride (1.12 g, 1.69 mmol), tert-butyl 5-methyl-8,11,14-trioxa-2,5-diazahexadecan-16-ylcarbamate 339c (0.61 g, 1.69 mmol) and HATU (0.77 g, 2.03 mmol) in DMF (8 mL) and the mixture stirred for 2 hours at room temperature. The mixture was diluted with water and extracted with ethyl acetate. The extract was washed with water and brine, dried (Mg$_2$SO$_4$) and evaporated. The residue was purified by Combiflash chromatography system (methanol/dichloromethane gradient) to give product as a yellow oil (1.46 g, 94%); MS (ES, m/z): 920 [M+H]$^+$.

Example 347

(S)-16-(3-(4-(cyclopentyloxy)-2-(4-(1,2,3,4-tetrahydronaphthalen-1-ylcarbamoyl)pyridin-2-yl)phenylcarbamoyl)phenyl)-4,7,10,13-tetraoxahexadecan-1-oic acid

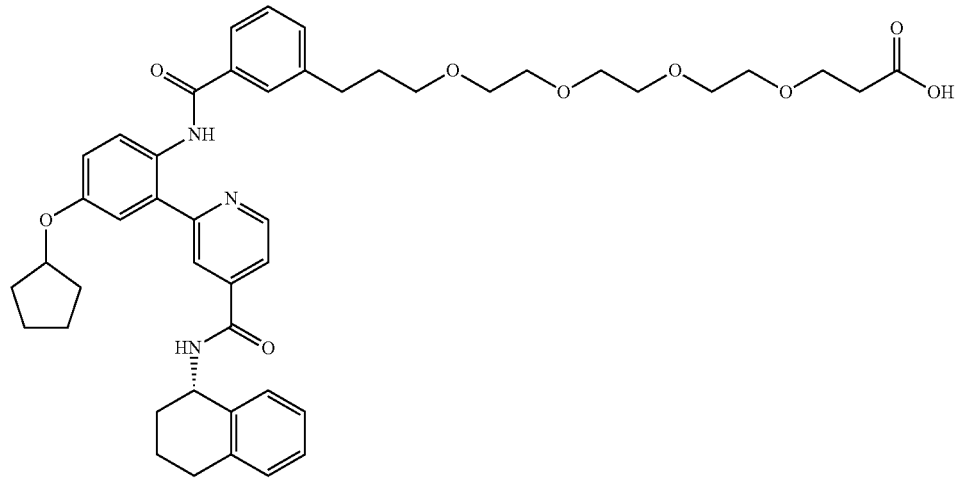 [SMILES: O=C(O)CCOCCOCCOCCOCCCc1cccc(C(=O)Nc2ccc(OC3CCCC3)cc2-c2cc(C(=O)N[C@H]3CCCc4ccccc43)ccn2)c1]

Example 347

This compound was prepared as described in Example 251 substituting 133a in place of 25b. MS (ES, m/z): 794 [M+H]$^+$

Example 348

Procedure for the Measurement of NaP2b-Mediated P$_i$ Transport

Materials.

HEK293 cells were obtained from the American Type Culture collection and propagated per their instructions. Expression clones for rat and human NaP2b (SLC34A2) were obtained from Open Biosystems (Catalog numbers MRN1768-9510282, and MHS1010-99823026, respectively). The sequence of the human protein was mutated to insert a threonine after residue 37, and to introduce a N39D mutation.

Inhibition of P$_i$ Transport.

The rate of phosphate (Pi) uptake into HEK293 cells was measured using a modification of the method described by Mohrmann et al. (Mohrmann, I., Mohrmann, M., Biber, J., and Murer, H. (1986) Am. J. Phys. 250(3 Pt 1):G323-30.) Transfected HEK293 cells were treated with a pharmacological agent to minimize endogenous PiT-mediated phosphate transport activity, such that the only remaining sodium-dependent phosphate transport activity is that which was bestowed by introduction of the NaP2b genes.

Cells were seeded into 96-well plates at 25,000 cells/well and cultured overnight. Lipofectamine 2000 (Invitrogen) was used to introduce the NaP2b cDNA, and the cells were allowed to approach confluence during a second overnight incubation. Medium was aspirated from the cultures, and the cells were washed once with choline uptake buffer (14 mM Tris, 137 mM choline chloride, 5.4 mM KCl, 2.8 mM CaCl$_2$, 1.2 mM MgSO$_4$, 100 uM KH$_2$PO$_4$, 1 mg/mL Bovine Serum Albumin, pH 7.4). Cells were then overlayed with either choline uptake buffer or sodium uptake buffer (14 mM Tris, 137 mM sodium chloride, 5.4 mM KCl, 2.8 mM CaCl$_2$, 1.2 mM MgSO$_4$, 100 uM KH$_2$PO$_4$, PiT-silencing agent, 1 mg/mL Bovine Serum Albumin, pH 7.4) containing 6-9 uCi/mL $^{33}$P orthophosphoric acid (Perkin Elmer) and test compound. Each compound was tested at twelve concentrations ranging from 0.1 nM to 30 uM. Assays were run in duplicate.

After incubation for 3-30 minutes at room temperature, assay mixtures were removed, and the cells were washed twice with ice cold stop solution (137 mM sodium chloride, 14 mM Tris, pH 7.4). Cells were lysed by addition of 20 μL 0.1% Tween 80 followed by 100 μL scintillation fluid, and counted using a TopCount (Perkin Elmer).

pIC50 (the negative log of the IC50) values of the test compounds were calculated using GraphPad Prism. Preliminary studies showed that under these conditions, sodium-dependent Pi uptake was linear for at least 30 mM and tolerated 0.6% (v/v) DMSO without deleterious effects.

To ascertain if an inhibitor was competitive for binding with phosphate, the procedure was repeated, but raising the concentration of the substrate in the assay mixture from 0.1 to 2.1 mM phosphate. Compounds that maintained their potency for inhibition of NaPi2b in the presence of 2.1 vs 0.1 mM phosphate were considered to not be competitive with respect to phosphate.

TABLE 11

Inhibitory activity of compounds against rat and human NaP2b Values reported as pIC50.

| Example | pIC50 range for rat Nap2b | pIC50 range for human NaP2b* | Competitive with respect to Pi?** |
|---|---|---|---|
| PFA | 2-3 | | Yes |
| 1.10 | 5.1-6.0 | | |
| 1.1 | 5.1-6.0 | 5.1-6.0 | No |
| 1.11 | 4.5-5 | | |
| 1.12 | 5.1-6.0 | | |
| 1.13 | 5.1-6.0 | | |
| 1.14 | 5.1-6.0 | | |
| 1.15 | 5.1-6.0 | | |
| 1.16 | 4.5-5 | | |
| 1.17 | 5.1-6.0 | | |
| 1.18 | 5.1-6.0 | | |
| 1.19 | 4.5-5 | | |
| 1.2 | 4.5-5 | | |
| 1.20 | 4.5-5 | | |
| 1.21 | 4.5-5 | | |
| 1.22 | 5.1-6.0 | | |
| 1.23 | 5.1-6.0 | | |
| 1.24 | 5.1-6.0 | | |
| 1.25 | 5.1-6.0 | | |
| 1.26 | 5.1-6.0 | | |
| 1.27 | 4.5-5 | | |
| 1.28 | 5.1-6.0 | | |
| 1.29 | 5.1-6.0 | | |
| 1.30 | 5.1-6.0 | | |
| 1.3 | 5.1-6.0 | | |
| 1.31 | 5.1-6.0 | | |
| 1.32 | 5.1-6.0 | | |
| 1.33 | 5.1-6.0 | | |
| 1.34 | 5.1-6.0 | | |
| 1.35 | 5.1-6.0 | | |
| 1.36 | 5.1-6.0 | | |
| 1.36 | 5.1-6.0 | | |
| 1.37 | 5.1-6.0 | | |
| 1.38 | 4.5-5 | | |
| 1.39 | 5.1-6.0 | | |
| 1.4 | 5.1-6.0 | | |
| 1.40 | 5.1-6.0 | | |
| 1.42 | 5.1-6.0 | | |
| 1.43 | 5.1-6.0 | | |
| 1.44 | 5.1-6.0 | | |
| 1.45 | 5.1-6.0 | | |
| 1.46 | 5.1-6.0 | | |
| 1.47 | 5.1-6.0 | | |
| 1.48 | 5.1-6.0 | | |
| 1.49 | 5.1-6.0 | | |
| 1.5 | 5.1-6.0 | | |
| 1.6 | 5.1-6.0 | | |
| 1.7 | 5.1-6.0 | | |
| 1.8 | 4.5-5 | | |
| 1.9 | 4.5-5 | | |
| 2 | 4.5-5 | | |
| 3.1 | 5.1-6.0 | 5.1-6.0 | |
| 3.10 | 5.1-6.0 | 4.5-5 | |
| 3.2 | 4.5-5 | | |
| 3.3 | 4.5-5 | | |
| 3.4 | 4.5-5 | | |
| 3.5 | 5.1-6.0 | | |
| 3.6 | 4.5-5 | 4.5-5 | |
| 3.7 | 4.5-5 | 4.5-5 | |
| 3.8 | 4.5-5 | | |
| 3.9 | 4.5-5 | | |
| 4.10 | 4.5-5 | | |
| 4.1 | 4.5-5 | | |
| 4.11 | 5.1-6.0 | | |
| 4.12 | 5.1-6.0 | | |
| 4.13 | 5.1-6.0 | | |
| 4.14 | 5.1-6.0 | | |
| 4.15 | 5.1-6.0 | | |
| 4.16 | 4.5-5 | | |
| 4.17 | 4.5-5 | | |
| 4.18 | 4.5-5 | | |
| 4.19 | 5.1-6.0 | 5.1-6.0 | |
| 4.20.1 | 5.1-6.0 | | |
| 4.2 | 5.1-6.0 | | |
| 4.20.2 | 5.1-6.0 | | |
| 4.21 | 5.1-6.0 | | |
| 4.22 | 4.5-5 | | |
| 4.23 | 4.5-5 | | |
| 4.24 | 5.1-6.0 | | |
| 4.25 | 5.1-6.0 | | |
| 4.26 | 5.1-6.0 | >6.0 | |
| 4.27 | 5.1-6.0 | | |
| 4.28 | 5.1-6.0 | | |
| 4.29 | 5.1-6.0 | | |
| 4.30 | 5.1-6.0 | | |
| 4.3 | 5.1-6.0 | | |
| 4.31 | 4.5-5 | | |
| 4.32 | 5.1-6.0 | | |
| 4.4 | 4.5-5 | | |
| 4.5 | 5.1-6.0 | | |
| 4.6 | 4.5-5 | | |
| 4.7 | 4.5-5 | | |
| 4.8 | 5.1-6.0 | | |
| 4.9 | 4.5-5 | | |
| 5.1 | 5.1-6.0 | | |
| 5.2 | 4.5-5 | | |
| 6.1 | 4.5-5 | | |
| 6.2 | 4.5-5 | | |
| 7 | 4.5-5 | | |
| 8.10 | 4.5-5 | | |
| 8.1 | 4.5-5 | | |
| 8.1 | >6.0 | >6.0 | No |
| 8.11 | 4.5-5 | | |
| 8.12 | 4.5-5 | | |
| 8.13 | 4.5-5 | | |
| 8.14 | 5.1-6.0 | | |
| 8.15 | 5.1-6.0 | | |
| 8.16 | 5.1-6.0 | | |
| 8.17 | >6.0 | | |
| 8.18 | >6.0 | | No |
| 8.19 | 5.1-6.0 | | |
| 8.2 | 5.1-6.0 | | |
| 8.20 | 5.1-6.0 | | |
| 8.21 | 5.1-6.0 | 5.9 | |
| 8.22 | 5.1-6.0 | | |
| 8.23 | 5.1-6.0 | | |
| 8.25 | 5.1-6.0 | >6.0 | |
| 8.26 | 4.5-5 | | No |
| 8.27 | 4.5-5 | | |
| 8.3 | 5.1-6.0 | | |
| 8.4 | 5.1-6.0 | | |
| 8.5 | 5.1-6.0 | | |
| 8.6 | 5.1-6.0 | | |
| 8.7 | 5.1-6.0 | | |
| 8.8 | >6.0 | | |
| 8.9 | 5.1-6.0 | | |
| 9.1 | 5.1-6.0 | | |
| 9.2 | 5.1-6.0 | >6.0 | |
| 9.3 | 5.1-6.0 | | |
| 10.10 | 5.1-6.0 | | |
| 10.1 | 5.1-6.0 | >6.0 | No |
| 10.11 | 5.1-6.0 | | |
| 10.12 | 5.1-6.0 | | |
| 10.2 | 4.5-5 | | |
| 10.3 | 4.5-5 | | |
| 10.4 | 4.5-5 | | |
| 10.5 | 4.5-5 | | |
| 10.6 | 5.1-6.0 | | |
| 10.7 | 5.1-6.0 | | |
| 10.8 | 4.5-5 | | |
| 10.9 | 4.5-5 | | |
| 11.1 | 5.1-6.0 | | |
| 11.2 | 5.1-6.0 | | |
| 11.3 | 4.5-5 | | |
| 11.4 | 4.5-5 | | |
| 12.1 | 5.1-6.0 | | |
| 12.2 | 4.5-5 | | |
| 14 | 4.5-5 | | |

TABLE 11-continued

Inhibitory activity of compounds against rat and human NaP2b Values reported as pIC50.

| Example | pIC50 range for rat Nap2b | pIC50 range for human NaP2b* | Competitive with respect to Pi?** |
|---|---|---|---|
| 15 | 5.1-6.0 | | |
| 16 | 5.1-6.0 | | |
| 17 | 5.1-6.0 | | |
| 18 | 5.1-6.0 | | |
| 19 | 5.1-6.0 | | |
| 20 | 5.1-6.0 | | |
| 21 | 5.1-6.0 | | |
| 22 | 4.5-5 | | |
| 24 | 5.1-6.0 | | |
| 25 | >6.0 | >6.0 | |
| 26 | 5.1-6.0 | | |
| 27 | 5.1-6.0 | | |
| 28 | 5.1-6.0 | | |
| 29 | 5.1-6.0 | | |
| 30 | 5.1-6.0 | | |
| 31 | 4.5-5 | | |
| 32 | 4.5-5 | | |
| 33 | 4.5-5 | | |
| 34 | 4.5-5 | | |
| 35 | 5.1-6.0 | | |
| 36 | 5.1-6.0 | | |
| 37 | >6.0 | >6.0 | No |
| 38 | 4.5-5 | | |
| 39 | 5.1-6.0 | | |
| 40 | 4.5-5 | | |
| 41 | 4.5-5 | | |
| 42 | 4.5-5 | | |
| 43 | 4.5-5 | | |
| 44 | 4.5-5 | | |
| 45 | 4.5-5 | | |
| 46 | 4.5-5 | | |
| 47 | 4.5-5 | | |
| 48 | 5.1-6.0 | | |
| 49 | 5.1-6.0 | | |
| 50 | 5.1-6.0 | | |
| 51 | 5.1-6.0 | | |
| 53 | 5.1-6.0 | | |
| 54 | 4.5-5 | | |
| 55 | 5.1-6.0 | | |
| 56 | 4.5-5 | | |
| 57 | 4.5-5 | | |
| 58 | 5.1-6.0 | | |
| 59 | 5.1-6.0 | | |
| 60 | 4.5-5 | | |
| 61 | 4.5-5 | | |
| 62 | 4.5-5 | | |
| 63 | 5.1-6.0 | | |
| 64 | 4.5-5 | | |
| 65 | 4.5-5 | | |
| 66 | 4.5-5 | | |
| 67 | 4.5-5 | | |
| 68 | 4.5-5 | | |
| 69 | 4.5-5 | | |
| 70 | 4.5-5 | | |
| 71 | 4.5-5 | | |
| 72 | 4.5-5 | | |
| 73 | 4.5-5 | | |
| 74 | 4.5-5 | | |
| 75 | 4.5-5 | | |
| 76 | 4.5-5 | | |
| 77 | 5.1-6.0 | | |
| 78 | 4.5-5 | | |
| 79 | 4.5-5 | | |
| 80 | 5.1-6.0 | 5.1-6.0 | No |
| 81 | 5.1-6.0 | | |
| 82 | 5.1-6.0 | | |
| 83 | 5.1-6.0 | | |
| 84 | 5.1-6.0 | | |
| 85 | 5.1-6.0 | | |
| 86 | 5.1-6.0 | | |
| 87 | 4.5-5 | | |
| 88 | 4.5-5 | | |
| 89 | 5.1-6.0 | | |
| 90 | 4.5-5 | | |
| 91 | 4.5-5 | | |
| 92 | 5.1-6.0 | | |
| 93 | 4.5-5 | | |
| 94 | 4.5-5 | | |
| 95 | 4.5-5 | | |
| 96 | 4.5-5 | | |
| 97 | 5.1-6.0 | 5.1-6.0 | |
| 98 | 4.5-5 | | |
| 99 | 4.5-5 | | |
| 100 | 5.1-6.0 | | |
| 101 | 5.1-6.0 | | |
| 102 | 4.5-5 | | |
| 103 | 4.5-5 | | |
| 104 | 4.5-5 | | |
| 105 | 5.1-6.0 | | |
| 106 | 4.5-5 | | |
| 108 | 4.5-5 | | |
| 109 | 5.1-6.0 | | |
| 110 | 5.1-6.0 | | |
| 111 | 4.5-5 | | |
| 112 | 5.1-6.0 | | |
| 113 | 5.1-6.0 | | |
| 114 | 5.1-6.0 | | |
| 115 | >6.0 | >6.0 | |
| 116 | 5.1-6.0 | | |
| 117 | 5.1-6.0 | 5.1-6.0 | |
| 118 | 5.1-6.0 | | |
| 119 | >6.0 | | |
| 270 | 5.1-6.0 | | |
| 331 | 5.1-6.0 | | |
| 330 | 5.1-6.0 | | |
| 332 | >6.0 | >6.0 | |
| 263 | 5.1-6.0 | >6.0 | |
| 294 | >6.0 | >6.0 | |
| 290 | 4.5-5.0 | 5.1-6.0 | |
| 291 | 5.1-6.0 | >6.0 | |
| 292 | 5.1-6.0 | >6.0 | |
| 295 | 5.1-6.0 | | |
| 296 | 5.1-6.0 | 5.1-6.0 | |
| 293 | 5.1-6.0 | 5.1-6.0 | |
| 297 | 5.1-6.0 | 5.1-6.0 | |
| 272 | 5.1-6.0 | 5.1-6.0 | |
| 287 | 5.1-6.0 | 5.1-6.0 | |
| 288 | 5.1-6.0 | 5.1-6.0 | |
| 257 | 5.1-6.0 | >6.0 | |
| 258 | 5.1-6.0 | | |
| 259 | 5.1-6.0 | 5.1-6.0 | |
| 260 | 5.1-6.0 | >6.0 | |
| 262 | 5.1-6.0 | 5.1-6.0 | |
| 271 | 5.1-6.0 | >6.0 | |
| 298 | 5.1-6.0 | 5.1-6.0 | |
| 304 | >6.0 | >6.0 | |
| 306 | >6.0 | >6.0 | |
| 299 | 5.1-6.0 | >6.0 | |
| 300 | 5.1-6.0 | >6.0 | |
| 320 | >6.0 | | |
| 321 | 5.1-6.0 | | |
| 322 | 5.1-6.0 | | |
| 323 | >6.0 | | |
| 324 | >6.0 | | |
| 326 | >6.0 | | |
| 325 | >6.0 | | |
| 225 | 4.5-5.0 | | |
| 224 | 5.1-6.0 | | |
| 344 | >6.0 | | |
| 343 | 5.1-6.0 | | |
| 342 | 5.1-6.0 | | |
| 345 | 5.1-6.0 | | |
| 347 | >6.0 | | |
| 133 | 5.1-6.0 | | |
| 346 | 5.1-6.0 | | |
| 341 | 5.1-6.0 | | |
| 340 | 5.1-6.0 | | |
| 289 | 5.1-6.0 | 5.1-6.0 | |

TABLE 11-continued

Inhibitory activity of compounds against rat and human NaP2b Values reported as pIC50.

| Example | pIC50 range for rat Nap2b | pIC50 range for human NaP2b* | Competitive with respect to Pi?** |
|---|---|---|---|
| 226 | >6.0 | 5.1-6.0 | |
| 253 | >6.0 | >6.0 | |
| 223 | 4.5-5.0 | <4.5 | |
| 339 | >6.0 | >6.0 | |
| 273 | 5.1-6.0 | 5.1-6.0 | |
| 274 | 5.1-6.0 | 5.1-6.0 | |
| 338 | 5.1-6.0 | 5.1-6.0 | |
| 247 | 5.1-6.0 | 5.1-6.0 | |
| 239 | >6.0 | >6.0 | |
| 261 | >6.0 | >6.0 | |
| 337 | 5.1-6.0 | 5.1-6.0 | |
| 179 | 5.1-6.0 | 5.1-6.0 | |
| 178 | 5.1-6.0 | 5.1-6.0 | |
| 182 | >6.0 | >6.0 | |
| 285 | >6.0 | >6.0 | |
| 205 | >6.0 | >6.0 | |
| 284 | 5.1-6.0 | 5.1-6.0 | |
| 232 | 4.5-5.0 | 4.5-5.0 | |
| 177 | 5.1-6.0 | 5.1-6.0 | |
| 176 | 5.1-6.0 | 5.1-6.0 | |
| 175 | 5.1-6.0 | 5.1-6.0 | |
| 336 | 5.1-6.0 | 5.1-6.0 | |
| 269 | 5.1-6.0 | >6.0 | |
| 266 | 5.1-6.0 | 5.1-6.0 | |
| 335 | 5.1-6.0 | 5.1-6.0 | |
| 174 | 5.1-6.0 | >6.0 | |
| 172 | 5.1-6.0 | >6.0 | |
| 171 | 5.1-6.0 | >6.0 | |
| 170 | 5.1-6.0 | >6.0 | |
| 169 | >6.0 | >6.0 | |
| 203 | 5.1-6.0 | 5.1-6.0 | |
| 268 | >6.0 | >6.0 | |
| 267 | >6.0 | >6.0 | |
| 281 | >6.0 | >6.0 | |
| 202 | 5.1-6.0 | >6.0 | |
| 275 | 5.1-6.0 | 5.1-6.0 | |
| 276 | 5.1-6.0 | 5.1-6.0 | |
| 277 | 5.1-6.0 | 5.1-6.0 | |
| 278 | 5.1-6.0 | 5.1-6.0 | |
| 303 | 5.1-6.0 | >6.0 | |
| 201 | 5.1-6.0 | 5.1-6.0 | |
| 230 | 5.1-6.0 | 5.1-6.0 | |
| 243 | 4.5-5.0 | 4.5-5.0 | |
| 231 | 4.5-5.0 | 4.5-5.0 | |
| 167 | 4.5-5.0 | 4.5-5.0 | |
| 251 | 5.1-6.0 | >6.0 | |
| 173 | >6.0 | >6.0 | |
| 164 | 5.1-6.0 | >6.0 | |
| 163 | 5.1-6.0 | 5.1-6.0 | |
| 222 | >6.0 | >6.0 | |
| 214 | 5.1-6.0 | 5.1-6.0 | |
| 213 | 4.5-5.0 | 5.1-6.0 | |
| 242 | >6.0 | >6.0 | |
| 200 | 5.1-6.0 | >6.0 | |
| 159 | >6.0 | >6.0 | |
| 279 | 5.1-6.0 | 5.1-6.0 | |
| 280 | >6.0 | >6.0 | |
| 282 | >6.0 | 5.1-6.0 | |
| 283 | >6.0 | 5.1-6.0 | |
| 302 | >6.0 | >6.0 | |
| 212 | >6.0 | >6.0 | |
| 229 | >6.0 | >6.0 | |
| 227 | 5.1-6.0 | 5.1-6.0 | |
| 132 | >6.0 | >6.0 | |
| 236 | >6.0 | >6.0 | |
| 286 | >6.0 | >6.0 | |
| 161 | 5.1-6.0 | 5.1-6.0 | |
| 181 | >6.0 | >6.0 | |
| 168 | >6.0 | >6.0 | |
| 166 | 5.1-6.0 | 5.1-6.0 | |
| 265 | >6.0 | >6.0 | |
| 199 | 5.1-6.0 | | |
| 198 | 4.5-5.0 | | |
| 334 | 4.5-5.0 | | |
| 328 | 5.1-6.0 | 5.1-6.0 | |
| 160 | >6.0 | >6.0 | |
| 158 | >6.0 | >6.0 | |
| 255 | 5.1-6.0 | | |
| 245 | 4.5-5.0 | | |
| 128 | 5.1-6.0 | | |
| 241 | 5.1-6.0 | | |
| 228 | 5.1-6.0 | | |
| 237 | 5.1-6.0 | | |
| 252 | >6.0 | >6.0 | |
| 197 | 5.1-6.0 | | |
| 196 | 5.1-6.0 | 5.1-6.0 | |
| 240 | 5.1-6.0 | | |
| 333 | 5.1-6.0 | | |
| 157.1 | 5.1-6.0 | | |
| 256 | 5.1-6.0 | | |
| 165 | 5.1-6.0 | | |
| 157 | >6.0 | | |
| 195 | 5.1-6.0 | | |
| 194 | >6.0 | | |
| 327 | 5.1-6.0 | | |
| 154 | 4.5-5.0 | | |
| 153 | 4.5-5.0 | | |
| 152 | 5.1-6.0 | | |
| 151 | 5.1-6.0 | | |
| 150 | 4.5-5.0 | | |
| 155 | 4.5-5.0 | | |
| 246 | 5.1-6.0 | | |
| 127 | 4.5-5.0 | | |
| 250 | 5.1-6.0 | | |
| 149 | 5.1-6.0 | | |
| 148 | 5.1-6.0 | | |
| 142 | >6.0 | 5.1-6.0 | |
| 193 | 4.5-5.0 | | |
| 192 | >6.0 | >6.0 | |
| 191 | 4.5-5.0 | | |
| 190 | 5.1-6.0 | 5.1-6.0 | |
| 180 | 5.1-6.0 | | |
| 144 | >6.0 | >6.0 | |
| 145 | 4.5-5.0 | | |
| 147 | 5.1-6.0 | | |
| 221 | 4.5-5.0 | | |
| 131 | >6.0 | | |
| 189 | 5.1-6.0 | | |
| 235 | >6.0 | | |
| 146 | 5.1-6.0 | | |
| 329 | 5.1-6.0 | | |
| 254 | >6.0 | >6.0 | |
| 244 | 5.1-6.0 | 5.1-6.0 | |
| 220 | >6.0 | 5.1-6.0 | |
| 219 | >6.0 | >6.0 | |
| 162 | >6.0 | >6.0 | |
| 234 | >6.0 | >6.0 | |
| 143 | >6.0 | >6.0 | |
| 129 | 5.1-6.0 | | |
| 188 | 5.1-6.0 | 5.1-6.0 | |
| 216 | >6.0 | >6.0 | |
| 215 | >6.0 | >6.0 | |
| 211 | 5.1-6.0 | | |
| 249 | 5.1-6.0 | | |
| 187 | >6.0 | 5.1-6.0 | |
| 233 | 5.1-6.0 | 5.1-6.0 | |
| 218 | 5.1-6.0 | | |
| 141 | 5.1-6.0 | | |
| 140 | 5.1-6.0 | | |
| 139 | 4.5-5.0 | | |
| 264 | 4.5-5.0 | | |
| 217 | >6.0 | | |
| 138 | 5.1-6.0 | 5.1-6.0 | |
| 137 | 5.1-6.0 | | |
| 136 | 5.1-6.0 | | |
| 135 | 5.1-6.0 | | |
| 134 | 5.1-6.0 | | |
| 185 | 5.1-6.0 | >6.0 | |

TABLE 11-continued

Inhibitory activity of compounds against rat and human NaP2b Values reported as pIC50.

| Example | pIC50 range for rat Nap2b | pIC50 range for human NaP2b* | Competitive with respect to Pi?** |
|---|---|---|---|
| 121 | 5.1-6.0 | | |
| 125 | 5.1-6.0 | | |
| 210 | 4.5-5.0 | | |
| 126 | >6.0 | 5.1-6.0 | |
| 186 | 5.1-6.0 | | |
| 124 | 5.1-6.0 | | |
| 123 | 5.1-6.0 | | |
| 122 | 5.1-6.0 | 5.1-6.0 | |
| 208 | 4.5-5.0 | | |
| 207 | 4.5-5.0 | | |
| 130 | 5.1-6.0 | | |
| 120 | 5.1-6.0 | | |
| 248 | 4.5-5.0 | | |
| 184 | 5.1-6.0 | | |
| 183 | 5.1-6.0 | 5.1-6.0 | |
| 238 | 4.5-5.0 | | |
| 209 | 5.1-6.0 | | |

*A blank indicates not tested
**Indicates compound is considered to not be competitive with respect to phosphate. A blank indicates not tested for competitive inhibition.

Example 349

In Vivo Assay

Bolus Phosphorus Challenge

It has been demonstrated that the hyperphosphatemic response to a single oral dose of phosphorus is significantly dampened in mice deficient in the Nap2b gene (Sabbagh et al, J. Am. Soc Nephrol., 20(11):2348-58 (2009)). By pretreating animals with a low phosphorus diet followed by the subsequent dosing of a phosphorus bolus, serum phosphorus levels were monitored after 30 minutes as a surrogate for intestinal phosphorus absorption. These investigators showed that as a result of Nap2b deletion, the rise in serum phosphorus was reduced by about 40%. This indicates that the theoretical maximum effect on phosphorus absorption a Nap2b inhibitor could have in mice is 40% as indicated by the serum Pi. The in vivo bolus phosphorus challenge model used here mimics this model in rats.

Male, 7-week-old Sprague-Dawley rats (Charles-River laboratories international, Hollister, Calif.) were allowed to acclimatize for a minimum of 3 days before switching to a synthetic low-phosphorus diet (TD.85010, Harlan Teklad, Madison, Wis.) which contains 0.1% phosphorus and 0.6% calcium. At day 5, testing compounds or vehicle alone (as indicated) were orally administered at the indicated dose in a volume of 5 ml/kg, followed by a bolus gavage of monobasic sodium phosphate (1 mmol in 1 ml) 15 min after compound dosing. Serum was collected via retroorbital bleeding 30 min post phosphate bolus and phosphate levels were determined utilizing an ACE ALERA blood chemistry analyzer (Alfa Wassermann Diagnostic Technologies, West Caldwell, N.J.).

The extent of inhibition by test compounds on the elevation of serum phosphate levels in response to the bolus of phosphorus is shown in Table 12 (data are expressed as % Inhibition, with 6-10 animals per data point). The differences between groups were evaluated by one-way analysis of variance with Dunnett's post hoc tests.

TABLE 12

Inhibition of Uptake of Phosphorus from the Intestine as Measured using the Bolus Phosphorus Challenge Model

| Example | Drug Dose | % Inhibition of Serum P elevation | Significance |
|---|---|---|---|
| 21 | 30 | 10-20 | n.s. |
| 1.32 | 30 | 20-30 | *** |
| 4.4 | 30 | 40-50 | *** |
| 51 | 30 | 10-20 | n.s. |
| 80 | 30 | 20-30 | *** |
| 14 | 30 | 10-20 | n.s. |
| 1.1 | 30 | 20-30 | ** |

*$p < 0.05$, versus vehicle by Dunnett's post hoc test.
**$p < 0.01$, versus vehicle by Dunnett's post hoc test.
***$p < 0.001$, versus vehicle by Dunnett's post hoc test.

Example 350

In Vivo Evaluation Procedure

Co-Dosing in Chow

Male, 7-week-old Sprague-Dawley rats (Charles-River laboratories international, Hollister, Calif.) were allowed to acclimate for a minimum of 3 days. The experiment was initiated by switching animals to a synthetic diet (0.6% phosphorus and 0.6% calcium, Harlan Teklad TD.84122) for four days. After this time, the animals were placed into metabolic cages for daily monitoring of food and water consumption, as well as urine and fecal collections. Test compounds were incorporated into the powdered diet listed above containing 3% chocolate flavoring (w/w, BioServ #7345) at 1.3 mg test compound per gram of diet to achieve an average daily nominal dose of 100 mg/kg/day. The actual dose received by each animal was later determined by measuring prepared diet consumption and body weight. Urine samples were collected in three daily periods from 24-48, 48-72, and 72-96 hours of drug dosing. Averaging these three 24 h periods allows for the more representative measurements of urination, fecal excretion, food consumption and water uptake for each animal. Phosphorus levels in the urine were determined by anion exchange chromatography using a Dionex ICS-3000 ion chromatography system. Urine samples were diluted 1:500 or 1:1000 and injected onto an IonPac AS18 analytical column (2×250 mm) using a potassium hydroxide eluent. Elution of urine phosphate ions was monitored via conductivity detector and reported as ppm relative to a standard ion solution containing phosphate. Daily urinary P output relative to the P consumed in the prepared diet for each animal was calculated. The percentage inhibition of phosphorus absorption was estimated by determining the reduction of this ratio compared to the control group (animals with no drug in chow). The differences between the means of control and treated groups were evaluated by t tests. In all experiments, one group was always included that had Renvela powder blended into their chow at 0.9% targeting a dose of 750 mg/kg. Typically this resulted in an approximately 15% inhibition of Urine Pout/P consumed.

TABLE 13

Inhibition of Uptake of Phosphorus from the Intestine as Measured using the Co-Dosing in Chow Model

| Example | Mean drug dose, mg/kg/day | Mean % inhibition Urine Pout/P consumed | t-test |
|---|---|---|---|
| 25 | 74 | 10-30 | *** |
| 37 | 101 | ≤10 | * |
| 188 | 110 | 10-30 | ** |
| 162 | 100 | 10-30 | *** |
| 144 | 100 | ≤10 | * |
| 142 | 100 | ≤10 | ns |
| 252 | 90 | 10-30 | * |
| 237 | 130 | ≤10 | ns |
| 265 | 120 | ≤10 | * |
| 166 | 120 | 10-30 | *** |
| 181 | 120 | ≤10 | ** |
| 161 | 120 | ≤10 | * |
| 286 | 130 | 10-30 | ** |
| 200 | 100 | 10-30 | * |
| 163 | 100 | ≤10 | ns |
| 164 | 100 | ≤10 | ns |
| 173 | 90 | ≤10 | ns |
| 251 | 50 | ≤10 | ns |
| 203 | 100 | ≤10 | ** |
| 335 | 100 | ≤10 | ** |
| 269 | 100 | ≤10 | ** |
| 327 | 100 | 10-30 | ** |
| 261 | 100 | 10-30 | * |
| 300 | 50 | ≤10 | * |
| 299 | 50 | 10-30 | ** |
| 298 | 50 | 10-30 | *** |
| 272 | 50 | ≤10 | ns |

*p < 0.05 versus control;
**p < 0.01 versus control;
***p < 0.001 versus control

Example 351

Stability of Compounds in Simulated Gastric and Intestinal Fluid

Test compounds were incubated at 1-20 µM in simulated gastric fluid (SGF; standard USP solution with 3 mg/mL pepsin) or simulated intestinal fluid (SIF; standard USP solution with 3 mg/mL pancreatin) for 3 hr or 6 hr. HPLC-UV or HPLC-MS were used to determine test compound levels using peak area %. Results (Table 14) were reported as the percentage of test compound remaining after incubation in a given condition relative to test compound present at t=0 in the same condition.

TABLE 14

Percentage of Compound Remaining in Simulated Gastric and Intestinal Fluids

| Example | Incubation Time | % remaining, SIF | % remaining, SGF |
|---|---|---|---|
| 117 | 6 hr | >80% | >80% |
| 25 | 6 hr | 80 | >80% |
| 8.25 | 6 hr | >80% | >80% |
| 26 | 6 hr | 60-80% | >80% |
| 37 | 6 hr | >80% | >80% |
| 8.21 | 6 hr | >80% | >80% |
| 8.1 | 6 hr | >80% | 60-80% |
| 8.6 | 6 hr | >80% | >80% |
| 209 | 6 hr | 60-80% | >80% |
| 238 | 6 hr | >80% | >80% |
| 248 | 6 hr | >80% | >80% |
| 126 | 6 hr | >80% | >80% |
| 210 | 6 hr | >80% | >80% |
| 137 | 6 hr | >80% | >80% |
| 138 | 6 hr | 40-60% | >80% |
| 264 | 6 hr | >80% | 40-60% |
| 162 | 6 hr | >80% | >80% |
| 254 | 6 hr | >80% | >80% |
| 146 | 6 hr | 60-80% | >80% |
| 235 | 6 hr | >80% | >80% |
| 131 | 6 hr | >80% | >80% |
| 147 | 6 hr | >80% | >80% |
| 144 | 6 hr | >80% | >80% |
| 191 | 6 hr | >80% | >80% |
| 193 | 6 hr | >80% | >80% |
| 142 | 6 hr | >80% | >80% |
| 148 | 6 hr | >80% | >80% |
| 149 | 6 hr | >80% | >80% |
| 250 | 6 hr | >80% | >80% |
| 246 | 6 hr | >80% | >80% |
| 150 | 6 hr | >80% | >80% |
| 151 | 6 hr | 40-60% | >80% |
| 152 | 6 hr | >80% | >80% |
| 327 | 6 hr | >80% | >80% |
| 157 | 6 hr | >80% | >80% |
| 165 | 6 hr | >80% | >80% |
| 256 | 6 hr | >80% | >80% |
| 157.1 | 6 hr | >80% | >80% |
| 157.1 | 6 hr | >80% | >80% |
| 333 | 6 hr | >80% | >80% |
| 240 | 6 hr | >80% | >80% |
| 196 | 6 hr | >80% | >80% |
| 252 | 6 hr | >80% | >80% |
| 237 | 6 hr | >80% | >80% |
| 255 | 6 hr | >80% | >80% |
| 158 | 6 hr | 20-40% | >80% |
| 160 | 6 hr | 40-60% | >80% |
| 328 | 6 hr | >80% | >80% |
| 199 | 6 hr | >80% | >80% |
| 265 | 6 hr | >80% | >80% |
| 166 | 6 hr | >80% | >80% |
| 168 | 6 hr | >80% | >80% |
| 181 | 6 hr | >80% | >80% |
| 161 | 6 hr | >80% | >80% |
| 286 | 6 hr | >80% | >80% |
| 200 | 6 hr | >80% | >80% |
| 163 | 6 hr | 60-80% | >80% |
| 164 | 6 hr | 60-80% | >80% |
| 173 | 6 hr | >80% | >80% |
| 251 | 6 hr | >80% | >80% |
| 275 | 6 hr | >80% | >80% |
| 202 | 6 hr | >80% | >80% |
| 281 | 6 hr | 20-40% | >80% |
| 203 | 6 hr | >80% | >80% |
| 169 | 6 hr | 60-80% | >80% |
| 170 | 6 hr | 60-80% | >80% |
| 171 | 6 hr | >80% | >80% |
| 172 | 6 hr | >80% | >80% |
| 174 | 6 hr | >80% | >80% |
| 335 | 6 hr | >80% | >80% |
| 269 | 6 hr | >80% | >80% |
| 205 | 6 hr | >80% | >80% |
| 285 | 6 hr | >80% | 60-80% |
| 182 | 6 hr | >80% | >80% |
| 261 | 6 hr | 60-80% | >80% |
| 261 | 6 hr | >80% | >80% |
| 239 | 6 hr | >80% | 60-80% |
| 339 | 6 hr | >80% | <20% |
| 253 | 6 hr | >80% | 60-80% |

Example 352

Determination of Compound Cmax and AUC

Sprague-Dawley rats were orally gavaged with test article at a nominal dose of 2.5 or 10 mg/kg and blood was collected at 0.5, 1, 2 and 4 h. Blood samples were processed to plasma using K$_2$EDTA as an anticoagulant. Plasma samples were treated with acetonitrile containing an internal standard, precipitated proteins removed by centrifugation. Supernatants were analyzed by LC-MS/MS and compound concentrations were determined by interpolation from a standard curve prepared in plasma. Table 15 illustrates data from the pharmacokinetic profiling of selected example compounds. All compounds were orally dosed at the dosage shown, and pharmacokinetic parameters determined.

TABLE 15

Pharmacokinetic Profiling of Selected Example Compounds

| Example | Actual Oral Dose (mg/kg) | Cmax (ng/mL) | AUC (ng × hr/mL) |
|---|---|---|---|
| 8.1 | 3-15 | <10 | <30 |
| 37 | 3-15 | <10 | <30 |
| 26 | 3-15 | <30 | <30 |
| 25 | 3-15 | <30 | <30 |
| 8.25 | 3-15 | <30 | >50 |
| 8.6 | 3-15 | <50 | >50 |
| 1.1 | 3-15 | <50 | >50 |
| 8.21 | 3-15 | <30 | <30 |
| 80 | 3-15 | <10 | <10 |
| 80 | 3-15 | <10 | <30 |
| 209 | 3-15 | <30 | <30 |
| 238 | 3-15 | <10 | <10 |
| 248 | 3-15 | <10 | <10 |
| 126 | 3-15 | <10 | <30 |
| 210 | 3-15 | <10 | <30 |
| 137 | 3-15 | <10 | <10 |
| 138 | 3-15 | <10 | <10 |
| 264 | 3-15 | <10 | <10 |
| 141 | 3-15 | >50 | >50 |
| 218 | 3-15 | <10 | <30 |
| 233 | 3-15 | <10 | <10 |
| 249 | 3-15 | <10 | <30 |
| 211 | 3-15 | <10 | <30 |
| 215 | 3-15 | <10 | <10 |
| 216 | 3-15 | <10 | <10 |
| 188 | 3-15 | <10 | <10 |
| 143 | 3-15 | <10 | <10 |
| 234 | 3-15 | <10 | <30 |
| 162 | 3-15 | <10 | <10 |
| 254 | 3-15 | <10 | <10 |
| 146 | 3-15 | <10 | <10 |
| 131 | 3-15 | <30 | <50 |
| 147 | 3-15 | <10 | <10 |
| 144 | 3-15 | <10 | <10 |
| 191 | 3-15 | <10 | <10 |
| 193 | 3-15 | <10 | <30 |
| 142 | 3-15 | <10 | <10 |
| 148 | 3-15 | <10 | <10 |
| 149 | 3-15 | <10 | <10 |
| 250 | 3-15 | <10 | <10 |
| 246 | 3-15 | <10 | <10 |
| 150 | 3-15 | <10 | <10 |
| 151 | 3-15 | <10 | <10 |
| 152 | 3-15 | <10 | <10 |
| 327 | 3-15 | <10 | <10 |
| 195 | 3-15 | <10 | <10 |
| 157 | 3-15 | <10 | <10 |
| 165 | 3-15 | <10 | <30 |
| 256 | 3-15 | <10 | <10 |
| 157.1 | 3-15 | <10 | <30 |
| 333 | 3-15 | <30 | <50 |
| 240 | 3-15 | <10 | <10 |
| 196 | 3-15 | >50 | >50 |
| 252 | 3-15 | <30 | <30 |
| 255 | 3-15 | <10 | <10 |
| 158 | 3-15 | <10 | <10 |
| 160 | 3-15 | <10 | <10 |
| 199 | 3-15 | <10 | <10 |
| 265 | 3-15 | <30 | <30 |
| 166 | 3-15 | <10 | <10 |
| 166 | 3-15 | <10 | <10 |
| 166 | 15-40 | >50 | <50 |
| 168 | 3-15 | <10 | <30 |
| 181 | 3-15 | <30 | <30 |
| 161 | 3-15 | <10 | <10 |
| 161 | 3-15 | <10 | <10 |
| 286 | 3-15 | <10 | <10 |
| 286 | 3-15 | <10 | <10 |
| 200 | 3-15 | <30 | <30 |
| 251 | 3-15 | <10 | <10 |
| 281 | 3-15 | <10 | <10 |
| 335 | 3-15 | <10 | >50 |
| 269 | 3-15 | <10 | <10 |
| 285 | 3-15 | <30 | <50 |
| 261 | 3-15 | <50 | >50 |
| 239 | 15-40 | <10 | <30 |
| 339 | 3-15 | <10 | <30 |
| 253 | 15-40 | <10 | <10 |
| 300 | 15-40 | <10 | <30 |
| 299 | 15-40 | <30 | <30 |
| 298 | 15-40 | <30 | <30 |
| 271 | 15-40 | <30 | >50 |
| 262 | 15-40 | <10 | <50 |
| 272 | 15-40 | <10 | <10 |
| 297 | 3-15 | <10 | <30 |
| 294 | 3-15 | <10 | >50 |

LLOQ = Lower Limit of Quantification

Example 353

Fecal Recovery of Orally Administered Compounds

Quantitative determination of test compound level in feces after oral gavage was performed using the same set of animals used to determine test compound concentration in plasma (Example 352). The animals were kept in metabolic cages and feces were collected from the time of dosing until 48 hr after dosing. Upon collection, feces were dried by lyophilization and ground to a visually homogenous powder. Duplicate samples of ground feces from each individual animal were weighed out and extracted using organic solvent. Extracted samples were then diluted into mobile phase and test compound levels were quantitatively determined by LC-MS/MS analysis as described in Example 352 except that the standard curve was prepared in a feces matrix. Extraction conditions were not optimized for individual compounds, and thus may represent a minimal level of recovery.

TABLE 16

Fraction of Orally Administered Compound Recovered in Feces 48 Hours after Dosing

| Example | % recovered in feces |
|---|---|
| 8.1 | <20 |
| 37 | <20 |
| 26 | <20 |
| 25 | 20-80 |
| 8.3 | <20 |
| 8.6 | 20-80 |
| 1.1 | 20-80 |
| 8.21 | >80 |
| 80 | 20-80 |
| 137 | <20 |
| 138 | <20 |

TABLE 16-continued

Fraction of Orally Administered Compound
Recovered in Feces 48 Hours after Dosing

| Example | % recovered in feces |
|---|---|
| 264 | <20 |
| 162 | 20-80 |
| 265 | <20 |
| 166 | >80 |
| 181 | >80 |
| 161 | >80 |
| 286 | <20 |
| 200 | 20-80 |
| 251 | >80 |
| 335 | >80 |
| 269 | <20 |
| 261 | <20 |
| 300 | 20-80 |
| 299 | 20-80 |
| 298 | >80 |
| 271 | 20-80 |
| 262 | 20-80 |
| 272 | >80 |
| 294 | >80 |

Example 354

In Vivo Evaluation Procedure

CKD Rats

To assess the ability of selected example compounds to impact the progression of chronic kidney disease (CKD), 5/6 nephrectomy (5/6Nx) rat model of CKD was used. A commonly used model to study various aspects of CKD, the 5/6Nx rat is not normally hyperphosphatemic unless challenged with phosphate in the diet and co-administration of active vitamin D (Shobeiri et. al., Am J Nephrol 2010; 31:471-481, Vascular Calcification in Animal Models of CKD: A Review). (Lopez et al. 2006, J Am Soc Nephrol 17: 795-804. Calcimimetic R-568 Decreases Extraosseous Calcifications in Uremic Rats Treated with Calcitriol). 5/6 Nx rats were obtained from Charles River Labs (CRL, Hollister, Calif.). Upon arrival, the surgeries and extent of kidney damage in the animals were assessed by measuring serum creatinine, P, Ca, and BUN. Based on this analysis, rats with inconsistent kidney function were removed from the study and the remainder of the cohort was divided in to evenly stratified test groups. The remaining animals were then placed on the same synthetic diet used in the drug-in-chow studies (Example 350), except the P levels were adjusted to 0.9% P. Drugs are blended into this chow to achieve the required dosing rate. At this time, rats were also started on an activated Vitamin D regimen in which they were injected intraperitoneally with calcitriol at 80 ng/kg three times a week. Once a week, serum was collected via retro orbital bleeding for analysis of serum P and creatinine utilizing an ACE ALERA blood chemistry analyzer. As reported by the Lopez group, substantial hyperphosphatemia was achieved after two weeks as well as measurable vascular and soft tissue calcification. Additionally, serum creatinine is doubled compared to untreated 5/6Nx rats and serum FGF-23 levels are significantly elevated. The data in Table 14 details the results for three independent studies in these 5/6 Nx rats. Unless otherwise indicated, the data shown is from the serum collected at 2 weeks after initiation of the treatment regimen. In addition, for study #3, during the third week of the study, the animals were placed in metabolic cages for two days, and urine collected for the final 24 hours. Using the measured levels of serum and urine creatinine, the creatinine clearance was calculated, and found to be 1.9 for vehicle, 1.9 for Renvela, 2.3 for Example 166 and 2.8 mL/min/kg for the combination group. The difference between the combination group and vehicle was statistically significant, with a p<0.05.

These results support the concept that treatment of 5/6Nx kidney damaged animals with a NaP2b inhibitor results in a reduced rate of progression of loss of kidney function, as shown by the improved trends in accepted markers of kidney disease progression, including serum creatinine, and glomerular filtration rate (GFR; creatinine clearance). The improvement appears to be mediated by reductions in serum P as well as overall P homeostasis, as evidenced by reduced levels of serum FGF23, a recognized indicator of whole-body P and recognized indicate of CKD progression (Zisman, A. L. and Wolf, M, Recent advances in the rapidly evolving field of fibroblast growth factor 23 in chronic kidney disease, Curr Opin Nephrol Hypertens. 2010 July; 19(4):335-42.) It is worth noting that in study #3, the treatment with the combination of Example 166 with the P binder Renvela results in greater than expected improvement (statistically significant improvements in serum P, serum Cre, FGF-23 and GFR), suggesting that these agents may be working synergistically through distinct but overlapping mechanisms.

TABLE 14

Parameters for CKD rats after two weeks of treatment

| Drug in chow | Study # | n | Ser P, mg/dL | Ser CRE, mg/dL | FGF23, pg/mL | Avg % weight gain |
|---|---|---|---|---|---|---|
| Vehicle | 1 | 7 | 12 | 1.5 | >15,000 | 17 |
| Renvela | 1 | 7 | 9.2* | 1.1 | >15,000 | 23 |
| Example 25 | 1 | 6 | 10 | 1.3 | ~10,000 | 18 |
| Example 261 | 1 | 5 | 9.7 | 1.0 | >15,000 | 23 |
| Vehicle | 2 | 9 | 12.6 | 1.6 | $2.2 \times 10^5$ | 21 |
| Renvela | 2 | 8 | 10 | 1.3 | $1.3 \times 10^5$ | 29 |
| Example 166 | 2 | 8 | 11 | 1.2 | $1.0 \times 10^5$ | 27 |
| Vehicle | 3 | 10 | 11§ | 1.2§ | $2.8 \times 10^{5\S\S}$ | 27§§ |
| Renvela | 3 | 11 | 11§ | 1.3§ | $1.7 \times 10^{5\S\S}$ | 32§§ |
| Example 166 | 3 | 11 | 10§ | 1.0§ | $1.2 \times 10^{5\S\S}$ | 35§§ |
| Example 166 + renvela | 3 | 10 | 8.4**§ | 0.9*§ | $1.1 \times 10^{5*\S\S}$ | 33§§ |

Ser P = Serum P, mg/dL
Ser CRE = serum Creatinine, mg/dL
FGF23 = serum FGF23 levels, pg/mL, measured using the Mouse FGF-23 (C-Terminal) ELISA kit from Immutopics (San Clemente, California)
Avg % weight gain = average % body weight since initiation of study
§Data taken at 3 weeks after initiation of study
§§Data taken at 4 weeks after initiation of study
*p < 0.05, versus vehicle
**p < 0.01, versus vehicle All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (I):

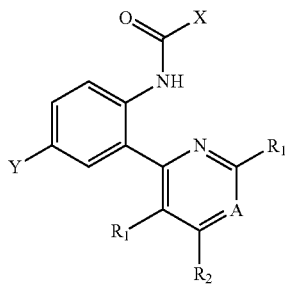

(I)

or a stereoisomer, prodrug or pharmaceutically acceptable salt thereof,
wherein:
A is —CR$_1$— or —N—;
X is substituted aryl or substituted heteroaryl;
Y is halogen, optionally substituted alkylamino, optionally substituted alkoxy, optionally substituted thioalkyl, optionally substituted cycloalkyl, optionally substituted heterocyclyl, optionally substituted aryl, —O(optionally substituted cycloalkyl), —O(optionally substituted heterocyclyl) or —O(optionally substituted aryl);
each R$_1$ is, independently, hydrogen, halogen, C$_{1-6}$alkyl or C$_{1-6}$haloalkyl;
R$_2$ is —C(=O)NR$_{2a}$R$_{2b}$, —NR$_{2a}$C(=O)R$_{2b}$, —C(=O)R$_{2b}$, —NR$_{2a}$R$_{2b}$, —OR$_{2b}$ or —R$_{2b}$;
R$_{2a}$ is hydrogen or optionally substituted C$_{1-6}$alkyl; and
R$_{2b}$ is optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, or optionally substituted heteroarylalkyl.

2. A compound of claim 1 wherein Y is halogen.
3. A compound of claim 2 wherein Y is chloro.
4. A compound of claim 1 wherein Y is alkylamino.
5. A compound of claim 4 wherein Y is diethylamino.
6. A compound of claim 1 wherein Y is alkoxy.
7. A compound of claim 1 wherein Y is heterocyclyl.
8. A compound of claim 7 wherein Y is 1-piperidinyl and the compound has the structure:

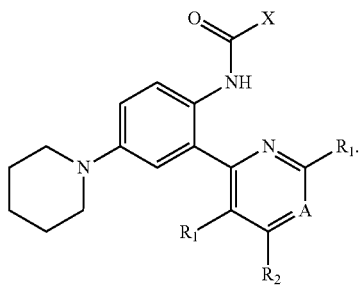

9. A compound of claim 1 wherein Y is —O(cycloalkyl).
10. A compound of claim 1 wherein X is —ZR$_3$, and wherein Z is aryl or heteroaryl and R$_3$ is a non-hydrogen substituent.
11. A compound of claim 10 wherein Z is aryl.

12. A compound of claim 11 wherein Z is phenyl.
13. A compound of claim 12 wherein the compound has the structure:

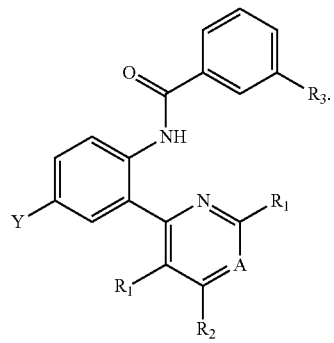

14. A compound of claim 10 wherein Z is heteroaryl.
15. A compound of claim 14 wherein Z is pyridinyl.
16. A compound of claim 15 wherein the compound has the structure:

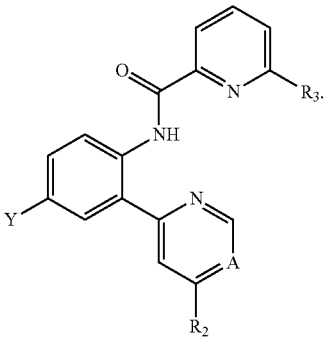

17. A compound of claim 10 wherein R$_3$ is:
(a) -(optionally substituted C$_{1-6}$alkyl)-S(O)$_{0-2}$(optionally substituted C$_{1-6}$alkyl)C(=O)NR$_7$R$_4$,
(b) -(optionally substituted C$_{1-6}$alkyl)-S(O)$_{0-2}$(optionally substituted C$_{1-6}$alkyl)NR$_7$R$_4$,
(c) -(optionally substituted C$_{1-6}$alkyl)-S(O)$_{0-2}$(optionally substituted C$_{1-6}$alkyl)C(=O)OR$_5$,
(d) -(optionally substituted C$_{1-6}$alkyl)-S(O)$_{0-2}$(optionally substituted C$_{1-6}$alkyl)OR$_5$,
(e) -(optionally substituted C$_{1-6}$alkyl)-S(O)$_{0-2}$(optionally substituted C$_{1-6}$alkyl)R$_6$,
(f) -(optionally substituted C$_{1-6}$alkyl)-S(O)$_{0-2}$R$_6$,
(g) -(optionally substituted C$_{1-6}$alkyl)-S(O)$_{0-2}$NR$_7$R$_4$,
(h) -(optionally substituted C$_{1-6}$alkyl)-S(O)$_{0-2}$(CH$_2$CH$_2$O)$_x$R$_5$, or
(i) -(optionally substituted C$_{1-6}$alkyl)-S(O)$_{0-2}$(CH$_2$CH$_2$O)$_x$(CH$_2$)$_2$NHSO$_2$(phenyl)R$_5$,
wherein:
R$_4$ is hydrogen, hydroxyl, alkoxy, optionally substituted C$_{1-6}$alkyl, optionally substituted aryl, optionally substituted heterocyclyl or optionally substituted heteroaryl;
R$_5$ is hydrogen, optionally substituted C$_{1-6}$alkyl, optionally substituted aryl, optionally substituted heterocyclyl or optionally substituted heteroaryl;
R$_6$ is optionally substituted aryl, optionally substituted heterocyclyl or optionally substituted heteroaryl;

R$_7$ is hydrogen or optionally substituted C$_{1-6}$alkyl; and
x is an integer from 2 to 10.

18. A compound of claim 17 wherein R$_3$ is:
(a) —CH$_2$S(O)$_{0-2}$(optionally substituted C$_{1-6}$alkyl)C(=O)NR$_7$R$_4$,
(b) —CH$_2$S(O)$_{0-2}$(optionally substituted C$_{1-6}$alkyl)NR$_7$R$_4$,
(c) —CH$_2$S(O)$_{0-2}$(optionally substituted C$_{1-6}$alkyl)C(=O)OR$_5$,
(d) —CH$_2$S(O)$_{0-2}$(optionally substituted C$_{1-6}$alkyl)OR$_5$,
(e) —CH$_2$S(O)$_{0-2}$(optionally substituted C$_{1-6}$alkyl)R$_6$,
(f) —CH$_2$S(O)$_{0-2}$R$_6$,
(g) —CH$_2$S(O)$_{0-2}$NR$_7$R$_4$,
(h) —CH$_2$S(O)$_{0-2}$(CH$_2$CH$_2$O)$_x$R$_5$, or
(i) —CH$_2$S(O)$_{0-2}$(CH$_2$CH$_2$O)$_x$(CH$_2$)$_2$NHSO$_2$(phenyl)R$_5$.

19. A compound of claim 10 wherein R$_3$ is:
(a) -(optionally substituted C$_{1-6}$alkyl)NR$_7$(CH$_2$CH$_2$O)$_x$R$_5$, or
(b) -(optionally substituted C$_{1-6}$alkyl)NR$_7$(CH$_2$CH$_2$O)$_x$(CH$_2$)$_2$NHSO$_2$(phenyl)R$_5$,
wherein:
R$_5$ is hydrogen, optionally substituted C$_{1-6}$alkyl, optionally substituted aryl, optionally substituted heterocyclyl or optionally substituted heteroaryl;
R$_7$ is hydrogen or optionally substituted C$_{1-6}$alkyl; and
x is an integer from 2 to 10.

20. A compound of claim 19 wherein R$_3$ is:
(a) —CH$_2$NR$_7$(CH$_2$CH$_2$O)$_x$R$_5$, or
(b) —CH$_2$NR$_7$(CH$_2$CH$_2$O)$_x$(CH$_2$)$_2$NHSO$_2$(phenyl)R$_5$.

21. A compound of claim 10 wherein R$_3$ is:
(a) —C(=O)NR$_7$(optionally substituted C$_{1-6}$alkyl)C(=O)NR$_7$R$_4$,
(b) —C(=O)NR$_7$(optionally substituted C$_{1-6}$alkyl)NR$_7$R$_4$,
(c) —C(=O)NR$_7$(optionally substituted C$_{1-6}$alkyl)C(=O)OR$_5$,
(d) —C(=O)NR$_7$(optionally substituted C$_{1-6}$alkyl)OR$_5$,
(e) —C(=O)NR$_7$(optionally substituted C$_{1-6}$alkyl)R$_6$,
(f) —C(=O)NR$_7$(CH$_2$CH$_2$O)$_x$R$_5$, or
(g) —C(=O)NR$_7$(CH$_2$CH$_2$O)$_x$(CH$_2$)$_2$NHSO$_2$(phenyl)R$_5$,
wherein:
R$_4$ is hydrogen, hydroxyl, alkoxy, optionally substituted C$_{1-6}$alkyl, optionally substituted aryl, optionally substituted heterocyclyl or optionally substituted heteroaryl;
R$_5$ is hydrogen, optionally substituted C$_{1-6}$alkyl, optionally substituted aryl, optionally substituted heterocyclyl or optionally substituted heteroaryl;
R$_6$ is optionally substituted aryl, optionally substituted heterocyclyl or optionally substituted heteroaryl;
R$_7$ is hydrogen or optionally substituted C$_{1-6}$alkyl; and
x is an integer from 2 to 10.

22. A compound of claim 10 wherein R$_3$ is:
(a) —O(optionally substituted C$_{1-6}$alkyl)C(=O)NR$_7$R$_4$,
(b) —O(optionally substituted C$_{1-6}$alkyl)NR$_7$R$_4$,
(c) —O(optionally substituted C$_{1-6}$alkyl)C(=O)OR$_5$,
(d) —O(optionally substituted C$_{1-6}$alkyl)OR$_5$,
(e) —O(optionally substituted C$_{1-6}$alkyl)R$_6$,
(f) —O(CH$_2$CH$_2$O)$_x$R$_5$, or
(g) —O(CH$_2$CH$_2$O)$_x$(CH$_2$)$_2$NHSO$_2$(phenyl)R$_5$,
wherein:
R$_4$ is hydrogen, hydroxyl, alkoxy, optionally substituted C$_{1-6}$alkyl, optionally substituted aryl, optionally substituted heterocyclyl or optionally substituted heteroaryl;
R$_5$ is hydrogen, optionally substituted C$_{1-6}$alkyl, optionally substituted aryl, optionally substituted heterocyclyl or optionally substituted heteroaryl;
R$_6$ is optionally substituted aryl, optionally substituted heterocyclyl or optionally substituted heteroaryl;
R$_7$ is hydrogen or optionally substituted C$_{1-6}$alkyl; and
x is an integer from 2 to 10.

23. A compound of claim 10 wherein R$_3$ is:
(a) —S(optionally substituted C$_{1-6}$alkyl)C(=O)NR$_7$R$_4$,
(b) —S(optionally substituted C$_{1-6}$alkyl)NR$_7$R$_4$,
(c) —S(optionally substituted C$_{1-6}$alkyl)C(=O)OR$_5$,
(d) —S(optionally substituted C$_{1-6}$alkyl)OR$_5$,
(e) —S(optionally substituted C$_{1-6}$alkyl)R$_6$,
(f) —S(CH$_2$CH$_2$O)$_x$R$_5$, or
(g) —S(CH$_2$CH$_2$O)$_x$(CH$_2$)$_2$NHSO$_2$(phenyl)R$_5$,
wherein:
R$_4$ is hydrogen, hydroxyl, alkoxy, optionally substituted C$_{1-6}$alkyl, optionally substituted aryl, optionally substituted heterocyclyl or optionally substituted heteroaryl;
R$_5$ is hydrogen, optionally substituted C$_{1-6}$alkyl, optionally substituted aryl, optionally substituted heterocyclyl or optionally substituted heteroaryl;
R$_6$ is optionally substituted aryl, optionally substituted heterocyclyl or optionally substituted heteroaryl;
R$_7$ is hydrogen or optionally substituted C$_{1-6}$alkyl; and
x is an integer from 2 to 10.

24. A compound of claim 10 wherein R$_3$ is:
(a) —NR$_7$(optionally substituted C$_{1-6}$alkyl)C(=O)NR$_7$R$_4$,
(b) —NR$_7$(optionally substituted C$_{1-6}$alkyl)NR$_7$R$_4$,
(c) —NR$_7$(optionally substituted C$_{1-6}$alkyl)C(=O)OR$_5$,
(d) —NR$_7$(optionally substituted C$_{1-6}$alkyl)OR$_5$,
(e) —NR$_7$(optionally substituted C$_{1-6}$alkyl)R$_6$,
(f) —NR$_7$(CH$_2$CH$_2$O)$_x$R$_5$, or
(g) —NR$_7$(CH$_2$CH$_2$O)$_x$(CH$_2$)$_2$NHSO$_2$(phenyl)R$_5$,
wherein:
R$_4$ is hydrogen, hydroxyl, alkoxy, optionally substituted C$_{1-6}$alkyl, optionally substituted aryl, optionally substituted heterocyclyl or optionally substituted heteroaryl;
R$_5$ is hydrogen, optionally substituted C$_{1-6}$alkyl, optionally substituted aryl, optionally substituted heterocyclyl or optionally substituted heteroaryl;
R$_6$ is optionally substituted aryl, optionally substituted heterocyclyl or optionally substituted heteroaryl;
R$_7$ is hydrogen or optionally substituted C$_{1-6}$alkyl; and
x is an integer from 2 to 10.

25. A compound of claim 10 wherein R$_3$ is:
(a) -(optionally substituted C$_{1-6}$alkyl)-(OCH$_2$CH$_2$)$_y$OR$_5$, or
(b) -(optionally substituted C$_{1-6}$alkyl)-(OCH$_2$CH$_2$)$_y$O(CH$_2$)$_2$NHSO$_2$(phenyl)R$_5$,
wherein:
R$_5$ is hydrogen, optionally substituted C$_{1-6}$alkyl, optionally substituted aryl, optionally substituted heterocyclyl or optionally substituted heteroaryl; and
y is an integer from 1 to 10.

26. A compound of claim 25 wherein R$_3$ is:
(a) —(CH$_2$)$_3$(OCH$_2$CH$_2$)$_y$OR$_5$, or
(b) —(CH$_2$)$_3$(OCH$_2$CH$_2$)$_y$O(CH$_2$)$_2$NHSO$_2$(phenyl)R$_5$.

27. A compound of claim 1 wherein A is —CH—.

28. A compound of claim 1 wherein A is N.

29. A compound of claim 1 wherein each R$_1$ is hydrogen.

30. A compound of claim 1 wherein R$_2$ is —C(=O)NR$_{2a}$R$_{2b}$.

31. A compound of claim 30 wherein R$_{2a}$ is hydrogen.

32. A compound of claim 30 wherein $R_{2b}$ is:

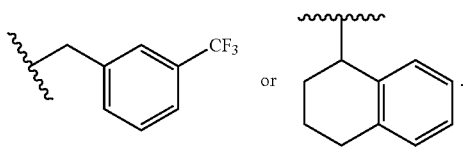 [SMILES: *Cc1cccc(C(F)(F)F)c1 ; *C1CCCc2ccccc21]

33. A pharmaceutical composition comprising a compound of claim 1, or a stereoisomer, pharmaceutically acceptable salt or prodrug thereof, and a pharmaceutically acceptable carrier, diluent or excipient.

34. The pharmaceutical composition of claim 33, further comprising one or more additional biologically active agents.

35. The pharmaceutical composition of claim 34, wherein the additional biologically active agent is selected from vitamin $D_2$, vitamin $D_3$, active vitamin D and active vitamin D analogs.

36. The pharmaceutical composition of claim 34, wherein the additional biologically active agent is a phosphate binder, and the compound does not interfere with the phosphate binder.

37. The pharmaceutical composition of claim 36, wherein the phosphate binder is selected from the group consisting of sevelamer carbonate, sevelamer hydrochloride, lanthanum carbonate, calcium carbonate, calcium acetate, MCI-196, ferric citrate, iron magnesium hydroxy carbonate, APS1585, SBR-759 and PA-21.

38. The pharmaceutical composition of claim 33, wherein the compound is substantially active as an inhibitor of Na/phosphate co-transport and the Na/phosphate co-transport is mediated by NaPi2b.

39. A method of inhibiting phosphate transport in a mammal, comprising administering to the mammal an effective amount of a compound of claim 1.

40. The method of claim 39, wherein the method inhibits sodium-mediated phosphate uptake.

41. The method of claim 39, wherein the method is selected from the group consisting of:
 (a) a method for treating hyperphosphatemia;
 (b) a method for treating a renal disease;
 (c) a method for delaying time to dialysis;
 (d) a method for attenuating intima localized vascular calcification;
 (e) a method for reducing the hyperphosphatemic effect of active vitamin D;
 (f) a method for reducing FGF23 levels;
 (g) a method for attenuating hyperparathyroidism;
 (h) a method for improving endothelial dysfunction induced by postprandial serum phosphate;
 (i) a method for reducing urinary phosphorous;
 (j) a method for normalizing serum phosphorus levels;
 (k) a method for treating proteinura; and
 (l) a method for reducing serum PTH and phosphate concentrations or levels.

42. The method of claim 41, wherein the renal disease is chronic kidney disease or end stage renal disease.

43. The method of claim 41, wherein the method for treating a renal disease further comprises administering to the mammal an effective amount of a phosphate binder.

44. A method of treating hyperphosphatemia in a mammal in need thereof, comprising administering to the mammal an effective amount of a compound of claim 1.

* * * * *